(12) United States Patent
Yang et al.

(10) Patent No.: US 11,795,177 B2
(45) Date of Patent: Oct. 24, 2023

(54) SUBSTITUTED QUINOLINE ANALOGS AS ALDEHYDE DEHYDROGENASE 1A1 (ALDH1A1) INHIBITORS

(71) Applicant: THE UNITED STATES OF AMERICA, AS REPRESENTED BY THE SECRETARY, DEPARTMENT OF HEALTH AND HUMAN SERVICES, Bethesda, MD (US)

(72) Inventors: Shyh Ming Yang, Doylestown, PA (US); David J. Maloney, Points of Rocks, MD (US); Natalia Martinez, Rockville, MD (US); Adam Yasgar, Washington, DC (US); Anton Simeonov, Bethesda, MD (US)

(73) Assignee: The United States of America, as Represented by the Secretary, Department of Health and Human Services, Bethesda, MD (US)

( * ) Notice: Subject to any disclaimer, the term of this patent is extended or adjusted under 35 U.S.C. 154(b) by 0 days.

(21) Appl. No.: 17/682,654

(22) Filed: Feb. 28, 2022

(65) Prior Publication Data
US 2023/0079399 A1 Mar. 16, 2023

Related U.S. Application Data

(62) Division of application No. 16/760,345, filed as application No. PCT/US2018/058257 on Oct. 30, 2018, now Pat. No. 11,505,559.
(Continued)

(51) Int. Cl.
C07D 491/113 (2006.01)
C07D 215/54 (2006.01)
C07D 401/04 (2006.01)
C07D 401/06 (2006.01)
C07D 401/12 (2006.01)
C07D 401/14 (2006.01)
C07D 409/14 (2006.01)
C07D 413/04 (2006.01)
(Continued)

(52) U.S. Cl.
CPC ........ C07D 491/113 (2013.01); C07D 215/54 (2013.01); C07D 401/04 (2013.01); C07D 401/06 (2013.01); C07D 401/12 (2013.01); C07D 401/14 (2013.01); C07D 409/14 (2013.01); C07D 413/04 (2013.01); C07D 471/04 (2013.01); C07D 491/107 (2013.01); C07D 495/04 (2013.01); C07D 495/10 (2013.01); C07D 519/00 (2013.01)

(58) Field of Classification Search
CPC .............. C07D 491/113; C07D 215/54; C07D 401/04; C07D 401/06; C07D 401/12; C07D 401/14; C07D 409/14; C07D 413/04; C07D 471/04; C07D 491/107; C07D 495/04; C07D 495/10; C07D 519/00
USPC ...................................... 514/210.16
See application file for complete search history.

(56) References Cited

U.S. PATENT DOCUMENTS 3,966,746 A 6/1976 Hoehn et al.
2013/0267501 A1 10/2013 Mochly-Rosen et al.
(Continued)

FOREIGN PATENT DOCUMENTS

WO 2004024728 A2 3/2004
WO 2005058834 A2 6/2005
WO 2010056865 A1 5/2010

OTHER PUBLICATIONS

Tanwar et al., Design, development of new synthetic methodology, and biological evaluation of substituted quinolines as new antitubercular leads, Bioorganic & Medicinal Chemistry Letters, 26, 2016, 5960-5966 (Year: 2016).*
(Continued)

Primary Examiner — Kristin A Vajda
(74) Attorney, Agent, or Firm — CANTOR COLBURN LLP

(57) ABSTRACT

The disclosure provides compounds of Formula I, which may be useful as aldehyde dehydrogenase inhibitors and the pharmaceutically acceptable salts thereof. The variables, J, $R^4$, G, Q, and ring A are defined herein. Aldehyde dehydrogenase inhibitors of Formula I are useful for treating a variety of conditions including cancer and inflammation. The disclosure includes methods for using compounds and salts of Formula I to treat colon cancer, pancreatic cancer, nasopharyngeal carcinoma, thyroid cancer, prostate cancer, ovarian cancer, head and neck squamous cell carcinoma, lung cancer, hepatocellular carcinoma, leukemia, brain tumors breast cancer, atherosclerosis, ischaemic heart disease, acne vulgaris, asthma, autoimmune diseases, autoinflammatory diseases, chronic prostatitis, glomerulonephritis, inflammatory bowel disease, pelvic inflammatory disease, reperfusion injury, rheumatoid arthritis, sarcoidosis, transplant rejection, vasculitis, and interstitial cystitis. The disclosure also includes pharmaceutical compositions containing a compound or salt of Formula I.

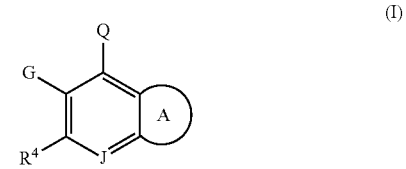

22 Claims, No Drawings

Related U.S. Application Data

(60) Provisional application No. 62/578,899, filed on Oct. 30, 2017.

(51) Int. Cl.
    *C07D 471/04*     (2006.01)
    *C07D 491/107*     (2006.01)
    *C07D 495/04*     (2006.01)
    *C07D 495/10*     (2006.01)
    *C07D 519/00*     (2006.01)

(56) References Cited

U.S. PATENT DOCUMENTS

2015/0306108 A1     10/2015     Hurley et al.
2021/0179630 A1     6/2021     Yang et al.

OTHER PUBLICATIONS

Wasa et al., Pd(0)/PR3-Catalyzed Arylation of Nicotinic and Isonicotinic Acid Derivatives, 2010, Angew Chem Int Ed Engl., 49(7), 1275-1277 (Year: 2010).*

Atechian et al., "New Vistas in Quinoline Synthesis," Science Direct, Tetrahedron 63 (2007), 2811-2823.

Bose et al., "Diversity-Oriented Synthesis of Quinolines via Friedlander Annulation Reaction Under Mild Catalytic Conditions," Journal of Combinatorial Chemistry, (2010), vol. 12, (No. 1), 100-110.

Chukhajian et al., "Cyclization of Dialkyl(3-Phenylpropen-2-YL-(3-Phenylpropyn-2-YL-)Ammonium Bromides by the Action of an Aqueous Alkali Solution. Aqueous-Alkaline Cleavage of the Cyclization Products—N,N-Dialkyl-4(9)-Phenyl-3a,4-Dihydro-Benzo[f]Isoindolinium Bromides," Chemistry of Heterocyclic Compounds, (2012), vol. 48, (No. 9), 1314-1320.

European Search Report for EP Application No. 18804792.2-1110; dated Jul. 8, 2021; 5 pages.

Ife et al., "Reversible Inhibitors of the Gastric (H+/K+)-ATPase. 3. 3-Substituted-4-(phenylamino)Quinolines," Journal of Medicinal Chemistry, (1992), vol. 35, (No. 18), 3413-3422.

International Preliminary Report on Patentability; International Application No. PCT/US2018/058257; International Filing Date—Oct. 30, 2018; dated May 5, 2020; 10 pages.

International Search Report; International Application No. PCT/US2018/058257; International Filing Date—Oct. 30, 2018; dated Feb. 11, 2019.

Tkachenko et al., "Study of Three-Component Reactions Between 5-Amino-3-Methylisoxazole, N-Arylamides of Acetoacetic Acid, and Aromatic Aldehydes," Chemistry of Heterocyclic Compounds, (2014), vol. 50, (No. 8), 1166-1176.

Written Opinion; International Application No. PCT/US2018/058257; International Filing Date—Oct. 30, 2018; dated Feb. 11, 2019.

Anzini Maurizio et al: "Mapping and fitting the peripheral benzodiazepine receptor binding site by carboxamide derivatives. comparison of different approaches to quantitative ligand-receptor interaction modeling", Journal of Medicinal Chemistry, American Chemical Society, US, vol. 44, No. 8, Jan. 1, 2001, pp. 1134-1150.

European Search Report for European Application No. 22207287.8, dated Feb. 22, 2023, 16 pages.

Gopi, P., et al: "Effective water mediated green synthesis of polysubstituted quinolines without energy expenditure", Montash Chem., vol. 148, No. 6, Sep. 14, 2016, pp. 1043-1049.

Kumar Gautam et al: "Synthesis and biological evaluation of dihydroquinoline carboxamide derivatives as anti-tubercular agents", European Journal of Medicinal Chemistry, vol. 157, Jul. 23, 2018, pp. 1-13.

Palakshi Reddy, et al: "Nickel oxide nanoparticles catalyzed synthesis of poly-substituted quinolines via Friedlander heteroannulation reaction", Chinese Chemical Letters, vol. 25, No. 12, Jun. 30, 2014, pp. 1595-1600.

Senadi, G. et al: Palladium (II)-catalysed regioselective synthesis of 3,4-disubstituted quinolines and 2,3,5-trisubstituted pyrroles from alkenes via anti-Markovnikov selectivity, Chemical Communications, vol. 51, No. 72, Jan. 1, 2015, pp. 13795-13798.

Tkachenko, V. et al: "The unexpected influence of aryl substituents in N-aryl-3-oxobutanamides on the behavior of their multicomponent reactions with 5-amino-3-methylisoxazole and salicylaldehyde", Beilstein Journal of Organic Chemistry, vol. 10, Dec. 3, 2014 (Dec. 3, 2014), pp. 3019-3030.

Vijayalakshmi, S., et al: "Synthesis of 6-chloro-7-phenyldibenzo[b,h][1,6]Naphthyridines", Dec. 1, 2000, pp. 1-6.

Wang Qiang et al: "Switchable intramolecular oxidative amidation of 4-arylquinoline-3-carboxamides: divergent access to dibenzo[c,f][2,7]naphthyridinones and spirocyclohexadienones", Organic Chemistry Frontiers, vol. 5, No. 4, Jan. 1, 2018, pp. 549-554.

Yan, X., et al: "Copper(I)-catalysed amidation and successive oxidation of benzylic C(sp3)-H bond: synthesis of 1H-pyrrolo[3,4-b]quinoline-1,3(2H)-diones", Tetrahedron, vol. 72, No. 29, May 25, 2016, pp. 4245-4251.

Yvenkateswarlu et al: "A simple and efficient protocol for the synthesis of quinolines catalyzed by chloramine-T", Organic communications, Jul. 1, 2012, pp. 120-127.

* cited by examiner

SUBSTITUTED QUINOLINE ANALOGS AS ALDEHYDE DEHYDROGENASE 1A1 (ALDH1A1) INHIBITORS

CROSS REFERENCE TO RELATED APPLICATIONS

This application is a Divisional of U.S. application Ser. No. 16/760,345, filed Apr. 29, 2020, which is a National Stage application of PCT/US2018/058257, filed Oct. 30, 2018, which claims priority to U.S. Provisional Application No. 62/578,899, filed Oct. 30, 2017, and all the benefits accruing therefrom under 35 U.S.C. § 119, the content of which is incorporated by reference in its entirety.

BACKGROUND

Aldehyde dehydrogenases (ALDH) constitute a family of enzymes that play a critical role in oxidizing various cytotoxic xenogenic and biogenic aldehydes. There are at least 19 members/isozymes of the ALDH family, where the various isozymes may exhibit different substrate specificity and/or cellular location relative to other members of the family.

Increased expression of various ALDH isozymes have been reported in various human cancers and are associated with cancer relapse. Family member ALDH1A1 is a cancer stem cell marker, and its expression correlates with poor prognosis in a number of malignancies. In addition, ALDH1A1 appears to be an important factor in tumor aggressiveness. In addition, tumors and cancer stem cells resistant to chemotherapy and radiation are associated with high expression of ALDH1A1. Although the majority of the research community has considered ALDH1A1 as a marker of cancer stem cells and a predictor of the prognosis, this enzyme plays an important role in the biology of tumors and cancer stem cells. Initial evidence using non-specific ALDH inhibitors and siRNA confirms the involvement of ALDH1A1 in the first line of targets for targeted drug development in order to enhance the efficacy of chemotherapy and radiation.

ALDH1A1 has also been shown to play a role metabolism and obesity. ALDH1A1 is expressed predominantly in white adipose tissues in mice and humans. White adipose tissue selective ALDH1A1 knockdown in obese mice limited weight gain and improved glucose homeostasis. ALDH1A1 inhibitors are therefore desirable as anti-obesity agents.

Therefore, this disclosure provides compounds and compositions that inhibit aldehyde dehydrogenases, such as aldehyde dehydrogenase 1A1, for use for the treatment of various conditions, such as cancer, inflammation, or obesity

SUMMARY

The disclosure provides compounds of Formula I, which may be useful as aldehyde dehydrogenase inhibitors

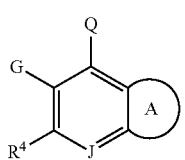

(Formula I)

and the pharmaceutically acceptable salts thereof.

Within Formula I the following conditions apply.

G is

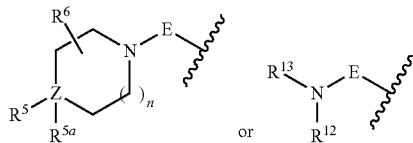

E is —C(O)—, $SO_2$—, or —$CH_2$—.
J is N or CH.
n is 0, 1, or 2.
Q is:
(i) an optionally substituted phenyl group substituted at the para position with $R^1$;
(ii) an optionally substituted N-linked 3- to 7-membered heterocycloalkyl group having 0 additional heteroatoms or having N, S, $SO_2$, or O at one additional ring position, and optionally substituted at one carbon atom with $R^1R^2$ or at a ring N with $R^1$, which N-linked 3- to 7-membered heterocycloalkyl group is optionally fused to a 4-6 membered carbocyclic or heterocyclic group;
(iii) an optionally substituted ($C_3$-$C_7$cycloalkyl)-$NR^9$— or an optionally substituted (heteroycloalkyl)-$NR^9$— where $R^9$ is hydrogen, $C_1$-$C_4$alkyl, $C_1$-$C_4$alkoxy, $C_1$-$C_2$haloalkyl, $C_1$-$C_2$haloalkoxy, and $C_3$-$C_6$cycloalkyl; or
(iv) an optionally substituted 5- or 6-membered heteroaryl group having 1, 2, 3, or 4 heteroatoms independently chosen from N, O, and S; or
(v) a cyclohexenyl group substituted at one carbon with $R^1$ and $R^2$;
$R^1$, when present, is hydrogen, halogen, hydroxyl, $C_1$-$C_6$alkyl, optionally substituted $C_3$-$C_6$cycloalkyl optionally substituted phenyl, optionally substituted phenyl$SO_2$—, optionally substituted benzyl, or an optionally substituted 5- or 6-membered heterocyclic ring.
$R^2$, when present, is hydrogen, hydroxyl, halogen, cyano, or $C_1$-$C_4$alkyl; or
$R^1$ and $R^2$ are joined to form an a oxo group, a $C_3$-$C_6$cycloalkyl ring or a 3- to 6-membered heterocycloalkyl ring; each of which $R^1/R^2$ ring is optionally fused to a 5- to 6-membered aryl or heteroaryl ring and is optionally substituted with one or more substituents independently chosen from halogen, hydroxyl, cyano, amino, $C_1$-$C_6$alkyl, and phenyl.
Each alkyl in the definition of $R^1$ and $R^2$ is straight or branched, can contain one or more double or triple bonds, can have one or more $CH_2$ group replaced by an O, S, or NH, and is optionally substituted by one or more substituents independently chosen from hydroxyl, amino, cyano, halo, oxo, and $C_3$-$C_6$cycloalkyl.
The A ring

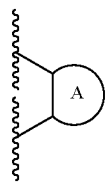

is phenyl ring or 5- or 6-memberd heteroaryl ring having 1, 2, or 3 heteroatoms independently chosen from N, O, and S, which A ring is optionally substituted with one or more $R^{11}$ substituents, where $R^{11}$ is independently chosen from halogen, hydroxyl, cyano, amino, nitro, $C_1$-$C_6$alkyl, $C_1$-$C_6$alkoxy, $C_1$-$C_2$haloalkyl, and $C_1$-$C_2$haloalkoxy.

$R^4$ is hydrogen, halogen, hydroxyl, cyano, or $C_1$-$C_4$alkyl.

Z is N, O, S, $SO_2$, or C.

$R^5$ is absent when Z is O, S, or $SO_2$, or $R^5$ is hydrogen, fluoro, cyano, trifluoromethyl, furanyl, thiophenyl, pyridyl, oxazolyl, phenyl, $C_1$-$C_4$alkyl, $C_1$-$C_4$alkyl-O—, $C_1$-$C_4$alkyl-$SO_2$—, $C_3$-$C_6$cycloalkyl, $C_3$-$C_6$cycloalkylO—, $C_3$-$C_6$cycloalkylC(O)—, $C_3$-$C_6$cycloalkylOC(O)—, $C_3$-$C_6$cycloalkyl-$SO_2$—, $C_1$-$C_4$alkyl-NH—$SO_2$—, ($C_1$-$C_4$alkyl)($C_1$-$C_4$alkyl)N—$SO_2$—, (4- to 6-membered heterocycloalkyl)$SO_2$—, or 5- or 6-membered heterocycle, or a group $R^7C(O)$—, where $R^7$ is $C_1$-$C_6$alkyl, $C_1$-$C_6$alkylO—, $C_1$-$C_6$alkylNH—, ($C_1$-$C_6$alkyl)($C_1$-$C_6$alkyl)N—, $C_3$-$C_6$cycloalkyl, 4- to 6-membered heterocycloalkyl, or 5- to 6-membered heteroaryl; each of which $R^5$ other than hydrogen, fluoro, cyano, and trifluoromethyl, is optionally substituted and $R^{5a}$ is absent when Z is O, S, $SO_2$, or N, or $R^{5a}$ is hydrogen, halogen, or methyl.

Or, $R^5$ and $R^{5a}$ are joined to form a $C_3$-$C_6$cycloalkyl ring or a 4- to 6-membered heterocycloalkyl ring; which $R^5/R^{5a}$ ring is optionally substituted with one or more substituents independently chosen from halogen, methyl, and methoxy.

$R^6$ is 0 or 1 or more substituents independently chosen from halogen, halogen, methyl, and methoxy.

$R^{12}$ is hydrogen or methyl.

$R^{13}$ is $C_3$-$C_6$cycloalkyl, phenyl, a 4-6 membered carbon-linked heterocycloalkyl group having 1 or 2 heteroatoms chosen from N, O, and S; or a 5- or 6-membered carbon-linked heteroaryl group having 1, 2, or 3 heteroatoms chosen from N, O, and S; where $R^{13}$ is optionally substituted with one or more substituents independently chosen from halogen, hydroxyl, cyano, amino, $C_1$-$C_4$alkyl, $C_1$-$C_4$alkoxy, trifluoromethyl, and trifluoromethoxy, and optionally substituted with one $C_1$-$C_6$alkyl substituent which has one or more $CH_2$ group replaced by an O, S, NH, or N($C_1$-$C_6$alkyl) and/or is substituted by one or more substituents independently chosen from hydroxyl, amino, cyano, halo, oxo, and $C_3$-$C_6$cycloalkyl.

This disclosure also provides pharmaceutical compositions comprising a compound or salt of Formula I. The compound or salt of Formula I can be the only active agent, or the compound or salt of Formula I can be a first active agent and can be combined with one or more additional active agents.

This disclosure further provides a process for making a compound of Formula I or a pharmaceutical composition comprising a compound of Formula I.

This disclosure further provides a process method of treating a disorder associated with ALDH1A1, comprising administering a sufficient amount of a compound of Formula I to a patient having an ALDH1A1 associated disorder to inhibit ALDH1A1 activity in the patient.

DETAILED DESCRIPTION

Terminology

In order for the present disclosure to be more readily understood, certain terms and phrases are defined below and throughout the specification.

The articles "a" and "an" are used herein to refer to one or to more than one (i.e., to at least one) of the grammatical object of the article. By way of example, "an element" means one element or more than one element.

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

It should also be understood that, unless clearly indicated to the contrary, in any methods claimed herein that include more than one step or act, the order of the steps or acts of the method is not necessarily limited to the order in which the steps or acts of the method are recited.

In the claims, as well as in the specification above, all transitional phrases such as "comprising," "including," "carrying," "having," "containing," "involving," "holding," "composed of," or the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03. The open-end phrases such as "comprising" include and encompass the close-ended phrases. Comprising may be amended to the more limiting phrases "consisting essentially of" of "consisting of" as needed.

The definition of each expression, e.g., alkyl, m, n, or the like, when it occurs more than once in any structure, is intended to be independent of its definition elsewhere in the same structure.

It will be understood that "substitution" or "substituted with" includes the implicit proviso that such substitution is in accordance with permitted valence of the substituted atom and the substituent, and that the substitution results in a stable compound, e.g., a compound which does not spontaneously undergo transformation such as by rearrangement, cyclization, elimination, or other reaction.

The term "substituted" is also contemplated to include all permissible substituents of organic compounds. In a broad aspect, the permissible substituents include acyclic and cyclic, branched and unbranched, carbocyclic and heterocyclic, aromatic and nonaromatic substituents of organic compounds. Illustrative substituents include, for example, those described herein below. The permissible substituents may be one or more and the same or different for appropriate organic compounds. For purposes of this disclosure, the heteroatoms such as nitrogen may have hydrogen substituents and/or any permissible substituents of organic compounds described herein which satisfy the valences of the heteroatoms. This disclosure is not intended to be limited in any manner by the permissible substituents of organic compounds. "H—" is not considered a substituent.

Suitable groups that may be present on a "substituted" or "optionally substituted" position include, but are not limited to, e.g., halogen; cyano; —OH; oxo; —NH$_2$; nitro; azido; alkanoyl (such as a $C_2$-$C_6$ alkanoyl group); C(O)NH$_2$; alkyl groups (including cycloalkyl and (cycloalkyl)alkyl groups) having 1 to about 8 carbon atoms, or 1 to about 6 carbon atoms; alkenyl and alkynyl groups including groups having one or more unsaturated linkages and from 2 to about 8, or 2 to about 6 carbon atoms; alkoxy groups having one or more oxygen linkages and from 1 to about 8, or from 1 to about 6 carbon atoms; aryloxy such as phenoxy; alkylthio groups including those having one or more thioether linkages and from 1 to about 8 carbon atoms, or from 1 to about 6 carbon atoms; alkylsulfinyl groups including those having one or more sulfinyl linkages and from 1 to about 8 carbon atoms, or from 1 to about 6 carbon atoms; alkylsulfonyl groups including those having one or more sulfonyl linkages and from 1 to about 8 carbon atoms, or from 1 to about 6 carbon atoms; aminoalkyl groups including groups having one or more N atoms and from 1 to about 8, or from 1 to about 6 carbon atoms; mono- or dialkylamino groups including groups having alkyl groups from 1 to about 6 carbon atoms; mono- or dialkylcarboxamido groups (i.e. alkylNHC(O)—, (alkyl$_1$)(alkyl$_2$)NC(O)—, alkylC(O)NH—, or alkyl$_1$C(O)N(alkyl$_2$)-) having alkyl groups from about 1 to about 6 carbon atoms; carbocyclyl such as aryl having 6 or more carbons and one or more rings, (e.g., phenyl, biphenyl, naphthyl, or the like, each ring either substituted or unsubstituted aromatic); or a saturated, unsaturated, or aromatic heterocycle having 1 to 3 separate or fused rings with 3 to about 8 members per ring and one or more N, O or S atoms, e.g. coumarinyl, quinolinyl, isoquinolinyl, quinazolinyl, pyridyl, pyrazinyl, pyrimidinyl, furanyl, pyrrolyl, thienyl, thiazolyl, triazinyl, oxazolyl, isoxazolyl, imidazolyl, indolyl, benzofuranyl, benzothiazolyl, tetrahydrofuranyl, tetrahydropyranyl, piperidinyl, morpholinyl, piperazinyl, and pyrrolidinyl. Such heterocycles may be further substituted, e.g. with hydroxy, alkyl, alkoxy, halogen and amino. In certain embodiments "optionally substituted" includes one or more substituents independently chosen from halogen, hydroxyl, oxo, amino, cyano, —CHO, —CO$_2$H, —C(O)NH$_2$, $C_1$-$C_6$-alkyl, $C_2$-$C_6$-alkenyl, $C_1$-$C_6$-alkoxy, $C_2$-$C_6$-alkanoyl, $C_1$-$C_6$-alkylester, (mono- and di-$C_1$-$C_6$-alkylamino)$C_0$-$C_2$-alkyl, (mono- and di-$C_1$-$C_6$-alkylamino)(CO)$C_0$-$C_2$-alkyl, $C_1$-$C_2$-haloalkyl, $C_1$-$C_2$haloalkoxy, and heterocyclic substituents of 5-6 members and 1 to 3 N, O or S atoms, i.e. pyridyl, pyrazinyl, pyrimidinyl, furanyl, pyrrolyl, thienyl, thiazolyl, triazinyl, oxazolyl, isoxazolyl, imidazolyl, tetrahydrofuranyl, tetrahydropyranyl, piperidinyl, morpholinyl, piperazinyl, and pyrrolidinyl, each of which heterocycle can be substituted by amino, $C_1$-$C_6$-alkyl, $C_1$-$C_6$-alkoxy, or —CONH$_2$. In certain embodiments "optionally substituted" includes halogen, hydroxyl, cyano, nitro, oxo, —CONH$_2$, amino, ono- or di-$C_1$-$C_4$alkylcarboxamide, and $C_1$-$C_6$hydrocarbyl, which $C_1$-$C_6$hydrocarbyl group, a hydrocarbon chain in which carbon atoms are joined by single, double or triple bonds, and any one carbon atom can be replaced by O, NH, or N($C_1$-$C_4$alkyl) and which hydrocarbyl group is optionally substituted with one or more substituents independently chosen from hydroxyl, halogen, and amino. When the substituent is oxo (=O) then 2 hydrogen atoms are replaced. When an oxo group substitutes an aryl or heteroaryl group, aromaticity of the group is lost. When an oxo group substitutes a heteroaryl group the resulting heterocyclic group can sometimes have tautomeric forms. For example a pyridyl group substituted by oxo at the 2- or 4-position can sometimes be written as a hydroxypyridine.

The term "saturated," as used herein, pertains to compounds and/or groups which do not have any carbon-carbon double bonds or carbon-carbon triple bonds.

The term "unsaturated," as used herein, pertains to compounds and/or groups which have at least one carbon-carbon double bond or carbon-carbon triple bond.

The term "aliphatic," as used herein, pertains to compounds and/or groups which are linear or branched, but not cyclic (also known as "acyclic" or "open-chain" groups).

Compounds of Formula I include compounds of the formula having isotopic substitutions at any position. Isotopes include those atoms having the same atomic number but different mass numbers. By way of general example, and without limitation, isotopes of hydrogen include tritium and deuterium and isotopes of carbon include $^{11}C$, $^{13}C$, and $^{14}C$. Compounds of Formula I also require enrichment of deuteration (substitution of a hydrogen atom with deuterium) at identified positions.

The term "cyclic," as used herein, pertains to compounds and/or groups which have one ring, or two or more rings (e.g., spiro, fused, bridged).

"Cyclolalkyl" is a saturated carbocyclic ring having the indicated number of carbon ring atoms, for example $C_{(3-6)}$ cycloalkyl is a cyclopropyl, cyclobutyl, cyclopentyl, or cyclohexyl group The term "aromatic" refers to a planar or polycyclic structure characterized by a cyclically conjugated molecular moiety containing 4n+2 electrons, wherein n is the absolute value of an integer. Aromatic molecules containing fused, or joined, rings also are referred to as bicyclic aromatic rings. For example, bicyclic aromatic rings containing heteroatoms in a hydrocarbon ring structure are referred to as bicyclic heteroaryl rings.

The term "hydrocarbon" as used herein refers to an organic compound consisting entirely of hydrogen and carbon.

For purposes of this disclosure, the chemical elements are identified in accordance with the Periodic Table of the Elements, CAS version, Handbook of Chemistry and Physics, 67th Ed., 1986-87, inside cover.

The term "heteroatom" as used herein is art-recognized and refers to an atom of any element other than carbon or hydrogen. Illustrative heteroatoms include boron, nitrogen, oxygen, phosphorus, sulfur and selenium.

The term "alkyl" means a branched or unbranched aliphatic radical containing the indicated number of carbon atoms. Representative examples of alkyl include, but are not limited to, methyl, ethyl, n-propyl, iso-propyl, n-butyl, secbutyl, iso-butyl, tert-butyl, n-pentyl, isopentyl, neopentyl, n-hexyl, 2-methylcyclopentyl, and 1-cyclohexylethyl.

The term "carbocyclyl" as used herein means monocyclic or multicyclic (e.g., bicyclic, tricyclic, etc.) hydrocarbons containing from 3 to 12 carbon atoms that is completely saturated or has one or more unsaturated bonds, and for the avoidance of doubt, the degree of unsaturation does not result in an aromatic ring system (e.g. phenyl). Examples of carbocyclyl groups include 1-cyclopropyl, 1-cyclobutyl, 2-cyclopentyl, 1-cyclopentenyl, 3-cyclohexyl, 1-cyclohexenyl and 2-cyclopentenylmethyl.

The term "heterocycloalkyl," means a saturated ring group usually having 4- to 7-ring atoms with 1 or 2 ring atoms independently chosen from N, O, and S: Examples of heterocycloalkyl groups includes azepines, azetidinyl, morpholinyl, pyranyl, oxopiperidinyl, oxopyrrolidinyl, piperazinyl, piperidinyl, pyrrolidinyl, quinicludinyl, thiomorpholinyl, tetrahydropyranyl and tetrahydrofuranyl.

The term "heterocyclic group" means a cyclic group containing at least on ring heteroatom chosen from N, O, and S. The heterocyclic group can be fully saturated, i.e. a heterocycloalkyl group, partially unsaturated, e.g. a heterocycloalkenyl group, or aromatic, e.g. a heteroaryl group. The heterocyclic group can contain one ring having 4 to 7 ring members and one, two, three, or four heteroatoms independently chosen from N, O, and S. It is preferred that not more than two heteroatoms are O or S and O and S atoms are not adjacent. The heterocyclic group can also contain two fused ring or two rings in spiro orientation; only one ring in a two ring heterocyclic group is required to contain a heteroatom.

The term "aryl," as used herein means a phenyl group, naphthyl or anthracenyl group. The aryl groups of the present disclosure can be optionally substituted with 1, 2, 3, 4 or 5 substituents.

The term "halo" or "halogen" means —Cl, —Br, —I or —F.

The term "haloalkyl" means an alkyl group, as defined herein, wherein at least one hydrogen is replaced with a halogen, as defined herein. Representative examples of haloalkyl include, but are not limited to, chloromethyl, 2-fluoroethyl, trifluoromethyl, pentafluoroethyl, and 2-chloro-3-fluoropentyl.

The term "hydroxyl" as used herein means an —OH group.

The term "alkoxy" as used herein means an alkyl group, as defined herein, appended to the parent molecular moiety through an oxygen atom. Representative examples of alkoxy include, but are not limited to, methoxy, ethoxy, propoxy, 2-propoxy, butoxy, tert-butoxy, pentyloxy, and hexyloxy.

The term "haloalkoxy" as used herein means an alkoxy group, as defined herein, wherein at least one hydrogen is replaced with a halogen, as defined herein. Representative examples of haloalkoxy include, but are not limited to, chloromethoxy, 2-fluoroethoxy, trifluoromethoxy, and pentafluoroethoxy.

The term "cyano" as used herein means a —C≡N group.

The term "nitro" as used herein means a —$NO_2$ group.

The abbreviations Me, Et, Ph, Tf, Nf, Ts, and Ms represent methyl, ethyl, phenyl, trifluoromethanesulfonyl, nonafluorobutanesulfonyl, p-toluenesulfonyl and methanesulfonyl, respectively. A more comprehensive list of the abbreviations utilized by organic chemists of ordinary skill in the art appears in the first issue of each volume of the *Journal of Organic Chemistry*; this list is typically presented in a table entitled Standard List of Abbreviations.

As used herein, the term "aldehyde dehydrogenase" or "ALDH" refers to an enzyme that oxidizes an aldehyde (e.g., a xenogenic aldehyde, a biogenic aldehyde, or an aldehyde produced from a compound that is ingested, inhaled, or absorbed) to its corresponding acid in an $NAD^+$-dependent or an $NADP^+$-dependent reaction. For example, ALDH oxidizes aldehydes derived from the breakdown of compounds, e.g., toxic compounds that are ingested, that are absorbed, that are inhaled, that are produced as a result of oxidative stress, or that are produced during normal metabolism, e.g., conversion of retinaldehyde to retinoic acid. An example of a biogenic aldehyde is acetaldehyde produced as a product of alcohol dehydrogenase activity on ingested ethanol. An aldehyde dehydrogenase can also exhibit esterase activity and/or reductase activity.

The term "ALDH" encompasses ALDH found in the cytosol, in the mitochondria, microsome, or other cellular compartment. The term "ALDH" encompasses ALDH found primarily in one or a few tissues, e.g., cornea, saliva, liver, etc., or in stem cells and embryos. The term "ALDH" encompasses any of the known ALDH isozymes, including ALDH1, ALDH2, ALDH3, ALDH4, ALDH5, etc.

As used herein, "ALDH1" refers to a cytosolic aldehyde dehydrogenase that oxidizes an aldehyde (e.g., a xenogenic aldehyde, a biogenic aldehyde, or an aldehyde produced from a compound that is ingested, inhaled, or absorbed) to its corresponding acid in an $NAD^+$-dependent reaction.

The term "ALDH1" encompasses ALDH1 from various species Amino acid sequences of ALDH1 from various species are publicly available. See, e.g., GenBank Accession Nos. AAC51652 (*Homo sapiens* ALDH1); NP_000680 (*Homo sapiens* ALDH1); AAH61526 (*Rattus norvegicus* ALDH1); AAI05194 (*Bos taurus* ALDH1); and NP_036051 (*Mus musculus* ALDH1). The term "ALDH1" as used herein also encompasses fragments, fusion proteins, and variants (e.g., variants having one or more amino acid substitutions, addition, deletions, and/or insertions) that retain ALDH1 enzymatic activity. The term "ALDH1" encompasses an aldehyde dehydrogenase that oxidizes aromatic aldehydes, including those of the retinaldehyde, naphthaldehyde, phenanthrenealdehyde, and coumarinaldehyde series, as well as complex polyaromatic aldehydes. The term "ALDH1" encompasses a cytosolic aldehyde dehydrogenase.

The term "ALDH1" encompasses an enzymatically active polypeptide having at least about 75%, at least about 80%, at least about 85%, at least about 90%, at least about 95%, at least about 98%, at least about 99%, or 100%, amino acid sequence identity to the amino acid sequence set forth in SEQ ID NO:3 or SEQ ID NO:4 of U.S. Patent Application Publication No. 2013/0267501, which is hereby incorporated by reference in its entirety.

As used herein, the term "administering" means providing a pharmaceutical agent or composition to a subject, and includes, but is not limited to, administering by a medical professional and self-administering.

As used throughout this application, the term "pharmaceutically effective amount of a compound for pharmaceutical use" shall mean an amount of compound that exhibits the intended pharmaceutical or therapeutic or diagnostic effect when administered. Examples of methods of administration include, but are not limited to, oral administration (e.g., ingestion, buccal or sublingual administration), anal or rectal administration, topical application, aerosol application, inhalation, intraperitoneal administration, intravenous administration, transdermal administration, intradermal administration, subdermal administration, intramuscular administration, intrauterine administration, vaginal administration, administration into a body cavity, surgical administration, administration into the lumen or parenchyma of an organ, and parenteral administration. The compositions can be administered in any form by any means. Examples of forms of administration include, but are not limited to, injections, solutions, creams, gels, implants, ointments, emulsions, suspensions, microspheres, powders, particles, microparticles, nanoparticles, liposomes, pastes, patches, capsules, suppositories, tablets, transdermal delivery devices, sprays, suppositories, aerosols, or other means familiar to one of ordinary skill in the art.

In some embodiments, the compositions can be combined with other components. Examples include, but are not limited to, coatings, depots, matrices for time release and osmotic pump components.

The term "solvate" refers to the compound formed by the interaction of a solvent and a compound. Suitable solvates are pharmaceutically acceptable solvates, such as hydrates, including monohydrates and hemi-hydrates. "Pharmaceutically acceptable salt" refers to a salt of a compound that is pharmaceutically acceptable and that possesses the desired pharmacological activity of the parent compound. Such salts may include: (i) acid addition salts, formed with inorganic acids such as hydrochloric acid, hydrobromic acid, sulfuric acid, nitric acid, phosphoric acid, or the like; or formed with organic acids such as acetic acid, propionic acid, hexanoic acid, cyclopentanepropionic acid, glycolic acid, pyruvic acid, lactic acid, malonic acid, succinic acid, malic acid, maleic acid, fumaric acid, tartaric acid, citric acid, benzoic acid, 3-(4-hydroxybenzoyl) benzoic acid, cinnamic acid, mandelic acid, methanesulfonic acid, or the like; or (ii) salts formed when an acidic proton present in the parent compound either is replaced by a metal ion, e.g., an alkali metal ion, an alkaline earth ion, or an aluminum ion; or coordinates with an organic base such as ethanolamine, diethanolamine, triethanolamine, N-methylglucamine, dicyclohexylamine, or the like.

In some embodiments, the one or more compounds, or compositions of the present disclosure, are administered to persons or animals to provide substances in any dose range that will produce desired physiological or pharmacological results. Dosage will depend upon the substance or substances administered, the therapeutic endpoint desired, the diagnostic endpoint desired, the desired effective concentration at the site of action or in a body fluid, and the type of administration. Information regarding appropriate doses of substances are known to persons of ordinary skill in the art and may be found in references such as L. S. Goodman and A. Gilman, eds, The Pharmacological Basis of Therapeutics, Macmillan Publishing, New York, and Katzung, Basic & Clinical Pharmacology, Appleton & Lang, Norwalk, Conn. (6.sup.th Ed. 1995). In some embodiments, the compounds and compositions of the present disclosure may be administered to a subject. Suitable subjects include a cell, population of cells, tissue or organism. In certain embodiments, the subject is a mammal such as a human. The compounds may be administered in vitro or in vivo.

The disclosure includes methods in which one or more compounds are an admixture or otherwise combined with one or more compounds and may be in the presence or absence of commonly used excipients (or "pharmaceutically acceptable carriers"); for example, but not limited to: i) diluents and carriers such as starch, mannitol, lactose, dextrose, sucrose, sorbitol, cellulose, or the like; ii) binders such as starch paste, gelatin, magnesium aluminum silicate, methylcellulose, alginates, gelatin, sodium carboxymethyl-cellulose, polyvinylpyrrolidone or the like; iii) lubricants such as stearic acid, talcum, silica, polyethylene glycol, polypropylene glycol or the like; iv) absorbents, colorants, sweeteners or the like; v) disintegrates, (e.g., calcium carbonate and sodium bicarbonate) such as effervescent mixtures or the like; vi) excipients (e.g. cyclodextrins or the like); vii) surface active agents (e.g., cetyl alcohol, glycerol monostearate), adsorptive carriers (e.g., kaolin and bentonite), emulsifiers or the like. Examples of carriers include, without limitation, any liquids, liquid crystals, solids or semi-solids, such as water or saline, gels, creams, salves, solvents, diluents, fluid ointment bases, ointments, pastes, implants, liposomes, micelles, giant micelles, or the like, which are suitable for use in the compositions.

Furthermore, the disclosure includes compositions prepared using conventional mixing, granulating, or coating methods and may contain 0.01 to 90% of the active ingredients. In some embodiments, the one or more compounds are for pharmaceutical use or for diagnostic use. Such methods can be used, for example, to prepare a bio-enhanced pharmaceutical composition in which the solubility of the compound(s) is (are) enhanced. In some embodiments, the resulting compositions contain a pharmaceutically effective amount of a compound for pharmaceutical or diagnostic use. The resulting compositions (formulations) may be presented in unit dosage form and may be prepared by methods known in the art of pharmacy. All methodology includes the act of bringing the active ingredient(s) into association with the carrier which constitutes one or more ingredients. Therefore, compositions (formulations) are prepared by blending active ingredient(s) with a liquid carrier or a finely divided solid carrier, and/or both, and then, if needed, shaping the product into a desired formulation.

"Therapeutically effective amount" or "effective amount" refers to the amount of a compound that, when administered to a subject for treating or diagnosing or monitoring a disease, or at least one of the clinical symptoms of a disease or disorder, is sufficient to affect such treatment for the disease, disorder, or symptom. The "therapeutically effective amount" can vary depending on the compound, the disease, disorder, and/or symptoms of the disease or disorder, severity of the disease, disorder, and/or symptoms of the disease or disorder, the age of the subject to be treated, and/or the weight of the subject to be treated. An appropriate amount in any given instance can be readily apparent to those skilled in the art or capable of determination by routine experimentation.

"Treating" or "treatment" of any disease or disorder refers to arresting or ameliorating a disease, disorder, or at least one of the clinical symptoms of a disease or disorder, reducing the risk of acquiring a disease, disorder, or at least one of the clinical symptoms of a disease or disorder, reducing the development of a disease, disorder or at least one of the clinical symptoms of the disease or disorder, or reducing the risk of developing a disease or disorder or at least one of the clinical symptoms of a disease or disorder. "Treating" or "treatment" also refers to inhibiting the disease or disorder, either physically, (e.g., stabilization of a discernible symptom), physiologically, (e.g., stabilization of a physical parameter), or both, or inhibiting at least one physical parameter which may not be discernible to the subject. Further, "treating" or "treatment" refers to monitoring, delaying or preventing the onset or reoccurrence of the disease or disorder or at least symptoms thereof in a subject which may be exposed to or predisposed to or may have previously suffered from a disease or disorder even though that subject does not yet experience or display symptoms of the disease or disorder.

Typical compositions of the disclosure contain compound from about 90 to about 80% by weight, from about 80 to about 70% by weight, from about 70 to about 60% by weight, from about 60 to about 50% by weight, from about 50 to about 40% by weight, from about 40 to about 30% by weight, from about 30 to 20% by weight, from about 20 to about 10% by weight, from about 10 to about 4% by weight, from about 4.0% to about 2.0% by weight, from about 2.0% to about 1.0% by weight, and even from about 1.0% to about 0.01% by weight. The effective amount of compounds or compositions of the disclosure may range from about 0.1 to 100 milligrams (mg) per kilogram (kg) of subject weight. In certain embodiments, the compounds or compositions of the disclosure are administered at from about 0.0001 mg/kg to 0.1 mg/kg (e.g. diagnostic monitoring), or from 0.1 mg/kg to 2 mg/kg, or from about 2 mg/kg to 5 mg/kg; in other embodiments, from about 5 mg/kg to 10 mg/kg, from about 10 mg/kg to 20 mg/kg, from about 20 mg/kg to 30 mg/kg, from about 30 mg/kg to 40 mg/kg, from about 40 mg/kg to 50 mg/kg, from about 50 mg/kg to 75 mg/kg or from about 75 mg/kg to 100 mg/kg.

As used herein, the term "subject" means a human or non-human animal selected for treatment or therapy.

As used herein, the phrase "subject suspected of having" means a subject exhibiting one or more clinical indicators of a disease or condition.

It should be understood that the ingredients particularly mentioned above are merely examples and that some embodiments of formulations comprising the compositions of the present disclosure include other suitable components and agents. The invention further includes packages, vessels, or any other type of container that contain a compound of the present invention.

Overview

In certain embodiments, the disclosure relates to compounds of Formula I. In certain embodiments, these compounds inhibit an aldehyde dehydrogenase, such as aldehyde dehydrogenase 1A1. In certain embodiments, the compounds demonstrate low-nM inhibition and excellent selectivity. In certain embodiments, the disclosure relates to a method of treating cancer, inflammation, or obesity comprising administering to a subject in need thereof an effective amount of a compound of Formula I.

In addition to compounds and salts of Formula I, as disclosed in the SUMMARY section the disclosure includes compounds and salts of Formula I, in which the variables, e.g., A, E, J, Q, $R^4$, $R^5$, $R^{5a}$, and $R^6$ carry the following definitions.

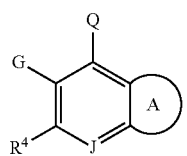
(Formula I)

where G is

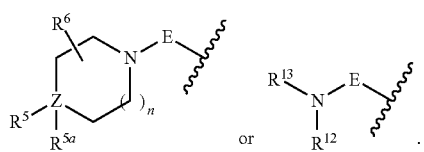

Formula I includes compounds and salts of Formula I-1 and Formula I-2

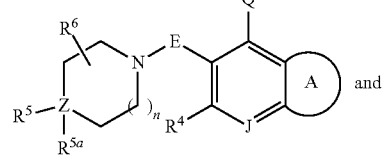
(Formula I-1)

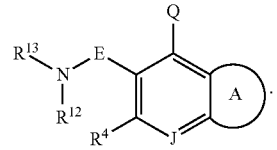
(Formula I-2)

Any of the following variable definitions can be combined so long as a stable compound results.

(1) Q is

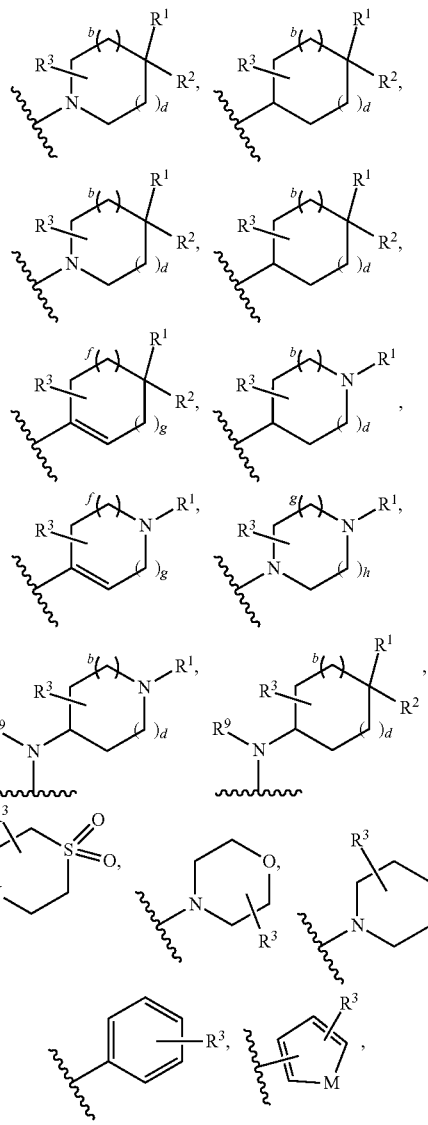

-continued

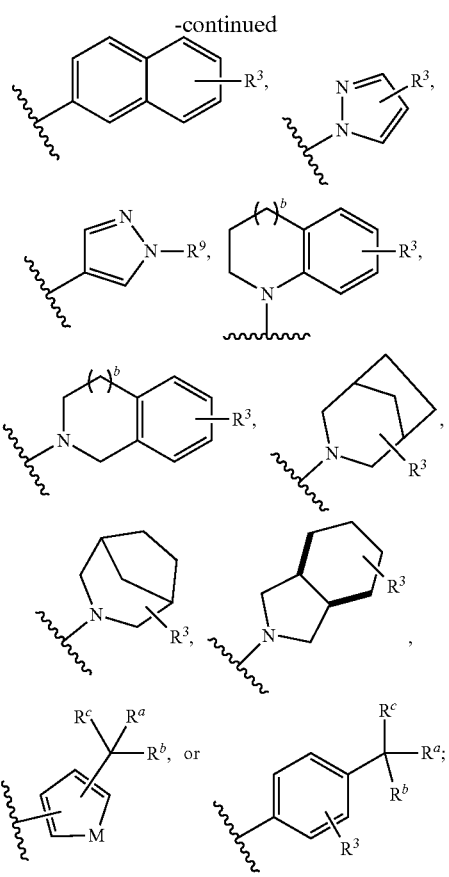

wherein b, d, and f, are each an independent integer from 0 to 2; g and h are each an independent integer from 1 to 2;

M is O, S, NH, N($C_1$-$C_4$alkyl), or N($C_3$-$C_5$cycloalkyl);

$R^3$ is independently chosen at each occurrence and is 0 or 1 or more substituents independently chosen from halogen, hydroxyl, cyano, amino, $C_1$-$C_6$alkyl, $C_1$-$C_6$alkoxy, $C_3$-$C_6$cycloalkyl, trifluoromethyl, and phenyl;

$R^a$ and $R^b$ are independently selected from hydrogen, $C_1$-$C_4$alkyl, ($C_3$-$C_6$cycloalkyl)$C_{(0-2)}$alkyl,

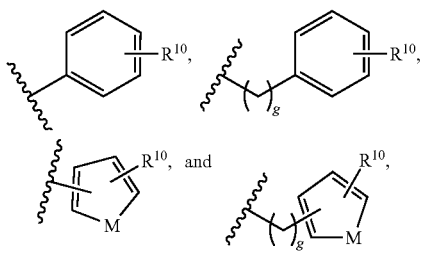

or $R^a$ and $R^b$ can be joined to form a 3- to 6-membered carbocyclic ring, or a 4- to 6-membered heterocycloalkyl ring having one heteroatom chosen from oxygen, sulfur, and nitrogen; wherein $R^{10}$ is 0 or one or more substituents independently selected from halogen, hydroxyl, oxo, cyano, $OCF_3$, $CF_3$, $C_1$-$C_4$alkyl, $C_1$-$C_4$alkoxy, and $C_3$-$C_6$ cycloalkyl; and $R^c$ is hydrogen, CN, F, OH, $HOCH_2$—, $HO(CH_3)CH$—, $HO(Me_2)C$—, $HC(=O)$—, $C_1$-$C_3$alkylC(=O), $C_1$-$C_4$alkyl, or ($C_{(3-6)}$cycloalkyl)$C_{(0-2)}$alkyl.

(2) $R^1$, when present, is hydrogen, halogen, hydroxyl, cyano, —$CF_3$, $C_1$-$C_4$alkyl optionally substituted with $R^{10}$, $C_1$-$C_4$alkoxy optionally substituted with $R^{10}$, $C_3$-$C_6$cycloalkyl optionally substituted with $R^{10}$, $C_3$-$C_6$cycloalkoxy optionally substituted with $R^{10}$, HC(O)—, $HOCH_2$-, $HO(CH_3)CH$—, $HO(Me_2)C$—, $C_1$-$C_3$alkylC(=O)—,

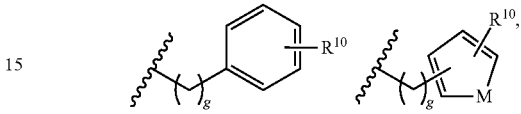

phenyl substituted with 0 to 2 $R^{10}$ substituents, pyridinyl substituted with 0 to 2 $R^{10}$ substituents, thiophenyl substituted with 0 to 1 $R^{10}$ substituents, furanyl substituted with 0 to 1 $R^{10}$ substituents; or $R^1$ and $R^2$ can be taken together to form a $C_3$-$C_6$ cycloalkyl ring substituted with 0 to 2 $R^{10}$ substituents, a 4-membered heterocycloalkyl ring containing a heteroatom selected from N, O and S and substituted with 0 to 2 $R^{10}$ substituents, or a 5- to 7-membered heterocycloalkyl ring containing 1 to 2 heteroatom selected from N, O, and S and substituted with 0 to 2 $R^{10}$ substituents.

(3) $R^1$, when present, is (i) hydrogen, (ii) $C_1$-$C_4$alkyl, $C_3$-$C_6$ cycloalkyl, $C_1$-$C_3$alkylC(O)—, $C_3$-$C_6$ cycloalkylC(O)—

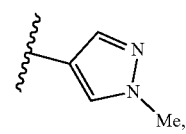 [SMILES: *c1cnn(C)c1]

phenyl, pyridinyl, thiazolyl, oxazolyl, furanyl, thiophenyl, phenylC(O)—, heteroarylC(O)—$C_1C_4$alkyl $SO_2$, $C_3$-$C_6$ cycloalkyl$SO_2$—, phenyl$SO_2$—, heteroaryl$SO_2$—, each of which is substituted with 0 or 1 or 2 groups independently chosen from halogen, cyano, methyl, ethyl, methoxy, ethoxy, and trifluoromethyl; or (iii)

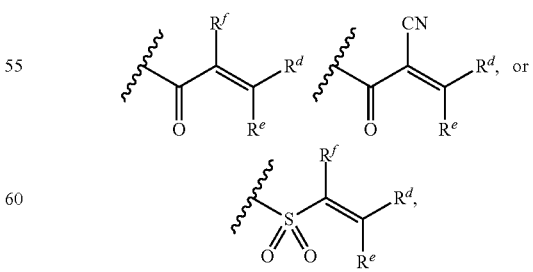

wherein $R^d$, $R^e$, and $R^f$ are independently hydrogen, F, Cl, $C_1$-$C_4$alkyl, or $C_3$-$C_6$cycloalkyl; and one of $R^d$ or $R^e$ can be $C_1$-$C_4$alkoxy, ($C_1$-$C_4$alkyl)$_2$N—,

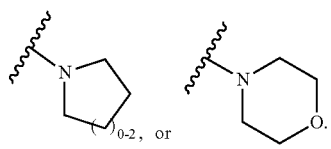 [SMILES: *N1CCCC1 ; *N1CCOCC1]

(4) A compound or salt of Formula I in which n is 1.

(5) $R^1$ is present and is not hydrogen.

(6) E is —C(O)—.

(7) J is N.

(8) A compound or salt of Formula I, of subformulae Formula I-A.

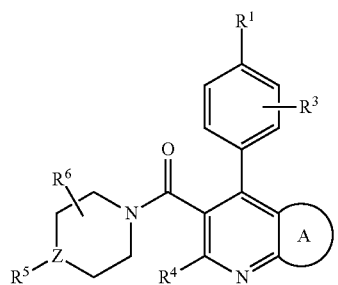

(Formula I-A)

or a pharmaceutically acceptable salt thereof, wherein $R^3$ is independently chosen at each occurrence and is 0 or 1 or more substituents independently chosen from halogen, hydroxyl, cyano, amino, $C_1$-$C_6$alkyl, $C_1$-$C_6$alkoxy, $C_3$-$C_6$cycloalkyl, trifluoromethyl, and phenyl and $R^1$, A, $R^4$, $R^5$ and $R^6$ may carry any of the definitions set forth for these variables in this disclosure.

(9) $R^1$ is (CN)C(CH$_3$)$_2$—,

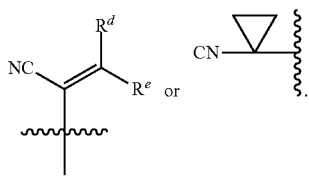

Included are compounds and salts of Formula I-A having this definition of $R^1$. $R^d$ and $R^e$ are independently hydrogen, F, Cl, $C_1$-$C_4$alkyl, or $C_3$-$C_6$cycloalkyl; and one of $R^d$ or $R^e$ can be $C_1$-$C_4$alkoxy, ($C_1$-$C_4$alkyl)$_2$N—,

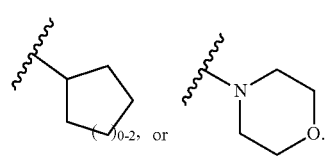

(10) A compound or salt of Formula I, of subformula Formula I-B

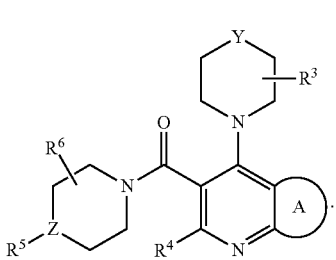

(Formula I-B)

(11) A compound or salt of Formula I, of subformula Formula I-C, -D, -E, or -F. $R^{11}$ is optional in each of these formulae.

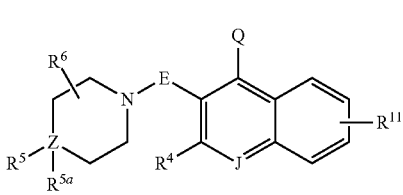

(Formula I-C)

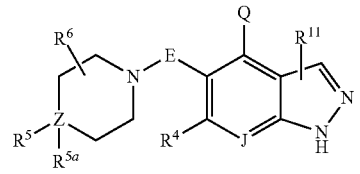

(Formula I-D)

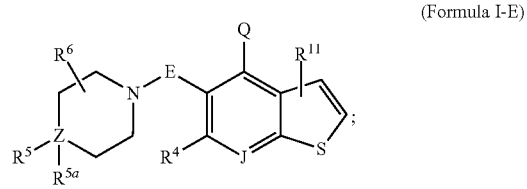

(Formula I-E)

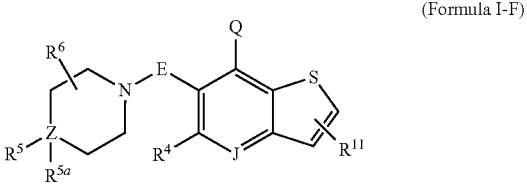

(Formula I-F)

(12) A compound or salt of Formula I, of subformula Formula I-G, -H, -I, or -J. $R^{11}$ is optional in Formula I-G.

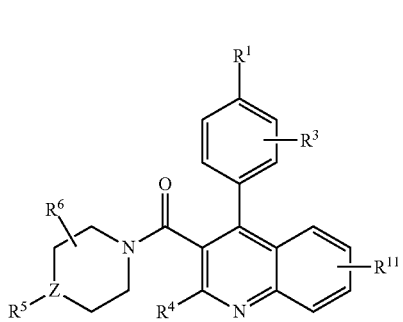

(Formula I-G)

-continued
(Formula (I-H))
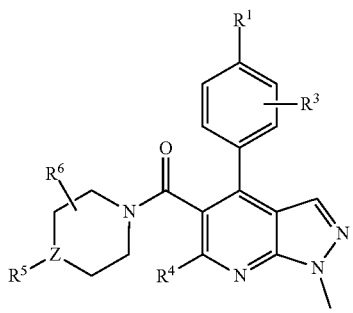
R[11] is optional
(Formula I-I)
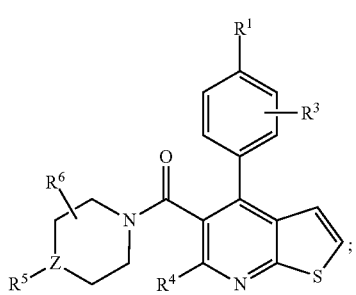
(Formula I-J)
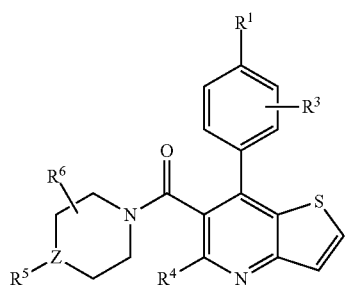
(13) A compound or salt of Formula I, of subformula Formula I-K, -L, -LL -M, or -N.
(Formula I-K)
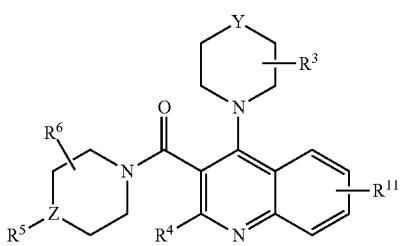
-continued
(Formula I-L)
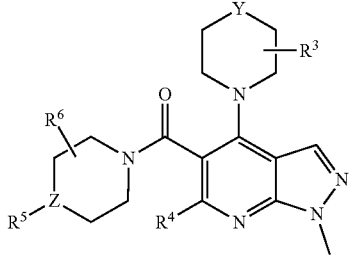
(Formula I-LL)
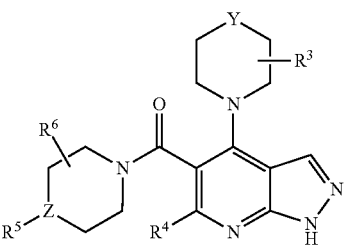
R[11] is 1 to 3 independently chosen substituents.
(Formula I-M)
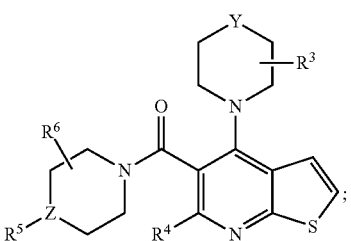
(Formula I-N)
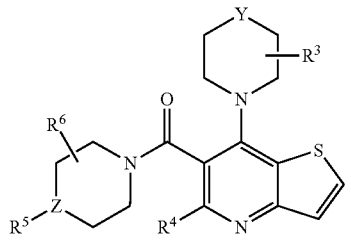
(14) A compound or salt of Formula I, of subformula Formula I-O or I-P.
(Formula I-O)
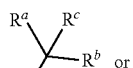
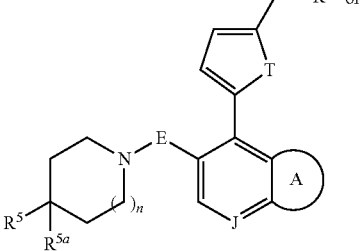

-continued

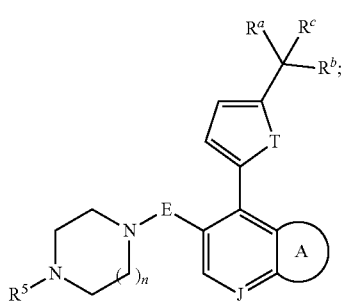

(Formula I-P)

where T is S, O, N(CH₃) or NH.

(15) A compound or salt of Formula I, of subformula Formula I-Q or I-R.

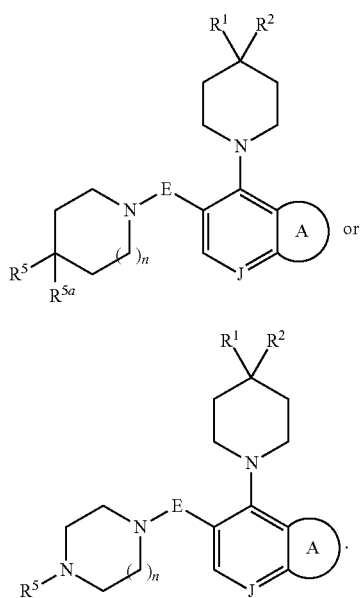

(Formula I-Q)

(Formula I-R)

(16) Y is $CR^1R^2$ and $R^1/R^2$ are taken together to form an unfused $C_3$-$C_6$cycloalkyl, a cyclopentyl fused to a phenyl group, or an unfused 3- to 6-membered heterocycloalkyl ring, each or which is optionally substituted with one or more substituents independently chosen from halogen, hydroxyl, oxo, $C_1$-$C_2$alkyl, $C_1$-$C_2$alkoxy.

(17) Y is $CR^1R^2$ and $R^1/R^2$ are taken together to form an unfused heterocycloalkyl ring chosen from an oxetanyl, tetrahydrofuranyl, tetrahydropyranyl, a 1,3-dioxanyl ring, a 1,4-dioxanyl ring, and a 1,3-dioxolanyl ring, each or which is optionally substituted with one or more substituents independently chosen from halogen, hydroxyl, $C_1$-$C_2$alkyl, $C_1$-$C_2$alkoxy.

(18) $R^1$ and $R^2$ are taken together to form a tetrahydrofuranyl, tetrahydropyranyl, 1,3-dioxolanyl, or 1,3-dioxanyl ring.

(19) Y is $CR^1R^2$ and $R^1$ is chosen from cyano, halogen, $C_1$-$C_2$alkoxy, $C_1$-$C_2$alkanoyl, $CH_2CHC(O)$—, $CH_2CHSO_2$—, $C_1$-$C_2$alkylsulfonyl, $C_1$-$C_2$haloalkyl, phenyl, and pyridyl.

(20) Y is $NR^1$ and $R^1$ is $C_1$-$C_2$alkanoyl, $CH_2CHC(O)$—, $C_1$-$C_2$alkylsulfonyl, or phenylsulfonyl.

(21) $R^1$ is cyano and $R^2$ is methyl.

(22) $R^1$ is phenyl, thienyl, or benzyl, each of which is optionally substituted with one or more substituents independently chosen from $C_1$-$C_2$alkyl, $C_1$-$C_2$alkoxy, $CF_3$, and halogen, and $R^2$ is cyano.

(23) $R^1$ is phenyl and $R^2$ is $CH_3C(O)$—, $(OH)CH_2$—, $CHO$—, $(CH_3)_2(OH)C$—, or $CH_3CH(OH)$—.

(24) $R^2$ is hydrogen.

(25) Y is $NR^1$ and $R^1$ is chosen from $CH_3C(O)$—, $C_1$-$C_2$alkylsulfonyl, $CH_2CHC(O)$—, $CH_2CHSO_2$—, pyridyl, and phenyl$SO_2$—.

(26) Y is $SO_2$.

(27) Y is O.

(28) The A-ring is substituted with 1, 2, or 3 substituents independently chosen from chloro, fluoro, methyl, and methoxy.

(29) $R^3$ is 0 or 1 or more substituents independently chosen from fluoro, trifluoromethyl, and $C_1$-$C_3$alkyl.

(30) $R^9$ is hydrogen, $C_1$-$C_4$alkyl, or $C_3$-$C_6$cycloalkyl.

(31) $R^{11}$ is 1, 2, or 3 substituents independently chosen from chloro, fluoro, methyl, and methoxy. In some embodiments $R^{11}$ is 1 fluoro substituent.

(32) $R^3$ is 0 substituents.

(33) $R^4$ is hydrogen.

(34) $R^6$ is 0 substituents.

(35) Z is N or C and $R^5$ is (i) hydrogen, fluoro, cyano, or trifluoromethyl, (ii) furanyl, thiophenyl, oxazolyl, phenyl, pyridyl, $C_1$-$C_4$alkyl, each of which is substituted with 0 to 2 halogen, cyano, $C_1$-$C_4$alkyl, methoxy, $C_3$-$C_5$cycloalkvl, or trifluoromethyl, or (iii)

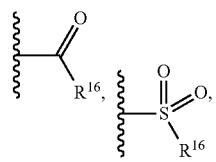

branched or unbranched

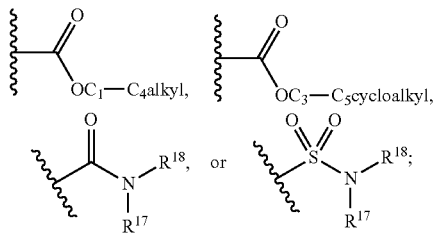

wherein $R^{16}$ is $C_1$-$C_4$alkyl, $C_3$-$C_6$cycloalkyl, $HOCH_2$—, $C_1$-$C_2$alkylOCH$_2$—$C_1$-$C_4$alkylNH—, $C_3$-$C_6$cycloalkylNH—, and

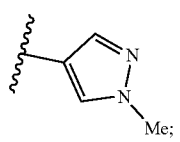

and $R^{17}$ and $R^{18}$ are each independently hydrogen, $C_1$-$C_4$alkyl, or $C_3$-$C_6$cycloalkyl, and $R^{17}$ and $R^{18}$ can be taken together to form a 3 to 7-membered heterocycloalkyl ring containing 1 to 2 heteroatoms selected from N, O, and S, where the heteroatoms are not attached to the same carbon.

(35) Z is N and $R^5$ is cyclopropylC(O)—, $CH_3SO_2$—, $(CH_3)_2NC(O)$—, or $(CH_3)_2NSO_2$—.

The disclosure includes a compound of Formula I-S

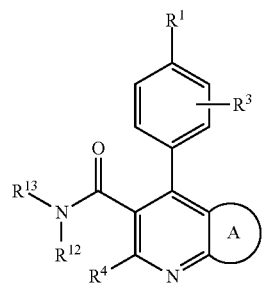

(Formula I-S)

or a pharmaceutically acceptable salt thereof. A ring, $R^1$, $R^3$, $R^4$, $R^{12}$, and $R^{13}$ may carry any definition set forth herein for these variables. In certain embodiments $R^1$ is (CN)C$(CH_3)_2$—,

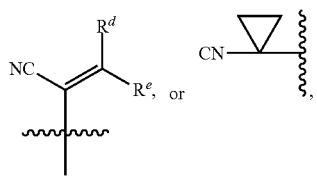

where $R^d$ and $R^e$ are independently hydrogen, F, Cl, $C_1$-$C_4$alkyl, or $C_3$-$C_6$cycloalkyl; and one of $R^d$ or $R^e$ can be $C_1$-$C_4$alkoxy, $(C_1$-$C_4$alkyl$)_2$N—,

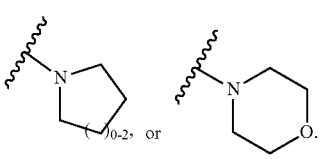

The disclosure includes a compound of Formula I-T

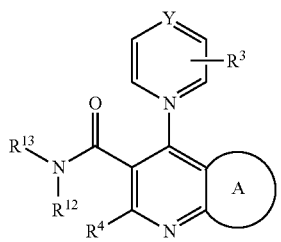

(Formula I-T)

or a pharmaceutically acceptable salt thereof.

The disclosure further includes compound or salt thereof of any of the following formulae:

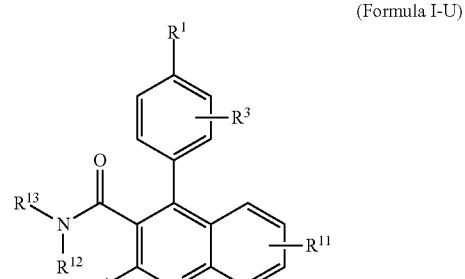

(Formula I-U)

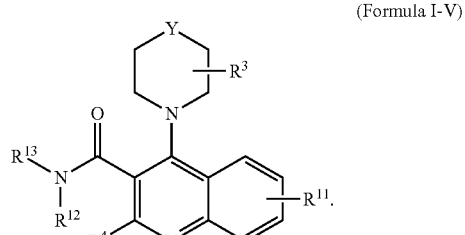

(Formula I-V)

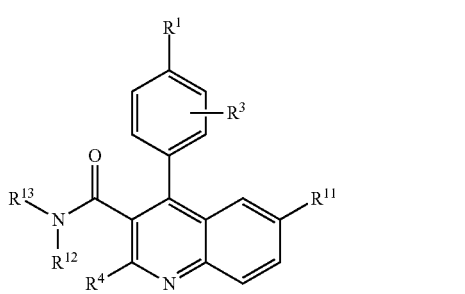

(Formula I-W)

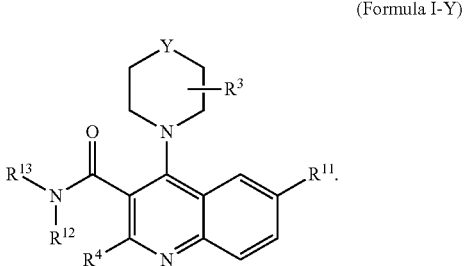

(Formula I-Y)

In certain embodiments compound is a compound of Formula I-U or I-W in which $R^1$ is

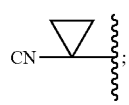

and $R^{11}$ is F, Cl, or methoxy.

The disclosure includes compounds and salts thereof of Formula I-U, I-V, I-W, or I-Y in which the following conditions are met.

Y is —C($R^1$)($R^2$)—, $R^1$ is —CN and $R^2$ is phenyl; and $R^{11}$ is F, Cl, or methoxy.

$R^{12}$ is hydrogen and $R^{13}$ is $C_3$-$C_6$cycloalkyl substituted with hydroxyl; or $R^{13}$ is

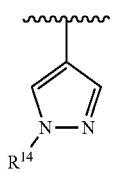

where $R^{14}$ is —$CH_2C(O)N(CH_3)_2$, —$CH_2C(O)N(H)(CH_3)$, —$CH_2C(O)NH_2$, —$CH_2C(O)N(H)(cyclopropyl)$, or —$C_1$-$C_4$alkylOH.

Pharmaceutical Compositions

While it is possible for compounds of the present disclosure to be administered as the raw chemical, it is also possible to present them as a pharmaceutical formulation. Accordingly, the present disclosure provides a pharmaceutical formulation comprising a compound or a pharmaceutically acceptable salt, prodrug or solvate thereof, together with one or more pharmaceutically acceptable carriers thereof and optionally one or more other therapeutic ingredients. The carrier(s) must be "acceptable" in the sense of being compatible with the other ingredients of the formulation and not deleterious to the recipient thereof. Proper formulation is dependent upon the route of administration chosen. Any of the well-known techniques, carriers, and excipients can be used as suitable and as understood in the art; e.g., in Remington's Pharmaceutical Sciences. The pharmaceutical compositions of the present disclosure can be manufactured in a manner that is itself known, e.g., by means of conventional mixing, dissolving, granulating, dragee-making, levigating, emulsifying, encapsulating, entrapping or compression processes, for example.

The formulations include those suitable for oral, parenteral (including subcutaneous, intradermal, intramuscular, intravenous, intraarticular, and intramedullary), intraperitoneal, transmucosal, transdermal, rectal and topical (including dermal, buccal, sublingual and intraocular) administration although the most suitable route depends upon for example the condition and disorder of the recipient. The formulations can conveniently be presented in unit dosage form and can be prepared by any of the methods well known in the art. All methods include the step of bringing into association a compound of the present disclosure or a pharmaceutically acceptable salt, prodrug or solvate thereof ("active ingredient") with the carrier which constitutes one or more accessory ingredients. In general, the formulations are prepared by uniformly and intimately bringing into association the active ingredient with liquid carriers or finely divided solid carriers or both and then, if necessary, shaping the product into the desired formulation.

The compounds can be formulated for parenteral administration by injection, e.g., by bolus injection or continuous infusion. Formulations for injection can be presented in unit dosage form, e.g., in ampoules or in multi-dose containers, with an added preservative. The compositions can take such forms as suspensions, solutions or emulsions in oily or aqueous vehicles, and can contain formulatory agents such as suspending, stabilizing and/or dispersing agents. The formulations can be presented in unit-dose or multi-dose containers, for example sealed ampoules and vials, and can be stored in powder form or in a freeze-dried (lyophilized) condition requiring only the addition of the sterile liquid carrier, for example, saline or sterile pyrogen-free water, immediately prior to use. Extemporaneous injection solutions and suspensions can be prepared from sterile powders, granules and tablets of the kind previously described.

Formulations for parenteral administration include aqueous and non-aqueous (oily) sterile injection solutions of the active compounds which can contain antioxidants, buffers, bacteriostats and solutes which render the formulation isotonic with the blood of the intended recipient; and aqueous and non-aqueous sterile suspensions which can include suspending agents and thickening agents. Suitable lipophilic solvents or vehicles include fatty oils such as sesame oil, or synthetic fatty acid esters, such as ethyl oleate or triglycerides, or liposomes. Aqueous injection suspensions can contain substances which increase the viscosity of the suspension, such as sodium carboxymethyl cellulose, sorbitol, or dextran. Optionally, the suspension can also contain suitable stabilizers or agents which increase the solubility of the compounds to allow for the preparation of highly concentrated solutions.

In addition to the formulations described previously, the compounds of the present disclosure can also be formulated as a depot preparation. Such long acting formulations can be administered by implantation (for example subcutaneously or intramuscularly) or by intramuscular injection. Thus, for example, the compounds can be formulated with suitable polymeric or hydrophobic materials (for example as an emulsion in an acceptable oil) or ion exchange resins, or as sparingly soluble derivatives, for example, as a sparingly soluble salt.

In certain embodiments, the disclosure relates to a pharmaceutical composition comprising any one of the aforementioned compounds, and a pharmaceutically acceptable carrier.

In certain embodiments, the disclosure relates to a pharmaceutical composition made by mixing any of the compositions described herein and a pharmaceutically acceptable carrier.

In certain embodiments, the disclosure relates to any one of the aforementioned compositions, wherein the compound is present in an amount of at least 1.0% by weight.

In certain embodiments, the disclosure relates to any one of the aforementioned compositions, wherein the compound is present in an amount of from about 1.0% to about 10.0% by weight.

In certain embodiments, the disclosure relates to any one of the aforementioned compositions, wherein the compound is present in an amount of from about 10.0% to about 75.0% by weight.

In certain embodiments, the disclosure relates to any one of the aforementioned compositions, wherein the compound is present in an amount of from about 75.0% to about 99% by weight.

Methods and Processes

In certain embodiments, the disclosure relates to a method of treating an ALDH1A1 disorder, comprising administering to a subject in need thereof a therapeutically effective amount of a compound described herein.

In certain embodiments, the disclosure relates to any of the methods described herein, wherein the ALDH1A1 disorder is selected from the group consisting of cancer, inflammation or a disease or disorder associated with inflammation, and obesity.

In certain embodiments, the disclosure relates to any of the methods described herein, wherein the ALDH1A1 disorder is selected from the group consisting of colon cancer, pancreatic cancer, nasopharyngeal carcinoma, thyroid cancer, prostate cancer, ovarian cancer, head and neck squamous cell carcinoma, lung cancer, hepatocellular carcinoma, leukemia, brain tumors, estrogen-dependent growth of uterine fibroids, and breast cancer.

The disclosure provides a method of treating an ALDH1A1 disorder by administering a compound of the disclosure to a patient having an ALDHAl disorder where the disorder is acquired chemoresistance or lysosomal autophagy in cancer cells. Autophagy is a process in which cellular material, such as damaged organelles and misfolded proteins, is delivered to lysosomes for degradation. While autophagy can have tumor suppression activity at an early stage of tumor development, it can also be harnessed by the cells of established tumors for cytoprotection. In this case autophagy can be targeted by anticancer agent to promote apoptosis and decrease chemoresistance.

In certain embodiments, the disclosure relates to any of the methods described herein, wherein the ALDH1A1 disorder is selected from the group consisting of atherosclerosis, ischaemic heart disease, acne vulgaris, asthma, autoimmune diseases, autoinflammatory diseases, celiac disease, chronic prostatitis, glomerulonephritis, hypersensitivities, inflammatory bowel disease, pelvic inflammatory disease, reperfusion injury, rheumatoid arthritis, sarcoidosis, transplant rejection, vasculitis, and interstitial cystitis.

In certain embodiments, the disclosure relates to a method of preventing or treating cancer in a subject in need thereof comprising administering a therapeutically effective amount of any one of the compounds described herein. In certain embodiments, the methods are useful for treating a wide variety of cancers, including carcinomas, sarcomas, leukemias, and lymphomas. Thus, the subject can have a cancer such as a carcinoma, a sarcoma, a leukemia, or a lymphoma. In some embodiments, the individual has lung cancer resulting from prolonged exposure to cigarette smoke.

Carcinomas that can be treated using a subject method include, but are not limited to, esophageal carcinoma, hepatocellular carcinoma, basal cell carcinoma (a form of skin cancer), squamous cell carcinoma (various tissues), bladder carcinoma, including transitional cell carcinoma (a malignant neoplasm of the bladder), bronchogenic carcinoma, colon carcinoma, colorectal carcinoma, gastric carcinoma, lung carcinoma, including small cell carcinoma and non-small cell carcinoma of the lung, adrenocortical carcinoma, thyroid carcinoma, pancreatic carcinoma, breast carcinoma, ovarian carcinoma, prostate carcinoma, adenocarcinoma, sweat gland carcinoma, sebaceous gland carcinoma, papillary carcinoma, papillary adenocarcinoma, cystadenocarcinoma, medullary carcinoma, renal cell carcinoma, ductal carcinoma in situ or bile duct carcinoma, choriocarcinoma, seminoma, embryonal carcinoma, Wilm's tumor, cervical carcinoma, uterine carcinoma, testicular carcinoma, osteogenic carcinoma, epithelieal carcinoma, and nasopharyngeal carcinoma, etc.

Specifically, the disclosure relates to the treatment, detection, or prognosis associated with a patient suffering from a head and neck squamous cell carcinoma (HNSCC), which are the most frequent malignancies of the upper aerodigestive tract. ALDH1-positive HNSCC patients have worse prognosis, which was associated with common clinicopathological features and poor prognostic factors. When isolated from HNSCC patients, ALDH1-positive cells (HNSCC-ALDH1+ cells) display radioresistance and represent a reservoir for generating tumors.

ALDH1A1 is also hypothesized to be a marker for normal and malignant human colonic stem cells (CSCs). In addition, ALDH1A1 may be used to track CSC overpopulation during colon tumorigenesis. Moreover, higher numbers of ALDH1A1-expressing cells in an adenoma is associated with a higher risk for metachronous adenoma, independent of adenoma size or histopathology. However, cytoplasmic and stromal expression of ALDH1A1 is not significantly associated with prognosis either in colon cancer or in rectal cancer. Furthermore, cytoplasmic expression of ALDH1A1 does not predict therapeutic vulnerability to palliative chemotherapy in patients with metastatic diseases. Interestingly, nuclear expression of ALDH1A1 is observed in a small subgroup of patients with colon and rectal cancer. In patients with colon cancer, nuclear expression is significantly associated with shortened overall survival. Besides nuclear localization, ALDH1A1 is present in the secretome of metastatic colon cancer cells. While not wishing to be bound by any particular theory, it is possible that extracellular ALDH1A1 protects the CSC against the hostile environment in the extracellular space, e.g. chemotherapeutic agents or oxidative conditions.

In addition, non-small cell lung cancers (NSCLC) express very high levels of ALDH1A1 in comparison with SCLC; the elevated expression of ALDH1A1 may be associated with malignant transformation to adenocarcinoma.

In papillary thyroid carcinoma (PTC), ALDH1A1 does not appear to be a marker for CSC, but it expression occurs in high levels in PTC. High ALDH1A1 expression in PTC is associated with a reduced lymph node recurrence-free survival (LN-RFS) and distant recurrence-free survival (DRFS) in PTC patients, relative to patients having low ALDH1A1 expression. Multivariate analysis confirmed that ALDH1A1 expression was an independent prognostic factor for LN-RFS and DRFS in PTC patients.

In addition, ALDH1A1 is up-regulated in clonal subpopulations of pancreatic cancer cell line, MiaPaCa-2. ALDH1A1 expression is highest in more highly-invading pancreatic cancer cells lines and data suggest that ALDH1A1 may be promote pancreatic cancer metastasis. Analysis of human tissue sections revealed ALDH1A1 to be abundantly expressed in the pancreatic cancer tissue. Moreover, high expression of ALDH1A1 in these cancers is found to be significantly associated with proliferation of the tumor cells. Cell populations with high ALDH activity are much more efficient at promoting tumor-initiation and have enhanced tumorigenic potential than cells that are high in CD133 expression (CD133(+)) and with low ALDH activity. Although CD133(+) cells may alone possess tumorigenic potential, they are significantly less tumorigenic than cells with high ALDH expression. In addition, high levels of ALDH1A1 expression contribute to the intrinsic and acquired resistance of in human pancreatic adenocarcinoma (MiaPaCa-2) cells to gemcitabine. Knock-down of ALDH1A1 expression with siRNA along with gemcitabine treatment results in a significant decrease in cell viability and an increase in apoptotic cell death in the gemcitabine-resistant MiaPaCa-2 (MiaPaCa-2/GR) cells. Additional studies showed that a combination treatment (dasatinib and gemcitabine) results in inhibition of cell proliferation and decreased survival of MiaPaCa-2/P (parental) and MIA PaCa-2/GR by reducing ALDH1A1 expression in ALDH1A1-enriched pancreatic cancer MiaPaCa-2 cells. In addition, using adoptive therapy with ALDH1A1-specific CD8(+) T cells eliminated ALDH enzymatically-active (or ALDH bright) cells, inhibited pancreatic tumor growth and metastases, or prolonged survival of xenograft-bearing immunodeficient mice. While not wishing to be bound by any particular theory, the available data strongly support the potential of ALDH1A1-based immunotherapy to selectively target CSCs in human cancer.

The association between ALDH1A1 expression and clinicopathological/prognostic parameters in breast cancer patients has also been evaluated. Through overall and sub-category analyses using data from 15 publications that included 921 ALDH1A1-positive cases and 2353 controls, ALDH1A1 was proposed to be a biomarker that predicts tumor progression and poor survival of breast cancer patients. ALDH1A1 has also been suggested as being predictive for the prognosis of triple-negative breast cancer (TNBC), a subtype of breast cancer characterized by poor outcomes. In addition, the ALDH1A1 phenotype is an independent predictor of early tumor relapse (i.e., incidence of early local recurrence and distant metastasis) of invasive ductal carcinoma. ALDH1A1 expression has been shown to be associated with severity of breast cancer. More specifically, tumors associated with advanced stage, were node-positive, or of larger size are found to have higher ALDH1A1 expression in the tumor tissue. ALDH1A1 expression is also correlated with worse disease-free survival and overall survival in patients who had been treated with neoadjuvant chemotherapy. BRCA1-related breast cancers show more frequent epithelial and stromal (peritumoral) ALDH1A1 expression leading to the suggestion that ALDH1A1 may be a diagnostic marker and a therapeutic target of BRCA1-related breast cancer. Using ellipticine, an inhibitor of ALDH1A1 as a model, molecular simulation and docking studies revealed that amino acids present in the active site of human ALDH1A1, viz. Asn-117, Asn-121, Glu-249, Cys-302 and Gln-350, interact with ellipticine. At high concentrations (3 mM), ellipticine decreased the expression of ALDH1A1-positive breast cancer stem cells (BCSCs) in the SUM159 cell line. Ellipticine also reduced the formation of mammospheresby MCF7 and SUM159 breast cancer cell lines. Interestingly, when treated with a combination of ellipticine and paclitaxel, the percentage of ALDH1A1-positive BCSCs was decreased significantly in vitro.

Ovarian CSCs may be identified by their expression of ALDH1A1. High ALDH1 expression is significantly associated with poor clinical outcomes in serous ovarian cancer patients (P=0.0036). More recent data indicate that there is a link between ALDH1 and EGFR expression in high-grade serous ovarian carcinoma (HGSC) Immunopositivity for both ALDH1 and EGFR identifies a subgroup of highly aggressive, poor-prognosis cancers. In addition, ALDH enzymatically-active (or ALDH bright) tumor cells exhibit CSC properties and are resistant to chemotherapy. Finally, inhibition of ALDH1A1 results in disruption of ovarian cancer cell spheroid formation and cell viability.

ALDH1A1 is also a marker for malignant prostate stem cells and predictor of prostate cancer (PCa) patient outcome. ALDH1A1-expressing PCa cells exhibit high clonogenic and tumorigenic capacities. In addition, xenograft experiments showed that PCa in mice resemble histopathologic characteristics and heterogeneity of the parental PCa cells in humans. While ALDH1A1-expressing cells are sparse in normal human prostate tissues and limited to the basal component in normal prostates, in tumor specimens, increased ALDH1A1 expression is found not only in secretory type cancer epithelial cells but also in neuroendocrine tumor populations. Finally, high ALDH1A1 expression in PCa correlates positively with Gleason score (P=0.01) and pathologic stage (P=0.01), and is inversely associated with overall survival and cancer-specific survival of PCa patients (P=0.00093 and 0.00017, respectively). ALDH1A1 is also a valuable biomarker for prognosis. The crucial role of ALDH1A1 enzymatic activity in CSC maintenance was demonstrated by DEAB (an ALDH inhibitor) induced repression of sphere formation by RWPE-2, CWR-R1 and DU-145 PCa cell lines.

In addition, ALDH1A1 has been recently suggested to be a novel CSC marker and a valuable predictor of poor survival and enhanced invasiveness and metastatic ability in nasopharyngeal carcinoma (NPC). Furthermore, ALDH1A1 expression in the invasive front (which underlies the biological aggressiveness and epithelial-mesenchymal transition (EMT) in human malignancies) links closely with EMT characteristics and tumor aggressiveness, confirming the prognostic value of ALDH1A1 as a marker in NPC patients. Finally, ALDH1A1 expression is high in spindle cells (cells that are prominently found in the invasive tumor front and the surrounding stroma) and may be responsible for the aggressive patterns and unfavorable prognosis in NPC patients.

Sarcomas that can be treated using a subject method include, but are not limited to, fibrosarcoma, myxosarcoma, liposarcoma, chondrosarcoma, chordoma, osteogenic sarcoma, osteosarcoma, angiosarcoma, endotheliosarcoma, lymphangiosarcoma, lymphangioendotheliosarcoma, synovioma, mesothelioma, Ewing's sarcoma, leiomyosarcoma, rhabdomyosarcoma, and other soft tissue sarcomas.

Other solid tumors that can be treated using a subject method include, but are not limited to, glioma, astrocytoma, medulloblastoma, craniopharyngioma, ependymoma, pinealoma, hemangioblastoma, acoustic neuroma, oligodendroglioma, menangioma, melanoma, neuroblastoma, and retinoblastoma.

Leukemias that can be treated using a subject method include, but are not limited to, a) chronic myeloproliferative syndromes (neoplastic disorders of multipotential hematopoietic stem cells); b) acute myelogenous leukemias (neoplastic transformation of a multipotential hematopoietic stem cell or a hematopoietic cell of restricted lineage potential; c) chronic lymphocytic leukemias (CLL; clonal proliferation of immunologically immature and functionally incompetent small lymphocytes), including B-cell CLL, T-cell CLL prolymphocytic leukemia, and hairy cell leukemia; and d) acute lymphoblastic leukemias (characterized by accumulation of lymphoblasts). Lymphomas that can be treated using a subject method include, but are not limited to, B-cell lymphomas (e.g., Burkitt's lymphoma); Hodgkin's lymphoma; or the like.

In certain embodiments, the disclosure relates to a method of preventing or treating a disease associated with chronic free radicals in a subject in need thereof comprising administering a therapeutically effective amount of any one of the compounds described herein. Chronic free radical-associated disorders that are amenable to treatment with a subject method include neurodegenerative diseases such as Parkinson's Disease and Alzheimer's Disease; amyotrophic lateral sclerosis (ALS); peripheral artery disease, or the like. In some embodiments, a chronic free radical-associated disease is treated by chronic (e.g., daily) treatment with a compound.

In certain embodiments, the disclosure relates to a method of preventing or treating a cardiovascular disorder in a subject in need thereof comprising administering a therapeutically effective amount of any one of the compounds described herein. In certain embodiments, cardiovascular disorders include angina, heart failure, insensitivity to nitroglycerin in angina and heart failure, hypertension, and heart disease.

In certain embodiments, the disclosure relates to a method of preventing or treating diabetes in a subject in need thereof comprising administering a therapeutically effective amount of any one of the compounds described herein. Subjects suitable for treatment with the inventive methods include individuals having Type 1 or Type 2 diabetes. Subjects suitable for treatment include individuals who have been diagnosed with Type 1 diabetes mellitus, where such individuals include those having a fasting blood glucose level greater than about 126 mg/dL. Such individuals include those having blood glucose levels of greater than about 200 mg/dL following a two-hour glucose tolerance test (75 g anhydrous glucose orally). Subjects suitable for treatment include individuals who have been diagnosed with Type 2 diabetes; individuals who have not yet been diagnosed with Type 2 diabetes, but who are at risk of developing Type 2 diabetes, e.g., individuals having a body mass index (weight in kilograms divided by height (in meters) squared) greater than 25, e.g., individuals having a body mass index from about 25 to about 27, from about 27 to about 30, or greater than 30.

In certain embodiments, the disclosure relates to a method of preventing or treating obesity in a subject in need thereof comprising administering a therapeutically effective amount of any one of the compounds described herein. ALDH1A1 has been implicated in obesity. More specifically, Aldh1a1-deficient mice are protected from diet-induced obesity and diabetes. In addition Aldh1a1-deficient mice display significantly decreased fasting glucose concentrations compared with WT controls as a result of attenuated hepatic glucose production. The same study also showed that Aldh1a1 deficiency resulted in increased AMP-activated protein kinase a activity, decreased expression of lipogenic targets of AMP-activated protein kinase a and significantly attenuated hepatic triacylglycerol synthesis.

In certain embodiments, the disclosure relates to a method of preventing or treating inflammation or a disease or disorder associated with inflammation in a subject in need thereof comprising administering a therapeutically effective amount of any one of the compounds described herein. Examples of diseases or disorders associated with inflammation include: cancer (described herein), atherosclerosis, ischaemic heart disease, acne vulgaris, asthma, autoimmune diseases, autoinflammatory diseases, celiac disease, chronic prostatitis, glomerulonephritis, hypersensitivities, inflammatory bowel disease, pelvic inflammatory disease, reperfusion injury, rheumatoid arthritis, sarcoidosis, transplant rejection, vasculitis, and interstitial cystitis.

Specifically, ALDH1A1 significantly induced in CD14(+) macrophages from the intestinal mucosa of patients with Crohn's disease (CD) than from controls and this is associated with generation of retinoic acid, which in turn may increase the inflammatory phenotype of these cells. Therefore inhibition of ALDH1A1 may reduce the generation of RA by CD14(+) macrophages, offering a new therapeutic options for patients with CD.

In certain embodiments, the disclosure relates to any one of the aforementioned methods, wherein the subject is a mammal.

In certain embodiments, the disclosure relates to any one of the aforementioned methods, wherein the subject is a human.

In certain embodiments, the disclosure relates to a process for making a pharmaceutical composition comprising mixing any of the compounds described herein and a pharmaceutically acceptable carrier.

Combination Therapy

The compounds of the disclosure can be combined with other therapeutic agents. The compound and other therapeutic agent may be administered simultaneously or sequentially. When the other therapeutic agents are administered simultaneously they can be administered in the same or separate formulations, but are administered at the same time. The other therapeutic agents are administered sequentially with one another and with the compounds, when the administration of the other therapeutic agents and the compounds is temporally separated. The separation in time between the administration of these compounds may be a matter of minutes or it may be longer. In some instances the compounds are administered with multiple therapeutic agents, i.e., 2, 3, 4 or even more different agents.

EXAMPLES

This invention is further illustrated by the following examples, which should not be construed as limiting.

General Methods for Examples

All air or moisture sensitive reactions were performed under positive pressure of nitrogen with oven-dried glassware. Chemical reagents and anhydrous solvents were obtained from commercial sources and used as-is. Preparative purification was performed on a Waters semi-preparative HPLC. The column used was a Phenomenex Luna C18 (5 micron, 30×75 mm) at a flow rate of 45 mL/min. The mobile phase consisted of acetonitrile and water (each containing 0.1% trifluoroacetic acid). A gradient of 10% to 50% acetonitrile over 8 minutes was used during the purification. Fraction collection was triggered by UV detection (220 nm). Analytical analysis for purity was determined by two different methods denoted as Final QC Methods 1 and 2. Method 1: Analysis was performed on an Agilent 1290 Infinity Series HPLC. UHPLC Long Gradient Equivalent 4% to 100% acetonitrile (0.05% trifluoroacetic acid) in water over 3 minutes run time of 4.5 minutes with a flow rate of 0.8 mL/min. A Phenomenex Luna C18 column (3 micron, 3×75 mm) was used at a temperature of 50° C. Method 2: analysis was performed on an Agilent 1260 with a 7 minute gradient of 4% to 100% acetonitrile (containing 0.025% trifluoroacetic acid) in water (containing 0.05% trifluoroacetic acid) over 8 minute run time at a flow rate of 1 mL/min. A Phenomenex Luna C18 column (3 micron, 3×75 mm) was used at a temperature of 50° C. Purity determination was performed using an Agilent Diode Array Detector for both Method 1 and Method 2. Mass determination was performed using an Agilent 6130 mass spectrometer with electrospray ionization in the positive mode. All of the analogs for assay have purity greater than 95% based on both analytical methods. $^1$H spectra were recorded on Varian 400 (100) and 600 MHz spectrometers. High resolution mass spectrometry was recorded on Agilent 6210 Time-of-Flight LC/MS system.

Example 1. (4-(cyclopropanecarbonyl)piperazin-1-yl)(6-methoxy-4-(1,4-dioxa-8-azaspiro[4.5]decan-8-yl)quinolin-3-yl)methanone, TFA (Cpd. 1)

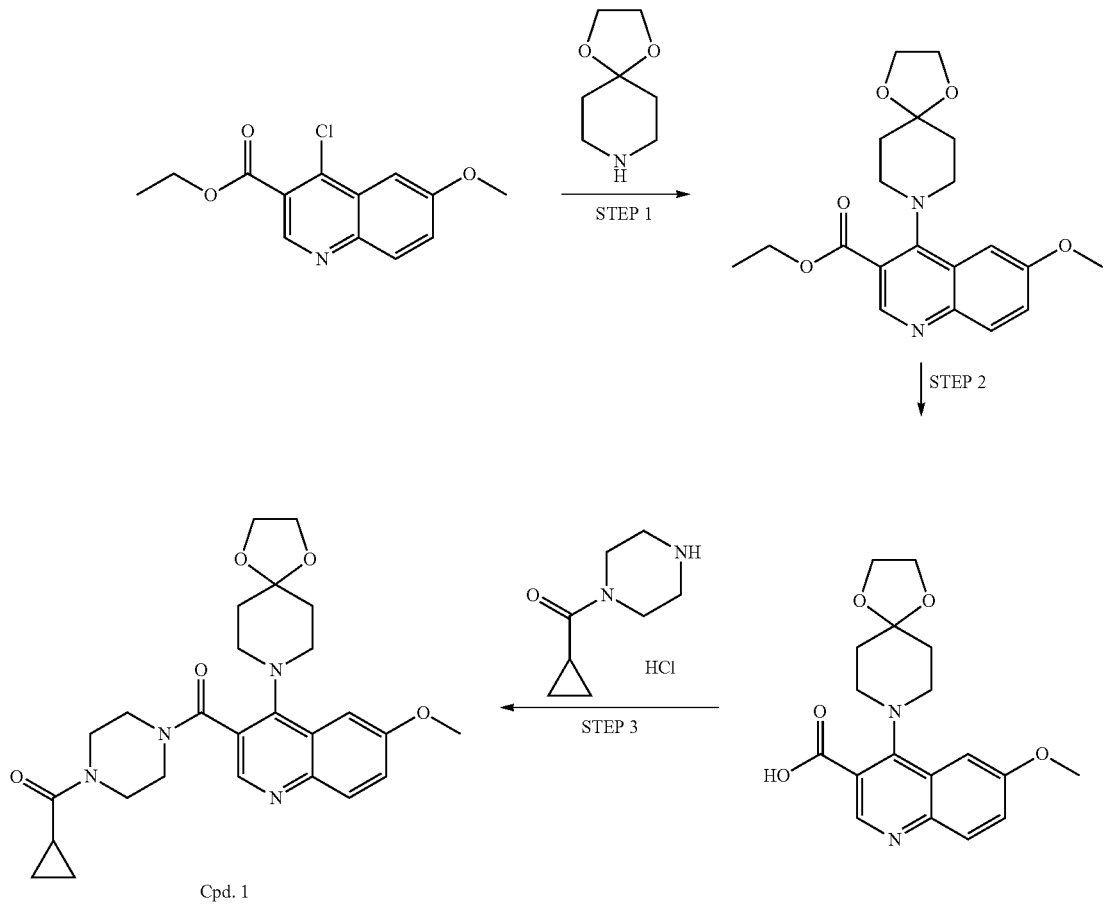

Cpd. 1

STEP 1: Synthesis of Ethyl 6-methoxy-4-(1,4-dioxa-8-azaspiro[4.5]decan-8-yl)quinoline-3-carboxylate. In a microwave vial was placed ethyl 4-chloro-6-methoxyquinoline-3-carboxylate (266 mg, 1 mmol) and 1,4-dioxa-8-azaspiro[4.5]decane (215 mg, 1.50 mmol). Then EtOH (2 ml) and Hunig's base (0.262 ml, 1.50 mmol) were added sequentially. The tube was sealed and heated at 80° C. for 3 h. After cooling to rt, the mixture was concentrated and purified by silica gel chromatography using 40-70% EtOAc/hexane as the eluent to give ethyl 6-methoxy-4-(1,4-dioxa-8-azaspiro[4.5]decan-8-yl)quinoline-3-carboxylate (360 mg, 0.967 mmol, 97% yield) $^1$H NMR (400 MHz, Chloroform-d) δ 8.76 (s, 1H), 7.97 (d, J=9.0 Hz, 1H), 7.40 (d, J=2.8 Hz, 1H), 7.37 (dd, J=9.0, 2.8 Hz, 1H), 4.45 (q, J=7.1 Hz, 2H), 4.04 (s, 4H), 3.94 (s, 3H), 3.45-3.32 (m, 4H), 2.03-1.89 (m, 4H), 1.45 (t, J=7.1 Hz, 3H); LC-MS (Method 1): $t_R$=2.86 min, m/z (M+H)$^+$=373.

STEP 2: Synthesis of 6-Methoxy-4-(1,4-dioxa-8-azaspiro[4.5]decan-8-yl)quinoline-3-carboxylic acid. To a solution of ethyl 6-methoxy-4-(1,4-dioxa-8-azaspiro[4.5]decan-8-yl)quinoline-3-carboxylate (360 mg, 0.967 mmol) in THF (4 ml)/MeOH (1 ml) was added NaOH$_{(aq)}$ (6N in H$_2$O, 1 mL, 6 mmol). The mixture was heated to 60° C. and stirred for overnight. After cooling to rt, 1N HCl$_{(aq)}$ was added until the pH of aqueous layer is ca. 4-5. The mixture was concentrated to removal most of solvent. The solid was triturated with small amount of ice-water and dried to give 6-methoxy-4-(1,4-dioxa-8-azaspiro[4.5]decan-8-yl)quinoline-3-carboxylic acid (two crops, 335 mg, 0.973 mmol, >99% yield). $^1$H NMR (400 MHz, DMSO-d$_6$) δ 8.91 (s, 1H), 8.06 (dd, J=9.3, 1.2 Hz, 1H), 7.67 (dd, J=9.2, 2.5 Hz, 1H), 7.40 (d, J=2.7 Hz, 1H), 3.98 (d, J=1.1 Hz, 7H), 3.62-3.54 (m, 4H), 1.98 (dd, J=6.9, 4.5 Hz, 4H). (acid OH not shown); LC-MS (Method 1): $t_R$=2.58 min, m/z (M+H)$^+$=345.

STEP 3: Synthesis of (4-(Cyclopropanecarbonyl)piperazin-1-yl)(6-methoxy-4-(1,4-dioxa-8-azaspiro[4.5]decan-8-yl)quinolin-3-yl)methanone, TFA. To a mixture of 6-methoxy-4-(1,4-dioxa-8-azaspiro[4.5]decan-8-yl)quinoline-3-carboxylic acid (34.4 mg, 0.1 mmol), cyclopropyl (piperazin-1-yl)methanone, HCl (28.6 mg, 0.15 mmol), and HATU (95 mg, 0.25 mmol) was added DMF (1 ml) and then Hunig's base (0.105 ml, 0.60 mmol). The mixture was stirred at rt for 1 h. The mixture was filtered through filter and submitted for purification by semi-preparative HPLC to give (4-(cyclopropanecarbonyl)piperazin-1-yl)(6-methoxy-4-(1,4-dioxa-8-azaspiro[4.5]decan-8-yl)quinolin-3-yl) methanone, TFA (30.9 mg, 0.052 mmol, 52.0% yield). $^1$H NMR (400 MHz, DMSO-d$_6$) δ 8.66 (s, 1H), 7.95 (d, J=9.2 Hz, 1H), 7.68-7.52 (m, 1H), 7.33 (d, J=2.8 Hz, 1H), 3.94 (d, J=3.9 Hz, 7H), 3.87-3.13 (m, 12H), 2.10-1.75 (m, 5H), 0.73 (d, J=6.3 Hz, 4H); LC-MS (Method 2): $t_R$=3.56 min, m/z (M+H)$^+$=481; HRMS calculated for C$_{26}$H$_{33}$N$_4$O$_5$ (M+H)$^+$: 481.2445, found: 481.2423.

Example 2. (6-methoxy-4-(1,4-dioxa-8-azaspiro[4.5]decan-8-yl)quinolin-3-yl)(4-methoxypiperidin-1-yl)methanone, TFA (Cpd. 2)

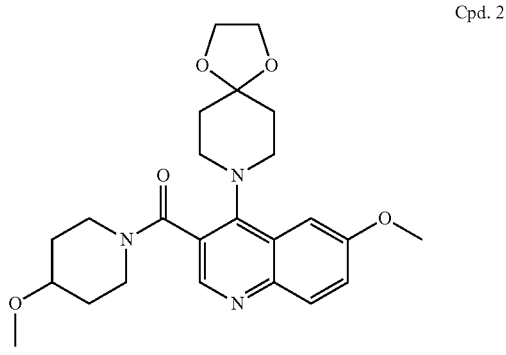 [SMILES: COc1ccc2ncc(C(=O)N3CCC(OC)CC3)c(N3CCC4(CC3)OCCO4)c2c1]

Cpd. 2

The title compound was prepared following the similar procedure as described in Example 1. $^1$H NMR (400 MHz, DMSO-d$_6$) δ 8.62 (d, J=9.8 Hz, 1H), 7.94 (dd, J=9.2, 2.4 Hz, 1H), 7.58 (dt, J=9.3, 2.8 Hz, 1H), 7.32 (d, J=2.9 Hz, 1H), 4.09-3.09 (m, 19H), 2.09-1.26 (m, 8H); LC-MS (Method 2): t$_R$=3.64 min, m/z (M+H)$^+$=442; HRMS calculated for C$_{24}$H$_{32}$N$_3$O$_5$ (M+H)$^+$: 442.2336, found: 442.2343.

Example 3. (4-(cyclopropanecarbonyl)piperazin-1-yl)(6-methoxy-4-(4-methoxypiperidin-1-yl)quinolin-3-yl)methanone, TFA (Cpd. 3)

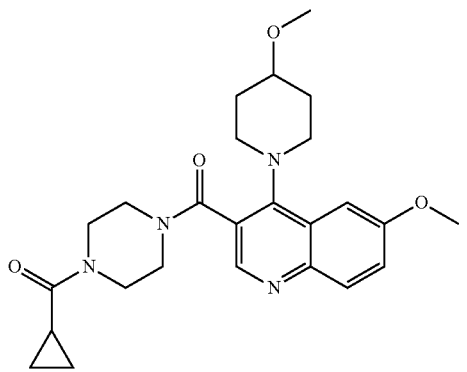

Cpd. 3

The title compound was prepared following the similar procedure as described in Example 1. $^1$H NMR (400 MHz, DMSO-d$_6$) δ 8.64 (s, 1H), 7.95 (d, J=9.2 Hz, 1H), 7.60 (dd, J=9.2, 2.6 Hz, 1H), 7.32 (d, J=2.8 Hz, 1H), 3.95 (s, 3H), 3.89-3.32 (m, 12H), 3.30 (s, 3H), 3.09 (t, J=10.3 Hz, 1H), 2.17-1.67 (m, 5H), 0.74 (d, J=4.8 Hz, 4H); LC-MS (Method 2): t$_R$=3.54 min, m/z (M+H)$^+$=453; HRMS calculated for C$_{25}$H$_{33}$N$_4$O$_4$ (M+H)$^+$: 453.2496, found: 453.2498.

Example 4. (6-methoxy-4-(4-methoxypiperidin-1-yl)quinolin-3-yl)(4-methoxypiperidin-1-yl)methanone, TFA (Cpd. 4)

Cpd. 4

The title compound was prepared following the similar procedure as described in Example 1. $^1$H NMR (400 MHz, DMSO-d$_6$) δ 8.61 (d, J=9.7 Hz, 1H), 7.94 (dd, J=9.3, 2.4 Hz, 1H), 7.59 (d, J=9.2 Hz, 1H), 7.31 (d, J=2.8 Hz, 1H), 4.03 (dt, J=12.4, 5.3 Hz, 1H), 3.94 (s, 3H), 3.88-3.31 (m, 7H), 3.29 (s, 3H), 3.25 (s, 3H), 3.22-3.02 (m, 2H), 2.20-1.30 (m, 8H); LC-MS (Method 2): t$_R$=3.63 min, m/z (M+H)$^+$=414; HRMS calculated for C$_{23}$H$_{32}$N$_3$O$_4$ (M+H)$^+$: 414.2387, found: 414.2379.

Example 5. 1-(4-(6-methoxy-4-(1,4-dioxa-8-azaspiro[4.5]decan-8-yl)quinoline-3-carbonyl)piperazin-1-yl)-2-methylpropan-1-one, TFA (Cpd. 5)

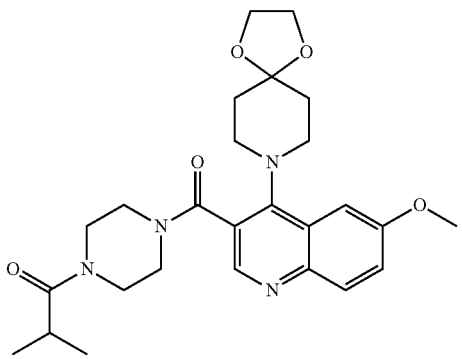

Cpd. 5

The title compound was prepared following the similar procedure as described in Example 1. $^1$H NMR (400 MHz, DMSO-d$_6$) δ 8.60 (d, J=6.8 Hz, 1H), 7.94 (dd, J=9.2, 3.1 Hz, 1H), 7.57 (dd, J=8.9, 2.7 Hz, 1H), 7.33 (d, J=2.8 Hz, 1H), 3.94 (d, J=2.9 Hz, 7H), 3.80-2.72 (m, 13H), 2.03-1.78 (m, 4H), 1.08-0.88 (m, 6H); LC-MS (Method 2): t$_R$=3.64 min, m/z (M+H)$^+$=483; HRMS calculated for C$_{26}$H$_{35}$N$_4$O$_5$ (M+H)$^+$: 483.2602, found: 483.2623.

Example 6. 1-(4-(6-methoxy-4-(1,4-dioxa-8-azaspiro[4.5]decan-8-yl)quinoline-3-carbonyl)piperazin-1-yl)propan-1-one, TFA (Cpd. 6)

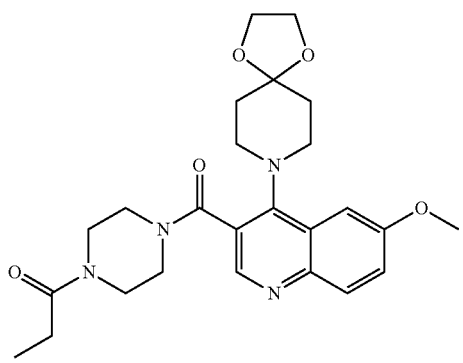

Cpd. 6

The title compound was prepared following the similar procedure as described in Example 1. $^1$H NMR (400 MHz, DMSO-d$_6$) δ 8.61 (s, 1H), 7.94 (dd, J=9.2, 2.3 Hz, 1H), 7.57 (dd, J=9.2, 2.6 Hz, 1H), 7.33 (d, J=2.8 Hz, 1H), 3.94 (d, J=2.8 Hz, 7H), 3.82-3.09 (m, 12H), 2.41-2.23 (m, 2H), 2.03-1.74 (m, 4H), 0.98 (dt, J=10.5, 7.4 Hz, 3H); LC-MS (Method 2): t$_R$=3.45 min, m/z (M+H)$^+$=469; HRMS calculated for C$_{25}$H$_{33}$N$_4$O$_5$ (M+H)$^+$: 469.2445, found: 469.2439.

Example 7. (6-methoxy-4-(1,4-dioxa-8-azaspiro[4.5]decan-8-yl)quinolin-3-yl)(4-(1-methyl-1H-pyrazole-4-carbonyl)piperazin-1-yl)methanone, TFA (Cpd. 7)

Cpd. 7

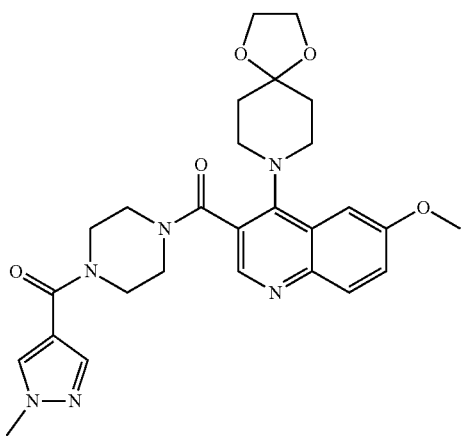

The title compound was prepared following the similar procedure as described in Example 1. $^1$H NMR (400 MHz, DMSO-d$_6$) δ 8.61 (d, J=2.9 Hz, 1H), 8.08 (s, 1H), 7.94 (d, J=9.2 Hz, 1H), 7.67 (s, 1H), 7.56 (d, J=9.7 Hz, 1H), 7.33 (d, J=2.8 Hz, 1H), 3.94 (d, J=2.6 Hz, 7H), 3.83 (s, 3H), 3.81-3.13 (m, 12H), 2.04-1.76 (m, 4H); LC-MS (Method 2): t$_R$=3.37 min, m/z (M+H)$^+$=521; HRMS calculated for C$_{27}$H$_{33}$N$_6$O$_5$ (M+H)$^+$: 521.2507, found: 521.2511.

Example 8. (4-isopropylpiperazin-1-yl)(6-methoxy-4-(1,4-dioxa-8-azaspiro[4.5]decan-8-yl)quinolin-3-yl)methanone, TFA (Cpd. 8)

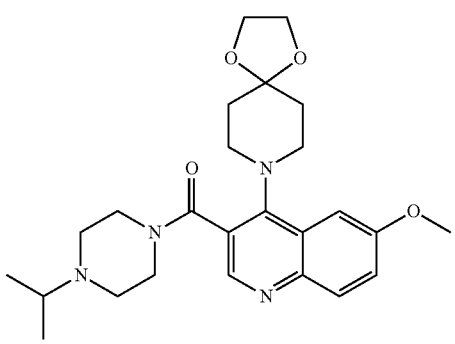

Cpd. 8

The title compound was prepared following the similar procedure as described in Example 1. $^1$H NMR (400 MHz, DMSO-d$_6$) δ 9.61 (s, 1H, salt NH), 8.68-8.49 (m, 1H), 7.93 (dt, J=9.3, 2.6 Hz, 1H), 7.50 (s, 1H), 7.32 (s, 1H), 4.70 (d, J=13.7 Hz, 1H), 3.97-3.90 (m, 7H), 3.84-2.75 (m, 12H), 1.89 (q, J=13.1, 7.4 Hz, 4H), 1.40-1.14 (m, 6H); LC-MS (Method 2): t$_R$=3.02 min, m/z (M+H)$^+$=455; HRMS calculated for C$_{25}$H$_{35}$N$_4$O$_4$ (M+H)$^+$: 455.2653, found: 455.2666.

Example 9. (4-cyclopentylpiperazin-1-yl)(6-methoxy-4-(1,4-dioxa-8-azaspiro[4.5]decan-8-yl)quinolin-3-yl)methanone, TFA (Cpd. 9)

Cpd. 9

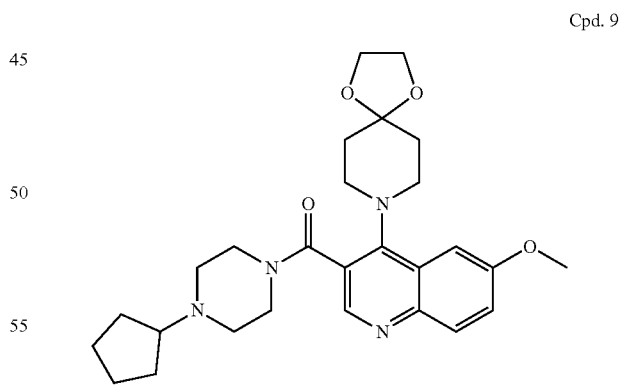

The title compound was prepared following the similar procedure as described in Example 1. $^1$H NMR (400 MHz, DMSO-d$_6$) δ 9.84 (s, 1H, salt NH), 8.59 (d, J=10.9 Hz, 1H), 7.93 (dd, J=9.3, 3.0 Hz, 1H), 7.50 (s, 1H), 7.32 (d, J=6.4 Hz, 1H), 4.64 (t, J=11.5 Hz, 1H), 3.93 (d, J=3.5 Hz, 7H), 3.83-2.74 (m, 12H), 2.13-1.35 (m, 12H); LC-MS (Method 2): t$_R$=3.18 min, m/z (M+H)$^+$=481; HRMS calculated for C$_{27}$H$_{37}$N$_4$O$_4$ (M+H)$^+$: 481.2809, found: 481.2805.

Example 10. (6-methoxy-4-(1,4-dioxa-8-azaspiro[4.5]decan-8-yl)quinolin-3-yl)(4-phenylpiperidin-1-yl)methanone, TFA (Cpd. 10)

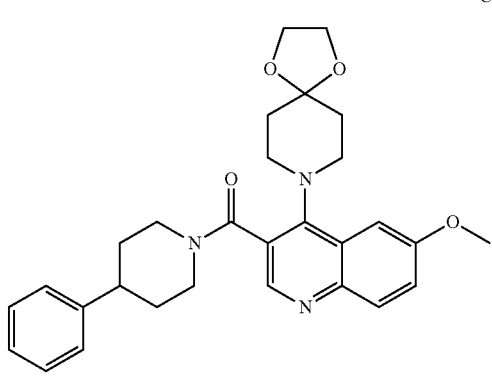

Cpd. 10

The title compound was prepared following the similar procedure as described in Example 1. $^1$H NMR (400 MHz, DMSO-$d_6$) δ 8.68 (d, J=5.2 Hz, 1H, 2 set), 7.95 (dd, J=9.2, 4.5 Hz, 1H), 7.59 (d, J=9.1 Hz, 1H), 7.37-7.15 (m, 6H), 4.71 (m, 1H), 3.97 (d, J=12.6 Hz, 7H), 3.80-2.80 (m, 8H), 2.10-1.44 (m, 8H); LC-MS (Method 2): $t_R$=4.65 min, m/z (M+H)$^+$=488; HRMS calculated for $C_{29}H_{34}N_3O_4$ (M+H)$^+$: 488.2544, found: 488.2538.

Example 11. (6-methoxy-4-(1,4-dioxa-8-azaspiro[4.5]decan-8-yl)quinolin-3-yl)(4-(pyrrolidin-1-yl)piperidin-1-yl)methanone, TFA (Cpd. 11)

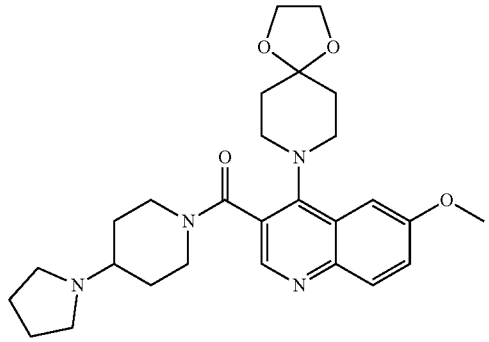

Cpd. 11

The title compound was prepared following the similar procedure as described in Example 1. $^1$H NMR (400 MHz, DMSO-$d_6$) δ 9.67 (s, 1H, salt NH), 8.58-8.37 (m, 1H), 7.96-7.87 (m, 1H), 7.47 (d, J=10.6 Hz, 1H), 7.32 (dd, J=11.5, 2.7 Hz, 1H), 4.74-4.54 (m, 1H), 3.93 (m, 7H), 3.89-2.72 (m, 12H), 2.28-1.30 (m, 12H); LC-MS (Method 2): $t_R$=3.05 min, m/z (M+H)$^+$=481; HRMS calculated for $C_{27}H_{37}N_4O_4$ (M+H)$^+$: 481.2809, found: 481.2809.

Example 12. (6-methoxy-4-(1,4-dioxa-8-azaspiro[4.5]decan-8-yl)quinolin-3-yl)(4-(trifluoromethyl)piperidin-1-yl)methanone, TFA (Cpd. 12)

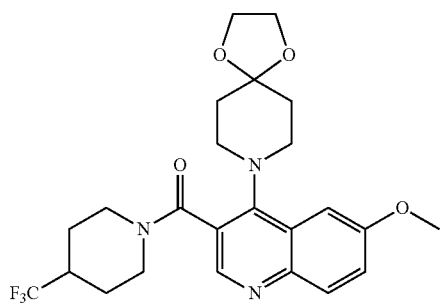

Cpd. 12

The title compound was prepared following the similar procedure as described in Example 1. $^1$H NMR (400 MHz, DMSO-$d_6$) δ 8.71-8.52 (m, 1H), 7.94 (td, J=9.0, 3.2 Hz, 1H), 7.58 (d, J=9.1 Hz, 1H), 7.33 (t, J=3.5 Hz, 1H), 4.65 (t, J=16.5 Hz, 1H), 3.94 (d, J=2.2 Hz, 7H), 3.84-2.55 (m, 8H), 2.07-1.23 (m, 8H); LC-MS (Method 2): $t_R$=4.27 min, m/z (M+H)$^+$= 480; HRMS calculated for $C_{24}H_{29}F_3N_3O_4$ (M+H)$^+$: 480.2105, found: 480.2086.

Example 13. (6-methoxy-4-(1,4-dioxa-8-azaspiro[4.5]decan-8-yl)quinolin-3-yl)(4-(methylsulfonyl)piperazin-1-yl)methanone, TFA (Cpd. 13)

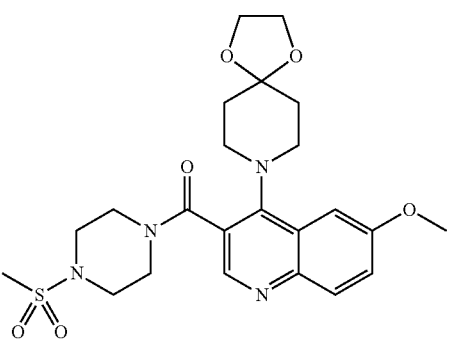

Cpd. 13

The title compound was prepared following the similar procedure as described in Example 1. $^1$H NMR (400 MHz, DMSO-$d_6$) δ 8.60 (d, J=4.5 Hz, 1H), 7.97-7.90 (m, 1H), 7.55 (d, J=9.0 Hz, 1H), 7.33 (d, J=2.7 Hz, 1H), 3.94 (s, 7H), 3.91-3.02 (m, 12H), 2.92 (s, 3H), 2.04-1.77 (m, 4H); LC-MS (Method 2): $t_R$=3.52 min, m/z (M+H)$^+$=491; HRMS calculated for $C_{23}H_{31}SN_4O_6$ (M+H)$^+$: 491.1959, found: 491.1946.

Example 14. (6-methoxy-4-(1,4-dioxa-8-azaspiro[4.5]decan-8-yl)quinolin-3-yl)(4-(pyridin-3-yl)piperazin-1-yl)methanone, TFA (Cpd. 14)

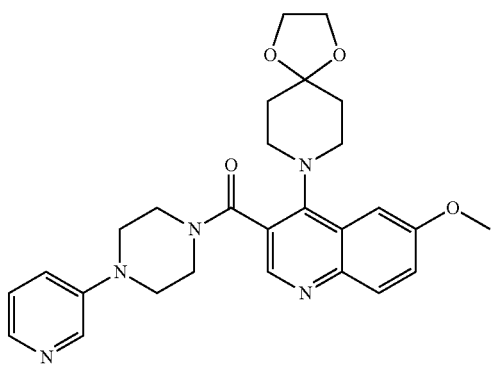

Cpd. 14

The title compound was prepared following the similar procedure as described in Example 1. $^1$H NMR (400 MHz, DMSO-$d_6$) δ 8.62 (s, 1H), 8.43 (d, J=2.9 Hz, 1H), 8.17 (d, J=5.1 Hz, 1H), 7.94 (dd, J=9.4, 3.4 Hz, 1H), 7.88 (s, 1H), 7.68 (t, J=7.1 Hz, 1H), 7.56 (dd, J=9.0, 2.6 Hz, 1H), 7.34 (d, J=2.7 Hz, 1H), 3.94 (s, 3H), 3.93 (s, 4H), 3.90-3.08 (m, 12H), 2.06-1.75 (m, 4H); LC-MS (Method 2): $t_R$=3.10 min, m/z (M+H)$^+$=490; HRMS calculated for $C_{27}H_{32}N_5O_4$ (M+H)$^+$: 490.2449, found: 490.2448.

Example 15. (6-methoxy-4-(1,4-dioxa-8-azaspiro[4.5]decan-8-yl)quinolin-3-yl)(4-(pyridin-4-yl)piperazin-1-yl)methanone, TFA (Cpd. 15)

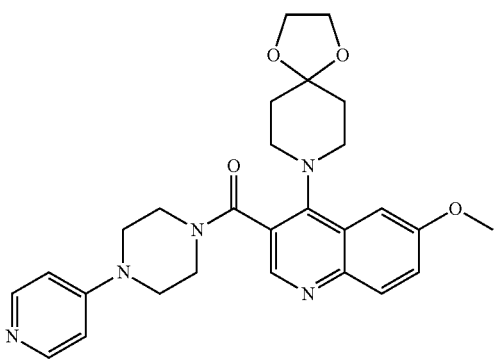

Cpd. 15

The title compound was prepared following the similar procedure as described in Example 1. $^1$H NMR (400 MHz, DMSO-$d_6$) δ 13.40 (s, 1H, salt NH), 8.59 (d, J=2.8 Hz, 1H), 8.28 (d, J=7.2 Hz, 2H), 7.97-7.89 (m, 1H), 7.54 (s, 1H), 7.33 (d, J=2.8 Hz, 1H), 7.19 (d, J=6.9 Hz, 2H), 3.93 (d, J=5.0 Hz, 7H), 3.91-3.06 (m, 12H), 2.02-1.76 (m, 4H); LC-MS (Method 2): $t_R$=3.08 min, m/z (M+H)$^+$=490; HRMS calculated for $C_{27}H_{32}N_5O_4$ (M+H)$^+$: 490.2449, found: 490.2450.

Example 16. 6-methoxy-N-(1-methylpiperidin-4-yl)-4-(1,4-dioxa-8-azaspiro[4.5]decan-8-yl)quinoline-3-carboxamide, TFA (Cpd. 16)

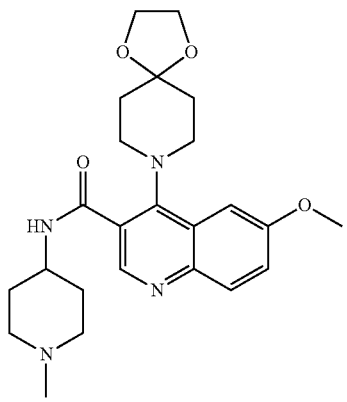

Cpd. 16

The title compound was prepared following the similar procedure as described in Example 1. $^1$H NMR (400 MHz, DMSO-$d_6$) δ 9.33 (s, 1H, salt NH), 8.76 (d, J=7.3 Hz, 1H), 8.59 (m, 1H), 7.98-7.88 (m, 1H), 7.50 (s, 1H), 7.34 (dd, J=5.4, 2.7 Hz, 1H), 3.93 (s, 8H), 3.55-3.02 (m, 8H), 2.76 (dd, J=6.8, 4.7 Hz, 3H), 2.18-1.55 (m, 8H); LC-MS (Method 2): $t_R$=2.99 min, m/z (M+H)$^+$=441; HRMS calculated for $C_{24}H_{33}N_4O_4$ (M+H)$^+$: 441.2496, found: 441.2483.

Example 17. (4-(cyclopropanecarbonyl)piperazin-1-yl)(6-methoxy-4-(8-azaspiro[4.5]decan-8-yl)quinolin-3-yl)methanone, TFA (Cpd. 17)

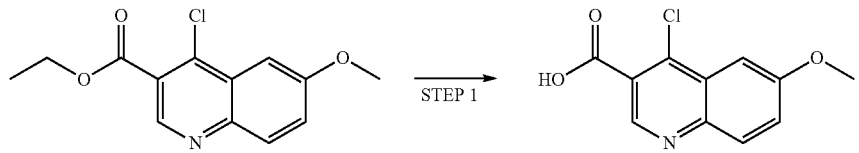

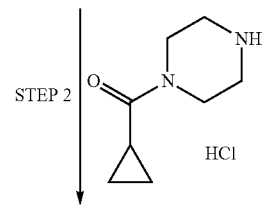

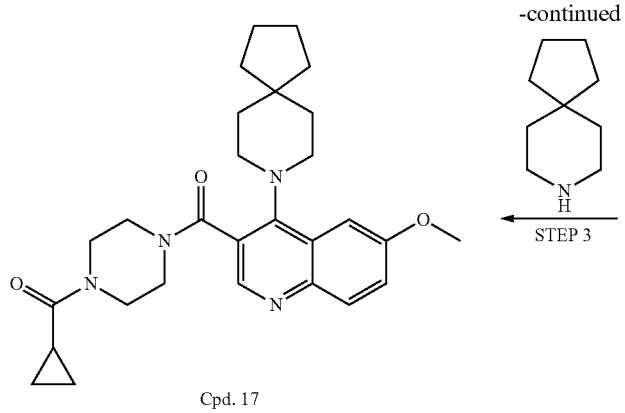

Cpd. 17

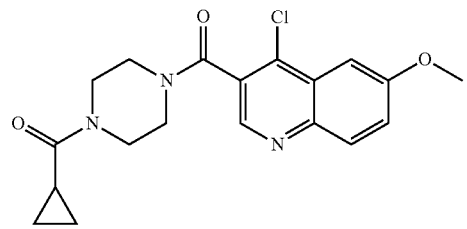

STEP 3

STEP 1: Synthesis of 4-Chloro-6-methoxyquinoline-3-carboxylic acid. To a solution of ethyl 4-chloro-6-methoxyquinoline-3-carboxylate (531 mg, 2 mmol) in THF (4 ml) was added 1N NaOH$_{(aq)}$ (2 mL, 2 mmol) at 0° C. The mixture was then warmed to rt and stirred for 2 h. 1N HCl$_{(aq)}$ (2 mL, 2 mmol) was added dropwise and then hexane (10 mL) was added. The solid was filtered and washed with small amount of H$_2$O (1 mL×3), and then dried to give 4-chloro-6-methoxyquinoline-3-carboxylic acid (450 mg, 1.42 mmol, 71.0% yield). This material contained ca. 20-25% of ethyl 4-hydroxy-6-methoxyquinoline-3-carboxylate, which was used for next step without further purification. LC-MS (Method 1): $t_R$=2.75 min, m/z (M+H)$^+$=238.

STEP 2: Synthesis of (4-Chloro-6-methoxyquinolin-3-yl)(4-(cyclopropanecarbonyl)piperazin-1-yl)methanone. To 4-chloro-6-methoxyquinoline-3-carboxylic acid (450 mg, 1.42 mmol), cyclopropyl(piperazin-1-yl)methanone, HCl (298 mg, 1.562 mmol) and HATU (702 mg, 1.846 mmol) was added DMF (3 ml) and then Hunig's base (0.620 ml, 3.55 mmol) at rt. The mixture was stirred for 2 h. The mixture was poured into H$_2$O (100 mL). The solid was filtered, washed with H$_2$O (2 mL×3), and dried to give (4-chloro-6-methoxyquinolin-3-yl)(4-(cyclopropanecarbonyl)piperazin-1-yl)methanone (460 mg, 1.23 mmol, 87% yield). The material was used without further purification. LC-MS (Method 1): $t_R$=2.97 min, m/z (M+H)$^+$=374.

STEP 3: Synthesis of (4-(Cyclopropanecarbonyl)piperazin-1-yl)(6-methoxy-4-(8-azaspiro[4.5]decan-8-yl)quinolin-3-yl)methanone, TFA. In a microwave tube was placed (4-chloro-6-methoxyquinolin-3-yl)(4-(cyclopropanecarbonyl)piperazin-1-yl)methanone (18.69 mg, 0.05 mmol) and 8-azaspiro[4.5]decane (69.6 mg, 0.50 mmol). Then, DMF (1 ml) was added. The tube was sealed and heated at 150° C. for 1 h under microwave irradiation. The mixture was filtered through a filter and submitted for purification by semi-preparative HPLC to give (4-(cyclopropanecarbonyl)piperazin-1-yl)(6-methoxy-4-(8-azaspiro[4.5]decan-8-yl)quinolin-3-yl)methanone (13.4 mg, 0.028 mmol, 56.2% yield). $^1$H NMR (400 MHz, DMSO-d$_6$) δ 8.60 (s, 1H), 7.94 (d, J=9.0 Hz, 1H), 7.64-7.55 (m, 1H), 7.37 (d, J=2.7 Hz, 1H), 3.94 (s, 3H), 3.90-3.08 (m, 12H), 2.08-1.37 (m, 13H), 0.79-0.61 (m, 4H); LC-MS (Method 2): $t_R$=4.58 min, (M+H)$^+$=477; HRMS calculated for C$_{28}$H$_{37}$N$_4$O$_3$ (M+H)$^+$: 477.2860, found: 477.2876.

Example 18. (4-(cyclopropanecarbonyl)piperazin-1-yl)(4-(4,4-dimethylpiperidin-1-yl)-6-methoxyquinolin-3-yl)methanone, TFA (Cpd. 18)

Cpd. 18

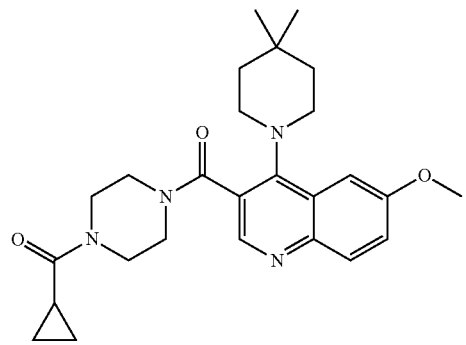

The title compound was prepared following the similar procedure as described in Example 17. $^1$H NMR (400 MHz, DMSO-d$_6$) δ 8.65-8.59 (m, 1H), 7.97-7.92 (m, 1H), 7.60 (d, J=9.4 Hz, 1H), 7.36 (d, J=2.7 Hz, 1H), 3.94 (s, 3H), 3.90-3.10 (m, 12H), 2.10-1.43 (m, 5H), 1.03 (s, 6H), 0.78-0.63 (m, 4H); LC-MS (Method 2): $t_R$=4.26 min, m/z (M+H)$^+$= 451; HRMS calculated for C$_{26}$H$_{35}$N$_4$O$_3$ (M+H)$^+$: 451.2704, found: 451.2713.

Example 19. (4-(cyclopropanecarbonyl)piperazin-1-yl)(6-methoxy-4-(4-(methylsulfonyl)piperazin-1-yl)quinolin-3-yl)methanone, TFA (Cpd. 19)

Cpd. 19

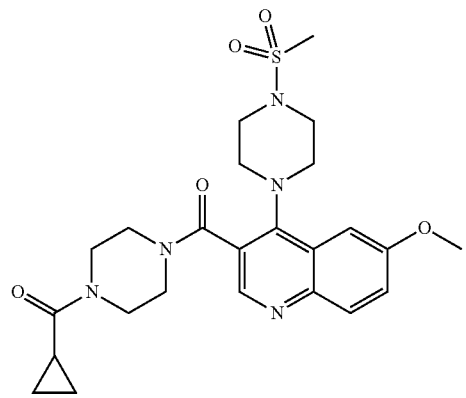

The title compound was prepared following the similar procedure as described in Example 17. ¹H NMR (400 MHz, DMSO-d$_6$) δ 8.59 (s, 1H), 7.96 (d, J=9.2 Hz, 1H), 7.53 (dd, J=9.0, 3.8 Hz, 1H), 7.38 (d, J=2.8 Hz, 1H), 3.95 (s, 3H), 3.88-3.07 (m, 16H), 2.99 (s, 3H), 2.14-1.79 (m, 1H), 0.83-0.60 (m, 4H); LC-MS (Method 2): t$_R$=3.33 min, m/z (M+H)$^+$= 502; HRMS calculated for C$_{24}$H$_{32}$N$_5$O$_5$S (M+H)$^+$: 502.2119, found: 502.2132.

Example 20. (4-(cyclopropanecarbonyl)piperazin-1-yl)(6-methoxy-4-(4-(pyridin-4-yl)piperazin-1-yl)quinolin-3-yl)methanone, TFA (Cpd. 20)

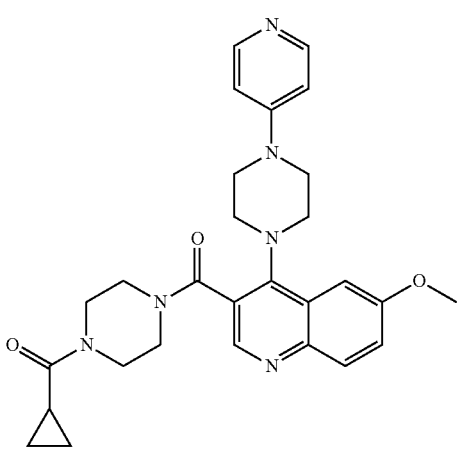

Cpd. 20

The title compound was prepared following the similar procedure as described in Example 17. ¹H NMR (400 MHz, DMSO-d$_6$) δ 13.42 (s, 1H, salt NH), 8.56 (s, 1H), 8.30 (d, J=7.0 Hz, 2H), 7.97 (d, J=9.1 Hz, 1H), 7.53 (dd, J=9.2, 2.8 Hz, 1H), 7.47 (d, J=2.8 Hz, 1H), 7.25 (d, J=7.4 Hz, 2H), 4.03 (t, J=11.0 Hz, 2H), 3.95 (s, 3H), 3.94-3.16 (m, 14H), 2.01 (s, 1H), 0.73 (s, 4H); LC-MS (Method 2): t$_R$=2.87 min, m/z (M+H)$^+$=501; HRMS calculated for C$_{28}$H$_{33}$N$_6$O$_3$ (M+H)$^+$: 501.2609, found: 501.2613.

Example 21. (4-(cyclopropanecarbonyl)piperazin-1-yl)(6-methoxy-4-((1-methylpiperidin-4-yl)amino)quinolin-3-yl)methanone, TFA (Cpd. 21)

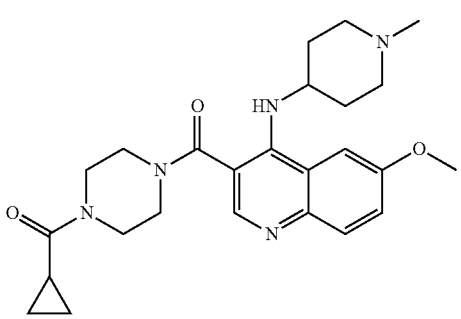

Cpd. 21

The title compound was prepared following the similar procedure as described in Example 17. ¹H NMR (400 MHz, DMSO-d$_6$) δ 9.49 (s, 1H, salt NH), 8.55 (s, 1H), 8.23 (s, 1H), 7.99 (d, J=2.7 Hz, 1H), 7.89 (d, J=9.2 Hz, 1H), 7.67 (dd, J=9.2, 2.3 Hz, 1H), 3.96 (s, 3H), 3.94-3.17 (m, 13H), 2.81 (d, J=3.7 Hz, 3H), 2.09-1.90 (m, 5H), 0.85-0.63 (m, 4H); LC-MS (Method 2): t$_R$=2.65 min, m/z (M+H)$^+$=452; HRMS calculated for C$_{25}$H$_{34}$N$_5$O$_3$ (M+H)$^+$: 452.2656, found: 452.2670.

Example 22. (4-(cyclobutylamino)-6-methoxyquinolin-3-yl)(4-(cyclopropanecarbonyl)piperazin-1-yl)methanone, TFA (Cpd. 22)

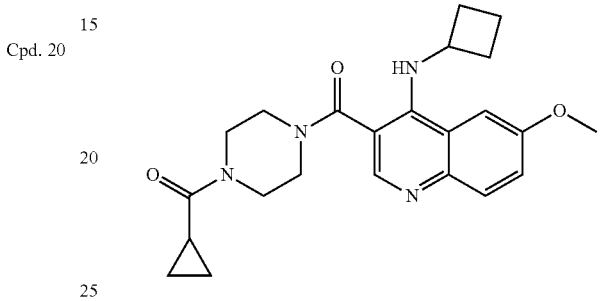

Cpd. 22

The title compound was prepared following the similar procedure as described in Example 17. ¹H NMR (400 MHz, DMSO-d6) δ 8.64 (s, 2H), 8.51 (s, 1H), 7.98 (d, J=2.4 Hz, 1H), 7.85 (d, J=9.2 Hz, 1H), 7.63 (dd, J=9.2, 2.5 Hz, 1H), 4.20 (h, J=9.0, 8.4 Hz, 1H), 3.97 (s, 3H), 3.58 (m, 8H), 2.41-2.17 (m, 4H), 2.10-1.53 (m, 3H), 0.87-0.55 (m, 4H); LC-MS (Method 2): t$_R$=3.59 min, m/z (M+H)$^+$=409; HRMS calculated for C$_{23}$H$_{29}$N$_4$O$_3$ (M+H)$^+$: 409.2234, found: 409.2245.

Example 23. 1-(4-(3-(4-(cyclopropanecarbonyl)piperazine-1-carbonyl)-6-methoxyquinolin-4-yl)piperazin-1-yl)ethanone, TFA (Cpd. 23)

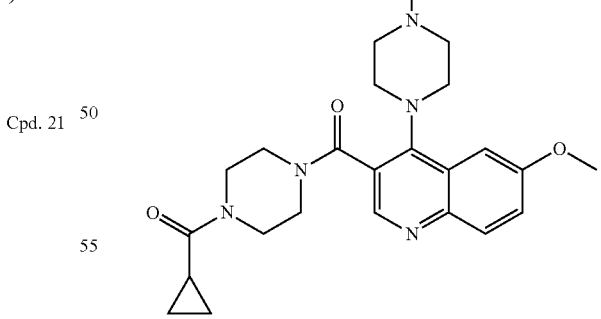

Cpd. 23

The title compound was prepared following the similar procedure as described in Example 17. ¹H NMR (400 MHz, DMSO-d$_6$) δ 8.63 (s, 1H), 7.96 (dd, J=9.2, 1.7 Hz, 1H), 7.56 (d, J=8.6 Hz, 1H), 7.40 (d, J=2.8 Hz, 1H), 3.95 (s, 3H), 3.87-2.99 (m, 16H), 2.06 (s, 3H), 1.93 (d, J=24.7 Hz, 1H), 0.83-0.55 (m, 4H); LC-MS (Method 2): t$_R$=3.09 min, m/z (M+H)$^+$=466; HRMS calculated for C$_{25}$H$_{32}$N$_5$O$_4$ (M+H)$^+$: 466.2449, found: 466.2449.

Example 24. (4-(cyclopropanecarbonyl)piperazin-1-yl)(6-methoxy-4-(1-oxa-8-azaspiro[4.5]decan-8-yl)quinolin-3-yl)methanone, TFA (Cpd. 24)

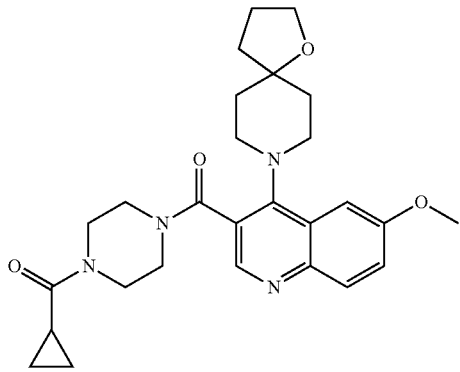

Cpd. 24

The title compound was prepared following the similar procedure as described in Example 17. $^1$H NMR (400 MHz, DMSO-d$_6$) δ 8.62 (s, 1H), 7.94 (dd, J=9.2, 1.5 Hz, 1H), 7.62-7.55 (m, 1H), 7.34 (d, J=2.8 Hz, 1H), 3.94 (s, 3H), 3.77 (td, J=6.7, 1.5 Hz, 2H), 3.74-3.06 (m, 12H), 2.10-1.60 (m, 9H), 0.84-0.60 (m, 4H); LC-MS (Method 2): t$_R$=3.82 min, m/z (M+H)$^+$=479; HRMS calculated for C$_{27}$H$_{35}$N$_4$O$_4$ (M+H)$^+$: 479.2653, found: 479.2649.

Example 25. 1-(3-(4-(cyclopropanecarbonyl)piperazine-1-carbonyl)-6-methoxyquinolin-4-yl)piperidine-4-carbonitrile, TFA (Cpd. 25)

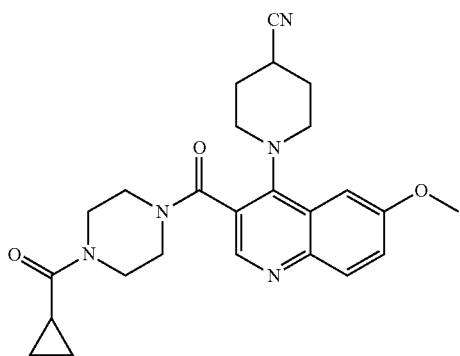

Cpd. 25

The title compound was prepared following the similar procedure as described in Example 17. $^1$H NMR (400 MHz, DMSO-d$_6$) δ 8.61 (s, 1H), 7.97-7.92 (m, 1H), 7.56 (dd, J=7.9, 4.1 Hz, 1H), 7.31 (d, J=2.7 Hz, 1H), 3.96 (s, 3H), 3.90-2.99 (m, 12H), 2.26-1.81 (m, 6H), 0.85-0.54 (m, 4H); LC-MS (Method 2): t$_R$=3.43 min, m/z (M+H)$^+$=448; HRMS calculated for C$_{25}$H$_{30}$N$_5$O$_3$ (M+H)$^+$: 448.2343, found: 448.2355.

Example 26. (4-(cyclopropanecarbonyl)piperazin-1-yl)(6-methoxy-4-(4-methoxy-4-methylpiperidin-1-yl)quinolin-3-yl)methanone, TFA (Cpd. 26)

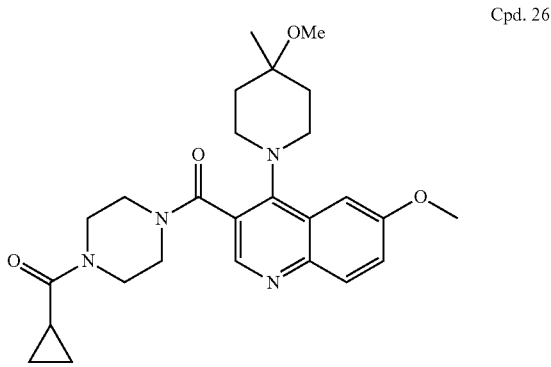 [SMILES: COc1ccc2ncc(C(=O)N3CCN(C(=O)C4CC4)CC3)c(N3CCC(C)(OC)CC3)c2c1]

Cpd. 26

The title compound was prepared following the similar procedure as described in Example 17. $^1$H NMR (400 MHz, DMSO-d$_6$) δ 8.59 (s, 1H), 7.94 (dd, J=9.2, 1.5 Hz, 1H), 7.61-7.54 (m, 1H), 7.33 (d, J=2.7 Hz, 1H), 3.94 (s, 3H), 3.48 (m, 12H), 3.15 (s, 3H), 2.10-1.61 (m, 5H), 1.21 (s, 3H), 0.84-0.62 (m, 4H); LC-MS (Method 2): t$_R$=3.76 min, m/z (M+H)$^+$=467; HRMS calculated for C$_{26}$H$_{34}$N$_4$O$_4$Na (M+Na)$^+$: 489.2472, found: 489.2496.

Example 27. 1-(3-(4-(cyclopropanecarbonyl)piperazine-1-carbonyl)-6-methoxyquinolin-4-yl)-4-methylpiperidine-4-carbonitrile, TFA (Cpd. 27)

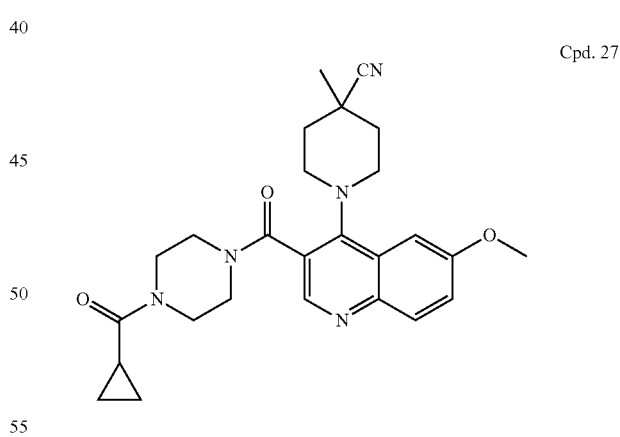

Cpd. 27

The title compound was prepared following the similar procedure as described in Example 17. $^1$H NMR (400 MHz, DMSO-d$_6$) δ 8.59 (s, 1H), 7.95 (d, J=9.2 Hz, 1H), 7.60-7.51 (m, 1H), 7.30 (d, J=2.8 Hz, 1H), 3.95 (s, 3H), 3.87-3.08 (m, 12H), 2.15-1.71 (m, 5H), 1.46 (s, 3H), 0.74 (dd, J=4.7, 2.6 Hz, 4H); LC-MS (Method 2): t$_R$=3.68 min, m/z (M+H)$^+$=462; HRMS calculated for C$_{26}$H$_{32}$N$_5$O$_3$ (M+H)$^+$: 462.2500, found: 462.2522.

Example 28. (4-(cyclopropanecarbonyl)piperazin-1-yl)(6-methoxy-4-(4-(trifluoromethyl)piperidin-1-yl)quinolin-3-yl)methanone, TFA (Cpd. 28)

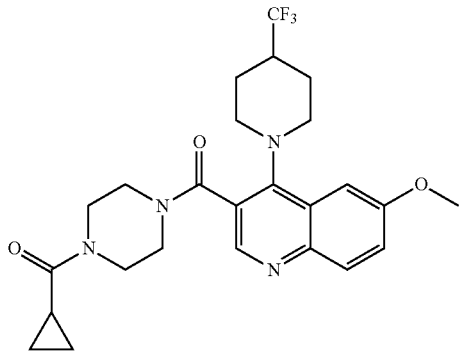

Cpd. 28

The title compound was prepared following the similar procedure as described in Example 17. $^1$H NMR (400 MHz, DMSO-d$_6$) δ 8.60 (d, J=3.4 Hz, 1H), 7.95 (dd, J=9.2, 1.5 Hz, 1H), 7.56 (d, J=9.4 Hz, 1H), 7.29 (d, J=2.8 Hz, 1H), 3.94 (s, 3H), 3.91-2.62 (m, 13H), 2.12-1.55 (m, 5H), 0.79-0.55 (m, 4H); LC-MS (Method 2): t$_R$=4.21 min, m/z (M+H)$^+$=491; HRMS calculated for C$_{26}$H$_{33}$F$_3$N$_4$O$_3$ (M+H)$^+$: 491.2265, found: 491.2268.

Example 29. (4-(cyclopropanecarbonyl)piperazin-1-yl)(4-(1,1-dioxidothiomorpholino)-6-methoxyquinolin-3-yl)methanone, TFA (Cpd. 29)

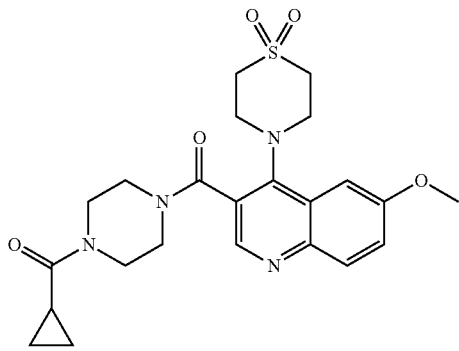

Cpd. 29

The title compound was prepared following the similar procedure as described in Example 17. $^1$H NMR (400 MHz, DMSO-d$_6$) δ 8.55 (s, 1H), 7.93-7.88 (m, 1H), 7.58 (dd, J=9.1, 2.7 Hz, 1H), 7.52 (d, J=2.6 Hz, 1H), 3.93 (s, 3H), 3.91-3.31 (m, 12H), 3.20 (s, 4H), 2.02 (s, 1H), 0.86-0.61 (m, 4H); LC-MS (Method 2): t$_R$=3.19 min, m/z (M+H)$^+$=473; HRMS calculated for C$_{23}$H$_{29}$SN$_4$O$_5$ (M+H)$^+$: 473.1853, found: 473.1871.

Example 30. (4-(cyclopropanecarbonyl)piperazin-1-yl)(6-methyl-4-(1,4-dioxa-8-azaspiro[4.5]decan-8-yl)quinolin-3-yl)methanone, TFA (Cpd. 30)

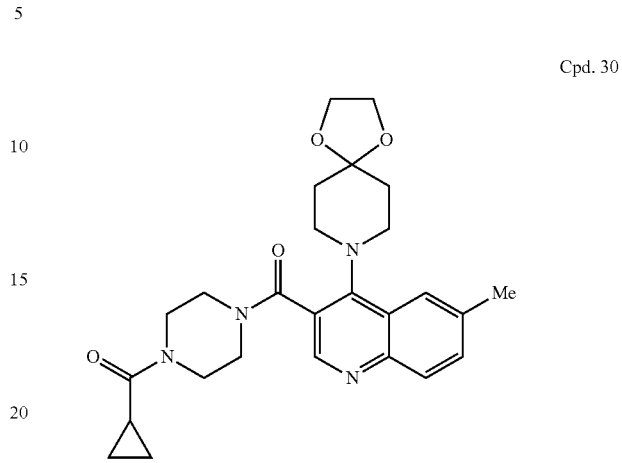

Cpd. 30

The title compound was prepared following the similar procedure as described in Example 1. $^1$H NMR (400 MHz, DMSO-d$_6$) δ 8.74 (s, 1H), 7.92 (d, J=8.5 Hz, 2H), 7.82 (dd, J=8.5, 1.7 Hz, 1H), 3.96 (s, 4H), 3.87-3.25 (m, 12H), 2.56 (s, 3H), 2.18-1.68 (m, 5H), 0.91-0.59 (m, 4H); LC-MS (Method 2): t$_R$=3.51 min, m/z (M+H)$^+$=465; HRMS calculated for C$_{26}$H$_{33}$N$_4$O$_4$ (M+H)$^+$: 465.2496, found: 465.2490.

Example 31. (4-(cyclopropanecarbonyl)piperazin-1-yl)(6-fluoro-4-(1,4-dioxa-8-azaspiro[4.5]decan-8-yl)quinolin-3-yl)methanone, TFA (Cpd. 31)

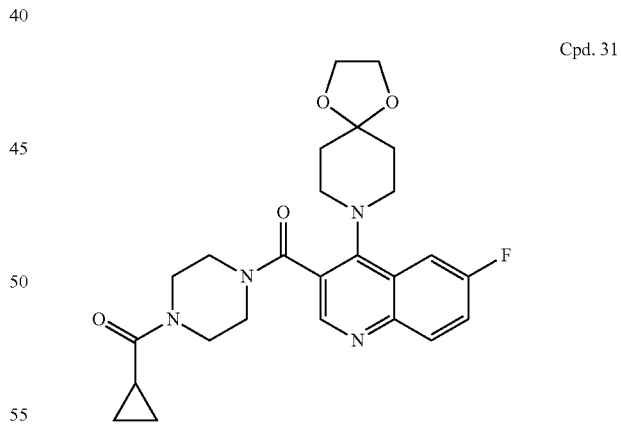

Cpd. 31

The title compound was prepared following the similar procedure as described in Example 1. $^1$H NMR (400 MHz, DMSO-d$_6$) δ 8.69 (d, J=4.0 Hz, 1H), 8.07 (dd, J=8.9, 5.3 Hz, 1H), 7.80 (t, J=9.9 Hz, 2H), 3.97-3.91 (m, 4H), 3.90-3.08 (m, 12H), 2.12-1.65 (m, 5H), 0.90-0.54 (m, 4H); LC-MS (Method 2): t$_R$=3.49 min, m/z (M+H)$^+$=469; HRMS calculated for C$_{25}$H$_{30}$FN$_4$O$_4$ (M+H)$^+$: 469.2246, found: 469.2260.

Example 32. (4,4-difluoropiperidin-1-yl)(6-methoxy-4-(1,4-dioxa-8-azaspiro[4.5]decan-8-yl)quinolin-3-yl)methanone, TFA (Cpd. 32)

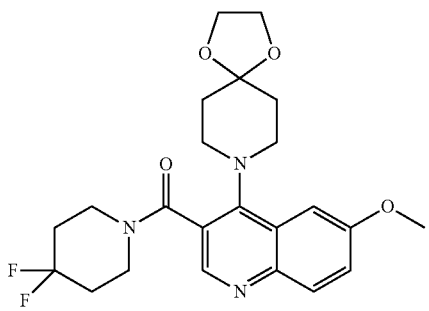
Cpd. 32

The title compound was prepared following the similar procedure as described in Example 1. $^1$H NMR (400 MHz, DMSO-d$_6$) δ 8.66 (s, 1H), 7.94 (d, J=9.2 Hz, 1H), 7.56 (d, J=9.1 Hz, 1H), 7.33 (d, J=2.8 Hz, 1H), 4.12-4.01 (m, 1H), 3.94 (s, 7H), 3.68-3.14 (m, 7H), 2.26-1.76 (m, 8H); LC-MS (Method 2): t$_R$=3.92 min, m/z (M+H)$^+$=448; HRMS calculated for C$_{23}$H$_{27}$F$_2$N$_3$O$_4$Na (M+Na)$^+$: 470.1862, found: 470.1871.

Example 33. ((2S*,6R*)-2,6-dimethylmorpholino)(6-methoxy-4-(1,4-dioxa-8-azaspiro[4.5]decan-8-yl)quinolin-3-yl)methanone, TFA (Cpd. 33)

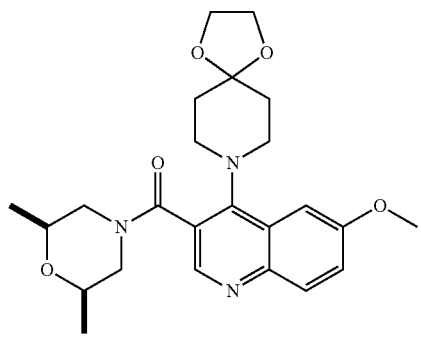
Cpd. 33

The title compound was prepared following the similar procedure as described in Example 1. $^1$H NMR (400 MHz, DMSO-d$_6$) δ 8.55 (s, 1H), 7.93 (d, J=9.1 Hz, 1H), 7.55 (s, 1H), 7.33 (dd, J=5.4, 2.8 Hz, 1H), 4.43 (dd, J=40.6, 12.9 Hz, 1H), 3.94 (s, 7H), 3.75-3.08 (m, 8H), 2.98-2.62 (m, 1H), 2.05-1.77 (m, 4H), 1.17 (dd, J=6.2, 4.5 Hz, 3H), 0.97 (dd, J=6.2, 1.7 Hz, 3H); LC-MS (Method 2): t$_R$=3.80 min, m/z (M+H)$^+$=442; HRMS calculated for C$_{24}$H$_{32}$N$_3$O$_5$ (M+H)$^+$: 442.2336, found: 442.2348.

Example 34. (4-(cyclopropanecarbonyl)piperazin-1-yl)(44(2S*,6R*)-2,6-dimethylmorpholino)-6-methoxyquinolin-3-yl)methanone, TFA (Cpd. 34)

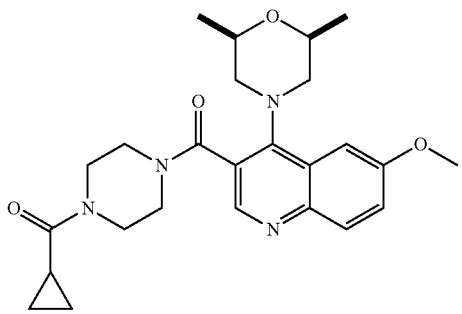
Cpd. 34

The title compound was prepared following the similar procedure as described in Example 17. $^1$H NMR (400 MHz, DMSO-d$_6$) δ 8.60 (s, 1H), 7.94 (dd, J=9.2, 1.6 Hz, 1H), 7.55 (d, J=9.1 Hz, 1H), 7.37 (d, J=2.8 Hz, 1H), 4.03 (t, J=8.4 Hz, 1H), 3.93 (s, 3H), 3.91-3.27 (m, 10H), 3.18 (s, 1H), 2.94 (t, J=10.9 Hz, 1H), 2.75 (t, J=11.8 Hz, 1H), 1.98 (d, J=27.8 Hz, 1H), 1.12 (dd, J=6.2, 3.0 Hz, 6H), 0.74 (d, J=4.5 Hz, 4H); LC-MS (Method 2): t$_R$=3.67 min, m/z (M+H)$^+$=453; HRMS calculated for C$_{25}$H$_{33}$N$_4$O$_4$ (M+H)$^+$: 453.2496, found: 453.2493.

Example 35. (4-(cyclopropanecarbonyl)piperazin-1-yl)(6-methoxy-4-(4-methyl-1H-pyrazol-1-yl)quinolin-3-yl)methanone, TFA (Cpd. 35)

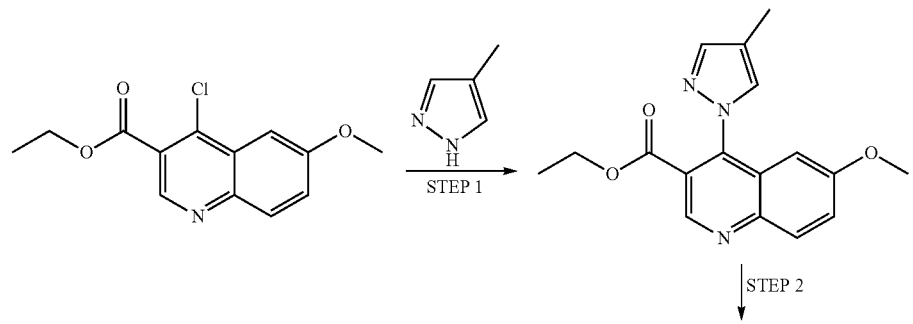

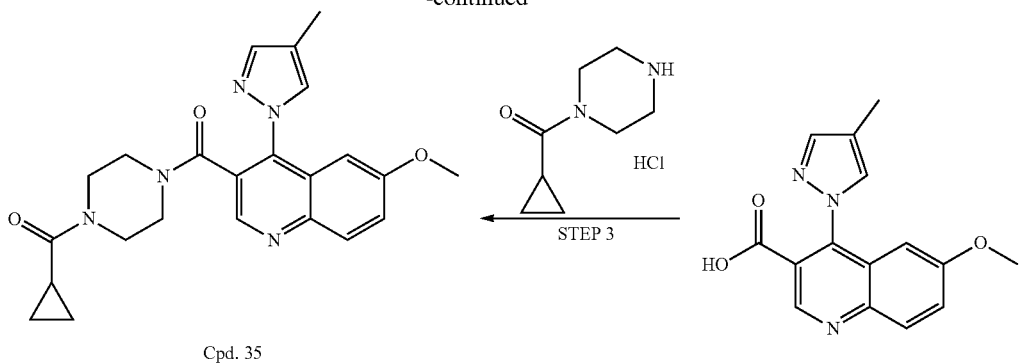

Cpd. 35

STEP 1: Synthesis of Ethyl 6-methoxy-4-(4-methyl-1H-pyrazol-1-yl)quinoline-3-carboxylate. In a microwave vial was placed ethyl 4-chloro-6-methoxyquinoline-3-carboxylate (266 mg, 1) and 4-methyl-1H-pyrazole (164 mg, 2.0 mmol), and $K_2CO_3$ (276 mg, 2.0 mmol). Then DMSO (2 ml) was added. The tube was sealed and heated at 100° C. for 2 h. The mixture was poured into EtOAc/$H_2O$ (30 mL/30 mL). The organic layer was dried ($Na_2SO_4$) and filtered. After removal of solvent, the product was purified by silica gel chromatography using 20-40% EtOAc/hexane as the eluent to give ethyl 6-methoxy-4-(4-methyl-1H-pyrazol-1-yl)quinoline-3-carboxylate (295 mg, 0.948 mmol, 95% yield). LC-MS (Method 1): $t_R$=3.33 min, m/z (M+H)$^+$=312.

STEP 2: Synthesis of 6-Methoxy-4-(4-methyl-1H-pyrazol-1-yl)quinoline-3-carboxylic acid. To a solution of ethyl 6-methoxy-4-(4-methyl-1H-pyrazol-1-yl)quinoline-3-carboxylate (295 mg, 0.948 mmol) in THF (2 ml)/MeOH (0.5 ml) was added NaOH$_{(aq)}$ (1N in $H_2O$, 2 mL, 2 mmol). The mixture was heated to 50° C. and stirred for 3 h. After cooling to rt, 1N HCl$_{(aq)}$ (2 mL) was added until the pH of aqueous layer is ca. 5. Then, hexane (5 mL) was added and the solid was filtered, washed with ice-water (1 mL×3), and dried to give 6-methoxy-4-(4-methyl-1H-pyrazol-1-yl)quinoline-3-carboxylic acid (164 mg, 0.579 mmol, 61.1% yield) as a pale yellow solid. LC-MS (Method 1): $t_R$=2.81 min, m/z (M+H)$^+$=284.

STEP 3: Synthesis of (4-(Cyclopropanecarbonyl)piperazin-1-yl)(6-methoxy-4-(4-methyl-1H-pyrazol-1-yl)quinolin-3-yl)methanone, TFA. To a mixture of 6-methoxy-4-(4-methyl-1H-pyrazol-1-yl)quinoline-3-carboxylic acid (28.3 mg, 0.1 mmol), cyclopropyl(piperazin-1-yl)methanone, HCl (28.6 mg, 0.150 mmol), and HATU (76 mg, 0.20 mmol) was added DMF (1 ml) and then Hunig's base (0.105 ml, 0.60 mmol). The mixture was stirred at rt for 1 h. The mixture was filtered through filter and submitted for purification by semi-preparative HPLC to give (4-(cyclopropanecarbonyl)piperazin-1-yl)(6-methoxy-4-(4-methyl-1H-pyrazol-1-yl)quinolin-3-yl)methanone, TFA (26.1 mg, 0.049 mmol, 48.9% yield). $^1$H NMR (400 MHz, DMSO-d$_6$) δ 8.75 (s, 1H), 8.08 (d, J=9.2 Hz, 1H), 7.92 (s, 1H), 7.76 (s, 1H), 7.56 (dd, J=9.2, 2.7 Hz, 1H), 7.20 (d, J=2.8 Hz, 1H), 3.81 (s, 3H), 3.73-2.80 (m, 8H), 2.14 (s, 3H), 2.05-1.71 (m, 1H), 0.71 (t, J=3.4 Hz, 4H); LC-MS (Method 2): $t_R$=4.25 min, m/z (M+H)$^+$=420; HRMS calculated for $C_{23}H_{26}N_5O_3$ (M+H)$^+$: 420.2030, found: 420.2043.

Example 36. (1,1-dioxidothiomorpholino)(6-methoxy-4-(1,4-dioxa-8-azaspiro[4.5]decan-8-yl)quinolin-3-yl)methanone, TFA (Cpd. 36)

Cpd. 36

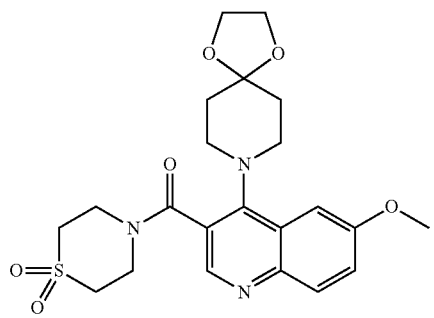

The title compound was prepared following the similar procedure as described in Example 1. $^1$H NMR (400 MHz, DMSO-d$_6$) δ 8.72 (s, 1H), 7.93 (d, J=9.2 Hz, 1H), 7.54 (dd, J=9.2, 2.6 Hz, 1H), 7.32 (d, J=2.8 Hz, 1H), 4.57 (d, J=14.2 Hz, 1H), 3.94 (s, 7H), 3.76-2.96 (m, 11H), 2.05-1.72 (m, 4H); LC-MS (Method 2): $t_R$=3.36 min, m/z (M+H)$^+$=462; HRMS calculated for $C_{22}H_{28}N_3O_6S$ (M+H)$^+$: 462.1693, found: 462.1704.

Example 37. (6-methoxy-4-(1,4-dioxa-8-azaspiro[4.5]decan-8-yl)quinolin-3-yl)(1,4-dioxa-8-azaspiro[4.5]decan-8-yl)methanone, TFA (Cpd. 37)

Cpd. 37

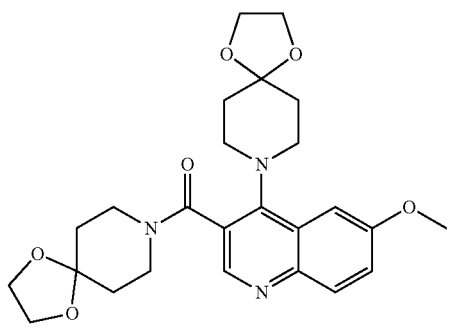

The title compound was prepared following the similar procedure as described in Example 1. $^1$H NMR (400 MHz, DMSO-d$_6$) δ 8.61 (s, 1H), 7.93 (d, J=9.2 Hz, 1H), 7.55 (d, J=9.6 Hz, 1H), 7.33 (d, J=2.7 Hz, 1H), 3.92 (d, J=14.9 Hz, 11H), 3.65-3.11 (m, 8H), 2.05-1.47 (m, 8H); LC-MS (Method 2): $t_R$=3.70 min, m/z (M+H)$^+$=470; HRMS calculated for $C_{25}H_{32}N_3O_6$ (M+H)$^+$: 470.2286, found: 470.2281.

Example 38. 1-(4-(6-methoxy-4-(1,4-dioxa-8-azaspiro[4.5]decan-8-yl)quinoline-3-carbonyl)piperazin-1-yl)ethanone, TFA (Cpd. 38)

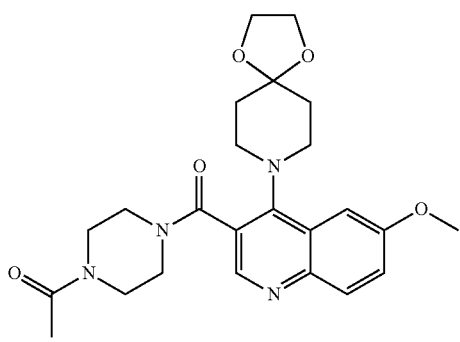

Cpd. 38

The title compound was prepared following the similar procedure as described in Example 1. $^1$H NMR (400 MHz, DMSO-d$_6$) δ 8.61 (s, 1H), 7.94 (d, J=9.2 Hz, 1H), 7.57 (dd, J=9.2, 2.4 Hz, 1H), 7.33 (d, J=2.7 Hz, 1H), 3.94 (d, J=2.2 Hz, 7H), 3.82-3.06 (m, 12H), 2.11-1.74 (m, 7H); LC-MS (Method 2): t$_R$=3.29 min, m/z (M+H)$^+$=455; HRMS calculated for C$_{24}$H$_{31}$N$_4$O$_5$ (M+H)$^+$: 455.2289, found: 455.2304.

Example 39. (6-methoxy-4-(1,4-dioxa-8-azaspiro[4.5]decan-8-yl)quinolin-3-yl)(morpholino)methanone, TFA (Cpd. 39)

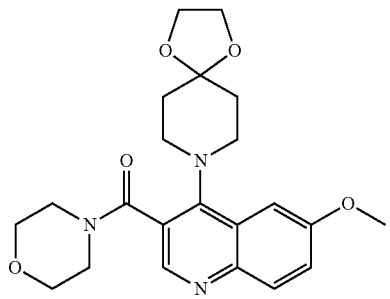

Cpd. 39

The title compound was prepared following the similar procedure as described in Example 1. $^1$H NMR (400 MHz, DMSO-d$_6$) δ 8.55 (s, 1H), 7.92 (d, J=9.1 Hz, 1H), 7.53 (s, 1H), 7.33 (d, J=2.8 Hz, 1H), 3.94 (d, J=3.7 Hz, 7H), 3.80-3.12 (m, 12H), 2.04-1.78 (m, 4H); LC-MS (Method 2): t$_R$=3.39 min, m/z (M+H)$^+$=414; HRMS calculated for C$_{22}$H$_{28}$N$_3$O$_5$ (M+H)$^+$: 414.2023, found: 414.2021.

Example 40. Ethyl 4-(6-methoxy-4-(1,4-dioxa-8-azaspiro[4.5]decan-8-yl)quinoline-3-carbonyl)piperazine-1-carboxylate, TFA (Cpd. 40)

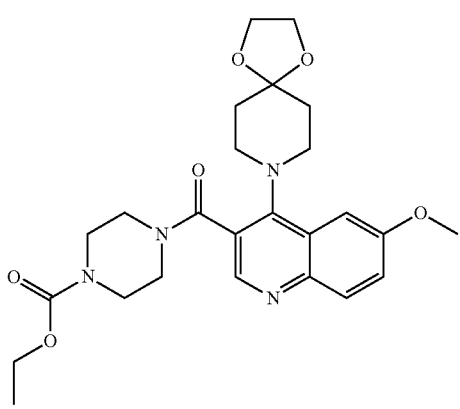

Cpd. 40

The title compound was prepared following the similar procedure as described in Example 1. $^1$H NMR (400 MHz, DMSO-d$_6$) δ 8.60 (s, 1H), 7.94 (d, J=9.2 Hz, 1H), 7.57 (d, J=9.2 Hz, 1H), 7.33 (d, J=2.7 Hz, 1H), 4.06 (q, J=7.1 Hz, 2H), 3.94 (d, J=2.2 Hz, 7H), 3.80-3.10 (m, 12H), 2.04-1.73 (m, 4H), 1.18 (t, J=7.1 Hz, 3H); LC-MS (Method 2): t$_R$=3.81 min, m/z (M+H)$^+$=485; HRMS calculated for C$_{25}$H$_{33}$N$_4$O$_6$ (M+H)$^+$: 485.2395, found: 485.2403.

Example 41. (4-(cyclopropanecarbonyl)piperazin-1-yl)(6-methoxy-4-(1-methyl-1H-pyrazol-4-yl)quinolin-3-yl)methanone, TFA (Cpd. 41)

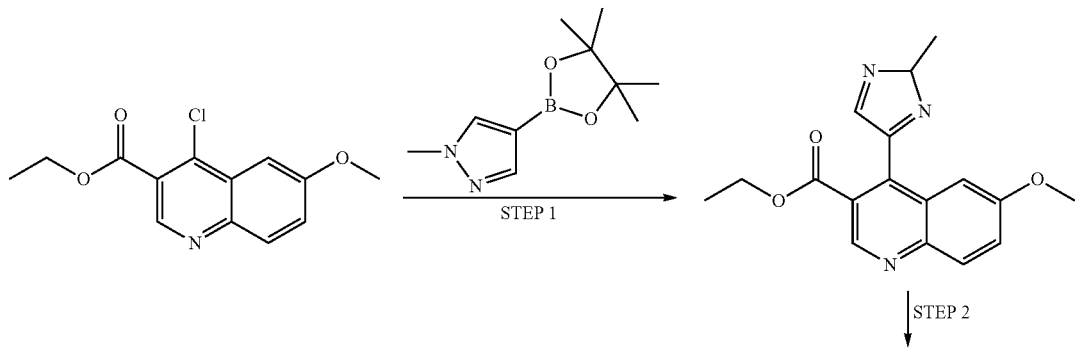

STEP 2

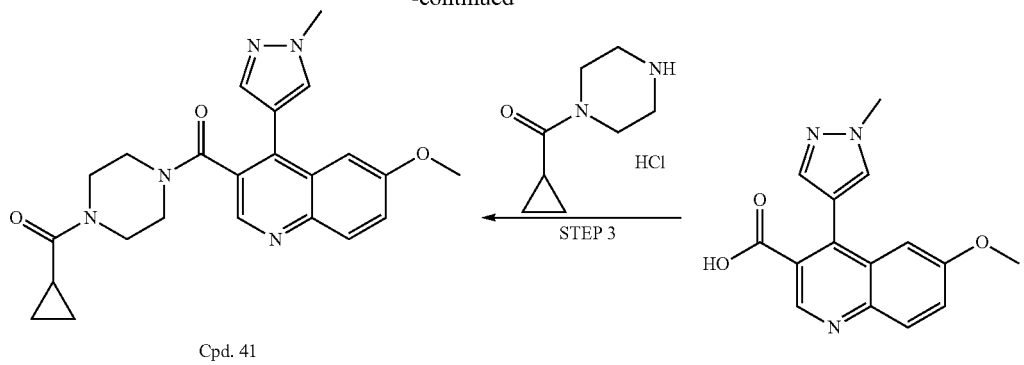

Cpd. 41

STEP 1: Synthesis of Ethyl 6-methoxy-4-(1-methyl-1H-pyrazol-4-yl)quinoline-3-carboxylate. In a microwave tube was placed ethyl 4-chloro-6-methoxyquinoline-3-carboxylate (266 mg, 1 mmol), 1-methyl-4-(4,4,5,5-tetramethyl-1,3,2-dioxaborolan-2-yl)-1H-pyrazole (312 mg, 1.500 mmol), PdCl$_2$(dppf) (73.2 mg, 0.10 mmol), and K$_2$CO$_3$ (622 mg, 4.50 mmol). The tube was sealed. The air was removed and re-filled with N$_2$ (3 times). Then, DMF (3 ml) was added and the mixture was heated (pre-heated oil bath) at 110° C. for 1.5 h. The mixture was poured into EtOAc/H$_2$O (50 mL/50 mL). The organic layer was washed with H$_2$O (50 mL), dried (Na$_2$SO$_4$), and filtered. After removal of solvent, the product was purified by silica gel chromatography using 80-100% EtOAc/hexane as the eluent to give ethyl 6-methoxy-4-(1-methyl-1H-pyrazol-4-yl)quinoline-3-carboxylate (243 mg, 0.781 mmol, 78% yield) as a pale yellow solid. LC-MS (Method 1): $t_R$=2.89 min, m/z (M+H)$^+$=312.

STEP 2: Synthesis of 6-Methoxy-4-(1-methyl-1H-pyrazol-4-yl)quinoline-3-carboxylic acid. To a solution of ethyl 6-methoxy-4-(1-methyl-1H-pyrazol-4-yl)quinoline-3-carboxylate (243 mg, 0.781 mmol) in THF (2 ml)/MeOH (0.5 ml) was added NaOH$_{(aq)}$ (1N in H$_2$O, 1.5 mL, 1.5 mmol). The mixture was heated to 50° C. and stirred for 3 h. After cooling to rt, 1N HCl$_{(aq)}$ (1.5 mL) was added until the pH of aqueous layer is ca. 5. The mixture was concentrated to removal most of solvent. The solid was triturated with small amount of ice-water and dried to give 6-methoxy-4-(1-methyl-1H-pyrazol-4-yl)quinoline-3-carboxylic acid (190 mg, 0.671 mmol, 86% yield) as a brown solid. LC-MS (Method 1): $t_R$=2.37 min, m/z (M+H)$^+$=284.

STEP 3: Synthesis of (4-(Cyclopropanecarbonyl)piperazin-1-yl)(6-methoxy-4-(1-methyl-1H-pyrazol-4-yl)quinolin-3-yl)methanone, TFA. To a mixture of 6-methoxy-4-(1-methyl-1H-pyrazol-4-yl)quinoline-3-carboxylic acid (28.3 mg, 0.1 mmol), cyclopropyl(piperazin-1-yl)methanone, HCl (28.6 mg, 0.150 mmol), and HATU (76 mg, 0.20 mmol) was added DMF (Volume: 1 ml) and then Hunig's base (0.105 ml, 0.60 mmol). The mixture was stirred at rt for 1 h. The mixture was filtered through filter and submitted for purification by semi-preparative HPLC to give (4-(cyclopropanecarbonyl)piperazin-1-yl)(6-methoxy-4-(1-methyl-1H-pyrazol-4-yl)quinolin-3-yl)methanone, TFA (33.8 mg, 0.063 mmol, 63.4% yield). $^1$H NMR (400 MHz, DMSO-d$_6$) δ 8.65 (d, J=2.1 Hz, 1H), 8.05 (s, 1H), 8.01 (d, J=9.1 Hz, 1H), 7.76 (s, 1H), 7.51 (ddd, J=9.1, 2.8, 1.2 Hz, 1H), 7.41 (d, J=2.7 Hz, 1H), 3.96 (s, 3H), 3.86 (s, 3H), 3.81-2.72 (m, 8H), 1.94 (s, 1H), 0.69 (d, J=4.6 Hz, 4H); LC-MS (Method 2): $t_R$=3.40 min, m/z (M+H)$^+$=420; HRMS calculated for C$_{23}$H$_{26}$N$_5$O$_3$ (M+H)$^+$: 420.2030, found: 420.2035.

Example 42. (4-(1,4-dioxa-8-azaspiro[4.5]decan-8-yl)quinolin-3-yl)(4-(cyclopropanecarbonyl)piperazin-1-yl)methanone, TFA (Cpd. 42)

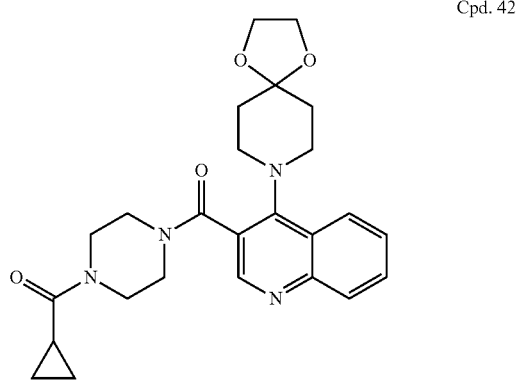 [SMILES: O=C(c1cnc2ccccc2c1N1CCC2(CC1)OCCO2)N1CCN(C(=O)C2CC2)CC1]

Cpd. 42

The title compound was prepared following the similar procedure as described in Example 1. $^1$H NMR (400 MHz, DMSO-d$_6$) δ 8.74 (s, 1H), 8.18 (d, J=8.5 Hz, 1H), 8.00 (d, J=8.3 Hz, 1H), 7.93 (t, J=7.7 Hz, 1H), 7.72 (t, J=7.7 Hz, 1H), 3.95 (d, J=1.6 Hz, 4H), 3.56 (q, J=69.1, 57.6 Hz, 12H), 2.13-1.74 (m, 5H), 0.85-0.64 (m, 4H); LC-MS (Method 2): $t_R$=3.34 min, m/z M+H)$^+$=451; HRMS calculated for C$_{25}$H$_{31}$N$_4$O$_4$ (M+H)$^+$: 451.2340, found: 451.2324.

Example 43. N-ethyl-4-(6-methoxy-4-(1,4-dioxa-8-azaspiro[4.5]decan-8-yl)quinoline-3-carbonyl)piperazine-1-carboxamide, TFA (Cpd. 43)

Cpd. 43

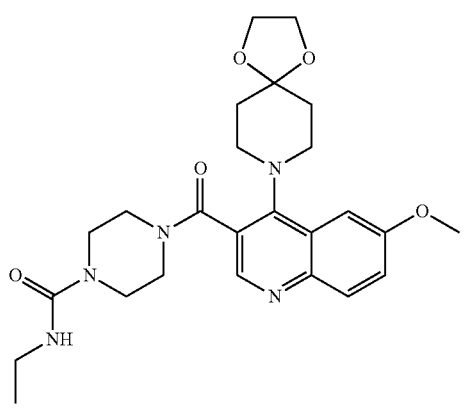

The title compound was prepared following the similar procedure as described in Example 1. $^1$H NMR (400 MHz, DMSO-d$_6$) δ 8.58 (s, 1H), 7.94 (d, J=9.2 Hz, 1H), 7.56 (d, J=9.2 Hz, 1H), 7.33 (d, J=2.8 Hz, 1H), 6.58 (d, J=5.3 Hz, 1H), 3.94 (m, 7H), 3.73-3.12 (m, 12H), 3.04 (dd, J=7.3, 5.2 Hz, 2H), 2.05-1.75 (m, 4H), 1.00 (t, J=7.1 Hz, 3H); LC-MS (Method 2): t$_R$=3.41 min, m/z (M+H)$^+$=484; HRMS calculated for C$_{25}$H$_{34}$N$_5$O$_5$ (M+H)$^+$: 484.2554, found: 484.2552.

Example 44. (4-(cyclopropanecarbonyl)piperazin-1-yl)(4-(4,4-difluoropiperidin-1-yl)-6-methoxyquinolin-3-yl)methanone, TFA (Cpd. 44)

Cpd. 44

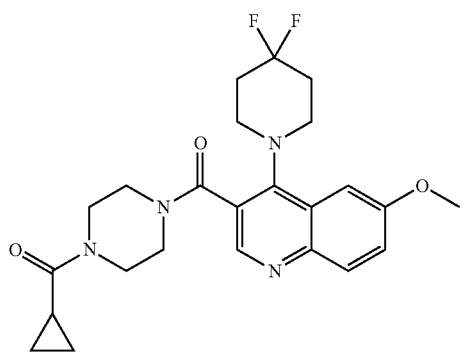

The title compound was prepared following the similar procedure as described in Example 17. $^1$H NMR (400 MHz, DMSO-d$_6$) δ 8.58 (s, 1H), 7.95 (dd, J=9.2, 2.2 Hz, 1H), 7.51 (d, J=9.2 Hz, 1H), 7.35 (d, J=2.7 Hz, 1H), 3.96 (s, 3H), 3.87-3.07 (m, 12H), 2.38-1.84 (m, 5H), 0.74 (d, J=4.5 Hz, 4H); LC-MS (Method 2): t$_R$=3.84 min, m/z (M+H)$^+$=459; HRMS calculated for C$_{24}$H$_{29}$F$_2$N$_4$O$_3$ (M+H)$^+$: 459.2202, found: 459.2179.

Example 45. (6-chloro-4-(1,4-dioxa-8-azaspiro[4.5]decan-8-yl)quinolin-3-yl)(4-(cyclopropanecarbonyl)piperazin-1-yl)methanone, TFA (Cpd. 45)

Cpd. 45

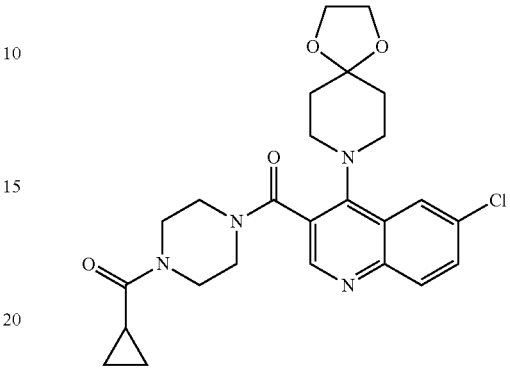

The title compound was prepared following the similar procedure as described in Example 1. $^1$H NMR (400 MHz, DMSO-d$_6$) δ 8.64 (s, 1H), 8.04 (d, J=2.3 Hz, 1H), 8.00 (d, J=9.0 Hz, 1H), 7.83 (dd, J=8.9, 2.2 Hz, 1H), 3.98-3.89 (m, 4H), 3.88-3.07 (m, 12H), 2.07-1.74 (m, 5H), 0.74 (dd, J=4.7, 2.8 Hz, 4H); LC-MS (Method 2): t$_R$=3.78 min, m/z (M+H)$^+$=485; HRMS calculated for C$_{25}$H$_{30}$ClN$_4$O$_4$ (M+H)$^+$: 485.1950, found: 485.1938.

Example 46. (4-(cyclopropanecarbonyl)piperazin-1-yl)(6-methoxy-4-(6-azaspiro[2.5]octan-6-yl)quinolin-3-yl)methanone, TFA (Cpd. 46)

Cpd. 46

The title compound was prepared following the similar procedure as described in Example 17. $^1$H NMR (400 MHz, DMSO-d$_6$) δ 8.62 (s, 1H), 7.94 (d, J=9.3 Hz, 1H), 7.58 (d, J=9.3 Hz, 1H), 7.39 (d, J=2.8 Hz, 1H), 3.94 (s, 3H), 3.88-3.10 (m, 12H), 1.97 (d, J=31.5 Hz, 1H), 1.63 (d, J=36.5 Hz, 4H), 0.74 (d, J=4.5 Hz, 4H), 0.41 (d, J=2.5 Hz, 4H); LC-MS (Method 2): t$_R$=4.10 min, m/z (M+H)$^+$=449; HRMS calculated for C$_{26}$H$_{33}$N$_4$O$_3$ (M+H)$^+$: 449.2547, found: 449.2548.

Example 47. (4-(cyclopropanecarbonyl)piperazin-1-yl)(7-methoxy-4-(1,4-dioxa-8-azaspiro[4.5]decan-8-yl)quinolin-3-yl)methanone, TFA (Cpd. 47)

Cpd. 47

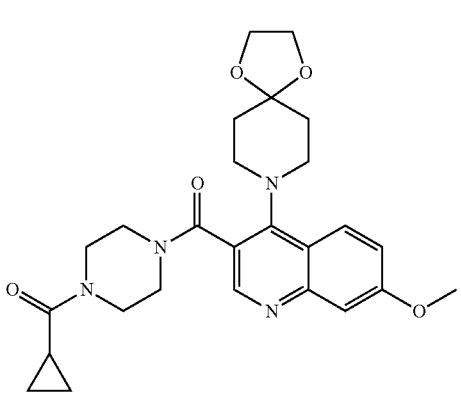

The title compound was prepared following the similar procedure as described in Example 1. $^1$H NMR (400 MHz, DMSO-d$_6$) δ 8.69 (s, 1H), 8.10 (d, J=9.3 Hz, 1H), 7.41-7.28 (m, 2H), 3.99-3.90 (m, 7H), 3.89-3.24 (m, 12H), 1.91 (dddd, J=76.2, 12.4, 7.3, 3.6 Hz, 5H), 0.84-0.60 (m, 4H); LC-MS (Method 2): t$_R$=3.54 min, m/z (M+H)$^+$=481; HRMS calculated for C$_{26}$H$_{33}$N$_4$O$_5$ (M+H)$^+$: 481.2445, found: 481.2459.

Example 48. (4-(cyclopropanecarbonyl)piperazin-1-yl)(6,7-dimethoxy-4-(1,4-dioxa-8-azaspiro[4.5]decan-8-yl)quinolin-3-yl)methanone, TFA (Cpd. 48)

Cpd. 48

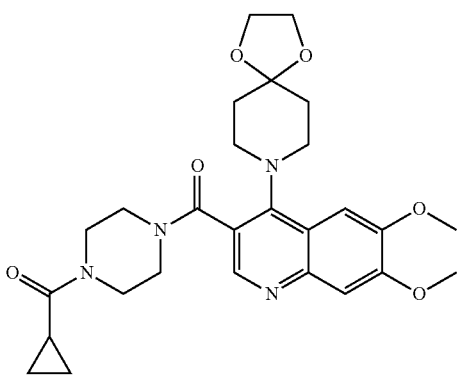

The title compound was prepared following the similar procedure as described in Example 1. $^1$H NMR (400 MHz, DMSO-d$_6$) δ 8.59 (s, 1H), 7.35 (s, 1H), 7.27 (s, 1H), 3.97 (s, 7H), 3.94 (s, 3H), 3.53 (m, 12H), 2.09-1.80 (m, 5H), 0.74 (d, J=4.6 Hz, 4H); LC-MS (Method 2): t$_R$=3.56 min, m/z (M+H)$^+$=511; HRMS calculated for C$_{27}$H$_{35}$N$_4$O$_6$ (M+H)$^+$: 511.2551, found: 511.2537.

Example 49. 1-(4-(6-fluoro-4-(1,4-dioxa-8-azaspiro[4.5]decan-8-yl)quinoline-3-carbonyl)piperazin-1-yl)-2-methylpropan-1-one, TFA (Cpd. 49)

Cpd. 49

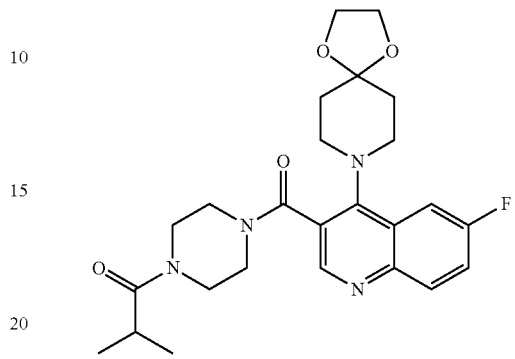

The title compound was prepared following the similar procedure as described in Example 1. $^1$H NMR (400 MHz, DMSO-d$_6$) δ 8.64 (s, 1H), 8.06 (dd, J=9.4, 5.4 Hz, 1H), 7.76 (d, J=9.5 Hz, 2H), 3.93 (s, 4H), 3.81-2.75 (m, 13H), 2.03-1.73 (m, 4H), 1.08-0.87 (m, 6H); LC-MS (Method 2): t$_R$=3.67 min, m/z (M+H)$^+$=471; HRMS calculated for C$_{25}$H$_{32}$FN$_4$O$_4$ (M+H)$^+$: 471.2402, found: 471.2417.

Example 50. (4,4-difluoropiperidin-1-yl)(6-fluoro-4-(1,4-dioxa-8-azaspiro[4.5]decan-8-yl)quinolin-3-yl)methanone, TFA (Cpd. 50)

Cpd. 50

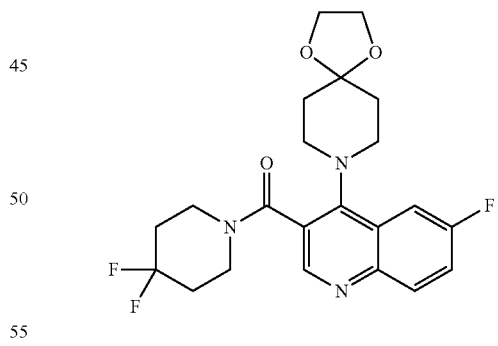

The title compound was prepared following the similar procedure as described in Example 1. $^1$H NMR (400 MHz, DMSO-d$_6$) δ 8.74-8.65 (m, 1H), 8.10-8.00 (m, 1H), 7.76 (d, J=9.9 Hz, 2H), 4.13-3.99 (m, 1H), 3.98-3.84 (m, 4H), 3.65-3.06 (m, 7H), 2.27-1.67 (m, 8H); LC-MS (Method 2): t$_R$=3.94 min, m/z (M+H)$^+$=436; HRMS calculated for C$_{22}$H$_{24}$F$_3$N$_{33}$O$_3$Na (M+Na)$^+$: 458.1662, found: 458.1667.

Example 51. 1-(4-(6-fluoro-4-(1,4-dioxa-8-azaspiro[4.5]decan-8-yl)quinoline-3-carbonyl)piperazin-1-yl)ethanone, TFA (Cpd. 51)

Cpd. 51

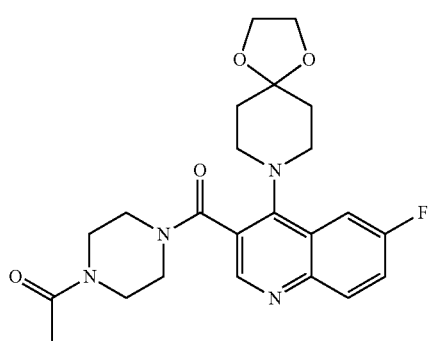

The title compound was prepared following the similar procedure as described in Example 1. $^1$H NMR (400 MHz, DMSO-d$_6$) δ 8.65 (d, J=2.7 Hz, 1H), 8.06 (dd, J=9.4, 5.4 Hz, 1H), 7.82-7.71 (m, 2H), 3.93 (s, 4H), 3.83-3.06 (m, 12H), 2.02 (s, 3H, 2 peaks due to rotamer of amide bond), 1.97-1.72 (m, 4H); LC-MS (Method 2): t$_R$=3.29 min, m/z (M+H)$^+$=443; HRMS calculated for C$_{23}$H$_{28}$FN$_4$O$_4$ (M+H)$^+$: 443.2089, found: 443.2095.

Example 52. (6-fluoro-4-(1,4-dioxa-8-azaspiro[4.5]decan-8-yl)quinolin-3-yl)(4-(methylsulfonyl)piperazin-1-yl)methanone, TFA (Cpd. 52)

Cpd. 52

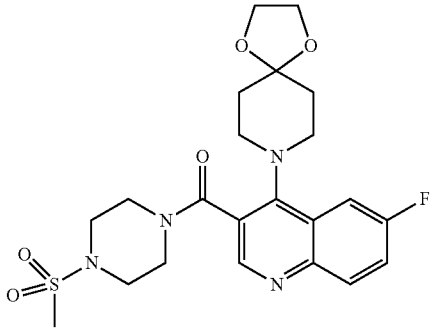

The title compound was prepared following the similar procedure as described in Example 1. $^1$H NMR (400 MHz, DMSO-d$_6$) δ 8.63 (d, J=3.6 Hz, 1H), 8.06 (dd, J=10.0, 5.4 Hz, 1H), 7.81-7.70 (m, 2H), 3.93 (m, 5H), 3.72-3.04 (m, 11H), 2.92 (s, 3H), 2.03-1.70 (m, 4H); LC-MS (Method 2): t$_R$=3.51 min, m/z (M+H)$^+$=479; HRMS calculated for C$_{22}$H$_{28}$FN$_4$O$_5$S (M+H)$^+$: 479.1759, found: 479.1772.

Example 53. (1,1-dioxidothiomorpholino)(6-fluoro-4-(1,4-dioxa-8-azaspiro[4.5]decan-8-yl)quinolin-3-yl)methanone, TFA (Cpd. 53)

Cpd. 53

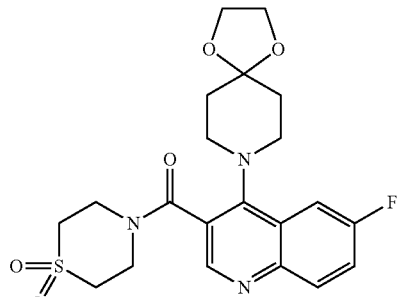

The title compound was prepared following the similar procedure as described in Example 1. $^1$H NMR (400 MHz, DMSO-d$_6$) δ 8.78 (s, 1H), 8.11-8.01 (m, 1H), 7.75 (dd, J=9.6, 7.1 Hz, 2H), 4.58 (d, J=14.4 Hz, 1H), 3.99-3.84 (m, 6H), 3.64 (m, 2H), 3.41 (m, 5H), 3.30-3.19 (m, 1H), 3.17-2.97 (m, 1H), 2.03-1.66 (m, 4H); LC-MS (Method 2): t$_R$=3.35 min, m/z (M+H)$^+$=450; HRMS calculated for C$_{21}$H$_{25}$FN$_3$O$_5$S (M+H)$^+$: 450.1493, found: 450.1507.

Example 54. Ethyl 4-(6-fluoro-4-(1,4-dioxa-8-azaspiro[4.5]decan-8-yl)quinoline-3-carbonyl)piperazine-1-carboxylate, TFA (Cpd. 54)

Cpd. 54

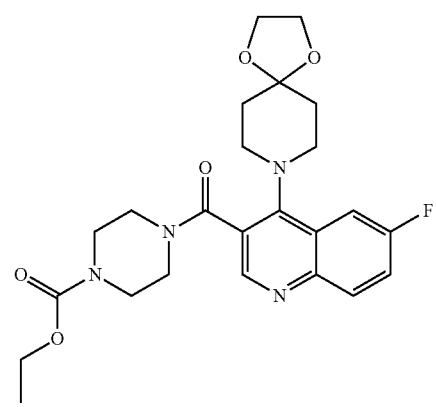

The title compound was prepared following the similar procedure as described in Example 1. $^1$H NMR (400 MHz, DMSO-d$_6$) δ 8.63 (s, 1H), 8.09-8.01 (m, 1H), 7.76 (d, J=9.6 Hz, 2H), 4.05 (q, J=7.1 Hz, 2H), 3.93 (q, J=2.5 Hz, 4H), 3.79-3.55 (m, 2H), 3.56-3.28 (m, 8H), 3.15 (d, J=9.4 Hz, 2H), 2.04-1.71 (m, 4H), 1.18 (t, J=7.1 Hz, 3H); LC-MS (Method 2): t$_R$=3.78 min, m/z (M+H)$^+$=473; HRMS calculated for C$_{24}$H$_{30}$FN$_4$O$_5$ (M+H)$^+$: 473.2195, found: 473.2199.

Example 55. ((2S*,6R*)-2,6-dimethylmorpholino)(6-fluoro-4-(1,4-dioxa-8-azaspiro[4.5]decan-8-yl)quinolin-3-yl)methanone, TFA (Cpd. 55)

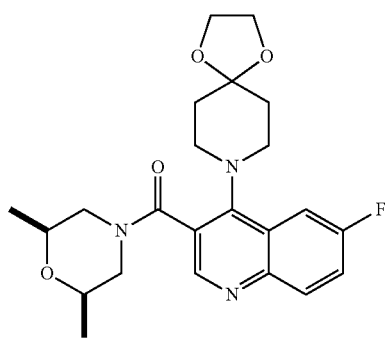

Cpd. 55

The title compound was prepared following the similar procedure as described in Example 1. $^1$H NMR (400 MHz, DMSO-d6) δ 8.60 (d, J=10.6 Hz, 1H), 8.06 (dd, J=9.9, 5.3 Hz, 1H), 7.75 (t, J=8.6 Hz, 2H), 4.56-4.31 (m, 1H), 3.94 (d, J=3.5 Hz, 4H), 3.79-2.38 (m, 9H), 2.06-1.74 (m, 4H), 1.17 (dd, J=6.2, 4.6 Hz, 3H), 0.97 (dd, J=6.2, 1.4 Hz, 3H); LC-MS (Method 2): $t_R$=3.79 min, m/z (M+H)$^+$=430; HRMS calculated for $C_{23}H_{29}FN_3O_4$ (M+H)$^+$: 430.2137, found: 430.2125.

Example 56. N-ethyl-4-(6-fluoro-4-(1,4-dioxa-8-azaspiro[4.5]decan-8-yl)quinoline-3-carbonyl)piperazine-1-carboxamide, TFA (Cpd. 56)

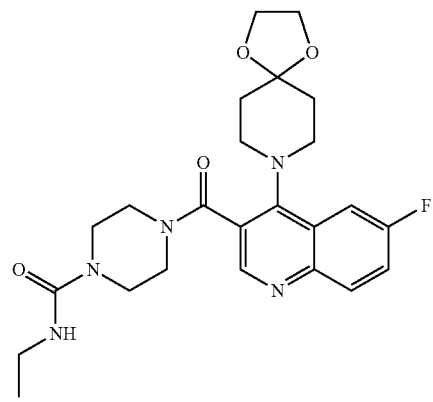

Cpd. 56

The title compound was prepared following the similar procedure as described in Example 1. $^1$H NMR (400 MHz, DMSO-d6) δ 8.62 (s, 1H), 8.11-8.01 (m, 1H), 7.77 (dd, J=9.5, 7.1 Hz, 2H), 6.58 (s, 1H), 3.93 (q, J=2.5 Hz, 4H), 3.73-2.96 (m, 4H), 2.04-1.71 (m, 4H), 1.00 (t, J=7.1 Hz, 3H); LC-MS (Method 2): $t_R$=3.38 min, m/z (M+H)$^+$=472; HRMS calculated for $C_{24}H_{31}FN_5O_4$ (M+H)$^+$: 472.23557, found: 472.2346.

Example 57. Cyclopropyl(4-((6-methoxy-4-(1,4-dioxa-8-azaspiro[4.5]decan-8-yl)quinolin-3-yl)methyl)piperazin-1-yl)methanone, TFA (Cpd. 57)

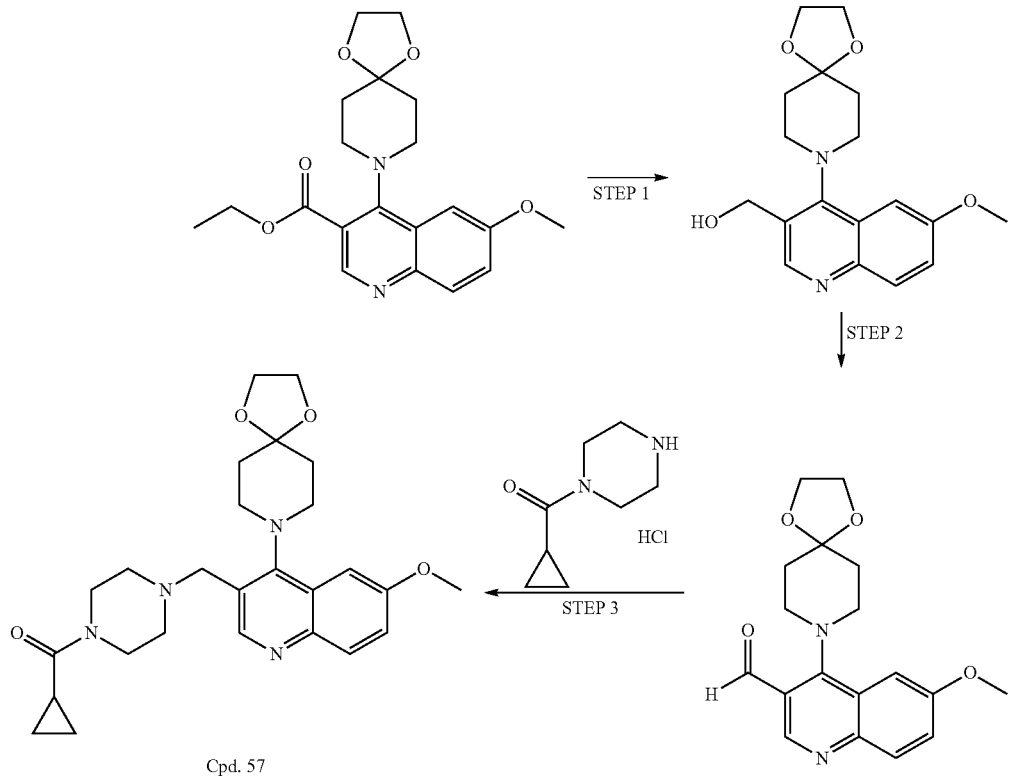

Cpd. 57

STEP 1: Synthesis of (6-Methoxy-4-(1,4-dioxa-8-azaspiro[4.5]decan-8-yl)quinolin-3-yl)methanol. In a microwave vail was placed ethyl 6-methoxy-4-(1,4-dioxa-8-azaspiro[4.5]decan-8-yl)quinoline-3-carboxylate (149 mg, 0.4 mmol). The vail was sealed and the air was removed and refilled with $N_2$. Then, $LiBH_4$ (87 mg, 4.0 mmol) (2M in THF, 2 mL, 4 mmol) was added. The mixture was heated at 60° C. for 3 h. After cooling to rt, the mixture was poured into $EtOAc/H_2O$ (5 mL/5 mL). The aqueous layer was extracted with EtOAc (5 mL×2). The combined organic layer was dried ($Na_2SO_4$) and filtered. After removal of solvent, the product was purified by silica gel chromatography using 0-10% MeOH/EtOAc as the eluent to give (6-methoxy-4-(1,4-dioxa-8-azaspiro[4.5]decan-8-yl)quinolin-3-yl)methanol (54 mg, 0.163 mmol, 40.9% yield). LC-MS (Method 1): $t_R$=2.61 min, m/z (M+H)$^+$=331.

STEP 2: Synthesis of 6-Methoxy-4-(1,4-dioxa-8-azaspiro[4.5]decan-8-yl)quinoline-3-carbaldehyde. To a solution of (6-methoxy-4-(1,4-dioxa-8-azaspiro[4.5]decan-8-yl)quinolin-3-yl)methanol (54 mg, 0.163 mmol) in $CH_2Cl_2$ (2 ml) was added Dess-Martin periodinane (139 mg, 0.327 mmol). The mixture was stirred at rt for 2 h. The mixture was concentrated and the residue was purified by silica gel chromatography using 50-80% EtOAc/hexane as the eluent to give 6-methoxy-4-(1,4-dioxa-8-azaspiro[4.5]decan-8-yl)quinoline-3-carbaldehyde (23 mg, 0.070 mmol, 42.9% yield). LC-MS (Method 1): $t_R$=2.55 min, m/z (M+H)$^+$=329.

STEP 3: Synthesis of Cyclopropyl(4-((6-methoxy-4-(1,4-dioxa-8-azaspiro[4.5]decan-8-yl)quinolin-3-yl)methyl)piperazin-1-yl)methanone, TFA. To 6-methoxy-4-(1,4-dioxa-8-azaspiro[4.5]decan-8-yl)quinoline-3-carbaldehyde (23 mg, 0.07 mmol) and cyclopropyl(piperazin-1-yl)methanone, HCl (26.7 mg, 0.14 mmol) was added $CH_2Cl_2$ (1 ml) and then $Et_3N$ (0.06 ml, 0.42 mmol). The mixture was stirred for 3-5 min and sodium triacetoxyborohydride (29.7 mg, 0.14 mmol) was added. The mixture was stirred at rt for 4 h. The mixture was concentrated, re-dissolved in MeOH, filtered through a filter, and submitted for purification by semi-preparative HPLC to give cyclopropyl(4-((6-methoxy-4-(1,4-dioxa-8-azaspiro[4.5]decan-8-yl)quinolin-3-yl)methyl)piperazin-1-yl)methanone, TFA (11.4 mg, 0.020 mmol, 28.0% yield). $^1$H NMR (400 MHz, DMSO-d$_6$) δ 8.73 (br s, 1H), 7.97 (d, J=9.2 Hz, 1H), 7.61 (br s, 1H), 7.38 (d, J=2.7 Hz, 1H), 4.50 (br s, 2H), 3.97 (s, 4H), 3.95 (s, 3H), 3.90-3.15 (m, 12H), 1.93 (s, 5H), 0.71 (br s, 4H); LC-MS (Method 2): $t_R$=3.63 min, m/z (M+H)$^+$=467; HRMS calculated for $C_{26}H_{35}N_4O_4$ (M+H)$^+$: 467.2653, found: 467.2671.

Example 58. (6-fluoro-4-(1,4-dioxa-8-azaspiro[4.5]decan-8-yl)quinolin-3-yl)(morpholino)methanone, TFA (Cpd. 58)

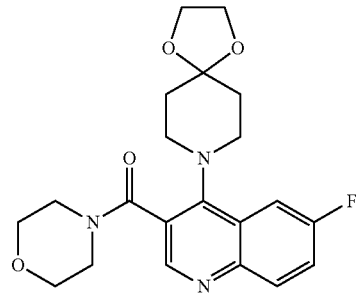

Cpd. 58

The title compound was prepared following the similar procedure as described in Example 1. $^1$H NMR (400 MHz, DMSO-d$_6$) δ 8.61 (s, 1H), 8.10-8.01 (m, 1H), 7.76 (t, J=8.6 Hz, 2H), 3.93 (q, J=2.6 Hz, 4H), 3.79-3.10 (m, 12H), 2.03-1.69 (m, 4H); LC-MS (Method 2): $t_R$=3.32 min, m/z (M+H)$^+$=402; HRMS calculated for $C_{21}H_{25}FN_3O_4$ (M+H)$^+$: 402.1824, found: 402.1833.

Example 59. (4-(cyclopropanecarbonyl)piperazin-1-yl)(6-fluoro-4-(6-azaspiro[2.5]octan-6-yl)quinolin-3-yl)methanone, TFA (Cpd. 59)

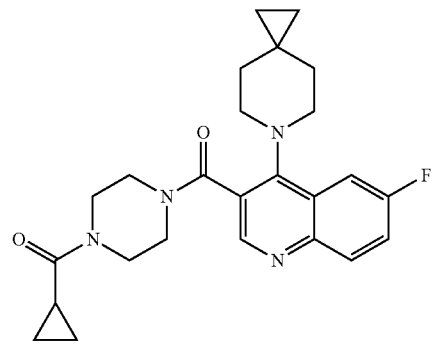

Cpd. 59

The title compound was prepared following the similar procedure as described in Example 17. $^1$H NMR (400 MHz, DMSO-d$_6$) δ 8.64 (s, 1H), 8.06 (dd, J=10.0, 5.5 Hz, 1H), 7.78 (d, J=9.5 Hz, 2H), 4.40-3.01 (m, 12H), 1.97 (m, 1H), 1.59 (m, 4H), 0.73 (d, J=4.6 Hz, 4H), 0.38 (br s, 4H); LC-MS (Method 2): $t_R$=4.16 min, m/z (M+H)$^+$=437; HRMS calculated for $C_{25}H_{29}FN_4O_2Na$ (M+Na)$^+$: 459.2167, found: 459.2182.

Example 60. (4-(cyclopropanecarbonyl)piperazin-1-yl)(44(2S*,6R*)-2,6-dimethylmorpholino)-6-fluoroquinolin-3-yl)methanone, TFA (Cpd. 60)

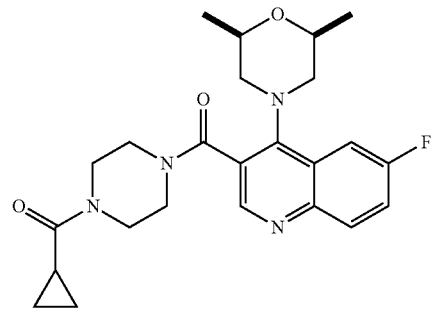

Cpd. 60

The title compound was prepared following the similar procedure as described in Example 17. $^1$H NMR (400 MHz, DMSO-d$_6$) δ 8.65 (s, 1H), 8.07 (dd, J=9.2, 5.3 Hz, 1H), 7.86-7.68 (m, 2H), 4.09-2.61 (m, 14H), 1.97 (m, 1H), 1.09 (t, J=6.7 Hz, 6H), 0.74 (d, J=4.5 Hz, 4H); LC-MS (Method 2): $t_R$=3.72 min, m/z (M+H)$^+$=441; HRMS calculated for $C_{24}H_{30}FN_4O_3$ (M+H)$^+$: 441.2296, found: 441.2289.

Example 61. (4-(cyclopropanecarbonyl)piperazin-1-yl)(6-fluoro-4-(4-methoxy-4-methylpiperidin-1-yl)quinolin-3-yl)methanone, TFA (Cpd. 61)

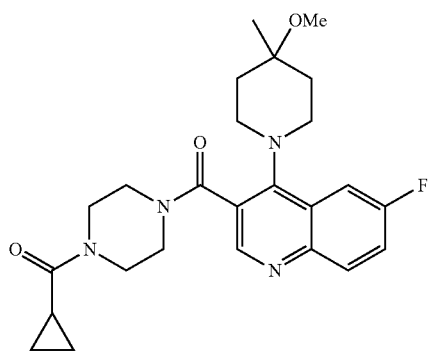

Cpd. 61

The title compound was prepared following the similar procedure as described in Example 17. $^1$H NMR (400 MHz, DMSO-$d_6$) δ 8.63 (d, J=5.1 Hz, 1H), 8.05 (dd, J=9.2, 5.4 Hz, 1H), 7.77 (tt, J=7.5, 4.9 Hz, 2H), 3.98-3.18 (m, 12H), 3.14 (s, 3H), 2.08-1.60 (m, 5H), 1.19 (s, 3H), 0.82-0.59 (m, 4H); LC-MS (Method 2): $t_R$=3.77 min, m/z (M+H)$^+$=455; HRMS calculated for $C_{25}H_{32}FN_4O_3$ (M+H)$^+$: 455.2453, found: 455.2445.

Example 62. (4-(cyclopropanecarbonyl)piperazin-1-yl)(6-fluoro-4-(8-azaspiro[4.5]decan-8-yl)quinolin-3-yl)methanone, TFA (Cpd. 62)

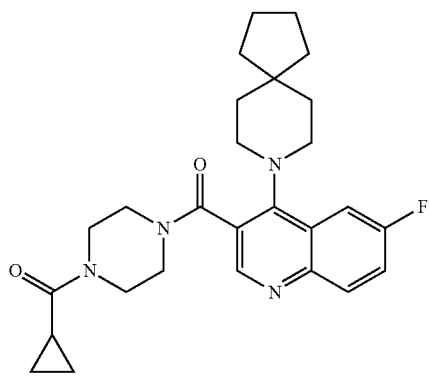

Cpd. 62

The title compound was prepared following the similar procedure as described in Example 17. $^1$H NMR (400 MHz, DMSO-$d_6$) δ 8.63 (s, 1H), 8.05 (dd, J=9.1, 5.4 Hz, 1H), 7.77 (t, J=8.8 Hz, 2H), 4.02-2.81 (m, 12H), 2.11-0.97 (m, 13H), 0.74 (d, J=4.6 Hz, 4H); LC-MS (Method 2): $t_R$=4.65 min, m/z (M+H)$^+$=465; HRMS calculated for $C_{27}H_{34}FN_4O_2$ (M+H)$^+$: 465.2660, found: 465.2645.

Example 63. (4-(cyclopropanecarbonyl)piperazin-1-yl)(4-(4,4-difluoropiperidin-1-yl)-6-fluoroquinolin-3-yl)methanone, TFA (Cpd. 63)

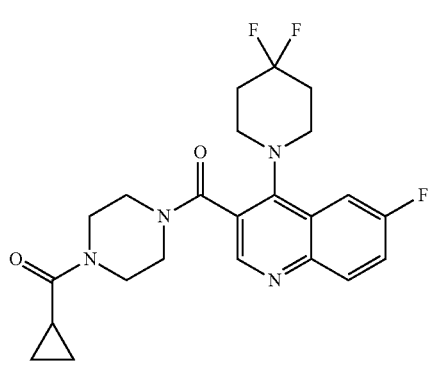

Cpd. 63

The title compound was prepared following the similar procedure as described in Example 17. $^1$H NMR (400 MHz, DMSO-$d_6$) δ 8.64 (s, 1H), 8.08 (dd, J=9.2, 5.5 Hz, 1H), 7.83 (dd, J=10.4, 2.8 Hz, 1H), 7.73 (t, J=8.8 Hz, 1H), 4.36-2.98 (m, 12H), 2.42-1.71 (m, 5H), 0.74 (d, J=4.6 Hz, 4H); LC-MS (Method 2): $t_R$=3.96 min, m/z (M+H)$^+$=447; HRMS calculated for $C_{23}H_{26}F_3N_4O_2$ (M+H)$^+$: 447.2002, found: 447.2024.

Example 64. 1-(3-(4-(cyclopropanecarbonyl)piperazine-1-carbonyl)-6-fluoroquinolin-4-yl)-4-methylpiperidine-4-carbonitrile, TFA (Cpd. 64)

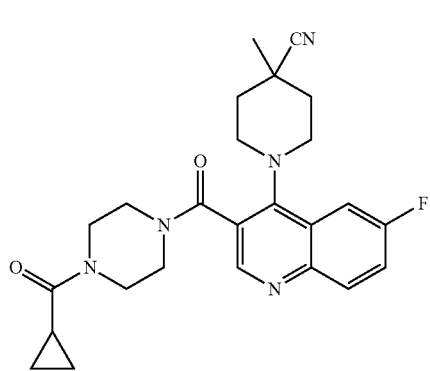

Cpd. 64

The title compound was prepared following the similar procedure as described in Example 17. $^1$H NMR (400 MHz, DMSO-$d_6$) δ 8.69-8.58 (m, 1H), 8.07 (dd, J=10.3, 5.5 Hz, 1H), 7.81-7.66 (m, 2H), 4.14-2.97 (m, 12H), 2.15-1.71 (m, 5H), 1.45 (s, 3H), 0.74 (d, J=4.7 Hz, 4H); LC-MS (Method 2): $t_R$=3.74 min, m/z (M+H)$^+$=450; HRMS calculated for $C_{25}H_{29}FN_5O_2$(M+H)$^+$: 450.2300, found: 450.2313.

Example 65. (4-(cyclopropanecarbonyl)piperazin-1-yl)(4-(4,4-dimethylpiperidin-1-yl)-6-fluoroquinolin-3-yl)methanone, TFA (Cpd. 65)

Example 67. 1-(3-(4-(cyclopropanecareonyl)piperazine-1-carbonyl)-6-methoxyquinolin-4-yl)piperidin-4-one (Cpd. 67)

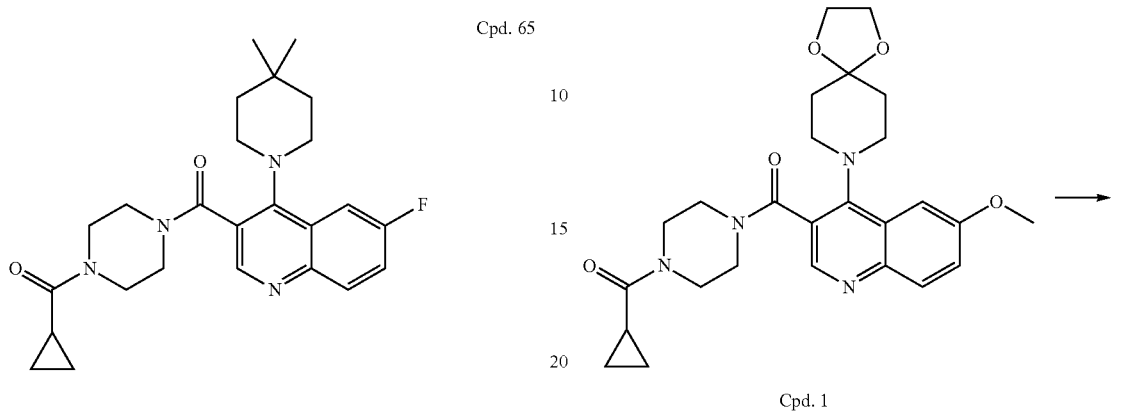

The title compound was prepared following the similar procedure as described in Example 17. $^1$H NMR (400 MHz, DMSO-d$_6$) δ 8.63 (s, 1H), 8.05 (dd, J=9.2, 5.4 Hz, 1H), 7.76 (t, J=8.7 Hz, 2H), 4.35-3.03 (m, 12H), 2.13-1.17 (m, 5H), 1.01 (s, 6H), 0.74 (d, J=4.6 Hz, 4H); LC-MS (Method 2): t$_R$=4.29 min, m/z (M+H)$^+$=439; HRMS calculated for C$_{25}$H$_{32}$FN$_4$O$_2$ (M+H)$^+$: 439.2504, found: 439.2516.

Example 66. (4-(cyclopropanecarbonyl)piperazin-1-yl)(6-fluoro-4-(1-oxa-8-azaspiro[4.5]decan-8-yl)quinolin-3-yl)methanone, TFA (Cpd. 66)

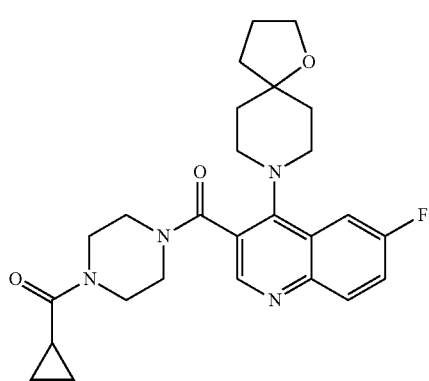

The title compound was prepared following the similar procedure as described in Example 17. $^1$H NMR (400 MHz, DMSO-d6) δ 8.64 (s, 1H), 8.05 (dd, J=9.1, 5.4 Hz, 1H), 7.83-7.69 (m, 2H), 4.34-2.96 (m, 14H), 2.09-1.57 (m, 9H), 0.74 (d, J=4.5 Hz, 4H); LC-MS (Method 2): t$_R$=3.82 min, m/z (M+H)$^+$=467; HRMS calculated for C$_{26}$H$_{32}$FN$_4$O$_3$ (M+H)$^+$: 467.2453, found: 467.2447.

To a microwave tube was placed (4-(cyclopropanecarbonyl)piperazin-1-yl)(6-methoxy-4-(1,4-dioxa-8-azaspiro[4.5]decan-8-yl)quinolin-3-yl)methanone (90 mg, 0.187 mmol) and p-toluenesulfonic acid-mono-hydrate (35.6 mg, 0.187 mmol). Then, Acetone (5 ml) and Water (0.5 ml) were added. The tube was sealed and heated at 55° C. for 48 h. K$_2$CO$_3$ (276 mg, 2 mmol) was added and stirred for 15 min. The mixture was filtered through a filter and the filtrate was concentrated. After removal of solvent, the product was dissolved in CH$_2$Cl$_2$, dried (Na$_2$SO$_4$), and filtered. After removal of solvent, the product was dissolved in DMF (2 mL), filtered through a filter and then submitted for purification by semi-preparative HPLC under basic condition to give 1-(3-(4-(cyclopropanecarbonyl)piperazine-1-carbonyl)-6-methoxyquinolin-4-yl)piperidin-4-one (11 mg, 0.025 mmol, 13.46% yield). $^1$H NMR (400 MHz, DMSO-d$_6$) δ 8.46 (s, 1H), 7.92 (d, J=9.0 Hz, 1H), 7.51-7.39 (m, 2H), 3.94 (s, 3H), 3.90-3.21 (m, 12H), 2.65-2.50 (m, 4H), 1.95 (m, 1H), 0.80-0.58 (m, 4H); LC-MS (Method 2): t$_R$=3.14 min, m/z (M+H)$^+$=437, HRMS calculated for C$_{24}$H$_{29}$N$_4$O$_4$ (M+H)$^+$: 437.2183, found: 437.2185.

Example 68. (4-(cyclopropanecarbonyl)piperazin-1-yl)(6-fluoro-4-(2-oxa-7-azaspiro[3.5]nonan-7-yl)quinolin-3-yl)methanone (Cpd. 68)

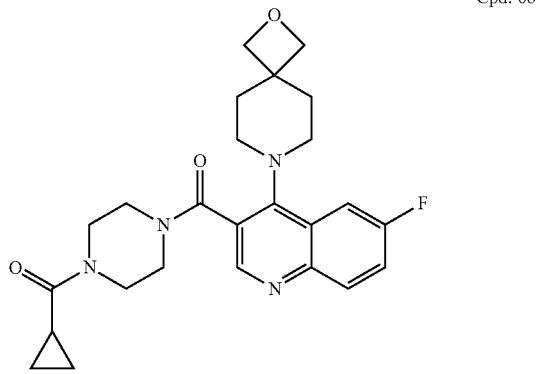

The title compound was prepared following the similar procedure as described in Example 17. ¹H NMR (400 MHz, DMSO-d₆) δ 8.53 (s, 1H), 8.09-7.99 (m, 1H), 7.73-7.62 (m, 2H), 4.43-4.30 (m, 4H), 3.30 (m, 8H), 3.13 (d, J=8.8 Hz, 2H), 2.90 (d, J=8.4 Hz, 2H), 2.15-1.83 (m, 5H), 0.74 (dd, J=4.8, 2.9 Hz, 4H); LC-MS (Method 2): $t_R$=3.31 min, m/z (M+H)⁺=453, HRMS calculated for $C_{25}H_{30}FN_4O_3$ (M+H)⁺: 453.2296, found: 453.2300.

Example 69. (4-(cyclopropanecarbonyl)-1,4-diazepan-1-yl)(6-fluoro-4-(1,4-dioxa-8-azaspiro[4.5]decan-8-yl)quinolin-3-yl)methanone, TFA (Cpd. 69)

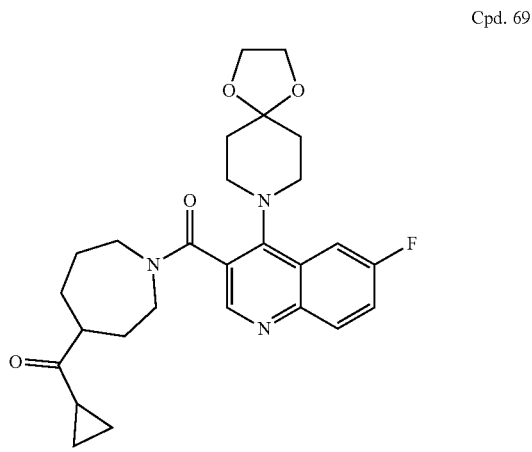 [SMILES: O=C(C1CC1)C1CCCN(C(=O)c2cnc3ccc(F)cc3c2N2CCC3(CC2)OCCO3)CC1]

The title compound was prepared following the similar procedure as described in Example 1. ¹H NMR (400 MHz, DMSO-d6) δ 8.65-8.40 (m, 1H), 8.05 (dd, J=9.9, 5.0 Hz, 1H), 7.77 (s, 2H), 4.00-3.03 (m, 16H), 1.97-1.67 (m, 7H), 0.87-0.42 (m, 4H); LC-MS (Method 2): $t_R$=3.50 min, m/z (M+H)⁺=483; HRMS calculated for $C_{26}H_{32}FN_4O_4$ (M+H)⁺: 483.2402, found: 483.2407.

Example 70. 1-(4-(6-fluoro-4-(1,4-dioxa-8-azaspiro[4.5]decan-8-yl)quinoline-3-carbonyl)piperazin-1-yl)propan-1-one, TFA (Cpd. 70)

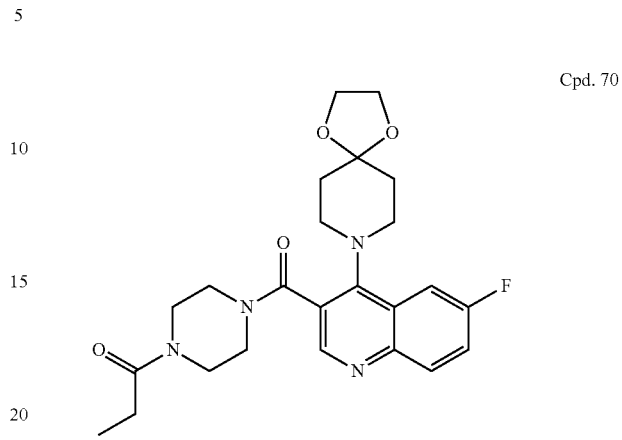

The title compound was prepared following the similar procedure as described in Example 1. ¹H NMR (400 MHz, DMSO-d₆) δ 8.65 (d, J=4.0 Hz, 1H), 8.10-7.99 (m, 1H), 7.76 (m, 2H), 4.01-3.85 (m, 4H), 3.82-3.05 (m, 12H), 2.42-2.20 (m, 2H), 2.04-1.72 (m, 4H), 0.98 (m, 3H); LC-MS (Method 2): $t_R$=3.42 min, m/z (M+H)⁺=457; HRMS calculated for $C_{24}H_{30}FN_4O_4$ (M+H)⁺: 457.2246, found: 457.2255.

Example 71. (4-(azepan-1-yl)-6-fluoroquinolin-3-yl)(4-(cyclopropanecarbonyl)piperazin-1-yl)methanone, TFA (Cpd. 71)

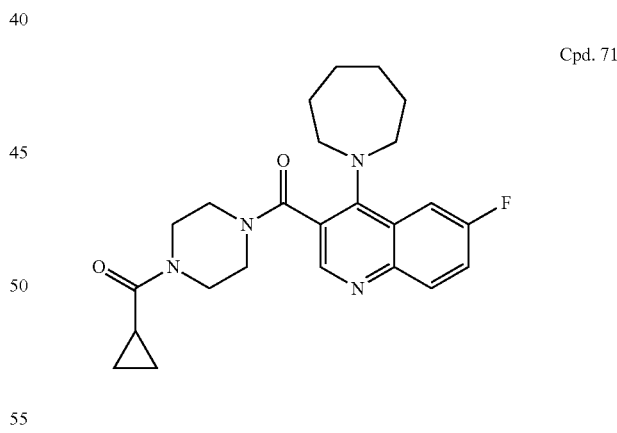

The title compound was prepared following the similar procedure as described in Example 17. ¹H NMR (400 MHz, DMSO-d₆) δ 8.64 (s, 1H), 8.04 (dd, J=9.2, 5.4 Hz, 1H), 7.96 (d, J=10.5 Hz, 1H), 7.80 (d, J=9.3 Hz, 1H), 3.92-3.23 (m, 12H), 2.07-1.49 (m, 9H), 0.74 (d, J=4.6 Hz, 4H); LC-MS (Method 2): $t_R$=3.93 min, m/z (M+H)⁺=425; HRMS calculated for $C_{24}H_{30}FN_4O_2$ (M+H)⁺: 425.2347, found: 425.2340.

Example 72. (4-(cyclopropanecarbonyl)piperazin-1-yl)(6-fluoro-4-(4-phenylpiperidin-1-yl)quinolin-3-yl)methanone, TFA (Cpd. 72)

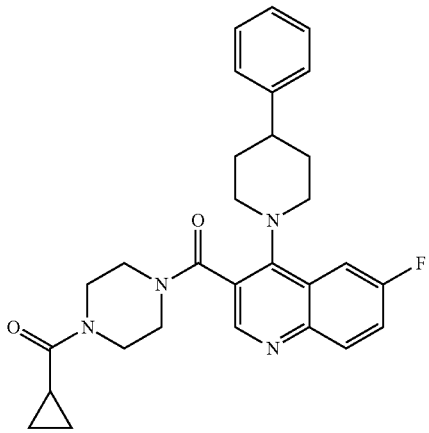

Cpd. 72

The title compound was prepared following the similar procedure as described in Example 17. ¹H NMR (400 MHz, DMSO-d$_6$) δ 8.65 (s, 1H), 8.07 (dd, J=9.2, 5.4 Hz, 1H), 7.84 (d, J=10.2 Hz, 1H), 7.78 (s, 1H), 7.41-7.26 (m, 4H), 7.25-7.16 (m, 1H), 3.98-3.24 (m, 11H), 3.16 (m, 1H), 2.81 (s, 1H), 2.17-1.78 (m, 5H), 0.74 (dd, J=4.7, 2.9 Hz, 4H); LC-MS (Method 2): t$_R$=4.58 min, m/z (M+H)$^+$=487; HRMS calculated for C$_{29}$H$_{32}$FN$_4$O$_2$ (M+H)$^+$: 487.2504, found: 487.2508.

Example 73. (4-(cyclopropanecarbonyl)piperazin-1-yl)(6-fluoro-8-methyl-4-(1,4-dioxa-8-azaspiro[4.5]decan-8-yl)quinolin-3-yl)methanone, TFA (Cpd. 73)

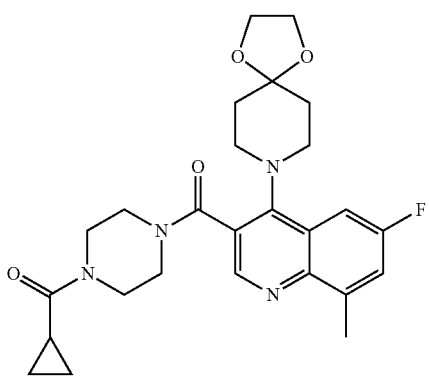

Cpd. 73

The title compound was prepared following the similar procedure as described in Example 1. ¹H NMR (400 MHz, DMSO-d$_6$) δ 8.57 (s, 1H), 7.58 (m, 2H), 3.92 (s, 4H), 3.87-3.25 (m, 10H), 3.13-3.01 (m, 2H), 2.70 (s, 3H), 2.08-1.70 (m, 5H), 0.74 (dd, J=4.7, 2.8 Hz, 4H); LC-MS (Method 2): t$_R$=3.81 min, m/z (M+H)$^+$=483; HRMS calculated for C$_{26}$H$_{32}$FN$_4$O$_4$ (M+H)$^+$: 483.2402, found: 483.2408.

Example 74. (4-(cyclopropanecarbonyl)piperazin-1-yl)(6-fluoro-4-(4-isopropylpiperidin-1-yl)quinolin-3-yl)methanone, TFA (Cpd. 74)

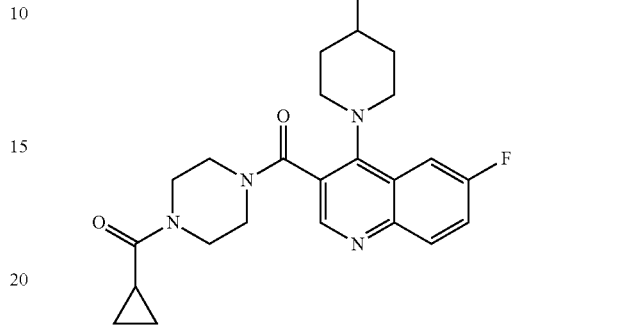

Cpd. 74

The title compound was prepared following the similar procedure as described in Example 17. ¹H NMR (400 MHz, DMSO-d$_6$) δ 8.63 (s, 1H), 8.05 (dd, J=9.3, 5.4 Hz, 1H), 7.77 (td, J=8.7, 2.7 Hz, 1H), 7.71 (dd, J=10.4, 2.8 Hz, 1H), 4.50-2.82 (m, 12H), 2.07-1.15 (m, 7H), 0.91 (dd, J=6.7, 1.6 Hz, 6H), 0.74 (dd, J=4.7, 3.0 Hz, 4H); LC-MS (Method 2): t$_R$=4.64 min, m/z M+H)$^+$=453; HRMS calculated for C$_{26}$H$_{34}$FN$_4$O$_2$ (M+H)$^+$: 453.2660, found: 453.2666.

Example 75. (4-(cyclopropanecarbonyl)piperazin-1-yl)(6-fluoro-4-(3-azaspiro[5.5]undecan-3-yl)quinolin-3-yl)methanone, TFA (Cpd. 75)

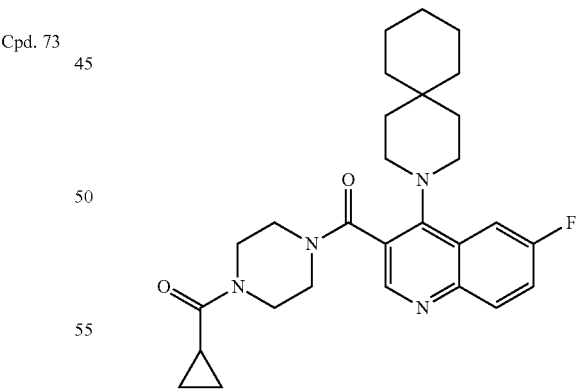

Cpd. 75

The title compound was prepared following the similar procedure as described in Example 17. ¹H NMR (400 MHz, DMSO-d$_6$) δ 8.63 (s, 1H), 8.05 (dd, J=9.5, 5.4 Hz, 1H), 7.76 (d, J=9.6 Hz, 2H), 4.21-3.01 (m, 12H), 1.96 (m, 2H), 1.77-1.50 (m, 5H), 1.42 (s, 8H), 0.74 (d, J=4.7 Hz, 4H); LC-MS (Method 2): t$_R$=4.87 min, m/z (M+H)$^+$=479; HRMS calculated for C$_{28}$H$_{36}$FN$_4$O$_2$ (M+H)$^+$: 479.2817, found: 479.2832.

Example 76. (4-(cyclopropanecarbonyl)piperazin-1-yl)(6-fluoro-4-(4-fluoropiperidin-1-yl)quinolin-3-yl)methanone, TFA (Cpd. 76)

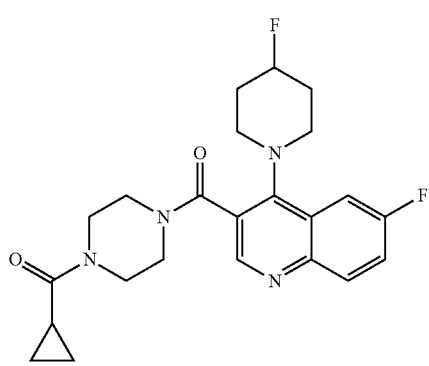

The title compound was prepared following the similar procedure as described in Example 17. $^1$H NMR (400 MHz, DMSO-$d_6$) δ 8.63 (s, 1H), 8.07 (dd, J=10.1, 5.4 Hz, 1H), 7.80-7.68 (m, 2H), 4.93 (d, J=48.4 Hz, 1H), 4.40-2.92 (m, 12H), 2.29-1.79 (m, 5H), 0.74 (dd, J=4.8, 2.9 Hz, 4H); LC-MS (Method 2): $t_R$=3.61 min, m/z (M+H)$^+$=429; HRMS calculated for $C_{23}H_{27}F_2N_4O_2$ (M+H)$^+$: 429.2097, found: 429.2114.

Example 77. (4-(cyclopropanecarbonyl)piperazin-1-yl)(4-(4,4-dimethylcyclohex-1-en-1-yl)-6-fluoroquinolin-3-yl)methanone (Cpd. 77)

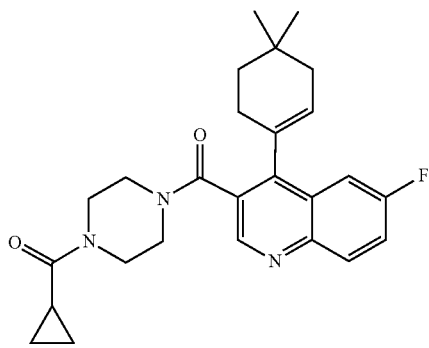

The title compound was prepared following the similar procedure as described in Example 41. $^1$H NMR (400 MHz, Chloroform-d) δ 8.70 (s, 1H), 8.12 (dd, J=10.1, 5.4 Hz, 1H), 7.57-7.44 (m, 2H), 5.60 (s, 1H), 4.06-2.99 (m, 8H), 2.61-1.81 (m, 4H), 1.17-0.65 (m, 13H); LC-MS (Method 2): $t_R$=5.50 min, m/z (M+H)$^+$=436; HRMS calculated for $C_{26}H_{31}FN_3O_2$ (M+H)$^+$: 436.2395, found: 436.2391.

Example 78. (4-(cyclopropanecarbonyl)piperazin-1-yl)(6,8-difluoro-4-(1,4-dioxa-8-azaspiro[4.5]decan-8-yl)quinolin-3-yl)methanone, TFA (Cpd. 78)

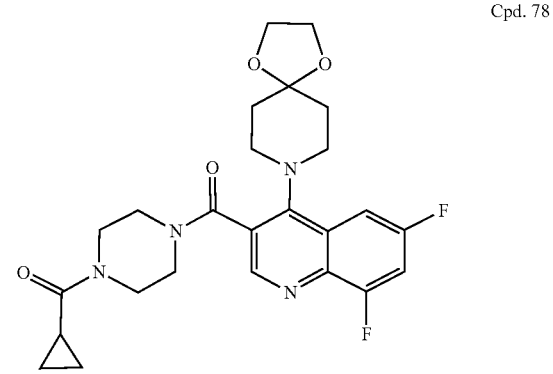 [SMILES: O=C(c1cnc2c(F)cc(F)cc2c1N1CCC2(CC1)OCCO2)N1CCN(C(=O)C2CC2)CC1]

The title compound was prepared following the similar procedure as described in Example 1. $^1$H NMR (400 MHz, DMSO-$d_6$) δ 8.58 (s, 1H), 7.74 (ddd, J=11.1, 8.9, 2.7 Hz, 1H), 7.55 (dt, J=10.0, 2.0 Hz, 1H), 3.92 (t, J=2.2 Hz, 4H), 3.88-3.21 (m, 10H), 3.04 (ddd, J=11.7, 7.2, 3.5 Hz, 2H), 2.07-1.62 (m, 5H), 0.74 (d, J=4.4 Hz, 4H); LC-MS (Method 2): $t_R$=4.11 min, m/z (M+H)$^+$=487; HRMS calculated for $C_{25}H_{29}F_2N_4O_4$ (M+H)$^+$: 487.2151, found: 487.2146.

Example 79. (4-(cyclopropanecarbonyl)piperazin-1-yl)(6-fluoro-4-(2-azaspiro[4.5]decan-2-yl)quinolin-3-yl)methanone, TFA (Cpd. 79)

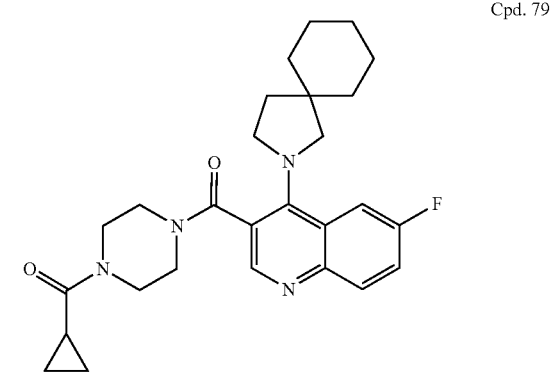 [SMILES: O=C(c1cnc2ccc(F)cc2c1N1CCC2(CCCCC2)C1)N1CCN(C(=O)C2CC2)CC1]

The title compound was prepared following the similar procedure as described in Example 17. $^1$H NMR (400 MHz, DMSO-$d_6$) δ 8.48 (s, 1H), 8.28 (dd, J=11.1, 2.6 Hz, 1H), 7.93 (dd, J=9.3, 5.4 Hz, 1H), 7.86 (td, J=9.4, 8.5, 2.5 Hz, 1H), 3.96-3.30 (m, 12H), 2.00 (s, 1H), 1.85 (s, 2H), 1.57-1.29 (m, 10H), 0.75 (q, J=7.9, 5.5 Hz, 4H); LC-MS (Method 2): $t_R$=4.36 min, m/z (M+H)$^+$=465; HRMS calculated for $C_{27}H_{34}FN_4O_2$ (M+H)$^+$: 465.2660, found: 465.2663.

Example 80. (4-(cyclopropanecarbonyl)piperazin-1-yl)(6-fluoro-4-(2-azaspiro[3.5]nonan-2-yl)quinolin-3-yl)methanone, TFA (Cpd. 80)

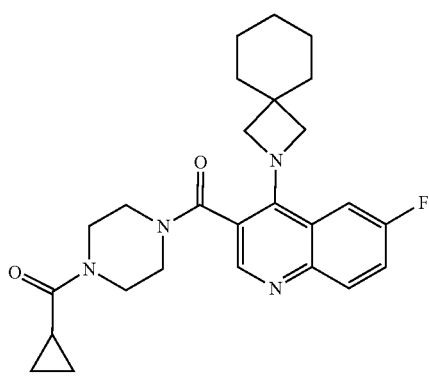

Cpd. 80

The title compound was prepared following the similar procedure as described in Example 17. $^1$H NMR (400 MHz, DMSO-$d_6$) δ 8.47 (s, 1H), 8.01 (dd, J=10.7, 2.6 Hz, 1H), 7.97-7.81 (m, 2H), 3.96-3.41 (m, 12H), 2.06-1.22 (m, 11H), 0.75 (d, J=4.9 Hz, 4H); LC-MS (Method 2): $t_R$=4.27 min, m/z (M+H)$^+$=451; HRMS calculated for $C_{26}H_{31}FN_4O_2Na$ (M+Na)$^+$: 473.2323, found: 473.2325.

Example 81. (4-(cyclopropanecarbonyl)piperazin-1-yl)(4-(4,4-diethylpiperidin-1-yl)-6-fluoroquinolin-3-yl)methanone, TFA (Cpd. 81)

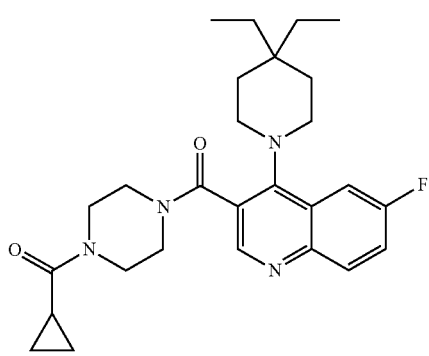

Cpd. 81

The title compound was prepared following the similar procedure as described in Example 17. $^1$H NMR (400 MHz, DMSO-$d_6$) δ 8.62 (s, 1H), 8.05 (dd, J=10.1, 5.4 Hz, 1H), 7.87-7.67 (m, 2H), 4.22-2.96 (m, 12H), 2.13-1.31 (m, 9H), 0.88-0.56 (m, 10H); LC-MS (Method 2): $t_R$=4.74 min, m/z (M+H)$^+$=467; HRMS calculated for $C_{27}H_{36}FN_4O_2$ (M+H)$^+$: 467.2817, found: 467.2836.

Example 82. (4-(3-azabicyclo[3.2.1]octan-3-yl)-6-fluoroquinolin-3-yl)(4-(cyclopropanecarbonyl)piperazin-1-yl)methanone, TFA (Cpd. 82)

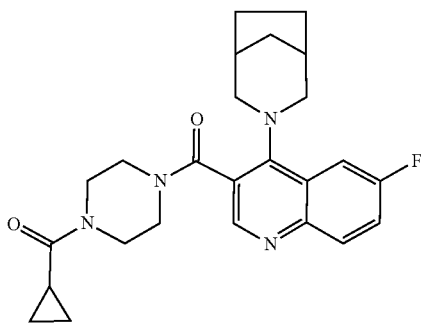

Cpd. 82

The title compound was prepared following the similar procedure as described in Example 17. $^1$H NMR (400 MHz, DMSO-$d_6$) δ 8.61 (s, 1H), 8.08 (dd, J=9.2, 5.5 Hz, 1H), 7.99 (dd, J=10.6, 2.9 Hz, 1H), 7.73 (td, J=8.6, 2.8 Hz, 1H), 4.19-3.16 (m, 10H), 3.08 (d, J=11.4 Hz, 1H), 2.88 (d, J=9.9 Hz, 1H), 2.37-1.42 (m, 9H), 0.73 (d, J=4.7 Hz, 4H); LC-MS (Method 2): $t_R$=4.18 min, m/z (M+H)$^+$=437; HRMS calculated for $C_{25}H_{29}FN_4O_2Na$ (M+Na)$^+$: 459.2167, found: 459.2162.

Example 83. (4-(cyclopropanecarbonyl)piperazin-1-yl)(6-fluoro-4-((3aR*,7aS*)-hexahydro-1H-isoindol-2(3H)-yl)quinolin-3-yl)methanone (Cpd. 83)

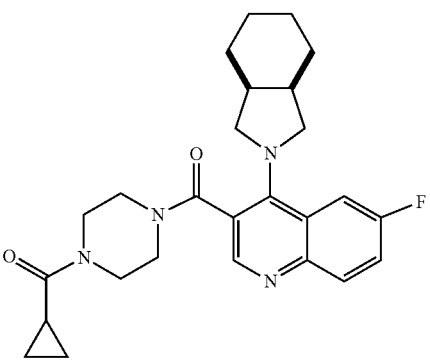

Cpd. 83

The title compound was prepared following the similar procedure as described in Example 17. $^1$H NMR (400 MHz, DMSO-$d_6$) δ 8.26 (s, 1H), 8.08-8.00 (m, 1H), 7.88 (dd, J=9.2, 5.9 Hz, 1H), 7.61 (t, J=8.2 Hz, 1H), 3.94-3.36 (m, 12H), 2.31-1.08 (m, 11H), 0.73 (d, J=4.7 Hz, 4H); LC-MS (Method 2): $t_R$=4.03 min, m/z (M+H)$^+$=451; HRMS calculated for $C_{26}H_{32}FN_4O_2$ (M+H)$^+$: 451.2504, found: 451.2520.

Example 84. (4-(4-(tert-butyl)phenyl)-6-fluoroquinolin-3-yl)(4-(cyclopropanecarbonyl)piperazin-1-yl)methanone, TFA (Cpd. 84)

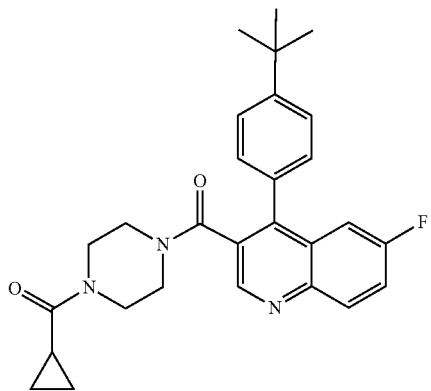

Cpd. 84

The title compound was prepared following the similar procedure as described in Example 41. $^1$H NMR (400 MHz, DMSO-d$_6$) δ 8.83 (s, 1H), 8.21 (dd, J=9.2, 5.6 Hz, 1H), 7.77 (td, J=8.7, 2.9 Hz, 1H), 7.60 (d, J=7.8 Hz, 2H), 7.48 (d, J=8.0 Hz, 1H), 7.41 (dd, J=10.3, 2.8 Hz, 1H), 7.36 (d, J=8.1 Hz, 1H), 4.00-1.75 (m, 9H), 1.31 (s, 9H), 0.64 (s, 4H); LC-MS (Method 2): t$_R$=5.71 min, m/z (M+H)$^+$=460; HRMS calculated for C$_{28}$H$_{31}$FN$_3$O$_2$ (M+H)$^+$: 460.2395, found: 460.2415.

Example 85. 1-(3-(4-(cyclopropylsulfonyl)piperazine-1-carbonyl)-6-fluoroquinolin-4-yl)-4-methylpiperidine-4-carbonitrile, TFA (Cpd. 85)

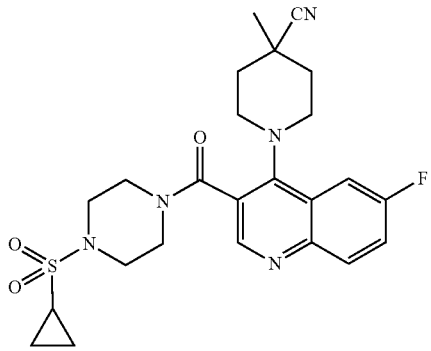

Cpd. 85

The title compound was prepared following the similar procedure as described in Example 1. $^1$H NMR (400 MHz, DMSO-d$_6$) δ 8.64 (d, J=3.5 Hz, 1H), 8.07 (dd, J=10.0, 5.6 Hz, 1H), 7.74 (dt, J=7.8, 2.5 Hz, 2H), 3.95-3.03 (m, 12H), 2.62 (ddt, J=12.5, 8.0, 3.9 Hz, 1H), 2.10-1.92 (m, 3H), 1.92-1.74 (m, 1H), 1.45 (s, 3H), 1.07-0.84 (m, 4H); LC-MS (Method 2): t$_R$=4.01 min, m/z (M+H)$^+$=486; HRMS calculated for C$_{24}$H$_{29}$FN$_5$O$_3$S (M+H)$^+$: 486.1970, found: 486.1970.

Example 86. 1-(6-fluoro-3-(4-(methylsulfonyl)piperazine-1-carbonyl)quinolin-4-yl)-4-methylpiperidine-4-carbonitrile, TFA (Cpd. 86)

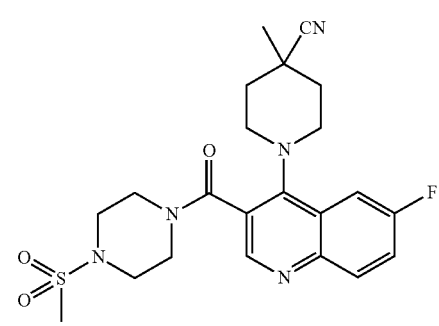

Cpd. 86

The title compound was prepared following the similar procedure as described in Example 1. $^1$H NMR (400 MHz, DMSO-d6) δ 8.63 (s, 1H), 8.07 (dd, J=10.1, 5.5 Hz, 1H), 7.74 (m, 2H), 3.97-3.03 (m, 12H), 2.91 (s, 3H), 2.14-1.70 (m, 4H), 1.45 (s, 3H); LC-MS (Method 2): t$_R$=3.72 min, m/z (M+H)$^+$=460; HRMS calculated for C$_{22}$H$_{27}$FN$_5$O$_3$S (M+H)$^+$: 460.1813, found: 460.1804.

Example 87. 1-(3-(4-acetylpiperazine-1-carbonyl)-6-fluoroquinolin-4-yl)-4-methylpiperidine-4-carbonitrile, TFA (Cpd. 87)

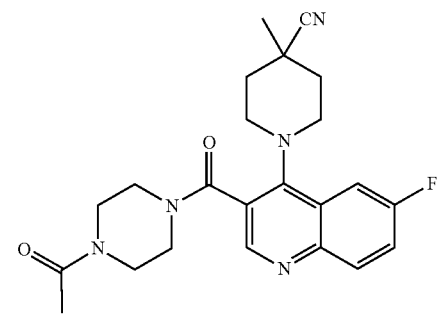

Cpd. 87

The title compound was prepared following the similar procedure as described in Example 1. LC-MS (Method 2): t$_R$=3.45 min, m/z (M+H)$^+$=424; HRMS calculated for C$_{23}$H$_{27}$FN$_5$O$_2$ (M+H)$^+$: 424.2143, found: 424.2144.

Example 88. Ethyl 4-(4-(4-cyano-4-methylpiperidin-1-yl)-6-fluoroquinoline-3-carbonyl)piperazine-1-carboxylate, TFA (Cpd. 88)

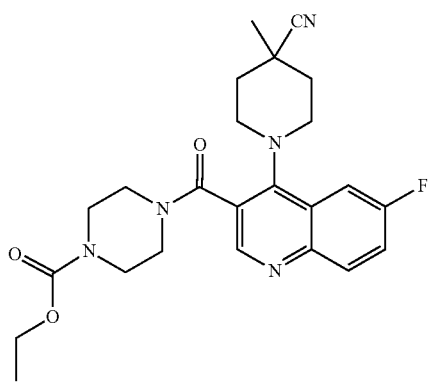

The title compound was prepared following the similar procedure as described in Example 1. $^1$H NMR (400 MHz, DMSO-$d_6$) δ 8.61 (d, J=7.0 Hz, 1H), 8.07 (dd, J=10.3, 5.5 Hz, 1H), 7.83-7.58 (m, 2H), 4.05 (q, J=7.1 Hz, 2H), 3.80-3.03 (m, 12H), 2.10-1.71 (m, 4H), 1.45 (s, 3H), 1.17 (td, J=7.2, 2.9 Hz, 3H); LC-MS (Method 2): $t_R$=4.04 min, m/z (M+H)$^+$=454; HRMS calculated for $C_{24}H_{28}FN_5O_3Na$ (M+Na)$^+$: 476.2068, found: 476.2068.

Example 89. 4-(4-(4-cyano-4-methylpiperidin-1-yl)-6-fluoroquinoline-3-carbonyl)-N-ethylpiperazine-1-carboxamide, TFA (Cpd. 89)

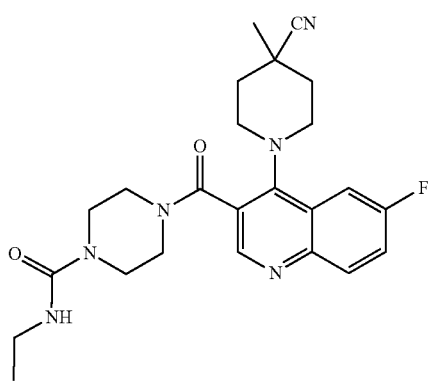

The title compound was prepared following the similar procedure as described in Example 1. $^1$H NMR (400 MHz, DMSO-$d_6$) δ 8.70-8.50 (m, 1H), 8.07 (dd, J=10.5, 5.4 Hz, 1H), 7.74 (d, J=9.5 Hz, 2H), 6.58 (s, 1H), 3.95-2.91 (m, 14H), 2.11-1.71 (m, 4H), 1.44 (s, 3H), 1.00 (td, J=7.1, 1.2 Hz, 3H); LC-MS (Method 2): $t_R$=3.59 min, m/z (M+H)$^+$=453; HRMS calculated for $C_{24}H_{30}FN_6O_2$ (M+H)$^+$: 453.2409, found: 453.2421.

Example 90. 4-(4-(4-cyano-4-methylpiperidin-1-yl)-6-fluoroquinoline-3-carbonyl)-N-isopropylpiperazine-1-carboxamide, TFA (Cpd. 90)

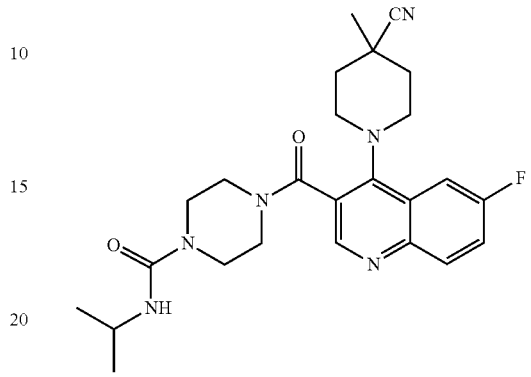

The title compound was prepared following the similar procedure as described in Example 1. $^1$H NMR (400 MHz, DMSO-$d_6$) δ 8.60 (s, 1H), 8.07 (dd, J=10.2, 5.4 Hz, 1H), 7.85-7.59 (m, 2H), 6.29 (d, J=7.6 Hz, 1H), 3.87-2.99 (m, 13H), 2.15-1.69 (m, 4H), 1.44 (s, 3H), 1.04 (d, J=6.6 Hz, 6H); LC-MS (Method 2): $t_R$=3.81 min, m/z (M+H)$^+$=467; HRMS calculated for $C_{25}H_{32}FN_6O_2$ (M+H)$^+$: 467.2565, found: 467.2555.

Example 91. 1-(6-fluoro-3-(4-propionylpiperazine-1-carbonyl)quinolin-4-yl)-4-methylpiperidine-4-carbonitrile, TFA (Cpd. 91)

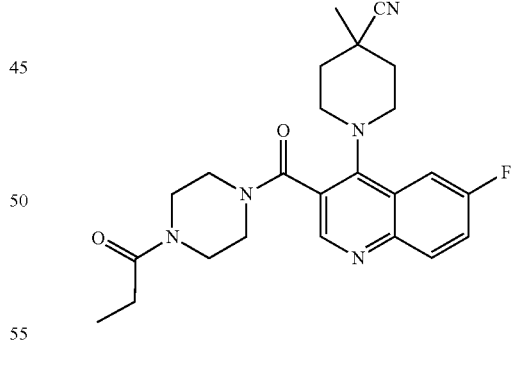

The title compound was prepared following the similar procedure as described in Example 1. $^1$H NMR (400 MHz, DMSO-$d_6$) δ 8.62 (d, J=3.0 Hz, 1H), 8.07 (dd, J=10.2, 5.3 Hz, 1H), 7.74 (d, J=10.4 Hz, 2H), 3.92-2.81 (m, 12H), 2.41-2.22 (m, 2H), 2.09-1.69 (m, 4H), 1.45 (s, 3H), 0.99 (dd, J=12.1, 5.6 Hz, 3H); LC-MS (Method 2): $t_R$=3.66 min, m/z (M+H)$^+$=438; HRMS calculated for $C_{24}H_{28}FN_5O_2Na$ (M+Na)$^+$: 460.2119, found: 460.2130.

Example 92. 1-(6-fluoro-3-(4-isobutyrylpiperazine-1-carbonyl)quinolin-4-yl)-4-methylpiperidine-4-carbonitrile, TFA (Cpd. 92)

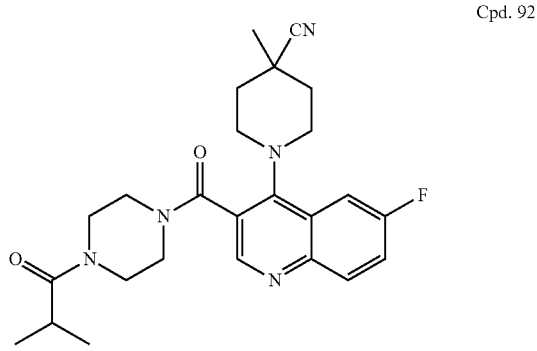 [SMILES: CC(C)C(=O)N1CCN(C(=O)c2cnc3ccc(F)cc3c2N2CCC(C)(C#N)CC2)CC1]

Cpd. 92

The title compound was prepared following the similar procedure as described in Example 1. $^1$H NMR (400 MHz, DMSO-d$_6$) δ 8.62 (s, 1H), 8.07 (dd, J=10.2, 5.4 Hz, 1H), 7.85-7.57 (m, 2H), 3.90-2.71 (m, 13H), 2.18-1.69 (m, 4H), 1.45 (s, 3H), 0.98 (q, J=6.7 Hz, 6H); LC-MS (Method 2): t$_R$=3.88 min, m/z (M+H)$^+$=452; HRMS calculated for C$_{25}$H$_{30}$FN$_5$O$_2$Na (M+Na)$^+$: 474.2276, found: 474.2292.

Example 93. 1-(3-(4-(cyclopropanecarbonyl)piperazine-1-carbonyl)quinolin-4-yl)-4-methylpiperidine-4-carbonitrile, TFA (Cpd. 93)

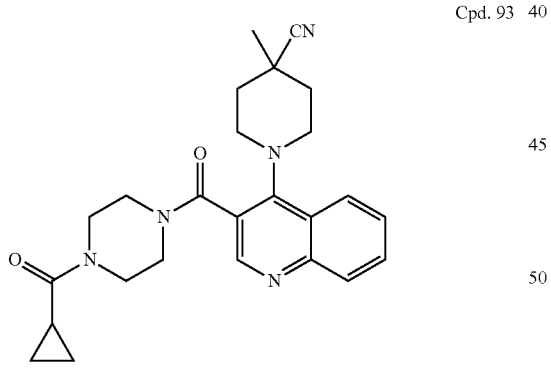

Cpd. 93

The title compound was prepared following the similar procedure as described in Example 1. $^1$H NMR (400 MHz, DMSO-d$_6$) δ 8.74 (s, 1H), 8.15 (d, J=8.5 Hz, 1H), 8.01 (dd, J=8.4, 1.2 Hz, 1H), 7.91 (t, J=7.8 Hz, 1H), 7.71 (t, J=7.7 Hz, 1H), 3.98-3.10 (m, 12H), 2.16-1.67 (m, 5H), 1.46 (s, 3H), 0.74 (dd, J=4.8, 2.4 Hz, 4H); LC-MS (Method 2): t$_R$=3.46 min, m/z (M+H)$^+$=432; HRMS calculated for C$_{25}$H$_{30}$N$_5$O$_2$ (M+H)$^+$: 432.2394, found: 432.2376.

Example 94. 4-methyl-1-(3-(4-propionylpiperazine-1-carbonyl)quinolin-4-yl)piperidine-4-carbonitrile, TFA (Cpd. 94)

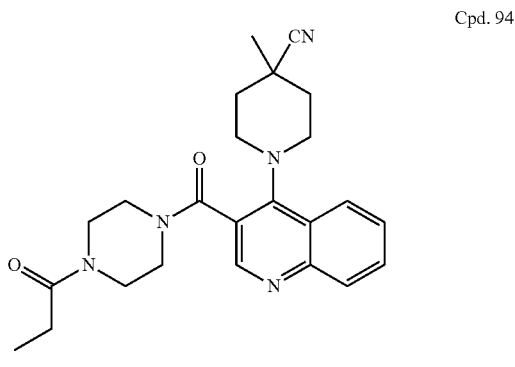 [SMILES: CCC(=O)N1CCN(C(=O)c2cnc3ccccc3c2N2CCC(C)(C#N)CC2)CC1]

Cpd. 94

The title compound was prepared following the similar procedure as described in Example 1. $^1$H NMR (400 MHz, DMSO-d$_6$) δ 8.71 (s, 1H), 8.13 (d, J=8.5 Hz, 1H), 8.00 (dd, J=8.5, 1.2 Hz, 1H), 7.88 (d, J=8.6 Hz, 1H), 7.69 (t, J=7.7 Hz, 1H), 3.91-3.11 (m, 12H), 2.42-2.21 (m, 2H), 2.03-2.06 (m, 3H), 1.86-1.70 (m, 1H), 1.46 (s, 3H), 1.07-0.89 (m, 3H); LC-MS (Method 2): t$_R$=3.35 min, m/z (M+H)$^+$=420; HRMS calculated for C$_{24}$H$_{30}$N$_5$O$_2$ (M+H)$^+$: 420.2394, found: 420.2409.

Example 95. 1-(3-(4-isobutyrylpiperazine-1-carbonyl)quinolin-4-yl)-4-methylpiperidine-4-carbonitrile, TFA (Cpd. 95)

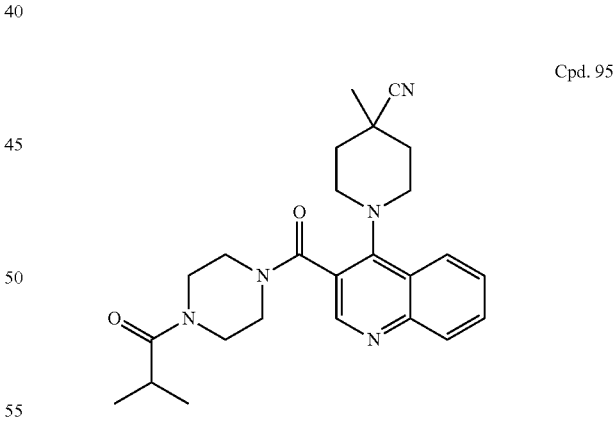

Cpd. 95

The title compound was prepared following the similar procedure as described in Example 1. $^1$H NMR (400 MHz, DMSO-d$_6$) δ 8.72 (s, 1H), 8.14 (d, J=8.6 Hz, 1H), 8.00 (d, J=8.4 Hz, 1H), 7.90 (t, J=7.7 Hz, 1H), 7.70 (t, J=7.8 Hz, 1H), 4.43-2.73 (m, 13H), 2.15-1.70 (m, 4H), 1.46 (s, 3H), 0.99 (d, J=8.3 Hz, 6H); LC-MS (Method 2): t$_R$=3.57 min, m/z (M+H)$^+$=434; HRMS calculated for C$_{25}$H$_{31}$N$_5$O$_2$Na (M+Na)$^+$: 456.2370, found: 456.2374.

Example 96. 1-(3-(4-acetylpiperazine-1-carbonyl)quinolin-4-yl)-4-methylpiperidine-4-carbonitrile, TFA (Cpd. 96)

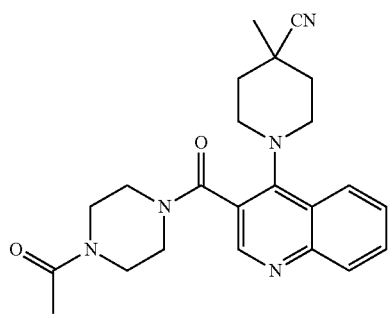

The title compound was prepared following the similar procedure as described in Example 1. $^1$H NMR (400 MHz, DMSO-d$_6$) δ 8.74 (s, 1H), 8.14 (d, J=8.5 Hz, 1H), 8.01 (dd, J=8.5, 1.2 Hz, 1H), 7.90 (t, J=7.7 Hz, 1H), 7.71 (t, J=7.6 Hz, 1H), 3.91-3.14 (m, 12H), 2.15-1.93 (m, 6H), 1.86-1.69 (m, 1H), 1.46 (s, 3H); LC-MS (Method 2): $t_R$=3.12 min, m/z (M+H)$^+$=406; HRMS calculated for C$_{25}$H$_{28}$N$_5$O$_2$ (M+H)$^+$: 406.2238, found: 406.2233.

Example 97. 4-methyl-1-(3-(4-(methylsulfonyl)piperazine-1-carbonyl)quinolin-4-yl)piperidine-4-carbonitrile, TFA (Cpd. 97)

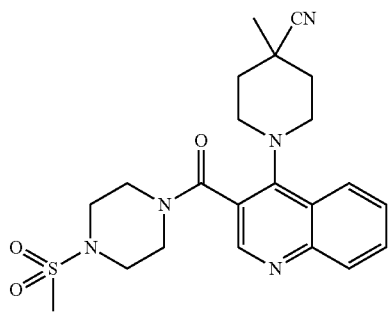

The title compound was prepared following the similar procedure as described in Example 1. $^1$H NMR (400 MHz, DMSO-d$_6$) δ 8.71 (s, 1H), 8.13 (d, J=8.5 Hz, 1H), 8.00 (dd, J=8.5, 1.2 Hz, 1H), 7.88 (t, J=7.6 Hz, 1H), 7.69 (t, J=7.8 Hz, 1H), 3.94-3.01 (m, 12H), 2.92 (s, 3H), 2.15-1.75 (m, 4H), 1.46 (s, 3H); LC-MS (Method 2): $t_R$=3.38 min, m/z (M+H)$^+$=442; HRMS calculated for C$_{22}$H$_{28}$N$_5$O$_3$S (M+H)$^+$: 442.1907, found: 442.1894.

Example 98. 1-(3-(4-(cyclopropylsulfonyl)piperazine-1-carbonyl)quinolin-4-yl)-4-methylpiperidine-4-carbonitrile, TFA (Cpd. 98)

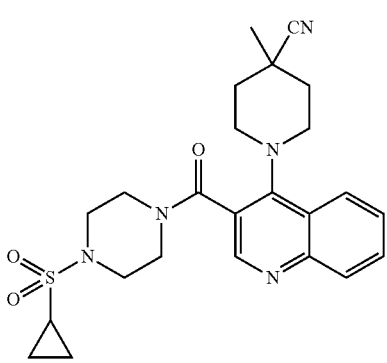

The title compound was prepared following the similar procedure as described in Example 1. $^1$H NMR (400 MHz, DMSO-d$_6$) δ 8.71 (s, 1H), 8.13 (d, J=8.4 Hz, 1H), 8.00 (d, J=8.4 Hz, 1H), 7.88 (s, 1H), 7.69 (t, J=7.7 Hz, 1H), 4.01-3.08 (m, 12H), 2.70-2.56 (m, 1H), 2.15-1.72 (m, 4H), 1.46 (s, 3H), 1.09-0.83 (m, 4H); LC-MS (Method 2): $t_R$=3.68 min, m/z (M+H)$^+$=468; HRMS calculated for C$_{24}$H$_{30}$N$_5$O$_3$S (M+H)$^+$: 468.2064, found: 468.2078.

Example 99. 4-(4-(4-cyano-4-methylpiperidin-1-yl)quinoline-3-carbonyl)-N-ethylpiperazine-1-carboxamide, TFA (Cpd. 99)

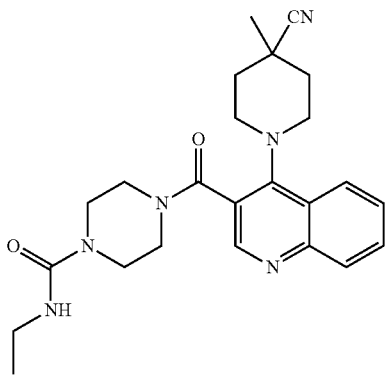

The title compound was prepared following the similar procedure as described in Example 1. $^1$H NMR (400 MHz, DMSO-d$_6$) δ 8.71 (s, 1H), 8.13 (d, J=8.5 Hz, 1H), 8.00 (dd, J=8.5, 1.3 Hz, 1H), 7.89 (t, J=7.6 Hz, 1H), 7.70 (t, J=7.7 Hz, 1H), 6.59 (t, J=5.3 Hz, 1H), 3.81-3.14 (m, 12H), 3.11-2.96 (m, 2H), 2.15-1.68 (m, 4H), 1.45 (s, 3H), 1.00 (t, J=7.1 Hz, 3H); LC-MS (Method 2): $t_R$=3.28 min, m/z (M+H)$^+$=435; HRMS calculated for C$_{24}$H$_{31}$N$_6$O$_2$ (M+H)$^+$: 435.2503, found: 435.2510.

Example 100. Ethyl 4-(4-(4-cyano-4-methylpiperidin-1-yl)quinoline-3-carbonyl)piperazine-1-carboxylate, TFA (Cpd. 100)

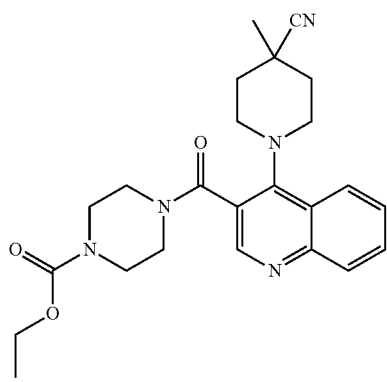

Cpd. 100

The title compound was prepared following the similar procedure as described in Example 1. $^1$H NMR (400 MHz, DMSO-$d_6$) δ 8.71 (s, 1H), 8.14 (d, J=8.6 Hz, 1H), 8.00 (dd, J=8.5, 1.2 Hz, 1H), 7.90 (t, J=7.8 Hz, 1H), 7.70 (t, J=7.7 Hz, 1H), 4.05 (q, J=7.1 Hz, 2H), 3.77-3.14 (m, 12H), 2.16-1.67 (m, 4H), 1.46 (s, 3H), 1.18 (t, J=7.1 Hz, 3H); LC-MS (Method 2): $t_R$=3.68 min, m/z (M+H)$^+$=436; HRMS calculated for $C_{24}H_{30}N_5O_2$ (M+H)$^+$: 436.2343, found: 436.2353.

Example 101. 1-(3-(4-(cyclopropanecarbonyl)piperazine-1-carbonyl)-7-methoxyquinolin-4-yl)-4-methylpiperidine-4-carbonitrile, TFA (Cpd. 101)

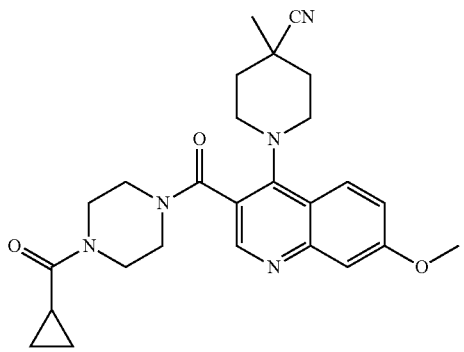

Cpd. 101

The title compound was prepared following the similar procedure as described in Example 1. $^1$H NMR (400 MHz, DMSO-$d_6$) δ 8.67 (s, 1H), 8.06 (d, J=9.9 Hz, 1H), 7.33 (p, J=2.4 Hz, 2H), 3.95 (s, 3H), 3.86-3.17 (m, 12H), 2.14-1.68 (m, 5H), 1.45 (s, 3H), 0.74 (d, J=4.6 Hz, 4H); LC-MS (Method 2): $t_R$=3.68 min, m/z (M+H)$^+$=462; HRMS calculated for $C_{26}H_{32}N_5O_3$ (M+H)$^+$: 462.2500, found: 462.2507.

Example 102. 1-(7-methoxy-3-(4-propionylpiperazine-1-carbonyl)quinolin-4-yl)-4-methylpiperidine-4-carbonitrile, TFA (Cpd. 102)

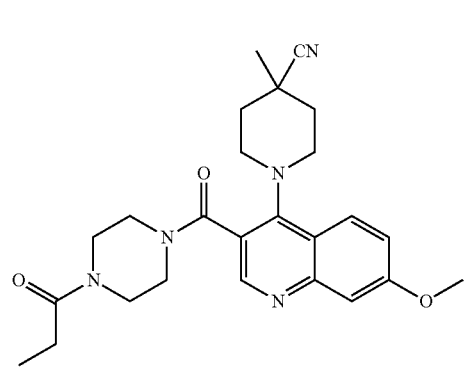

Cpd. 102

The title compound was prepared following the similar procedure as described in Example 1. $^1$H NMR (400 MHz, DMSO-$d_6$) δ 8.67 (s, 1H), 8.06 (d, J=10.0 Hz, 1H), 7.48-7.14 (m, 2H), 3.95 (s, 3H), 3.82-3.18 (m, 12H), 2.42-2.24 (m, 2H), 2.12-1.68 (m, 4H), 1.45 (s, 3H), 0.98 (q, J=7.9 Hz, 3H); LC-MS (Method 2): $t_R$=3.59 min, m/z (M+H)$^+$=450; HRMS calculated for $C_{25}H_{31}N_5O_3Na$ (M+Na)$^+$: 472.2319, found: 472.2341.

Example 103. 1-(3-(4-isobutyrylpiperazine-1-carbonyl)-7-methoxyquinolin-4-yl)-4-methylpiperidine-4-carbonitrile, TFA (Cpd. 103)

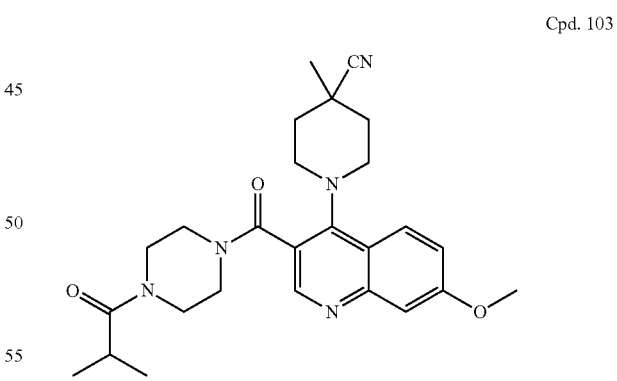

Cpd. 103

The title compound was prepared following the similar procedure as described in Example 1. $^1$H NMR (400 MHz, DMSO-$d_6$) δ 8.66 (s, 1H), 8.05 (d, J=9.9 Hz, 1H), 7.59-7.11 (m, 2H), 3.95 (s, 3H), 3.81-3.14 (m, 12H), 2.88 (m, 1H), 2.14-1.66 (m, 4H), 1.45 (s, 3H), 1.00 (s, 6H); LC-MS (Method 2): $t_R$=3.78 min, m/z (M+H)$^+$=464; HRMS calculated for $C_{26}H_{34}N_5O_3$ (M+H)$^+$: 464.2656, found: 464.2666.

Example 104. 1-(3-(4-acetylpiperazine-1-carbonyl)-7-methoxyquinolin-4-yl)-4-methylpiperidine-4-carbonitrile, TFA (Cpd. 104)

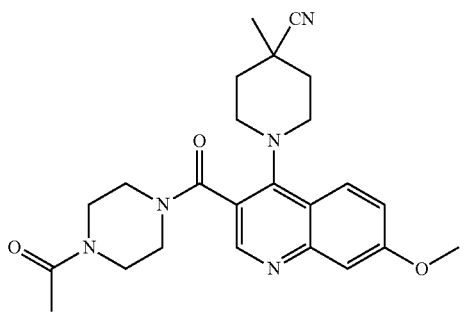

Cpd. 104

The title compound was prepared following the similar procedure as described in Example 1. $^1$H NMR (400 MHz, DMSO-$d_6$) δ 8.67 (s, 1H), 8.06 (d, J=10.0 Hz, 1H), 7.33 (h, J=2.7 Hz, 2H), 3.95 (s, 3H), 3.81-3.18 (m, 12H), 2.15-1.66 (m, 7H), 1.45 (s, 3H); LC-MS (Method 2): $t_R$=3.41 min, m/z (M+H)$^+$=436; HRMS calculated for $C_{24}H_{30}N_5O_3$ (M+H)$^+$: 436.2343, found: 436.2360.

Example 105. 1-(7-methoxy-3-(4-(methylsulfonyl)piperazine-1-carbonyl)quinolin-4-yl)-4-methylpiperidine-4-carbonitrile, TFA (Cpd. 105)

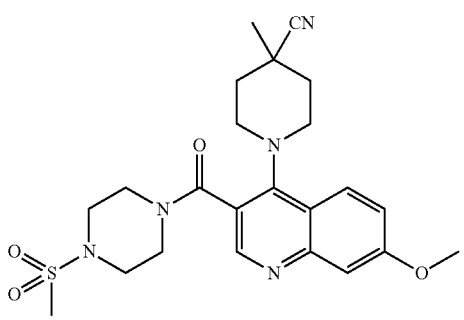

Cpd. 105

The title compound was prepared following the similar procedure as described in Example 1. $^1$H NMR (400 MHz, DMSO-$d_6$) δ 8.66 (s, 1H), 8.05 (d, J=9.8 Hz, 1H), 7.42-7.20 (m, 2H), 3.94 (s, 3H), 3.89-3.02 (m, 12H), 2.92 (s, 3H), 2.13-1.70 (m, 4H), 1.45 (s, 3H); LC-MS (Method 2): $t_R$=3.54 min, m/z (M+H)$^+$=472; HRMS calculated for $C_{23}H_{30}N_5O_3S$ (M+H)$^+$: 472.2013, found: 472.2019.

Example 106. 1-(3-(4-(cyclopropylsulfonyl)piperazine-1-carbonyl)-7-methoxyquinolin-4-yl)-4-methylpiperidine-4-carbonitrile, TFA (Cpd. 106)

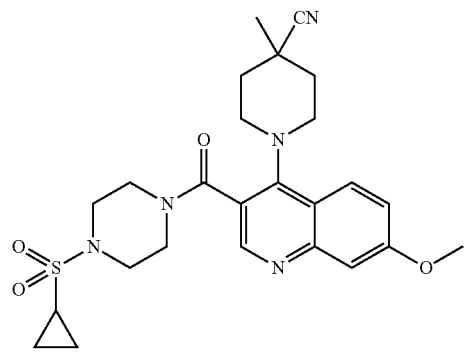

Cpd. 106

The title compound was prepared following the similar procedure as described in Example 1. $^1$H NMR (400 MHz, DMSO-$d_6$) δ 8.67 (s, 1H), 8.20-7.90 (m, 1H), 7.46-7.18 (m, 2H), 3.94 (s, 3H), 3.89-3.11 (m, 12H), 2.68-2.57 (m, 1H), 2.13-1.71 (m, 4H), 1.45 (s, 3H), 1.07-0.80 (m, 4H); LC-MS (Method 2): $t_R$=3.88 min, m/z (M+H)$^+$=498; HRMS calculated for $C_{25}H_{32}N_5O_4S$ (M+H)$^+$: 498.2170, found: 498.2186.

Example 107. 4-(4-(4-cyano-4-methylpiperidin-1-yl)-7-methoxyquinoline-3-carbonyl)-N-ethylpiperazine-1-carboxamide, TFA (Cpd. 107)

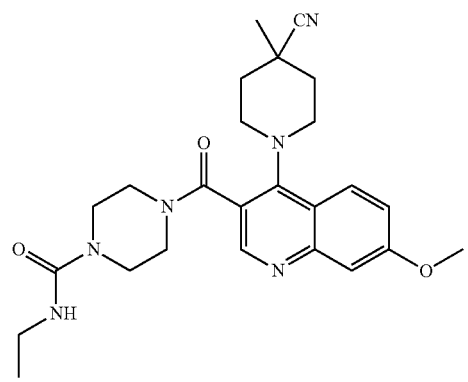

Cpd. 107

The title compound was prepared following the similar procedure as described in Example 1. $^1$H NMR (400 MHz, DMSO-$d_6$) δ 8.66 (s, 1H), 8.06 (d, J=10.1 Hz, 1H), 7.46-7.20 (m, 2H), 6.60 (t, J=5.3 Hz, 1H), 3.95 (s, 3H), 3.82-3.18 (m, 12H), 3.10-2.98 (m, 2H), 2.14-1.68 (m, 4H), 1.45 (s, 3H), 1.00 (t, J=7.1 Hz, 3H); LC-MS (Method 2): $t_R$=3.53 min, m/z (M+H)$^+$=465; HRMS calculated for $C_{27}H_{36}N_6O_3$ (M+H)$^+$: 465.2611, found: 465.2629.

Example 108. Ethyl 4-(4-(4-cyano-4-methylpiperidin-1-yl)-7-methoxyquinoline-3-carbonyl)piperazine-1-carboxylate, TFA (Cpd. 108)

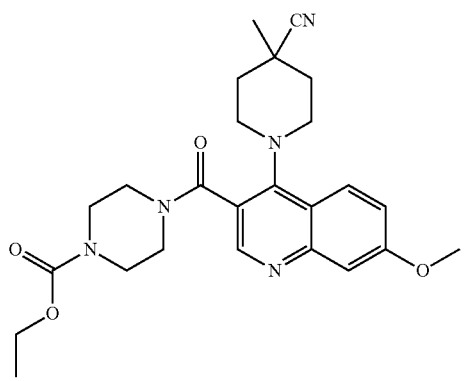

The title compound was prepared following the similar procedure as described in Example 1. $^1$H NMR (400 MHz, DMSO-$d_6$) δ 8.66 (s, 1H), 8.17-7.89 (m, 1H), 7.33 (h, J=2.6 Hz, 2H), 4.06 (q, J=7.1 Hz, 2H), 3.95 (s, 3H), 3.80-3.05 (m, 12H), 2.12-1.68 (m, 4H), 1.45 (s, 3H), 1.17 (td, J=7.0, 4.8 Hz, 3H); LC-MS (Method 2): $t_R$=3.93 min, m/z (M+H)$^+$=466; HRMS calculated for $C_{25}H_{32}N_5O_4$ (M+H)$^+$: 466.2449, found: 466.2451.

Example 109. 1-(3-(4-(cyclopropanecarbonyl)piperazine-1-carbonyl)-6,7-dimethoxyquinolin-4-yl)-4-methylpiperidine-4-carbonitrile, TFA (Cpd. 109)

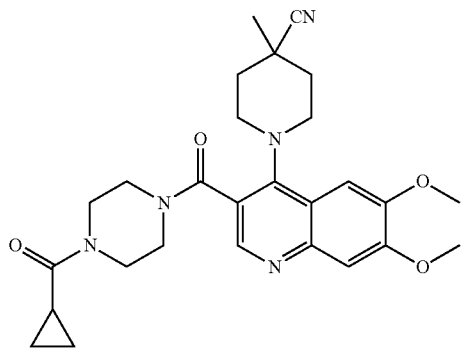

The title compound was prepared following the similar procedure as described in Example 1. $^1$H NMR (400 MHz, DMSO-$d_6$) δ 8.64 (s, 1H), 7.36 (s, 1H), 7.24 (s, 1H), 3.99 (s, 3H), 3.97 (s, 3H), 3.90-3.09 (m, 12H), 2.15-1.70 (m, 5H), 1.47 (s, 3H), 0.74 (dd, J=4.3, 2.5 Hz, 4H); LC-MS (Method 2): $t_R$=3.61 min, m/z (M+H)$^+$=492; HRMS calculated for $C_{27}H_{34}N_5O_4$ (M+H)$^+$: 492.2605, found: 492.2623.

Example 110. 1-(6,7-dimethoxy-3-(4-propionylpiperazine-1-carbonyl)quinolin-4-yl)-4-methylpiperidine-4-carbonitrile, TFA (Cpd. 110)

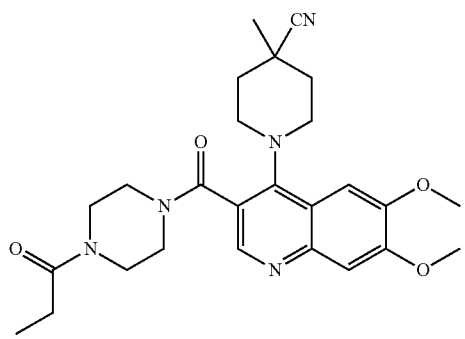

The title compound was prepared following the similar procedure as described in Example 1. $^1$H NMR (400 MHz, DMSO-$d_6$) δ 8.62 (s, 1H), 7.35 (s, 1H), 7.23 (s, 1H), 3.98 (s, 3H), 3.97 (s, 3H), 3.85-3.10 (m, 12H), 2.38 (d, J=7.4 Hz, 1H), 2.15-1.71 (m, 5H), 1.46 (s, 3H), 0.98 (q, J=7.9 Hz, 3H); LC-MS (Method 2): $t_R$=3.52 min, m/z (M+H)$^+$=480; HRMS calculated for $C_{26}H_{34}N_5O_4$ (M+H)$^+$: 480.2605, found: 480.2615.

Example 111. 1-(3-(4-isobutyrylpiperazine-1-carbonyl)-6,7-dimethoxyquinolin-4-yl)-4-methylpiperidine-4-carbonitrile, TFA (Cpd. 111)

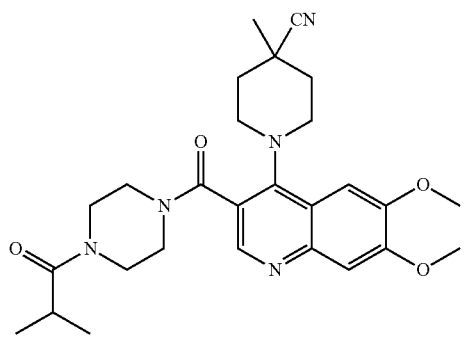

The title compound was prepared following the similar procedure as described in Example 1. $^1$H NMR (400 MHz, DMSO-$d_6$) δ 8.63 (s, 1H), 7.35 (s, 1H), 7.23 (s, 1H), 3.98 (s, 3H), 3.97 (s, 3H), 3.87-2.75 (m, 13H), 2.15-1.68 (m, 4H), 1.46 (s, 3H), 0.99 (d, J=7.1 Hz, 6H); LC-MS (Method 2): $t_R$=3.71 min, m/z (M+H)$^+$=494; HRMS calculated for $C_{27}H_{35}N_5O_4Na$ (M+Na)$^+$: 516.2581, found: 516.2562.

Example 112. 1-(3-(4-acetylpiperazine-1-carbonyl)-6,7-dimethoxyquinolin-4-yl)-4-methylpiperidine-4-carbonitrile, TFA (Cpd. 112)

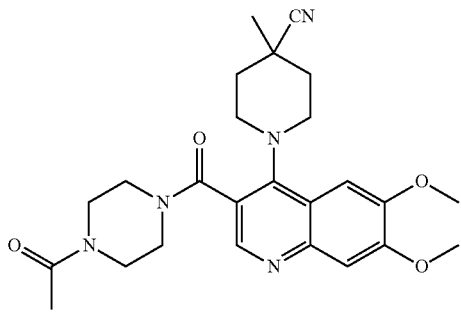

Cpd. 112

The title compound was prepared following the similar procedure as described in Example 1. $^1$H NMR (400 MHz, DMSO-d$_6$) δ 8.62 (s, 1H), 7.35 (s, 1H), 7.23 (s, 1H), 3.98 (s, 3H), 3.97 (s, 3H), 3.85-3.09 (m, 12H), 2.14-1.70 (m, 7H), 1.46 (s, 3H); LC-MS (Method 2): t$_R$=3.35 min, m/z (M+H)$^+$=466; HRMS calculated for C$_{25}$H$_{32}$N$_5$O$_4$ (M+H)$^+$: 466.2449, found: 466.2457.

Example 113. 1-(6,7-dimethoxy-3-(4-(methylsulfonyl)piperazine-1-carbonyl)quinolin-4-yl)-4-methylpiperidine-4-carbonitrile, TFA (Cpd. 113)

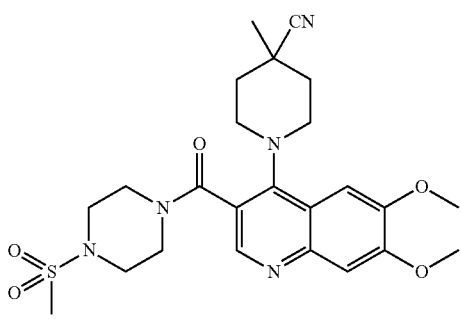

Cpd. 113

The title compound was prepared following the similar procedure as described in Example 1. $^1$H NMR (400 MHz, DMSO-d$_6$) δ 8.59 (s, 1H), 7.36 (s, 1H), 7.23 (s, 1H), 3.98 (s, 3H), 3.96 (s, 3H), 3.90-3.04 (m, 12H), 2.92 (s, 3H), 2.15-1.72 (m, 4H), 1.47 (s, 3H); LC-MS (Method 2): t$_R$=3.56 min, m/z (M+H)$^+$=502; HRMS calculated for C$_{24}$H$_{32}$N$_5$O$_5$S (M+H)$^+$: 502.2119, found: 502.2108.

Example 114. 1-(3-(4-(cyclopropylsulfonyl)piperazine-1-carbonyl)-6,7-dimethoxyquinolin-4-yl)-4-methylpiperidine-4-carbonitrile, TFA (Cpd. 114)

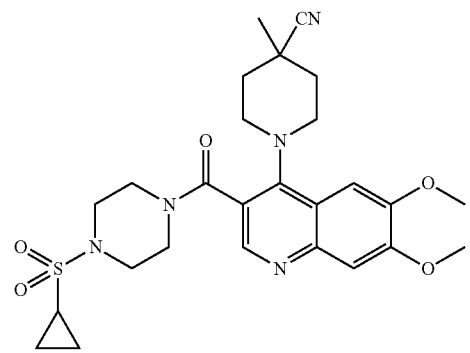

Cpd. 114

The title compound was prepared following the similar procedure as described in Example 1. $^1$H NMR (400 MHz, DMSO-d$_6$) δ 8.61 (s, 1H), 7.36 (s, 1H), 7.23 (s, 1H), 3.98 (s, 3H), 3.97 (s, 3H), 3.91-3.09 (m, 12H), 2.67-2.55 (m, 1H), 2.14-1.73 (m, 4H), 1.47 (s, 3H), 1.08-0.87 (m, 4H); LC-MS (Method 2): t$_R$=3.82 min, m/z (M+H)$^+$=528; HRMS calculated for C$_{26}$H$_{34}$N$_5$O$_5$S (M+H)$^+$: 528.2275, found: 528.2296.

Example 115. 4-(4-(4-cyano-4-methylpiperidin-1-yl)-6,7-dimethoxyquinoline-3-carbonyl)-N-ethylpiperazine-1-carboxamide, TFA (Cpd. 115)

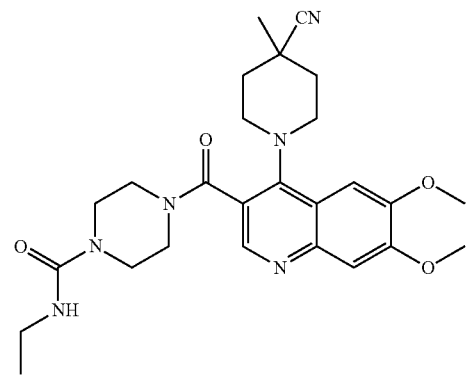

Cpd. 115

The title compound was prepared following the similar procedure as described in Example 1. $^1$H NMR (400 MHz, DMSO-$d_6$) δ 8.61 (s, 1H), 7.35 (s, 1H), 7.23 (s, 1H), 6.60 (t, J=5.3 Hz, 1H), 3.98 (s, 3H), 3.97 (s, 3H), 3.88-3.13 (m, 12H), 3.10-2.97 (m, 2H), 2.15-1.71 (m, 4H), 1.46 (s, 3H), 1.00 (t, J=7.1 Hz, 3H); LC-MS (Method 2): $t_R$=3.48 min, m/z (M+H)$^+$=495; HRMS calculated for $C_{26}H_{35}N_6O_4$ (M+H)$^+$: 495.2714, found: 495.2710.

Example 116. Ethyl 4-(4-(4-cyano-4-methylpiperidin-1-yl)-6,7-dimethoxyquinoline-3-carbonyl)piperazine-1-carboxylate, TFA (Cpd. 116)

Cpd. 116

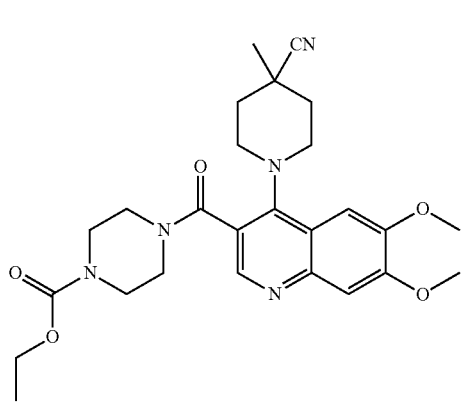

The title compound was prepared following the similar procedure as described in Example 1. $^1$H NMR (400 MHz, DMSO-$d_6$) δ 8.59 (s, 1H), 7.36 (s, 1H), 7.23 (s, 1H), 4.06 (q, J=7.1 Hz, 2H), 3.98 (s, 3H), 3.97 (s, 3H), 3.84-3.02 (m, 12H), 2.15-1.69 (m, 4H), 1.46 (s, 3H), 1.17 (td, J=7.1, 5.1 Hz, 3H); LC-MS (Method 2): $t_R$=3.87 min, m/z (M+H)$^+$=496; HRMS calculated for $C_{26}H_{34}N_5O_5$ (M+H)$^+$: 496.2554, found: 496.2544.

Example 117. 1-(6-chloro-3-(4-(cyclopropanecarbonyl)piperazine-1-carbonyl)quinolin-4-yl)-4-methylpiperidine-4-carbonitrile, TFA (Cpd. 117)

Cpd. 117

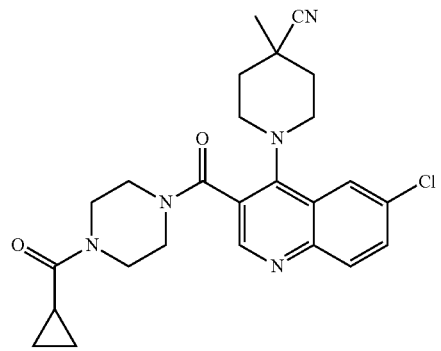

The title compound was prepared following the similar procedure as described in Example 1. $^1$H NMR (400 MHz, DMSO-$d_6$) δ 8.66 (s, 1H), 8.04 (d, J=2.3 Hz, 1H), 8.01 (d, J=9.0 Hz, 1H), 7.83 (dd, J=8.9, 2.3 Hz, 1H), 4.15-3.05 (m, 12H), 2.12-1.70 (m, 5H), 1.46 (s, 3H), 0.74 (dd, J=4.8, 2.4 Hz, 4H); LC-MS (Method 2): $t_R$=3.95 min, m/z (M+H)$^+$=466; HRMS calculated for $C_{25}H_{28}ClN_5O_2Na$ (M+Na)$^+$: 488.1824, found: 488.1824.

Example 118. 1-(6-chloro-3-(4-propionylpiperazine-1-carbonyl)quinolin-4-yl)-4-methylpiperidine-4-carbonitrile, TFA (Cpd. 118)

Cpd. 118

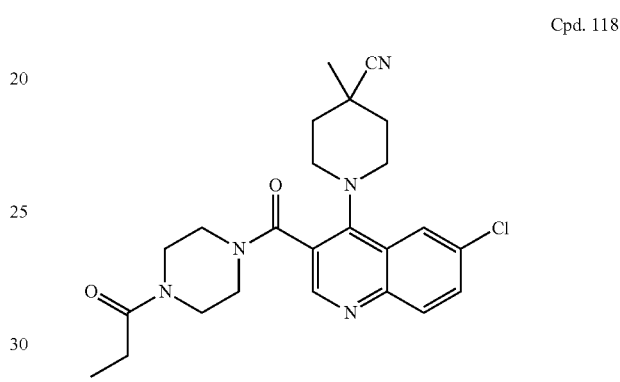

The title compound was prepared following the similar procedure as described in Example 1. $^1$H NMR (400 MHz, DMSO-$d_6$) δ 8.64 (s, 1H), 8.05-7.98 (m, 2H), 7.86-7.79 (m, 1H), 3.91-2.98 (m, 12H), 2.42-2.21 (m, 2H), 2.09-1.69 (m, 4H), 1.45 (s, 3H), 0.98 (t, J=7.3 Hz, 3H); LC-MS (Method 2): $t_R$=3.86 min, m/z (M+H)$^+$=454; HRMS calculated for $C_{24}H_{29}ClN_5O_2$(M+H)$^+$: 454.2004, found: 454.2012.

Example 119. 1-(6-chloro-3-(4-(methylsulfonyl)piperazine-1-carbonyl)quinolin-4-yl)-4-methylpiperidine-4-carbonitrile, TFA (Cpd. 119)

Cpd. 119

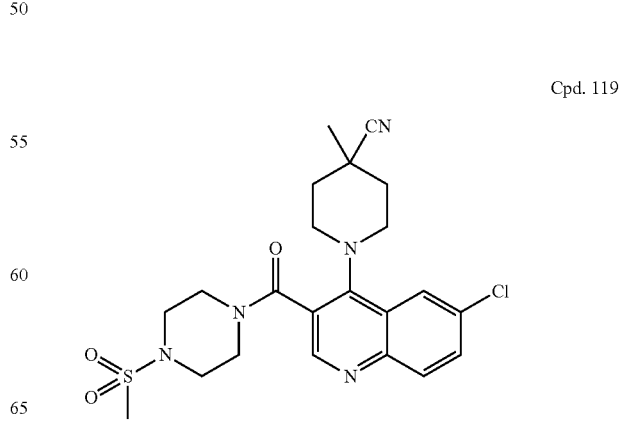

The title compound was prepared following the similar procedure as described in Example 1. $^1$H NMR (400 MHz, DMSO-$d_6$) δ 8.65 (d, J=1.4 Hz, 1H), 8.05-7.98 (m, 2H), 7.83 (dd, J=9.0, 2.3 Hz, 1H), 3.96-3.03 (m, 12H), 2.91 (s, 3H), 2.12-1.75 (m, 4H), 1.46 (s, 3H); LC-MS (Method 2): $t_R$=3.99 min, m/z (M+H)$^+$=476; HRMS calculated for $C_{22}H_{27}ClN_5O_3S$ (M+H)$^+$: 476.1518, found: 476.1528.

Example 120. 1-(6-chloro-3-(4-(cyclopropylsulfonyl)piperazine-1-carbonyl)quinolin-4-yl)-4-methylpiperidine-4-carbonitrile, TFA (Cpd. 120)

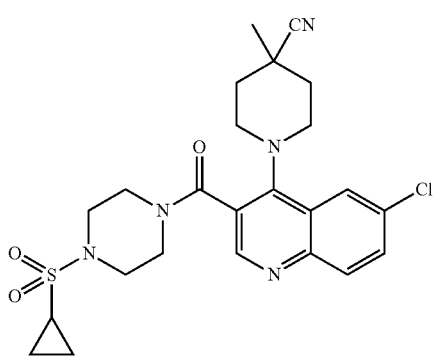

Cpd. 120

The title compound was prepared following the similar procedure as described in Example 1. $^1$H NMR (400 MHz, DMSO-$d_6$) δ 8.66 (s, 1H), 8.05-7.98 (m, 2H), 7.83 (dd, J=9.0, 2.2 Hz, 1H), 3.94-3.08 (m, 12H), 2.69-2.54 (m, 1H), 2.10-1.73 (m, 4H), 1.46 (s, 3H), 1.07-0.84 (m, 4H); LC-MS (Method 2): $t_R$=4.21 min, m/z (M+H)$^+$=503; HRMS calculated for $C_{24}H_{29}ClN_5O_3S$ (M+H)$^+$: 502.1674, found: 502.1682.

Example 121. 4-(6-chloro-4-(4-cyano-4-methylpiperidin-1-yl)quinoline-3-carbonyl)-N-ethylpiperazine-1-carboxamide, TFA (Cpd. 121)

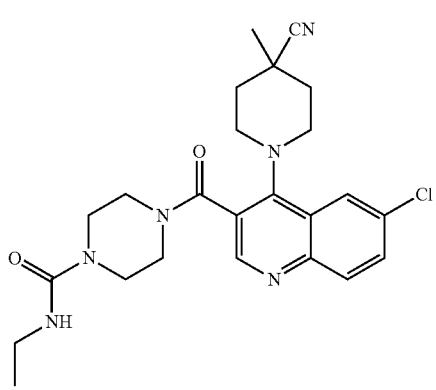

Cpd. 121

The title compound was prepared following the similar procedure as described in Example 1. $^1$H NMR (400 MHz, DMSO-$d_6$) δ 8.62 (s, 1H), 8.05-7.97 (m, 2H), 7.83 (dd, J=8.9, 2.3 Hz, 1H), 6.58 (s, 1H), 3.72-3.08 (m, 12H), 3.08-2.97 (m, 2H), 2.12-1.72 (m, 4H), 1.45 (s, 3H), 0.99 (t, J=7.1 Hz, 3H); LC-MS (Method 2): $t_R$=3.78 min, m/z (M+H)$^+$=469; HRMS calculated for $C_{24}H_{30}ClN_6O_2$ (M+H)$^+$: 469.2113, found: 469.2112.

Example 122. (4-(cyclopropanecarbonyl)piperazin-1-yl)(6,7-difluoro-4-(1,4-dioxa-8-azaspiro[4.5]decan-8-yl)quinolin-3-yl)methanone, TFA (Cpd. 122)

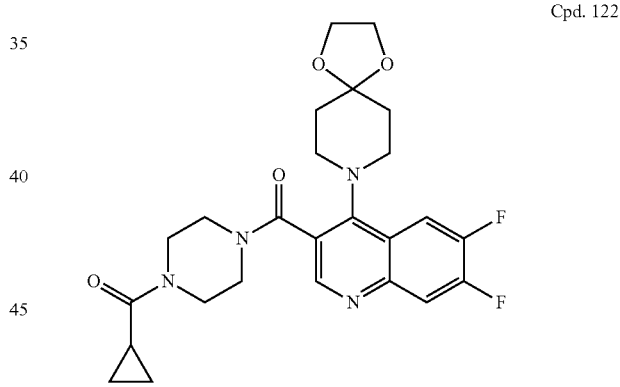

Cpd. 122

The title compound was prepared following the similar procedure as described in Example 1. $^1$H NMR (400 MHz, DMSO-$d_6$) δ 8.60 (s, 1H), 8.03-7.86 (m, 2H), 3.96-3.88 (m, 4H), 3.85-2.99 (m, 12H), 2.07-1.70 (m, 5H), 0.72 (d, J=4.6 Hz, 4H); LC-MS (Method 2): $t_R$=3.79 min, m/z (M+H)$^+$=487; HRMS calculated for $C_{25}H_{29}F_2N_4O_4$ (M+H)$^+$: 487.2151, found: 487.2152.

Example 123. (4-(cyclopropanecarbonyl)piperazin-1-yl)(6,8-difluoro-7-methoxy-4-(1,4-dioxa-8-azaspiro[4.5]decan-8-yl)quinolin-3-yl)methanone, Tfa (Cpd. 123) and Example 124. (4-(cyclopropanecarbonyl)piperazin-1-yl)(6,7,8-trifluoro-4-(1,4-dioxa-8-azaspiro[4.5]decan-8-yl)quinolin-3-yl)methanone, TFA (Cpd. 124)

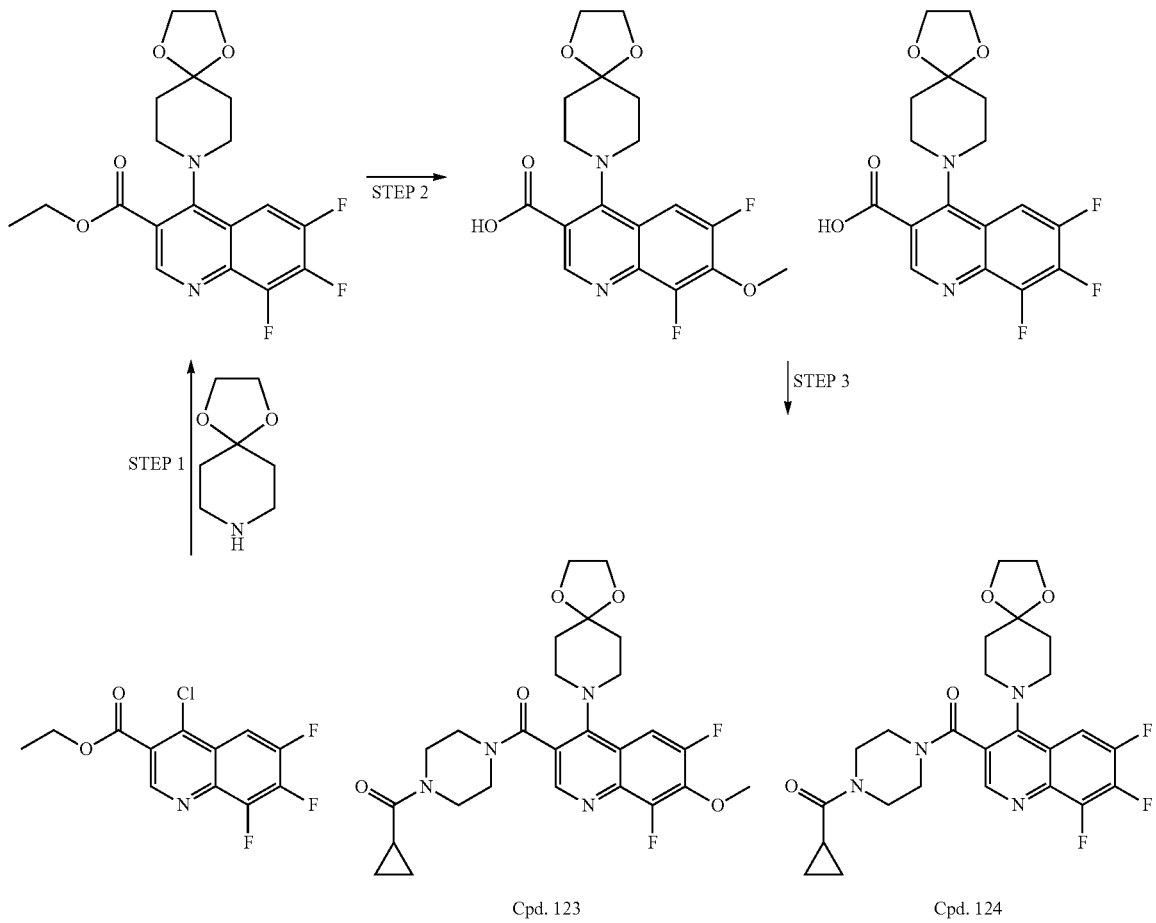

Cpd. 123

Cpd. 124

STEP 1: Synthesis of Ethyl 6,7,8-trifluoro-4-(1,4-dioxa-8-azaspiro[4.5]decan-8-yl)quinoline-3-carboxylate. In a microwave vial was placed ethyl 4-chloro-6,7,8-trifluoroquinoline-3-carboxylate (290 mg, 1 mmol) and 1,4-dioxa-8-azaspiro[4.5]decane (286 mg, 2.0 mmol). Then EtOH (4 ml) and Hunig's base (0.349 ml, 2.0 mmol) were added sequentially. The tube was sealed and heated at 80° C. for 3 h. After cooling to rt, the mixture was concentrated and purified by silica gel chromatography using 10-30% EtOAc/hexane as the eluent to give ethyl 6,7,8-trifluoro-4-(1,4-dioxa-8-azaspiro[4.5]decan-8-yl)quinoline-3-carboxylate (367 mg, 0.926 mmol, 93% yield). LC-MS (Method 1): $t_R$=3.48 min, m/z (M+H)$^+$=397.

STEP 2: Synthesis of 6,8-Difluoro-7-methoxy-4-(1,4-dioxa-8-azaspiro[4.5]decan-8-yl)quinoline-3-carboxylic acid, and 6,7,8-Trifluoro-4-(1,4-dioxa-8-azaspiro[4.5]decan-8-yl)quinoline-3-carboxylic acid. To a solution of ethyl 6,7,8-trifluoro-4-(1,4-dioxa-8-azaspiro[4.5]decan-8-yl)quinoline-3-carboxylate (396 mg, 0.999 mmol) in THF (3 ml)/MeOH (1 ml) was added 1N NaOH$_{(aq)}$ (3 mL). The mixture was heated at 50° C. for 15 min. The mixture was then stirred at rt for 6 h. Then, 1N HCl$_{(aq)}$ was added until the pH of water layer is ca. 4. The mixture was concentrated to remove the solvent, including water. The crude product was triturated with H$_2$O (2 mL×3), hexane (3 mL×2) and then dried to give 268 mg of a mixture of 6,7,8-trifluoro-4-(1,4-dioxa-8-azaspiro[4.5]decan-8-yl)quinoline-3-carboxylic acid (LC-MS (Method 1): $t_R$=2.72 min, m/z M+H)$^+$=381) and 6,8-difluoro-7-methoxy-4-(1,4-dioxa-8-azaspiro[4.5]decan-8-yl)quinoline-3-carboxylic acid (LC-MS (Method 1): $t_R$=3.07 min, m/z (M+H)$^+$=369). The mixture was used for next step without further purification.

STEP 3: Synthesis of (4-(Cyclopropanecarbonyl)piperazin-1-yl)(6,8-difluoro-7-methoxy-4-(1,4-dioxa-8-azaspiro[4.5]decan-8-yl)quinolin-3-yl)methanone, TFA (Cpd. 123) and (4-(Cyclopropanecarbonyl)piperazin-1-yl)(6,7,8-trifluoro-4-(1,4-dioxa-8-azaspiro[4.5]decan-8-yl)quinolin-3-yl)methanone, TFA (Cpd. 124). To a mixture of 6,7,8-trifluoro-4-(1,4-dioxa-8-azaspiro[4.5]decan-8-yl)quinoline-3-carboxylic acid (14.73 mg, 0.04 mmol), 6,8-difluoro-7-methoxy-4-(1,4-dioxa-8-azaspiro[4.5]decan-8-yl)quinoline-3-carboxylic acid (15.21 mg, 0.040 mmol), cyclopropyl (piperazin-1-yl)methanone, HCl (36.6 mg, 0.192 mmol), and HATU (73.0 mg, 0.192 mmol) was added DMF (1 ml) and then Hunig's base (0.14 ml, 0.80 mmol). The mixture was stirred at rt for 1.5 h. The mixture was filtered through a filter and submitted for purification by semi-preparative HPLC to give (4-(cyclopropanecarbonyl)piperazin-1-yl)(6,8-difluoro-7-methoxy-4-(1,4-dioxa-8-azaspiro[4.5]decan-8- yl)quinolin-3-yl)methanone, TFA (6.6 mg, 10.47 timol, 26.2% yield) (Cpd. 123, $^1$H NMR (400 MHz, DMSO-d$_6$) δ 8.55 (s, 1H), 7.60 (dd, J=12.3, 1.7 Hz, 1H), 4.08 (s, 3H), 3.95-3.85 (m, 4H), 3.84-2.94 (m, 12H), 2.09-1.61 (m, 5H), 0.72 (d, J=4.7 Hz, 4H); LC-MS (Method 2): t$_R$=4.09 min, m/z (M+H)$^+$=517; HRMS calculated for C$_{26}$H$_{31}$F$_2$N$_4$O$_5$ (M+H)$^+$: 517.2257, found: 517.2270) and (4-(cyclopropanecarbonyl)piperazin-1-yl)(6,7,8-trifluoro-4-(1,4-dioxa-8-azaspiro[4.5]decan-8-yl)quinolin-3-yl)methanone, TFA (9.6 mg, 0.016 mmol, 38.8% yield) (Cpd. 124, $^1$H NMR (400 MHz, DMSO-d$_6$) δ 8.63 (s, 1H), 7.77 (dd, J=11.2, 8.0 Hz, 1H), 3.94-3.88 (m, 4H), 3.87-2.93 (m, 12H), 2.09-1.67 (m, 5H), 0.72 (d, J=4.7 Hz, 4H); LC-MS (Method 2): t$_R$=4.65 min, m/z (M+H)$^+$=505; HRMS calculated for C$_{25}$H$_{28}$F$_3$N$_4$O$_4$ (M+H)$^+$: 505.2057, found: 505.2034).

Example 125. 1-(3-(4-(cyclopropanecarbonyl)piperazine-1-carbonyl)-6,8-difluoroquinolin-4-yl)-4-methylpiperidine-4-carbonitrile, TFA (Cpd. 125)

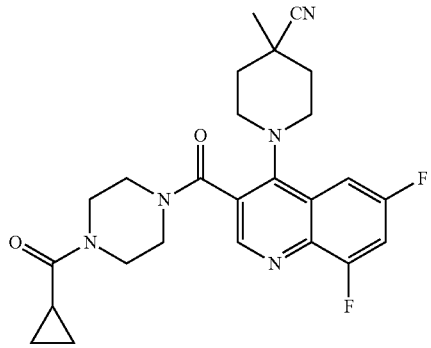

Cpd. 125

The title compound was prepared following the similar procedure as described in Example 1. $^1$H NMR (400 MHz, DMSO-d$_6$) δ 8.60 (s, 1H), 7.77 (ddd, J=11.4, 9.0, 2.7 Hz, 1H), 7.55 (dt, J=10.1, 2.0 Hz, 1H), 4.04-2.79 (m, 12H), 2.16-1.64 (m, 5H), 1.43 (s, 3H), 0.72 (d, J=4.8 Hz, 4H); LC-MS (Method 2): t$_R$=4.47 min, m/z (M+H)$^+$=468; HRMS calculated for C$_{25}$H$_{28}$F$_2$N$_5$O$_2$ (M+H)$^+$: 468.2206, found: 468.2223.

Example 126. 1-(3-(4-(cyclopropanecarbonyl)piperazine-1-carbonyl)-6,7-difluoroquinolin-4-yl)-4-methylpiperidine-4-carbonitrile, TFA (Cpd. 126)

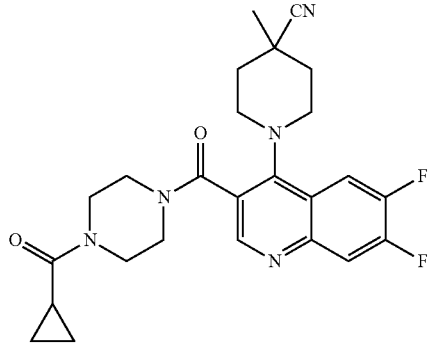

Cpd. 126

The title compound was prepared following the similar procedure as described in Example 1. $^1$H NMR (400 MHz, DMSO-d$_6$) δ 8.62 (s, 1H), 8.01 (dd, J=11.4, 7.8 Hz, 1H), 7.93 (dd, J=11.8, 8.7 Hz, 1H), 4.56-2.83 (m, 12H), 2.12-1.68 (m, 5H), 1.43 (s, 3H), 0.72 (d, J=4.8 Hz, 4H); LC-MS (Method 2): t$_R$=4.12 min, m/z (M+H)$^+$=468; HRMS calculated for C$_{25}$H$_{28}$F$_2$N$_5$O$_2$ (M+H)$^+$: 468.2206, found: 468.2229.

Example 127. 1-(3-(4-(cyclopropanecarbonyl)piperazine-1-carbonyl)-6,8-difluoro-7-methoxyquinolin-4-yl)-4-methylpiperidine-4-carbonitrile, TFA (Cpd. 127)

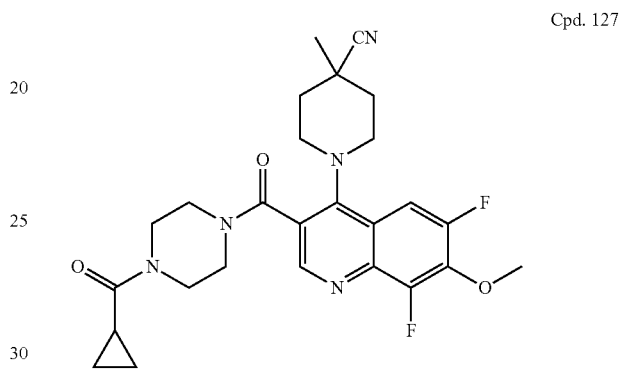

Cpd. 127

The title compound was prepared following the similar procedure as described in Example 123 and 124. LC-MS (Method 2): t$_R$=4.44 min, m/z (M+H)$^+$=498; HRMS calculated for C$_{26}$H$_{30}$F$_2$N$_5$O$_3$ (M+H)$^+$: 498.2311, found: 498.2312.

Example 128. 1-(3-(4-(cyclopropanecarbonyl)piperazine-1-carbonyl)-6,7,8-trifluoroquinolin-4-yl)-4-methylpiperidine-4-carbonitrile, TFA (Cpd. 128)

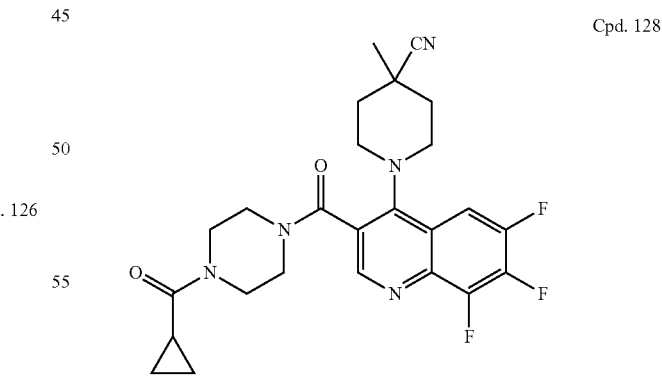

Cpd. 128

The title compound was prepared following the similar procedure as described in Example 123 and 124. $^1$H NMR (400 MHz, DMSO-d$_6$) δ 8.66 (s, 1H), 7.96-7.62 (m, 1H), 4.00-2.93 (m, 12H), 2.14-1.70 (m, 5H), 1.43 (s, 3H), 0.72 (d, J=4.9 Hz, 4H); LC-MS (Method 2): t$_R$=4.90 min, m/z (M+H)$^+$=486; HRMS calculated for C$_{25}$H$_{27}$F$_3$N$_5$O$_2$ (M+H)$^+$: 486.2111, found: 486.2100.

Example 129. (7-methoxy-4-(1,4-dioxa-8-azaspiro[4.5]decan-8-yl)quinolin-3-yl)(4-(methylsulfonyl)piperazin-1-yl)methanone, TFA (Cpd. 129)

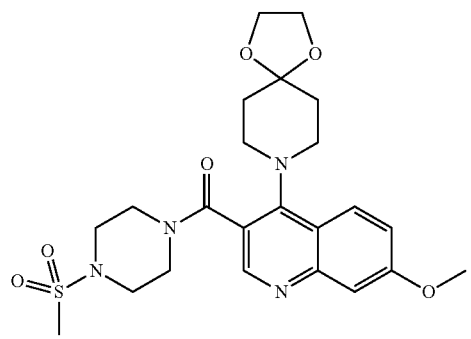

Cpd. 129

The title compound was prepared following the similar procedure as described in Example 1. $^1$H NMR (400 MHz, DMSO-d$_6$) δ 8.66 (d, J=1.4 Hz, 1H), 8.08 (d, J=9.2 Hz, 1H), 7.39-7.25 (m, 2H), 3.93 (m, 7H), 3.87-3.00 (m, 12H), 2.92 (s, 3H), 2.06-1.73 (m, 4H); LC-MS (Method 2): t$_R$=3.56 min, m/z (M+H)$^+$=491; HRMS calculated for C$_{23}$H$_{31}$N$_4$O$_6$S (M+H)$^+$: 491.1959, found: 491.1962.

Example 130. (6,7-dimethoxy-4-(1,4-dioxa-8-azaspiro[4.5]decan-8-yl)quinolin-3-yl)(4-(methylsulfonyl)piperazin-1-yl)methanone, TFA (Cpd. 130)

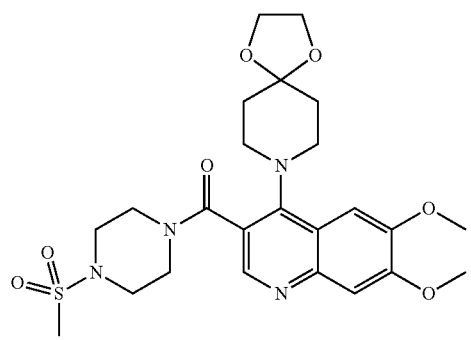

Cpd. 130

The title compound was prepared following the similar procedure as described in Example 1. $^1$H NMR (400 MHz, DMSO-d$_6$) δ 8.59 (s, 1H), 7.34 (s, 1H), 7.26 (s, 1H), 4.00-3.90 (m, 10H), 3.89-3.01 (m, 12H), 2.92 (s, 3H), 2.02-1.77 (m, 4H); LC-MS (Method 2): t$_R$=3.44 min, m/z M+H)$^+$=521; HRMS calculated for C$_{24}$H$_{33}$N$_4$O$_7$S (M+H)$^+$: 521.2064, found: 521.2066.

Example 131. (6,8-difluoro-4-(1,4-dioxa-8-azaspiro[4.5]decan-8-yl)quinolin-3-yl)(4-(methylsulfonyl)piperazin-1-yl)methanone, TFA (Cpd. 131)

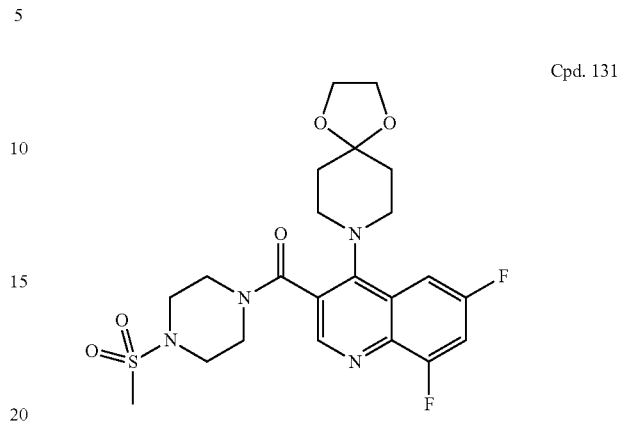

Cpd. 131

The title compound was prepared following the similar procedure as described in Example 1. $^1$H NMR (400 MHz, DMSO-d$_6$) δ 8.58 (s, 1H), 7.76 (ddd, J=10.5, 8.9, 2.7 Hz, 1H), 7.54 (dt, J=9.9, 1.9 Hz, 1H), 4.05-2.95 (m, 16H), 2.92 (s, 3H), 1.97-1.71 (m, 4H); LC-MS (Method 2): t$_R$=4.06 min, m/z (M+H)$^+$=497; HRMS calculated for C$_{22}$H$_{27}$F$_2$N$_4$O$_5$S (M+H)$^+$: 497.1665, found: 497.1663.

Example 132. (6,7-difluoro-4-(1,4-dioxa-8-azaspiro[4.5]decan-8-yl)quinolin-3-yl)(4-(methylsulfonyl)piperazin-1-yl)methanone, TFA (Cpd. 132)

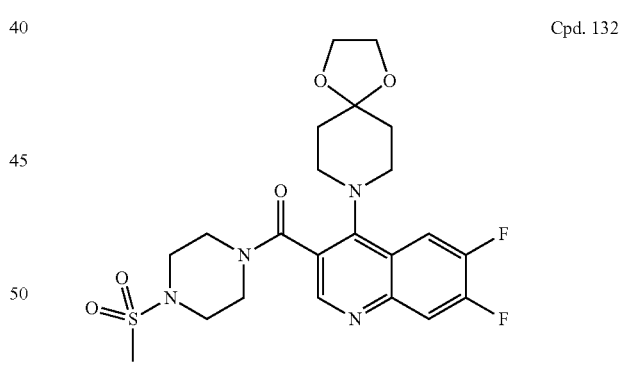

Cpd. 132

The title compound was prepared following the similar procedure as described in Example 1. $^1$H NMR (400 MHz, DMSO-d$_6$) δ 8.59 (s, 1H), 7.99 (dd, J=11.4, 7.8 Hz, 1H), 7.93 (dd, J=11.8, 8.8 Hz, 1H), 3.97-2.97 (m, 16H), 2.91 (s, 3H), 1.99-1.72 (m, 4H); LC-MS (Method 2): t$_R$=3.77 min, m/z (M+H)$^+$=497; HRMS calculated for C$_{22}$H$_{26}$F$_2$N$_4$O$_5$SNa (M+Na)$^+$: 519.1484, found: 519.1496.

Example 133. (6,8-difluoro-7-methoxy-4-(1,4-di-oxa-8-azaspiro[4.5]decan-8-yl)quinolin-3-yl)(4-(methylsulfonyl)piperazin-1-yl)methanone, TFA (Cpd. 133)

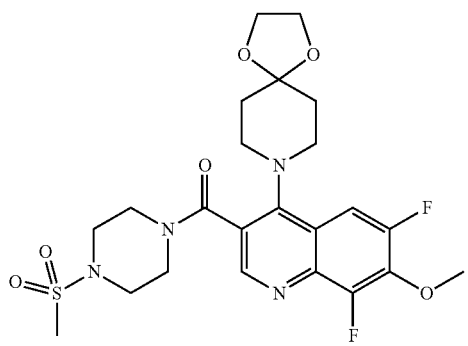

Cpd. 133

The title compound was prepared following the similar procedure as described in Example 123 and 124. $^1$H NMR (400 MHz, DMSO-d$_6$) δ 8.56 (s, 1H), 7.60 (dd, J=12.3, 1.7 Hz, 1H), 4.08 (s, 3H), 3.94-3.87 (m, 4H), 3.64-2.94 (m, 12H), 2.91 (s, 3H), 1.97-1.70 (m, 4H); LC-MS (Method 2): $t_R$=4.11 min, m/z (M+H)$^+$=527; HRMS calculated for C$_{23}$H$_{29}$F$_2$N$_4$O$_6$S (M+H)$^+$: 527.1770, found: 527.1785.

Example 134. (4-(methylsulfonyl)piperazin-1-yl)(6,7,8-trifluoro-4-(1,4-dioxa-8-azaspiro[4.5]decan-8-yl)quinolin-3-yl)methanone, TFA (Cpd. 134)

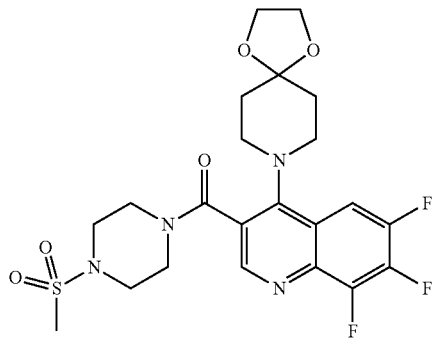

Cpd. 134

The title compound was prepared following the similar procedure as described in Example 123 and 124. $^1$H NMR (400 MHz, DMSO-d$_6$) δ 8.64 (s, 1H), 7.86-7.64 (m, 1H), 3.93-3.88 (m, 4H), 3.64-2.96 (m, 12H), 2.91 (s, 3H), 2.00-1.71 (m, 4H); LC-MS (Method 2): $t_R$=4.67 min, m/z (M+H)$^+$=515; HRMS calculated for C$_{22}$H$_{26}$F$_3$N$_4$O$_5$S (M+H)$^+$: 515.1571, found: 515.1566.

Example 135. 1-(6,8-difluoro-3-(4-(methylsulfonyl)piperazine-1-carbonyl)quinolin-4-yl)-4-methylpiperidine-4-carbonitrile, TFA (Cpd. 135)

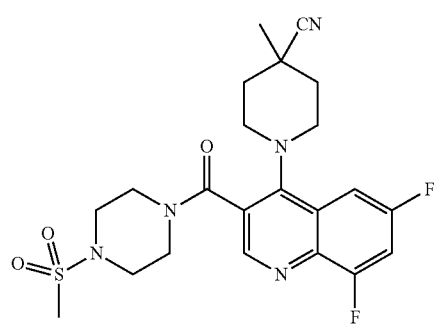

Cpd. 135

The title compound was prepared following the similar procedure as described in Example 1. $^1$H NMR (400 MHz, DMSO-d$_6$) δ 8.60 (s, 1H), 7.77 (ddd, J=10.4, 8.9, 2.7 Hz, 1H), 7.58-7.51 (m, 1H), 3.97-2.97 (m, 12H), 2.90 (s, 3H), 2.06-1.74 (m, 4H), 1.43 (s, 3H); LC-MS (Method 2): $t_R$=4.51 min, m/z (M+H)$^+$=478; HRMS calculated for C$_{22}$H$_{26}$F$_2$N$_5$O$_3$S (M+H)$^+$: 478.1719, found: 478.1735.

Example 136. 1-(6,7-difluoro-3-(4-(methylsulfonyl)piperazine-1-carbonyl)quinolin-4-yl)-4-methylpiperidine-4-carbonitrile, TFA (Cpd. 136)

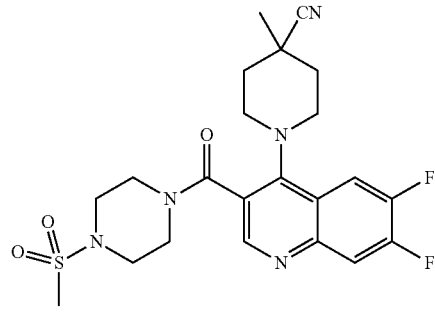

Cpd. 136

The title compound was prepared following the similar procedure as described in Example 1. $^1$H NMR (400 MHz, DMSO-d$_6$) δ 8.61 (s, 1H), 8.01 (dd, J=11.4, 7.8 Hz, 1H), 7.93 (dd, J=11.8, 8.7 Hz, 1H), 3.95-2.99 (m, 12H), 2.90 (s, 3H), 2.09-1.74 (m, 4H), 1.43 (s, 3H); LC-MS (Method 2): $t_R$=4.16 min, m/z (M+H)$^+$=478; HRMS calculated for C$_{22}$H$_{26}$F$_2$N$_5$O$_3$S (M+H)$^+$: 478.1719, found: 478.1734.

Example 137. 1-(6,8-difluoro-7-methoxy-3-(4-(methylsulfonyl)piperazine-1-carbonyl)quinolin-4-yl)-4-methylpiperidine-4-carbonitrile, TFA (Cpd. 137)

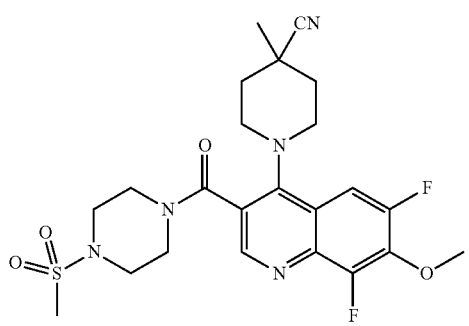

The title compound was prepared following the similar procedure as described in Example 123 and 124. LC-MS (Method 2): $t_R$=4.48 min, m/z (M+H)$^+$=508; HRMS calculated for $C_{23}H_{28}F_2N_5O_4S$ (M+H)$^+$: 508.1825, found: 508.1847.

Example 138. 4-methyl-1-(6,7,8-trifluoro-3-(4-(methylsulfonyl)piperazine-1-carbonyl)quinolin-4-yl)piperidine-4-carbonitrile, TFA (Cpd. 138)

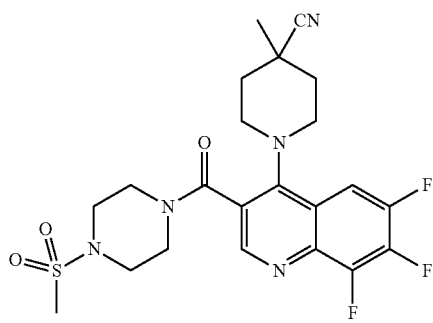

The title compound was prepared following the similar procedure as described in Example 123 and 124. $^1$H NMR (400 MHz, DMSO-d$_6$) δ 8.66 (s, 1H), 7.78 (dd, J=11.2, 7.7 Hz, 1H), 3.97-2.96 (m, 12H), 2.90 (s, 3H), 2.12-1.75 (m, 4H), 1.43 (s, 3H); LC-MS (Method 2): $t_R$=4.94 min, m/z (M+H)$^+$=496; HRMS calculated for $C_{22}H_{25}F_3N_5O_3S$ (M+H)$^+$: 496.1625, found: 496.1636.

Example 139. N-ethyl-4-(7-methoxy-4-(1,4-dioxa-8-azaspiro[4.5]decan-8-yl)quinoline-3-carbonyl)piperazine-1-carboxamide, TFA (Cpd. 139)

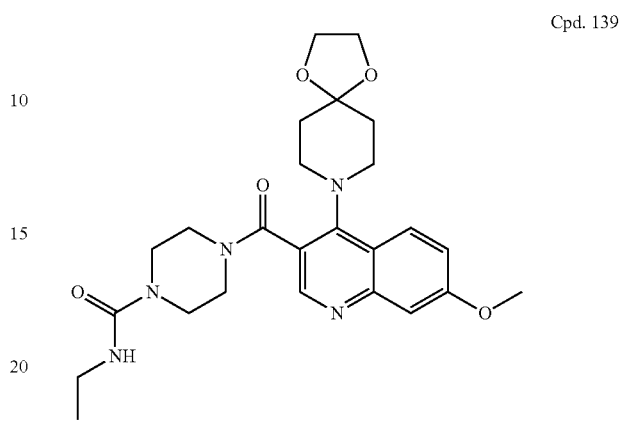

The title compound was prepared following the similar procedure as described in Example 1. $^1$H NMR (400 MHz, DMSO-d$_6$) δ 8.64 (s, 1H), 8.08 (d, J=9.3 Hz, 1H), 7.37-7.25 (m, 2H), 6.62 (t, J=5.4 Hz, 1H), 3.97-3.88 (m, 7H), 3.70-3.13 (m, 12H), 3.03 (qd, J=7.1, 5.1 Hz, 2H), 2.09-1.72 (m, 4H), 0.99 (t, J=7.1 Hz, 3H); LC-MS (Method 2): $t_R$=3.48 min, m/z (M+H)$^+$=484; HRMS calculated for $C_{25}H_{34}N_5O_5$ (M+H)$^+$: 484.2554, found: 484.2568.

Example 140. 4-(6,7-dimethoxy-4-(1,4-dioxa-8-azaspiro[4.5]decan-8-yl)quinoline-3-carbonyl)-N-ethylpiperazine-1-carboxamide, TFA (Cpd. 140)

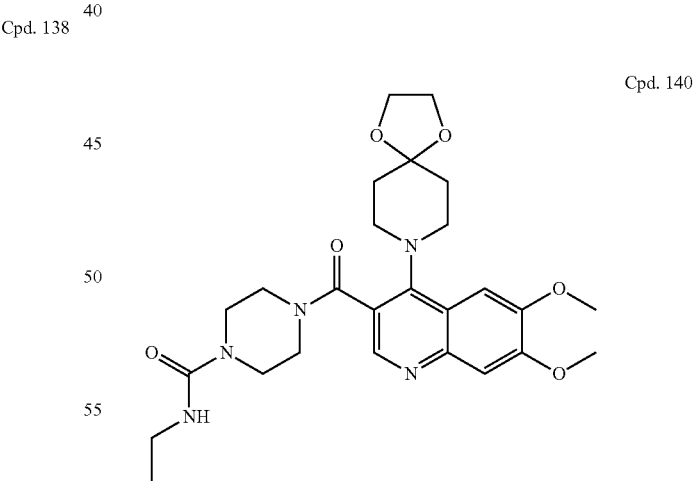

The title compound was prepared following the similar procedure as described in Example 1. $^1$H NMR (400 MHz, DMSO-d$_6$) δ 8.60 (s, 1H), 7.34 (d, J=1.2 Hz, 1H), 7.25 (s, 1H), 6.62 (t, J=5.4 Hz, 1H), 3.96 (s, 6H), 3.93 (s, 4H), 3.67-3.15 (m, 12H), 3.03 (qd, J=7.2, 5.2 Hz, 2H), 2.04-1.75 (m, 4H), 0.99 (t, J=7.1 Hz, 3H); LC-MS (Method 2): $t_R$=3.36 min, m/z (M+H)$^+$=514; HRMS calculated for $C_{26}H_{36}N_5O_6$ (M+H)$^+$: 514.2660, found: 514.2643.

Example 141. 4-(6,8-difluoro-4-(1,4-dioxa-8-azaspiro[4.5]decan-8-yl)quinoline-3-carbonyl)-N-ethylpiperazine-1-carboxamide, TFA (Cpd. 141)

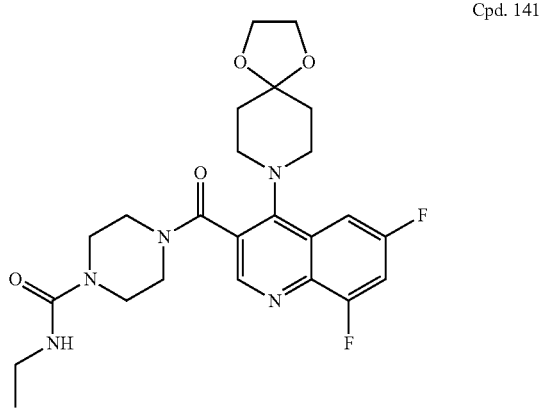 [SMILES: CCNC(=O)N1CCN(C(=O)c2cnc3c(F)cc(F)cc3c2N2CCC3(CC2)OCCO3)CC1]

Cpd. 141

The title compound was prepared following the similar procedure as described in Example 1. $^1$H NMR (400 MHz, DMSO-$d_6$) δ 8.54 (s, 1H), 7.75 (ddd, J=10.5, 8.9, 2.7 Hz, 1H), 7.64-7.44 (m, 1H), 6.60 (s, 1H), 4.03-2.89 (m, 18H), 1.97-1.67 (m, 4H), 0.98 (t, J=7.1 Hz, 3H); LC-MS (Method 2): $t_R$=3.87 min, m/z (M+H)$^+$=490; HRMS calculated for $C_{24}H_{30}F_2N_5O_4$ (M+H)$^+$: 490.2260, found: 490.2254.

Example 142. 4-(6,7-difluoro-4-(1,4-dioxa-8-azaspiro[4.5]decan-8-yl)quinoline-3-carbonyl)-N-ethylpiperazine-1-carboxamide, TFA (Cpd. 142)

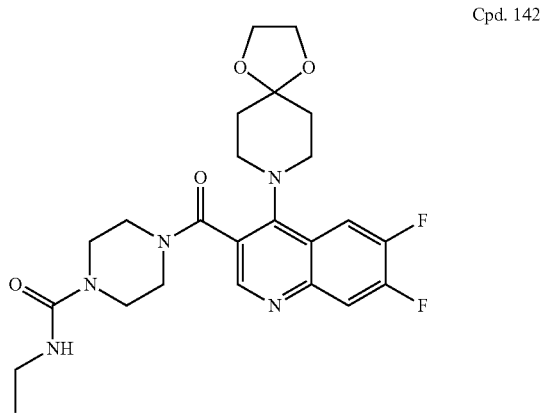 [SMILES: CCNC(=O)N1CCN(C(=O)c2cnc3cc(F)c(F)cc3c2N2CCC3(CC2)OCCO3)CC1]

Cpd. 142

The title compound was prepared following the similar procedure as described in Example 1. $^1$H NMR (400 MHz, DMSO-$d_6$) δ 8.57 (d, J=2.7 Hz, 1H), 7.96 (m, 2H), 6.60 (s, 1H), 3.95-2.93 (m, 18H), 2.00-1.66 (m, 4H), 0.98 (t, J=7.1 Hz, 3H); LC-MS (Method 2): $t_R$=4.22 min, m/z (M+H)$^+$=490; HRMS calculated for $C_{24}H_{30}F_2N_5O_4$ (M+H)$^+$: 490.2260, found: 490.2247.

Example 143. 4-(6,8-difluoro-7-methoxy-4-(1,4-dioxa-8-azaspiro[4.5]decan-8-yl)quinoline-3-carbonyl)-N-ethylpiperazine-1-carboxamide, TFA (Cpd. 143)

Cpd. 143

The title compound was prepared following the similar procedure as described in Example 123 and 124. LC-MS (Method 2): $t_R$=3.87 min, m/z (M+H)$^+$=520; HRMS calculated for $C_{25}H_{32}F_2N_5O_5$ (M+H)$^+$: 520.2366, found: 520.2379.

Example 144. N-ethyl-4-(6,7,8-trifluoro-4-(1,4-dioxa-8-azaspiro[4.5]decan-8-yl)quinoline-3-carbonyl)piperazine-1-carboxamide, TFA (Cpd. 144)

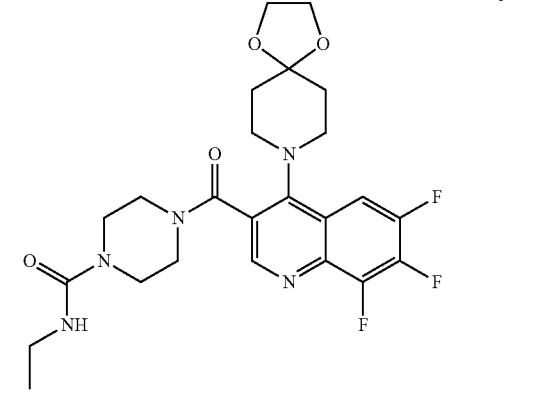

Cpd. 144

The title compound was prepared following the similar procedure as described in Example 123 and 124. $^1$H NMR (400 MHz, DMSO-$d_6$) δ 8.60 (s, 1H), 7.77 (ddd, J=11.6, 8.0, 1.9 Hz, 1H), 6.60 (s, 1H), 3.95-3.85 (m, 4H), 3.73-2.95 (m, 14H), 2.01-1.69 (m, 4H), 0.98 (t, J=7.1 Hz, 3H); LC-MS (Method 2): $t_R$=4.38 min, m/z (M+H)$^+$=508; HRMS calculated for $C_{24}H_{29}F_3N_5O_4$ (M+H)$^+$: 508.2166, found: 508.2151.

Example 145. 4-(4-(4-cyano-4-methylpiperidin-1-yl)-6,8-difluoroquinoline-3-carbonyl)-N-ethylpiperazine-1-carboxamide, TFA (Cpd. 145)

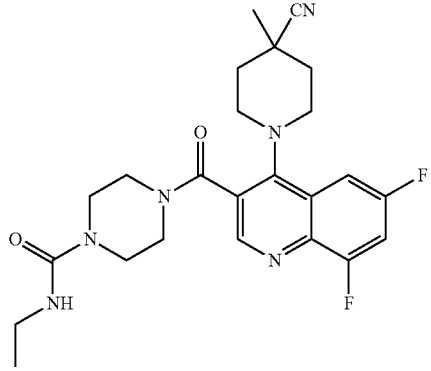
Cpd. 145

The title compound was prepared following the similar procedure as described in Example 1. $^1$H NMR (400 MHz, DMSO-$d_6$) δ 8.57 (s, 1H), 7.76 (ddd, J=10.5, 8.9, 2.7 Hz, 1H), 7.54 (ddd, J=10.1, 2.8, 1.3 Hz, 1H), 6.60 (s, 1H), 3.73-2.97 (m, 14H), 2.06-1.69 (m, 4H), 1.42 (s, 3H), 0.98 (t, J=7.2 Hz, 3H); LC-MS (Method 2): $t_R$=4.22 min, m/z (M+H)$^+$=471; HRMS calculated for $C_{24}H_{29}F_2N_6O_2$ (M+H)$^+$: 471.2315, found: 471.2294.

Example 146. 4-(4-(4-cyano-4-methylpiperidin-1-yl)-6,7-difluoroquinoline-3-carbonyl)-N-ethylpiperazine-1-carboxamide, TFA (Cpd. 146)

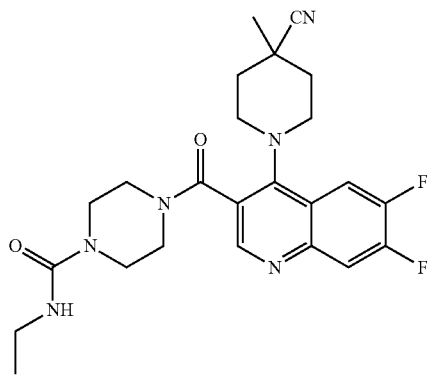
Cpd. 146

The title compound was prepared following the similar procedure as described in Example 1. $^1$H NMR (400 MHz, DMSO-$d_6$) δ 8.59 (d, J=2.1 Hz, 1H), 8.00 (dd, J=11.4, 7.9 Hz, 1H), 7.97-7.88 (m, 1H), 6.60 (s, 1H), 3.70-2.88 (m, 14H), 2.10-1.69 (m, 4H), 1.42 (s, 3H), 0.98 (t, J=7.1 Hz, 3H); LC-MS (Method 2): $t_R$=3.86 min, m/z (M+H)$^+$=471; HRMS calculated for $C_{24}H_{29}F_2N_6O_2$ (M+H)$^+$: 471.2315, found: 471.2314.

Example 147. 4-(4-(4-cyano-4-methylpiperidin-1-yl)-6,8-difluoro-7-methoxyquinoline-3-carbonyl)-N-ethylpiperazine-1-carboxamide, TFA (Cpd. 147)

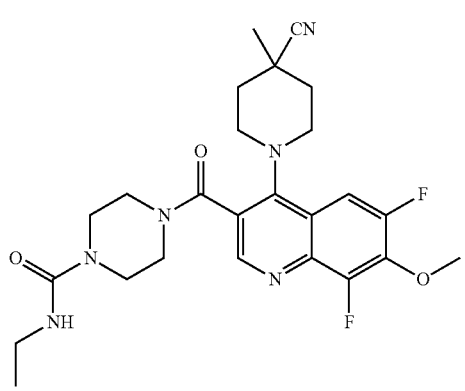
Cpd. 147

The title compound was prepared following the similar procedure as described in Example 123 and 124. LC-MS (Method 2): $t_R$=4.20 min, m/z (M+H)$^+$=501; HRMS calculated for $C_{25}H_{30}F_2N_6O_3Na$ (M+Na)$^+$: 523.2240, found: 523.2262.

Example 148. 4-(4-(4-cyano-4-methylpiperidin-1-yl)-6,7,8-trifluoroquinoline-3-carbonyl)-N-ethylpiperazine-1-carboxamide, TFA (Cpd. 148)

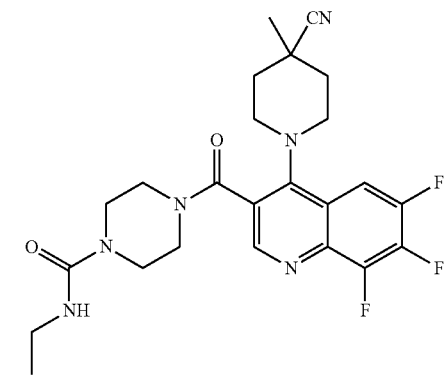
Cpd. 148

The title compound was prepared following the similar procedure as described in Example 123 and 124. $^1$H NMR (400 MHz, DMSO-$d_6$) δ 8.63 (s, 1H), 7.92-7.64 (m, 1H), 6.60 (s, 1H), 3.88-2.93 (m, 14H), 2.12-1.68 (m, 4H), 1.42 (s, 3H), 0.98 (t, J=7.1 Hz, 3H); LC-MS (Method 2): $t_R$=4.64 min, m/z (M+H)$^+$=489; HRMS calculated for $C_{24}H_{28}F_3N_6O_2$ (M+H)$^+$: 489.2220, found: 489.2214.

Example 149. N,N-diethyl-4-(6-fluoro-4-(1,4-dioxa-8-azaspiro[4.5]decan-8-yl)quinoline-3-carbonyl)piperazine-1-carboxamide, TFA (Cpd. 149)

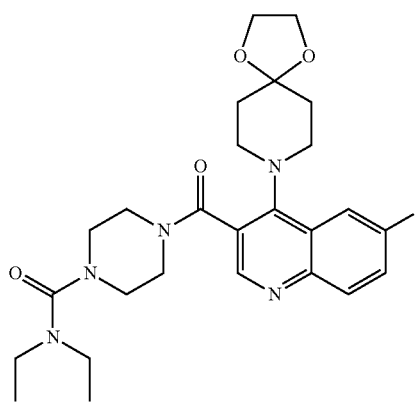

Cpd. 149

The title compound was prepared following the similar procedure as described in Example 1. $^1$H NMR (400 MHz, DMSO-d$_6$) δ 8.65 (s, 1H), 8.05 (dd, J=8.9, 5.3 Hz, 1H), 7.76 (d, J=10.7 Hz, 2H), 3.92 (p, J=1.5 Hz, 4H), 3.75-2.91 (m, 16H), 2.02-1.76 (m, 4H), 1.02 (t, J=7.0 Hz, 6H); LC-MS (Method 2): t$_R$=3.86 min, m/z (M+H)$^+$=500; HRMS calculated for C$_{26}$H$_{35}$FN$_5$O$_4$ (M+H)$^+$: 500.2668, found: 500.2655.

Example 150. (6-fluoro-4-(1,4-dioxa-8-azaspiro[4.5]decan-8-yl)quinolin-3-yl)(4-(pyrrolidine-1-carbonyl)piperazin-1-yl)methanone, TFA (Cpd. 150)

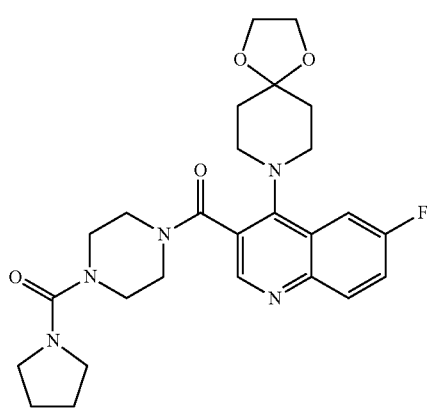

Cpd. 150

The title compound was prepared following the similar procedure as described in Example 1. $^1$H NMR (400 MHz, DMSO-d$_6$) δ 8.65 (s, 1H), 8.05 (dd, J=9.0, 5.4 Hz, 1H), 7.76 (d, J=10.4 Hz, 2H), 3.92 (p, J=1.5 Hz, 4H), 3.76-2.97 (m, 16H), 2.01-1.76 (m, 4H), 1.76-1.67 (m, 4H); LC-MS (Method 2): t$_R$=3.62 min, m/z (M+H)$^+$=498; HRMS calculated for C$_{26}$H$_{32}$FN$_5$O$_4$Na (M+Na)$^+$: 520.2331, found: 520.2338.

Example 151. (4-(ethylsulfonyl)piperazin-1-yl)(6-fluoro-4-(1,4-dioxa-8-azaspiro[4.5]decan-8-yl)quinolin-3-yl)methanone, TFA (Cpd. 151)

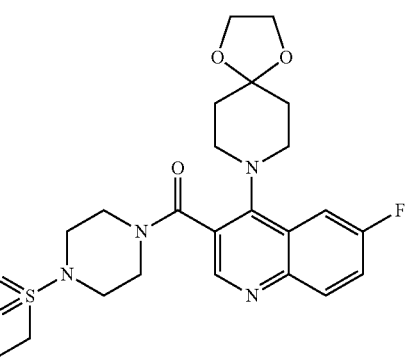

Cpd. 151

The title compound was prepared following the similar procedure as described in Example 1. $^1$H NMR (400 MHz, DMSO-d$_6$) δ 8.64 (s, 1H), 8.18-7.94 (m, 1H), 7.74 (d, J=10.4 Hz, 2H), 3.97-2.97 (m, 18H), 2.02-1.73 (m, 4H), 1.25-1.18 (m, 3H); LC-MS (Method 2): t$_R$=3.63 min, m/z (M+H)$^+$=493; HRMS calculated for C$_{23}$H$_{30}$FN$_4$O$_5$S (M+H)$^+$: 493.1915, found: 493.1909.

Example 152. 4-(6-fluoro-4-(1,4-dioxa-8-azaspiro[4.5]decan-8-yl)quinoline-3-carbonyl)-N,N-dimethylpiperazine-1-sulfonamide, TFA (Cpd. 152)

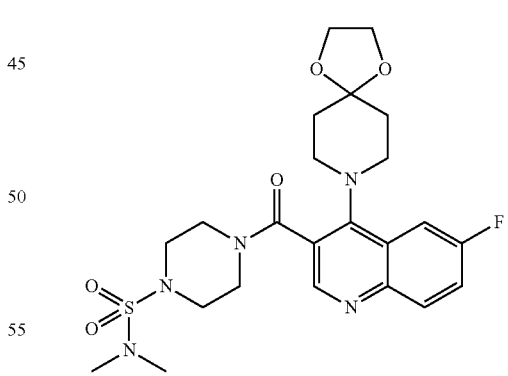

Cpd. 152

The title compound was prepared following the similar procedure as described in Example 1. $^1$H NMR (400 MHz, DMSO-d$_6$) δ 8.65 (s, 1H), 8.14-7.96 (m, 1H), 7.75 (t, J=9.5 Hz, 2H), 3.99-3.05 (m, 16H), 2.76 (s, 6H), 2.00-1.73 (m, 4H); LC-MS (Method 2): t$_R$=3.76 min, m/z (M+H)$^+$=508; HRMS calculated for C$_{23}$H$_{31}$FN$_5$O$_5$S (M+H)$^+$: 508.2024, found: 508.2029.

Example 153. (6-fluoro-4-(1,4-dioxa-8-azaspiro[4.5]decan-8-yl)quinolin-3-yl)(4-(pyrrolidin-1-ylsulfonyl)piperazin-1-yl)methanone, TFA (Cpd. 153)

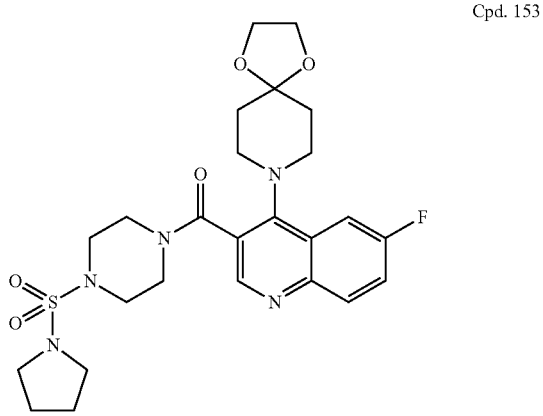 [SMILES: O=C(c1cnc2ccc(F)cc2c1N1CCC2(CC1)OCCO2)N1CCN(S(=O)(=O)N2CCCC2)CC1]

The title compound was prepared following the similar procedure as described in Example 1. $^1$H NMR (400 MHz, DMSO-$d_6$) δ 8.66 (s, 1H), 8.05 (dd, J=8.9, 5.5 Hz, 1H), 7.75 (d, J=10.4 Hz, 2H), 3.92 (p, J=1.4 Hz, 4H), 3.89-3.00 (m, 16H), 2.01-1.76 (m, 8H); LC-MS (Method 2): $t_R$=3.97 min, m/z (M+H)$^+$=534; HRMS calculated for $C_{25}H_{32}FN_5O_5SNa$ (M+Na)$^+$: 556.2000, found: 556.2020.

Example 154. 4-(4-(4-cyano-4-methylpiperidin-1-yl)-6-fluoroquinoline-3-carbonyl)-N,N-diethylpiperazine-1-carboxamide, TFA (Cpd. 154)

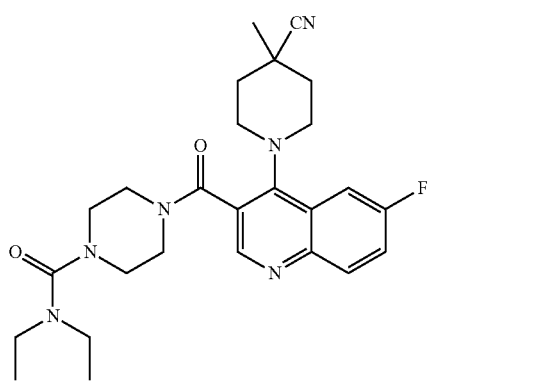

The title compound was prepared following the similar procedure as described in Example 1. $^1$H NMR (400 MHz, DMSO-$d_6$) δ 8.66 (s, 1H), 8.06 (dd, J=8.9, 5.4 Hz, 1H), 7.75 (d, J=11.0 Hz, 2H), 3.77-2.95 (m, 16H), 2.10-1.73 (m, 4H), 1.44 (s, 3H), 1.02 (t, J=7.0 Hz, 6H); LC-MS (Method 2): $t_R$=4.12 min, m/z (M+H)$^+$=481; HRMS calculated for $C_{26}H_{34}FN_6O_2$ (M+H)$^+$: 481.2722, found: 481.2711.

Example 155. 1-(6-fluoro-3-(4-(pyrrolidine-1-carbonyl)piperazine-1-carbonyl)quinolin-4-yl)-4-methylpiperidine-4-carbonitrile, TFA (Cpd. 155)

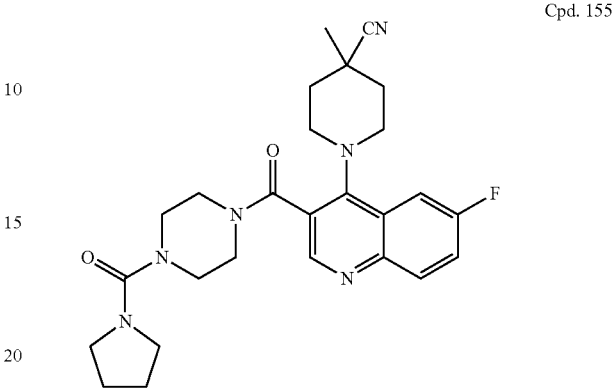

The title compound was prepared following the similar procedure as described in Example 1. $^1$H NMR (400 MHz, DMSO-$d_6$) δ 8.64 (s, 1H), 8.06 (dd, J=9.3, 5.2 Hz, 1H), 7.75 (t, J=8.9 Hz, 2H), 3.77-3.04 (m, 16H), 2.09-1.76 (m, 4H), 1.76-1.65 (m, 4H), 1.44 (s, 3H); LC-MS (Method 2): $t_R$=3.88 min, m/z (M+H)$^+$=479; HRMS calculated for $C_{26}H_{32}FN_6O_2$ (M+H)$^+$: 479.2565, found: 479.2546.

Example 156. 1-(3-(4-(ethylsulfonyl)piperazine-1-carbonyl)-6-fluoroquinolin-4-yl)-4-methylpiperidine-4-carbonitrile, TFA (Cpd. 156)

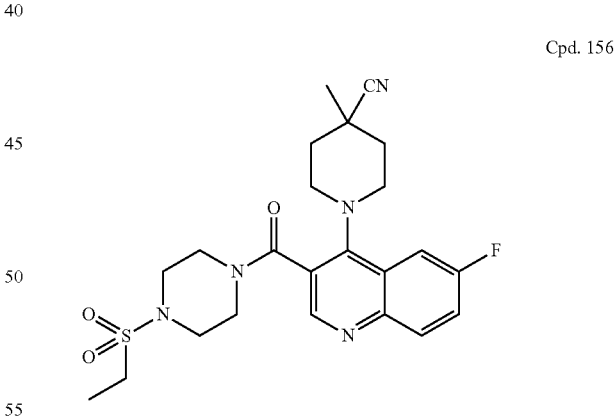

The title compound was prepared following the similar procedure as described in Example 1. $^1$H NMR (400 MHz, DMSO-$d_6$) δ 8.63 (t, J=1.5 Hz, 1H), 8.06 (ddd, J=9.7, 4.4, 2.0 Hz, 1H), 7.74 (t, J=8.5 Hz, 2H), 3.90-3.03 (m, 14H), 2.09-1.74 (m, 4H), 1.44 (s, 3H), 1.20 (t, J=7.4 Hz, 3H); LC-MS (Method 2): $t_R$=3.89 min, m/z (M+H)$^+$=474; HRMS calculated for $C_{23}H_{29}FN_5O_3S$ (M+H)$^+$: 474.1970, found: 474.1957.

Example 157. 4-(4-(4-cyano-4-methylpiperidin-1-yl)-6-fluoroquinoline-3-carbonyl)-N,N-dimethylpiperazine-1-sulfonamide, TFA (Cpd. 157)

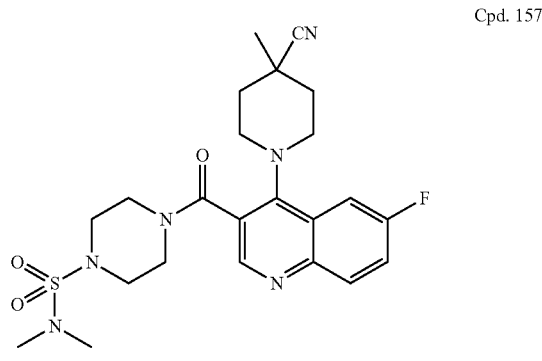 [SMILES: CN(C)S(=O)(=O)N1CCN(C(=O)c2cnc3ccc(F)cc3c2N2CCC(C)(C#N)CC2)CC1]

The title compound was prepared following the similar procedure as described in Example 1. $^1$H NMR (400 MHz, DMSO-$d_6$) δ 8.66 (s, 1H), 8.22-7.96 (m, 1H), 7.74 (m, 2H), 3.91-3.00 (m, 12H), 2.76 (s, 6H), 2.10-1.74 (m, 4H), 1.44 (s, 3H); LC-MS (Method 2): $t_R$=4.03 min, m/z (M+H)$^+$=489; HRMS calculated for $C_{23}H_{30}FN_6O_3S$ (M+H)$^+$: 489.2079, found: 489.2063.

Example 158. 1-(6-fluoro-3-(4-(pyrrolidin-1-ylsulfonyl)piperazine-1-carbonyl)quinolin-4-yl)-4-methylpiperidine-4-carbonitrile, TFA (Cpd. 158)

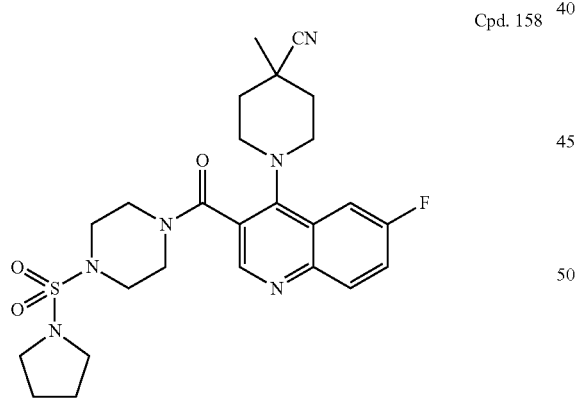

The title compound was prepared following the similar procedure as described in Example 1. $^1$H NMR (400 MHz, DMSO-$d_6$) δ 8.66 (s, 1H), 8.16-7.98 (m, 1H), 7.75 (td, J=8.9, 2.6 Hz, 2H), 3.92-3.00 (m, 16H), 2.10-1.72 (m, 8H), 1.44 (s, 3H); LC-MS (Method 2): $t_R$=4.25 min, m/z (M+H)$^+$=515; HRMS calculated for $C_{25}H_{32}FN_6O_3S$ (M+H)$^+$: 515.2235, found: 515.2257.

Example 159. 4-(6,8-difluoro-4-(1,4-dioxa-8-azaspiro[4.5]decan-8-yl)quinoline-3-carbonyl)-N,N-diethylpiperazine-1-carboxamide, TFA (Cpd. 159)

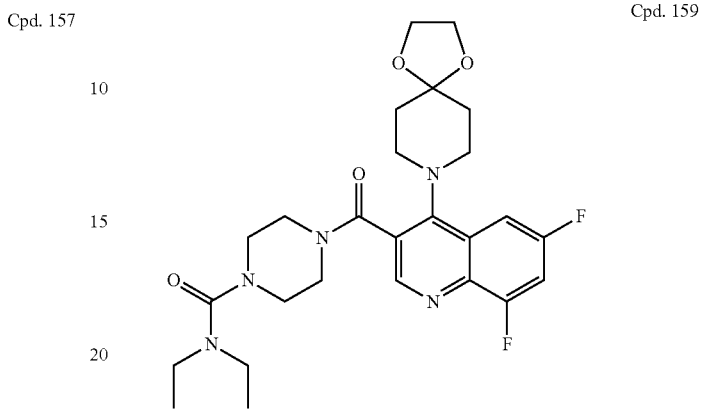

The title compound was prepared following the similar procedure as described in Example 1. $^1$H NMR (400 MHz, DMSO-$d_6$) δ 8.55 (s, 1H), 7.75 (ddd, J=10.5, 8.9, 2.7 Hz, 1H), 7.53 (ddd, J=10.1, 2.8, 1.3 Hz, 1H), 3.96-2.93 (m, 20H), 1.96-1.71 (m, 4H), 1.02 (t, J=7.0 Hz, 6H); LC-MS (Method 2): $t_R$=4.60 min, m/z (M+H)$^+$=518; HRMS calculated for $C_{26}H_{34}F_2N_5O_4$ (M+H)$^+$: 518.2530, found: 518.2565.

Example 160. (6,8-difluoro-4-(1,4-dioxa-8-azaspiro[4.5]decan-8-yl)quinolin-3-yl)(4-(pyrrolidine-1-carbonyl)piperazin-1-yl)methanone, TFA (Cpd. 160)

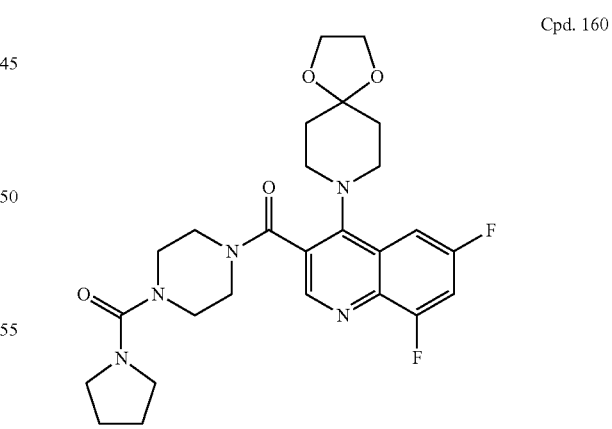

The title compound was prepared following the similar procedure as described in Example 1. $^1$H NMR (400 MHz, DMSO-$d_6$) δ 8.55 (s, 1H), 7.75 (ddd, J=11.4, 9.0, 2.7 Hz, 1H), 7.53 (dt, J=10.2, 2.0 Hz, 1H), 3.95-3.86 (m, 4H), 3.80-2.96 (m, 16H), 1.96-1.65 (m, 8H); LC-MS (Method 2): $t_R$=4.29 min, m/z (M+H)$^+$=516; HRMS calculated for $C_{26}H_{32}F_2N_5O_4$ (M+H)$^+$: 516.2417, found: 516.2406.

Example 161. (6,8-difluoro-4-(1,4-dioxa-8-azaspiro[4.5]decan-8-yl)quinolin-3-yl)(4-(ethylsulfonyl)piperazin-1-yl)methanone, TFA (Cpd. 161)

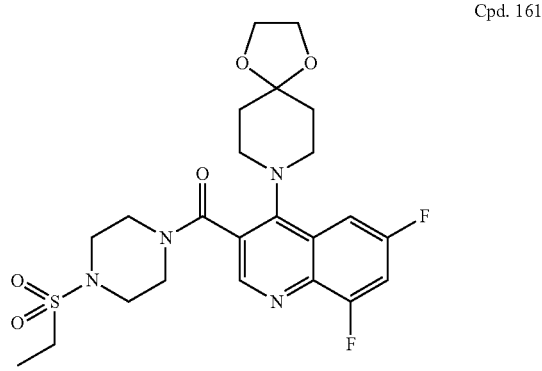 [SMILES: CCS(=O)(=O)N1CCN(C(=O)c2cnc3c(F)cc(F)cc3c2N2CCC3(CC2)OCCO3)CC1]

Cpd. 161

The title compound was prepared following the similar procedure as described in Example 1. $^1$H NMR (400 MHz, DMSO-$d_6$) δ 8.59 (s, 1H), 7.75 (ddd, J=10.5, 8.8, 2.7 Hz, 1H), 7.53 (ddd, J=10.1, 2.8, 1.4 Hz, 1H), 3.96-3.86 (m, 4H), 3.63-2.95 (m, 14H), 1.98-1.70 (m, 4H), 1.20 (t, J=7.4 Hz, 3H); LC-MS (Method 2): $t_R$=4.35 min, m/z (M+H)$^+$=511; HRMS calculated for $C_{23}H_{28}FN_4O_5SNa$ (M+Na)$^+$: 533.1641, found: 533.1657.

Example 162. 4-(6,8-difluoro-4-(1,4-dioxa-8-azaspiro[4.5]decan-8-yl)quinoline-3-carbonyl)-N,N-dimethylpiperazine-1-sulfonamide, TFA (Cpd. 162)

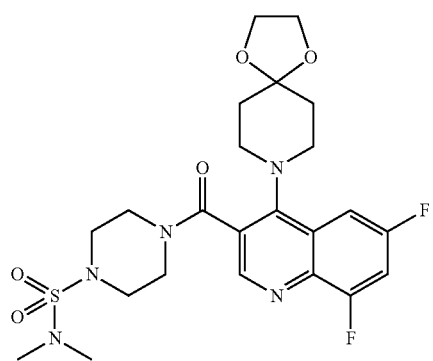

Cpd. 162

The title compound was prepared following the similar procedure as described in Example 1. $^1$H NMR (400 MHz, DMSO-$d_6$) δ 8.59 (s, 1H), 7.75 (ddd, J=10.4, 8.8, 2.7 Hz, 1H), 7.64-7.41 (m, 1H), 3.91 (qd, J=3.4, 1.5 Hz, 4H), 3.89-2.96 (m, 12H), 2.76 (s, 6H), 1.96-1.68 (m, 4H); LC-MS (Method 2): $t_R$=4.51 min, m/z (M+H)$^+$=526; HRMS calculated for $C_{23}H_{30}F_2N_5O_5S$ (M+H)$^+$: 526.1930, found: 526.1942.

Example 163. (6,8-difluoro-4-(1,4-dioxa-8-azaspiro[4.5]decan-8-yl)quinolin-3-yl)(4-(pyrrolidin-1-ylsulfonyl)piperazin-1-yl)methanone, TFA (Cpd. 163)

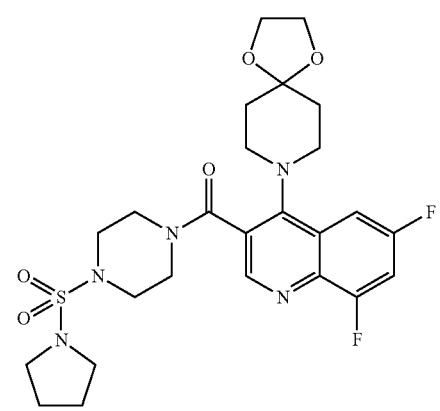

Cpd. 163

The title compound was prepared following the similar procedure as described in Example 1. $^1$H NMR (400 MHz, DMSO-$d_6$) δ 8.59 (s, 1H), 7.75 (ddd, J=10.5, 8.8, 2.7 Hz, 1H), 7.62-7.42 (m, 1H), 3.95-3.89 (m, 4H), 3.89-2.94 (m, 16H), 1.96-1.72 (m, 8H); LC-MS (Method 2): $t_R$=4.77 min, m/z (M+H)$^+$=552; HRMS calculated for $C_{25}H_{32}F_2N_5O_5S$ (M+H)$^+$: 552.2087, found: 552.2095.

Example 164. 4-(4-(4-cyano-4-methylpiperidin-1-yl)-6,8-difluoroquinoline-3-carbonyl)-N,N-diethylpiperazine-1-carboxamide, TFA (Cpd. 164)

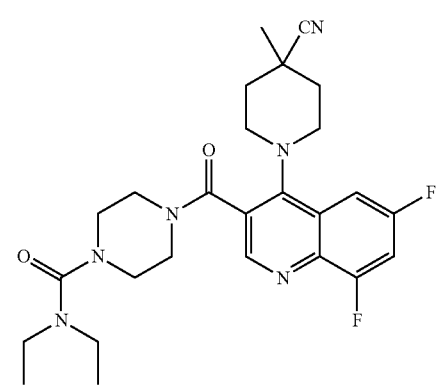

Cpd. 164

The title compound was prepared following the similar procedure as described in Example 1. $^1$H NMR (400 MHz, DMSO-$d_6$) δ 8.58 (s, 1H), 7.76 (ddd, J=10.5, 8.9, 2.7 Hz, 1H), 7.64-7.44 (m, 1H), 3.80-2.94 (m, 16H), 2.08-1.72 (m, 4H), 1.43 (s, 3H), 1.02 (t, J=7.0 Hz, 6H); LC-MS (Method 2): $t_R$=4.93 min, m/z (M+H)$^+$=499; HRMS calculated for $C_{26}H_{33}F_2N_6O_2$ (M+H)$^+$: 499.2628, found: 499.2634.

Example 165. 1-(6,8-difluoro-3-(4-(pyrrolidine-1-carbonyl)piperazine-1-carbonyl)quinolin-4-yl)-4-methylpiperidine-4-carbonitrile, TFA (Cpd. 165)

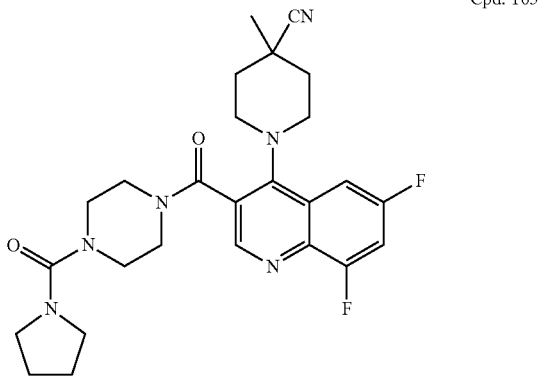

The title compound was prepared following the similar procedure as described in Example 1. ¹H NMR (400 MHz, DMSO-d₆) δ 8.58 (s, 1H), 7.76 (ddd, J=10.4, 8.9, 2.7 Hz, 1H), 7.54 (dt, J=10.2, 2.0 Hz, 1H), 3.80-2.98 (m, 16H), 2.05-1.76 (m, 4H), 1.76-1.63 (m, 4H), 1.43 (s, 3H); LC-MS (Method 2): $t_R$=4.62 min, m/z (M+H)⁺=497; HRMS calculated for $C_{26}H_{31}F_2N_6O_2$ (M+H)⁺: 497.2471, found: 491.2483.

Example 166. 1-(3-(4-(ethylsulfonyl)piperazine-1-carbonyl)-6,8-difluoroquinolin-4-yl)-4-methylpiperidine-4-carbonitrile, TFA (Cpd. 166)

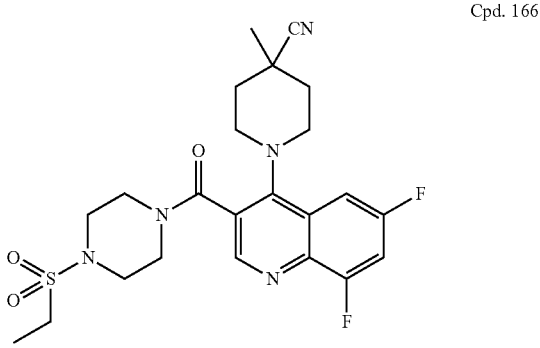 [SMILES: CCS(=O)(=O)N1CCN(C(=O)c2cnc3c(F)cc(F)cc3c2N2CCC(C)(C#N)CC2)CC1]

The title compound was prepared following the similar procedure as described in Example 1. ¹H NMR (400 MHz, DMSO-d₆) δ 8.61 (s, 1H), 7.77 (ddd, J=10.4, 8.9, 2.7 Hz, 1H), 7.64-7.42 (m, 1H), 3.95-2.98 (m, 14H), 2.07-1.70 (m, 4H), 1.43 (s, 3H), 1.20 (t, J=7.4 Hz, 3H); LC-MS (Method 2): $t_R$=4.71 min, m/z (M+H)⁺=492; HRMS calculated for $C_{23}H_{28}F_2N_5O_3S$ (M+H)⁺: 492.1875, found: 492.1878.

Example 167. 4-(4-(4-cyano-4-methylpiperidin-1-yl)-6,8-difluoroquinoline-3-carbonyl)-N,N-dimethylpiperazine-1-sulfonamide, TFA (Cpd. 167)

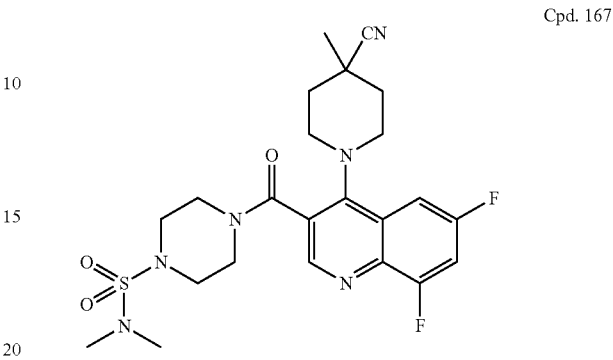

The title compound was prepared following the similar procedure as described in Example 1. ¹H NMR (400 MHz, DMSO-d₆) δ 8.62 (s, 1H), 7.77 (ddd, J=10.5, 8.9, 2.7 Hz, 1H), 7.54 (ddd, J=10.1, 2.7, 1.3 Hz, 1H), 3.96-2.99 (m, 12H), 2.76 (s, 6H), 2.07-1.73 (m, 4H), 1.43 (s, 3H); LC-MS (Method 2): $t_R$=4.86 min, m/z (M+H)⁺=507; HRMS calculated for $C_{23}H_{29}F_2N_6O_3S$ (M+H)⁺: 507.1984, found: 507.2000.

Example 168. 1-(6,8-difluoro-3-(4-(pyrrolidin-1-ylsulfonyl)piperazine-1-carbonyl)quinolin-4-yl)-4-methylpiperidine-4-carbonitrile, TFA (Cpd. 168)

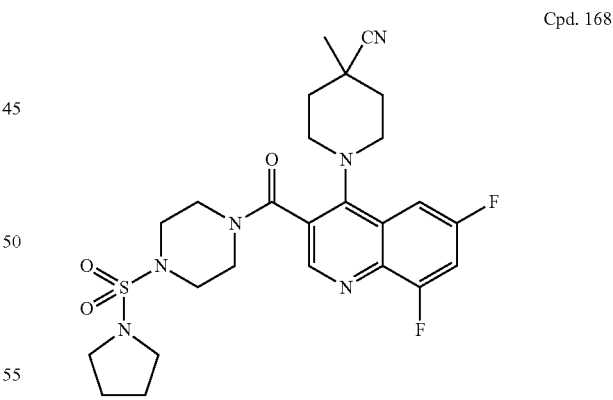

The title compound was prepared following the similar procedure as described in Example 1. ¹H NMR (400 MHz, DMSO-d₆) δ 8.62 (s, 1H), 7.77 (ddd, J=10.5, 8.9, 2.7 Hz, 1H), 7.66-7.42 (m, 1H), 3.95-2.95 (m, 16H), 2.04-1.73 (m, 8H), 1.43 (s, 3H); LC-MS (Method 2): $t_R$=5.11 min, m/z (M+H)⁺=533; HRMS calculated for $C_{25}H_{31}F_2N_6O_3S$ (M+H)⁺: 533.2141, found: 533.2146.

Example 169. 4-(6,7-difluoro-4-(1,4-dioxa-8-azasprio[4.5]decan-8-yl)quinoline-3-carbonyl)-N,N-diethylpiperazine-1-carboxamide, TFA (Cpd. 169)

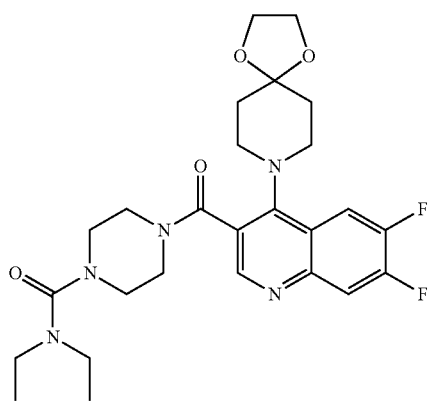

Cpd. 169

The title compound was prepared following the similar procedure as described in Example 1. $^1$H NMR (400 MHz, DMSO-d$_6$) δ 8.58 (t, J=1.7 Hz, 1H), 8.08-7.80 (m, 2H), 3.91 (p, J=1.6 Hz, 4H), 3.78-2.92 (m, 16H), 2.01-1.71 (m, 4H), 1.02 (t, J=7.0 Hz, 6H); LC-MS (Method 2): t$_R$=4.22 min, m/z (M+H)$^+$=518; HRMS calculated for C$_{26}$H$_{34}$F$_2$N$_5$O$_4$ (M+H)$^+$: 518.2573, found: 518.2573.

Example 170. (6,7-difluoro-4-(1,4-dioxa-8-azaspiro[4.5]decan-8-yl)quinolin-3-yl)(4-(pyrrolidine-1-carbonyl)piperazin-1-yl)methanone, TFA (Cpd. 170)

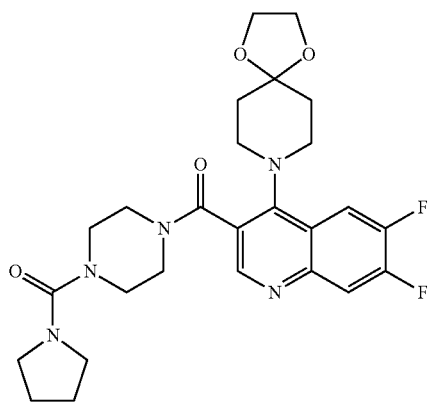

Cpd. 170

The title compound was prepared following the similar procedure as described in Example 1. $^1$H NMR (400 MHz, DMSO-d$_6$) δ 8.58 (d, J=2.9 Hz, 1H), 8.02-7.87 (m, 2H), 3.91 (qd, J=3.4, 1.7 Hz, 4H), 3.76-2.97 (m, 16H), 2.02-1.63 (m, 8H); LC-MS (Method 2): t$_R$=3.69 min, m/z (M+H)$^+$=516; HRMS calculated for C$_{26}$H$_{32}$F$_2$N$_5$O$_4$ (M+H)$^+$: 516.2417, found: 516.2417.

Example 171. (6,7-difluoro-4-(1,4-dioxa-8-azaspiro[4.5]decan-8-yl)quinolin-3-yl)(4-(ethylsulfonyl)piperazin-1-yl)methanone, TFA (Cpd. 171)

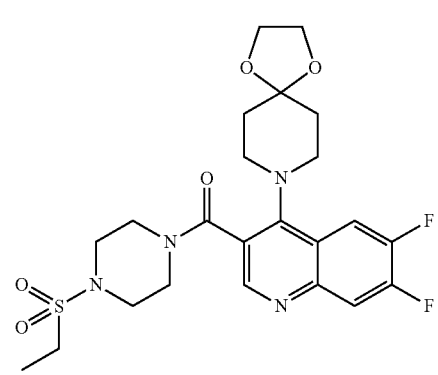

Cpd. 171

The title compound was prepared following the similar procedure as described in Example 1. $^1$H NMR (400 MHz, DMSO-d$_6$) δ 8.61 (d, J=1.0 Hz, 1H), 7.96 (m, 2H), 3.99-3.79 (m, 4H), 3.67-2.95 (m, 14H), 2.04-1.64 (m, 4H), 1.20 (t, J=7.4 Hz, 3H); LC-MS (Method 2): t$_R$=3.98 min, m/z (M+H)$^+$=511; HRMS calculated for C$_{23}$H$_{29}$F$_2$N$_4$O$_5$S (M+H)$^+$: 511.1821, found: 511.1819.

Example 172. 4-(6,7-difluoro-4-(1,4-dioxa-8-azaspiro[4.5]decan-8-yl)quinoline-3-carbonyl)-N,N-dimethylpiperazine-1-sulfonamide, TFA (Cpd. 172)

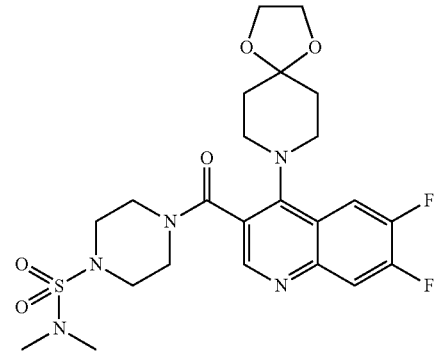

Cpd. 172

The title compound was prepared following the similar procedure as described in Example 1. $^1$H NMR (400 MHz, DMSO-d$_6$) δ 8.62 (d, J=1.6 Hz, 1H), 7.99 (dd, J=11.2, 7.7 Hz, 1H), 7.97-7.89 (m, 1H), 3.95-3.89 (m, 4H), 3.89-2.98 (m, 12H), 2.76 (s, 6H), 2.03-1.72 (m, 4H); LC-MS (Method 2): t$_R$=4.12 min, m/z (M+H)$^+$=526; HRMS calculated for C$_{23}$H$_{30}$F$_2$N$_5$O$_5$S (M+H)$^+$: 526.1930, found: 526.1946.

Example 173. (6,7-difluoro-4-(1,4-dioxa-8-azaspiro[4.5]decan-8-yl)quinolin-3-yl)(4-(pyrrolidin-1-ylsulfonyl)piperazin-1-yl)methanone, TFA (Cpd. 173)

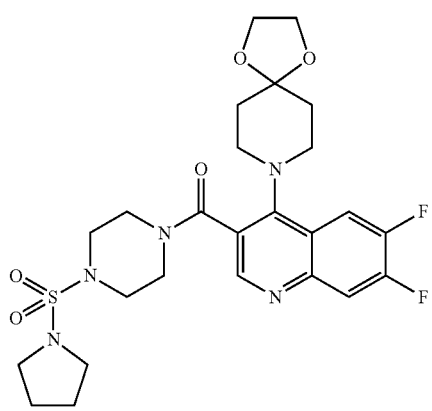

Cpd.173

The title compound was prepared following the similar procedure as described in Example 1. $^1$H NMR (400 MHz, DMSO-d$_6$) δ 8.62 (s, 1H), 7.99 (dd, J=11.3, 7.8 Hz, 1H), 7.96-7.89 (m, 1H), 3.91 (m, 4H), 3.89-2.95 (m, 16H), 2.01-1.67 (m, 8H); LC-MS (Method 2): t$_R$=4.37 min, m/z (M+H)$^+$=552; HRMS calculated for C$_{25}$H$_{32}$F$_2$N$_5$O$_5$S (M+H)$^+$: 552.2087, found: 552.2112.

Example 174. 4-(4-(4-cyano-4-methylpiperidin-1-yl)-6,7-difluoroquinoline-3-carbonyl)-N,N-diethylpiperazine-1-carboxamide, TFA (Cpd. 174)

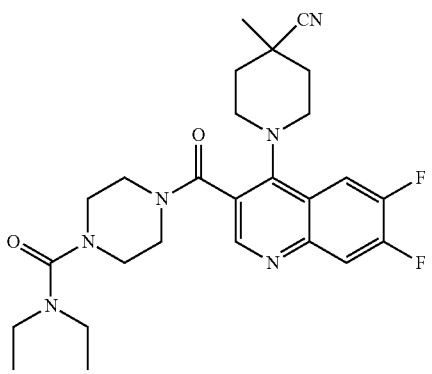

Cpd. 174

The title compound was prepared following the similar procedure as described in Example 1. $^1$H NMR (400 MHz, DMSO-d$_6$) δ 8.60 (s, 1H), 8.00 (dd, J=11.4, 7.9 Hz, 1H), 7.94 (dd, J=11.8, 8.7 Hz, 1H), 3.77-2.97 (m, 16H), 2.09-1.68 (m, 4H), 1.43 (s, 3H), 1.02 (t, J=7.0 Hz, 6H); LC-MS (Method 2): t$_R$=4.54 min, m/z (M+H)$^+$=499; HRMS calculated for C$_{26}$H$_{33}$F$_2$N$_6$O$_2$ (M+H)$^+$: 499.2628, found: 499.2630.

Example 175. 1-(6,7-difluoro-3-(4-(pyrrolidine-1-carbonyl)piperazine-1-carbonyl)quinolin-4-yl)-4-methylpiperidine-4-carbonitrile, TFA (Cpd. 175)

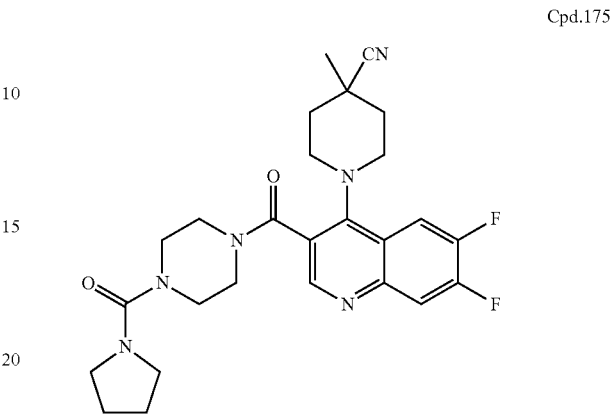

Cpd.175

The title compound was prepared following the similar procedure as described in Example 1. $^1$H NMR (400 MHz, DMSO-d6) δ 8.61 (s, 1H), 8.00 (dd, J=11.3, 7.8 Hz, 1H), 7.94 (dd, J=11.8, 8.7 Hz, 1H), 3.77-3.00 (m, 16H), 2.09-1.75 (m, 4H), 1.75-1.66 (m, 4H), 1.43 (s, 3H); LC-MS (Method 2): t$_R$=4.27 min, m/z (M+H)$^+$=497; HRMS calculated for C$_{26}$H$_{31}$F$_2$N$_6$O$_2$ (M+H)$^+$: 497.2471, found: 497.2450.

Example 176. 1-(3-(4-(ethylsulfonyl)piperazine-1-carbonyl)-6,7-difluoroquinolin-4-yl)-4-methylpiperidine-4-carbonitrile, TFA (Cpd. 176)

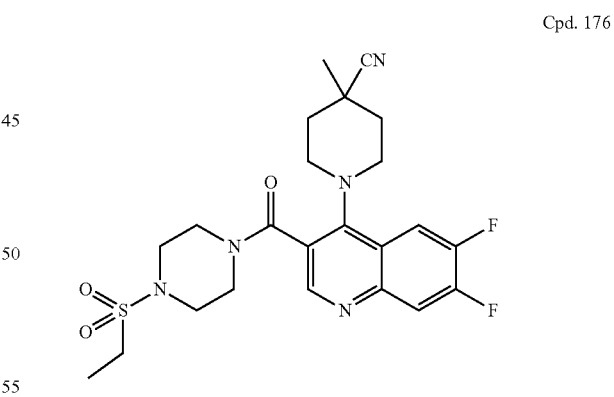

Cpd. 176

The title compound was prepared following the similar procedure as described in Example 1. $^1$H NMR (400 MHz, DMSO-d$_6$) δ 8.62 (s, 1H), 8.01 (dd, J=11.4, 7.9 Hz, 1H), 7.93 (dd, J=11.8, 8.7 Hz, 1H), 3.91-2.93 (m, 14H), 2.12-1.72 (m, 4H), 1.43 (s, 3H), 1.20 (t, J=7.4 Hz, 3H); LC-MS (Method 2): t$_R$=4.34 min, m/z (M+H)$^+$=492; HRMS calculated for C$_{23}$H$_{28}$F$_2$N$_5$O$_3$S (M+H)$^+$: 492.1875, found: 492.1879.

Example 177. 4-(4-(4-cyano-4-methylpiperidin-1-yl)-6,7-difluoroquinoline-3-carbonyl)-N,N-dimethylpiperazine-1-sulfonamide, TFA (Cpd. 177)

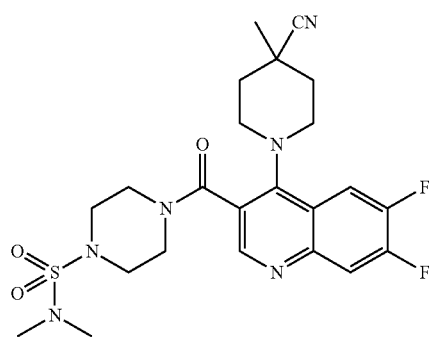

The title compound was prepared following the similar procedure as described in Example 1. $^1$H NMR (400 MHz, DMSO-d6) δ 8.64 (s, 1H), 8.01 (dd, J=11.4, 7.8 Hz, 1H), 7.94 (dd, J=11.8, 8.7 Hz, 1H), 3.92-2.98 (m, 12H), 2.76 (s, 6H), 2.10-1.72 (m, 4H), 1.43 (s, 3H); LC-MS (Method 2): $t_R$=4.48 min, m/z (M+H)$^+$=507; HRMS calculated for $C_{23}H_{29}F_2N_6O_3S$ (M+H)$^+$: 507.1984, found: 507.2000.

Example 178. 1-(6,7-difluoro-3-(4-(pyrrolidin-1-ylsulfonyl)piperazine-1-carbonyl)quinolin-4-yl)-4-methylpiperidine-4-carbonitrile, TFA (Cpd. 178)

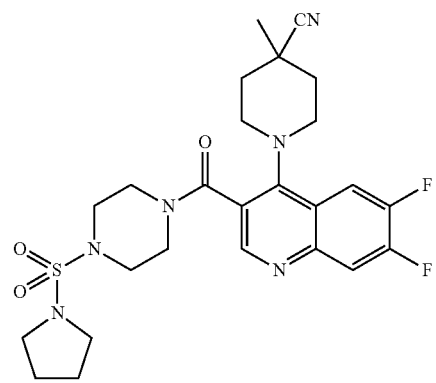

The title compound was prepared following the similar procedure as described in Example 1. $^1$H NMR (400 MHz, DMSO-d$_6$) δ 8.63 (s, 1H), 8.01 (dd, J=11.4, 7.9 Hz, 1H), 7.93 (dd, J=11.9, 8.8 Hz, 1H), 3.93-2.95 (m, 16H), 2.12-1.70 (m, 8H), 1.43 (s, 3H); LC-MS (Method 2): $t_R$=4.72 min, m/z (M+H)$^+$=533; HRMS calculated for $C_{25}H_{30}F_2N_6O_3SNa$ (M+Na)$^+$: 555.1960, found: 555.1988.

Example 179. 4-(6-fluoro-4-(1,4-dioxa-8-azaspiro[4.5]decan-8-yl)quinoline-3-carbonyl)-N,N-dimethylpiperazine-1-carboxamide, TFA (Cpd. 179)

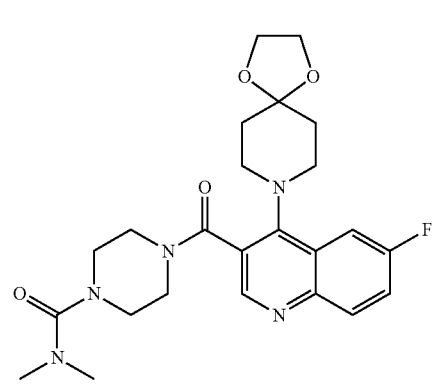

The title compound was prepared following the similar procedure as described in Example 1. $^1$H NMR (400 MHz, DMSO-d$_6$) δ 8.64 (s, 1H), 8.05 (dd, J=8.9, 5.4 Hz, 1H), 7.76 (d, J=10.2 Hz, 2H), 3.95-3.88 (m, 4H), 3.77-2.95 (m, 12H), 2.74 (s, 6H), 2.05-1.68 (m, 4H); LC-MS (Method 2): $t_R$=3.48 min, m/z (M+H)$^+$=472; HRMS calculated for $C_{24}H_{31}FN_5O_4$ (M+H)$^+$: 472.2355, found: 472.2377.

Example 180. 4-(6,8-difluoro-4-(1,4-dioxa-8-azaspiro[4.5]decan-8-yl)quinoline-3-carbonyl)-N,N-dimethylpiperazine-1-carboxamide, TFA (Cpd. 180)

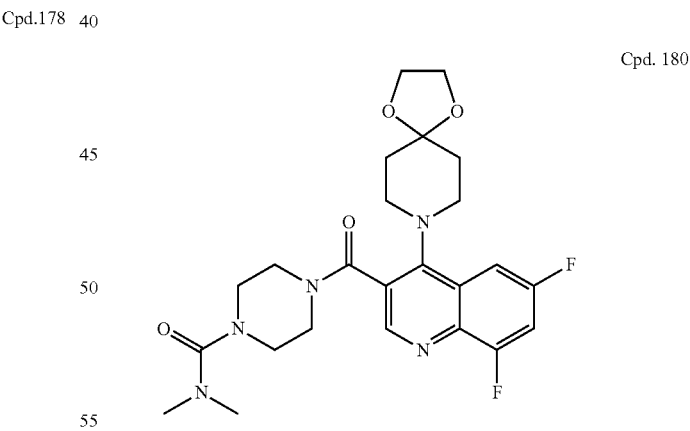

The title compound was prepared following the similar procedure as described in Example 1. $^1$H NMR (400 MHz, DMSO-d$_6$) δ 8.55 (s, 1H), 7.75 (ddd, J=10.5, 8.8, 2.7 Hz, 1H), 7.53 (ddd, J=10.1, 2.8, 1.4 Hz, 1H), 3.95-3.85 (m, 4H), 3.78-3.51 (m, 2H), 3.49-2.95 (m, 10H), 2.73 (s, 6H), 1.99-1.71 (m, 4H); LC-MS (Method 2): $t_R$=4.01 min, m/z (M+H)$^+$=490; HRMS calculated for $C_{24}H_{30}F_2N_5O_4$ (M+H)$^+$: 490.2260, found: 490.2255.

Example 181. 4-(6,7-difluoro-4-(1,4-dioxa-8-azaspiro[4.5]decan-8-yl)quinoline-3-carbonyl)-N,N-dimethylpiperazine-1-carboxamide, TFA (Cpd. 181)

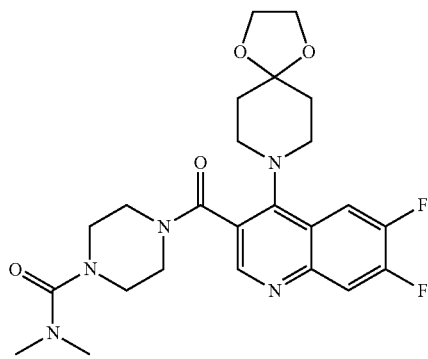

Cpd. 181

The title compound was prepared following the similar procedure as described in Example 1. $^1$H NMR (400 MHz, DMSO-$d_6$) δ 8.58 (s, 1H), 8.02-7.96 (m, 1H), 7.96-7.90 (m, 1H), 3.95-3.85 (m, 4H), 3.67 (m, 1H), 3.45-2.94 (m, 11H), 2.73 (s, 6H), 2.06-1.73 (m, 4H); LC-MS (Method 2): $t_R$=3.72 min, m/z (M+H)$^+$=490; HRMS calculated for $C_{24}H_{30}F_2N_5O_4$ (M+H)$^+$: 490.2260, found: 490.2275.

Example 182. 4-(4-(4-cyano-4-methylpiperidin-1-yl)-6-fluoroquinoline-3-carbonyl)-N,N-dimethylpiperazine-1-carboxamide, TFA (Cpd. 182)

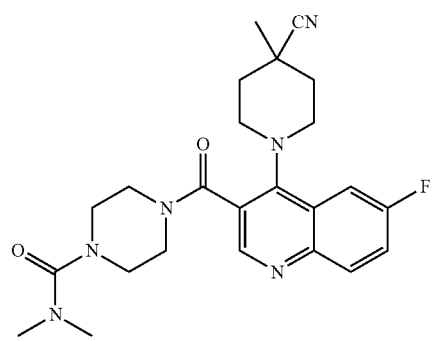

Cpd.182

The title compound was prepared following the similar procedure as described in Example 1. $^1$H NMR (400 MHz, DMSO-$d_6$) δ 8.64 (s, 1H), 8.10-8.00 (m, 1H), 7.80-7.68 (m, 2H), 3.79-3.00 (m, 12H), 2.73 (s, 6H), 2.13-1.69 (m, 4H), 1.44 (s, 3H); LC-MS (Method 2): $t_R$=3.66 min, m/z (M+H)$^+$=453; HRMS calculated for $C_{24}H_{30}FN_6O_2$ (M+H)$^+$: 453.2409, found: 453.2403.

Example 183. 4-(4-(4-cyano-4-methylpiperidin-1-yl)-6,8-difluoroquinoline-3-carbonyl)-N,N-dimethylpiperazine-1-carboxamide, TFA (Cpd. 183)

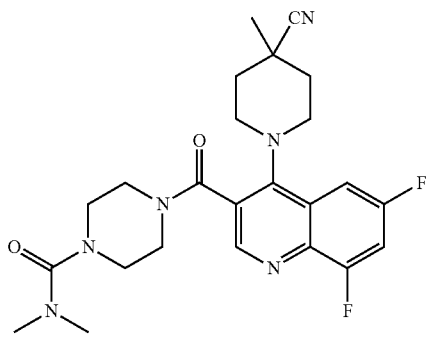

Cpd.183

The title compound was prepared following the similar procedure as described in Example 1. $^1$H NMR (400 MHz, DMSO-$d_6$) δ 8.58 (s, 1H), 7.76 (ddd, J=10.5, 8.9, 2.7 Hz, 1H), 7.54 (ddd, J=10.1, 2.8, 1.4 Hz, 1H), 3.79-2.97 (m, 12H), 2.73 (s, 6H), 2.09-1.69 (m, 4H), 1.43 (s, 3H); LC-MS (Method 2): $t_R$=4.34 min, m/z (M+H)$^+$=471; HRMS calculated for $C_{24}H_{29}F_2N_6O_2$ (M+H)$^+$: 471.2315, found: 471.2312.

Example 184. 4-(4-(4-cyano-4-methylpiperidin-1-yl)-6,7-difluoroquinoline-3-carbonyl)-N,N-dimethylpiperazine-1-carboxamide, TFA (Cpd. 184)

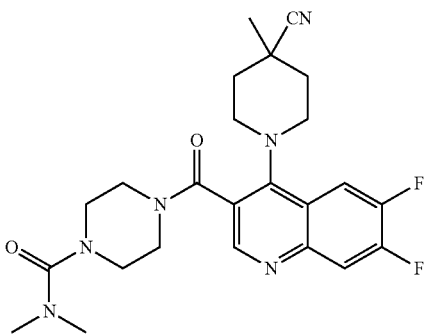

Cpd. 184

The title compound was prepared following the similar procedure as described in Example 1. $^1$H NMR (400 MHz, DMSO-$d_6$) δ 8.60 (s, 1H), 8.00 (dd, J=11.4, 7.9 Hz, 1H), 7.93 (dd, J=11.8, 8.7 Hz, 1H), 3.78-2.96 (m, 12H), 2.73 (s, 6H), 2.12-1.73 (m, 4H), 1.43 (s, 3H); LC-MS (Method 2): $t_R$=4.01 min, m/z (M+H)$^+$=471; HRMS calculated for $C_{24}H_{29}F_2N_6O_2$ (M+H)$^+$: 471.2315, found: 471.2326.

Example 185. (6-fluoro-4-(1,4-dioxa-8-azaspiro[4.5]decan-8-yl)quinolin-3-yl)(4-(methylsulfonyl)piperidin-1-yl)methanone, TFA (Cpd. 185)

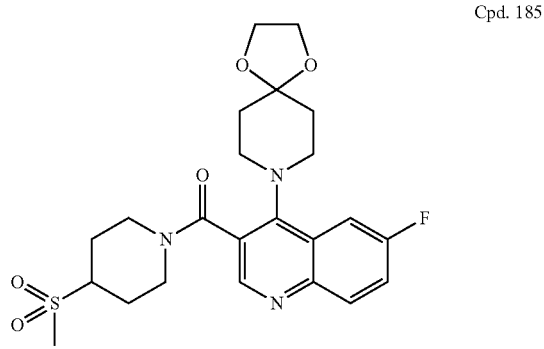 [SMILES: CS(=O)(=O)C1CCN(C(=O)c2cnc3ccc(F)cc3c2N2CCC3(CC2)OCCO3)CC1]

Cpd. 185

The title compound was prepared following the similar procedure as described in Example 1. $^1$H NMR (400 MHz, DMSO-$d_6$) δ 8.64 (two singlet, rotamers, 1H), 8.10-7.99 (m, 1H), 7.83-7.70 (m, 2H), 4.65 (d, J=10.3 Hz, 1H), 3.95-3.88 (m, 4H), 3.87-2.76 (m, 11H), 2.17 (t, J=12.4 Hz, 1H), 2.01-1.35 (m, 7H); LC-MS (Method 2): $t_R$=3.31 min, m/z (M+H)$^+$=478; HRMS calculated for $C_{23}H_{29}FN_3O_5S$ (M+H)$^+$: 478.1806, found: 478.1796.

Example 186. (6,8-difluoro-4-(1,4-dioxa-8-azaspiro[4.5]decan-8-yl)quinolin-3-yl)(4-(methylsulfonyl)piperidin-1-yl)methanone, TFA (Cpd. 186)

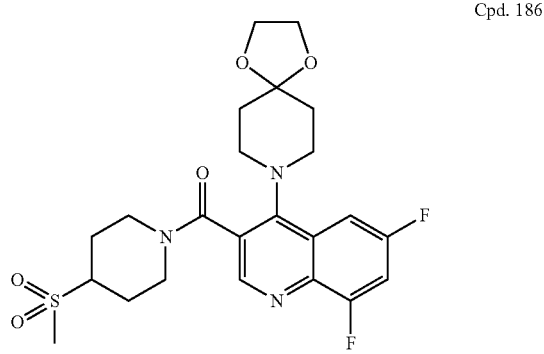 [SMILES: CS(=O)(=O)C1CCN(C(=O)c2cnc3c(F)cc(F)cc3c2N2CCC3(CC2)OCCO3)CC1]

Cpd. 186

The title compound was prepared following the similar procedure as described in Example 1. $^1$H NMR (400 MHz, DMSO-$d_6$) δ 8.55 (two singlet, rotamers, 1H), 7.75 (ddd, J=10.5, 8.8, 2.7 Hz, 1H), 7.54 (ddt, J=11.1, 7.2, 1.9 Hz, 1H), 4.67 (d, J=12.4 Hz, 1H), 3.96-3.84 (m, 4H), 3.83-2.73 (m, 11H), 2.23-1.40 (m, 8H); LC-MS (Method 2): $t_R$=3.83 min, m/z (M+H)$^+$=496; HRMS calculated for $C_{23}H_{27}F_2N_3O_5SNa$ (M+Na)$^+$: 518.1532, found: 518.1543.

Example 187. (6,7-difluoro-4-(1,4-dioxa-8-azaspiro[4.5]decan-8-yl)quinolin-3-yl)(4-(methylsulfonyl)piperidin-1-yl)methanone, TFA (Cpd. 187)

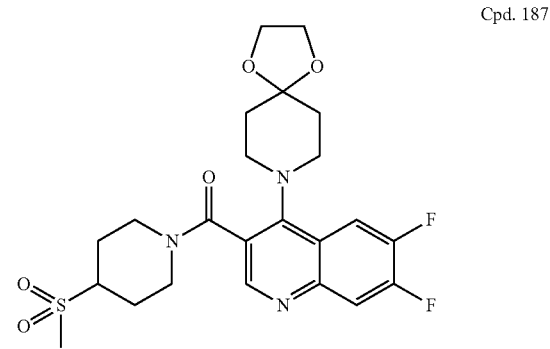 [SMILES: CS(=O)(=O)C1CCN(C(=O)c2cnc3cc(F)c(F)cc3c2N2CCC3(CC2)OCCO3)CC1]

Cpd. 187

The title compound was prepared following the similar procedure as described in Example 1. $^1$H NMR (400 MHz, DMSO-$d_6$) δ 8.58 (two singlet, rotamers, 1H), 7.96 (dddd, J=20.5, 11.8, 8.3, 6.0 Hz, 2H), 4.66 (d, J=12.6 Hz, 1H), 3.97-3.85 (m, 4H), 3.83-2.74 (m, 11H), 2.25-1.37 (m, 8H); LC-MS (Method 2): $t_R$=3.53 min, m/z (M+H)$^+$=496; HRMS calculated for $C_{23}H_{28}F_2N_3O_5S$ (M+H)$^+$: 496.1712, found: 496.1723.

Example 188. 1-(6-fluoro-3-(4-(methylsulfonyl)piperidine-1-carbonyl)quinolin-4-yl)-4-methylpiperidine-4-carbonitrile, TFA (Cpd. 188)

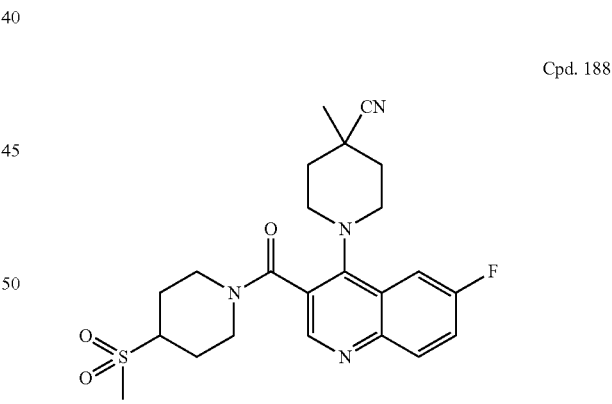

Cpd. 188

The title compound was prepared following the similar procedure as described in Example 1. $^1$H NMR (400 MHz, DMSO-$d_6$) δ 8.64 (two singlet, rotamers, 1H), 8.12-8.00 (m, 1H), 7.75 (t, J=8.9 Hz, 2H), 4.68 (d, J=12.8 Hz, 1H), 3.87-2.77 (m, 11H), 2.25-1.46 (m, 8H), 1.44 (s, 3H); LC-MS (Method 2): $t_R$=3.45 min, m/z (M+H)$^+$=459; HRMS calculated for $C_{23}H_{28}FN_4O_3S$ (M+H)$^+$: 459.1861, found: 459.1868.

Example 189. 1-(6,8-difluoro-3-(4-(methylsulfonyl)piperidine-1-carbonyl)quinolin-4-yl)-4-methylpiperidine-4-carbonitrile, TFA (Cpd. 189)

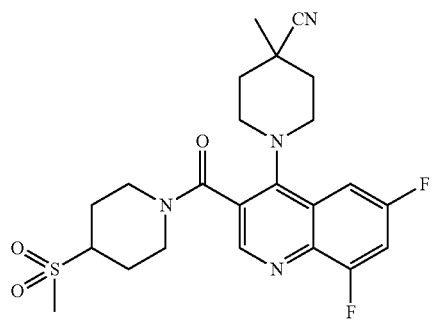

Cpd. 189

The title compound was prepared following the similar procedure as described in Example 1. $^1$H NMR (400 MHz, DMSO-d$_6$) δ 8.59 (two singlet, rotamers, 1H), 7.76 (ddd, J=10.5, 8.9, 2.7 Hz, 1H), 7.66-7.38 (m, 1H), 4.69 (d, J=13.4 Hz, 1H), 3.84-2.76 (m, 11H), 2.24-1.45 (m, 8H), 1.43 (s, 3H); LC-MS (Method 2): t$_R$=4.12 min, m/z (M+H)$^+$=477; HRMS calculated for C$_{23}$H$_{27}$F$_2$N$_4$O$_3$S (M+H)$^+$: 477.1766, found: 477.1745.

Example 190. 1-(6,7-difluoro-3-(4-(methylsulfonyl)piperidine-1-carbonyl)quinolin-4-yl)-4-methylpiperidine-4-carbonitrile, TFA (Cpd. 190)

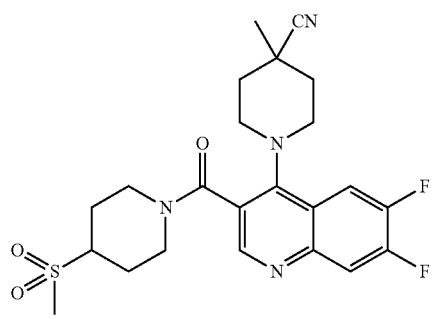

Cpd. 190

The title compound was prepared following the similar procedure as described in Example 1. $^1$H NMR (400 MHz, DMSO-d$_6$) δ 8.61 (two singlet, rotamers, 1H), 8.06-7.87 (m, 2H), 4.68 (d, J=13.1 Hz, 1H), 3.83-2.75 (m, 11H), 2.24-1.45 (m, 8H), 1.43 (s, 3H); LC-MS (Method 2): t$_R$=3.80 min, m/z (M+H)$^+$=477; HRMS calculated for C$_{23}$H$_{27}$F$_2$N$_4$O$_3$S (M+H)$^+$: 477.1766, found: 477.1750.

Example 191. (4-(cyclopropanecarbonyl)piperidin-1-yl)(6-fluoro-4-(1,4-dioxa-8-azaspiro[4.5]decan-8-yl)quinolin-3-yl)methanone, TFA (Cpd. 191)

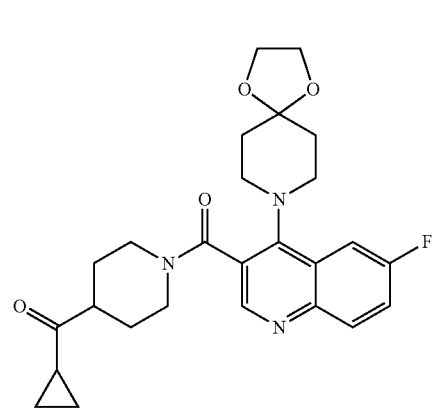

Cpd. 191

The title compound was prepared following the similar procedure as described in Example 1. $^1$H NMR (400 MHz, DMSO-d$_6$) δ 8.62 (two singlet due to rotamer, 1H), 8.20-7.92 (m, 1H), 7.76 (m, 2H), 4.45 (t, J=12.2 Hz, 1H), 3.99-3.84 (m, 4H), 3.71-2.77 (m, 8H), 2.24-2.10 (m, 1H), 2.08-1.27 (m, 8H), 0.92-0.71 (m, 4H); LC-MS (Method 2): t$_R$=3.83 min, m/z (M+H)$^+$=468; HRMS calculated for C$_{26}$H$_{31}$FN$_3$O$_4$ (M+H)$^+$: 468.2293, found: 468.2311.

Example 192. (4-(cyclopropanecarbonyl)piperidin-1-yl)(6,8-difluoro-4-(1,4-dioxa-8-azaspiro[4.5]decan-8-yl)quinolin-3-yl)methanone, TFA (Cpd. 192)

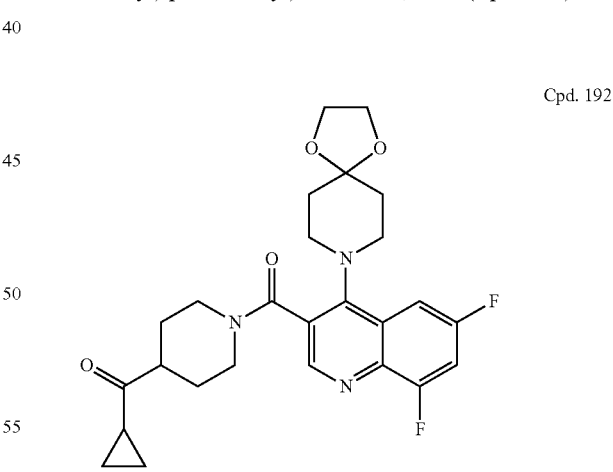

Cpd. 192

The title compound was prepared following the similar procedure as described in Example 1. $^1$H NMR (400 MHz, DMSO-d$_6$) δ 8.51 (two singlet due to rotamer, 1H), 7.74 (ddd, J=10.4, 8.8, 2.7 Hz, 1H), 7.53 (ddt, J=10.2, 4.0, 2.0 Hz, 1H), 4.46 (m, 1H), 3.95-3.85 (m, 4H), 3.65-2.76 (m, 8H), 2.16 (ddq, J=7.7, 6.0, 4.6 Hz, 1H), 2.06-1.25 (m, 8H), 0.92-0.72 (m, 4H); LC-MS (Method 2): t$_R$=4.60 min, m/z (M+H)$^+$=486; HRMS calculated for C$_{26}$H$_{30}$F$_2$N$_3$O$_4$ (M+H)$^+$: 486.2199, found: 486.2212.

Example 193. (4-(cyclopropanecarbonyl)piperidin-1-yl)(6,7-difluoro-4-(1,4-dioxa-8-azaspiro[4.5]decan-8-yl)quinolin-3-yl)methanone, TFA (Cpd. 193)

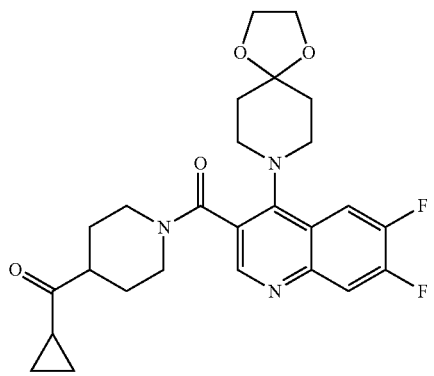

Cpd. 193

The title compound was prepared following the similar procedure as described in Example 1. $^1$H NMR (400 MHz, DMSO-d$_6$) δ 8.56 (two singlet due to rotamer, 1H), 8.08-7.74 (m, 2H), 4.45 (t, J=14.4 Hz, 1H), 3.96-3.84 (m, 4H), 3.68-2.78 (m, 8H), 2.23-2.09 (m, 1H), 2.07-1.26 (m, 8H), 0.92-0.69 (m, 4H); LC-MS (Method 2): t$_R$=4.18 min, m/z (M+H)$^+$=486; HRMS calculated for C$_{26}$H$_{30}$F$_2$N$_3$O$_4$ (M+H)$^+$: 486.2199, found: 486.2215.

Example 194. 1-(3-(4-(cyclopropanecarbonyl)piperidine-1-carbonyl)-6-fluoroquinolin-4-yl)-4-methylpiperidine-4-carbonitrile, TFA (Cpd. 194)

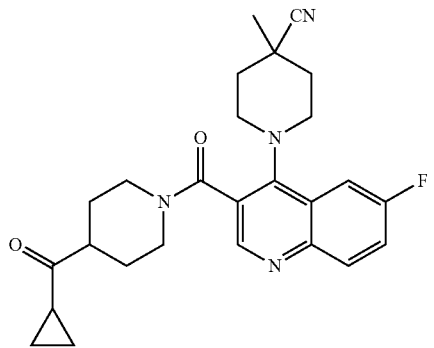

Cpd. 194

The title compound was prepared following the similar procedure as described in Example 1. $^1$H NMR (400 MHz, DMSO-d$_6$) δ 8.61 (two singlet due to rotamer, 1H), 8.06 (m, 1H), 7.74 (m, 2H), 4.54-4.41 (m, 1H), 3.68-2.77 (m, 8H), 2.24-2.10 (m, 1H), 2.10-1.48 (m, 8H), 1.43 (two singlet due to rotamer, 3H), 0.93-0.71 (m, 4H); LC-MS (Method 2): t$_R$=4.08 min, m/z (M+H)$^+$=449; HRMS calculated for C$_{26}$H$_{30}$FN$_4$O$_2$ (M+H)$^+$: 449.2347, found: 449.2341.

Example 195. 1-(3-(4-(cyclopropanecarbonyl)piperidine-1-carbonyl)-6,8-difluoroquinolin-4-yl)-4-methylpiperidine-4-carbonitrile, TFA (Cpd. 195)

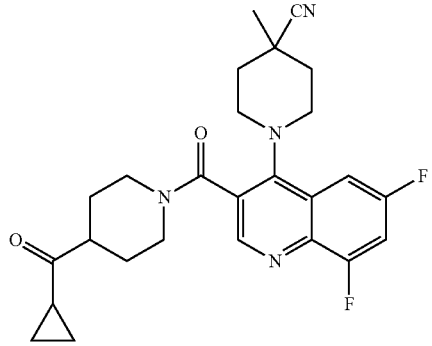

Cpd. 195

The title compound was prepared following the similar procedure as described in Example 1. $^1$H NMR (400 MHz, DMSO-d$_6$) δ 8.55 (two singlet due to rotamer, 1H), 7.75 (m, 1H), 7.64-7.42 (m, 1H), 4.54-4.37 (m, 1H), 3.63-2.76 (m, 8H), 2.23-2.11 (m, 1H), 2.07-1.48 (m, 8H), 1.42 (two singlet due to rotamer, 3H), 0.92-0.72 (m, 4H); LC-MS (Method 2): t$_R$=4.96 min, m/z (M+H)$^+$=467; HRMS calculated for C$_{26}$H$_{29}$F$_2$N$_4$O$_2$ (M+H)$^+$: 467.2253, found: 467.2246.

Example 196. 1-(3-(4-(cyclopropanecareonyl)piperidine-1-carbonyl)-6,7-difluoroquinolin-4-yl)-4-methylpiperidine-4-carbonitrile, TFA (Cpd. 196)

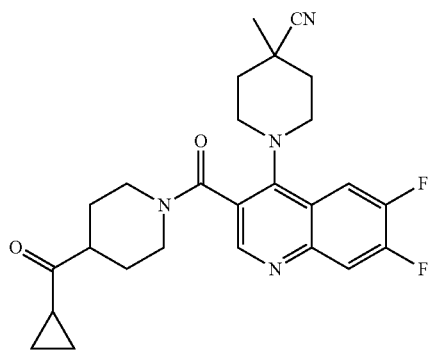

Cpd. 196

The title compound was prepared following the similar procedure as described in Example 1. $^1$H NMR (400 MHz, DMSO-d$_6$) δ 8.57 (two singlet due to rotamer, 1H), 8.10-7.66 (m, 2H), 4.46 (t, J=13.9 Hz, 1H), 3.64-2.75 (m, 8H), 2.16 (m, 1H), 2.10-1.47 (m, 8H), 1.43 (two singlet due to rotamer, 3H), 0.95-0.66 (m, 4H); LC-MS (Method 2): t$_R$=4.53 min, m/z (M+H)$^+$=467; HRMS calculated for C$_{26}$H$_{29}$F$_2$N$_4$O$_2$ (M+H)$^+$: 467.2253, found: 467.2251.

Example 197. 4-ethyl-1-(6-fluoro-3-(4-(methyl-sulfonyl)piperazine-1-carbonyl)quinolin-4-yl)piperidine-4-carbonitrile, TFA (Cpd. 197)

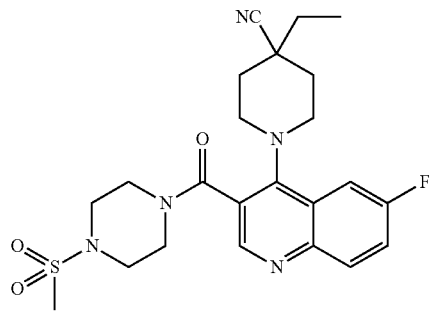
Cpd. 197

The title compound was prepared following the similar procedure as described in Example 17. $^1$H NMR (400 MHz, DMSO-$d_6$) δ 8.59 (d, J=3.7 Hz, 1H), 8.05 (dd, J=10.0, 5.5 Hz, 1H), 7.77-7.63 (m, 2H), 3.97-3.01 (m, 12H), 2.90 (s, 3H), 2.10-1.75 (m, 4H), 1.71 (q, J=7.4 Hz, 2H), 1.03 (t, J=7.4 Hz, 3H); LC-MS (Method 2): $t_R$=4.11 min, m/z (M+H)$^+$=474; HRMS calculated for $C_{27}H_{32}FN_4O_3S$ (M+H)$^+$: 511.2174, found: 511.2182.

Example 198. (4-(4-benzylpiperidin-1-yl)-6-fluoro-quinolin-3-yl)(4-(methylsulfonyl)piperazin-1-yl)methanone, TFA (Cpd. 198)

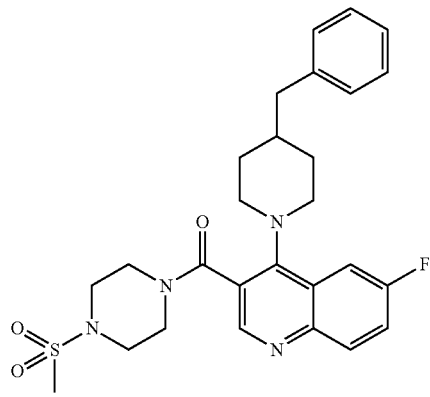
Cpd. 198

The title compound was prepared following the similar procedure as described in Example 17. $^1$H NMR (400 MHz, DMSO-$d_6$) δ 8.56 (s, 1H), 8.03 (dd, J=9.1, 5.5 Hz, 1H), 7.77-7.63 (m, 2H), 7.32-7.10 (m, 5H), 4.02-2.97 (m, 12H), 2.89 (s, 3H), 2.60 (t, J=6.4 Hz, 2H), 1.81-1.31 (m, 5H); LC-MS (Method 2): $t_R$=4.90 min, m/z (M+H)$^+$=511; HRMS calculated for $C_{27}H_{32}FN_4O_3S$ (M+H)$^+$: 511.2174, found: 511.2182.

Example 199. 1'-(6-fluoro-3-(4-(methylsulfonyl)piperazine-1-carbonyl)quinolin-4-yl)spiro[indene-1,4'-piperidin]-3(2H)-one, TFA (Cpd. 199)

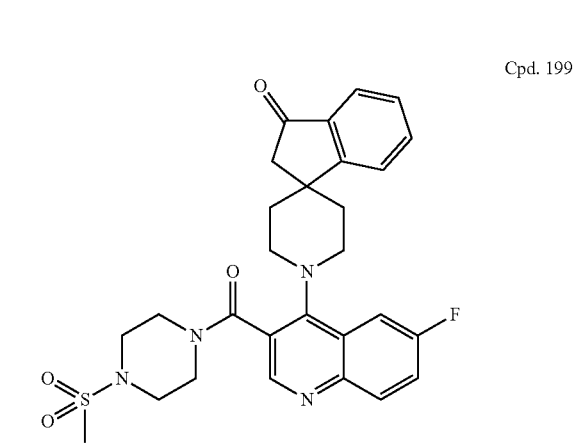 [SMILES: CS(=O)(=O)N1CCN(C(=O)c2cnc3ccc(F)cc3c2N2CCC3(CC2)CC(=O)c2ccccc23)CC1]
Cpd. 199

The title compound was prepared following the similar procedure as described in Example 17. $^1$H NMR (400 MHz, DMSO-$d_6$) δ 8.61 (s, 1H), 8.07 (dd, J=9.2, 5.5 Hz, 1H), 7.95 (t, J=8.9 Hz, 2H), 7.80-7.69 (m, 2H), 7.63 (d, J=7.5 Hz, 1H), 7.47 (t, J=7.4 Hz, 1H), 4.03-3.01 (m, 12H), 2.90 (s, 3H), 2.72 (s, 2H), 2.46 (m, 2H), 1.69-1.53 (m, 2H); LC-MS (Method 2): $t_R$=4.20 min, m/z (M+H)$^+$=537; HRMS calculated for $C_{28}H_{30}FN_4O_4S$ (M+H)$^+$: 537.1966, found: 537.1984.

Example 200. (4-(4-benzylpiperidin-1-yl)-6-fluoro-quinolin-3-yl)(4-(cyclopropanecarbonyl)piperazin-1-yl)methanone, TFA (Cpd. 200)

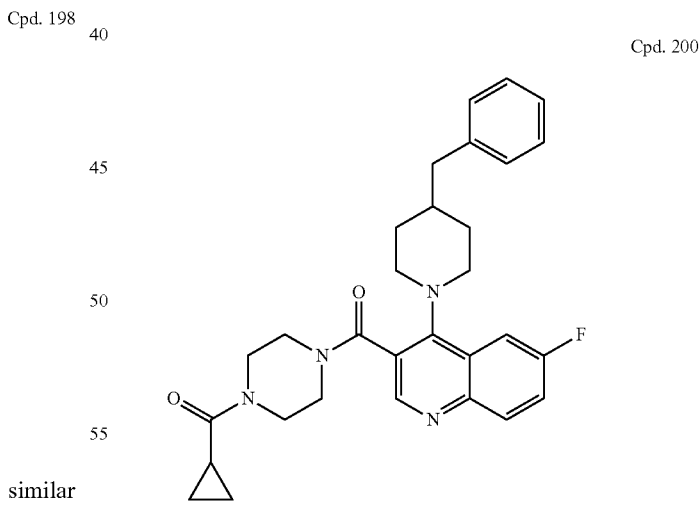
Cpd. 200

The title compound was prepared following the similar procedure as described in Example 17. $^1$H NMR (400 MHz, DMSO-$d_6$) δ 8.59 (s, 1H), 8.03 (dd, J=9.2, 5.5 Hz, 1H), 7.80-7.63 (m, 2H), 7.33-7.11 (m, 5H), 3.92-2.84 (m, 12H), 2.60 (t, J=7.8 Hz, 2H), 2.07-1.30 (m, 6H), 0.71 (d, J=4.9 Hz, 4H); LC-MS (Method 2): $t_R$=4.86 min, m/z (M+H)$^+$=501; HRMS calculated for $C_{30}H_{34}FN_4O_2$ (M+H)$^+$: 501.2660, found: 501.2683.

Example 201. 1'-(6-fluoro-3-(4-(methylsulfonyl)piperazine-1-carbonyl)quinolin-4-yl)spiro[indene-2,4'-piperidin]-1(3H)-one, TFA (Cpd. 201)

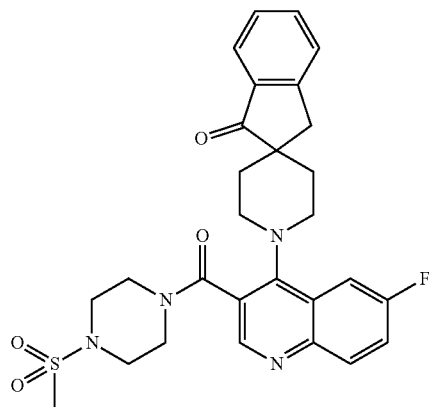

Cpd. 201

The title compound was prepared following the similar procedure as described in Example 17. $^1$H NMR (400 MHz, DMSO-$d_6$) δ 8.62 (s, 1H), 8.07 (dd, J=9.6, 5.5 Hz, 1H), 7.81-7.66 (m, 4H), 7.63 (d, J=7.6 Hz, 1H), 7.45 (t, J=7.3 Hz, 1H), 3.99-3.01 (m, 14H), 2.92 (s, 3H), 2.15-1.84 (m, 2H), 1.56 (t, J=14.8 Hz, 2H); LC-MS (Method 2): $t_R$=4.36 min, m/z (M+H)$^+$=537; HRMS calculated for $C_{28}H_{30}FN_4O_4S$ (M+H)$^+$: 537.1966, found: 537.1974.

Example 202. 1-(3-(4-(cyclopropanecarbonyl)piperazine-1-carbonyl)-6-fluoroquinolin-4-yl)-4-ethylpiperidine-4-carbonitrile, TFA (Cpd. 202)

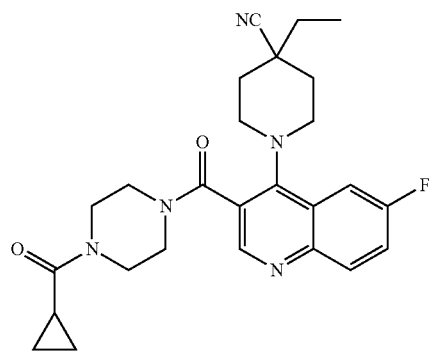

Cpd. 202

The title compound was prepared following the similar procedure as described in Example 17. LC-MS (Method 2): $t_R$=4.08 min, m/z (M+H)$^+$=464; HRMS calculated for $C_{26}H_{31}FN_5O_2$ (M+H)$^+$: 464.2456, found: 464.2477.

Example 203. 1'-(3-(4-(cyclopropanecarbonyl)piperazine-1-carbonyl)-6-fluoroquinolin-4-yl)spiro[indene-1,4'-piperidin]-3(2H)-one, TFA (Cpd. 203)

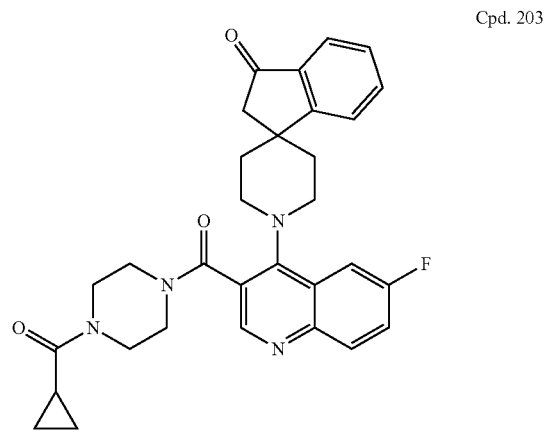 [SMILES: O=C1CC2(CCN(c3c(C(=O)N4CCN(C(=O)C5CC5)CC4)cnc4ccc(F)cc34)CC2)c2ccccc21]

Cpd. 203

The title compound was prepared following the similar procedure as described in Example 17. $^1$H NMR (400 MHz, DMSO-$d_6$) δ 8.62 (s, 1H), 8.07 (dd, J=9.2, 5.5 Hz, 1H), 7.99-7.90 (m, 2H), 7.74 (td, J=7.5, 1.3 Hz, 2H), 7.63 (d, J=7.6 Hz, 1H), 7.50-7.43 (m, 1H), 3.50-2.80 (m, 12H), 2.70 (s, 2H), 2.25 (m, 1H), 2.10-1.82 (m, 2H), 1.62 (m, 2H), 0.72 (d, J=4.2 Hz, 4H); LC-MS (Method 2): $t_R$=4.16 min, m/z (M+H)$^+$=527; HRMS calculated for $C_{31}H_{32}FN_4O_3$ (M+H)$^+$: 527.2453, found: 527.2461.

Example 204. 1'-(3-(4-(cyclopropanecarbonyl)piperazine-1-carbonyl)-6-fluoroquinolin-4-yl)spiro[indene-2,4'-piperidin]-1(3H)-one, TFA (Cpd. 204)

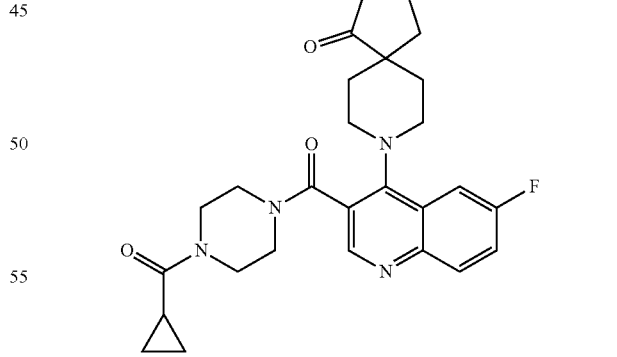

Cpd. 204

The title compound was prepared following the similar procedure as described in Example 17. $^1$H NMR (400 MHz, DMSO-$d_6$) δ 8.64 (s, 1H), 8.07 (dd, J=9.7, 5.5 Hz, 1H), 7.83-7.66 (m, 4H), 7.64 (d, J=7.6 Hz, 1H), 7.45 (t, J=7.4 Hz, 1H), 3.89-3.06 (m, 14H), 2.17-1.80 (m, 3H), 1.66-1.44 (m, 2H), 0.72 (d, J=4.6 Hz, 4H); LC-MS (Method 2): $t_R$=4.16 min, m/z (M+H)$^+$=527; HRMS calculated for $C_{31}H_{32}FN_4O_3$ (M+H)$^+$: 527.2453, found: 527.2453.

Example 205. 1-(5-(4-(cyclopropanecarbonyl)piperazine-1-carbonyl)-1-methyl-1H-pyrazolo[3,4-b]pyridin-4-yl)-4-methylpiperidine-4-carbonitrile, TFA (Cpd. 205)

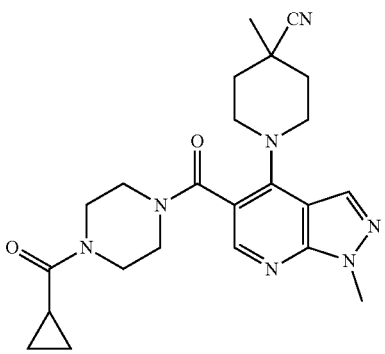

Cpd. 205

The title compound was prepared following the similar procedure as described in Example 1. $^1$H NMR (400 MHz, DMSO-$d_6$) δ 8.23 (s, 1H), 8.08 (s, 1H), 3.95 (s, 3H), 3.92-3.09 (m, 12H), 1.99-1.80 (m, 3H), 1.71-1.58 (m, 2H), 1.39 (s, 3H), 0.71 (d, J=4.7 Hz, 4H); LC-MS (Method 2): $t_R$=3.52 min, m/z (M+H)$^+$=436; HRMS calculated for $C_{23}H_{30}N_7O_2$ (M+H)$^+$: 436.2455, found: 436.2465.

Example 206. 4-methyl-1-(1-methyl-5-(4-(methylsulfonyl)piperazine-1-carbonyl)-1H-pyrazolo[3,4-b]pyridin-4-yl)piperidine-4-carbonitrile, TFA (Cpd. 206)

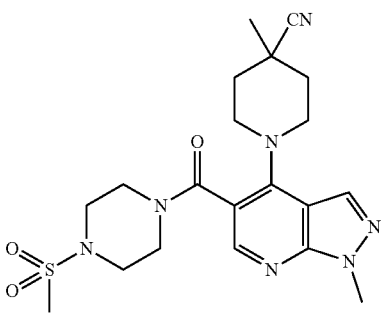

Cpd. 206

The title compound was prepared following the similar procedure as described in Example 1. $^1$H NMR (400 MHz, DMSO-$d_6$) δ 8.24 (s, 1H), 8.08 (s, 1H), 4.04-4.01 (m, 2H), 3.94 (s, 3H), 3.86-2.88 (m, 10H), 2.87 (s, 3H), 2.01-1.97 (m, 2H), 1.72-1.57 (m, 2H), 1.40 (s, 3H); LC-MS (Method 2): $t_R$=3.48 min, m/z (M+H)$^+$=446; HRMS calculated for $C_{20}H_{28}N_7O_3S$ (M+H)$^+$: 446.1969, found: 446.1982.

Example 207. 1-(5-(4-(ethylsulfonyl)piperazine-1-carbonyl)-1-methyl-1H-pyrazolo[3,4-b]pyridin-4-yl)-4-methylpiperidine-4-carbonitrile, TFA (Cpd. 207)

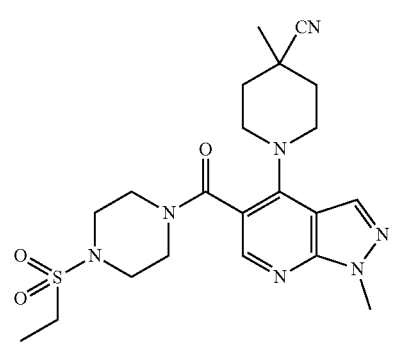

Cpd. 207

The title compound was prepared following the similar procedure as described in Example 1. $^1$H NMR (400 MHz, DMSO-$d_6$) δ 8.23 (s, 1H), 8.08 (s, 1H), 3.94 (s, 3H), 3.89-2.92 (m, 14H), 2.01-1.97 (m, 2H), 1.76-1.51 (m, 2H), 1.39 (s, 3H), 1.18 (t, J=7.4 Hz, 3H); LC-MS (Method 2): $t_R$=3.69 min, m/z (M+H)$^+$=460; HRMS calculated for $C_{21}H_{30}N_7O_3S$ (M+H)$^+$: 460.2125, found: 460.2131.

Example 208. 1-(3-(4-(cyclopropanecarbonyl)piperazine-1-carbonyl)-6-fluoroquinolin-4-yl)-4-phenylpiperidine-4-carbonitrile, TFA (Cpd. 208)

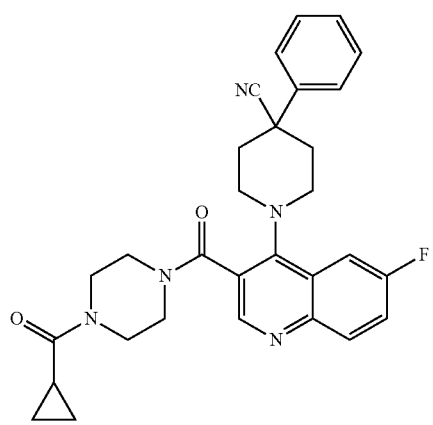

Cpd. 208

The title compound was prepared following the similar procedure as described in Example 17. $^1$H NMR (400 MHz, DMSO-$d_6$) δ 8.64 (s, 1H), 8.07 (dd, J=9.2, 5.5 Hz, 1H), 7.89 (d, J=10.1 Hz, 1H), 7.73 (t, J=8.9 Hz, 1H), 7.69-7.62 (m, 2H), 7.51-7.43 (m, 2H), 7.42-7.35 (m, 1H), 3.95-3.24 (m, 12H), 2.60-1.81 (m, 5H), 0.72 (d, J=4.9 Hz, 4H); LC-MS (Method 2): $t_R$=4.45 min, m/z (M+H)$^+$=512; HRMS calculated for $C_{30}H_{31}FN_5O_2$ (M+H)$^+$: 512.2456, found: 512.2470.

Example 209. 1-(6-fluoro-3-(4-(methylsulfonyl)piperazine-1-carbonyl)quinolin-4-yl)-4-phenylpiperidine-4-carbonitrile, TFA (Cpd. 209)

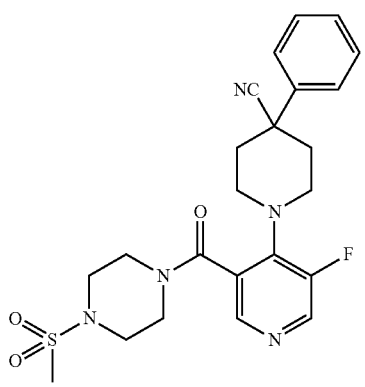

Cpd. 209

The title compound was prepared following the similar procedure as described in Example 17. $^1$H NMR (400 MHz, DMSO-d$_6$) δ 8.63 (d, J=3.4 Hz, 1H), 8.07 (dd, J=9.2, 5.5 Hz, 1H), 7.89 (dd, J=10.2, 2.8 Hz, 1H), 7.73 (td, J=8.8, 2.8 Hz, 1H), 7.69-7.62 (m, 2H), 7.52-7.43 (m, 2H), 7.43-7.35 (m, 1H), 3.96-2.97 (m, 12H), 2.90 (s, 3H), 2.57-2.21 (m, 4H); LC-MS (Method 2): t$_R$=4.44 min, m/z (M+H)$^+$=522; HRMS calculated for C$_{27}$H$_{29}$FN$_5$O$_3$S (M+H)$^+$: 522.1970, found: 522.1971.

Example 210. 1-(4-(6-fluoro-3-(4-(methylsulfonyl)piperazine-1-carbonyl)quinolin-4-yl)phenyl)cyclopropanecarbonitrile, TFA (Cpd. 210)

added LiOH$_{(aq)}$ (1.5 N, 10 mL, 15 mmol) and stirred at rt for 3 h. The mixture was added with 1N HCl$_{(aq)}$ to pH about 5. The solid formed which is 4-OH ethyl ester from starting material was filtered out and washed with H$_2$O. The product in the aqueous layer was concentrated to remove all the water and dried to give 4-bromo-6-fluoroquinoline-3-carboxylic acid, which contained NaCl salt. The material was used for next step without further purification. LC-MS (Method 1): t$_R$=2.85 min, m/z (M+H)$^+$=270.

STEP 2: Synthesis of (4-Bromo-6-fluoroquinolin-3-yl)(4-(methylsulfonyl)piperazin-1-yl)methanone, To a mixture of 4-bromo-6-fluoroquinoline-3-carboxylic acid (405 mg, 1.50 mmol) (this material contained some 4-OH impurity), 1-(methylsulfonyl)piperazine (246 mg, 1.5 mmol), and HATU (759 mg, 1.995 mmol) was added DMF (3 ml) and then Hunig's base (1.048 ml, 6.0 mmol). The mixture was stirred at rt for 3 h. The mixture was poured into H$_2$O (80 mL) and the resulting solid was filtered, washed with H$_2$O (2 mL×3), and then dried to give (4-bromo-6-fluoroquinolin-3-yl)(4-(methylsulfonyl)piperazin-1-yl)methanone (176 mg, 0.423 mmol, 28.2% yield). LC-MS (Method 1): t$_R$=2.91 min, m/z (M+H)$^+$=416.

STEP 3: Synthesis of 1-(4-(6-Fluoro-3-(4-(methylsulfonyl)piperazine-1-carbonyl)quinolin-4-yl)phenyl)cyclopropanecarbonitrile, TFA. In a 2-neck flask was placed (4-bromo-6-fluoroquinolin-3-yl)(4-(methylsulfonyl)piperazin-1-yl)methanone (20.81 mg, 0.05 mmol), (4-(1-cyanocyclopropyl)phenyl)boronic acid (18.70 mg, 0.10 mmol), PdCl$_2$(dppf)-CH$_2$Cl$_2$ adduct (4.08 mg, 5.0 μmol), and K$_2$CO$_3$ (41.5 mg, 0.30 mmol). The air was removed and re-filled with N$_2$ (2-3 times). Then a mixture of 1,4-Dioxane (1 ml) and water (0.5 ml) was added and stirred at 95° C. (pre-heated) for 1 h. The organic layer was separated and the aqueous layer was extracted with EtOAc (5 mL×2). The combined organic was dried (Na$_2$SO$_4$) and filtered. After removal of solvent, the product was filtered through a

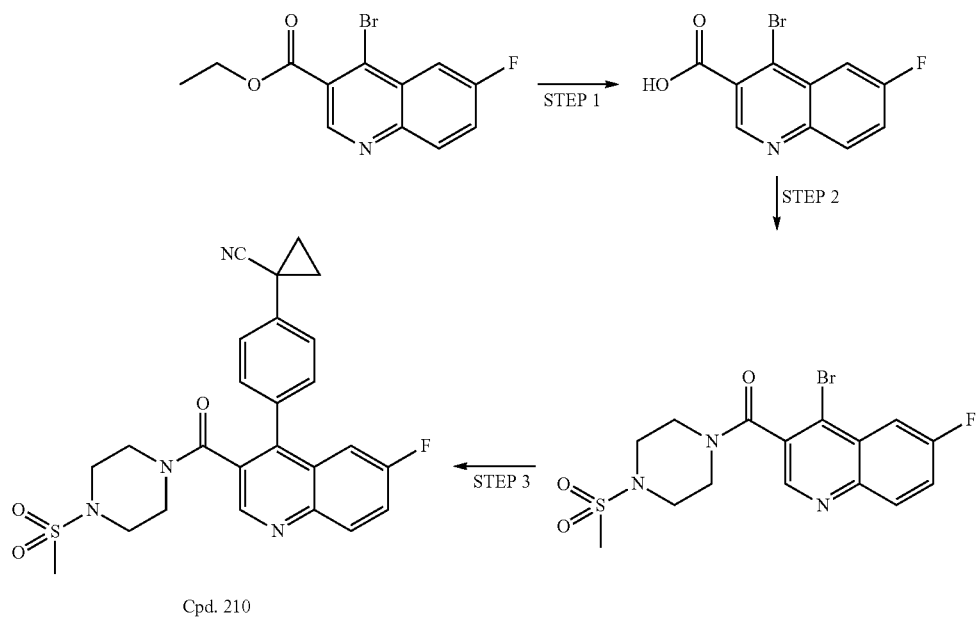

Cpd. 210

STEP 1: Synthesis of 4-Bromo-6-fluoroquinoline-3-carboxylic acid. To a suspension of ethyl 4-bromo-6-fluoroquinoline-3-carboxylate (0.894 g, 3 mmol) (ca. 70% purity contained ca. 30% of 4-OH Ethyl ester) in THF (10 ml) was PL-Thio-resin, eluted with EtOAc, concentrated, re-dissolved in DMF, and submitted for purification by semi-preparative HPLC to give 1-(4-(6-fluoro-3-(4-(methylsulfonyl)piperazine-1-carbonyl)quinolin-4-yl)phenyl)

cyclopropanecarbonitrile, TFA (6.2 mg, 10.46 µmol, 20.93% yield). ¹H NMR (400 MHz, DMSO-d₆) δ 8.85 (s, 1H), 8.21 (dd, J=9.2, 5.6 Hz, 1H), 7.77 (ddd, J=9.3, 8.2, 2.9 Hz, 1H), 7.57 (d, J=8.3 Hz, 1H), 7.53 (d, J=8.1 Hz, 1H), 7.46 (d, J=8.3 Hz, 1H), 7.38 (d, J=8.1 Hz, 1H), 7.28 (dd, J=10.2, 2.8 Hz, 1H), 3.67-2.86 (m, 6H), 2.75 (s, 3H), 2.53 (d, J=9.0 Hz, 1H), 2.09 (d, J=9.4 Hz, 1H), 1.82 (q, J=4.1 Hz, 2H), 1.67-1.58 (m, 2H); LC-MS (Method 2): $t_R$=4.71 min, m/z (M+H)⁺=479; HRMS calculated for $C_{25}H_{24}FN_4O_3S$ (M+H)⁺: 479.1548, found: 479.1562.

Example 211. 2-(4-(6-fluoro-3-(4-(methylsulfonyl)piperazine-1-carbonyl)quinolin-4-yl)phenyl)-2-methylpropanenitrile, TFA (Cpd. 211)

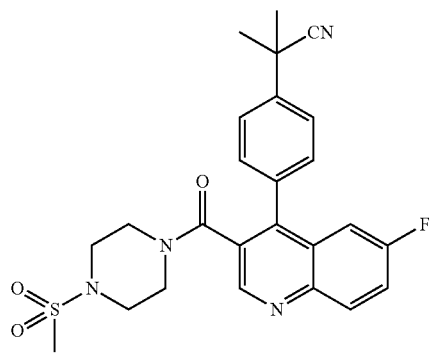

Cpd. 211

The title compound was prepared following the similar procedure as described in Example 210. ¹H NMR (400 MHz, DMSO-d₆) δ 8.86 (s, 1H), 8.21 (dd, J=9.2, 5.6 Hz, 1H), 7.84-7.72 (m, 2H), 7.70 (d, J=8.1 Hz, 1H), 7.58 (d, J=8.1 Hz, 1H), 7.42 (d, J=8.1 Hz, 1H), 7.27 (dd, J=10.2, 2.8 Hz, 1H), 3.79-2.91 (m, 6H), 2.76 (s, 3H), 2.55-2.47 (m, 1H), 2.25-2.11 (m, 1H), 1.74 (s, 6H); LC-MS (Method 2): $t_R$=4.85 min, m/z (M+H)⁺=481; HRMS calculated for $C_{25}H_{25}FN_4O_3SNa$ (M+Na)⁺: 503.1524, found: 503.1541.

Example 212. 2-(4-(6-fluoro-3-(4-(methylsulfonyl)piperazine-1-carbonyl)quinolin-4-yl)phenyl)acetonitrile, TFA (Cpd. 212)

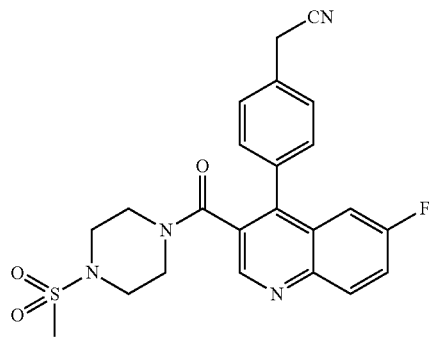

Cpd. 212

The title compound was prepared following the similar procedure as described in Example 210. ¹H NMR (400 MHz, DMSO-d₆) δ 8.86 (s, 1H), 8.21 (dd, J=9.2, 5.6 Hz, 1H), 7.78 (ddd, J=9.2, 8.2, 2.9 Hz, 1H), 7.64-7.45 (m, 3H), 7.39 (d, J=7.9 Hz, 1H), 7.28 (dd, J=10.2, 2.8 Hz, 1H), 4.15 (s, 2H), 3.62-2.85 (m, 6H), 2.75 (s, 3H), 2.59-2.50 (m, 1H), 2.16 (d, J=10.0 Hz, 1H); LC-MS (Method 2): $t_R$=4.35 min, m/z (M+H)⁺=453; HRMS calculated for $C_{23}H_{22}FN_4O_3S$ (M+H)⁺: 453.1391, found: 453.1386.

Example 213. 2-(1-(3-(4-(cyclopropanecarbonyl)piperazine-1-carbonyl)-6-fluoroquinolin-4-yl)piperidin-4-yl)acetonitrile, TFA (Cpd. 213)

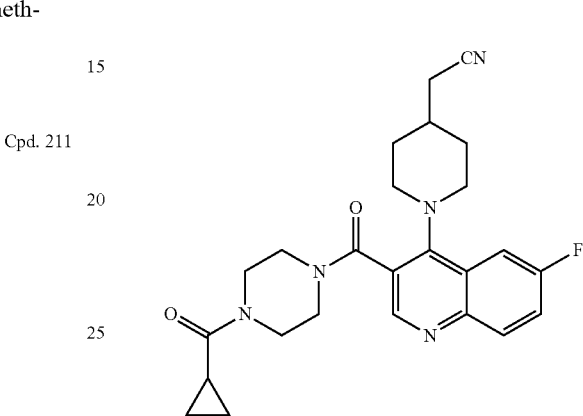

Cpd. 213

The title compound was prepared following the similar procedure as described in Example 17. ¹H NMR (400 MHz, DMSO-d₆) δ 8.61 (s, 1H), 8.05 (dd, J=9.2, 5.4 Hz, 1H), 7.81-7.51 (m, 2H), 3.93-2.81 (m, 12H), 2.59 (d, J=6.4 Hz, 2H), 2.06-1.35 (m, 6H), 0.73 (dd, J=4.7, 2.8 Hz, 4H); LC-MS (Method 2): $t_R$=3.42 min, m/z (M+H)⁺=450; HRMS calculated for $C_{25}H_{29}FN_5O_2$ (M+H)⁺: 450.2300, found: 450.2313.

Example 214. 2-(1-(6-fluoro-3-(4-(methylsulfonyl)piperazine-1-carbonyl)quinolin-4-yl)piperidin-4-yl)acetonitrile, TFA (Cpd. 214)

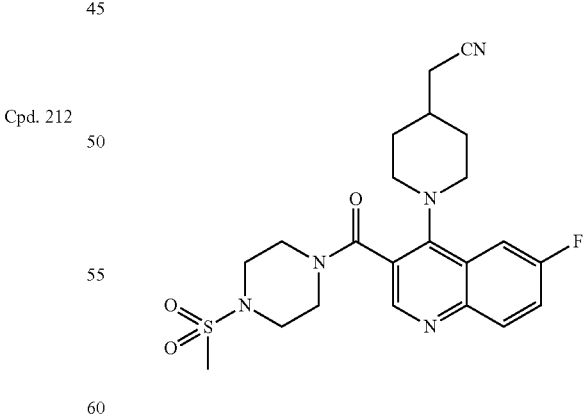

Cpd. 214

The title compound was prepared following the similar procedure as described in Example 17. ¹H NMR (400 MHz, DMSO-d₆) δ 8.59 (s, 1H), 8.05 (dd, J=9.2, 5.5 Hz, 1H), 7.84-7.51 (m, 2H), 4.01-2.92 (m, 12H), 2.91 (s, 3H), 2.60 (d, J=6.3 Hz, 2H), 1.96-1.36 (m, 5H); LC-MS (Method 2): $t_R$=3.38 min, m/z (M+H)⁺=460; HRMS calculated for $C_{22}H_{27}FN_5O_3S$ (M+H)⁺: 460.1813, found: 460.1820

Example 215. 1-(1-(3-(4-(cyclopropanecarbonyl) piperazine-1-carbonyl)-6-fluoroquinolin-4-yl)-4-phenylpiperidin-4-yl)ethanone, TFA (Cpd. 215)

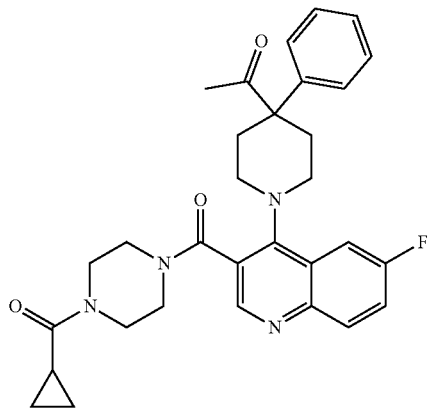

Cpd. 215

The title compound was prepared following the similar procedure as described in Example 17. $^1$H NMR (400 MHz, DMSO-d$_6$) δ 8.56 (s, 1H), 8.03 (dd, J=9.1, 5.4 Hz, 1H), 7.74 (t, J=8.3 Hz, 2H), 7.40 (d, J=4.3 Hz, 4H), 7.29 (dt, J=8.6, 4.2 Hz, 1H), 3.91-3.02 (m, 12H), 2.47-1.95 (m, 5H), 1.93 (s, 3H), 0.73 (d, J=4.7 Hz, 4H); LC-MS (Method 2): t$_R$=4.34 min, m/z (M+H)$^+$=529; HRMS calculated for C$_{31}$H$_{34}$FN$_4$O$_3$ (M+H)$^+$: 529.2609, found: 529.2611.

Example 216. 1-(1-(6-fluoro-3-(4-(methylsulfonyl)piperazine-1-carbonyl)quinolin-4-yl)-4-phenylpiperidin-4-yl)ethanone, TFA (Cpd. 216)

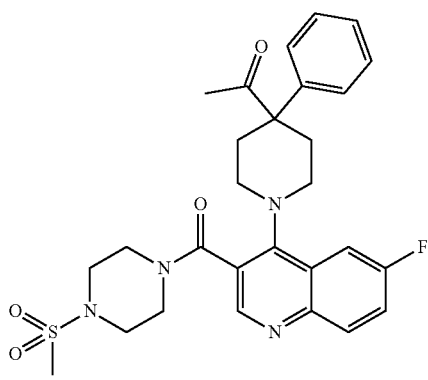

Cpd. 216

The title compound was prepared following the similar procedure as described in Example 17. $^1$H NMR (400 MHz, DMSO-d$_6$) δ 8.56 (s, 1H), 8.03 (dd, J=9.1, 5.5 Hz, 1H), 7.75 (t, J=9.1 Hz, 2H), 7.46-7.23 (m, 5H), 3.90-2.96 (m, 12H), 2.92 (s, 3H), 2.61-2.23 (m, 4H), 1.93 (s, 3H); LC-MS (Method 2): t$_R$=4.36 min, m/z (M+H)$^+$=539; HRMS calculated for C$_{28}$H$_{32}$FN$_4$O$_4$S (M+H)$^+$: 539.2123, found: 539.2135.

Example 217. 4-methyl-1-(5-(4-(methylsulfonyl)piperazine-1-carbonyl)thieno[2,3-b]pyridin-4-yl)piperidine-4-carbonitrile, TFA (Cpd. 217)

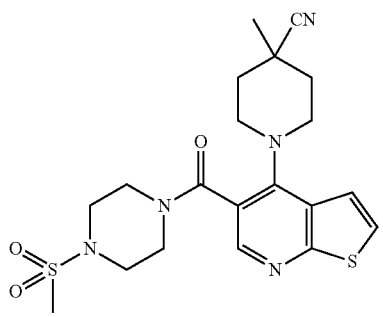

Cpd. 217

The title compound was prepared following the similar procedure as described in Example 1. $^1$H NMR (400 MHz, DMSO-d$_6$) δ 8.21 (s, 1H), 7.79 (d, J=6.1 Hz, 1H), 7.41 (d, J=6.1 Hz, 1H), 4.03-2.99 (m, 12H), 2.88 (s, 3H), 2.02-1.59 (m, 4H), 1.40 (s, 3H); LC-MS (Method 2): t$_R$=3.86 min, m/z (M+H)$^+$=448; HRMS calculated for C$_{20}$H$_{26}$N$_5$O$_3$S$_2$ (M+H)$^+$: 448.1472, found: 448.1483.

Example 218. 1-(5-(4-(ethylsulfonyl)piperazine-1-carbonyl)thieno[2,3-b]pyridin-4-yl)-4-methylpiperidine-4-carbonitrile, TFA (Cpd. 218)

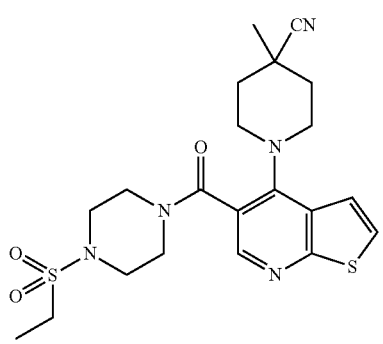

Cpd. 218

The title compound was prepared following the similar procedure as described in Example 1. $^1$H NMR (400 MHz, DMSO-d$_6$) δ 8.22 (s, 1H), 7.79 (d, J=6.1 Hz, 1H), 7.40 (d, J=6.1 Hz, 1H), 4.00-3.11 (m, 12H), 3.06 (q, J=7.4 Hz, 2H), 2.02-1.55 (m, 4H), 1.40 (s, 3H), 1.19 (t, J=7.4 Hz, 3H); LC-MS (Method 2): t$_R$=4.07 min, m/z (M+H)$^+$=462; HRMS calculated for C$_{21}$H$_{28}$N$_5$O$_3$S$_2$ (M+H)$^+$: 462.1628, found: 462.1644.

Example 219. 1-(5-(4-(cyclopropanecarbonyl)piperazine-1-carbonyl)thieno[2,3-b]pyridin-4-yl)-4-methylpiperidine-4-carbonitrile, TFA (Cpd. 219)

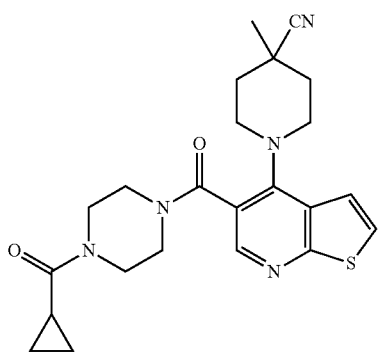

Cpd. 219

The title compound was prepared following the similar procedure as described in Example 1. $^1$H NMR (400 MHz, DMSO-$d_6$) δ 8.22 (s, 1H), 7.79 (d, J=6.1 Hz, 1H), 7.41 (d, J=6.1 Hz, 1H), 4.23-3.08 (m, 12H), 2.05-1.54 (m, 5H), 1.40 (s, 3H), 0.71 (dd, J=5.6, 2.8 Hz, 4H); LC-MS (Method 2): $t_R$=3.85 min, m/z (M+H)$^+$=438; HRMS calculated for $C_{23}H_{27}N_5O_2SNa$ (M+Na)$^+$: 460.1778, found: 460.1788.

Example 220. 1-(4-(6-fluoro-3-(4-(methylsulfonyl)piperazine-1-carbonyl)quinolin-4-yl)piperazin-1-yl)prop-2-en-1-one (Cpd. 220)

Hunig's base (1.048 ml, 6.0 mmol) were added sequentially. The tube was sealed and heated at 80° C. for overnight. After cooling to rt, the mixture was concentrated and purified by silica gel chromatography using 15-30-45% EtOAc/hexane as the eluent to give ethyl 4-(4-(tert-butoxycarbonyl)piperazin-1-yl)-6-fluoroquinoline-3-carboxylate (800 mg, 1.983 mmol, 99% yield).

STEP 2: Synthesis of 4-(4-(tert-Butoxycarbonyl)piperazin-1-yl)-6-fluoroquinoline-3-carboxylic acid. To a solution of ethyl 4-(4-(tert-butoxycarbonyl)piperazin-1-yl)-6-fluoroquinoline-3-carboxylate (800 mg, 1.983 mmol) in THF (6 ml)/MeOH (1 ml) was added 1.5 N LiOH$_{(aq)}$ (6 mL, 9 mmol). The mixture was heated at 50° C. for 5 h. After cooling to rt, 1N HCl$_{(aq)}$ was added until the pH of water layer is ca. 4-5. Then hexane (20 mL) was added. No solid was formed. The mixture was then concentrated to remove all the solvent and then dried to give 4-(4-(tert-butoxycarbonyl)piperazin-1-yl)-6-fluoroquinoline-3-carboxylic acid (1.202 g, 1.857 mmol, 94% yield). This material is contained with NaCl salt and was used without further purification. LC-MS (Method 1): $t_R$=2.75 min, m/z (M+H)$^+$=376.

STEP 3: Synthesis of tert-Butyl 4-(6-fluoro-3-(4-(methylsulfonyl)piperazine-1-carbonyl)quinolin-4-yl)piperazine-1-carboxylate. To a mixture of 4-(4-(tert-butoxycarbonyl)piperazin-1-yl)-6-fluoroquinoline-3-carboxylic acid (647 mg, 1 mmol), 1-(methylsulfonyl)piperazine (181 mg, 1.10 mmol), and HATU (570 mg, 1.50 mmol) was added DMF (3 ml) and then Hunig's base (0.524 ml, 3.0 mmol). The mixture was stirred at rt for 1.5 h. The mixture was poured into EtOAc/H$_2$O (30 mL/30 mL). The organic layer was dried (Na$_2$SO$_4$) and filtered. After removal of solvent, the product was purified by silica gel chromatography using 0-5% MeOH/EtOAc as the eluent to give tert-butyl 4-(6-fluoro-3-(4-(methylsulfonyl)piperazine-1-carbonyl)quinolin-4-yl)piperazine-1-carboxylate (510 mg, 0.978 mmol, 98% yield). LC-MS (Method 1): $t_R$=2.88 min, m/z (M+H)$^+$=522.

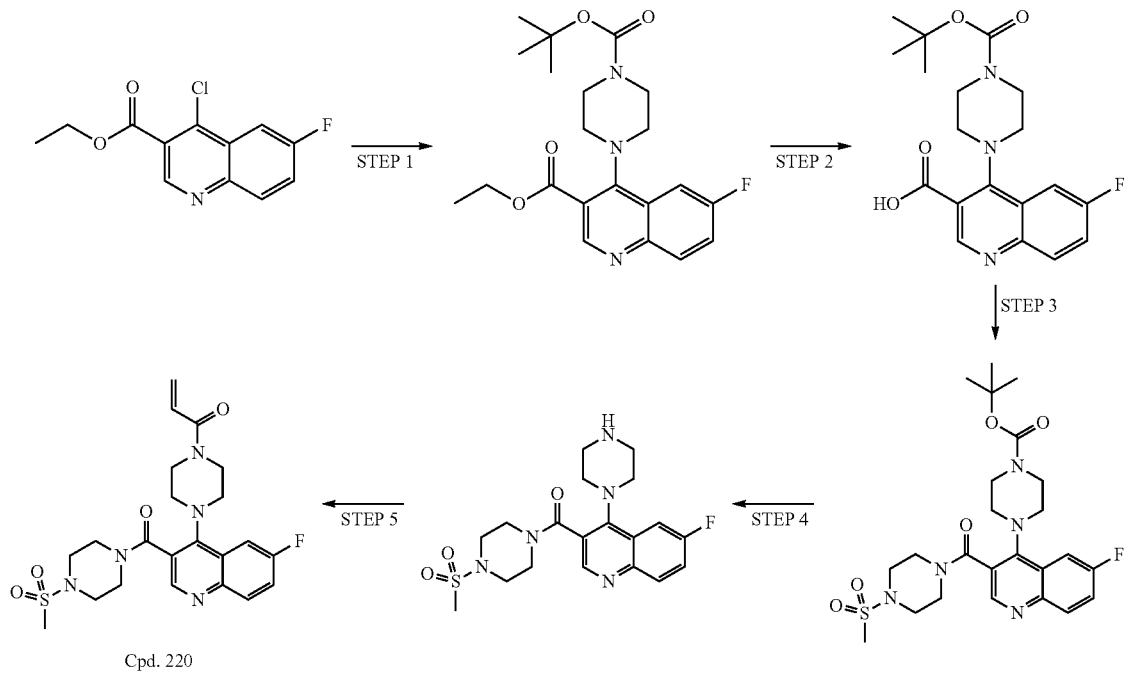 [SMILES: CCOC(=O)c1cnc2ccc(F)cc2c1Cl ; CCOC(=O)c1cnc2ccc(F)cc2c1N1CCN(C(=O)OC(C)(C)C)CC1 ; CC(C)(C)OC(=O)N1CCN(c2c(C(=O)O)cnc3ccc(F)cc23)CC1 ; C=CC(=O)N1CCN(c2c(C(=O)N3CCN(S(C)(=O)=O)CC3)cnc3ccc(F)cc23)CC1 ; CS(=O)(=O)N1CCN(C(=O)c2cnc3ccc(F)cc3c2N2CCNCC2)CC1 ; CC(C)(C)OC(=O)N1CCN(c2c(C(=O)N3CCN(S(C)(=O)=O)CC3)cnc3ccc(F)cc23)CC1]

Cpd. 220

STEP 1: Synthesis of ethyl 4-(4-(tert-Butoxycarbonyl)piperazin-1-yl)-6-fluoroquinoline-3-carboxylate. In a microwave vial was placed ethyl 4-chloro-6-fluoroquinoline-3-carboxylate (507 mg, 2 mmol) and tert-butyl piperazine-1-carboxylate (447 mg, 2.40 mmol). Then EtOH (4 ml) and STEP 4: Synthesis of (6-Fluoro-4-(piperazin-1-yl)quinolin-3-yl)(4-(methylsulfonyl)piperazin-1-yl)methanone, 2HCl. To a solution of tert-butyl 4-(6-fluoro-3-(4-(methylsulfonyl)piperazine-1-carbonyl)quinolin-4-yl)piperazine-1-carboxylate (510 mg, 0.978 mmol) in 1,4-Dioxane (5 ml)/CH$_2$Cl$_2$ (8 ml) was added HCl (4N in dioxane, 4 mL, 16 mmol). Salt formed right after HCl solution was added. The deprotection process proceeded slowly with stirring suspension. The suspension was stirred at rt for overnight and checked by HPLC to ensure the completion of deprotection. The mixture was concentrated to remove most of solvent. Then hexane (30 mL) was added and the solid was filtered, washed with hexane (mL×3), and dried to give (6-fluoro-4-(piperazin-1-yl)quinolin-3-yl)(4-(methylsulfonyl)piperazin-1-yl)methanone, 2HCl as a pale yellow solid. LC-MS (Method 1): $t_R$=2.27 min, m/z (M+H)$^+$=422.

STEP 5: Synthesis of 1-(4-(6-Fluoro-3-(4-(methylsulfonyl)piperazine-1-carbonyl)quinolin-4-yl)piperazin-1-yl)prop-2-en-1-one. To a solution of (6-fluoro-4-(piperazin-1-yl)quinolin-3-yl)(4-(methylsulfonyl)piperazin-1-yl)methanone, 2HCl (49.4 mg, 0.1 mmol) in CH$_2$Cl$_2$ (1 ml) was added Et$_3$N (0.139 ml, 1.0 mmol) and then acryloyl chloride (45.3 mg, 0.50 mmol). The mixture was stirred at rt for 30 min. The mixture was poured into EtOAc/H$_2$O (10 mL/10 mL). The organic layer was dried (Na$_2$SO$_4$) and filtered. After removal of solvent, the product was purified by silica gel chromatography using 0-10% MeOH/EtOAc as the eluent to give 1-(4-(6-fluoro-3-(4-(methylsulfonyl)piperazine-1-carbonyl)quinolin-4-yl)piperazin-1-yl)prop-2-en-1-one (23 mg, 0.048 mmol, 48.4% yield). LC-MS (Method 2): $t_R$=3.19 min, m/z (M+H)$^+$=476; HRMS calculated for C$_{22}$H$_{27}$FN$_5$O$_4$S (M+H)$^+$: 476.1762, found: 476.1763.

Example 221. (6-fluoro-4-(4-(vinylsulfonyl)piperazin-1-yl)quinolin-3-yl)(4-(methylsulfonyl)piperazin-1-yl)methanone (Cpd. 221)

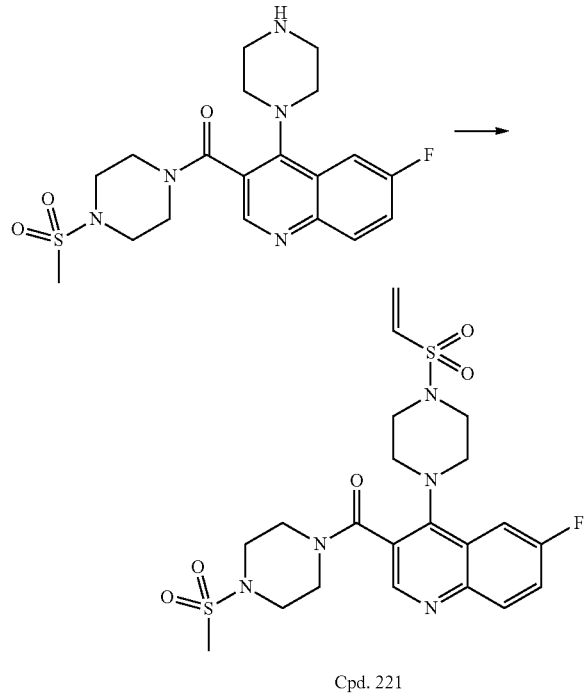

Cpd. 221

To a solution of (6-fluoro-4-(piperazin-1-yl)quinolin-3-yl)(4-(methylsulfonyl)piperazin-1-yl)methanone, 2HCl (49.4 mg, 0.1 mmol) in CH$_2$Cl$_2$ (1 ml) was added Et$_3$N (0.139 ml, 1.0 mmol) and then ethenesulfonyl chloride (63.3 mg, 0.50 mmol). The mixture was stirred at rt for 30 min. The mixture was poured into EtOAc/H$_2$O (10 mL/10 mL). The organic layer was dried (Na$_2$SO$_4$) and filtered. After removal of solvent, the product was purified by silica gel chromatography using 0-5% MeOH/EtOAc as the eluent to give (6-fluoro-4-(4-(vinylsulfonyl)piperazin-1-yl)quinolin-3-yl)(4-(methylsulfonyl)piperazin-1-yl)methanone (24 mg, 0.047 mmol, 46.9% yield). LC-MS (Method 2): $t_R$=3.59 min, m/z (M+H)$^+$=512; HRMS calculated for C$_{21}$H$_{27}$FN$_5$O$_5$S$_2$ (M+H)$^+$: 512.1432, found: 512.1440.

Example 222. (e)-3-cyclopropyl-2-(4-(6-fluoro-3-(4-(methylsulfonyl)piperazine-1-carbonyl)quinolin-4-yl)piperazine-1-carbonyl)acrylonitrile (Cpd. 222)

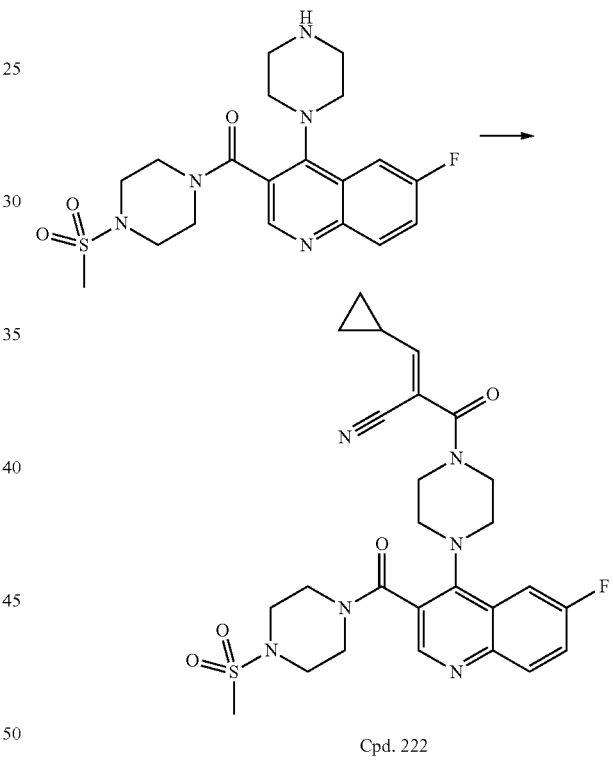

Cpd. 222

To a mixture of (6-fluoro-4-(piperazin-1-yl)quinolin-3-yl)(4-(methylsulfonyl)piperazin-1-yl)methanone, 2HCl (49.4 mg, 0.1 mmol), (E)-2-cyano-3-cyclopropylacrylic acid (27.4 mg, 0.20 mmol), and HATU (114 mg, 0.30 mmol) was added DMF (1 ml) and then Hunig's base (0.087 ml, 0.50 mmol). The mixture was stirred at rt for 1.5 h. The mixture was poured into EtOAc/H$_2$O (10 mL/10 mL). The aqueous layer was extracted with EtOAc (10 mL). The combined organic layer was dried (Na$_2$SO$_4$) and filtered. After removal of solvent, the product was purified by silica gel chromatography using 80-100% EtOAc/hexane as the eluent to give (E)-3-cyclopropyl-2-(4-(6-fluoro-3-(4-(methylsulfonyl)piperazine-1-carbonyl)quinolin-4-yl)piperazine-1-carbonyl)acrylonitrile (43 mg, 0.080 mmol, 80% yield). LC-MS (Method 2): $t_R$=3.80 min, m/z (M+H)$^+$=541; HRMS calculated for $C_{26}H_{30}FN_6O_4S$ (M+H)$^+$: 541.2028, found: 541.2023.

Example 223. (R)-1-(6-fluoro-3-(3-methyl-4-(methylsulfonyl)piperazine-1-carbonyl)quinolin-4-yl)-4-methylpiperidine-4-carbonitrile, TFA (Cpd. 223)

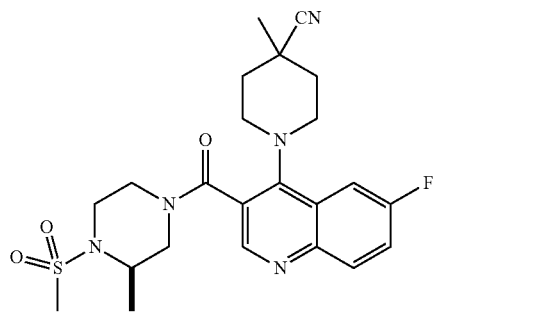

Cpd. 223

The title compound was prepared following the similar procedure as described in Example 1. $^1$H NMR (400 MHz, DMSO-d$_6$) δ 8.76-8.44 (m, 1H), 8.16-7.93 (m, 1H), 7.89-7.50 (m, 2H), 4.52-2.84 (m, 14H), 2.13-1.71 (m, 4H), 1.44 (2 set of s, 3H), 1.32-1.03 (m, 3H) (rotamers observed); LC-MS (Method 2): $t_R$=3.92 min, m/z (M+H)$^+$=474; HRMS calculated for $C_{23}H_{29}FN_5O_3S$ (M+H)$^+$: 474.1970, found: 474.1983.

Example 224. (R)-1-(3-(4-(cyclopropanecareonyl)-3-methylpiperazine-1-carbonyl)-6-fluoroquinolin-4-yl)-4-methylpiperidine-4-carbonitrile, TFA (Cpd. 224)

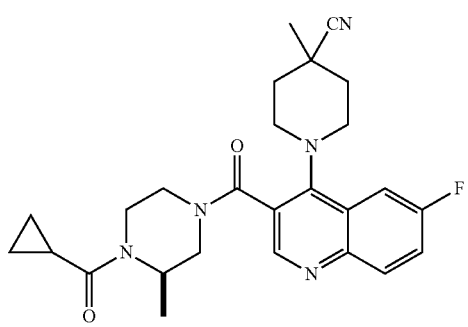

Cpd. 224

The title compound was prepared following the similar procedure as described in Example 1. $^1$H NMR (400 MHz, DMSO-d$_6$) δ 8.62 (m, 1H), 8.13-7.97 (m, 1H), 7.73 (m, 2H), 4.80-2.72 (m, 11H), 2.13-1.62 (m, 4H), 1.44 (2 set of s, 3H), 1.35-1.00 (m, 4H), 0.71 (s, 4H) (rotamers observed); LC-MS (Method 2): $t_R$=3.82 min, m/z (M+H)$^+$=464; HRMS calculated for $C_{26}H_{31}FN_5O_2$ (M+H)$^+$: 464.2456, found: 464.2475.

Example 225. 1-(3-((3R*,5S*)-3,5-dimethyl-4-(methylsulfonyl)piperazine-1-carbonyl)-6-fluoroquinolin-4-yl)-4-methylpiperidine-4-carbonitrile, TFA (Cpd. 225)

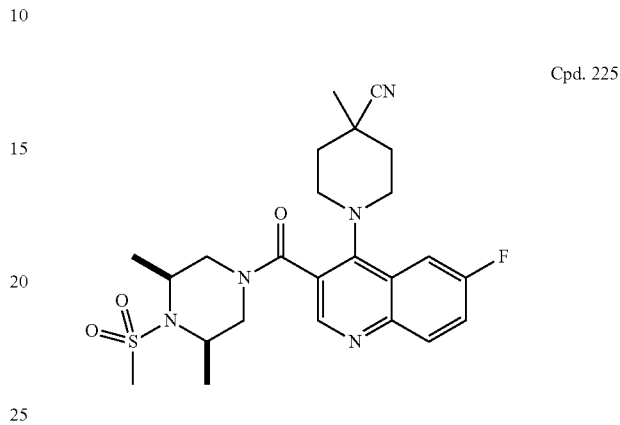

Cpd. 225

The title compound was prepared following the similar procedure as described in Example 1. $^1$H NMR (400 MHz, DMSO-d$_6$) δ 8.64 (m, 1H), 8.06 (m, 1H), 7.85-7.64 (m, 2H), 4.45-3.01 (m, 10H), 2.99 (2 set of s, 3H), 2.11-1.73 (m, 4H), 1.44 (2 set of s, 3H), 1.37-1.31 (m, 3H), 1.24-1.16 (m, 3H) (rotamers observed); LC-MS (Method 2): $t_R$=3.81 min, m/z (M+H)$^+$=488; HRMS calculated for $C_{24}H_{31}FN_5O_3S$ (M+H)$^+$: 488.2126, found: 488.2127.

Example 226. (S)-1-(6-fluoro-3-(3-methyl-4-(methylsulfonyl)piperazine-1-carbonyl)quinolin-4-yl)-4-methylpiperidine-4-carbonitrile, TFA (Cpd. 226)

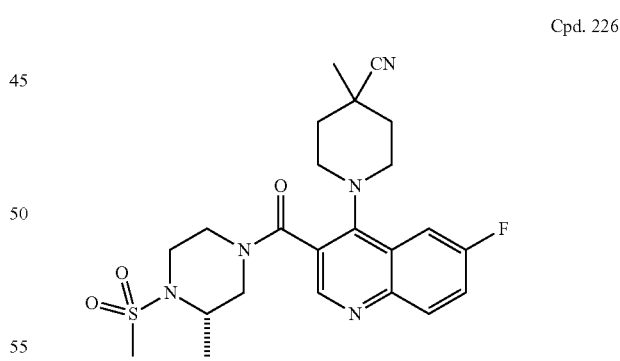

Cpd. 226

The title compound was prepared following the similar procedure as described in Example 1. $^1$H NMR (400 MHz, DMSO-d$_6$) δ 8.72-8.46 (m, 1H), 8.15-7.93 (m, 1H), 7.80-7.59 (m, 2H), 4.53-3.01 (m, 11H), 3.00-2.95 (m, 3H), 2.12-1.72 (m, 4H), 1.44 (2 set of s, 3H), 1.33-1.02 (m, 3H). (rotamers observed); LC-MS (Method 2): $t_R$=3.89 min, m/z (M+H)$^+$=474; HRMS calculated for $C_{23}H_{29}FN_5O_3S$ (M+H)$^+$: 474.1970, found: 474.1979.

Example 227. (S)-1-(3-(4-(cyclopropanecarbonyl)-3-methylpiperazine-1-carbonyl)-6-fluoroquinolin-4-yl)-4-methylpiperidine-4-carbonitrile, TFA (Cpd. 227)

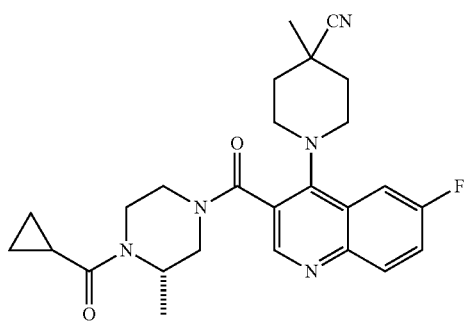

The title compound was prepared following the similar procedure as described in Example 1. $^1$H NMR (400 MHz, DMSO-d$_6$) δ 8.61 (m, 1H), 8.06 (m, 1H), 7.80-7.54 (m, 2H), 4.84-2.72 (m, 11H), 2.19-1.62 (m, 4H), 1.44 (2 set of s, 3H), 1.15 (m, 4H), 0.71 (m, 4H). (rotamers observed); LC-MS (Method 2): t$_R$=3.80 min, m/z (M+H)$^+$=464; HRMS calculated for C$_{26}$H$_{31}$FN$_5$O$_2$ (M+H)$^+$: 464.2456, found: 464.2445.

Example 228. 1-(3-((3R*,5S*)-4-(cyclopropanecarbonyl)-3,5-dimethylpiperazine-1-carbonyl)-6-fluoroquinolin-4-yl)-4-methylpiperidine-4-carbonitrile, TFA (Cpd. 228)

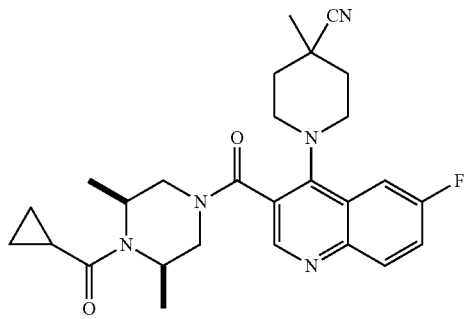

The title compound was prepared following the similar procedure as described in Example 1. $^1$H NMR (400 MHz, DMSO-d$_6$) δ 8.67 (2 set of s, 1H), 8.07 (m, 1H), 7.87-7.59 (m, 2H), 4.73-2.89 (m, 10H), 2.14-1.74 (m, 4H), 1.44 (2 set of s, 3H), 1.36-0.94 (m, 7H), 0.72 (m, 4H). (rotamers observed); LC-MS (Method 2): t$_R$=3.95 min, m/z (M+H)$^+$=478; HRMS calculated for C$_{27}$H$_{33}$FN$_5$O$_2$ (M+H)$^+$: 478.2613, found: 478.2631.

Example 229. 1-(3-(3,3-dimethyl-4-(methylsulfonyl)piperazine-1-carbonyl)-6-fluoroquinolin-4-yl)-4-methylpiperidine-4-carbonitrile, TFA (Cpd. 229)

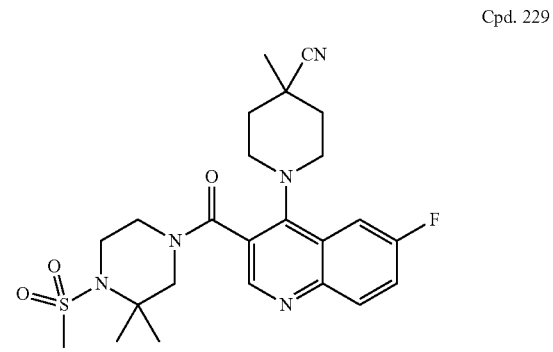 [SMILES: CC1(C#N)CCN(c2c(C(=O)N3CCN(S(C)(=O)=O)C(C)(C)C3)cnc3ccc(F)cc23)CC1]

The title compound was prepared following the similar procedure as described in Example 1. $^1$H NMR (400 MHz, DMSO-d$_6$) δ 8.60 (2 set of s, 1H), 8.06 (m, 1H), 7.73 (m, 2H), 4.04-3.02 (m, 10H), 2.99 (s, 3H), 2.08-1.69 (m, 4H), 1.53-1.39 (m, 6H), 1.32 (2 set of s, 3H). (rotamers observed); LC-MS (Method 2): t$_R$=3.92 min, m/z (M+H)$^+$=488; HRMS calculated for C$_{24}$H$_{31}$FN$_5$O$_3$S (M+H)$^+$: 488.2126, found: 488.2139.

Example 230. 1-(6-fluoro-3-(4-(methylsulfonyl)-4,7-diazaspiro[2.5]octane-7-carbonyl)quinolin-4-yl)-4-methylpiperidine-4-carbonitrile, TFA (Cpd. 230)

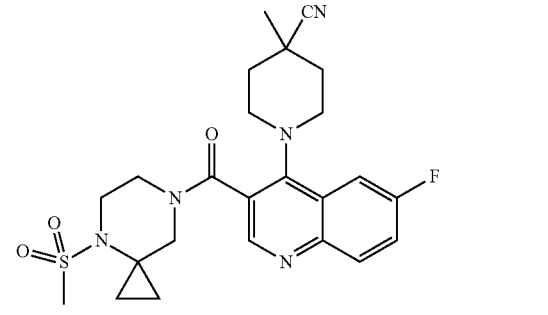

The title compound was prepared following the similar procedure as described in Example 1. $^1$H NMR (400 MHz, DMSO-d$_6$) δ 8.57 (s, 1H), 8.06 (m, 1H), 7.73 (m, 2H), 3.99-3.08 (m, 10H), 3.06 (2 set of s, 3H), 2.08-1.70 (m, 4H), 1.44 (2 set of s, 3H), 1.40-0.56 (m, 4H). (rotamers observed); LC-MS (Method 2): t$_R$=3.89 min, m/z (M+H)$^+$=486; HRMS calculated for C$_{24}$H$_{29}$FN$_5$O$_3$S (M+H)$^+$: 486.1970, found: 486.1972.

Example 231. 1-(3-(4-(cyclopropanecarbonyl)-3,3-dimethylpiperazine-1-carbonyl)-6-fluoroquinolin-4-yl)-4-methylpiperidine-4-carbonitrile, TFA (Cpd. 231)

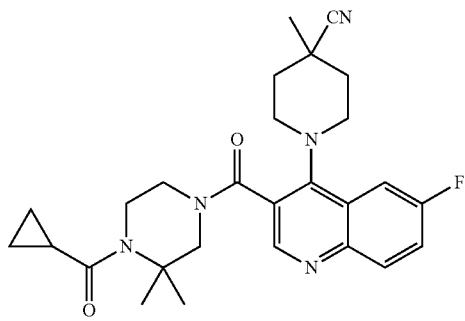

The title compound was prepared following the similar procedure as described in Example 1. LC-MS (Method 2): $t_R$=4.00 min, m/z (M+H)$^+$=478; HRMS calculated for $C_{27}H_{33}FN_5O_2$ (M+H)$^+$: 478.2613, found: 478.2604.

Example 232. 1-(3-(4-(cyclopropanecarbonyl)-4,7-diazaspiro[2.5]octane-7-carbonyl)-6-fluoroquinolin-4-yl)-4-methylpiperidine-4-carbonitrile, TFA (Cpd. 232)

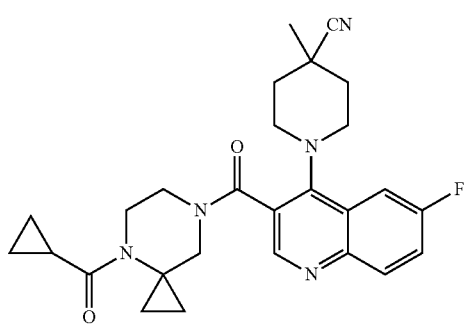

The title compound was prepared following the similar procedure as described in Example 1. $^1$H NMR (400 MHz, DMSO-d$_6$) δ 8.57 (2 set of s, 1H), 8.05 (m, 1H), 7.73 (m, 2H), 4.03-2.99 (m, 10H), 2.11-1.72 (m, 4H), 1.44 (2 set of s, 3H), 1.40-0.59 (m, 9H). (rotamers observed); LC-MS (Method 2): $t_R$=4.00 min, m/z (M+H)$^+$=476; HRMS calculated for $C_{27}H_{31}FN_5O_2$(M+H)$^+$:476.2456, found: 476.2472.

Example 233. 1-(6-(4-(cyclopropanecarbonyl)piperazine-1-carbonyl)thieno[3,2-b]pyridin-7-yl)-4-methylpiperidine-4-carbonitrile, TFA (Cpd. 233)

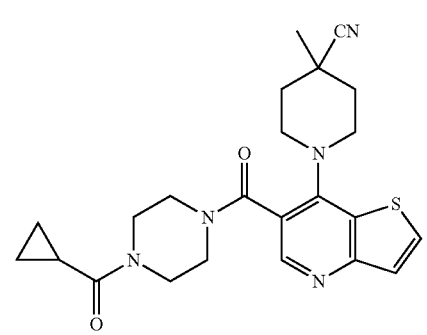

The title compound was prepared following the similar procedure as described in Example 1. $^1$H NMR (400 MHz, DMSO-d$_6$) δ 8.44 (s, 1H), 8.27 (d, J=5.6 Hz, 1H), 7.53 (d, J=5.6 Hz, 1H), 3.95-3.15 (m, 12H), 2.11-1.82 (m, 3H), 1.77-1.59 (m, 2H), 1.41 (s, 3H), 0.72 (dd, J=4.6, 1.8 Hz, 4H); LC-MS (Method 2): $t_R$=3.49 min, m/z (M+H)$^+$=438; HRMS calculated for $C_{23}H_{28}N_5O_2S$ (M+H)$^+$: 438.1958, found: 438.1972.

Example 234. 4-methyl-1-(6-(4-(methylsulfonyl)piperazine-1-carbonyl)thieno[3,2-b]pyridin-7-yl)piperidine-4-carbonitrile, TFA (Cpd. 234)

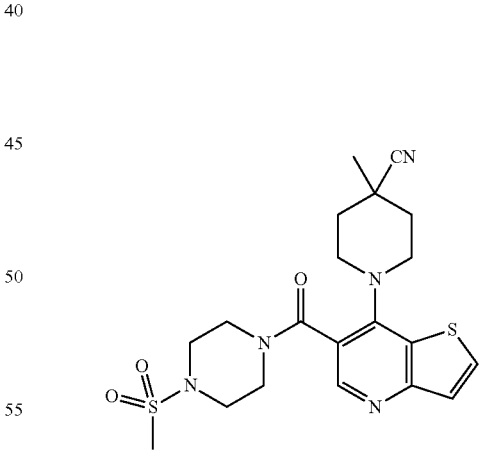

The title compound was prepared following the similar procedure as described in Example 1. LC-MS (Method 2): $t_R$=3.26 min, m/z (M+H)$^+$=448; HRMS calculated for $C_{20}H_{26}N_5O_3S_2$ (M+H)$^+$: 448.1472, found: 448.1480.

Example 235. 4-methyl-1-(5-(4-(methylsulfonyl)piperazine-1-carbonyl)-1H-pyrazolo[3,4-b]pyridin-4-yl)piperidine-4-carbonitrile, TFA (Cpd. 235)

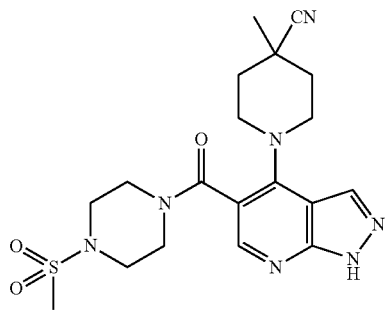

Cpd. 235

The title compound was prepared following the similar procedure as described in Example 1. $^1$H NMR (400 MHz, DMSO-$d_6$) δ 13.71-13.49 (m, 1H), 8.22 (d, J=1.5 Hz, 1H), 8.04 (s, 1H), 4.02 (d, J=13.5 Hz, 1H), 3.81 (d, J=13.4 Hz, 1H), 3.71 (d, J=13.9 Hz, 1H), 3.47 (t, J=10.6 Hz, 1H), 3.38-3.20 (m, 4H), 3.17-2.90 (m, 4H), 2.87 (s, 3H), 1.99 (d, J=13.5 Hz, 2H), 1.83-1.55 (m, 2H), 1.40 (s, 3H); LC-MS (Method 2): $t_R$=2.95 min, m/z (M+H)$^+$=432; HRMS calculated for $C_{19}H_{26}N_7O_3S$ (M+H)$^+$: 432.1812, found: 432.1824.

Example 236. 4-methyl-1-(5-(4-(methylsulfonyl)piperazine-1-carbonyl)-1H-pyrrolo[2,3-b]pyridin-4-yl)piperidine-4-carbonitrile, TFA (Cpd. 236)

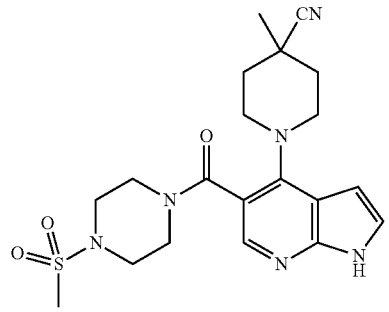

Cpd. 236

The title compound was prepared following the similar procedure as described in Example 1. LC-MS (Method 2): $t_R$=3.22 min, m/z (M+H)$^+$=431; HRMS calculated for $C_{20}H_{27}N_6O_3S$ (M+H)$^+$: 431.1860, found: 431.1866.

Example 237. 1-(5-(4-(cyclopropanecarbonyl)piperazine-1-carbonyl)-1H-pyrazolo[3,4-b]pyridin-4-yl)-4-methylpiperidine-4-carbonitrile, TFA (Cpd. 237)

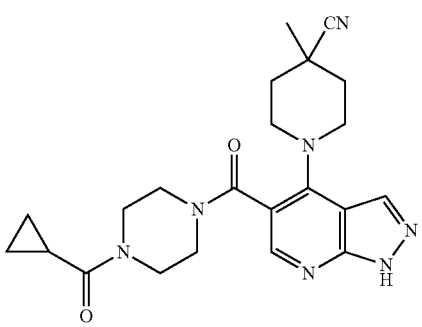

Cpd. 237

The title compound was prepared following the similar procedure as described in Example 1. $^1$H NMR (400 MHz, DMSO-$d_6$) δ 13.53 (s, 1H), 8.25 (s, 1H), 8.07 (s, 1H), 3.84-3.20 (m, 12H), 1.99-1.68 (m, 5H), 1.40 (s, 3H), 0.75-0.68 (m, 4H); LC-MS (Method 2): $t_R$=3.06 min, m/z M+H)$^+$= 422.

Example 238. (s)-1-(3-(4-(cyclopropanecarbonyl)-2-methylpiperazine-1-carbonyl)-6-fluoroquinolin-4-yl)-4-methylpiperidine-4-carbonitrile, TFA (Cpd. 238)

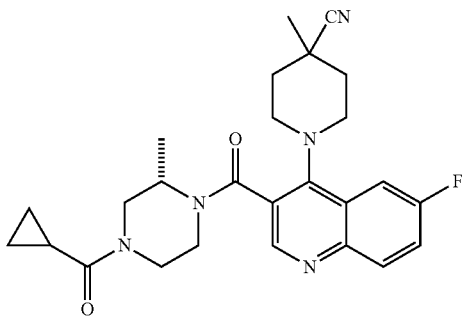

Cpd. 238

The title compound was prepared following the similar procedure as described in Example 1. $^1$H NMR (400 MHz, DMSO-$d_6$) δ 8.84-8.35 (m, 1H), 8.18-7.99 (m, 1H), 7.83-7.59 (m, 2H), 4.89-2.80 (m, 11H), 2.12-1.64 (m, 5H), 1.43 (2 set of s, 3H), 1.22-1.02 (m, 3H), 0.84-0.57 (m, 4H). (rotamers observed); LC-MS (Method 2): $t_R$=3.81 min, m/z (M+H)$^+$=464; HRMS calculated for $C_{26}H_{31}FN_5O_2$ (M+H)$^+$: 464.2456, found: 464.2470.

Example 239. (R)-1-(3-(4-(cyclopropanecarbonyl)-2-methylpiperazine-1-carbonyl)-6-fluoroquinolin-4-yl)-4-methylpiperidine-4-carbonitrile, TFA (Cpd. 239)

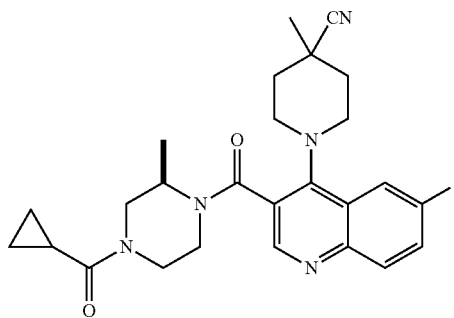

The title compound was prepared following the similar procedure as described in Example 1. $^1$H NMR (400 MHz, DMSO-d$_6$) δ 8.78-8.32 (m, 1H), 8.16-7.96 (m, 1H), 7.72 (m, 2H), 4.91-2.71 (m, 11H), 2.13-1.68 (m, 5H), 1.43 (2 set of s, 3H), 1.22-1.02 (m, 3H), 0.71 (m, 4H). (rotamers observed); LC-MS (Method 2): t$_R$=3.81 min, m/z (M+H)$^+$= 464; HRMS calculated for C$_{26}$H$_{31}$FN$_5$O$_2$ (M+H)$^+$: 464.2456, found: 464.2470.

Example 240. 1-(3-((2S*,6R*)-4-(cyclopropanecarbonyl)-2,6-dimethylpiperazine-1-carbonyl)-6-fluoroquinolin-4-yl)-4-methylpiperidine-4-carbonitrile, TFA (Cpd. 240)

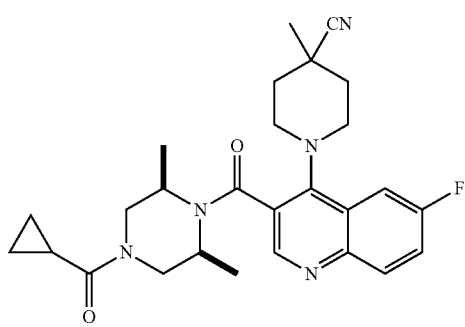

The title compound was prepared following the similar procedure as described in Example 1. LC-MS (Method 2): t$_R$=3.70 min, m/z (M+H)$^+$=478; HRMS calculated for C$_{27}$H$_{33}$FN$_5$O$_2$ (M+H)$^+$: 478.2613, found: 478.2630.

Example 241. (R)-1-(6-fluoro-3-(2-methyl-4-(methylsulfonyl)piperazine-1-carbonyl)quinolin-4-yl)-4-methylpiperidine-4-carbonitrile, TFA (Cpd. 241)

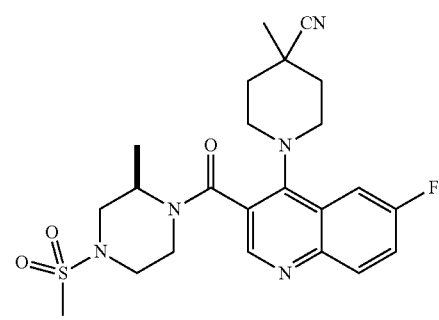

The title compound was prepared following the similar procedure as described in Example 1. LC-MS (Method 2): t$_R$=3.81 min, m/z (M+H)$^+$=474; HRMS calculated for C$_{23}$H$_{29}$FN$_5$O$_3$S (M+H)$^+$: 474.1970, found: 474.1993.

Example 242. 1-(3-(4-(cyclopropanecarbonyl)piperazine-1-carbonyl)-6-fluoroquinolin-4-yl)-4-(cyclopropylmethyl)piperidine-4-carbonitrile (Cpd. 242)

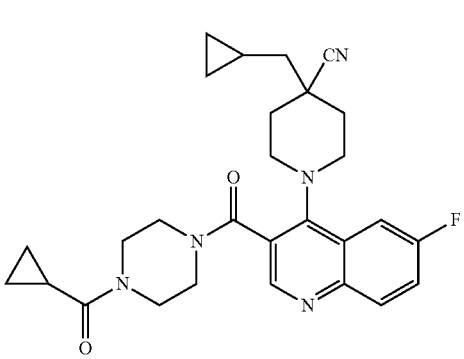

The title compound was prepared following the similar procedure as described in Example 1. LC-MS (Method 2): t$_R$=4.31 min, m/z (M+H)$^+$=490; HRMS calculated for C$_{28}$H$_{33}$FN$_5$O$_2$ (M+H)$^+$: 490.2613, found: 490.2626.

Example 243. 4-(cyclopropylmethyl)-1-(6-fluoro-3-(4-(methylsulfonyl)piperazine-1-carbonyl)quinolin-4-yl)piperidine-4-carbonitrile, TFA (Cpd. 243)

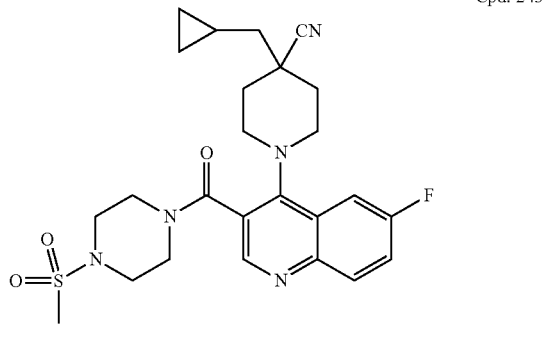

Cpd. 243

The title compound was prepared following the similar procedure as described in Example 1. $^1$H NMR (400 MHz, DMSO-d$_6$) δ 8.59 (s, 1H), 8.05 (dd, J=10.1, 5.6 Hz, 1H), 7.77-7.64 (m, 2H), 3.97-3.00 (m, 12H), 2.90 (s, 3H), 2.20-1.90 (m, 3H), 1.83 (td, J=12.6, 4.1 Hz, 1H), 1.63 (d, J=6.9 Hz, 2H), 0.86 (dd, J=9.6, 4.4 Hz, 1H), 0.57-0.43 (m, 2H), 0.20 (td, J=4.5, 2.3 Hz, 2H); LC-MS (Method 2): t$_R$=4.50 min, m/z (M+H)$^+$=500; HRMS calculated for C$_{25}$H$_{31}$FN$_5$O$_3$S (M+H)$^+$: 500.2126, found: 500.2120.

Example 244. 4-benzyl-1-(3-(4-(cyclopropanecarbonyl)piperazine-1-carbonyl)-6-fluoroquinolin-4-yl)piperidine-4-carbonitrile, TFA (Cpd. 244)

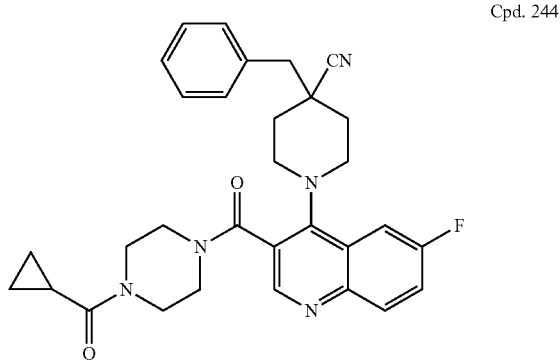 [SMILES: N#CC1(Cc2ccccc2)CCN(c2c(C(=O)N3CCN(C(=O)C4CC4)CC3)cnc3ccc(F)cc23)CC1]

Cpd. 244

The title compound was prepared following the similar procedure as described in Example 1. $^1$H NMR (400 MHz, DMSO-d$_6$) δ 8.55 (s, 1H), 8.05 (dd, J=9.1, 5.6 Hz, 1H), 7.75-7.62 (m, 2H), 7.39-7.22 (m, 5H), 3.78-3.00 (m, 14H), 2.21-1.78 (m, 5H), 0.70 (s, 4H); LC-MS (Method 2): t$_R$=4.61 min, m/z (M+H)$^+$=526; HRMS calculated for C$_{31}$H$_{33}$FN$_5$O$_2$ (M+H)$^+$: 526.2613, found: 526.2627.

Example 245. 4-benzyl-1-(6-fluoro-3-(4-(methylsulfonyl)piperazine-1-carbonyl)quinolin-4-yl)piperidine-4-carbonitrile, TFA (Cpd. 245)

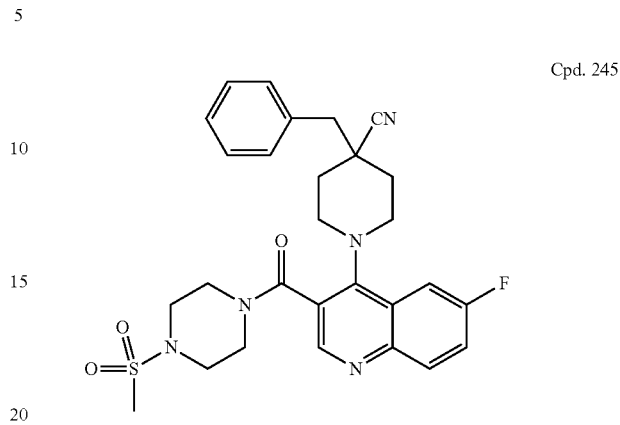

Cpd. 245

The title compound was prepared following the similar procedure as described in Example 1. $^1$H NMR (400 MHz, DMSO-d$_6$) δ 8.55 (s, 1H), 8.05 (dd, J=9.1, 5.5 Hz, 1H), 7.75-7.63 (m, 2H), 7.40-7.20 (m, 5H), 3.83-3.01 (m, 14H), 2.87 (s, 3H), 2.19-1.79 (m, 4H); LC-MS (Method 2): t$_R$=4.75 min, m/z (M+H)$^+$=536; HRMS calculated for C$_{28}$H$_{31}$FN$_5$O$_3$S (M+H)$^+$: 536.2126, found: 536.2148.

Example 246. 1'-(3-(4-(cyclopropanecarbonyl)piperazine-1-carbonyl)-6-fluoroquinolin-4-yl)spiro[indene-1,4'-piperidin]-2(3H)-one, TFA (Cpd. 246)

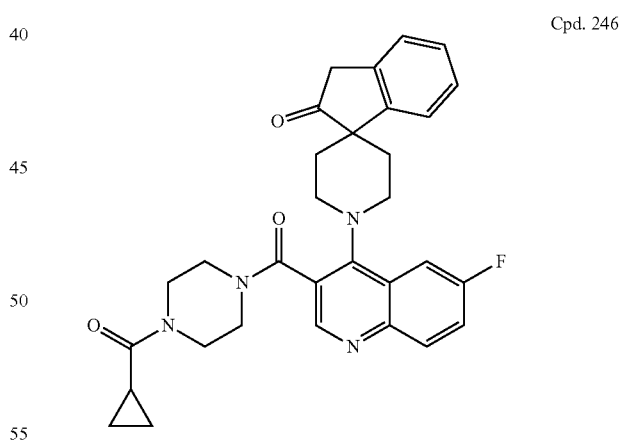

Cpd. 246

The title compound was prepared following the similar procedure as described in Example 17. $^1$H NMR (400 MHz, DMSO-d$_6$) δ 8.60 (s, 1H), 8.06 (dd, J=9.1, 5.5 Hz, 1H), 7.90-7.83 (m, 1H), 7.75 (t, J=9.0 Hz, 1H), 7.65-7.59 (m, 1H), 7.38-7.20 (m, 3H), 4.06-3.17 (m, 14H), 2.20-1.84 (m, 5H), 0.80-0.58 (m, 4H); LC-MS (Method 2): t$_R$=4.33 min, m/z (M+H)$^+$=527; HRMS calculated for C$_{31}$H$_{32}$FN$_4$O$_3$ (M+H)$^+$: 527.2453, found: 527.2458.

Example 247. 1'-(6-fluoro-3-(4-(methylsulfonyl) piperazine-1-carbonyl)quinolin-4-yl)spiro[indene-1, 4'-piperidin]-2(3H)-one, TFA (Cpd. 247)

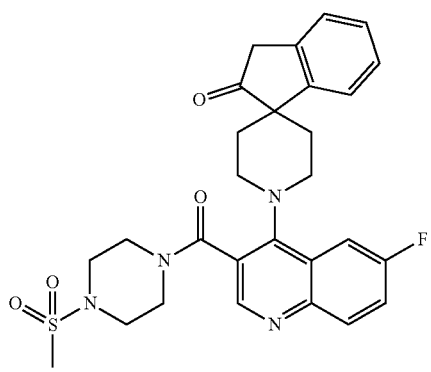

Cpd. 247

The title compound was prepared following the similar procedure as described in Example 17. $^1$H NMR (400 MHz, DMSO-$d_6$) δ 8.60 (s, 1H), 8.06 (dd, J=9.1, 5.5 Hz, 1H), 7.87 (d, J=10.4 Hz, 1H), 7.79-7.70 (m, 1H), 7.67-7.59 (m, 1H), 7.39-7.23 (m, 3H), 4.04-3.03 (m, 14H), 2.92 (s, 3H), 2.20-1.83 (m, 4H); LC-MS (Method 2): $t_R$=4.33 min, m/z (M+H)$^+$=537; HRMS calculated for $C_{28}H_{30}FN_4O_4S$ (M+H)$^+$: 537.1966, found: 537.1978.

Example 248. 8-(3-(4-(cyclopropanecarbonyl)piperazine-1-carbonyl)-6-fluoroquinolin-4-yl)-2-oxa-8-azaspiro[4.5]decan-1-one, TFA (Cpd. 248)

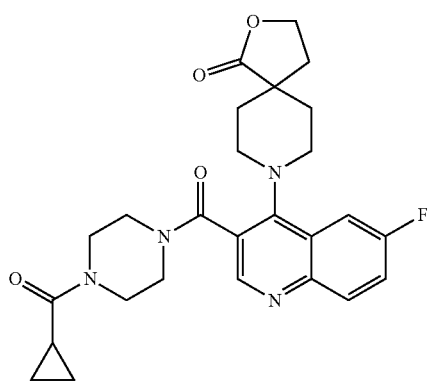

Cpd. 248

The title compound was prepared following the similar procedure as described in Example 17. $^1$H NMR (400 MHz, DMSO-$d_6$) δ 8.62 (s, 1H), 8.06 (dd, J=9.3, 5.3 Hz, 1H), 7.80-7.68 (m, 2H), 4.31 (t, J=7.0 Hz, 2H), 4.15-2.97 (m, 12H), 2.24 (t, J=7.0 Hz, 2H), 2.09-1.64 (m, 5H), 0.79-0.59 (m, 4H); LC-MS (Method 2): $t_R$=3.33 min, m/z (M+H)$^+$=481; HRMS calculated for $C_{26}H_{30}FN_4O_4$ (M+H)$^+$: 481.2246, found: 481.2261.

Example 249. 8-(6-fluoro-3-(4-(methylsulfonyl) piperazine-1-carbonyl)quinolin-4-yl)-2-oxa-8-azaspiro[4.5]decan-1-one, TFA (Cpd. 249)

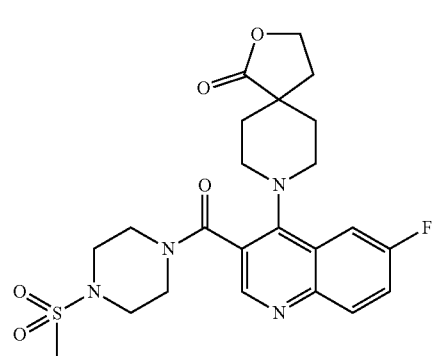

Cpd. 249

The title compound was prepared following the similar procedure as described in Example 17. $^1$H NMR (400 MHz, DMSO-$d_6$) δ 8.61 (s, 1H), 8.09-8.01 (m, 1H), 7.74 (t, J=9.1 Hz, 2H), 4.31 (t, J=7.0 Hz, 2H), 4.02-2.99 (m, 12H), 2.91 (s, 3H), 2.25 (t, J=7.0 Hz, 2H), 2.09-1.66 (m, 4H); LC-MS (Method 2): $t_R$=3.28 min, m/z (M+H)$^+$=491; HRMS calculated for $C_{23}H_{28}FN_4O_5S$ (M+H)$^+$: 491.1759, found: 491.1767.

Example 250. 8-(3-(4-(cyclopropanecarbonyl)piperazine-1-carbonyl)-6-fluoroquinolin-4-yl)-8-azaspiro[4.5]decan-1-one, TFA (Cpd. 250)

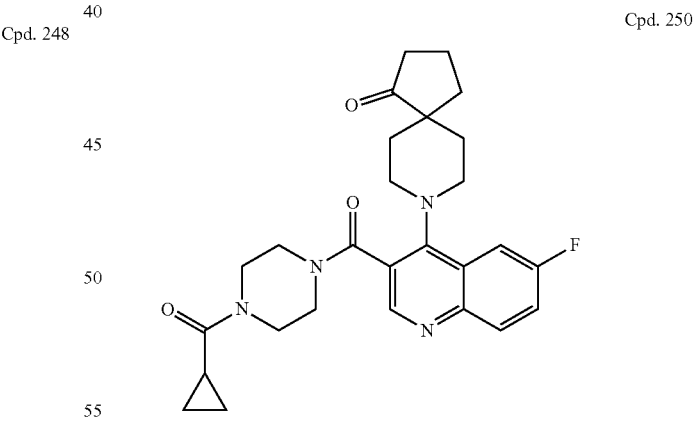

Cpd. 250

The title compound was prepared following the similar procedure as described in Example 17. $^1$H NMR (400 MHz, DMSO-$d_6$) δ 8.61 (s, 1H), 8.05 (dd, J=9.2, 5.4 Hz, 1H), 7.80-7.59 (m, 2H), 3.90-3.18 (m, 11H), 3.10 (t, J=11.4 Hz, 1H), 2.28 (t, J=7.5 Hz, 2H), 2.08-1.77 (m, 6H), 1.72 (m, 1H), 1.55 (m, 2H), 0.80-0.60 (m, 4H); LC-MS (Method 2): $t_R$=5.17 min, m/z M+H)$^+$=479; HRMS calculated for $C_{27}H_{32}FN_4O_3$ (M+H)$^+$: 479.2453, found: 479.2469.

Example 251. 8-(6-fluoro-3-(4-(methylsulfonyl)piperazine-1-carbonyl)quinolin-4-yl)-8-azaspiro[4.5]decan-1-one, TFA (Cpd. 251)

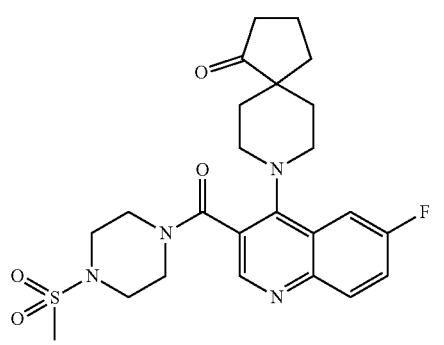

Cpd. 251

The title compound was prepared following the similar procedure as described in Example 17. ¹H NMR (400 MHz, DMSO-$d_6$) δ 8.59 (s, 1H), 8.05 (dd, J=9.1, 5.5 Hz, 1H), 7.82-7.62 (m, 2H), 3.92 (dd, J=11.8, 7.0 Hz, 1H), 3.63 (ddd, J=12.7, 7.4, 3.8 Hz, 1H), 3.54-3.34 (m, 2H), 3.29-3.20 (m, 4H), 3.12-307 (m, 4H), 2.91 (s, 3H), 2.28 (t, J=7.5 Hz, 2H), 1.98-1.78 (m, 5H), 1.73 (dt, J=13.9, 7.1 Hz, 1H), 1.55 (t, J=14.3 Hz, 2H); LC-MS (Method 2): $t_R$=5.07 min, m/z M+H)⁺=489; HRMS calculated for $C_{24}H_{30}FN_4O_4S$ (M+H)⁺: 489.1966, found: 489.1975.

Example 252. (4-(4-(cyclopropylsulfonyl)piperazin-1-yl)-6-fluoroquinolin-3-yl)(4-(methylsulfonyl)piperazin-1-yl)methanone, TFA (Cpd. 252)

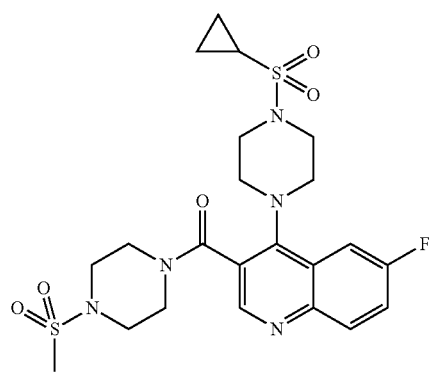

Cpd. 252

The title compound was prepared following the similar procedure as described in Example 221. ¹H NMR (400 MHz, DMSO-$d_6$) δ 8.64 (s, 1H), 8.08 (dd, J=9.2, 5.6 Hz, 1H), 7.82 (dd, J=10.2, 2.8 Hz, 1H), 7.72 (ddd, J=9.2, 8.2, 2.8 Hz, 1H), 3.94-3.89 (m, 1H), 3.74-3.63 (m, 1H), 3.60-3.00 (m, 14H), 2.91 (s, 3H), 2.74-2.63 (m, 1H), 1.08-0.88 (m, 4H); LC-MS (Method 2): $t_R$=3.78 min, m/z (M+H)⁺=526; HRMS calculated for $C_{22}H_{29}FN_5O_5S_2$ (M+H)⁺: 526.1589, found: 526.1600.

Example 253. (6-fluoro-4-(4-(1-hydroxyethyl)-4-phenylpiperidin-1-yl)quinolin-3-yl)(4-(methylsulfonyl)piperazin-1-yl)methanone (Cpd. 253)

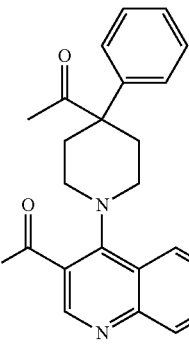

Cpd. 216

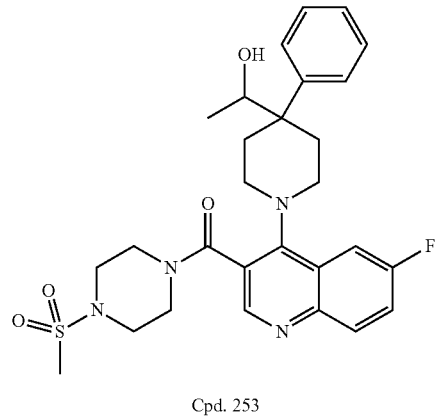

Cpd. 253

To a solution of 1-(1-(6-fluoro-3-(4-(methylsulfonyl)piperazine-1-carbonyl)quinolin-4-yl)-4-phenylpiperidin-4-yl)ethanone (25 mg, 0.046 mmol) in EtOH (2 ml)/EtOAc (2 ml) was added NaBH₄ (17.56 mg, 0.464 mmol). The mixture was stirred at rt for 2 h. The mixture was concentrated and than added EtOAc (5 mL)/H₂O (5 mL). The aqueous layer was extracted with EtOAc (3 mL×3). The combined organic layer was dried (Na₂SO₄) and filtered. After removal of solvent, the product was purified by silica gel chromatography using 0-5% MeOH/EtOAc as the eluent to give (6-fluoro-4-(4-(1-hydroxyethyl)-4-phenylpiperidin-1-yl)quinolin-3-yl)(4-(methylsulfonyl)piperazin-1-yl)methanone (24.5 mg, 0.045 mmol, 98% yield). ¹H NMR (400 MHz, Chloroform-d) δ 8.36 (d, J=1.8 Hz, 1H), 8.01 (dd, J=9.2, 5.5 Hz, 1H), 7.67 (dd, J=10.2, 2.9 Hz, 1H), 7.49-7.39 (m, 3H), 7.38-7.27 (m, 3H), 4.15-4.02 (m, 1H), 3.88-3.74 (m, 1H), 3.50-3.38 (m, 1H), 3.37-2.82 (m, 10H), 2.76 (d, J=2.8 Hz, 3H), 2.62 (t, J=17.0 Hz, 1H), 2.46-2.32 (m, 1H), 2.27-2.00 (m, 2H), 1.20 (d, J=6.0 Hz, 1H), 1.01 (dd, J=6.4, 4.6 Hz, 3H); LC-MS (Method 2): $t_R$=4.10 min, m/z (M+H)⁺=541; HRMS calculated for $C_{28}H_{34}FN_4O_4S$ (M+H)⁺: 541.2279, found: 541.2288.

Example 254. (6-fluoro-4-(4-(phenylsulfonyl)piperazin-1-yl)quinolin-3-yl)(4-(methylsulfonyl)piperazin-1-yl)methanone (Cpd. 254)

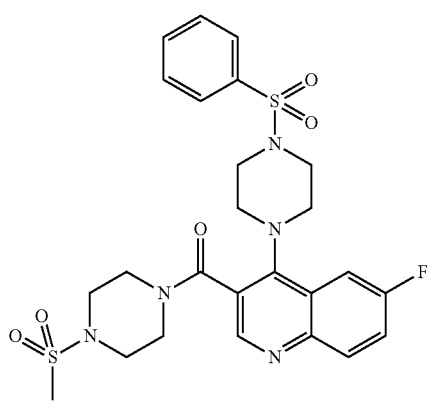

The title compound was prepared following the similar procedure as described in Example 221. ¹H NMR (400 MHz, Chloroform-d) δ 8.47 (s, 1H), 8.05 (ddd, J=8.5, 5.5, 1.0 Hz, 1H), 7.86-7.79 (m, 2H), 7.73-7.66 (m, 1H), 7.65-7.58 (m, 2H), 7.51-7.42 (m, 2H), 4.25 (ddd, J=14.0, 5.1, 2.4 Hz, 1H), 3.71-3.02 (m, 15H), 2.85 (s, 3H); LC-MS (Method 2): $t_R$=4.36 min, m/z M+H)⁺=562; HRMS calculated for $C_{25}H_{29}FN_5O_5S_2$ (M+H)⁺: 562.1589, found: 562.1592.

Example 255. (4-(cyclopropanecarbonyl)piperazin-1-yl)(6-fluoro-4-(4-(hydroxymethyl)-4-phenylpiperidin-1-yl)quinolin-3-yl)methanone, TFA (Cpd. 255)

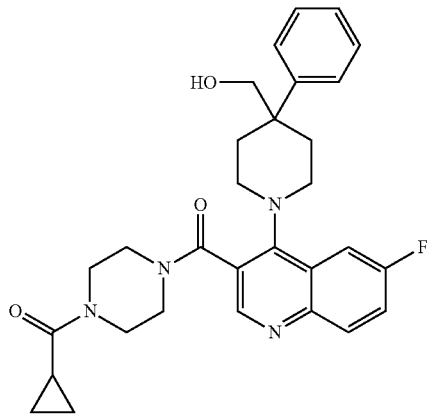

The title compound was prepared following the similar procedure as described in Example 17. ¹H NMR (400 MHz, DMSO-d₆) δ 8.52 (s, 1H), 8.06-7.98 (m, 1H), 7.80-7.70 (m, 2H), 7.43-7.37 (m, 2H), 7.32 (t, J=7.7 Hz, 2H), 7.16 (t, J=7.3 Hz, 1H), 3.41 (s, 2H), 3.86-3.01 (m, 14H), 2.35-1.77 (m, 4H), 0.73 (d, J=4.4 Hz, 4H); LC-MS (Method 2): $t_R$=3.63 min, m/z (M+H)⁺=517; HRMS calculated for $C_{30}H_{34}FN_4O_3$ (M+H)⁺: 517.2609, found: 517.2628.

Example 256. (6-fluoro-4-(4-(hydroxymethyl)-4-phenylpiperidin-1-yl)quinolin-3-yl)(4-(methylsulfonyl)piperazin-1-yl)methanone, TFA (Cpd. 256)

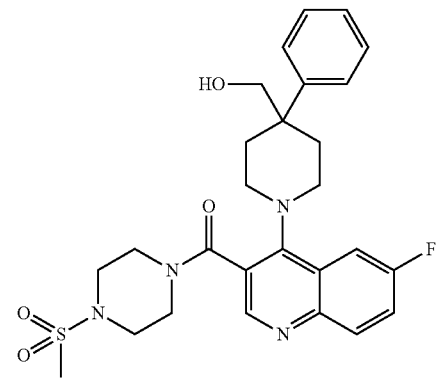

The title compound was prepared following the similar procedure as described in Example 17. ¹H NMR (400 MHz, DMSO-d₆) δ 8.55 (s, 1H), 8.02 (dd, J=10.1, 5.5 Hz, 1H), 7.79-7.67 (m, 2H), 7.45-7.29 (m, 4H), 7.25-7.17 (m, 1H), 3.89-3.81 (m, 1H), 3.43 (s, 2H), 3.54-2.93 (m, 14H), 2.88 (s, 3H), 2.33-2.04 (m, 2H); LC-MS (Method 2): $t_R$=3.86 min, m/z (M+H)⁺=527; HRMS calculated for $C_{27}H_{32}FN_4O_4S$ (M+H)⁺: 527.2123, found: 527.2128.

Example 257. 1-(6-fluoro-3-(4-(methylsulfonyl)piperazine-1-carbonyl)quinolin-4-yl)-4-phenylpiperidine-4-carbaldehyde (Cpd. 257)

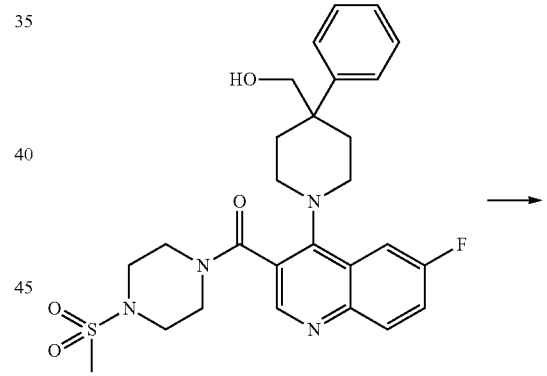

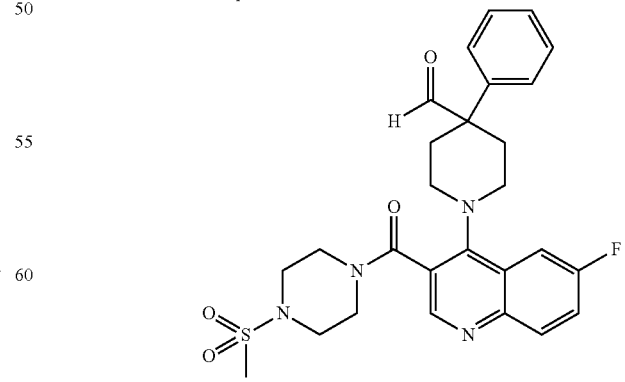

To a suspension of (6-fluoro-4-(4-(hydroxymethyl)-4-phenylpiperidin-1-yl)quinolin-3-yl)(4-(methylsulfonyl)piperazin-1-yl)methanone (30 mg, 0.057 mmol) in CH$_2$Cl$_2$ (2 ml) was added Dess-Martin periodinane (48.3 mg, 0.114 mmol). The mixture was stirred at rt for 1 h. Then 2N Na$_2$CO$_{3(aq)}$ (5 mL) was added. The mixture was extracted with EtOAc (5 mL×3). The combined organic layer was dried (Na$_2$SO$_4$) and filtered. After removal of solvent, the product was purified by silica gel chromatography using 0-10% MeOH/EtOAc as the eluent to give 1-(6-fluoro-3-(4-(methylsulfonyl)piperazine-1-carbonyl)quinolin-4-yl)-4-phenylpiperidine-4-carbaldehyde (22.6 mg, 0.043 mmol, 76% yield). $^1$H NMR (400 MHz, Chloroform-d) δ 9.46 (s, 1H), 8.44 (s, 1H), 8.05 (dd, J=9.2, 5.5 Hz, 1H), 7.64 (dd, J=10.0, 2.8 Hz, 1H), 7.51-7.40 (m, 3H), 7.39-7.31 (m, 3H), 4.08 (ddd, J=13.4, 6.2, 3.4 Hz, 1H), 3.81 (d, J=11.4 Hz, 1H), 3.63-3.07 (m, 10H), 2.86 (s, 3H), 2.64 (d, J=13.5 Hz, 2H), 2.33-2.29 (m, 2H); LC-MS (Method 2): $t_R$=4.50 min, m/z (M+H)$^+$=525; HRMS calculated for C$_{27}$H$_{30}$FN$_4$O$_4$S (M+H)$^+$: 525.1966, found: 525.1979.

Example 258. (6-fluoro-4-(4-(2-hydroxypropan-2-yl)-4-phenylpiperidin-1-yl)quinolin-3-yl)(4-(methylsulfonyl)piperazin-1-yl)methanone, TFA (Cpd. 258)

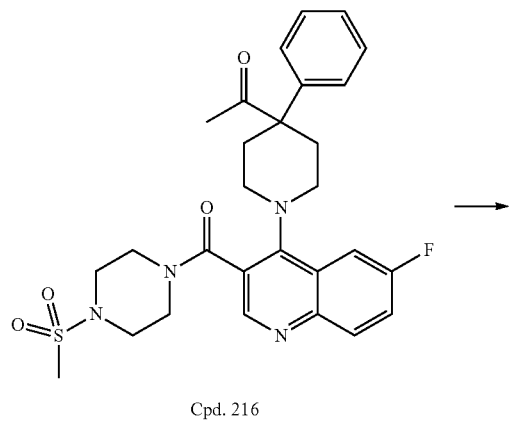

Cpd. 216

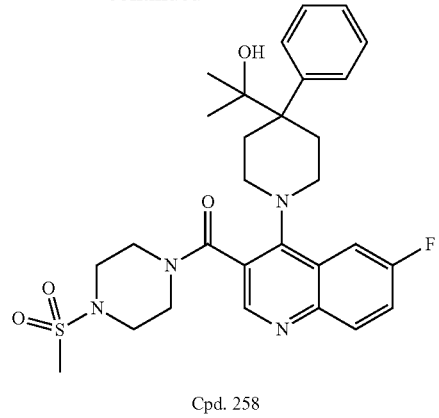

Cpd. 258

To a solution of 1-(1-(6-fluoro-3-(4-(methylsulfonyl)piperazine-1-carbonyl)quinolin-4-yl)-4-phenylpiperidin-4-yl)ethanone (29.6 mg, 0.055 mmol) in THF (2 ml) was added MeMgBr (3M in Et$_2$O, 0.33 mL, 1 mmol) at rt. The mixture was stirred for 2 h and then quenched with NH$_4$Cl$_{(aq)}$ (3 mL). The mixture was extracted with EtOAc (5 mL×3). The combined organic layer was dried (Na$_2$SO$_4$) and filtered. After removal of solvent, the product was purified by silica gel chromatography using 0-5% MeOH/EtOAc as the eluent to give product. This product still not pure enough and was dissolved in DMF and then submitted for purification by semi-preparative HPLC to give (6-fluoro-4-(4-(2-hydroxypropan-2-yl)-4-phenylpiperidin-1-yl)quinolin-3-yl)(4-(methylsulfonyl)piperazin-1-yl)methanone, TFA (1.1 mg, 1.645 μmol, 2.99% yield). $^1$H NMR (400 MHz, DMSO-d$_6$) δ 8.37 (s, 1H), 7.99 (dd, J=10.0, 5.6 Hz, 1H), 7.65 (ddd, J=10.3, 6.0, 2.9 Hz, 2H), 7.42-7.29 (m, 4H), 7.23-7.16 (m, 1H), 4.40 (s, 1H), 3.90-3.74 (m, 1H), 3.18-2.75 (m, 14H), 2.86 (s, 3H), 2.34-2.20 (m, 1H), 0.96 (s, 6H); LC-MS (Method 2): $t_R$=4.24 min, m/z (M+H)$^+$=555; HRMS calculated for C$_{29}$H$_{36}$FN$_4$O$_4$S (M+H)$^+$: 555.2436, found: 555.2439.

Example 259. 2-(4-(6-fluoro-3-(4-(methylsulfonyl)piperidine-1-carbonyl)quinolin-4-yl)phenyl)-2-methylpropanenitrile, TFA (Cpd. 259)

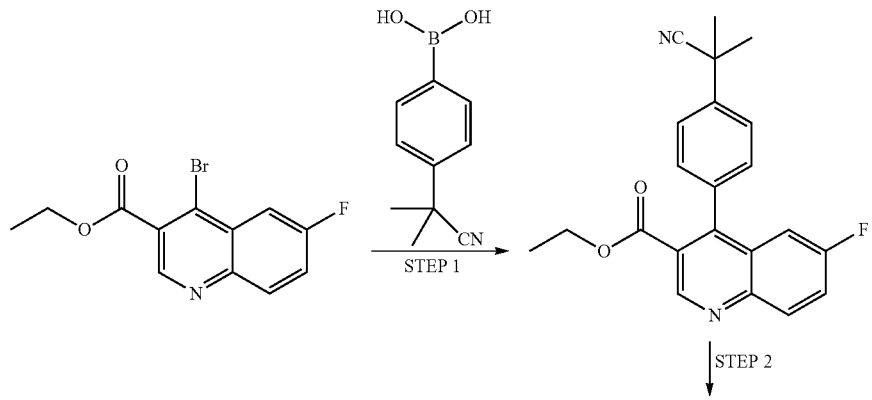

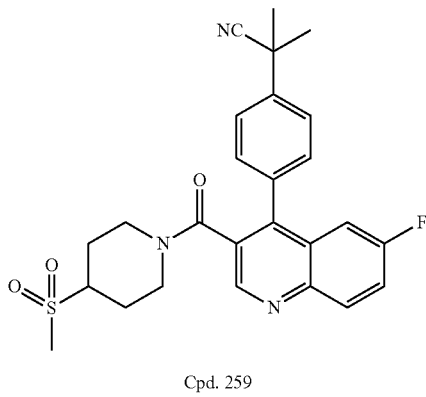

Cpd. 259

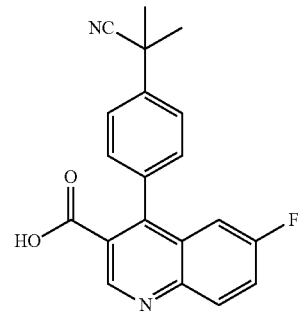

STEP 3

Step 1: Synthesis of Ethyl 4-(4-(2-cyanopropan-2-yl)phenyl)-6-fluoroquinoline-3-carboxylate In a 2-neck flask was placed ethyl 4-bromo-6-fluoroquinoline-3-carboxylate (894 mg, 3 mmol), (4-(2-cyanopropan-2-yl)phenyl)boronic acid (652 mg, 3.45 mmol), PdCl$_2$ (dppf)-CH$_2$Cl$_2$ adduct (245 mg, 0.30 mmol), and K$_2$CO$_3$ (954 mg, 6.90 mmol). The air was removed and re-filled with N$_2$ (2-3 times). Then added a mixture of 1,4-Dioxane (6 ml) and Water (3 ml) was added and stirred at 95° C. (pre-heated) for 2 h. The organic layer was separated and the aqueous layer was extracted with EtOAc (5 mL×2). The combined organic was dried (Na$_2$SO$_4$) and filtered. After removal of solvent, the product was purified by silica gel chromatography using 20-50% EtOAc/hexane as the eluent to give ethyl 4-(4-(2-cyanopropan-2-yl)phenyl)-6-fluoroquinoline-3-carboxylate (390 mg, 1.076 mmol, 35.9% yield). LC-MS (Method 1): t$_R$=3.66 min, m/z (M+H)$^+$=363.

Step 2: Synthesis of 4-(4-(2-Cyanopropan-2-yl)phenyl)-6-fluoroquinoline-3-carboxylic acid To a solution of ethyl 4-(4-(2-cyanopropan-2-yl)phenyl)-6-fluoroquinoline-3-carboxylate (390 mg, 1.076 mmol) in THF (9 ml)/MeOH (1 ml) was added 1 N NaOH$_{(aq)}$ (5 mL, 5 mmol). The mixture was then heated at 50° C. for 2 h. After cooling to rt, 1N HCl$_{(aq)}$ was added until the pH of water layer is ca. 3. Then hexane (30 mL) was added and the solid was filtered, triturated with small amount of water (2 mL×2), hexane (5 mL), and then dried to give 4-(4-(2-cyanopropan-2-yl)phenyl)-6-fluoroquinoline-3-carboxylic acid (346 mg, 1.035 mmol, 96% yield) as a solid. LC-MS (Method 1): t$_R$=3.26 min, m/z (M+H)$^+$=335.

Step 3: Synthesis of 2-(4-(6-Fluoro-3-(4-(methylsulfonyl)piperidine-1-carbonyl)quinolin-4-yl)phenyl)-2-methylpropanenitrile, TFA To a mixture of 4-(4-(2-cyanopropan-2-yl)phenyl)-6-fluoroquinoline-3-carboxylic acid (16.72 mg, 0.05 mmol), 4-(methylsulfonyl)piperidine (24.49 mg, 0.15 mmol), and HATU (76 mg, 0.20 mmol) was added DMF (2 ml) and then Hunig's base (0.087 ml, 0.50 mmol). The mixture was stirred at rt for 1.5 h. The mixture was filtered through a filter and submitted for purification by semi-preparative HPLC to give 2-(4-(6-fluoro-3-(4-(methylsulfonyl)piperidine-1-carbonyl)quinolin-4-yl)phenyl)-2-methylpropanenitrile, TFA (13.3 mg, 0.022 mmol, 44.8% yield). $^1$H NMR (400 MHz, DMSO-d$_6$) δ 8.80 (s, 1H), 8.20 (dd, J=9.3, 5.6 Hz, 1H), 7.77 (ddd, J=9.3, 8.2, 2.9 Hz, 1H), 7.68 (d, J=8.7 Hz, 2H), 7.62 (d, J=8.0 Hz, 1H), 7.44 (d, J=7.8 Hz, 1H), 7.32 (dd, J=10.2, 2.8 Hz, 1H), 4.44 (t, J=14.1 Hz, 1H), 2.79 (s, 3H), 3.39-2.32 (m, 4H), 1.99-1.93 (m, 1H), 1.74 (s, 3H), 1.73 (s, 3H), 1.65-1.57 (m, 1H), 0.71 (qd, J=12.3, 4.1 Hz, 1H), 0.38 (tt, J=13.3, 6.7 Hz, 1H). (major rotamer reported); LC-MS (Method 2): t$_R$=4.61 min, m/z (M+H)$^+$=480; HRMS calculated for C$_{26}$H$_{27}$FN$_3$O$_3$S (M+H)$^+$: 480.1752, found: 480.1742.

Example 260. 4-(4-(4-(1-cyanocyclopropyl)phenyl)-6-fluoroquinoline-3-carbonyl)-N,N-dimethylpiperazine-1-sulfonamide, TFA (Cpd. 260)

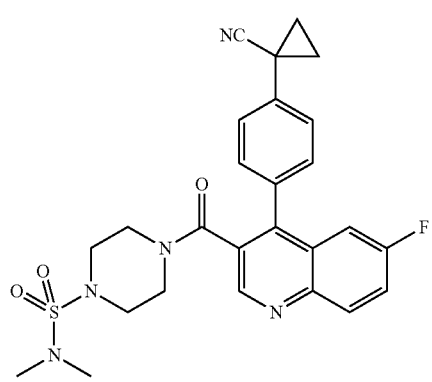

Cpd. 260

The title compound was prepared following the similar procedure as described in Example 259. $^1$H NMR (400 MHz, DMSO-d$_6$) δ 8.85 (s, 1H), 8.20 (dd, J=9.3, 5.6 Hz, 1H), 7.77 (ddd, J=9.3, 8.2, 2.9 Hz, 1H), 7.57-7.52 (m, 2H), 7.47 (d, J=8.2 Hz, 1H), 7.39 (d, J=8.1 Hz, 1H), 7.29 (dd, J=10.2, 2.8 Hz, 1H), 3.66 (d, J=12.6 Hz, 1H), 3.33-2.93 (m, 5H), 2.68 (s, 6H), 2.52 (t, J=9.0 Hz, 1H), 2.08 (t, J=8.7 Hz, 1H), 1.85-1.82 (m, 2H), 1.66-1.52 (m, 2H); LC-MS (Method 2): t$_R$=5.00 min, m/z (M+H)$^+$=508; HRMS calculated for C$_{26}$H$_{27}$FN$_5$O$_3$S (M+H)$^+$: 508.1813, found: 508.1838.

Example 261. 4-(4-(4-(2-cyanopropan-2-yl)phenyl)-6-fluoroquinoline-3-carbonyl)-N,N-dimethylpiperazine-1-sulfonamide, TFA (Cpd. 261)

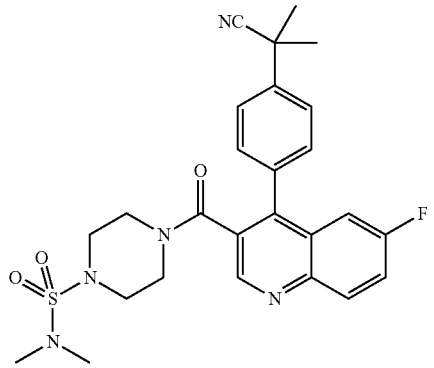

Cpd. 261

The title compound was prepared following the similar procedure as described in Example 259. $^1$H NMR (400 MHz, DMSO-d$_6$) δ 8.85 (s, 1H), 8.21 (dd, J=9.2, 5.6 Hz, 1H), 7.78 (ddd, J=9.2, 8.2, 2.9 Hz, 1H), 7.72 (t, J=8.2 Hz, 2H), 7.58 (d, J=8.0 Hz, 1H), 7.43 (d, J=8.1 Hz, 1H), 7.31 (dd, J=10.2, 2.8 Hz, 1H), 3.74-2.88 (m, 7H), 2.65 (s, 6H), 2.04 (t, J=9.0 Hz, 1H), 1.74 (s, 6H); LC-MS (Method 2): t$_R$=5.16 min, m/z (M+H)$^+$=510; HRMS calculated for C$_{26}$H$_{29}$FN$_5$O$_3$S (M+H)$^+$: 510.1970, found: 510.1980.

Example 262. 1-(4-(3-(4-(cyclopropanecarbonyl)piperazine-1-carbonyl)-6-fluoroquinolin-4-yl)phenyl)cyclopropanecarbonitrile, TFA (Cpd. 262)

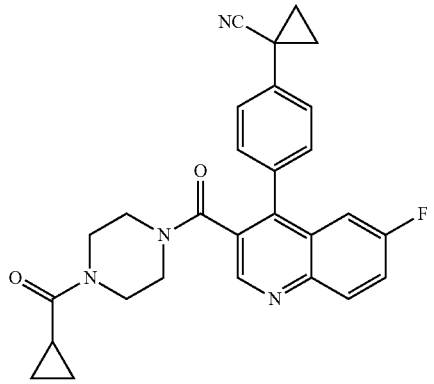

Cpd. 262

The title compound was prepared following the similar procedure as described in Example 259. $^1$H NMR (400 MHz, DMSO-d$_6$) δ 8.86 (s, 1H), 8.20 (dd, J=9.3, 5.6 Hz, 1H), 7.76 (ddd, J=9.2, 8.2, 2.9 Hz, 1H), 7.50-7.40 (d, J=42.8 Hz, 4H), 7.26 (dd, J=10.2, 2.9 Hz, 1H), 3.72-2.65 (m, 8H), 1.96-1.85 (m, 1H), 1.85-1.79 (m, 2H), 1.62-1.54 (m, 2H), 0.67-0.65 (m, 4H); LC-MS (Method 2): t$_R$=4.67 min, m/z (M+H)$^+$=469; HRMS calculated for C$_{28}$H$_{26}$FN$_4$O$_2$(M+H)$^+$: 469.2034, found: 469.2049.

Example 263. 4-(4-(4-(2-cyanopropan-2-yl)phenyl)-6-fluoroquinoline-3-carbonyl)-N,N-dimethylpiperazine-1-carboxamide, TFA (Cpd. 263)

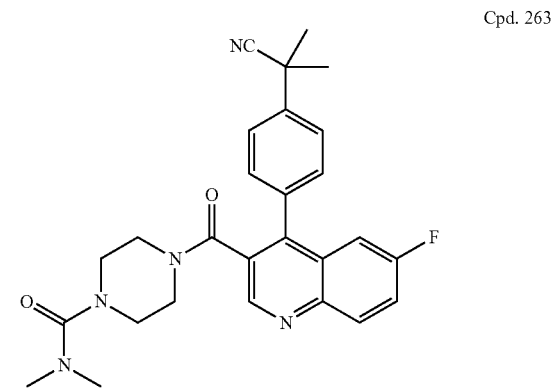 [SMILES: CN(C)C(=O)N1CCN(C(=O)c2cnc3ccc(F)cc3c2-c2ccc(C(C)(C)C#N)cc2)CC1]

Cpd. 263

The title compound was prepared following the similar procedure as described in Example 259. $^1$H NMR (400 MHz, DMSO-d$_6$) δ 8.84 (s, 1H), 8.20 (dd, J=9.3, 5.6 Hz, 1H), 7.77 (ddd, J=9.3, 8.2, 2.9 Hz, 1H), 7.70 (d, J=7.4 Hz, 2H), 7.57 (d, J=8.1 Hz, 1H), 7.45 (d, J=8.1 Hz, 1H), 7.33 (dd, J=10.2, 2.8 Hz, 1H), 3.62 (d, J=13.7 Hz, 1H), 3.27-2.84 (m, 6H), 2.64 (s, 6H), 1.94 (t, J=9.5 Hz, 1H), 1.72 (s, 6H); LC-MS (Method 2): t$_R$=4.71 min, m/z (M+H)$^+$=474; HRMS calculated for C$_{27}$H$_{29}$FN$_5$O$_2$ (M+H)$^+$: 474.2300, found: 474.2319.

Example 264. 2-(4-(3-(4-(cyclopropanecarbonyl)piperazine-1-carbonyl)-6-fluoroquinolin-4-yl)phenyl)-2-methylpropanenitrile, TFA (Cpd. 264)

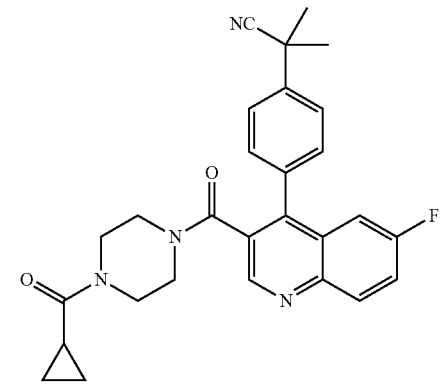

Cpd. 264

The title compound was prepared following the similar procedure as described in Example 259. $^1$H NMR (400 MHz, DMSO-d$_6$) δ 8.86 (s, 1H), 8.21 (dd, J=9.3, 5.6 Hz, 1H), 7.77 (ddd, J=9.3, 8.2, 2.9 Hz, 1H), 7.71 (d, J=7.2 Hz, 2H), 7.58 (d, J=8.1 Hz, 1H), 7.45 (d, J=8.0 Hz, 1H), 7.32 (dd, J=10.2, 2.8 Hz, 1H), 3.88-2.31 (m, 8H), 1.94-1.74 (m, 1H), 1.71 (s, 6H), 0.64 (d, J=7.9 Hz, 4H); LC-MS (Method 2): t$_R$=4.82 min, m/z (M+H)$^+$=471; HRMS calculated for C$_{28}$H$_{28}$FN$_4$O$_2$ (M+H)$^+$: 471.2191, found: 471.2198.

Example 265. 4-(4-(4-(1-cyanocyclopropyl)phenyl)-6-fluoroquinoline-3-carbonyl)-N,N-dimethylpiperazine-1-carboxamide, TFA (Cpd. 265)

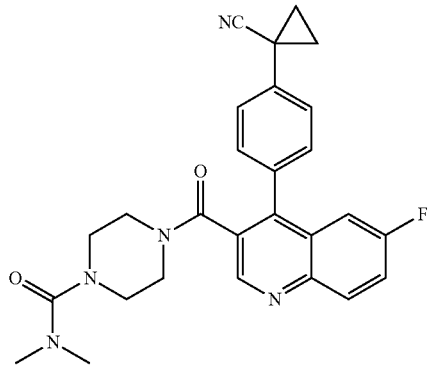

The title compound was prepared following the similar procedure as described in Example 259. $^1$H NMR (400 MHz, DMSO-d$_6$) δ 8.84 (s, 1H), 8.20 (dd, J=9.2, 5.6 Hz, 1H), 7.76 (ddd, J=9.2, 8.2, 2.9 Hz, 1H), 7.53-7.47 (m, 3H), 7.38 (d, J=8.1 Hz, 1H), 7.27 (dd, J=10.2, 2.8 Hz, 1H), 3.37-3.33 (m, 2H), 3.14-3.09 (m, 2H), 2.93-2.91 (m, 2H), 2.66 (s, 6H), 2.65-2.55 (m, 1H), 2.28-2.16 (m, 1H), 1.85-1.77 (m, 2H), 1.62-1.52 (m, 2H); LC-MS (Method 2): t$_R$=4.56 min, m/z (M+H)$^+$=472; HRMS calculated for C$_{27}$H$_{27}$FN$_5$O$_2$ (M+H)$^+$: 472.2143, found: 472.2155.

Example 266. 1-(4-(6-fluoro-3-(4-(methylsulfonyl)piperidine-1-carbonyl)quinolin-4-yl)phenyl)cyclopropanecarbonitrile, TFA (Cpd. 266)

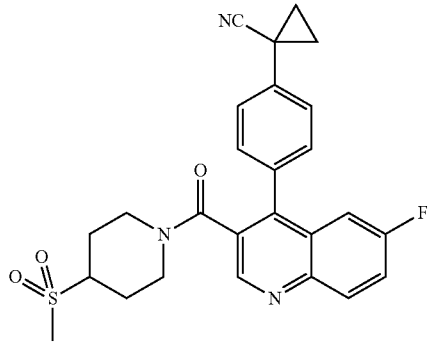

The title compound was prepared following the similar procedure as described in Example 259. $^1$H NMR (400 MHz, DMSO-d6) δ 8.79 (s, 1H), 8.19 (dd, J=9.2, 5.6 Hz, 1H), 7.80-7.70 (m, 1H), 7.57 (d, J=8.1 Hz, 1H), 7.52-7.39 (m, 3H), 7.33 (dd, J=10.2, 2.9 Hz, 1H), 4.46 (t, J=13.8 Hz, 1H), 3.16-3.05 (m, 1H), 2.77 (s, 3H), 2.66-2.39 (m, 3H), 2.05-1.37 (m, 6H), 0.80-0.73 (m, 1H), 0.28-0.24 (m, 1H). (major rotamer reported); LC-MS (Method 2): t$_R$=4.46 min, m/z (M+H)$^+$=478; HRMS calculated for C$_{26}$H$_{25}$FN$_3$O$_3$S (M+H)$^+$: 478.1595, found: 478.1612.

Example 267. 4-(4-chlorophenyl)-1-(3-(4-(cyclopropanecarbonyl)piperazine-1-carbonyl)-6-fluoroquinolin-4-yl)piperidine-4-carbonitrile, TFA (Cpd. 267)

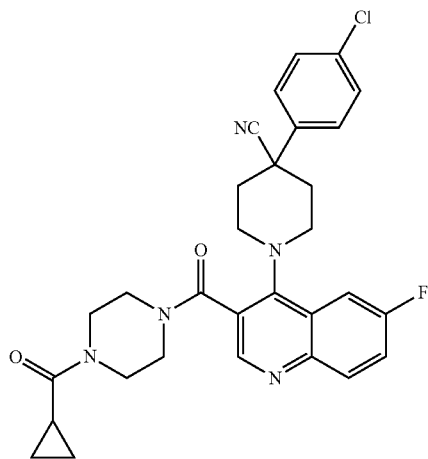

The title compound was prepared following the similar procedure as described in Example 17. $^1$H NMR (400 MHz, DMSO-d$_6$) δ 8.58 (s, 1H), 8.06 (dd, J=9.2, 5.6 Hz, 1H), 7.87 (dd, J=10.3, 2.9 Hz, 1H), 7.74-7.62 (m, 3H), 7.58-7.50 (m, 2H), 3.28 (s, 12H), 2.47 (p, J=1.9 Hz, 4H), 2.08-1.79 (m, 1H), 0.76-0.60 (m, 4H); LC-MS (Method 2): t$_R$=4.90 min, m/z (M+H)$^+$=547; HRMS calculated for C$_{30}$H$_{30}$ClFN$_5$O$_2$ (M+H)$^+$: 546.2067, found: 546.2073.

Example 268. 4-(4-(4-acetyl-4-phenylpiperidin-1-yl)-6-fluoroquinoline-3-carbonyl)-N,N-dimethylpiperazine-1-sulfonamide, TFA (Cpd. 268)

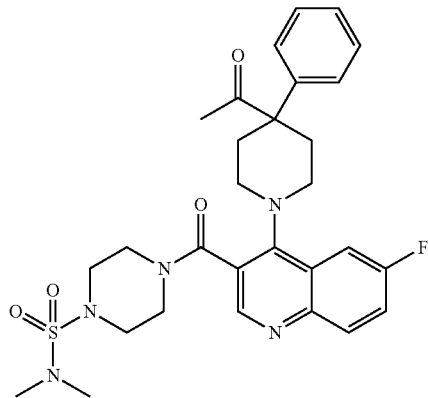

The title compound was prepared following the similar procedure as described in Example 1. LC-MS (Method 2): t$_R$=4.48 min, m/z (M+H)$^+$=568; HRMS calculated for C$_{29}$H$_{35}$FN$_5$O$_4$S (M+H)$^+$: 568.2388, found: 568.2413.

Example 269. 1-(6-fluoro-3-(4-(methylsulfonyl)piperidine-1-carbonyl)quinolin-4-yl)-4-phenylpiperidine-4-carbonitrile, TFA (Cpd. 269)

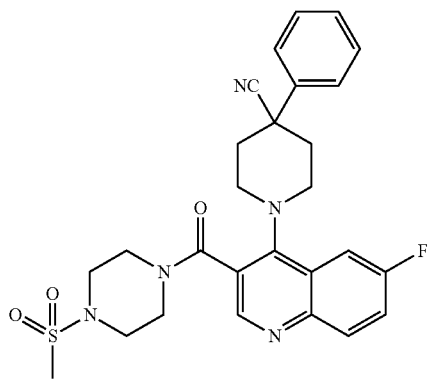

Cpd. 269

The title compound was prepared following the similar procedure as described in Example 1. $^1$H NMR (400 MHz, DMSO-d$_6$) δ 8.69 (s, 0.5H), 8.64 (s, 0.5H), 8.08 (dt, J=9.1, 5.5 Hz, 1H), 7.96-7.84 (m, 1H), 7.75 (t, J=8.6 Hz, 1H), 7.70-7.62 (m, 2H), 7.48 (ddt, J=7.9, 6.4, 1.3 Hz, 2H), 7.43-7.35 (m, 1H), 4.71 (d, J=13.4 Hz, 1H), 3.90-2.81 (m, 8H), 2.96 (s, 1.5H), 2.92 (s, 1.5H), 2.67-2.10 (m, 5H), 1.97 (d, J=12.7 Hz, 1H), 1.82-1.41 (m, 2H). (2 rotamers); LC-MS (Method 2): t$_R$=4.18 min, m/z (M+H)$^+$=521; HRMS calculated for C$_{28}$H$_{30}$FN$_4$O$_3$S (M+H)$^+$: 521.2017, found: 521.2023.

Example 270. 4-(4-(4-cyano-4-phenylpiperidin-1-yl)-6-fluoroquinoline-3-carbonyl)-N,N-dimethylpiperazine-1-sulfonamide, TFA (Cpd. 270)

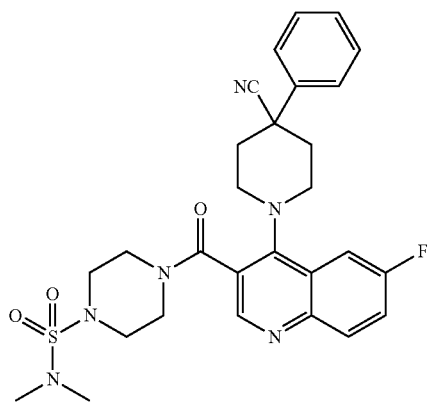

Cpd. 270

The title compound was prepared following the similar procedure as described in Example 1. $^1$H NMR (400 MHz, DMSO-d$_6$) δ 8.65 (s, 1H), 8.07 (dd, J=9.2, 5.5 Hz, 1H), 7.89 (dd, J=10.3, 2.8 Hz, 1H), 7.73 (td, J=8.7, 2.8 Hz, 1H), 7.69-7.62 (m, 2H), 7.52-7.44 (m, 2H), 7.44-7.35 (m, 1H), 3.94-3.10 (m, 12H), 2.76 (s, 6H), 2.57-2.15 (m, 4H); LC-MS (Method 2): t$_R$=4.67 min, m/z (M+H)$^+$=551; HRMS calculated for C$_{28}$H$_{32}$FN$_6$O$_3$S (M+H)$^+$: 551.2235, found: 551.2249.

Example 271. 4-(4-(4-acetyl-4-phenylpiperidin-1-yl)-6-fluoroquinoline-3-carbonyl)-N,N-dimethylpiperazine-1-carboxamide, TFA (Cpd. 271)

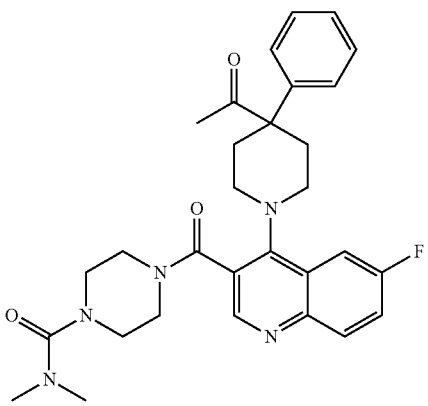

Cpd. 271

The title compound was prepared following the similar procedure as described in Example 1. LC-MS (Method 2): t$_R$=4.14 min, m/z (M+H)$^+$=532; HRMS calculated for C$_{30}$H$_{35}$FN$_5$O$_3$ (M+H)$^+$: 532.2718, found: 532.2740.

Example 272. 4-(4-(4-cyano-4-phenylpiperidin-1-yl)-6-fluoroquinoline-3-carbonyl)-N,N-dimethylpiperazine-1-carboxamide, TFA (Cpd. 272)

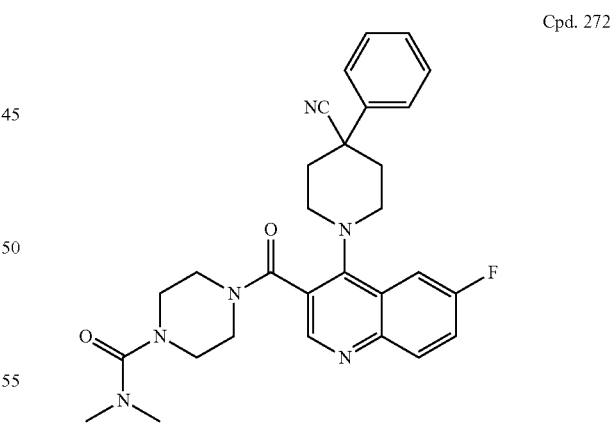

Cpd. 272

The title compound was prepared following the similar procedure as described in Example 1. $^1$H NMR (400 MHz, DMSO-d$_6$) δ 8.63 (s, 1H), 8.07 (dd, J=9.2, 5.5 Hz, 1H), 7.89 (dd, J=10.2, 2.8 Hz, 1H), 7.73 (td, J=8.7, 2.8 Hz, 1H), 7.69-7.61 (m, 2H), 7.52-7.42 (m, 2H), 7.42-7.35 (m, 1H), 3.79-3.01 (m, 12H), 2.73 (s, 6H), 2.59-2.49 (m, 1H), 2.38-2.18 (m, 3H); LC-MS (Method 2): t$_R$=4.28 min, m/z (M+H)$^+$=515; HRMS calculated for C$_{29}$H$_{32}$FN$_6$O$_2$ (M+H)$^+$: 515.2565, found: 515.2570.

Example 273. 1-(1-(6-fluoro-3-(4-(methylsulfonyl) piperidine-1-carbonyl)quinolin-4-yl)-4-phenylpiperidin-4-yl)ethanone, TFA (Cpd. 273)

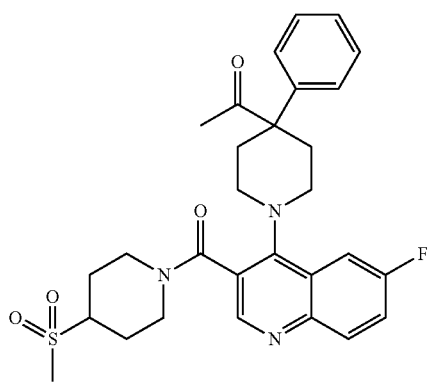

Cpd. 273

The title compound was prepared following the similar procedure as described in Example 1. $^1$H NMR (400 MHz, DMSO-d6) δ 8.66 (s, 0.5H), 8.59 (s, 0.5H), 8.04 (dt, J=9.2, 5.4 Hz, 1H), 7.86-7.70 (m, 2H), 7.41 (tdd, J=8.4, 6.3, 2.2 Hz, 4H), 7.31 (tt, J=6.3, 2.2 Hz, 1H), 4.61 (d, J=13.2 Hz, 1H), 2.96 (s, 1.5H), 2.94 (s, 1.5H), 3.86-2.27 (m, 12H), 2.24-2.13 (m, 2H), 1.93 (s, 3H), 1.79-1.36 (m, 2H). (2 rotamers, ca. 1:1); LC-MS (Method 2): $t_R$=4.07 min, m/z (M+H)$^+$=538; HRMS calculated for $C_{29}H_{33}FN_3O_4S$ (M+H)$^+$: 538.2170, found: 538.2188.

Example 274. 1-(6-fluoro-3-(4-(methylsulfonyl) piperazine-1-carbonyl)quinolin-4-yl)-4-(2-fluorophenyl)piperidine-4-carbonitrile, TFA (Cpd. 274)

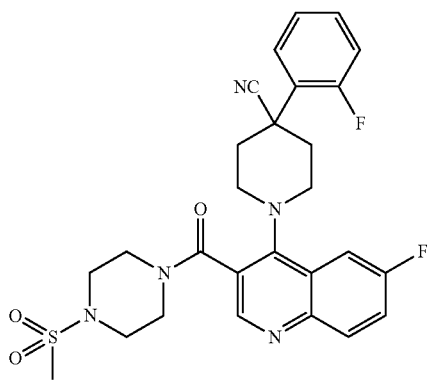

Cpd. 274

The title compound was prepared following the similar procedure as described in Example 17. $^1$H NMR (400 MHz, DMSO-d$_6$) δ 8.61 (s, 1H), 8.07 (dd, J=9.2, 5.6 Hz, 1H), 7.80 (dd, J=10.3, 2.9 Hz, 1H), 7.71 (ddd, J=9.2, 8.1, 2.9 Hz, 1H), 7.60 (td, J=8.0, 1.6 Hz, 1H), 7.49 (dddd, J=8.3, 7.0, 5.2, 1.6 Hz, 1H), 7.39-7.29 (m, 2H), 3.98-3.03 (m, 12H), 2.90 (s, 3H), 2.57-2.31 (m, 4H); LC-MS (Method 2): $t_R$=4.40 min, m/z (M+H)$^+$=540; HRMS calculated for $C_{27}H_{28}F_2N_5O_3S$ (M+H)$^+$: 540.1875, found: 540.1890.

Example 275. 4-(4-chlorophenyl)-1-(6-fluoro-3-(4-(methylsulfonyl)piperazine-1-carbonyl)quinolin-4-yl)piperidine-4-carbonitrile, TFA (Cpd. 275)

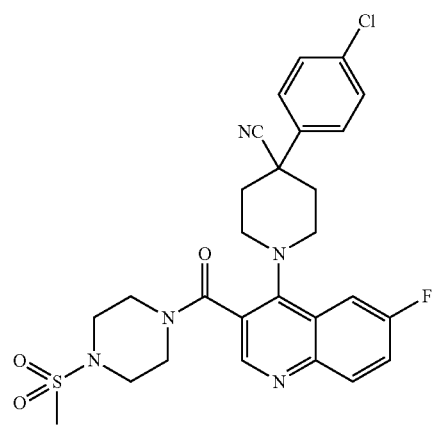

Cpd. 275

The title compound was prepared following the similar procedure as described in Example 17. LC-MS (Method 2): $t_R$=4.80 min, m/z (M+H)$^+$=557; HRMS calculated for $C_{27}H_{28}ClFN_5O_3S$ (M+H)$^+$: 556.1580, found: 556.1589.

Example 276. 1-(3-(4-(cyclopropanecareonyl)piperazine-1-carbonyl)-6-fluoroquinolin-4-yl)-4-(2-fluorophenyl)piperidine-4-carbonitrile, TFA (Cpd. 276)

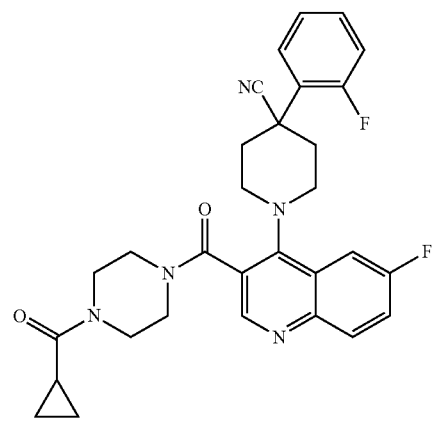

Cpd. 276

The title compound was prepared following the similar procedure as described in Example 17. $^1$H NMR (400 MHz, DMSO-d$_6$) δ 8.59 (s, 1H), 8.06 (dd, J=9.2, 5.6 Hz, 1H), 7.78 (dd, J=10.3, 2.9 Hz, 1H), 7.68 (ddd, J=9.2, 8.2, 2.9 Hz, 1H), 7.60 (td, J=8.1, 1.6 Hz, 1H), 7.49 (dddd, J=8.3, 7.0, 5.1, 1.6 Hz, 1H), 7.39-7.27 (m, 2H), 3.84-3.23 (m, 12H), 2.57-2.31 (m, 4H), 2.02-1.90 (m, 1H), 0.73 (d, J=4.6 Hz, 4H); LC-MS (Method 2): $t_R$=4.40 min, m/z (M+H)$^+$=530; HRMS calculated for $C_{30}H_{30}F_2N_5O_2$ (M+H)$^+$: 530.2362, found: 530.2361.

Example 277. 1-(6-fluoro-3-(4-(methylsulfonyl) piperazine-1-carbonyl)quinolin-4-yl)-4-(2-fluoro-4-methylphenyl)piperidine-4-carbonitrile, TFA (Cpd. 277)

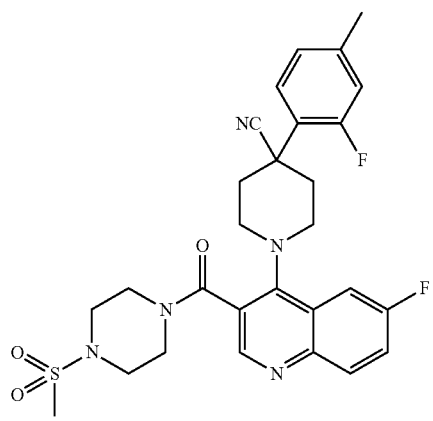

Cpd. 277

The title compound was prepared following the similar procedure as described in Example 17. $^1$H NMR (400 MHz, DMSO-$d_6$) δ 8.61 (s, 1H), 8.07 (dd, J=9.2, 5.5 Hz, 1H), 7.79 (dd, J=10.2, 2.9 Hz, 1H), 7.71 (ddd, J=9.2, 8.2, 2.8 Hz, 1H), 7.45 (t, J=8.3 Hz, 1H), 7.17 (dt, J=12.3, 1.4 Hz, 1H), 7.14-7.10 (m, 1H), 3.96-3.08 (m, 12H), 2.90 (s, 3H), 2.53-2.22 (m, 4H), 2.33 (s, 3H); LC-MS (Method 2): $t_R$=4.69 min, m/z (M+H)$^+$=554; HRMS calculated for $C_{28}H_{30}F_2N_5O_3S$ (M+H)$^+$: 554.2032, found: 554.2021.

Example 278. 1-(3-(4-(cyclopropanecarbonyl)piperazine-1-carbonyl)-6-fluoroquinolin-4-yl)-4-(4-fluorophenyl)piperidine-4-carbonitrile, TFA (Cpd. 278)

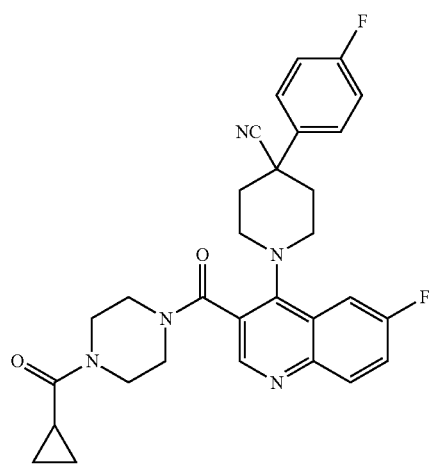

Cpd. 278

The title compound was prepared following the similar procedure as described in Example 17. $^1$H NMR (400 MHz, DMSO-$d_6$) δ 8.61 (s, 1H), 8.06 (dd, J=9.2, 5.5 Hz, 1H), 7.88 (dd, J=10.3, 2.9 Hz, 1H), 7.73-7.68 (m, 3H), 7.36-7.26 (m, 2H), 3.91-3.20 (m, 12H), 2.58-2.48 (m, 1H), 2.34-2.17 (m, 3H), 2.07-1.81 (m, 1H), 0.72 (s, 4H); LC-MS (Method 2): $t_R$=4.59 min, m/z M+H)$^+$=530; HRMS calculated for $C_{30}H_{30}F_2N_5O_2$ (M+H)$^+$: 530.2362, found: 530.2371.

Example 279. 1-(6-fluoro-3-(4-(methylsulfonyl) piperazine-1-carbonyl)quinolin-4-yl)-4-(4-fluorophenyl)piperidine-4-carbonitrile, TFA (Cpd. 279)

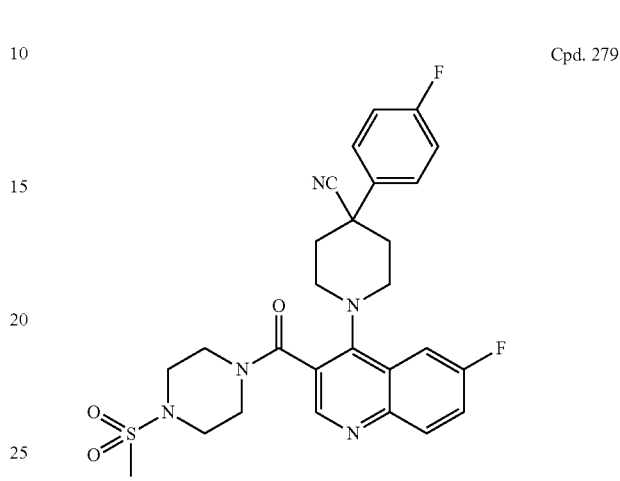

Cpd. 279

The title compound was prepared following the similar procedure as described in Example 17. $^1$H NMR (400 MHz, DMSO-$d_6$) δ 8.60 (d, J=1.2 Hz, 1H), 8.06 (dd, J=9.2, 5.6 Hz, 1H), 7.88 (dd, J=10.3, 2.9 Hz, 1H), 7.77-7.64 (m, 3H), 7.36-7.26 (m, 2H), 3.96-3.84 (m, 1H), 3.77-3.67 (m, 1H), 3.60 (d, J=13.2 Hz, 1H), 3.55-3.05 (m, 9H), 2.90 (s, 3H), 2.56-2.49 (m, 1H), 2.39-2.17 (m, 3H); LC-MS (Method 2): $t_R$=4.61 min, m/z (M+H)$^+$=540; HRMS calculated for $C_{27}H_{28}F_2N_5O_3S$ (M+H)$^+$: 540.1875, found: 540.1894.

Example 280. (6-fluoro-4-(4-(1-(hydroxymethyl) cyclopropyl)phenyl)quinolin-3-yl)(4-(methylsulfonyl)piperazin-1-yl)methanone, TFA (Cpd. 280)

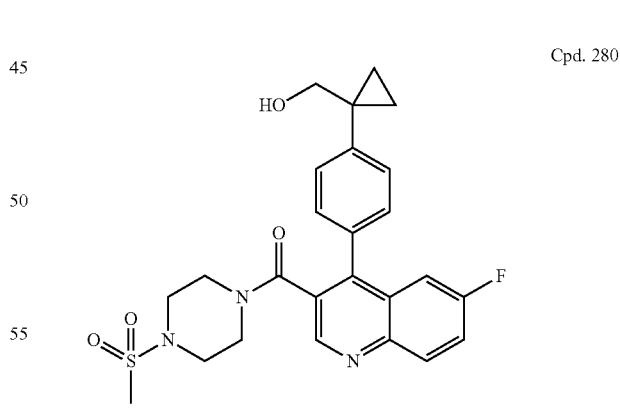

Cpd. 280

The title compound was prepared following the similar procedure as described in Example 210. $^1$H NMR (400 MHz, DMSO-$d_6$) δ 8.82 (s, 1H), 8.19 (dd, J=9.3, 5.6 Hz, 1H), 7.76 (ddd, J=9.3, 8.1, 2.9 Hz, 1H), 7.50 (d, J=8.2 Hz, 1H), 7.42 (d, J=7.8 Hz, 2H), 7.35 (dd, J=10.3, 2.8 Hz, 1H), 7.28 (d, J=7.3 Hz, 1H), 3.73 (d, J=13.8 Hz, 1H), 3.60 (s, 2H), 3.35-2.85 (m, 6H), 2.71 (s, 3H), 2.40 (t, J=8.9 Hz, 1H), 1.87 (dd, J=11.4, 6.9 Hz, 1H), 0.95-0.82 (m, 4H); LC-MS (Method 2): $t_R$=4.44 min, m/z (M+H)$^+$=484; HRMS calculated for $C_{25}H_{27}FN_3O_4S$ (M+H)$^+$: 484.1701, found: 484.1721.

Example 281. 4-(7-(4-(1-cyanocyclopropyl)phenyl)thieno[3,2-b]pyridine-6-carbonyl)-N,N-dimethylpiperazine-1-carboxamide, TFA (Cpd. 281)

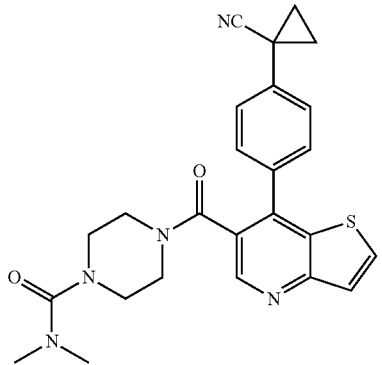

Cpd. 281

The title compound was prepared following the similar procedure as described in Example 41. $^1$H NMR (400 MHz, DMSO-d$_6$) δ 8.64 (s, 1H), 8.25 (d, J=5.6 Hz, 1H), 7.66 (d, J=5.6 Hz, 1H), 7.63-7.56 (m, 2H), 7.55-7.48 (m, 2H), 3.55 (s, 1H), 3.35 (s, 1H), 3.12 (br s, 2H), 2.92 (s, 3H), 2.66 (s, 6H), 2.12 (s, 1H), 1.84-1.76 (m, 2H), 1.61-1.53 (m, 2H); LC-MS (Method 2): $t_R$=4.31 min, m/z (M+H)$^+$=460; HRMS calculated for $C_{25}H_{26}N_5O_2S$ (M+H)$^+$: 460.1802, found: 460.1797.

Example 282. 1-(6-(4-(cyclopropanecarbonyl)piperazine-1-carbonyl)thieno[3,2-b]pyridin-7-yl)-4-phenylpiperidine-4-carbonitrile, TFA (Cpd. 282)

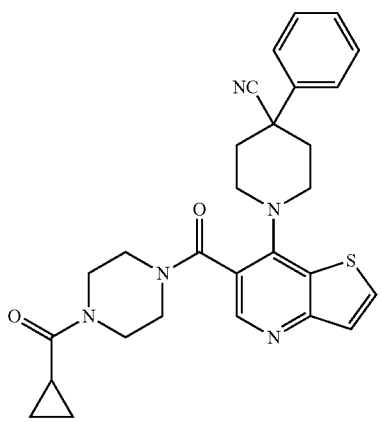

Cpd. 282

The title compound was prepared following the similar procedure as described in Example 1. $^1$H NMR (400 MHz, DMSO-d$_6$) δ 8.46 (s, 1H), 8.27 (d, J=5.6 Hz, 1H), 7.58-7.52 (m, 3H), 7.51-7.42 (m, 2H), 7.42-7.35 (m, 1H), 4.00 (d, J=13.9 Hz, 1H), 3.88-3.31 (m, 11H), 2.41-1.82 (m, 5H), 0.72 (d, J=4.2 Hz, 4H); LC-MS (Method 2): $t_R$=4.10 min, m/z (M+H)$^+$=500; HRMS calculated for $C_{28}H_{30}N_5O_2S$ (M+H)$^+$: 500.2115, found: 500.2123.

Example 283. 1-(4-(6-(4-(methylsulfonyl)piperidine-1-carbonyl)thieno[3,2-b]pyridin-7-ylphenyl)cyclopropanecarbonitrile, TFA (Cpd. 283)

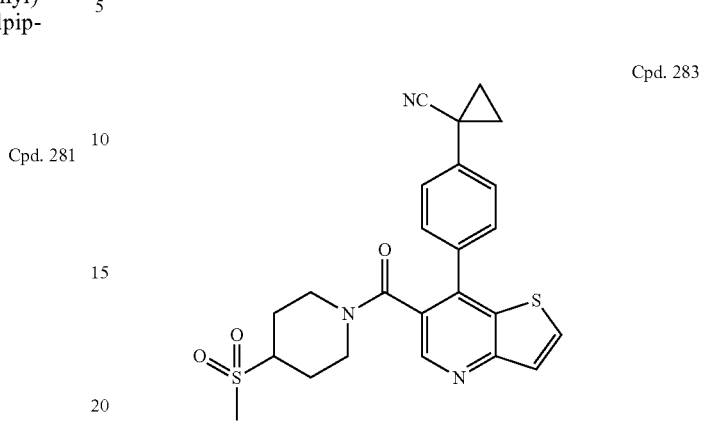

Cpd. 283

The title compound was prepared following the similar procedure as described in Example 41. $^1$H NMR (400 MHz, DMSO-d$_6$) δ 8.69 and 8.59 (2 set of s, 1H), 8.25 (d, J=5.6 Hz, 1H), 7.73-7.39 (m, 5H), 4.55-4.52 (m, 1H), 3.53-2.56 (m, 7H), 2.09--0.25 (m, 8H). (2 rotamers); LC-MS (Method 2): $t_R$=4.20 min, m/z (M+H)$^+$=466; HRMS calculated for $C_{24}H_{24}N_3O_3S_2$ (M+H)$^+$: 466.1254, found: 466.1252.

Example 284. 4-(7-(4-(1-cyanocyclopropyl)phenyl)thieno[3,2-b]pyridine-6-carbonyl)-N,N-dimethylpiperazine-1-sulfonamide, TFA (Cpd. 284)

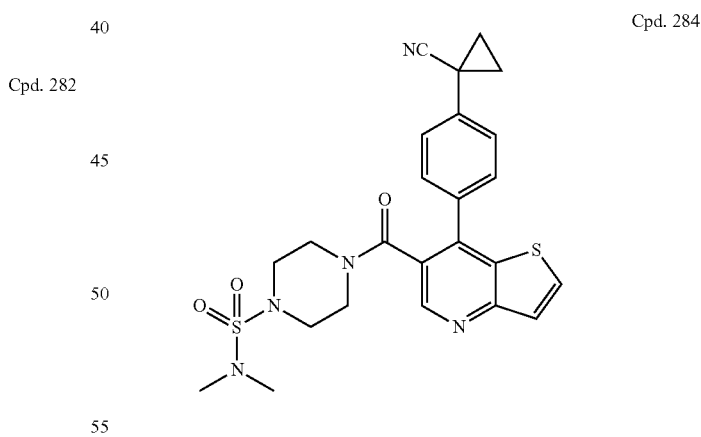

Cpd. 284

The title compound was prepared following the similar procedure as described in Example 41. $^1$H NMR (400 MHz, DMSO-d$_6$) δ 8.65 (s, 1H), 8.26 (d, J=5.6 Hz, 1H), 7.67 (d, J=5.6 Hz, 1H), 7.65-7.59 (m, 2H), 7.55-7.48 (m, 2H), 3.76 (s, 1H), 3.25 (s, 2H), 3.12-2.88 (m, 3H), 2.66 (s, 6H), 2.52 (br s, 1H), 1.88 (s, 1H), 1.83 (d, J=2.6 Hz, 2H), 1.61 (d, J=3.1 Hz, 2H); LC-MS (Method 2): $t_R$=4.72 min, m/z (M+H)$^+$=496; HRMS calculated for $C_{24}H_{26}N_5O_3S_2$ (M+H)$^+$: 496.1472, found: 496.1468.

Example 285. 1-(6-(4-(methylsulfonyl)piperazine-1-carbonyl)thieno[3,2-b]pyridin-7-yl)-4-phenylpiperidine-4-carbonitrile, TFA (Cpd. 285)

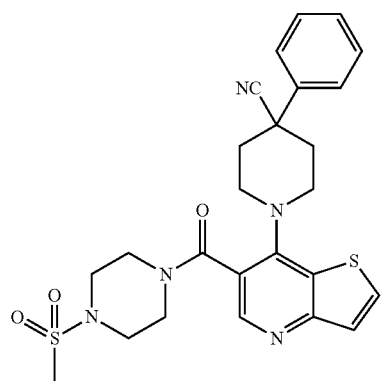

The title compound was prepared following the similar procedure as described in Example 1. $^1$H NMR (400 MHz, DMSO-$d_6$) δ 8.45 (s, 1H), 8.27 (d, J=5.6 Hz, 1H), 7.59-7.53 (m, 3H), 7.47 (ddd, J=7.9, 6.9, 1.3 Hz, 2H), 7.42-7.35 (m, 1H), 4.05-3.63 (m, 4H), 3.50 (t, J=12.3 Hz, 4H), 3.23 (t, J=5.2 Hz, 2H), 3.15-3.05 (m, 2H), 2.89 (s, 3H), 2.38-2.34 (m, 2H), 2.22 (td, J=12.7, 3.8 Hz, 1H), 2.12 (td, J=12.9, 4.0 Hz, 1H); LC-MS (Method 2): $t_R$=4.13 min, m/z (M+H)$^+$=510; HRMS calculated for $C_{25}H_{28}N_5O_3S_2$ (M+H)$^+$: 510.1628, found: 510.1633.

Example 286. 1-(4-(6-(4-(methylsulfonyl)piperazine-1-carbonyl)thieno[3,2-b]pyridin-7-ylphenyl)cyclopropanecarbonitrile, TFA (Cpd. 286)

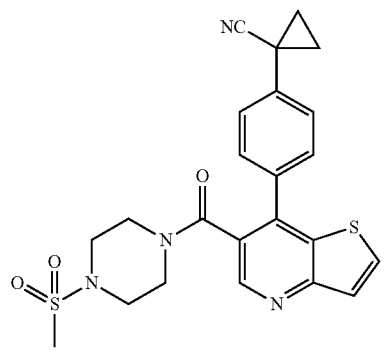

The title compound was prepared following the similar procedure as described in Example 41. $^1$H NMR (400 MHz, DMSO-$d_6$) δ 8.65 (s, 1H), 8.26 (d, J=5.6 Hz, 1H), 7.67 (d, J=5.6 Hz, 1H), 7.64-7.57 (m, 2H), 7.55-7.48 (m, 2H), 3.68 (s, 1H), 3.41 (s, 1H), 3.15 (br s, 2H), 3.04 (s, 1H), 2.91 (br s, 2H), 2.72 (s, 4H), 2.61-2.49 (m, 1H), 1.90 (br s, 1H), 1.81 (q, J=3.0 Hz, 2H), 1.67-1.58 (m, 2H); LC-MS (Method 2): $t_R$=4.44 min, m/z (M+H)$^+$=467; HRMS calculated for $C_{23}H_{23}N_4O_3S_2$ (M+H)$^+$: 467.1206, found: 467.1225.

Example 287. 4-(7-(4-cyano-4-phenylpiperidin-1-yl)thieno[3,2-b]pyridine-6-carbonyl)-N,N-dimethylpiperazine-1-sulfonamide, TFA (Cpd. 287)

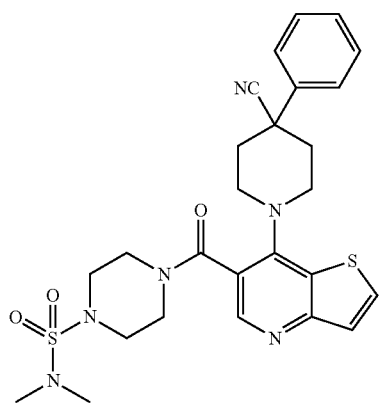

The title compound was prepared following the similar procedure as described in Example 1. $^1$H NMR (400 MHz, DMSO-$d_6$) δ 8.47 (s, 1H), 8.28 (d, J=5.6 Hz, 1H), 7.59-7.51 (m, 3H), 7.51-7.43 (m, 2H), 7.42-7.35 (m, 1H), 3.99 (d, J=13.5 Hz, 1H), 3.89-3.72 (m, 2H), 3.71-3.60 (m, 1H), 3.56-3.34 (m, 4H), 3.28 (t, J=5.2 Hz, 2H), 3.23-3.05 (m, 2H), 2.75 (s, 6H), 2.41-2.01 (m, 4H); LC-MS (Method 2): $t_R$=4.39 min, m/z (M+H)$^+$=539; HRMS calculated for $C_{26}H_{31}N_6O_3S_2$ (M+H)$^+$: 539.1894, found: 539.1895.

Example 288. 1-(4-(6-(4-(cyclopropanecarbonyl)piperazine-1-carbonyl)thieno[3,2-b]pyridin-7-yl)phenyl)cyclopropanecarbonitrile, TFA (Cpd. 288)

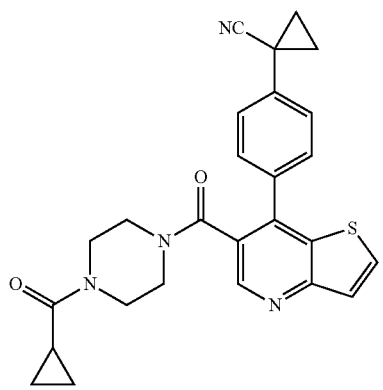

The title compound was prepared following the similar procedure as described in Example 41. $^1$H NMR (400 MHz, DMSO-$d_6$) δ 8.66 (s, 1H), 8.26 (d, J=5.6 Hz, 1H), 7.67 (d, J=5.6 Hz, 1H), 7.63-7.56 (m, 2H), 7.55-7.48 (m, 2H), 3.84-2.68 (m, 7H), 1.89 (d, J=8.0 Hz, 1H), 1.81 (m, 3H), 1.58 (q, J=4.7 Hz, 2H), 0.66 (d, J=6.3 Hz, 4H); LC-MS (Method 2): $t_R$=4.40 min, m/z M+H)$^+$=457; HRMS calculated for $C_{26}H_{24}N_4O_2SNa$ (M+Na)$^+$: 479.1512, found: 479.1528.

Example 289. 4-(7-(4-cyano-4-phenylpiperidin-1-yl)thieno[3,2-b]pyridine-6-carbonyl)-N,N-dimethylpiperazine-1-carboxamide, TFA (Cpd. 289)

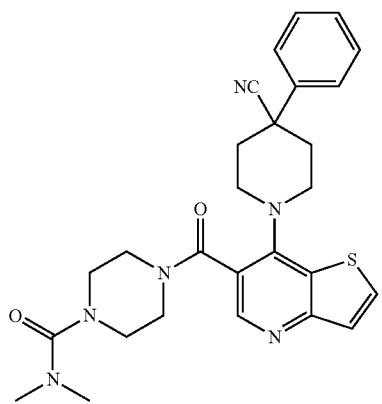

Cpd. 289

The title compound was prepared following the similar procedure as described in Example 1. $^1$H NMR (400 MHz, DMSO-d$_6$) δ 8.45 (s, 1H), 8.28 (d, J=5.6 Hz, 1H), 7.59-7.52 (m, 3H), 7.51-7.42 (m, 2H), 7.42-7.34 (m, 1H), 4.00 (d, J=13.7 Hz, 1H), 3.80 (d, J=13.3 Hz, 1H), 3.69 (s, 2H), 3.56-3.43 (m, 2H), 3.40 (t, J=5.2 Hz, 2H), 3.27-3.02 (m, 4H), 2.73 (s, 6H), 2.41-2.01 (m, 4H); LC-MS (Method 2): t$_R$=4.04 min, m/z (M+H)$^+$=503; HRMS calculated for C$_{27}$H$_{31}$N$_6$O$_2$S (M+H)$^+$: 503.2224, found: 503.2234.

Example 290. 1-(3-(4-(cyclopropanecarbonyl)piperazine-1-carbonyl)-6-fluoroquinolin-4-yl)-4-(2-fluoro-4-methylphenyl)piperidine-4-carbonitrile, TFA (Cpd. 290)

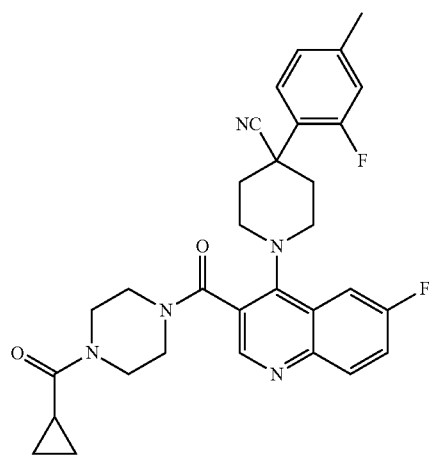

Cpd. 290

The title compound was prepared following the similar procedure as described in Example 17. $^1$H NMR (400 MHz, DMSO-d$_6$) δ 8.58 (s, 1H), 8.06 (dd, J=9.2, 5.6 Hz, 1H), 7.77 (dd, J=10.3, 2.9 Hz, 1H), 7.67 (ddd, J=9.1, 8.1, 2.9 Hz, 1H), 7.45 (t, J=8.3 Hz, 1H), 7.21-7.14 (m, 1H), 7.12 (ddd, J=7.9, 1.8, 0.8 Hz, 1H), 3.83-3.24 (m, 12H), 2.53-2.24 (m, 4H), 2.33 (s, 3H), 2.01-1.90 (m, 1H), 0.72 (d, J=4.0 Hz, 4H); LC-MS (Method 2): t$_R$=4.80 min, m/z (M+H)$^+$=544; HRMS calculated for C$_{31}$H$_{32}$F$_2$N$_5$O$_2$ (M+H)$^+$: 544.2519, found: 544.2522.

Example 291. (4-(cyclopropanecarbonyl)piperazin-1-yl)(6-fluoro-4-(4-hydroxy-4-phenylpiperidin-1-yl)quinolin-3-yl)methanone, TFA (Cpd. 291)

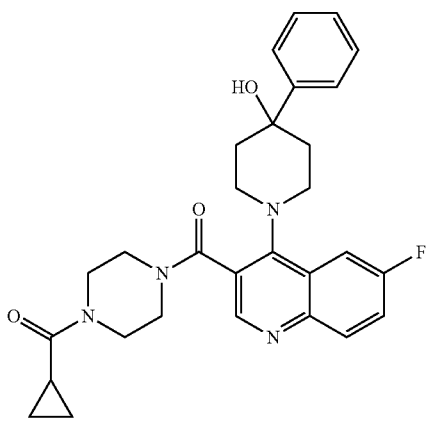

Cpd. 291

The title compound was prepared following the similar procedure as described in Example 17. $^1$H NMR (400 MHz, DMSO-d$_6$) δ 8.63 (s, 1H), 8.05 (dd, J=9.2, 5.5 Hz, 1H), 7.87 (dd, J=10.3, 2.8 Hz, 1H), 7.82-7.71 (m, 1H), 7.63-7.55 (m, 2H), 7.34 (dd, J=8.4, 7.0 Hz, 2H), 7.27-7.19 (m, 1H), 3.93-3.22 (m, 12H), 3.16 (d, J=10.7 Hz, 1H), 2.38 (td, J=12.5, 5.4 Hz, 1H), 2.18 (td, J=12.7, 4.3 Hz, 1H), 2.07-1.82 (m, 1H), 1.82-1.63 (m, 2H), 0.73 (dd, J=4.7, 2.8 Hz, 4H); LC-MS (Method 2): t$_R$=3.84 min, m/z (M+H)$^+$=503; HRMS calculated for C$_{29}$H$_{32}$FN$_4$O$_3$ (M+H)$^+$: 503.2453, found: 503.2446.

Example 292. (6-fluoro-4-(4-hydroxy-4-phenylpiperidin-1-yl)quinolin-3-yl)(4-(methylsulfonyl)piperazin-1-yl)methanone, TFA (Cpd. 292)

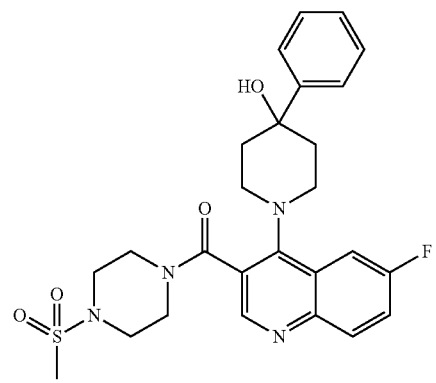

Cpd. 292

The title compound was prepared following the similar procedure as described in Example 17. $^1$H NMR (400 MHz, DMSO-d$_6$) δ 8.62 (s, 1H), 8.05 (dd, J=9.2, 5.5 Hz, 1H), 7.87 (dd, J=10.3, 2.8 Hz, 1H), 7.81-7.72 (m, 1H), 7.63-7.56 (m, 2H), 7.35 (dd, J=8.4, 7.0 Hz, 2H), 7.27-7.20 (m, 1H), 3.98-3.84 (m, 1H), 3.68-3.63 (m, 3H), 3.57-3.42 (m, 3H), 3.25 (t, J=5.3 Hz, 2H), 3.19-3.08 (m, 4H), 2.91 (s, 3H), 2.44-2.32 (m, 1H), 2.25-2.12 (m, 1H), 1.83-1.64 (m, 2H); LC-MS (Method 2): $t_R$=3.82 min, m/z (M+H)$^+$=513; HRMS calculated for $C_{26}H_{30}FN_4O_4S$ (M+H)$^+$: 513.1966, found: 513.1990.

Example 293. 1-(6-(4-(methylsulfonyl)piperidine-1-carbonyl)thieno[3,2-b]pyridin-7-yl)-4-phenylpiperidine-4-carbonitrile, TFA (Cpd. 293)

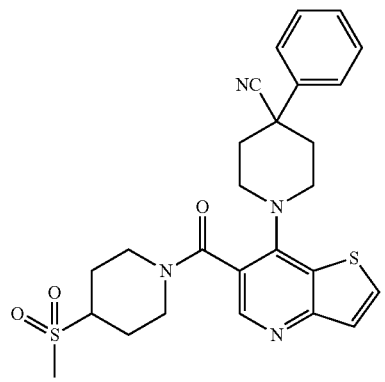

Cpd. 293

The title compound was prepared following the similar procedure as described in Example 1. $^1$H NMR (400 MHz, DMSO-d$_6$) δ 8.50 and 8.43 (2 set of s, 1H), 8.29 (dd, J=5.7, 1.7 Hz, 1H), 7.59-7.52 (m, 3H), 7.51-7.42 (m, 2H), 7.42-7.34 (m, 1H), 4.66 (s, 1H), 4.07-3.92 (m, 1H), 3.86-2.77 (m, 7H), 2.93 (2 set of s, 3H), 2.40-1.41 (m, 8H). (2 rotamers); LC-MS (Method 2): $t_R$=3.97 min, m/z (M+H)$^+$=509; HRMS calculated for $C_{26}H_{29}N_4O_3S_2$ (M+H)$^+$: 509.1676, found: 509.1690.

Example 294. 1-(4-(6-chloro-3-(4-(cyclopropanecarbonyl)piperazine-1-carbonyl)quinolin-4-yl)phenyl)cyclopropanecarbonitrile, TFA (Cpd. 294)

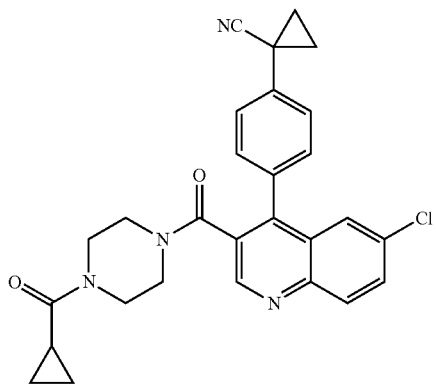

Cpd. 294

The title compound was prepared following the similar procedure as described in Example 41. $^1$H NMR (400 MHz, DMSO-d$_6$) δ 8.90 (s, 1H), 8.15 (d, J=9.0 Hz, 1H), 7.86 (dd, J=9.0, 2.4 Hz, 1H), 7.61-7.33 (m, 5H), 3.72-2.69 (m, 8H), 1.88 (br s, 1H), 1.85-1.79 (m, 2H), 1.60 (d, J=2.8 Hz, 2H), 0.66 (d, J=7.9 Hz, 4H); LC-MS (Method 2): $t_R$=4.99 min, m/z (M+H)$^+$=485; HRMS calculated for $C_{28}H_{26}ClN_4O_2$ (M+H)$^+$: 485.1739, found: 485.1743.

Example 295. 1-(4-(6-chloro-3-(4-(methylsulfonyl)piperidine-1-carbonyl)quinolin-4-yl)phenyl)cyclopropanecarbonitrile, TFA (Cpd. 295)

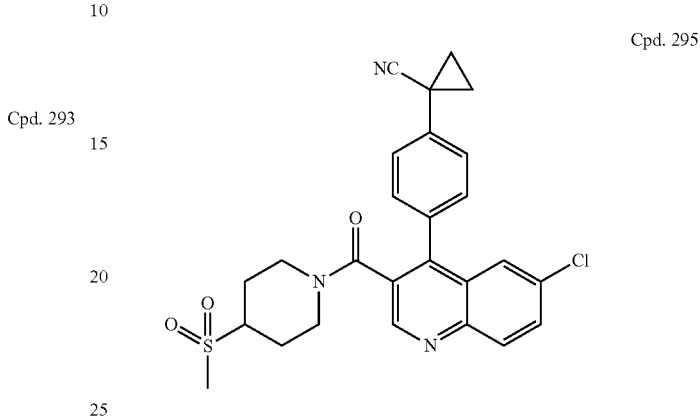

Cpd. 295

The title compound was prepared following the similar procedure as described in Example 41. $^1$H NMR (400 MHz, DMSO-d$_6$) δ 8.94 and 8.83 (2 set of s, 1H), 8.14 (dd, J=9.0, 2.4 Hz, 1H), 7.85 (dd, J=9.0, 2.3 Hz, 1H), 7.69-7.26 (m, 5H), 4.45 (t, J=13.6 Hz, 1H), 3.35-2.40 (m, 4H), 2.86 and 2.77 (2 set of s, 3H), 2.07-0.09 (m, 8H). (2 rotamers); LC-MS (Method 2): $t_R$=4.80 min, m/z (M+H)$^+$=494; HRMS calculated for $C_{26}H_{25}ClN_3O_3S$ (M+H)$^+$: 494.1300, found: 494.1303.

Example 296. 4-(6-chloro-4-(4-(1-cyanocyclopropyl)phenyl)quinoline-3-carbonyl)-N,N-dimethylpiperazine-1-carboxamide, TFA (Cpd. 296)

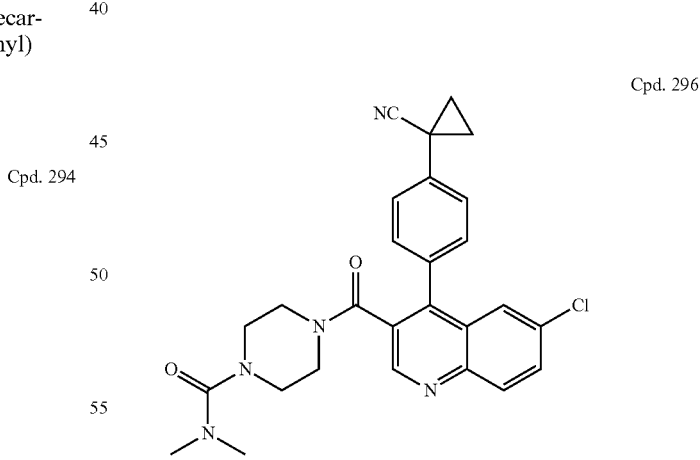

Cpd. 296

The title compound was prepared following the similar procedure as described in Example 41. $^1$H NMR (400 MHz, DMSO-d$_6$) δ 8.88 (s, 1H), 8.14 (d, J=9.0 Hz, 1H), 7.85 (dd, J=9.0, 2.4 Hz, 1H), 7.61-7.43 (m, 4H), 7.39 (d, J=8.1 Hz, 1H), 3.53-3.27 (m, 2H), 3.12 (d, J=11.3 Hz, 2H), 2.92 (d, J=10.9 Hz, 2H), 2.66-2.61 (m, 7H), 2.28-2.23 (m, 1H), 1.81-1.80 (m, 2H), 1.61-1.58 (m, 2H); LC-MS (Method 2): $t_R$=4.89 min, m/z (M+H)$^+$=488; HRMS calculated for $C_{27}H_{27}ClN_5O_2$ (M+H)$^+$: 488.1848, found: 488.1863.

Example 297. 1-(4-(6-chloro-3-(4-(methylsulfonyl)piperazine-1-carbonyl)quinolin-4-yl)phenyl)cyclopropanecarbonitrile, TFA (Cpd. 297)

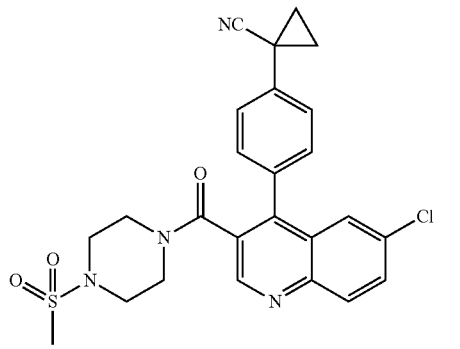

Cpd. 297

The title compound was prepared following the similar procedure as described in Example 41. ¹H NMR (400 MHz, DMSO-$d_6$) δ 8.89 (d, J=1.9 Hz, 1H), 8.15 (dd, J=9.2, 1.8 Hz, 1H), 7.86 (dd, J=9.0, 2.4 Hz, 1H), 7.62-7.50 (m, 3H), 7.47 (d, J=8.2 Hz, 1H), 7.38 (d, J=8.2 Hz, 1H), 3.70-2.86 (m, 6H), 2.76 (s, 3H), 2.54 (d, J=9.5 Hz, 1H), 2.11 (t, J=9.6 Hz, 1H), 1.82 (q, J=2.7 Hz, 2H), 1.71-1.57 (m, 2H); LC-MS (Method 2): $t_R$=5.02 min, m/z (M+H)⁺=495; HRMS calculated for $C_{25}H_{24}ClN_4O_3S$ (M+H)⁺: 495.1252, found: 495.1249.

Example 298. 4-(6-chloro-4-(4-(1-cyanocyclopropyl)phenyl)quinoline-3-carbonyl)-N,N-dimethylpiperazine-1-sulfonamide, TFA (Cpd. 298)

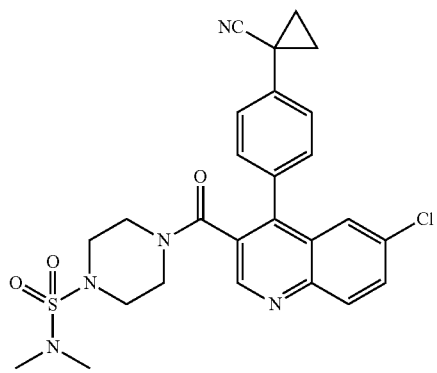

Cpd. 298

The title compound was prepared following the similar procedure as described in Example 41. ¹H NMR (400 MHz, DMSO-$d_6$) δ 8.89 (s, 1H), 8.15 (d, J=9.3 Hz, 1H), 7.86 (dd, J=9.0, 2.4 Hz, 1H), 7.62-7.51 (m, 3H), 7.48 (d, J=8.3 Hz, 1H), 7.39 (d, J=8.2 Hz, 1H), 3.71-2.93 (m, 6H), 2.68 (s, 6H), 2.53 (t, J=9.3 Hz, 1H), 2.09 (t, J=9.0 Hz, 1H), 1.84-1.83 (m, 2H), 1.64-1.62 (m, 2H); LC-MS (Method 2): $t_R$=5.33 min, m/z (M+H)⁺=524; HRMS calculated for $C_{26}H_{27}ClN_5O_3S$ (M+H)⁺: 524.1518, found: 524.1542.

Example 299. 2-methyl-2-(4-(2-(4-(methylsulfonyl)piperazine-1-carbonyl)naphthalen-1-yl)phenyl)propanenitrile (Cpd. 299)

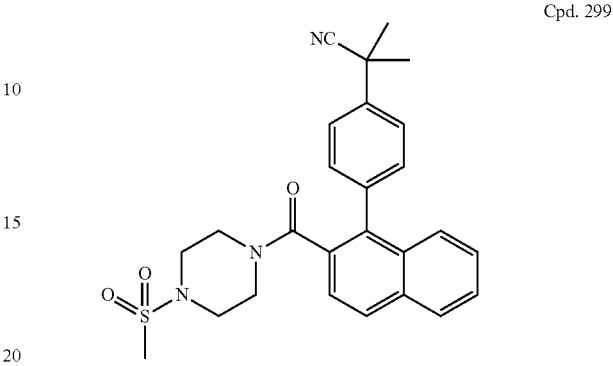

Cpd. 299

The title compound was prepared following the similar procedure as described in Example 210. ¹H NMR (400 MHz, DMSO-$d_6$) δ 8.03 (dd, J=8.2, 6.3 Hz, 2H), 7.71-7.66 (m, 1H), 7.63 (d, J=8.2 Hz, 1H), 7.61-7.42 (m, 5H), 7.38 (d, J=8.2 Hz, 1H), 3.54-2.89 (m, 6H), 2.76 (s, 3H), 2.46-2.43 (m, 1H), 2.38-2.25 (m, 1H), 1.73 (s, 6H); LC-MS (Method 2): $t_R$=5.38 min, m/z (M+H)⁺=462; HRMS calculated for $C_{26}H_{28}N_3O_3S$ (M+H)⁺: 462.1846, found: 462.1852.

Example 300. 1-(4-(2-(4-(methylsulfonyl)piperazine-1-carbonyl)naphthalen-1-yl)phenyl)cyclopropanecarbonitrile (Cpd. 300)

Cpd. 300

The title compound was prepared following the similar procedure as described in Example 210. ¹H NMR (400 MHz, Chloroform-d) δ 7.92 (t, J=8.9 Hz, 2H), 7.68 (d, J=8.4 Hz, 1H), 7.61-7.32 (m, 7H), 3.77-3.52 (m, 2H), 3.22-3.17 (m, 2H), 3.06-2.96 m, 2H), 2.73 (br s, 1H), 2.69 (s, 3H), 2.40 (t, J=9.4 Hz, 1H), 1.82-1.79 (m, 2H), 1.51-1.45 (m, 2H); LC-MS (Method 2): $t_R$=5.27 min, m/z (M+H)⁺=460; HRMS calculated for $C_{26}H_{26}N_3O_3S$ (M+H)⁺: 460.1689, found: 460.1695.

Example 301. (4-(4,4-dimethylcyclohex-1-en-1-yl)-6-fluoroquinolin-3-yl)(4-(methylsulfonyl)piperazin-1-yl)methanone, TFA (Cpd. 301)

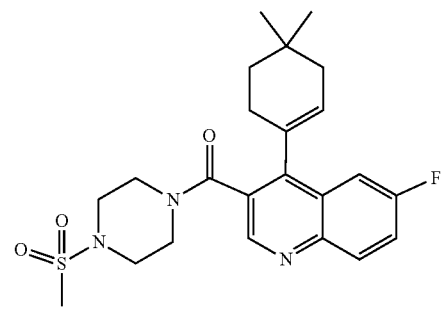

Cpd. 301

The title compound was prepared following the similar procedure as described in Example 41. $^1$H NMR (400 MHz, DMSO-$d_6$) δ 8.75 (s, 1H), 8.13 (dd, J=9.2, 5.6 Hz, 1H), 7.72 (ddd, J=9.3, 8.3, 2.9 Hz, 1H), 7.57-7.41 (m, 1H), 5.66 (t, J=3.7 Hz, 1H), 4.00-2.92 (m, 8H), 2.89 (s, 3H), 2.37-1.28 (m, 6H), 1.01 (s, 3H), 0.93 (s, 3H); LC-MS (Method 2): $t_R$=5.44 min, m/z (M+H)$^+$=446; HRMS calculated for $C_{23}H_{28}FN_3O_3SNa$ (M+Na)$^+$: 468.1728, found: 468.1731.

Example 302. 1-(3-(4-(cyclopropanecarbonyl)piperazine-1-carbonyl)-6-fluoroquinolin-4-yl)piperidine-4-carbonitrile, TFA (Cpd. 302)

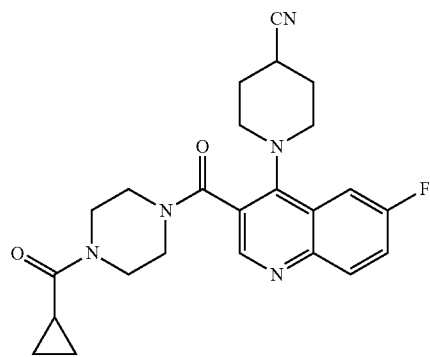

Cpd. 302

The title compound was prepared following the similar procedure as described in Example 17. $^1$H NMR (400 MHz, DMSO-$d_6$) δ 8.61 (s, 1H), 8.13-7.97 (m, 1H), 7.80-7.61 (m, 2H), 3.89-2.92 (m, 13H), 2.21-1.79 (m, 5H), 0.79-0.60 (m, 4H); LC-MS (Method 2): $t_R$=3.32 min, m/z (M+H)$^+$=436; HRMS calculated for $C_{24}H_{26}FN_5O_2Na$ (M+Na)$^+$: 458.1963, found: 458.1962.

Example 303. (4-(cyclopropanecarbonyl)piperazin-1-yl)(6-fluoro-4-(4-(methylsulfonyl)piperazin-1-yl)quinolin-3-yl)methanone, TFA (Cpd. 303)

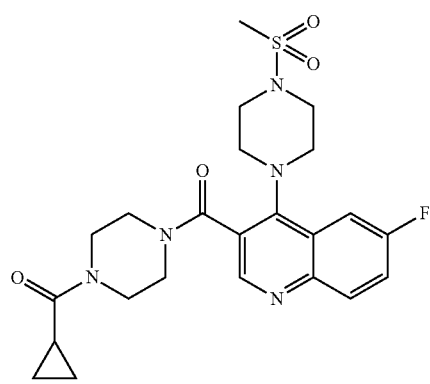

Cpd. 303

The title compound was prepared following the similar procedure as described in Example 17. $^1$H NMR (400 MHz, DMSO-$d_6$) δ 8.64 (s, 1H), 8.08 (dd, J=9.2, 5.6 Hz, 1H), 7.82 (dd, J=10.3, 2.9 Hz, 1H), 7.71 (ddd, J=9.2, 8.2, 2.9 Hz, 1H), 4.21-3.00 (m, 16H), 2.96 (s, 3H), 2.10-1.84 (m, 1H), 0.72 (d, J=4.4 Hz, 4H); LC-MS (Method 2): $t_R$=3.23 min, m/z (M+H)$^+$=490; HRMS calculated for $C_{23}H_{29}FN_5O_4S$ (M+H)$^+$: 490.1919, found: 490.1908.

Example 304. 1-(4-(3-(4-(cyclopropanecarbonyl)piperazine-1-carbonyl)-6-fluoroquinolin-4-yl)piperazin-1-yl)ethanone, TFA (Cpd. 304)

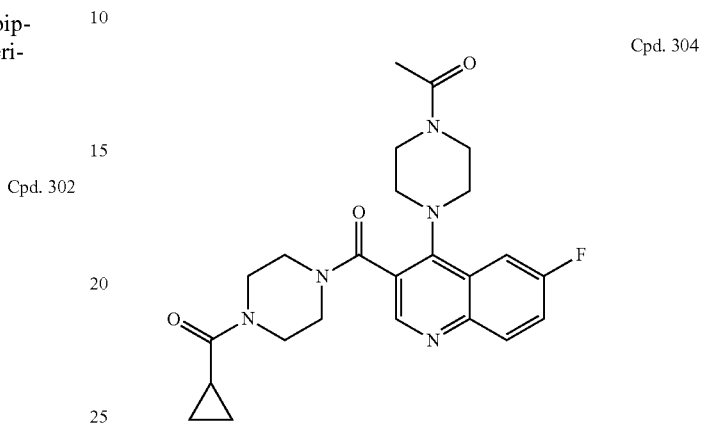

Cpd. 304

The title compound was prepared following the similar procedure as described in Example 17. $^1$H NMR (400 MHz, DMSO-$d_6$) δ 8.62 (s, 1H), 8.07 (dd, J=9.2, 5.5 Hz, 1H), 7.82 (dd, J=10.3, 2.8 Hz, 1H), 7.73 (ddd, J=9.2, 8.2, 2.8 Hz, 1H), 3.91-2.88 (m, 16H), 2.03 (s, 3H), 2.02-1.83 (m, 1H), 0.72 (d, J=4.2 Hz, 4H); LC-MS (Method 2): $t_R$=2.96 min, m/z (M+H)$^+$=454; HRMS calculated for $C_{24}H_{29}FN_5O_3$ (M+H)$^+$: 454.2249, found: 454.2227.

Example 305. 1-(6-fluoro-3-(4-(methylsulfonyl)piperazine-1-carbonyl)quinolin-4-yl)piperidine-4-carbonitrile, TFA (Cpd. 305)

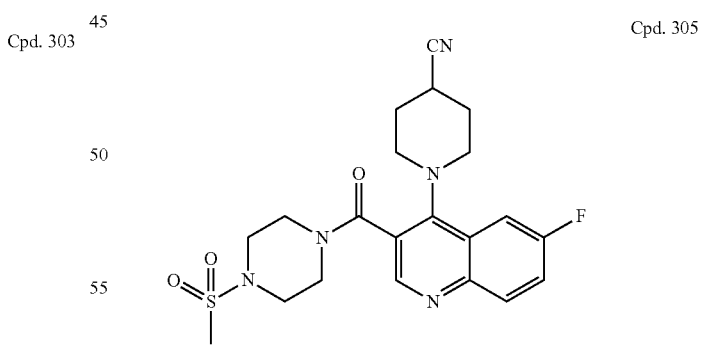

Cpd. 305

The title compound was prepared following the similar procedure as described in Example 17. $^1$H NMR (400 MHz, DMSO-$d_6$) δ 8.60 (s, 1H), 8.13-7.93 (m, 1H), 7.80-7.62 (m, 2H), 3.92 (dt, J=13.3, 4.7 Hz, 1H), 3.63 (ddd, J=12.5, 7.3, 3.9 Hz, 1H), 3.54-3.34 (m, 2H), 3.32-2.94 (m, 9H), 2.91 (s, 3H), 2.20-1.83 (m, 4H); LC-MS (Method 2): $t_R$=3.26 min, m/z (M+H)$^+$=446; HRMS calculated for $C_{21}H_{25}FN_5O_3S$ (M+H)$^+$: 446.1657, found: 446.1669.

Example 306. (4-(4-(tert-butyl)phenyl)-6-fluoroquinolin-3-yl)(4-(methylsulfonyl)piperazin-1-yl)methanone, TFA (Cpd. 306)

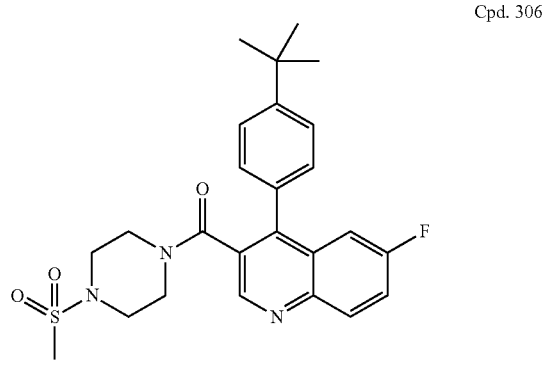 [SMILES: CC(C)(C)c1ccc(-c2c(C(=O)N3CCN(S(C)(=O)=O)CC3)cnc3ccc(F)cc23)cc1]

The title compound was prepared following the similar procedure as described in Example 210. $^1$H NMR (400 MHz, DMSO-d$_6$) δ 8.83 (s, 1H), 8.20 (dd, J=9.2, 5.6 Hz, 1H), 7.76 (ddd, J=9.2, 8.2, 2.9 Hz, 1H), 7.62 (d, J=8.2 Hz, 1H), 7.57 (d, J=8.1 Hz, 1H), 7.45 (d, J=8.2 Hz, 1H), 7.36-7.23 (m, 2H), 3.65-2.89 (m, 7H), 2.74 (s, 3H), 2.13 (t, J=8.4 Hz, 1H), 1.32 (s, 9H); LC-MS (Method 2): t$_R$=5.69 min, m/z (M+H)$^+$=470; HRMS calculated for C$_{25}$H$_{29}$FN$_3$O$_3$S (M+H)$^+$: 470.1908, found: 470.1922.

Example 307. (6-fluoro-4-(4-(methylsulfonyl)piperazin-1-yl)quinolin-3-yl)(4-(methylsulfonyl)piperazin-1-yl)methanone, TFA (Cpd. 307)

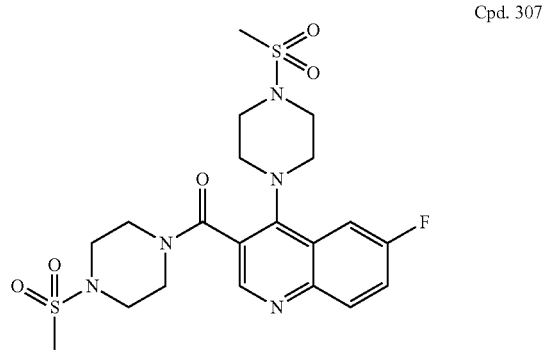 [SMILES: CS(=O)(=O)N1CCN(C(=O)c2cnc3ccc(F)cc3c2N2CCN(S(C)(=O)=O)CC2)CC1]

The title compound was prepared following the similar procedure as described in Example 17. $^1$H NMR (400 MHz, DMSO-d$_6$) δ 8.64 (s, 1H), 8.08 (dd, J=9.2, 5.5 Hz, 1H), 7.83 (dd, J=10.3, 2.9 Hz, 1H), 7.72 (ddd, J=9.2, 8.1, 2.9 Hz, 1H), 3.92 (dt, J=13.3, 4.6 Hz, 1H), 3.69 (ddd, J=12.5, 7.5, 3.5 Hz, 1H), 3.56-3.01 (m, 14H), 2.97 (s, 3H), 2.91 (s, 3H); LC-MS (Method 2): t$_R$=3.18 min, m/z (M+H)$^+$=500; HRMS calculated for C$_{20}$H$_{27}$FN$_5$O$_5$S$_2$ (M+H)$^+$: 500.1432, found: 500.1440.

Example 308. 1-(4-(6-fluoro-3-(4-(methylsulfonyl)piperazine-1-carbonyl)quinolin-4-yl)phenyl)cyclobutanecarbonitrile, TFA (Cpd. 308)

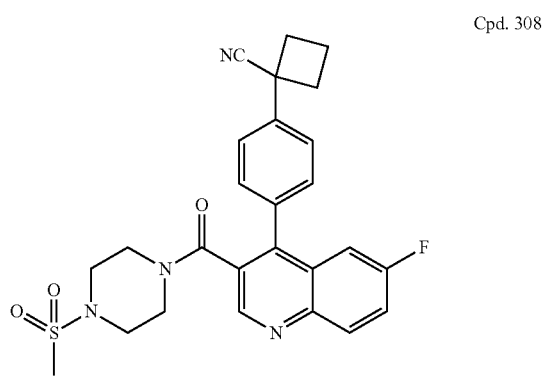 [SMILES: CS(=O)(=O)N1CCN(C(=O)c2cnc3ccc(F)cc3c2-c2ccc(C3(C#N)CCC3)cc2)CC1]

The title compound was prepared following the similar procedure as described in Example 210. $^1$H NMR (400 MHz, DMSO-d$_6$) δ 8.86 (s, 1H), 8.21 (dd, J=9.2, 5.6 Hz, 1H), 7.77 (ddd, J=9.2, 8.2, 2.9 Hz, 1H), 7.70 (d, J=8.1 Hz, 1H), 7.66 (d, J=8.1 Hz, 1H), 7.58 (d, J=8.2 Hz, 1H), 7.43 (d, J=8.1 Hz, 1H), 7.29 (dd, J=10.2, 2.8 Hz, 1H), 3.64-2.92 (m, 6H), 2.75 (s, 3H), 2.81-2.59 (m, 4H), 2.56-2.49 (m, 1H), 2.37-2.24 (m, 1H), 2.20 (t, J=9.2 Hz, 1H), 2.04 (dtt, J=11.3, 8.9, 4.5 Hz, 1H); LC-MS (Method 2): t$_R$=5.08 min, m/z (M+H)$^+$=493; HRMS calculated for C$_{26}$H$_{26}$FN$_4$O$_3$S (M+H)$^+$: 493.1704, found: 493.1709.

Example 309. 1-(4-(6-fluoro-3-(4-(methylsulfonyl)piperazine-1-carbonyl)quinolin-4-yl)phenyl)cyclopentanecarbonitrile, TFA (Cpd. 309)

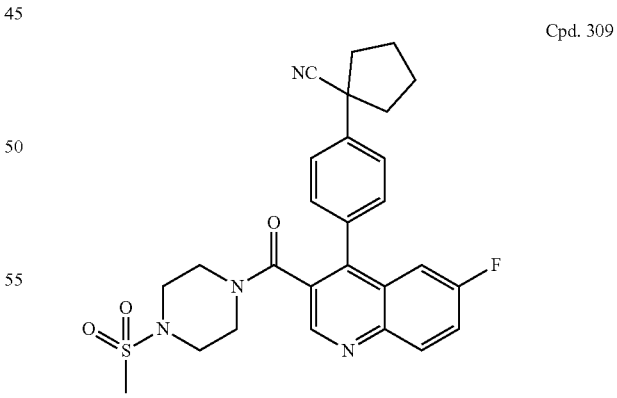

The title compound was prepared following the similar procedure as described in Example 210. LC-MS (Method 2): t$_R$=5.29 min, m/z (M+H)$^+$=507; HRMS calculated for C$_{27}$H$_{28}$FN$_4$O$_3$S (M+H)$^+$: 507.1861, found: 507.1851.

Example 310. 1-(6-chloro-3-(4-(methylsulfonyl)piperidine-1-carbonyl)quinolin-4-yl)-4-phenylpiperidine-4-carbonitrile, TFA (Cpd. 310)

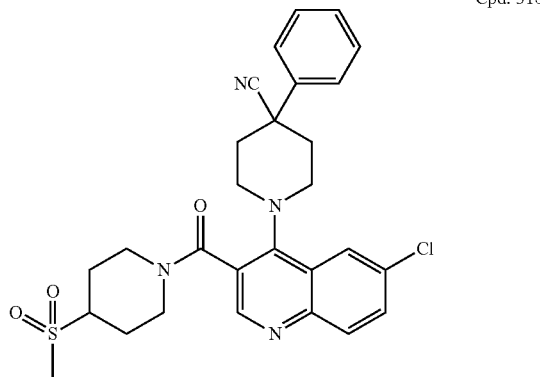

Cpd. 310

The title compound was prepared following the similar procedure as described in Example 1. $^1$H NMR (400 MHz, DMSO-d$_6$) δ 8.71 and 8.66 (2 set of s, 1H), 8.17 (dd, J=8.0, 2.3 Hz, 1H), 8.02 and 8.01 (2 set of d, J=8.0 Hz, 1H), 7.84 (dd, J=9.0, 2.3 Hz, 1H), 7.65 (dt, J=8.2, 1.2 Hz, 2H), 7.48 (ddd, J=7.9, 6.8, 1.5 Hz, 2H), 7.43-7.36 (m, 1H), 4.70 (m, 1H), 3.90-2.79 (m, 8H), 2.96 and 2.93 (2 set of s, 3H), 2.46-1.40 (m, 8H). (2 rotamers); LC-MS (Method 2): t$_R$=4.41 min, m/z (M+H)$^+$=537; HRMS calculated for C$_{28}$H$_{29}$ClN$_4$O$_3$SNa (M+Na)$^+$: 559.1541, found: 559.1534.

Example 311. 2-(3-fluoro-4-(6-fluoro-3-(4-(methylsulfonyl)piperazine-1-carbonyl)quinolin-4-yl)phenyl)-2-methylpropanenitrile, TFA (Cpd. 311)

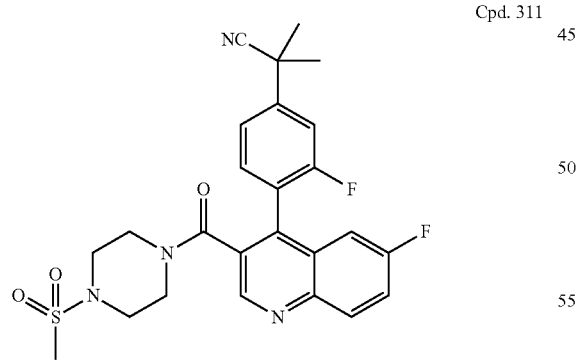

Cpd. 311

The title compound was prepared following the similar procedure as described in Example 210. $^1$H NMR (400 MHz, DMSO-d6) δ 8.96 (s, 1H), 8.24 (dd, J=9.3, 5.6 Hz, 1H), 7.80 (ddd, J=9.3, 8.3, 2.9 Hz, 1H), 7.63 (s, 1H), 7.56 (dd, J=8.0, 1.8 Hz, 1H), 7.46 (s, 1H), 7.14 (s, 1H), 3.69-2.54 (m, 11H), 1.76 (s, 3H), 1.75 (s, 3H); LC-MS (Method 2): t$_R$=4.92 min, m/z (M+H)$^+$=499; HRMS calculated for C$_{25}$H$_{25}$F$_2$N$_4$O$_3$S (M+H)$^+$: 499.1610, found: 499.1626.

Example 312. 4-(6-chloro-4-(4-cyano-4-phenylpiperidin-1-yl)quinoline-3-carbonyl)-N,N-dimethylpiperazine-1-carboxamide, TFA (Cpd. 312)

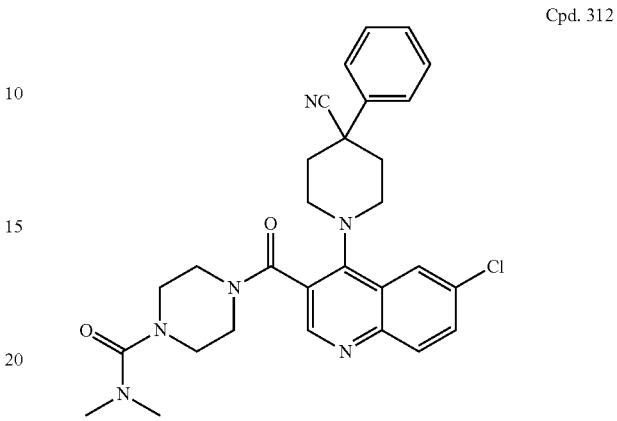

Cpd. 312

The title compound was prepared following the similar procedure as described in Example 1. $^1$H NMR (400 MHz, DMSO-d$_6$) δ 8.67 (s, 1H), 8.16 (d, J=2.3 Hz, 1H), 8.01 (d, J=8.9 Hz, 1H), 7.84 (dd, J=8.9, 2.3 Hz, 1H), 7.68-7.62 (m, 2H), 7.53-7.45 (m, 2H), 7.43-7.36 (m, 1H), 3.80-3.02 (m, 12H), 2.74 (s, 6H), 2.37-2.22 (m, 4H); LC-MS (Method 2): t$_R$=4.50 min, m/z M+H)$^+$=531; HRMS calculated for C$_{29}$H$_{32}$ClN$_6$O$_2$ (M+H)$^+$: 531.2270, found: 531.2271.

Example 313. 1-(6-chloro-3-(4-(cyclopropanecarbonyl)piperazine-1-carbonyl)quinolin-4-yl)-4-phenylpiperidine-4-carbonitrile, TFA (Cpd. 313)

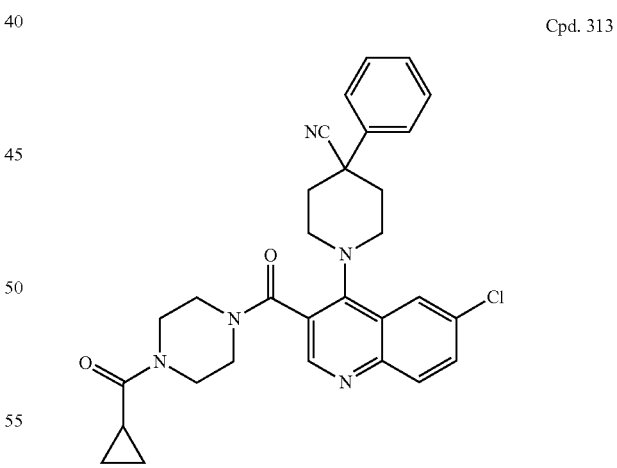

Cpd. 313

The title compound was prepared following the similar procedure as described in Example 1. $^1$H NMR (400 MHz, DMSO-d$_6$) δ 8.68 (s, 1H), 8.16 (d, J=2.3 Hz, 1H), 8.02 (d, J=9.0 Hz, 1H), 7.84 (dd, J=9.0, 2.3 Hz, 1H), 7.68-7.61 (m, 2H), 7.53-7.44 (m, 2H), 7.43-7.36 (m, 1H), 3.93-3.26 (m, 12H), 2.46-2.22 (m, 4H), 2.02-1.92 (m, 1H), 0.73 (d, J=4.8 Hz, 4H); LC-MS (Method 2): t$_R$=4.61 min, m/z (M+H)$^+$=528; HRMS calculated for C$_{30}$H$_{31}$ClN$_5$O$_2$ (M+H)$^+$: 528.2161, found: 528.2178.

Example 314. 4-(6-chloro-4-(4-cyano-4-phenylpiperidin-1-yl)quinoline-3-carbonyl)-N,N-dimethylpiperazine-1-sulfonamide, TFA (Cpd. 314)

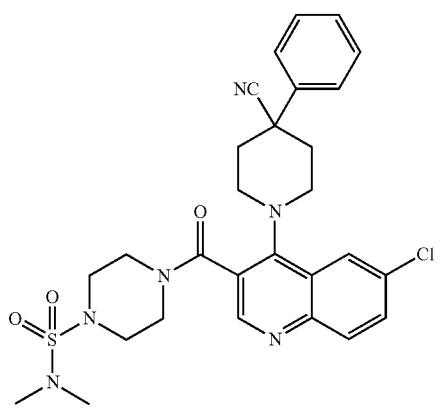

Cpd. 314

The title compound was prepared following the similar procedure as described in Example 1. $^1$H NMR (400 MHz, DMSO-d$_6$) δ 8.70 (s, 1H), 8.16 (d, J=2.3 Hz, 1H), 8.02 (d, J=9.0 Hz, 1H), 7.85 (dd, J=9.0, 2.3 Hz, 1H), 7.69-7.62 (m, 2H), 7.54-7.44 (m, 2H), 7.44-7.36 (m, 1H), 3.94-3.11 (m, 12H), 2.76 (s, 6H), 2.45-2.22 (m, 4H); LC-MS (Method 2): t$_R$=4.91 min, m/z M+H)$^+$=567; HRMS calculated for C$_{28}$H$_{31}$ClN$_6$O$_3$SNa (M+Na)$^+$: 589.1759, found: 589.1751.

Example 315. 1-(3-fluoro-4-(6-fluoro-3-(4-(methylsulfonyl)piperazine-1-carbonyl)quinolin-4-yl)phenyl)cyclopropanecarbonitrile, TFA (Cpd. 315)

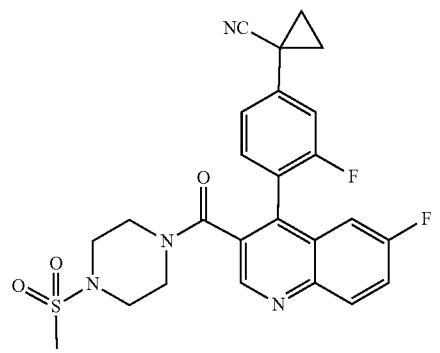

Cpd. 315

The title compound was prepared following the similar procedure as described in Example 210. $^1$H NMR (400 MHz, DMSO-d$_6$) δ 8.95 (s, 1H), 8.23 (dd, J=9.3, 5.5 Hz, 1H), 7.79 (ddd, J=9.3, 8.2, 2.8 Hz, 1H), 7.27 (d, J=107.2 Hz, 4H), 3.07 (d, J=184.5 Hz, 11H), 1.85 (td, J=4.1, 3.6, 2.2 Hz, 2H), 1.72-1.65 (m, 2H); LC-MS (Method 2): t$_R$=4.79 min, m/z (M+H)$^+$=497; HRMS calculated for C$_{25}$H$_{23}$F$_2$N$_4$O$_3$S (M+H)$^+$: 497.1453, found: 497.1453.

Example 316. 1-(6-chloro-3-(4-(methylsulfonyl)piperazine-1-carbonyl)quinolin-4-yl)-4-phenylpiperidine-4-carbonitrile, TFA (Cpd. 316)

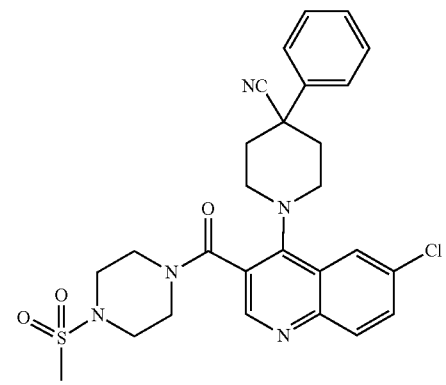

Cpd. 316

The title compound was prepared following the similar procedure as described in Example 1. $^1$H NMR (400 MHz, DMSO-d$_6$) δ 8.66 (s, 1H), 8.15 (d, J=2.3 Hz, 1H), 8.02 (d, J=9.0 Hz, 1H), 7.83 (dd, J=8.9, 2.3 Hz, 1H), 7.68-7.62 (m, 2H), 7.53-7.44 (m, 2H), 7.43-7.35 (m, 1H), 3.95-3.00 (m, 12H), 2.91 (s, 3H), 2.45-2.22 (m, 4H); LC-MS (Method 2): t$_R$=4.66 min, m/z M+H)$^+$=538; HRMS calculated for C$_{27}$H$_{28}$ClN$_5$O$_3$SNa (M+Na)$^+$: 560.1494, found: 560.1512.

Example 317. 1-(6-methoxy-3-(4-(methylsulfonyl)piperazine-1-carbonyl)quinolin-4-yl)-4-phenylpiperidine-4-carbonitrile, HCL (Cpd. 317)

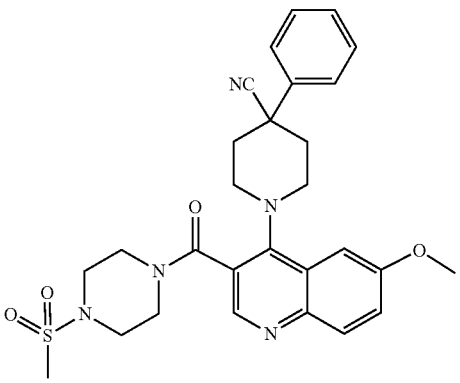

Cpd. 317

The title compound was prepared following the similar procedure as described in Example 1. $^1$H NMR (400 MHz, DMSO-d$_6$) δ 8.76 (s, 1H), 8.09 (d, J=9.2 Hz, 1H), 7.70-7.60 (m, 3H), 7.54-7.45 (m, 2H), 7.43-7.36 (m, 2H), 3.97 (s, 3H), 3.94-3.02 (m, 12H), 2.92 (s, 3H), 2.43-2.26 (m, 4H); MS M+H)$^+$=534; HRMS calculated for C$_{28}$H$_{32}$N$_5$O$_4$S (M+H)$^+$: 534.2170, found: 534.2169.

Example 318. 1-(7-methoxy-3-(4-(methylsulfonyl)piperazine-1-carbonyl)quinolin-4-yl)-4-phenylpiperidine-4-carbonitrile, HCl (Cpd. 318)

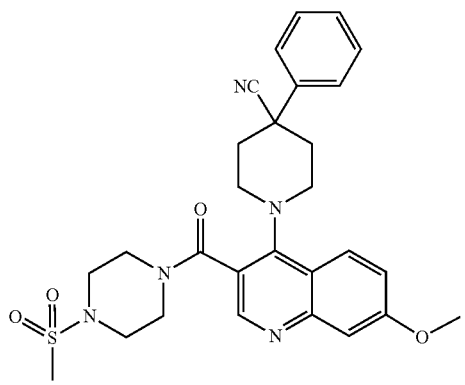

Cpd. 318

The title compound was prepared following the similar procedure as described in Example 1. $^1$H NMR (400 MHz, DMSO-d$_6$) δ 8.76 (d, J=4.2 Hz, 1H), 8.20 (d, J=9.4 Hz, 1H), 7.67-7.58 (m, 2H), 7.49 (dd, J=8.5, 6.9 Hz, 2H), 7.46-7.37 (m, 2H), 7.34 (dd, J=9.4, 2.5 Hz, 1H), 3.95 (s, 3H), 3.92-2.99 (m, 12H), 2.91 (s, 3H), 2.63-2.15 (m, 4H); MS M+H)$^+$=534; HRMS calculated for C$_{28}$H$_{31}$N$_5$O$_4$SNa (M+Na)$^+$: 556.1989, found: 556.1994.

Example 319. 1-(6,7-difluoro-3-(4-(methylsulfonyl)piperazine-1-carbonyl)quinolin-4-yl)-4-phenylpiperidine-4-carbonitrile, HCl (Cpd. 319)

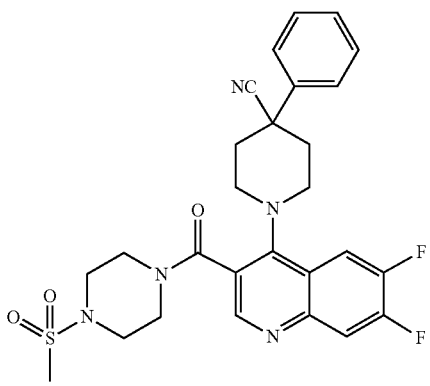

Cpd. 319

The title compound was prepared following the similar procedure as described in Example 1. $^1$H NMR (400 MHz, DMSO-d$_6$) δ 8.69 (d, J=3.0 Hz, 1H), 8.16 (dd, J=11.6, 8.6 Hz, 1H), 8.04 (dd, J=11.1, 7.8 Hz, 1H), 7.70-7.62 (m, 2H), 7.54-7.43 (m, 2H), 7.43-7.33 (m, 1H), 3.94-3.84 (m, 1H), 3.79-3.69 (m, 1H), 3.65 (d, J=13.3 Hz, 1H), 3.57-3.03 (m, 9H), 2.90 (s, 3H), 2.58 (td, J=12.7, 3.9 Hz, 1H), 2.36 (td, J=12.5, 11.8, 3.8 Hz, 1H), 2.31-2.16 (m, 2H); MS M+H)$^+$=540; HRMS calculated for C$_{27}$H$_{28}$F$_2$N$_5$O$_3$S (M+H)$^+$: 540.1875, found: 540.1869.

Example 320. 1-(6,8-difluoro-3-(4-(methylsulfonyl)piperazine-1-carbonyl)quinolin-4-yl)-4-phenylpiperidine-4-carbonitrile, HCl (Cpd. 320)

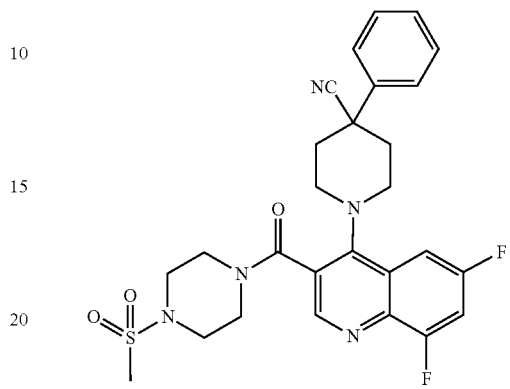

Cpd. 320

The title compound was prepared following the similar procedure as described in Example 1. $^1$H NMR (400 MHz, DMSO-d$_6$) δ 8.63 (s, 1H), 7.81-7.69 (m, 2H), 7.69-7.63 (m, 2H), 7.52-7.44 (m, 2H), 7.42-7.33 (m, 1H), 3.93 (dt, J=13.3, 4.8 Hz, 1H), 3.71 (dt, J=13.1, 5.1 Hz, 1H), 3.64-3.05 (m, 10H), 2.91 (s, 3H), 2.57-2.13 (m, 4H); MS M+H)$^+$=540; HRMS calculated for C$_{27}$H$_{28}$F$_2$N$_5$O$_3$S (M+H)$^+$: 540.1875, found: 540.1887.

Example 321. 1-(4-(6-methoxy-3-(4-(methylsulfonyl)piperazine-1-carbonyl)quinolin-4-yl)phenyl)cyclopropane-1-carbonitrile, HCl (Cpd. 321)

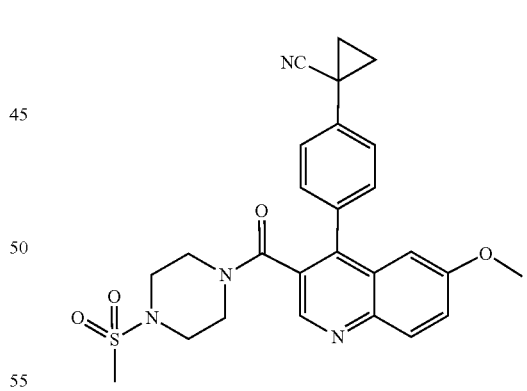

Cpd. 321

The title compound was prepared following the similar procedure as described in Example 259. $^1$H NMR (400 MHz, DMSO-d$_6$) δ 8.73 (d, J=0.8 Hz, 1H), 8.06 (d, J=9.2 Hz, 1H), 7.62-7.50 (m, 3H), 7.45 (d, J=8.2 Hz, 1H), 7.39 (d, J=8.2 Hz, 1H), 6.97 (d, J=2.8 Hz, 1H), 3.73 (s, 3H), 3.57 (s, 1H), 3.41 (t, J=9.0 Hz, 1H), 3.17 (d, J=8.3 Hz, 2H), 2.98 (t, J=12.7 Hz, 2H), 2.76 (s, 3H), 2.58-2.50 (m, 1H), 2.10 (t, J=8.7 Hz, 1H), 1.83 (dd, J=6.0, 2.7 Hz, 2H), 1.67-1.55 (m, 2H); MS (M+H)$^+$=491; HRMS calculated for C$_{26}$H$_{27}$N$_4$O$_4$S (M+H)$^+$: 491.1748, found: 491.1750.

Example 322. 1-(4-(7-methoxy-3-(4-(methylsulfonyl)piperazine-1-carbonyl)quinolin-4-yl)phenyl)cyclopropane-1-carbonitrile, HCl (Cpd. 322)

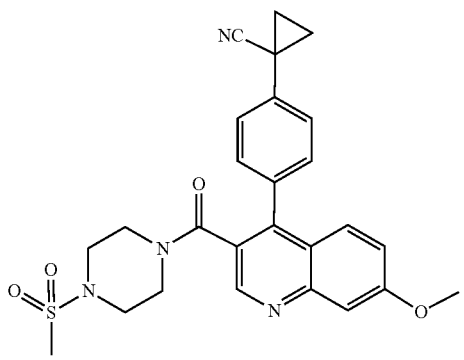

Cpd. 322

The title compound was prepared following the similar procedure as described in Example 259. $^1$H NMR (400 MHz, DMSO-d$_6$) δ 8.87 (s, 1H), 7.64-7.35 (m, 6H), 7.32 (dt, J=6.4, 2.3 Hz, 1H), 3.95 (s, 3H), 3.57 (s, 1H), 3.43 (d, J=8.6 Hz, 1H), 3.29-2.90 (m, 4H), 2.76 (s, 3H), 2.56 (d, J=10.4 Hz, 1H), 2.12 (s, 1H), 1.82 (q, J=4.6, 4.2 Hz, 2H), 1.66-1.58 (m, 2H); MS (M+H)$^+$=491; HRMS calculated for C$_{26}$H$_{27}$N$_4$O$_4$S (M+H)$^+$: 491.1748, found: 491.1751.

Example 323. 1-(4-(6,7-difluoro-3-(4-(methylsulfonyl)piperazine-1-carbonyl)quinolin-4-yl)phenyl)cyclopropane-1-carbonitrile, HCl (Cpd. 323)

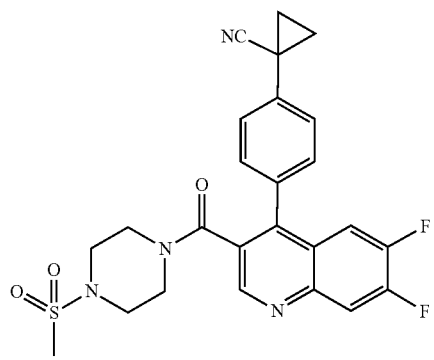

Cpd. 323

The title compound was prepared following the similar procedure as described in Example 259. $^1$H NMR (400 MHz, DMSO-d$_6$) δ 8.89 (s, 1H), 8.18 (dd, J=11.4, 7.9 Hz, 1H), 7.63-7.43 (m, 4H), 7.38 (d, J=8.1 Hz, 1H), 3.60 (d, J=13.0 Hz, 1H), 3.48-3.35 (m, 1H), 3.18 (d, J=9.3 Hz, 2H), 3.03-2.96 (m, 2H), 2.76 (s, 3H), 2.60-2.50 (m, 1H), 2.17-2.03 (m, 1H), 1.86-1.79 (m, 2H), 1.63 (td, J=5.5, 4.9, 3.1 Hz, 2H); MS M+H)$^+$=497; HRMS calculated for C$_{25}$H$_{23}$F$_2$N$_4$O$_3$S (M+H)$^+$: 497.1453, found: 497.1465.

Example 324. 1-(4-(6,8-difluoro-3-(4-(methylsulfonyl)piperazine-1-carbonyl)quinolin-4-yl)phenyl)cyclopropane-1-carbonitrile, HCl (Cpd. 324)

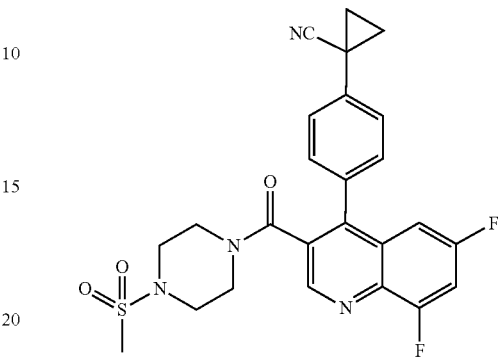

Cpd. 324

The title compound was prepared following the similar procedure as described in Example 259. $^1$H NMR (400 MHz, DMSO-d$_6$) δ 8.90 (s, 1H), 7.86 (ddd, J=11.0, 9.0, 2.6 Hz, 1H), 7.57 (d, J=8.1 Hz, 1H), 7.51 (d, J=8.1 Hz, 1H), 7.47 (d, J=8.2 Hz, 1H), 7.38 (d, J=8.1 Hz, 1H), 7.13 (dt, J=9.9, 1.9 Hz, 1H), 3.65-3.35 (m, 2H), 3.20 (q, J=12.3, 10.6 Hz, 2H), 3.10-2.90 (m, 2H), 2.76 (s, 3H), 2.55 (ddd, J=11.5, 8.1, 3.3 Hz, 1H), 2.13 (t, J=9.1 Hz, 1H), 1.82 (q, J=4.1, 3.6 Hz, 2H), 1.63 (q, J=3.9 Hz, 2H); MS M+H)$^+$=497; HRMS calculated for C$_{25}$H$_{23}$F$_2$N$_4$O$_3$S (M+H)$^+$: 497.1453, found: 497.1444.

Example 325. 4-(4-cyano-4-phenylpiperidin-1-yl)-6-fluoro-N-((1R,4R)-4-hydroxycyclohexyl)quinoline-3-carboxamide, TFA (Cpd. 325)

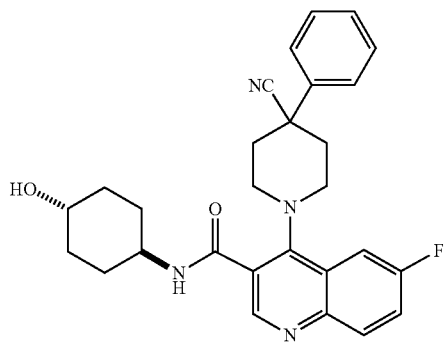

Cpd. 325

The title compound was prepared following the similar procedure as described in Example 1. $^1$H NMR (400 MHz, DMSO-d$_6$) δ 8.62 (s, 1H), 8.53 (d, J=7.6 Hz, 1H), 8.07 (dd, J=9.2, 5.4 Hz, 1H), 7.87 (dd, J=10.3, 2.7 Hz, 1H), 7.74 (td, J=8.7, 2.7 Hz, 1H), 7.66 (d, J=7.7 Hz, 2H), 7.47 (t, J=7.6 Hz, 2H), 7.38 (t, J=7.3 Hz, 1H), 3.79-3.64 (m, 1H), 3.54 (d, J=7.9 Hz, 4H), 3.40-3.35 (m, 1H), 2.47-2.35 (m, 2H), 2.26 (d, J=13.2 Hz, 2H), 1.97 (d, J=10.6 Hz, 2H), 1.83 (dd, J=9.7, 4.4 Hz, 2H), 1.41-1.17 (m, 4H). (OH not shown); LC-MS (Method 2): tR=3.98 min, m/z (M+H)+=473.

Example 326. 1-(6-fluoro-3-(3-hydroxyazetidine-1-carbonyl)quinolin-4-yl)-4-phenylpiperidine-4-carbonitrile, TFA (Cpd. 326)

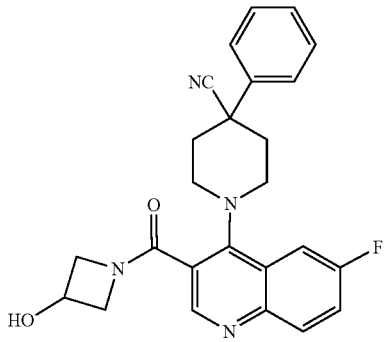

The title compound was prepared following the similar procedure as described in Example 1. ¹H NMR (400 MHz, DMSO-d₆) δ 8.67 (s, 1H), 8.06 (dd, J=9.2, 5.5 Hz, 1H), 7.89 (dd, J=10.3, 2.7 Hz, 1H), 7.75 (td, J=8.7, 2.7 Hz, 1H), 7.67 (d, J=7.7 Hz, 2H), 7.48 (t, J=7.6 Hz, 2H), 7.39 (t, J=7.4 Hz, 1H), 4.54 (td, J=6.9, 3.4 Hz, 1H), 4.30 (dd, J=10.5, 7.0 Hz, 1H), 4.22 (t, J=8.0 Hz, 1H), 3.90-3.78 (m, 2H), 3.62-3.42 (m, 4H), 2.46-2.35 (m, 2H), 2.26 (d, J=13.2 Hz, 2H). (OH not shown); LC-MS (Method 2): t$_R$=3.88 min, m/z (M+H)+=431.

Example 327. 1-(4-(4-cyano-4-phenylpiperidin-1-yl)-6-fluoroquinoline-3-carbonyl)-N-methylpiperidine-4-carboxamide, TFA (Cpd. 327)

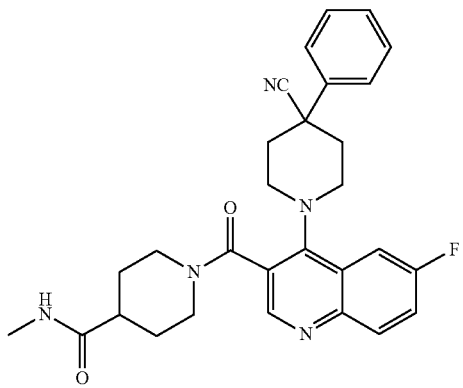

The title compound was prepared following the similar procedure as described in Example 1. ¹H NMR (400 MHz, DMSO-d₆) δ 8.63 and 8.62 (two s, 1H), 8.10-8.-5 (m, 1H), 7.93-7.87 (m, 1H), 7.80-7.61 (m, 4H), 7.47 (t, J=7.6 Hz, 2H), 7.39 (t, J=7.3 Hz, 1H), 4.52 (t, J=13.2 Hz, 1H), 3.78-2.79 (m, 8H), 2.70-2.11 (m, 7H), 1.91-1.35 (m, 4H). (two rotamers); LC-MS (Method 2): t$_R$=4.10 min, m/z (M+H)+=500.

Example 328. 1-(3-(2,2-dioxido-2-thia-6-azaspiro[3.3]heptane-6-carbonyl)-6-fluoroquinolin-4-yl)-4-phenylpiperidine-4-carbonitrile, TFA (Cpd. 328)

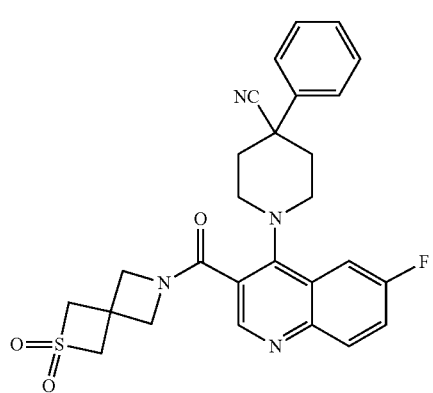

The title compound was prepared following the similar procedure as described in Example 1. ¹H NMR (400 MHz, DMSO-d₆) δ 8.65 (s, 1H), 8.06 (dd, J=9.2, 5.4 Hz, 1H), 7.87 (dd, J=10.3, 2.8 Hz, 1H), 7.75 (t, J=8.8 Hz, 1H), 7.66 (d, J=7.8 Hz, 2H), 7.48 (t, J=7.6 Hz, 2H), 7.39 (t, J=7.3 Hz, 1H), 4.07 (s, 1H), 4.02 (s, 1H), 4.00 (s, 1H), 3.96 (s, 1H), 3.91-3.81 (m, 1H), 3.62-3.41 (m, 4H), 2.46-2.35 (m, 4H), 2.27 (d, J=13.2 Hz, 2H), 2.06-1.86 (m, 2H). (OH not shown); LC-MS (Method 2): t$_R$=4.03 min, m/z (M+H)+=471.

Example 328. 1-(3-(2,2-dioxido-2-thia-6-azaspiro[3.3]heptane-6-carbonyl)-6-fluoroquinolin-4-yl)-4-phenylpiperidine-4-carbonitrile, TFA (Cpd. 328)

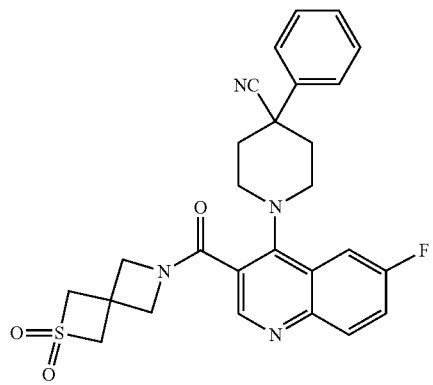

The title compound was prepared following the similar procedure as described in Example 1. ¹H NMR (400 MHz, DMSO-d₆) δ 8.07 (dd, J=9.2, 5.5 Hz, 1H), 7.88 (dd, J=10.3, 2.7 Hz, 1H), 7.75 (td, J=8.7, 2.7 Hz, 1H), 7.66 (d, J=7.7 Hz, 2H), 7.48 (t, J=7.6 Hz, 2H), 7.39 (t, J=7.4 Hz, 1H), 4.52 (d, J=13.5 Hz, 2H), 4.44 (d, J=13.4 Hz, 2H), 4.35 (d, J=5.9 Hz, 4H), 3.60-3.40 (m, 4H), 2.48-2.40 (m, 2H), 2.26 (d, J=13.2 Hz, 2H); LC-MS (Method 2): t$_R$=4.19 min, m/z (M+H)+=505.

Example 329. 1-(6-fluoro-3-(6-hydroxy-2-azaspiro[3.3]heptane-2-carbonyl)quinolin-4-yl)-4-phenylpiperidine-4-carbonitrile, TFA (Cpd. 329)

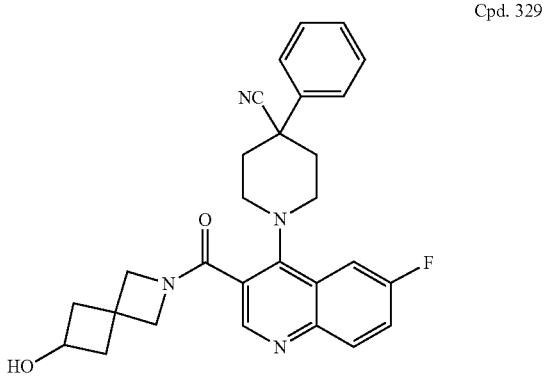 [SMILES: N#CC1(c2ccccc2)CCN(c2c(C(=O)N3CC4(CC(O)C4)C3)cnc3ccc(F)cc23)CC1]

The title compound was prepared following the similar procedure as described in Example 1. $^1$H NMR (400 MHz, DMSO-$d_6$) δ 8.65 (s, 1H), 8.06 (dd, J=9.2, 5.4 Hz, 1H), 7.87 (dd, J=10.3, 2.8 Hz, 1H), 7.75 (t, J=8.8 Hz, 1H), 7.66 (d, J=7.8 Hz, 2H), 7.48 (t, J=7.6 Hz, 2H), 7.39 (t, J=7.3 Hz, 1H), 4.07 (s, 1H), 4.02 (s, 1H), 4.00 (s, 1H), 3.96 (s, 1H), 3.91-3.81 (m, 1H), 3.62-3.41 (m, 4H), 2.46-2.35 (m, 4H), 2.27 (d, J=13.2 Hz, 2H), 2.06-1.86 (m, 2H). (OH not shown); LC-MS (Method 2): $t_R$=4.03 min, m/z (M+H)+=471.

Example 330. 4-(4-cyano-4-phenylpiperidin-1-yl)-6-fluoro-N-((1R,3R)-3-hydroxycyclobutyl)quinoline-3-carboxamide, TFA (Cpd. 330)

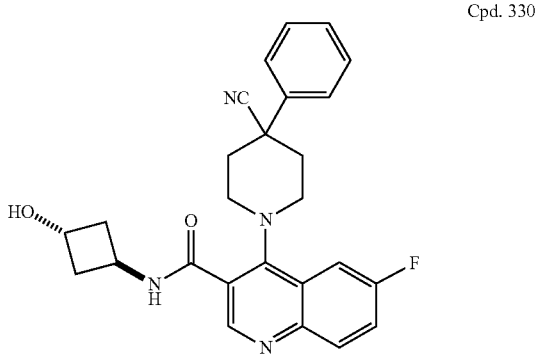

The title compound was prepared following the similar procedure as described in Example 1. $^1$H NMR (400 MHz, DMSO-$d_6$) δ 8.65 (s, 1H), 8.06 (dd, J=9.2, 5.4 Hz, 1H), 7.87 (dd, J=10.3, 2.8 Hz, 1H), 7.75 (t, J=8.8 Hz, 1H), 7.66 (d, J=7.8 Hz, 2H), 7.48 (t, J=7.6 Hz, 2H), 7.39 (t, J=7.3 Hz, 1H), 4.07 (s, 1H), 4.02 (s, 1H), 4.00 (s, 1H), 3.96 (s, 1H), 3.91-3.81 (m, 1H), 3.62-3.41 (m, 4H), 2.46-2.35 (m, 4H), 2.27 (d, J=13.2 Hz, 2H), 2.06-1.86 (m, 2H). (OH not shown); LC-MS (Method 2): $t_R$=4.03 min, m/z (M+H)+=471.

Example 331. 1-(6-fluoro-3-(4-hydroxypiperidine-1-carbonyl)quinolin-4-yl)-4-phenylpiperidine-4-carbonitrile, TFA (Cpd. 331)

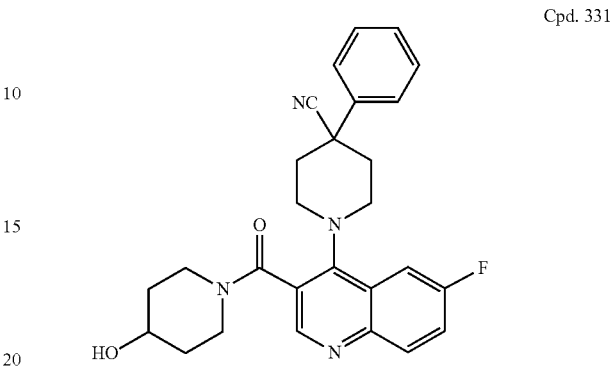

The title compound was prepared following the similar procedure as described in Example 1. $^1$H NMR (400 MHz, DMSO-$d_6$) δ 8.62 (s, 1H), 8.07 (ddd, J=8.4, 5.4, 2.4 Hz, 1H), 7.90 (dt, J=10.3, 3.4 Hz, 1H), 7.75 (td, J=8.7, 2.7 Hz, 1H), 7.66 (dt, J=7.4, 2.9 Hz, 2H), 7.47 (t, J=7.6 Hz, 2H), 7.39 (t, J=7.3 Hz, 1H), 4.21-3.01 (m, 9H), 2.59-2.16 (m, 4H), 1.94-1.62 (m, 2H), 1.59-1.27 (m, 2H). (OH not shown); LC-MS (Method 2): $t_R$=4.01 min, m/z (M+H)+=459.

Example 332. 1-(4-(3-(2,2-dioxido-2-thia-6-azaspiro[3.3]heptane-6-carbonyl)-6-fluoroquinolin-4-yl)phenyl)cyclopropane-1-carbonitrile, TFA (Cpd. 332)

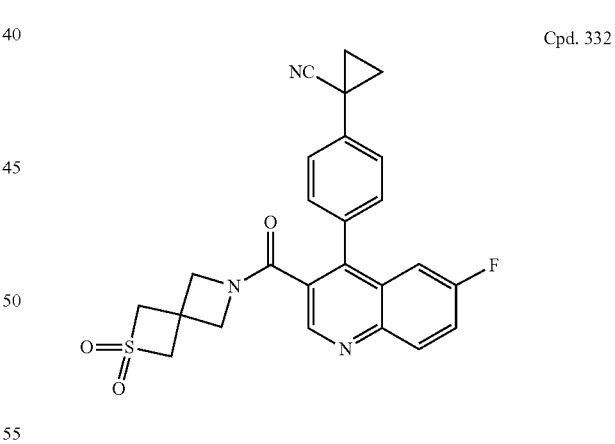

The title compound was prepared following the similar procedure as described in Example 41. $^1$H NMR (400 MHz, DMSO-$d_6$) δ 8.88 (s, 1H), 8.19 (dd, J=9.3, 5.6 Hz, 1H), 7.77 (td, J=8.7, 2.8 Hz, 1H), 7.49 (d, J=8.4 Hz, 2H), 7.44 (d, J=8.4 Hz, 2H), 7.25 (dd, J=10.2, 2.8 Hz, 1H), 4.34 (d, J=13.7 Hz, 2H), 4.20 (d, J=14.0 Hz, 2H), 4.07 (s, 2H), 3.97 (s, 2H), 1.85-1.82 (m, 2H), 1.65-1.61 (m, 2H); LC-MS (Method 2): $t_R$=4.45 min, m/z (M+H)+=462.

Example 333. 1-(4-(4-(1-cyanocyclopropyl)phenyl)-6-fluoroquinoline-3-carbonyl)-N-methylpiperidine-4-carboxamide, TFA (Cpd. 333)

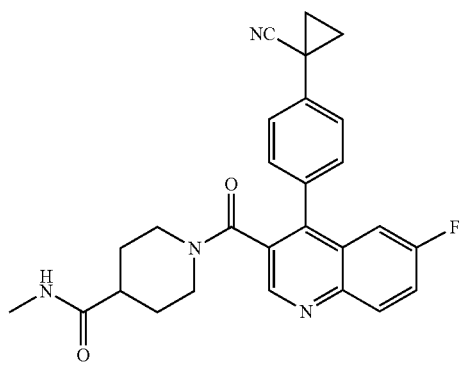

The title compound was prepared following the similar procedure as described in Example 41. LC-MS (Method 2): t$_R$=4.30 min, m/z (M+H)+=457.

Example 334. 1-(4-(6-fluoro-3-(3-hydroxyazetidine-1-carbonyl)quinolin-4-yl)phenyl)cyclopropane-1-carbonitrile, TFA (Cpd. 334)

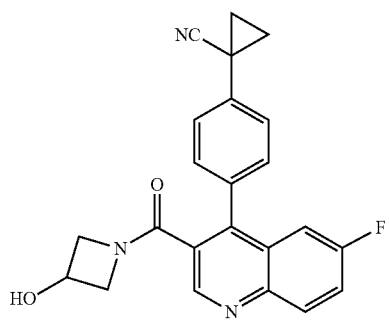

The title compound was prepared following the similar procedure as described in Example 41. $^1$H NMR (400 MHz, DMSO-d$_6$) δ 8.86 (s, 1H), 8.18 (dd, J=9.2, 5.6 Hz, 1H), 7.75 (td, J=8.7, 2.7 Hz, 1H), 7.52-7.46 (m, 2H), 7.43 (d, J=7.9 Hz, 2H), 7.22 (dd, J=10.3, 2.8 Hz, 1H), 4.28 (tt, J=6.7, 4.7 Hz, 1H), 4.01 (dd, J=10.3, 7.0 Hz, 1H), 3.91-3.81 (m, 1H), 3.53 (dd, J=10.5, 4.6 Hz, 1H), 3.43 (dd, J=9.4, 4.6 Hz, 1H), 1.84 (q, J=4.9 Hz, 2H), 1.63 (q, J=4.9 Hz, 2H). (OH not shown); LC-MS (Method 2): t$_R$=4.17 min, m/z (M+H)+=388.

Example 335. 1-(4-(6-fluoro-3-(6-hydroxy-2-azaspiro[3.3]heptane-2-carbonyl)quinolin-4-yl)phenyl)cyclopropane-1-carbonitrile (Cpd. 335)

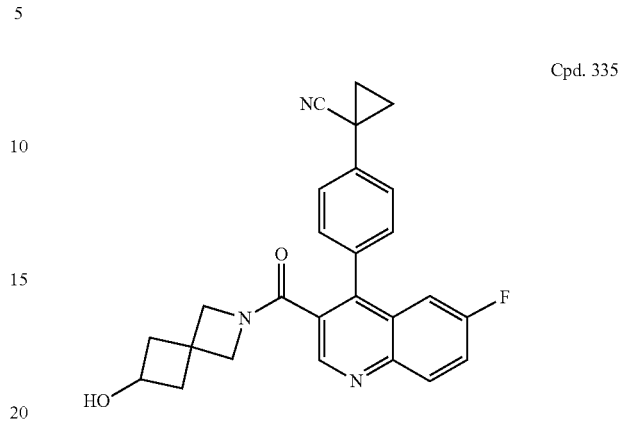

The title compound was prepared following the similar procedure as described in Example 41. $^1$H NMR (400 MHz, DMSO-d$_6$) δ 8.83 (d, J=4.2 Hz, 1H), 8.18 (dd, J=9.3, 5.6 Hz, 1H), 7.82-7.68 (m, 1H), 7.55-7.47 (m, 2H), 7.44 (d, J=8.2 Hz, 2H), 7.33-7.22 (m, 1H), 6.55 (br s, 1H), 4.94 (dd, J=6.2, 3.9 Hz, 1H), 3.73 (s, 1H), 3.69 (s, 1H), 3.58 (s, 1H), 3.52 (s, 1H), 2.23-2.03 (m, 2H), 1.92-1.55 (m, 6H); LC-MS (Method 2): t$_R$=4.29 min, m/z (M+H)+=428.

Example 336. 4-(4-(1-cyanocyclopropyl)phenyl)-6-fluoro-N-((1R,3R)-3-hydroxycyclobutyl)quinoline-3-carboxamide (Cpd. 336)

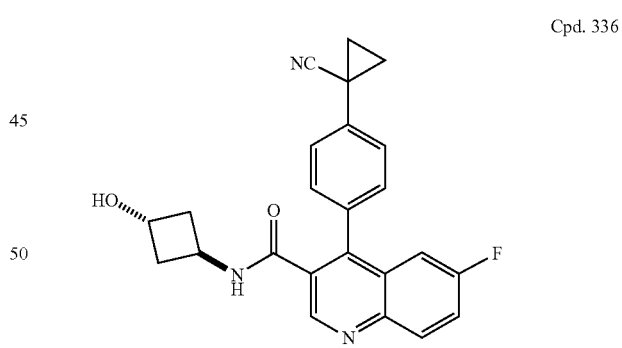

The title compound was prepared following the similar procedure as described in Example 41. $^1$H NMR (400 MHz, DMSO-d$_6$) δ 8.86 (s, 1H), 8.37 (d, J=6.9 Hz, 1H), 8.18 (dd, J=9.2, 5.6 Hz, 1H), 7.78-7.67 (m, 1H), 7.51-7.42 (m, 2H), 7.39 (d, J=8.4 Hz, 2H), 7.18 (dd, J=10.2, 2.8 Hz, 1H), 4.90 (d, J=5.8 Hz, 1H), 4.05 (dt, J=11.4, 5.3 Hz, 1H), 3.93 (q, J=6.2 Hz, 1H), 1.95-1.87 (m, 2H), 1.85-1.71 (m, 4H), 1.57 (q, J=5.1 Hz, 2H); LC-MS (Method 2): t$_R$=4.09 min, m/z (M+H)+=402.

Example 337. 4-(4-(1-cyanocyclopropyl)phenyl)-6-fluoro-N-((1R,3R)-3-hydroxycyclobutyl)quinoline-3-carboxamide (Cpd. 337)

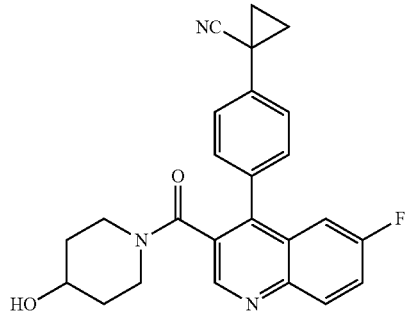

Cpd. 337

The title compound was prepared following the similar procedure as described in Example 41. $^1$H NMR (400 MHz, DMSO-d$_6$) δ 8.81 and 8.78 (two set of s, 1H), 8.24-8.11 (m, 1H), 7.79-7.66 (m, 1H), 7.60-7.32 (m, 4H), 7.29-7.21 (m, 1H), 4.67 and 4.61 (two set of d, J=3.4 Hz, 1H), 3.88-3.44 (m, 2H), 3.24-2.58 (m, 3H), 1.81 (dt, J=7.5, 3.7 Hz, 2H), 1.69-1.53 (m, 2H), 1.52-0.34 (m, 4H). (two rotamers); LC-MS (Method 2): t$_R$=4.27 min, m/z (M+H)+=416.

Example 338. 4-(4-(1-cyanocyclopropyl)phenyl)-6-fluoro-N-((1R,4R)-4-hydroxycyclohexyl)quinoline-3-carboxamide (Cpd. 338)

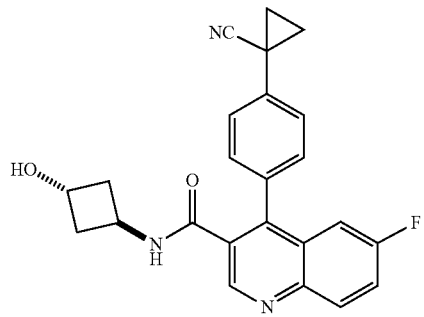

Cpd. 338

The title compound was prepared following the similar procedure as described in Example 41. $^1$H NMR (400 MHz, DMSO-d$_6$) δ 8.83 (s, 1H), 8.18 (dd, J=9.2, 5.6 Hz, 1H), 7.95 (d, J=8.1 Hz, 1H), 7.73 (td, J=8.7, 2.7 Hz, 1H), 7.51-7.42 (m, 2H), 7.41-7.33 (m, 2H), 7.16 (dd, J=10.2, 2.8 Hz, 1H), 4.43 (d, J=4.3 Hz, 1H), 3.43 (d, J=10.2 Hz, 1H), 3.27-3.13 (m, 1H), 1.80 (q, J=5.0 Hz, 2H), 1.65 (d, J=12.4 Hz, 2H), 1.55 (q, J=5.1 Hz, 2H), 1.44 (d, J=12.5 Hz, 2H), 1.15-1.00 (m, 2H), 0.99-0.79 (m, 2H); LC-MS (Method 2): t$_R$=4.26 min, m/z (M+H)+=430.

Example 339. 4-(4-cyano-4-phenylpiperidin-1-yl)-N-(1-(2-(dimethylamino)-2-oxo ethyl)-1H-pyrazol-4-yl)-6-fluoroquinoline-3-carboxamide, TFA (Cpd. 339)

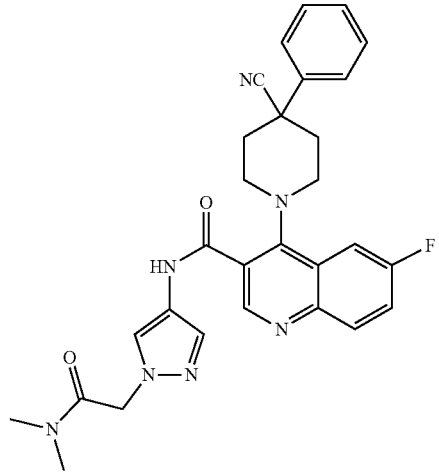

Cpd. 339

The title compound was prepared following the similar procedure as described in Example 1. $^1$H NMR (400 MHz, DMSO-d$_6$) δ 10.77 (s, 1H), 8.75 (s, 1H), 8.08 (dd, J=9.2, 5.5 Hz, 1H), 8.01 (s, 1H), 7.88 (dd, J=10.3, 2.8 Hz, 1H), 7.72 (td, J=8.8, 2.7 Hz, 1H), 7.68-7.59 (m, 2H), 7.54 (s, 1H), 7.45 (t, J=7.6 Hz, 2H), 7.37 (t, J=7.3 Hz, 1H), 5.09 (s, 2H), 3.57-3.52 (m, 4H), 3.00 (s, 3H), 2.83 (s, 3H), 2.64-2.35 (m, 2H), 2.24 (d, J=13.1 Hz, 2H); LC-MS (Method 2): t$_R$=5.66 min, m/z (M+H)+=526.

Example 340. 1-(4-(4-(1-cyanocyclopropyl)phenyl)-6-fluoroquinoline-3-carbonyl)-4-hydroxypiperidine-4-carbonitrile, TFA (Cpd. 340)

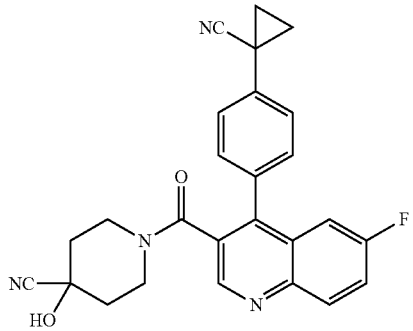

Cpd. 340

The title compound was prepared following the similar procedure as described in Example 41. $^1$H NMR (400 MHz, DMSO-d$_6$) δ 8.88 and 8.83 (two s, 1H), 8.19 (dd, J=9.3, 5.6 Hz, 1H), 7.75 (td, J=8.5, 2.6 Hz, 1H), 7.59-7.20 (m, 5H), 6.65 (s, 1H), 3.64-2.75 (m, 4H), 2.06-1.24 (m, 7H), 0.89 (q, J=10.1, 6.5 Hz, 1H). (two rotamers); LC-MS (Method 2): t$_R$=6.35 min, m/z (M+H)+=441.

Example 341. 1-(3-(4-cyano-4-hydroxypiperidine-1-carbonyl)-6-fluoroquinolin-4-yl)-4-phenylpiperidine-4-carbonitrile, TFA (Cpd. 341)

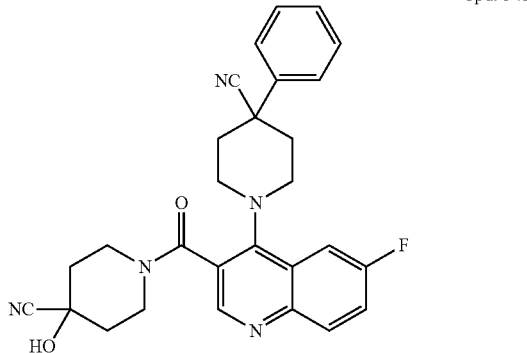

The title compound was prepared following the similar procedure as described in Example 1. $^1$H NMR (400 MHz, DMSO-$d_6$) δ 8.68 and 8.62 (two s, 1H), 8.08-8.04 (m, 1H), 7.87 (dd, J=9.8, 2.7 Hz, 1H), 7.75-7.61 (m, 3H), 7.47 (t, J=7.6 Hz, 2H), 7.38 (t, J=7.3 Hz, 1H), 6.84 and 6.76 (two s, 1H), 4.04-3.17 (m, 8H), 2.38-1.64 (m, 8H). (two rotamers); LC-MS (Method 2): $t_R$=6.04 min, m/z (M+H)+=484.

Example 342. N-(1-(2-amino-2-oxoethyl)-1H-pyrazol-4-yl)-4-(4-(1-cyanocyclopropyl)phenyl)-6-fluoroquinoline-3-carboxamide, TFA (Cpd. 342)

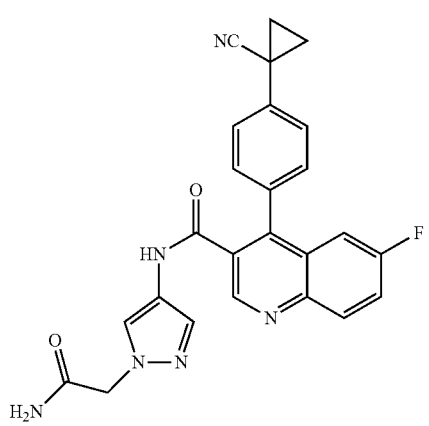

The title compound was prepared following the similar procedure as described in Example 41. $^1$H NMR (400 MHz, DMSO-$d_6$) δ 10.51 (s, 1H), 9.00 (s, 1H), 8.22 (dd, J=9.3, 5.6 Hz, 1H), 7.84 (s, 1H), 7.76 (td, J=8.7, 2.8 Hz, 1H), 7.42 (q, J=8.2 Hz, 6H), 7.34 (s, 1H), 7.20-7.10 (m, 2H), 4.66 (s, 2H), 1.79 (q, J=5.1 Hz, 2H), 1.59 (q, J=5.2 Hz, 2H); LC-MS (Method 2): $t_R$=5.66 min, m/z (M+H)+=455.

Example 343. 4-(4-(1-cyanocyclopropyl)phenyl)-6-fluoro-N-(1-(2-hydroxyethyl)-1H-pyrazol-4-yl)quinoline-3-carboxamide, TFA (Cpd. 343)

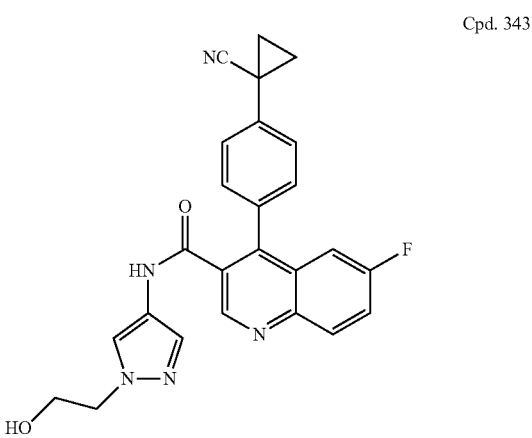 [SMILES: N#CC1(c2ccc(-c3c(C(=O)Nc4cnn(CCO)c4)cnc4ccc(F)cc34)cc2)CC1]

The title compound was prepared following the similar procedure as described in Example 41. $^1$H NMR (400 MHz, DMSO-$d_6$) δ 10.46 (s, 1H), 8.99 (s, 1H), 8.21 (dd, J=9.3, 5.6 Hz, 1H), 7.82 (s, 1H), 7.76 (td, J=8.8, 2.8 Hz, 1H), 7.43 (d, J=8.3 Hz, 2H), 7.40 (d, J=8.2 Hz, 2H), 7.32 (s, 1H), 7.14 (dd, J=10.2, 2.8 Hz, 1H), 4.04 (t, J=5.6 Hz, 2H), 3.65 (t, J=5.6 Hz, 2H), 1.79 (q, J=5.1 Hz, 2H), 1.58 (q, J=5.2 Hz, 2H). (OH not shown); LC-MS (Method 2): $t_R$=5.78 min, m/z (M+H)+=442.

Example 344. 4-(4-(1-cyanocyclopropyl)phenyl)-N-(1-(2-(cyclopropylamino)-2-oxoethyl)-1H-pyrazol-4-yl)-6-fluoroquinoline-3-carboxamide, TFA (Cpd. 344)

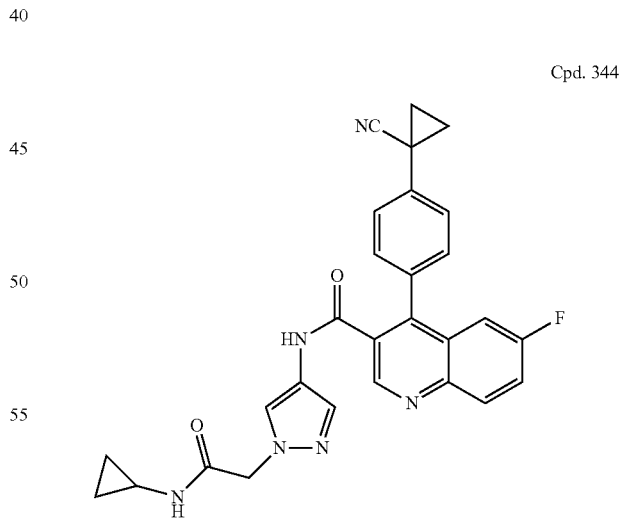

The title compound was prepared following the similar procedure as described in Example 41. $^1$H NMR (400 MHz, DMSO-$d_6$) δ 10.51 (s, 1H), 9.01 (s, 1H), 8.22 (dd, J=9.3, 5.6 Hz, 1H), 8.17 (d, J=4.2 Hz, 1H), 7.83 (s, 1H), 7.76 (td, J=8.8, 2.8 Hz, 1H), 7.44 (d, J=8.3 Hz, 2H), 7.40 (d, J=8.3 Hz, 2H), 7.33 (s, 1H), 7.14 (dd, J=10.2, 2.8 Hz, 1H), 4.61 (s, 2H), 2.60 (dq, J=7.3, 3.7 Hz, 1H), 1.79 (q, J=5.1 Hz, 2H), 1.59 (q, J=5.2 Hz, 2H), 0.60 (td, J=7.0, 4.9 Hz, 2H), 0.42-0.34 (m, 2H); LC-MS (Method 2): t$_R$=4.47 min, m/z (M+H)+=495.

Example 345. 4-(4-cyano-4-phenylpiperidin-1-yl)-6-fluoro-N-(1-(2-hydroxyethyl)-1H-pyrazol-4-yl)quinoline-3-carboxamide, TFA (Cpd. 345)

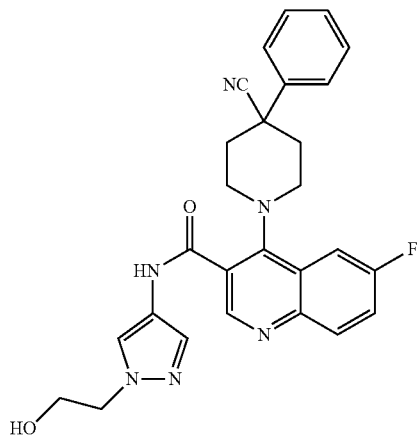

Cpd. 345

The title compound was prepared following the similar procedure as described in Example 1. $^1$H NMR (400 MHz, DMSO-d$_6$) δδ 10.76 (s, 1H), 8.78 (s, 1H), 8.09 (dd, J=9.2, 5.5 Hz, 1H), 8.05 (s, 1H), 7.90 (dd, J=10.3, 2.8 Hz, 1H), 7.76 (td, J=8.6, 2.7 Hz, 1H), 7.66-7.58 (m, 2H), 7.55 (s, 1H), 7.45 (t, J=7.6 Hz, 2H), 7.37 (dd, J=8.3, 6.3 Hz, 1H), 4.12 (t, J=5.6 Hz, 2H), 3.71 (t, J=5.6 Hz, 2H), 3.56 (d, J=8.0 Hz, 4H), 2.44-2.35 (m, 2H), 2.24 (d, J=13.1 Hz, 2H). (OH not shown); LC-MS (Method 2): t$_R$=4.03 min, m/z (M+H)+=485.

Example 346. 4-(4-(1-cyanocyclopropyl)phenyl)-N-(1-(2-(dimethylamino)-2-oxoethyl)-1H-pyrazol-4-yl)-6-fluoroquinoline-3-carboxamide, TFA (Cpd. 346)

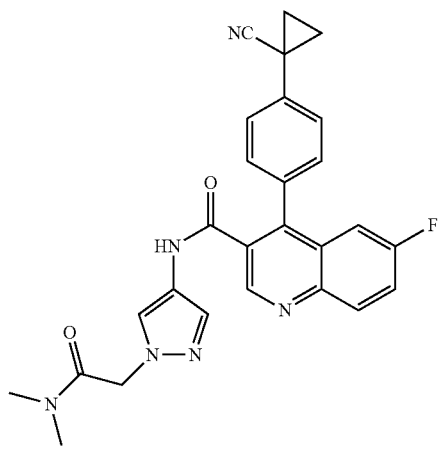

Cpd. 346

The title compound was prepared following the similar procedure as described in Example 41. $^1$H NMR (400 MHz, DMSO-d$_6$) δ 10.50 (s, 1H), 9.01 (s, 1H), 8.22 (dd, J=9.3, 5.6 Hz, 1H), 7.77 (d, J=3.8 Hz, 2H), 7.44 (d, J=8.4 Hz, 2H), 7.40 (d, J=8.3 Hz, 2H), 7.32 (s, 1H), 7.14 (dd, J=10.2, 2.8 Hz, 1H), 5.00 (s, 2H), 2.96 (s, 3H), 2.80 (s, 3H), 1.79 (q, J=5.0 Hz, 2H), 1.59 (q, J=5.2 Hz, 2H); LC-MS (Method 2): t$_R$=4.38 min, m/z (M+H)+=483.

Example 347. 4-(4-cyano-4-phenylpiperidin-1-yl)-N-(1-(2-(cyclopropylamino)-2-oxoethyl)-1H-pyrazol-4-yl)-6-fluoroquinoline-3-carboxamide (Cpd. 347)

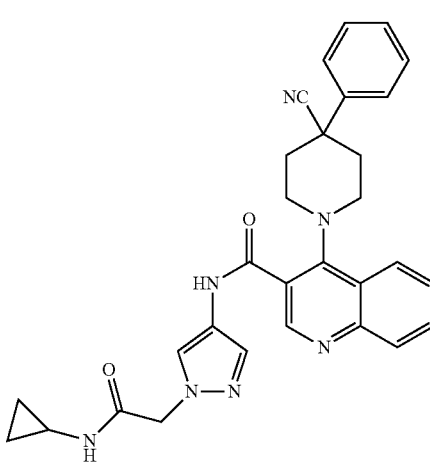

Cpd. 347

The title compound was prepared following the similar procedure as described in Example 1. $^1$H NMR (400 MHz, DMSO-d$_6$) δ δ 10.75 (s, 1H), 8.70 (s, 1H), 8.21 (d, J=4.1 Hz, 1H), 8.12-8.01 (m, 2H), 7.86 (dd, J=10.4, 2.8 Hz, 1H), 7.74-7.60 (m, 3H), 7.55 (s, 1H), 7.45 (t, J=7.6 Hz, 2H), 7.37 (t, J=7.3 Hz, 1H), 4.70 (s, 2H), 3.58-3.40 (m, 4H), 2.63 (dq, J=7.2, 3.8 Hz, 1H), 2.40 (td, J=12.2, 4.1 Hz, 2H), 2.22 (d, J=13.1 Hz, 2H), 0.61 (dt, J=6.9, 3.3 Hz, 2H), 0.46-0.34 (m, 2H); LC-MS (Method 2): t$_R$=4.17 min, m/z (M+H)+=538.

Example 348. 1-(3-(4-cyclopropyl-4-hydroxypiperidine-1-carbonyl)-6-fluoroquinolin-4-yl)-4-phenylpiperidine-4-carbonitrile (Cpd. 348)

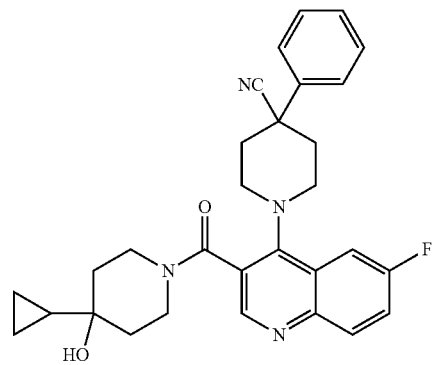

Cpd. 348

The title compound was prepared following the similar procedure as described in Example 1. $^1$H NMR (400 MHz, DMSO-d$_6$) δ 8.56 and 8.48 (two s, 1H), 8.07-8.02 (m, 1H), 7.89-7.77 (m, 1H), 7.68-7.63 (m, 3H), 7.47 (t, J=7.6 Hz, 2H), 7.38 (t, J=7.3 Hz, 1H), 4.48-4.29 (m, 1H), 4.02 (d, J=1.9 Hz, 1H), 3.69-3.00 (m, 7H), 2.46-2.13 (m, 4H), 1.64-1.55 (m, 3H), 1.38 (t, J=14.6 Hz, 1H), 0.86 (t, J=7.3 Hz, 1H), 0.36-0.21 (m, 2H), 0.25-0.11 (m, 2H). (two rotamers); LC-MS (Method 2): t$_R$=4.62 min, m/z (M+H)+=499.

Example 349. 1-(6-fluoro-3-(4-hydroxy-4-methylpiperidine-1-carbonyl)quinolin-4-yl)-4-phenylpiperidine-4-carbonitrile (Cpd. 349)

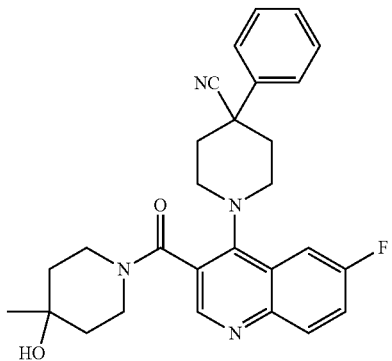

Cpd. 349

The title compound was prepared following the similar procedure as described in Example 1. $^1$H NMR (400 MHz, DMSO-d$_6$) δ 8.53 and 8.46 (two s, 1H), 8.06-8.02 (m, 1H), 7.86-7.81 (m, 1H), 7.71-7.61 (m, 3H), 7.47 (t, J=7.6 Hz, 2H), 7.38 (t, J=7.3 Hz, 1H), 4.44 and 4.40 (two s, 1H), 4.32-4.12 (m, 1H), 3.60-3.57 (m, 1H), 3.54-3.16 (m, 6H), 2.45-2.10 (m, 4H), 1.70-1.27 (m, 4H), 1.16 and 1.14 (two s, 3H). (two rotamers); LC-MS (Method 2): t$_R$=4.26 min, m/z (M+H)+=473.

Example 350. 1-(4-(6-fluoro-3-(4-hydroxy-4-methylpiperidine-1-carbonyl)quinolin-4-yl)phenyl)cyclopropane-1-carbonitrile (Cpd. 350)

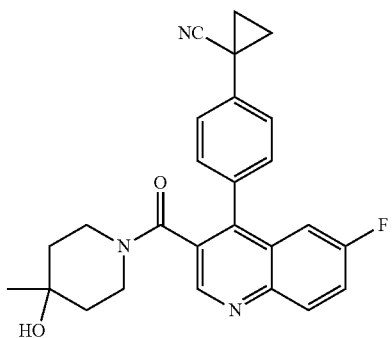

Cpd. 350

The title compound was prepared following the similar procedure as described in Example 41. $^1$H NMR (400 MHz, DMSO-d$_6$) δ 8.83 and 8.77 (two s, 1H), 8.18 (dd, J=9.3, 5.6 Hz, 1H), 7.74 (t, J=8.7 Hz, 1H), 7.60-7.15 (m, 5H), 4.28 and 4.24 (two s, 1H), 4.05 and 3.92 (two d, J=12.9 Hz, 1H), 3.17-2.74 (m, 3H), 1.85-1.79 (m, 2H), 1.70-1.24 (m, 4H), 1.14-0.81 (m, 4H), 0.75 and 0.11 (two set of td, J=12.6, 4.5 Hz, 1H). (two rotamers); LC-MS (Method 2): t$_R$=4.55 min, m/z (M+H)+=430.

Example 351. 1-(6-fluoro-3-(4-hydroxy-4-(hydroxymethyl)piperidine-1-carbonyl)quinolin-4-yl)-4-phenylpiperidine-4-carbonitrile (Cpd. 351)

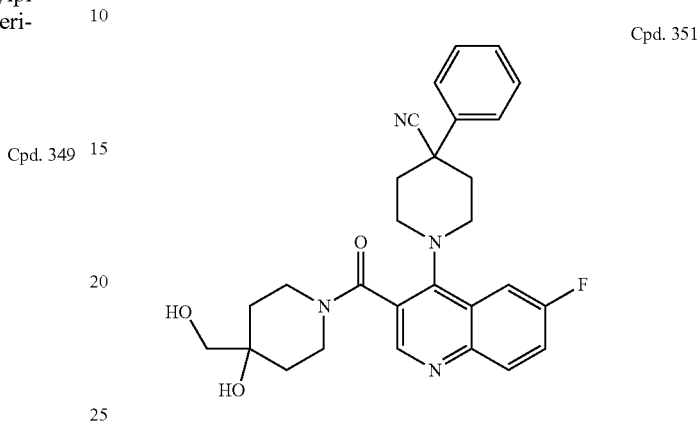

Cpd. 351

The title compound was prepared following the similar procedure as described in Example 1. $^1$H NMR (400 MHz, DMSO-d$_6$) δ 8.50 and 8.49 (two s, 1H), 8.06-8.02 (m, 1H), 7.84 (dd, J=10.3, 2.8 Hz, 1H), 7.71-7.61 (m, 3H), 7.47 (t, J=7.6 Hz, 2H), 7.38 (t, J=7.3 Hz, 1H), 4.60 and 4.55 (two t, J=5.8 Hz, 1H), 4.41-4.31 (m, 2H), 3.66-3.04 (m, 9H), 2.44-2.13 (m, 4H), 1.71-1.23 (m, 4H). (two rotamers); LC-MS (Method 2): t$_R$=3.95 min, m/z (M+H)+=489.

Example 352. N-(1-(2-amino-2-oxoethyl)-1H-pyrazol-4-yl)-4-(4-cyano-4-phenylpiperidin-1-yl)-6-fluoroquinoline-3-carboxamide (Cpd. 352)

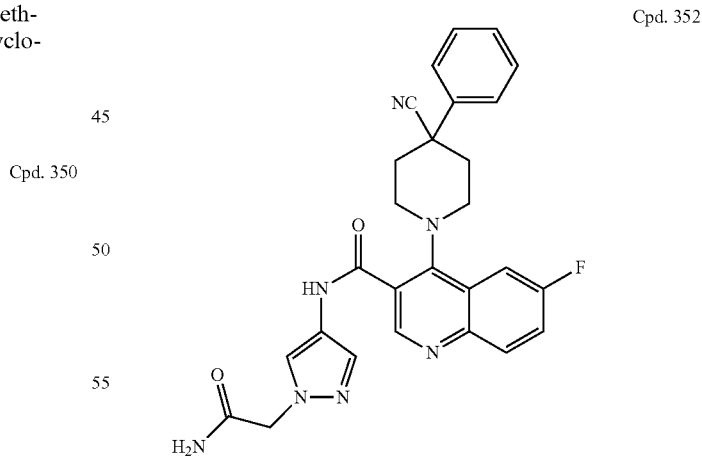

Cpd. 352

The title compound was prepared following the similar procedure as described in Example 1. $^1$H NMR (400 MHz, DMSO-d$_6$) δ 10.75 (s, 1H), 8.69 (s, 1H), 8.07 (q, J=4.8, 4.1 Hz, 2H), 7.86 (dd, J=10.3, 2.8 Hz, 1H), 7.74-7.59 (m, 3H), 7.56 (s, 1H), 7.47-7.42 (m, 2H), 7.40-7.32 (m, 1H), 7.21 (s, 1H), 4.74 (s, 2H), 3.59-3.39 (m, 4H), 2.44-2.33 (m, 2H), 2.22 (d, J=13.1 Hz, 2H); LC-MS (Method 2): t$_R$=3.92 min, m/z (M+H)+=498.

Example 353. 1-(4-(3-(4-cyclopropyl-4-hydroxypiperidine-1-carbonyl)-6-fluoroquinolin-4-yl)phenyl)cyclopropane-1-carbonitrile (Cpd. 353)

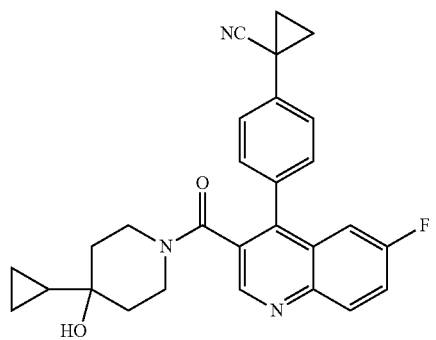

Cpd. 353

The title compound was prepared following the similar procedure as described in Example 41. $^1$H NMR (400 MHz, DMSO-$d_6$) δ 8.86 and 8.77 (two s, 1H), 8.18 (dd, J=9.3, 5.9 Hz, 1H), 7.79-7.67 (m, 1H), 7.59-7.15 (m, 5H), 4.18 and 4.09 (two d, J=13.0 Hz, 1H), 3.90 and 3.87 (two s 1H), 3.17-2.54 (m, 3H), 1.82 (d, J=2.7 Hz, 2H), 1.66-0.20 (m, 7H), 0.15-0.07 (m, 4H). (two rotamers); LC-MS (Method 2): $t_R$=4.92 min, m/z (M+H)+=456.

Example 354. 1-(4-(6-fluoro-3-(4-hydroxy-4-(hydroxymethyl)piperidine-1-carbonyl)quinolin-4-yl)phenyl)cyclopropane-1-carbonitrile (Cpd. 354)

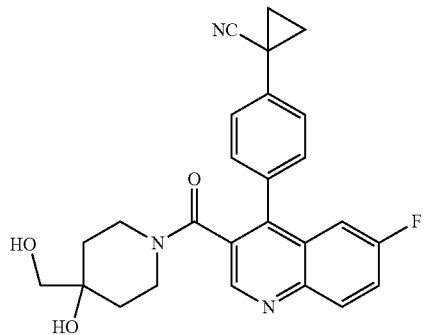

Cpd. 354

The title compound was prepared following the similar procedure as described in Example 41. $^1$H NMR (400 MHz, DMSO-$d_6$) δ 8.81 and 8.78 (two s, 1H), 8.18 (dd, J=9.2, 5.9 Hz, 1H), 7.78-7.69 (m, 1H), 7.56-7.14 (m, 5H), 4.54 and 4.43 (two t, J=5.8 Hz, 1H), 4.23-4.00 (m, 2H), 3.19-2.58 (m, 5H), 1.87-1.74 (m, 2H), 1.66-0.91 (m, 5H), 0.81 and 0.33 (two dt, J=12.0, 4.0 Hz, 1H). (two rotamers); LC-MS (Method 2): $t_R$=4.13 min, m/z (M+H)+=446.

Example 355. 4-(4-(1-cyanocyclopropyl)phenyl)-6-fluoro-N-(1-(2-(methylamino)-2-oxoethyl)-1H-pyrazol-4-yl)quinoline-3-carboxamide, TFA (Cpd. 355)

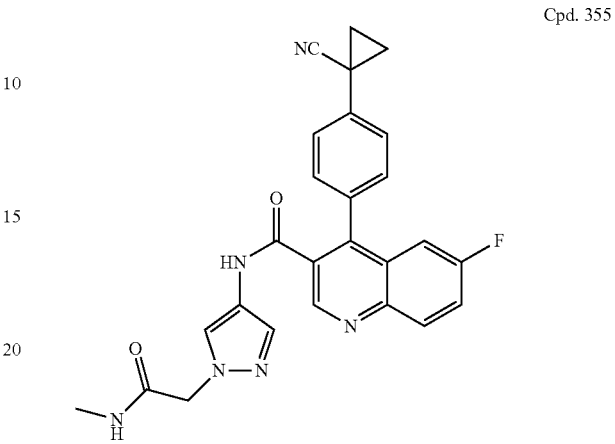

Cpd. 355

The title compound was prepared following the similar procedure as described in Example 41. $^1$H NMR (400 MHz, DMSO-$d_6$) δ 10.52 (s, 1H), 9.00 (s, 1H), 8.22 (dd, J=9.3, 5.6 Hz, 1H), 7.91 (q, J=4.7 Hz, 1H), 7.85 (s, 1H), 7.77 (td, J=8.7, 2.8 Hz, 1H), 7.44 (d, J=8.5 Hz, 2H), 7.40 (d, J=8.5 Hz, 2H), 7.35 (s, 1H), 7.14 (dd, J=10.2, 2.8 Hz, 1H), 4.66 (s, 2H), 2.57 (d, J=4.5 Hz, 3H), 1.79 (q, J=5.0, 4.6 Hz, 2H), 1.59 (q, J=5.1 Hz, 2H); LC-MS (Method 2): $t_R$=4.30 min, m/z (M+H)+=469.

Example 356. 1-(6-fluoro-3-(4-(methylsulfonyl)piperazine-1-carbonyl)quinolin-4-yl)-4-(thiophen-2-yl)piperidine-4-carbonitrile, TFA (Cpd. 356)

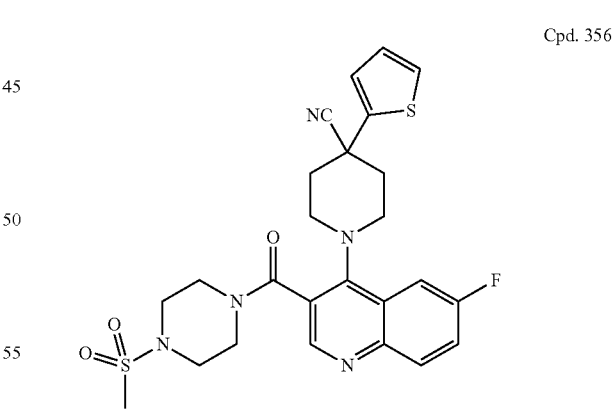

Cpd. 356

The title compound was prepared following the similar procedure as described in Example 1. $^1$H NMR (400 MHz, DMSO-$d_6$) δ 8.64 (s, 1H), 8.07 (dd, J=9.2, 5.5 Hz, 1H), 7.84 (dd, J=10.3, 2.8 Hz, 1H), 7.73 (td, J=8.7, 2.8 Hz, 1H), 7.61 (dd, J=5.1, 1.3 Hz, 1H), 7.32 (dd, J=3.7, 1.4 Hz, 1H), 7.10 (dd, J=5.2, 3.5 Hz, 1H), 3.91-3.01 (m, 12H), 2.90 (s, 3H), 2.57-2.23 (m, 4H); LC-MS (Method 2): $t_R$=4.42 min, m/z (M+H)+=528.

Example 357. (z)-3-cyclopropyl-2-(4-(6-fluoro-3-(4-(methylsulfonyl)piperazine-1-carbonyl)quinolin-4-yl)phenyl)acrylonitrile (Cpd. 357)

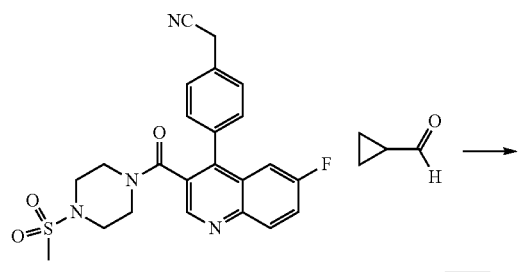

Cpd. 212

Cpd. 357

To a mixture of 2-(4-(6-fluoro-3-(4-(methylsulfonyl)piperazine-1-carbonyl)quinolin-4-yl)phenyl)acetonitrile (91 mg, 0.2 mmol) and $K_2CO_3$ (111 mg, 0.80 mmol) was added DMF (1 ml) and then cyclopropanecarbaldehyde (28.0 mg, 0.40 mmol). The mixture was sealed and heated at 80° C. for 3 hr. After cooling to rt, the mixture was concentrated and the residue was poured into $EtOAc/H_2O$ (5 mL/5 mL). The aqueous layer was extracted with EtOAc (5 mL×3). The combined organic layer was dried ($Na_2SO_4$) and filtered. After removal of solvent the product was purified by silica gel chromatography using 0-10% $MeOH/CH_2Cl_2$ as the eluent to give (Z)-3-cyclopropyl-2-(4-(6-fluoro-3-(4-(methylsulfonyl)piperazine-1-carbonyl)quinolin-4-yl)phenyl)acrylonitrile (48 mg, 0.095 mmol, 47.6% yield). $^1$H NMR (400 MHz, DMSO-$d_6$) δ 8.86 (s, 1H), 8.21 (dd, J=9.2, 5.6 Hz, 1H), 7.82-7.72 (m, 2H), 7.70 (d, J=8.0 Hz, 1H), 7.56 (d, J=8.2 Hz, 1H), 7.42 (d, J=8.1 Hz, 1H), 7.31 (dd, J=10.2, 2.8 Hz, 1H), 6.86 (d, J=10.7 Hz, 1H), 3.60-3.40 (m, 2H), 3.25-2.87 (m, 4H), 2.71 (s, 3H), 2.58 (br s, 1H), 2.13 (br s, 1H), 2.01-1.95 (m, 1H), 1.15 (dd, J=7.9, 2.9 Hz, 2H), 0.89 (p, J=3.5 Hz, 2H); LC-MS (Method 2): $t_R$=5.28 min, m/z (M+H)+=505.

TABLE 1

| Cpd. ID | Structure | Compound name |
|---|---|---|
| 1 | 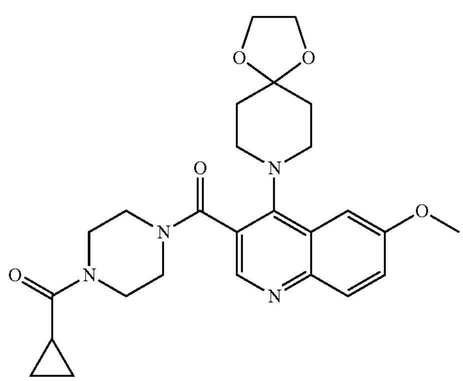 [SMILES: COc1ccc2ncc(C(=O)N3CCN(C(=O)C4CC4)CC3)c(N3CCC4(CC3)OCCO4)c2c1] | (4-(cyclopropanecarbonyl)piperazin-1-yl)(6-methoxy-4-(1,4-dioxa-8-azaspiro[4.5]decan-8-yl)quinolin-3-yl)methanone, TFA |
| 2 | 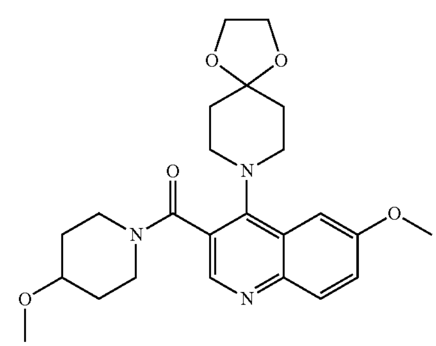 [SMILES: COc1ccc2ncc(C(=O)N3CCC(OC)CC3)c(N3CCC4(CC3)OCCO4)c2c1] | (6-methoxy-4-(1,4-dioxa-8-azaspiro[4.5]decan-8-yl)quinolin-3-yl)(4-methoxypiperidin-1-yl)methanone, TFA |

TABLE 1-continued

| Cpd. ID | Structure | Compound name |
| --- | --- | --- |
| 3 | 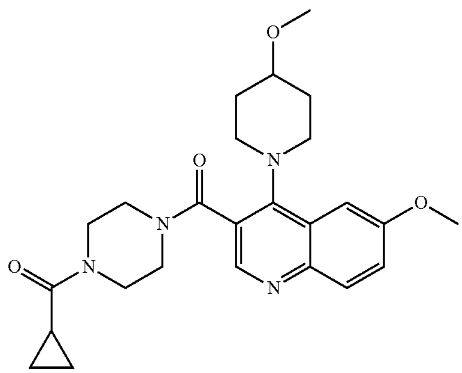 [SMILES: COc1ccc2ncc(C(=O)N3CCN(C(=O)C4CC4)CC3)c(N3CCC(OC)CC3)c2c1] | (4-(cyclopropanecarbonyl)piperazin-1-yl)(6-methoxy-4-(4-methoxypiperidin-1-yl)quinolin-3-yl)methanone, TFA |
| 4 | 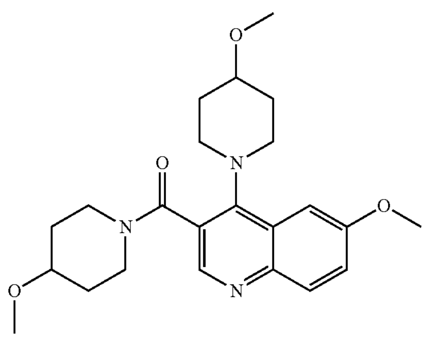 [SMILES: COc1ccc2ncc(C(=O)N3CCC(OC)CC3)c(N3CCC(OC)CC3)c2c1] | (6-methoxy-4-(4-methoxypiperidin-1-yl)quinolin-3-yl)(4-methoxypiperidin-1-yl)methanone, TFA |
| 5 | 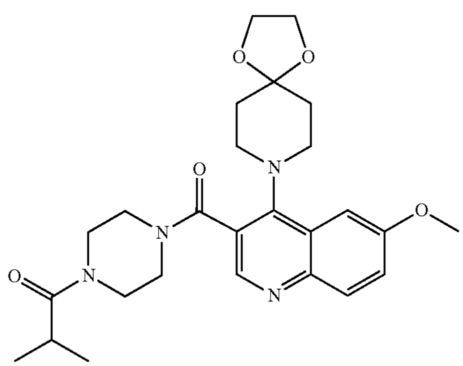 [SMILES: COc1ccc2ncc(C(=O)N3CCN(C(=O)C(C)C)CC3)c(N3CCC4(CC3)OCCO4)c2c1] | 1-(4-(6-methoxy-4-(1,4-dioxa-8-azaspiro[4.5]decan-8-yl)quinoline-3-carbonyl)piperazin-1-yl)-2-methylpropan-1-one, TFA |
| 6 | 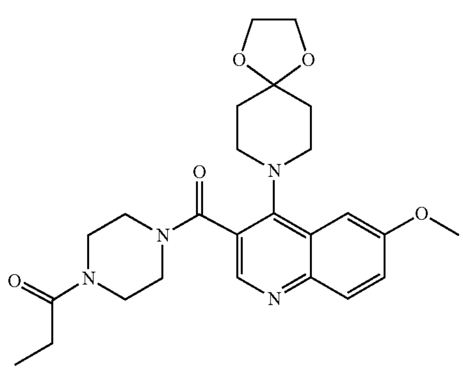 [SMILES: CCC(=O)N1CCN(C(=O)c2cnc3ccc(OC)cc3c2N2CCC3(CC2)OCCO3)CC1] | 1-(4-(6-methoxy-4-(1,4-dioxa-8-azaspiro[4.5]decan-8-yl)quinoline-3-carbonyl)piperazin-1-yl)propan-1-one, TFA |

TABLE 1-continued

| Cpd. ID | Structure | Compound name |
|---|---|---|
| 7 | 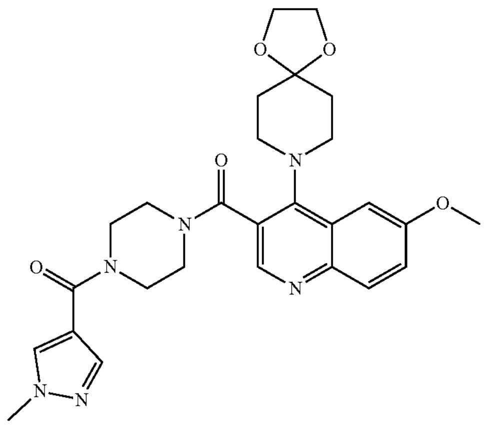 | (6-methoxy-4-(1,4-dioxa-8-azaspiro[4.5]decan-8-yl)quinolin-3-yl)(4-(1-methyl-1H-pyrazole-4-carbonyl)piperazin-1-yl)methanone, TFA |
| 8 | 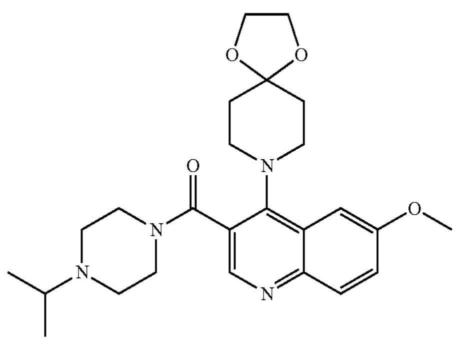 [SMILES: COc1ccc2ncc(C(=O)N3CCN(C(C)C)CC3)c(N3CCC4(CC3)OCCO4)c2c1] | (4-isopropylpiperazin-1-yl)(6-methoxy-4-(1,4-dioxa-8-azaspiro[4.5]decan-8-yl)quinolin-3-yl)methanone, TFA |
| 9 | 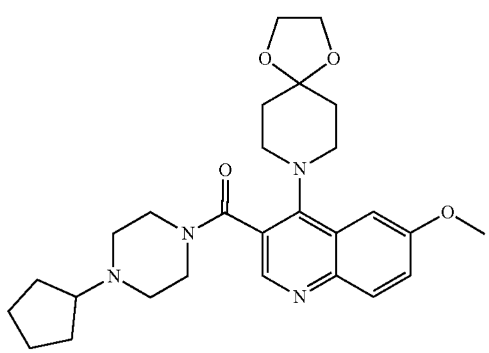 [SMILES: COc1ccc2ncc(C(=O)N3CCN(C4CCCC4)CC3)c(N3CCC4(CC3)OCCO4)c2c1] | (4-cyclopentylpiperazin-1-yl)(6-methoxy-4-(1,4-dioxa-8-azaspiro[4.5]decan-8-yl)quinolin-3-yl)methanone, TFA |
| 10 | 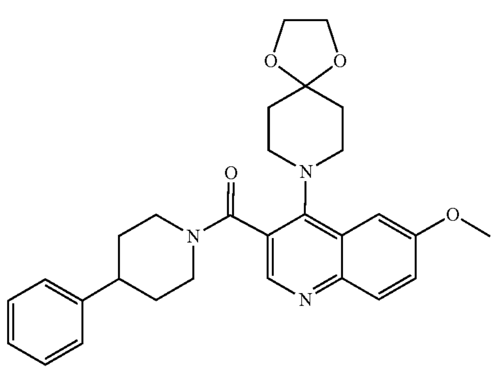 [SMILES: COc1ccc2ncc(C(=O)N3CCC(c4ccccc4)CC3)c(N3CCC4(CC3)OCCO4)c2c1] | (6-methoxy-4-(1,4-dioxa-8-azaspiro[4.5]decan-8-yl)quinolin-3-yl)(4-phenylpiperidin-1-yl)methanone, TFA |

TABLE 1-continued

| Cpd. ID | Structure | Compound name |
| --- | --- | --- |
| 11 | 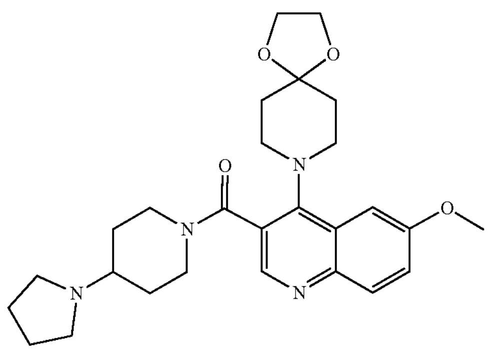 [SMILES: COc1ccc2ncc(C(=O)N3CCC(N4CCCC4)CC3)c(N3CCC4(CC3)OCCO4)c2c1] | (6-methoxy-4-(1,4-dioxa-8-azaspiro[4.5]decan-8-yl)quinolin-3-yl)(4-(pyrrolidin-1-yl)piperidin-1-yl)methanone, TFA |
| 12 | 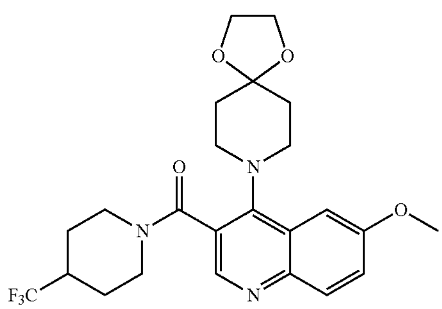 [SMILES: COc1ccc2ncc(C(=O)N3CCC(C(F)(F)F)CC3)c(N3CCC4(CC3)OCCO4)c2c1] | (6-methoxy-4-(1,4-dioxa-8-azaspiro[4.5]decan-8-yl)quinolin-3-yl)(4-(trifluoromethyl)piperidin-1-yl)methanone, TFA |
| 13 | 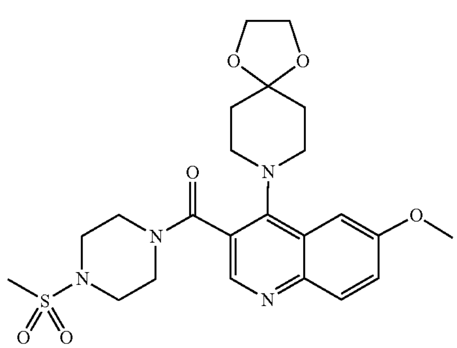 | (6-methoxy-4-(1,4-dioxa-8-azaspiro[4.5]decan-8-yl)quinolin-3-yl)(4-(methylsulfonyl)piperazin-1-yl)methanone, TFA |
| 14 | 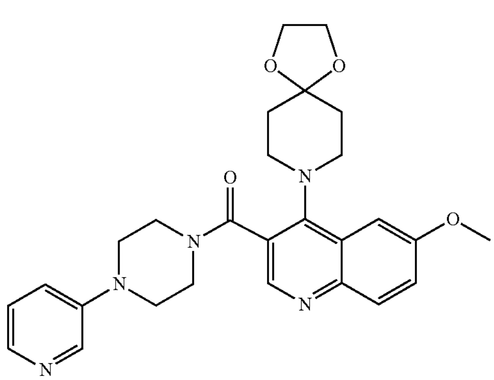 [SMILES: COc1ccc2ncc(C(=O)N3CCN(c4cccnc4)CC3)c(N3CCC4(CC3)OCCO4)c2c1] | (6-methoxy-4-(1,4-dioxa-8-azaspiro[4.5]decan-8-yl)quinolin-3-yl)(4-(pyridin-3-yl)piperazin-1-yl)methanone, TFA |

TABLE 1-continued

| Cpd. ID | Structure | Compound name |
|---|---|---|
| 15 | 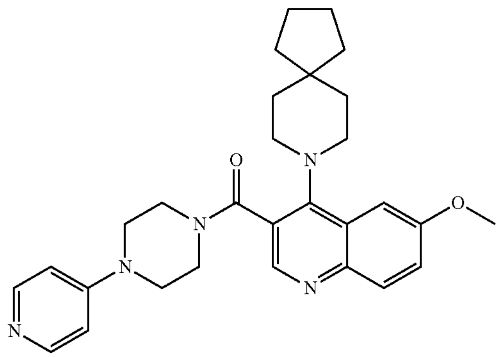 [SMILES: COc1ccc2ncc(C(=O)N3CCN(c4ccncc4)CC3)c(N3CCC4(CCCC4)CC3)c2c1] | (6-methoxy-4-(1,4-dioxa-8-azaspiro[4.5]decan-8-yl)quinolin-3-yl)(4-(pyridin-4-yl)piperazin-1-yl)methanone, TFA |
| 16 | 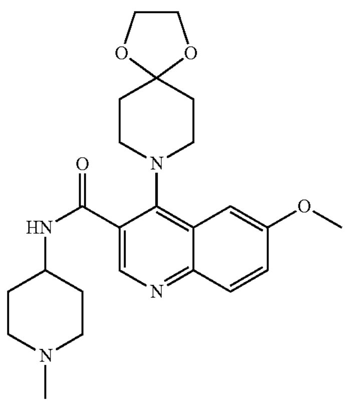 [SMILES: COc1ccc2ncc(C(=O)NC3CCN(C)CC3)c(N3CCC4(CC3)OCCO4)c2c1] | 6-methoxy-N-(1-methylpiperidin-4-yl)-4-(1,4-dioxa-8-azaspiro[4.5]decan-8-yl)quinoline-3-carboxamide, TFA |
| 17 | 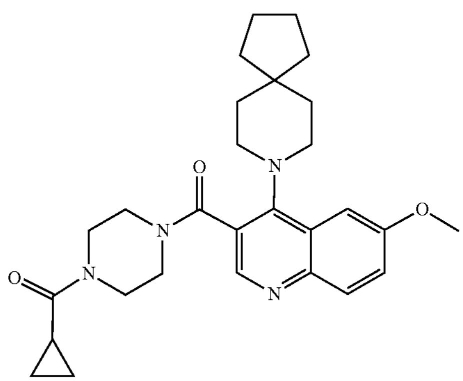 [SMILES: COc1ccc2ncc(C(=O)N3CCN(C(=O)C4CC4)CC3)c(N3CCC4(CCCC4)CC3)c2c1] | (4-(cyclopropanecarbonyl)piperazin-1-yl)(6-methoxy-4-(8-azaspiro[4.5]decan-8-yl)quinolin-3-yl)methanone, TFA |
| 18 | 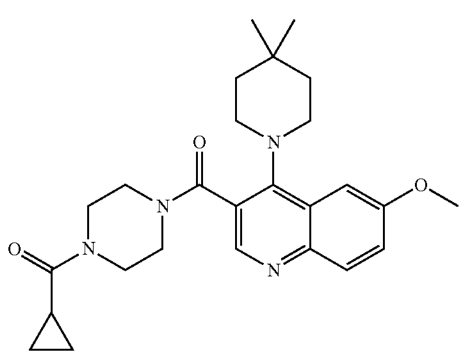 [SMILES: COc1ccc2ncc(C(=O)N3CCN(C(=O)C4CC4)CC3)c(N3CCC(C)(C)CC3)c2c1] | (4-(cyclopropanecarbonyl)piperazin-1-yl)(4-(4,4-dimethylpiperidin-1-yl)-6-methoxyquinolin-3-yl)methanone, TFA |

TABLE 1-continued

| Cpd. ID | Structure | Compound name |
|---|---|---|
| 19 | 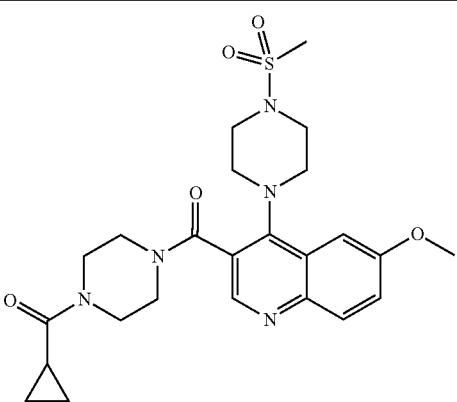 | (4-(cyclopropanecarbonyl)piperazin-1-yl)(6-methoxy-4-(4-(methylsulfonyl)piperazin-1-yl)quinolin-3-yl)methanone, TFA |
| 20 | 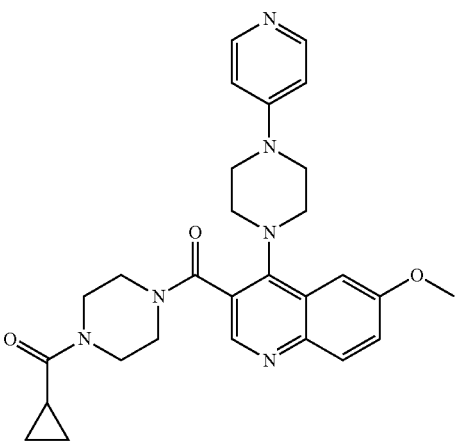 [SMILES: COc1ccc2ncc(C(=O)N3CCN(C(=O)C4CC4)CC3)c(N3CCN(c4ccncc4)CC3)c2c1] | (4-(cyclopropanecarbonyl)piperazin-1-yl)(6-methoxy-4-(4-(pyridin-4-yl)piperazin-1-yl)quinolin-3-yl)methanone, TFA |
| 21 | 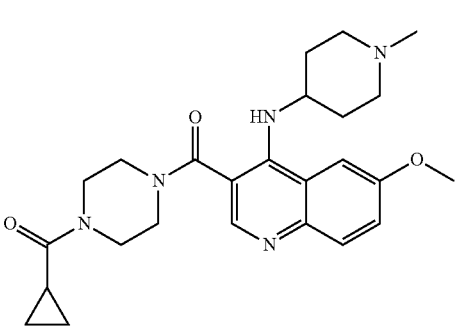 [SMILES: COc1ccc2ncc(C(=O)N3CCN(C(=O)C4CC4)CC3)c(NC3CCN(C)CC3)c2c1] | (4-(cyclopropanecarbonyl)piperazin-1-yl)(6-methoxy-4-((1-methylpiperidin-4-yl)amino)quinolin-3-yl)methanone, TFA |
| 22 | 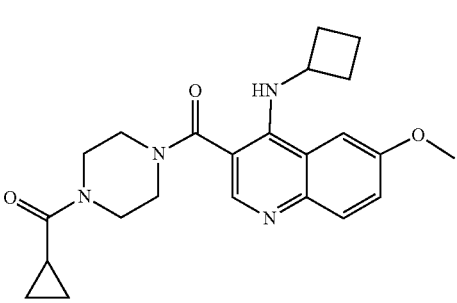 [SMILES: COc1ccc2ncc(C(=O)N3CCN(C(=O)C4CC4)CC3)c(NC3CCC3)c2c1] | (4-(cyclobutylamino)-6-methoxyquinolin-3-yl)(4-(cyclopropanecarbonyl)piperazin-1-yl)methanone, TFA |

TABLE 1-continued

| Cpd. ID | Structure | Compound name |
| --- | --- | --- |
| 23 | 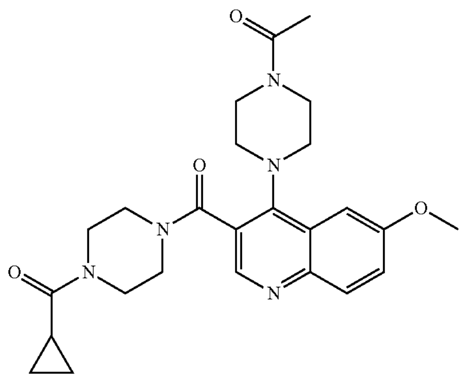 [SMILES: COc1ccc2ncc(C(=O)N3CCN(C(=O)C4CC4)CC3)c(N3CCN(C(C)=O)CC3)c2c1] | 1-(4-(3-(4-(cyclopropanecarbonyl)piperazine-1-carbonyl)-6-methoxyquinolin-4-yl)piperazin-1-yl)ethanone, TFA |
| 24 | 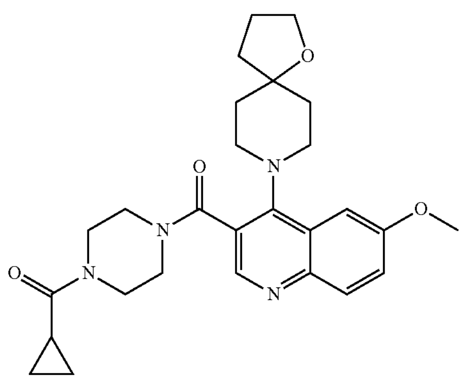 [SMILES: COc1ccc2ncc(C(=O)N3CCN(C(=O)C4CC4)CC3)c(N3CCC4(CCCO4)CC3)c2c1] | (4-(cyclopropanecarbonyl)piperazin-1-yl)(6-methoxy-4-(1-oxa-8-azaspiro[4.5]decan-8-yl)quinolin-3-yl)methanone, TFA |
| 25 | 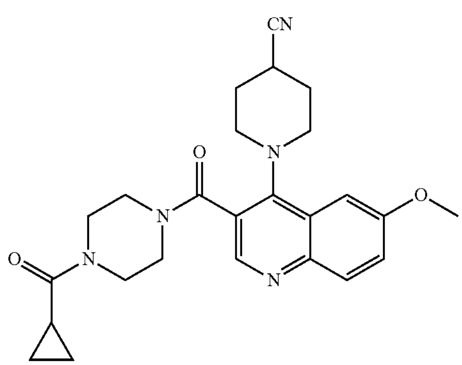 [SMILES: COc1ccc2ncc(C(=O)N3CCN(C(=O)C4CC4)CC3)c(N3CCC(C#N)CC3)c2c1] | 1-(3-(4-(cyclopropanecarbonyl)piperazine-1-carbonyl)-6-methoxyquinolin-4-yl)piperidine-4-carbonitrile, TFA |
| 26 | 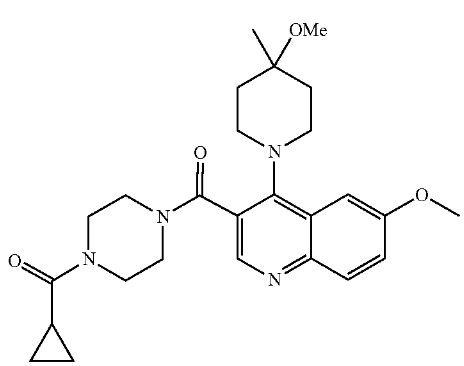 [SMILES: COc1ccc2ncc(C(=O)N3CCN(C(=O)C4CC4)CC3)c(N3CCC(C)(OC)CC3)c2c1] | (4-(cyclopropanecarbonyl)piperazin-1-yl)(6-methoxy-4-(4-methoxy-4-methylpiperidin-1-yl)quinolin-3-yl)methanone, TFA |

TABLE 1-continued

| Cpd. ID | Structure | Compound name |
|---|---|---|
| 27 | 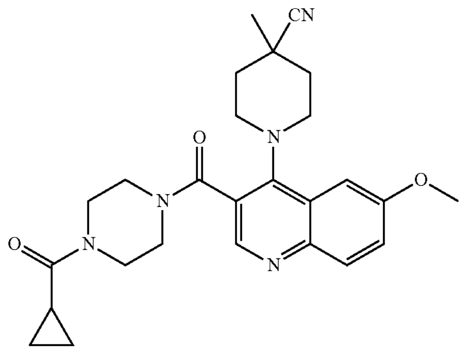 [SMILES: COc1ccc2ncc(C(=O)N3CCN(C(=O)C4CC4)CC3)c(N3CCC(C)(C#N)CC3)c2c1] | 1-(3-(4-(cyclopropanecarbonyl)piperazine-1-carbonyl)-6-methoxyquinolin-4-yl)-4-methylpiperidine-4-carbonitrile, TFA |
| 28 | 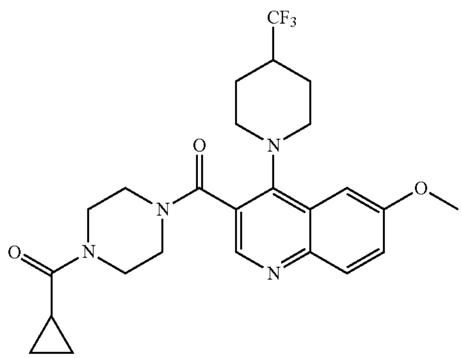 [SMILES: COc1ccc2ncc(C(=O)N3CCN(C(=O)C4CC4)CC3)c(N3CCC(C(F)(F)F)CC3)c2c1] | (4-(cyclopropanecarbonyl)piperazin-1-yl)(6-methoxy-4-(4-(trifluoromethyl)piperidin-1-yl)quinolin-3-yl)methanone, TFA |
| 29 | 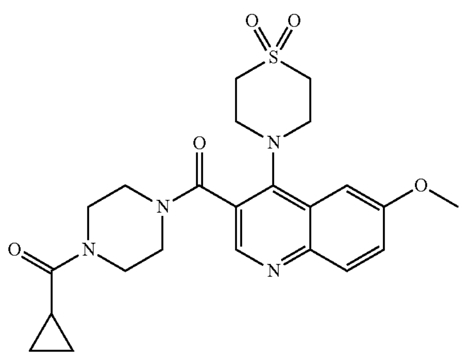 [SMILES: COc1ccc2ncc(C(=O)N3CCN(C(=O)C4CC4)CC3)c(N3CCS(=O)(=O)CC3)c2c1] | (4-(cyclopropanecarbonyl)piperazin-1-yl)(4-(1,1-dioxidothiomorpholino)-6-methoxyquinolin-3-yl)methanone, TFA |
| 30 | 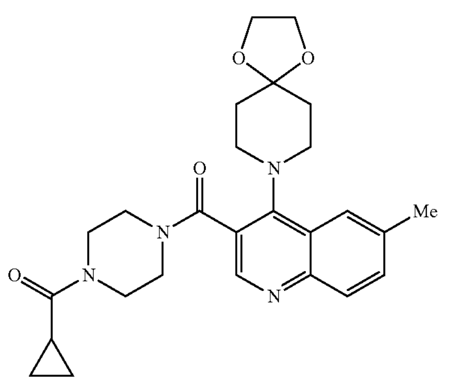 [SMILES: Cc1ccc2ncc(C(=O)N3CCN(C(=O)C4CC4)CC3)c(N3CCC4(CC3)OCCO4)c2c1] | (4-(cyclopropanecarbonyl)piperazin-1-yl)(6-methyl-4-(1,4-dioxa-8-azaspiro[4.5]decan-8-yl)quinolin-3-yl)methanone, TFA |

TABLE 1-continued

| Cpd. ID | Structure | Compound name |
|---|---|---|
| 31 | 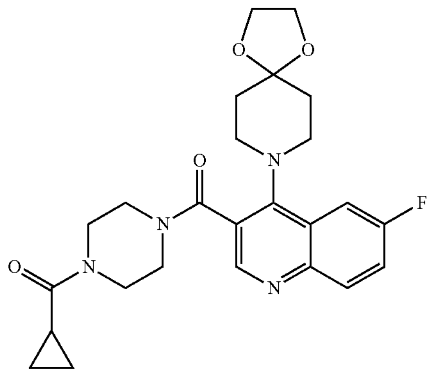 | (4-(cyclopropanecarbonyl)piperazin-1-yl)(6-fluoro-4-(1,4-dioxa-8-azaspiro[4.5]decan-8-yl)quinolin-3-yl)methanone, TFA |
| 32 | 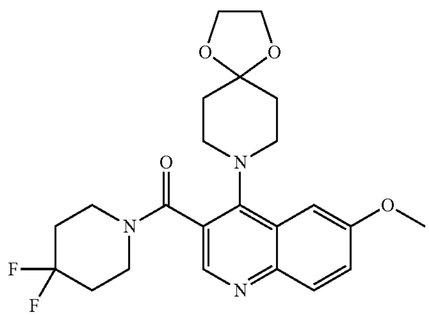 [SMILES: COc1ccc2ncc(C(=O)N3CCC(F)(F)CC3)c(N3CCC4(CC3)OCCO4)c2c1] | (4,4-difluoropiperidin-1-yl)(6-methoxy-4-(1,4-dioxa-8-azaspiro[4.5]decan-8-yl)quinolin-3-yl)methanone, TFA |
| 33 | 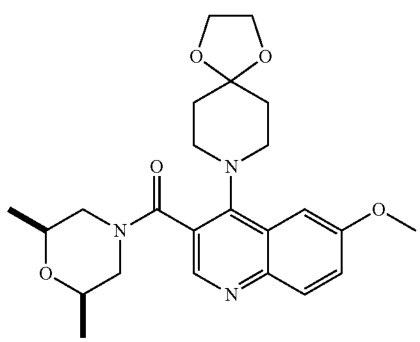 | ((2S*,6R*)-2,6-dimethylmorpholino)(6-methoxy-4-(1,4-dioxa-8-azaspiro[4.5]decan-8-yl)quinolin-3-yl)methanone, TFA |
| 34 | 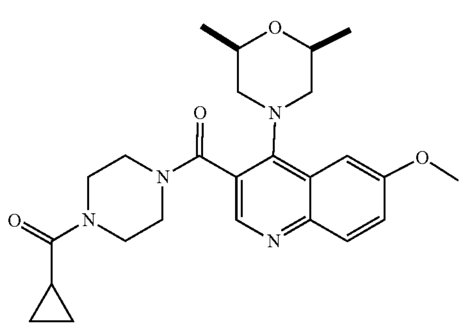 [SMILES: COc1ccc2ncc(C(=O)N3CCN(C(=O)C4CC4)CC3)c(N3C[C@@H](C)O[C@@H](C)C3)c2c1] | (4-(cyclopropanecarbonyl)piperazin-1-yl)(4-((2S*,6R*)-2,6-dimethylmorpholino)-6-methoxyquinolin-3-yl)methanone, TFA |

TABLE 1-continued

| Cpd. ID | Structure | Compound name |
|---|---|---|
| 35 | 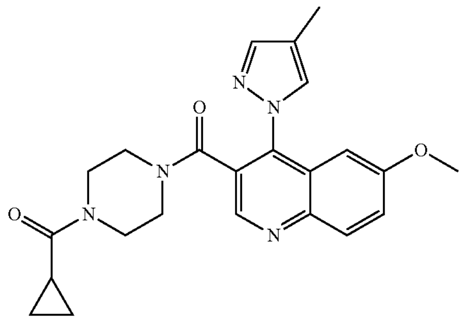 [SMILES: COc1ccc2ncc(C(=O)N3CCN(C(=O)C4CC4)CC3)c(-n3cc(C)cn3)c2c1] | (4-(cyclopropanecarbonyl)piperazin-1-yl)(6-methoxy-4-(4-methyl-1H-pyrazol-1-yl)quinolin-3-yl)methanone, TFA |
| 36 | 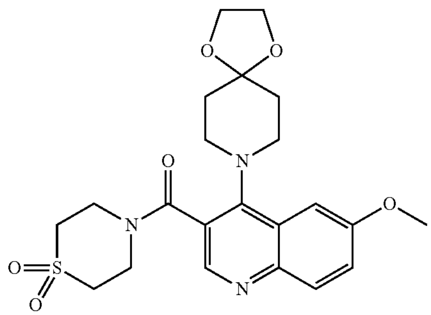 [SMILES: COc1ccc2ncc(C(=O)N3CCS(=O)(=O)CC3)c(N3CCC4(CC3)OCCO4)c2c1] | (1,1-dioxidothiomorpholino)(6-methoxy-4-(1,4-dioxa-8-azaspiro[4.5]decan-8-yl)quinolin-3-yl)methanone, TFA |
| 37 | 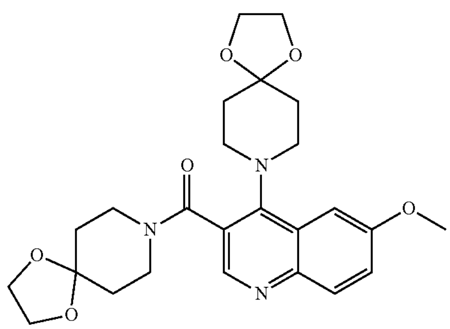 [SMILES: COc1ccc2ncc(C(=O)N3CCC4(CC3)OCCO4)c(N3CCC4(CC3)OCCO4)c2c1] | (6-methoxy-4-(1,4-dioxa-8-azaspiro[4.5]decan-8-yl)quinolin-3-yl)(1,4-dioxa-8-azaspiro[4.5]decan-8-yl)methanone, TFA |
| 38 | 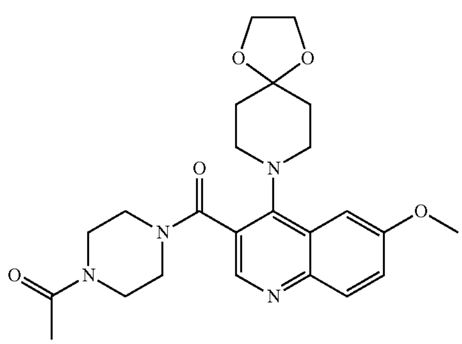 [SMILES: COc1ccc2ncc(C(=O)N3CCN(C(C)=O)CC3)c(N3CCC4(CC3)OCCO4)c2c1] | 1-(4-(6-methoxy-4-(1,4-dioxa-8-azaspiro[4.5]decan-8-yl)quinoline-3-carbonyl)piperazin-1-yl)ethanone, TFA |
| 39 | 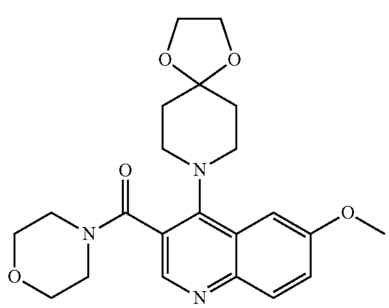 [SMILES: COc1ccc2ncc(C(=O)N3CCOCC3)c(N3CCC4(CC3)OCCO4)c2c1] | (6-methoxy-4-(1,4-dioxa-8-azaspiro[4.5]decan-8-yl)quinolin-3-yl)(morpholino)methanone, TFA |

TABLE 1-continued

| Cpd. ID | Structure | Compound name |
|---|---|---|
| 40 | 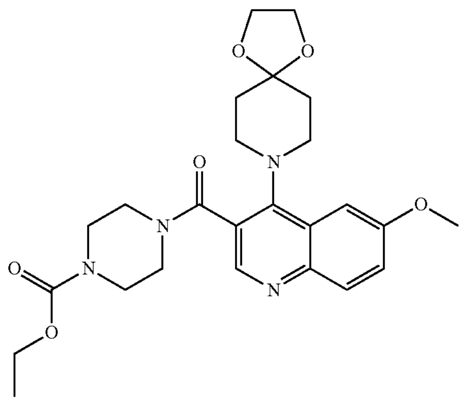 [SMILES: CCOC(=O)N1CCN(C(=O)c2cnc3ccc(OC)cc3c2N2CCC3(CC2)OCCO3)CC1] | Ethyl 4-(6-methoxy-4-(1,4-dioxa-8-azaspiro[4.5]decan-8-yl)quinoline-3-carbonyl)piperazine-1-carboxylate, TFA |
| 41 | 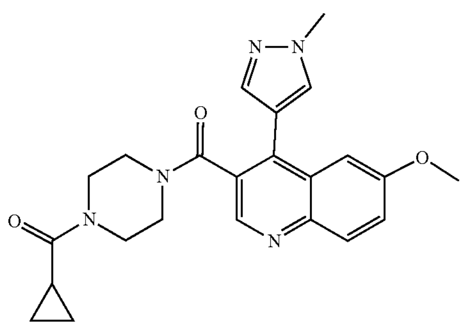 [SMILES: COc1ccc2ncc(C(=O)N3CCN(C(=O)C4CC4)CC3)c(-c3cnn(C)c3)c2c1] | (4-(cyclopropanecarbonyl)piperazin-1-yl)(6-methoxy-4-(1-methyl-1H-pyrazol-4-yl)quinolin-3-yl)methanone, TFA |
| 42 | 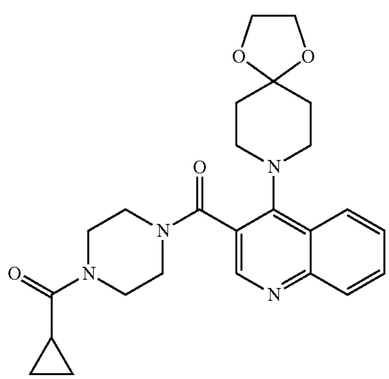 [SMILES: O=C(c1cnc2ccccc2c1N1CCC2(CC1)OCCO2)N1CCN(C(=O)C2CC2)CC1] | (4-(1,4-dioxa-8-azaspiro[4.5]decan-8-yl)quinolin-3-yl)(4-(cyclopropanecarbonyl)piperazin-1-yl)methanone, TFA |
| 43 | 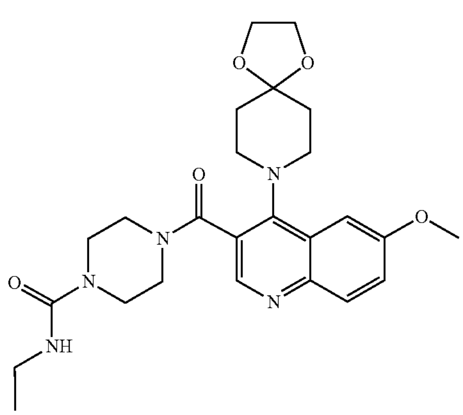 [SMILES: CCNC(=O)N1CCN(C(=O)c2cnc3ccc(OC)cc3c2N2CCC3(CC2)OCCO3)CC1] | N-ethyl-4-(6-methoxy-4-(1,4-dioxa-8-azaspiro[4.5]decan-8-yl)quinoline-3-carbonyl)piperazine-1-carboxamide, TFA |

TABLE 1-continued

| Cpd. ID | Structure | Compound name |
|---|---|---|
| 44 | 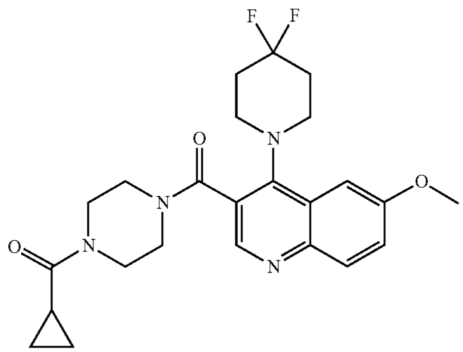 [SMILES: COc1ccc2ncc(C(=O)N3CCN(C(=O)C4CC4)CC3)c(N3CCC(F)(F)CC3)c2c1] | (4-(cyclopropanecarbonyl)piperazin-1-yl)(4-(4,4-difluoropiperidin-1-yl)-6-methoxyquinolin-3-yl)methanone, TFA |
| 45 | 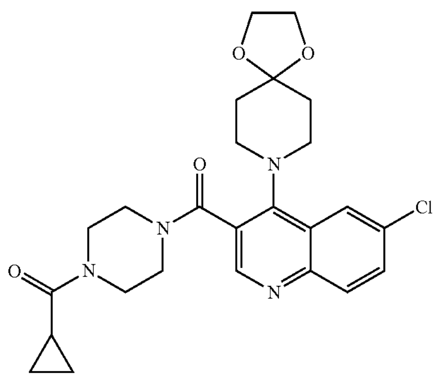 [SMILES: O=C(c1cnc2ccc(Cl)cc2c1N1CCC2(CC1)OCCO2)N1CCN(C(=O)C2CC2)CC1] | (6-chloro-4-(1,4-dioxa-8-azaspiro[4.5]decan-8-yl)quinolin-3-yl)(4-(cyclopropanecarbonyl)piperazin-1-yl)methanone, TFA |
| 46 | 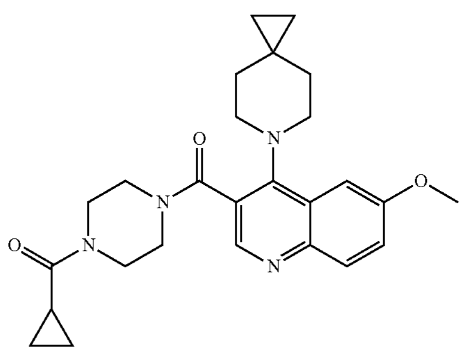 [SMILES: COc1ccc2ncc(C(=O)N3CCN(C(=O)C4CC4)CC3)c(N3CCC4(CC3)CC4)c2c1] | (4-(cyclopropanecarbonyl)piperazin-1-yl)(6-methoxy-4-(6-azaspiro[2.5]octan-6-yl)quinolin-3-yl)methanone, TFA |
| 47 | 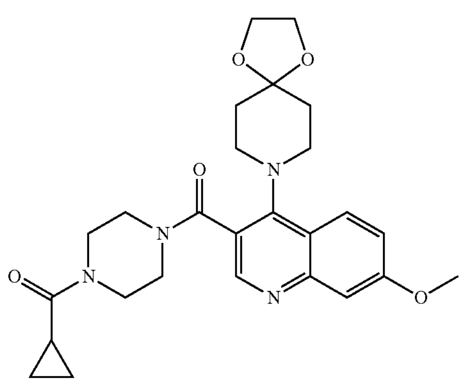 [SMILES: COc1ccc2c(N3CCC4(CC3)OCCO4)c(C(=O)N3CCN(C(=O)C4CC4)CC3)cnc2c1] | (4-(cyclopropanecarbonyl)piperazin-1-yl)(7-methoxy-4-(1,4-dioxa-8-azaspiro[4.5]decan-8-yl)quinolin-3-yl)methanone, TFA |

TABLE 1-continued

| Cpd. ID | Structure | Compound name |
|---|---|---|
| 48 | 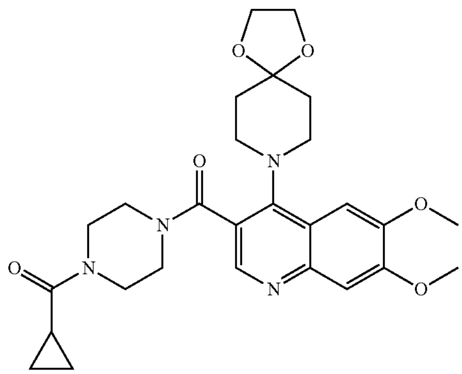 [SMILES: COc1cc2ncc(C(=O)N3CCN(C(=O)C4CC4)CC3)c(N3CCC4(CC3)OCCO4)c2cc1OC] | (4-(cyclopropanecarbonyl)piperazin-1-yl)(6,7-dimethoxy-4-(1,4-dioxa-8-azaspiro[4.5]decan-8-yl)quinolin-3-yl)methanone, TFA |
| 49 | 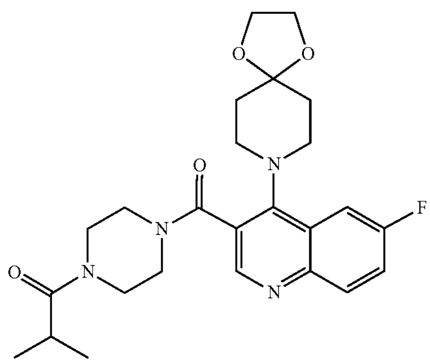 [SMILES: CC(C)C(=O)N1CCN(C(=O)c2cnc3ccc(F)cc3c2N2CCC3(CC2)OCCO3)CC1] | 1-(4-(6-fluoro-4-(1,4-dioxa-8-azaspiro[4.5]decan-8-yl)quinoline-3-carbonyl)piperazin-1-yl)-2-methylpropan-1-one, TFA |
| 50 | 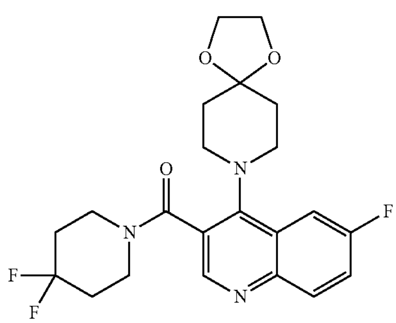 [SMILES: O=C(c1cnc2ccc(F)cc2c1N1CCC2(CC1)OCCO2)N1CCC(F)(F)CC1] | (4,4-difluoropiperidin-1-yl)(6-fluoro-4-(1,4-dioxa-8-azaspiro[4.5]decan-8-yl)quinolin-3-yl)methanone, TFA |
| 51 | 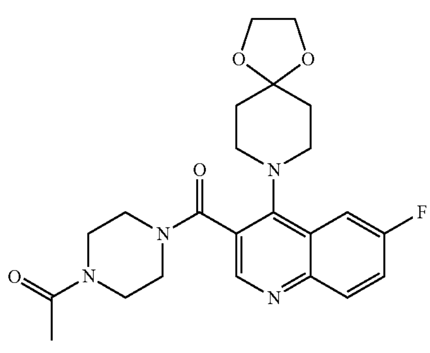 [SMILES: CC(=O)N1CCN(C(=O)c2cnc3ccc(F)cc3c2N2CCC3(CC2)OCCO3)CC1] | 1-(4-(6-fluoro-4-(1,4-dioxa-8-azaspiro[4.5]decan-8-yl)quinoline-3-carbonyl)piperazin-1-yl)ethanone, TFA |

TABLE 1-continued

| Cpd. ID | Structure | Compound name |
|---|---|---|
| 52 | 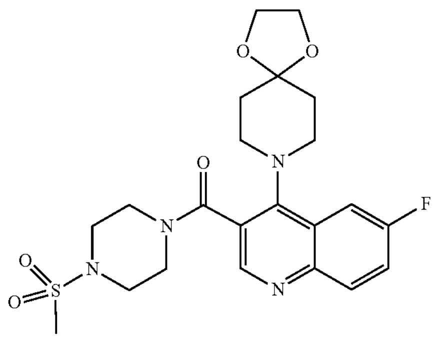 [SMILES: CS(=O)(=O)N1CCN(C(=O)c2cnc3ccc(F)cc3c2N2CCC3(CC2)OCCO3)CC1] | (6-fluoro-4-(1,4-dioxa-8-azaspiro[4.5]decan-8-yl)quinolin-3-yl)(4-(methylsulfonyl)piperazin-1-yl)methanone, TFA |
| 53 | 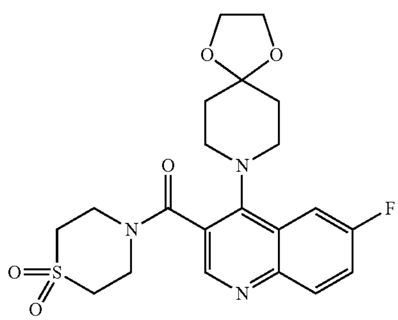 [SMILES: O=C(c1cnc2ccc(F)cc2c1N1CCC2(CC1)OCCO2)N1CCS(=O)(=O)CC1] | (1,1-dioxidothiomorpholino)(6-fluoro-4-(1,4-dioxa-8-azaspiro[4.5]decan-8-yl)quinolin-3-yl)methanone, TFA |
| 54 | 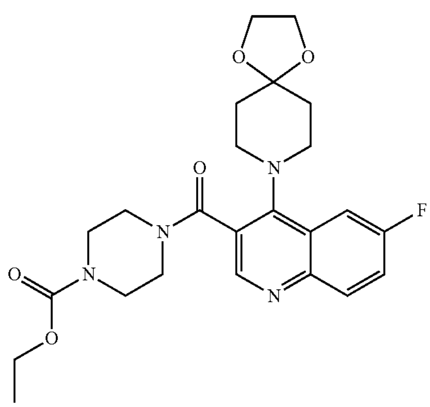 [SMILES: CCOC(=O)N1CCN(C(=O)c2cnc3ccc(F)cc3c2N2CCC3(CC2)OCCO3)CC1] | ethyl 4-(6-fluoro-4-(1,4-dioxa-8-azaspiro[4.5]decan-8-yl)quinoline-3-carbonyl)piperazine-1-carboxylate, TFA |
| 55 | 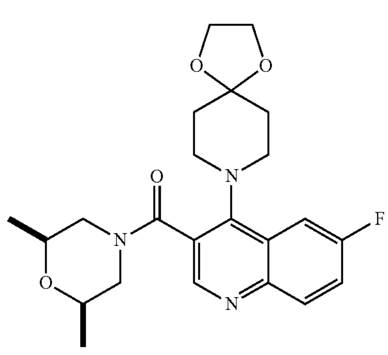 [SMILES: C[C@@H]1CN(C(=O)c2cnc3ccc(F)cc3c2N2CCC3(CC2)OCCO3)C[C@H](C)O1] | ((2S*,6R*)-2,6-dimethylmorpholino)(6-fluoro-4-(1,4-dioxa-8-azaspiro[4.5]decan-8-yl)quinolin-3-yl)methanone, TFA |

TABLE 1-continued

| Cpd. ID | Structure | Compound name |
|---|---|---|
| 56 | 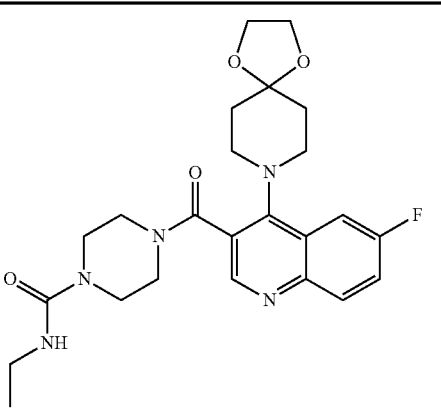 | N-ethyl-4-(6-fluoro-4-(1,4-dioxa-8-azaspiro[4.5]decan-8-yl)quinoline-3-carbonyl)piperazine-1-carboxamide, TFA |
| 57 | 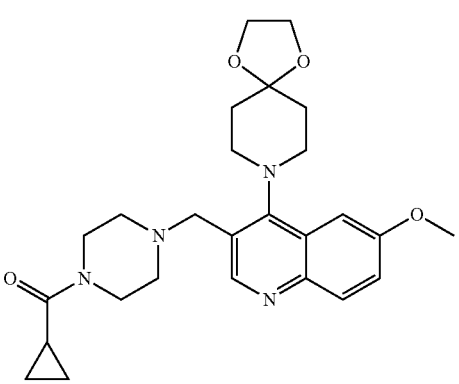 [SMILES: COc1ccc2ncc(CN3CCN(C(=O)C4CC4)CC3)c(N3CCC4(CC3)OCCO4)c2c1] | cyclopropyl(4-((6-methoxy-4-(1,4-dioxa-8-azaspiro[4.5]decan-8-yl)quinolin-3-yl)methyl)piperazin-1-yl)methanone, TFA |
| 58 | 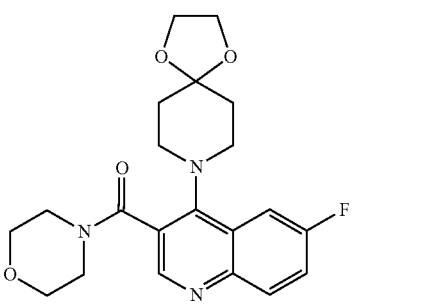 [SMILES: O=C(c1cnc2ccc(F)cc2c1N1CCC2(CC1)OCCO2)N1CCOCC1] | (6-fluoro-4-(1,4-dioxa-8-azaspiro[4.5]decan-8-yl)quinolin-3-yl)(morpholino)methanone, TFA |
| 59 | 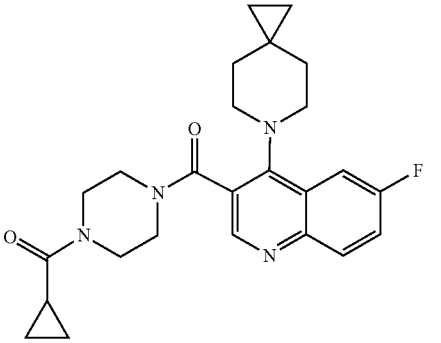 [SMILES: O=C(c1cnc2ccc(F)cc2c1N1CCC2(CC1)CC2)N1CCN(C(=O)C2CC2)CC1] | (4-(cyclopropanecarbonyl)piperazin-1-yl)(6-fluoro-4-(6-azaspiro[2.5]octan-6-yl)quinolin-3-yl)methanone, TFA |

TABLE 1-continued

| Cpd. ID | Structure | Compound name |
|---|---|---|
| 60 | 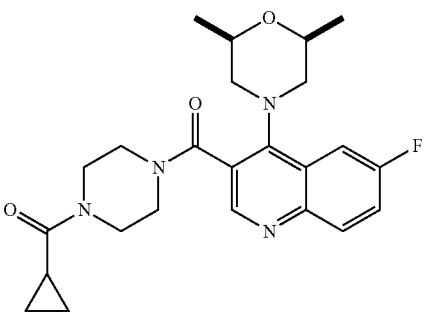 [SMILES: C[C@@H]1CN(c2c(C(=O)N3CCN(C(=O)C4CC4)CC3)cnc3ccc(F)cc23)C[C@H](C)O1] | YSM007-056 (4-(cyclopropanecarbonyl)piperazin-1-yl)(4-((2S*,6R*)-2,6-dimethylmorpholino)-6-fluoroquinolin-3-yl)methanone, TFA |
| 61 | 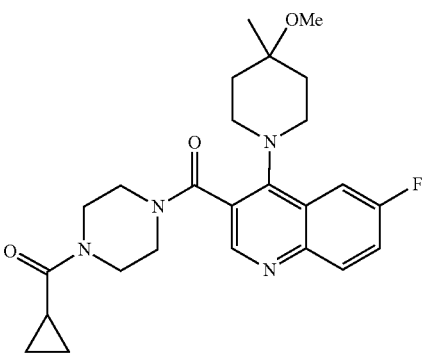 [SMILES: COC1(C)CCN(c2c(C(=O)N3CCN(C(=O)C4CC4)CC3)cnc3ccc(F)cc23)CC1] | (4-(cyclopropanecarbonyl)piperazin-1-yl)(6-fluoro-4-(4-methoxy-4-methylpiperidin-1-yl)quinolin-3-yl)methanone, TFA |
| 62 | 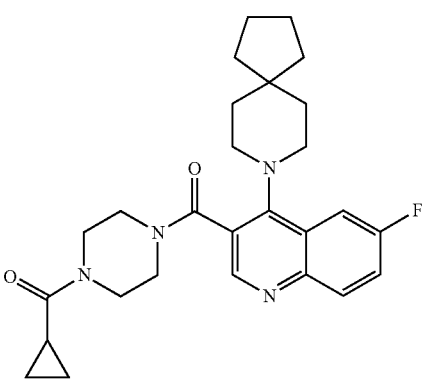 [SMILES: O=C(c1cnc2ccc(F)cc2c1N1CCC2(CCCC2)CC1)N1CCN(C(=O)C2CC2)CC1] | (4-(cyclopropanecarbonyl)piperazin-1-yl)(6-fluoro-4-(8-azaspiro[4.5]decan-8-yl)quinolin-3-yl)methanone, TFA |
| 63 | 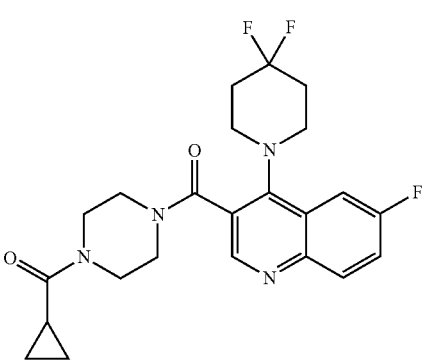 [SMILES: O=C(c1cnc2ccc(F)cc2c1N1CCC(F)(F)CC1)N1CCN(C(=O)C2CC2)CC1] | (4-(cyclopropanecarbonyl)piperazin-1-yl)(4-(4,4-difluoropiperidin-1-yl)-6-fluoroquinolin-3-yl)methanone, TFA |

TABLE 1-continued

| Cpd. ID | Structure | Compound name |
|---|---|---|
| 64 | 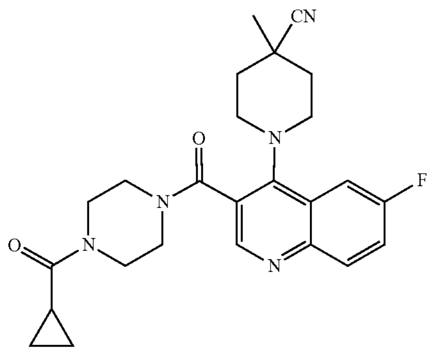 [SMILES: CC1(C#N)CCN(c2c(C(=O)N3CCN(C(=O)C4CC4)CC3)cnc3ccc(F)cc23)CC1] | 1-(3-(4-(cyclopropanecarbonyl)piperazine-1-carbonyl)-6-fluoroquinolin-4-yl)-4-methylpiperidine-4-carbonitrile, TFA |
| 65 | 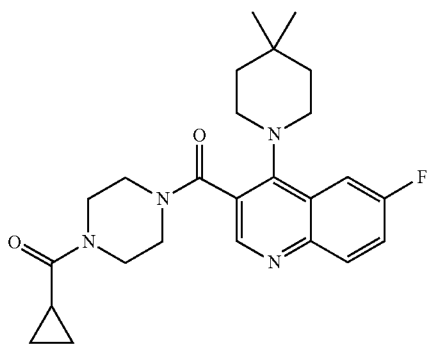 [SMILES: CC1(C)CCN(c2c(C(=O)N3CCN(C(=O)C4CC4)CC3)cnc3ccc(F)cc23)CC1] | (4-(cyclopropanecarbonyl)piperazin-1-yl)(4-(4,4-dimethylpiperidin-1-yl)-6-fluoroquinolin-3-yl)methanone, TFA |
| 66 | 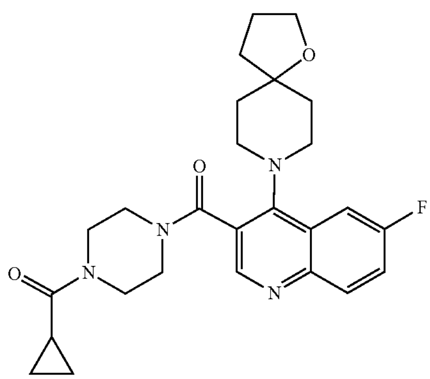 [SMILES: O=C(c1cnc2ccc(F)cc2c1N1CCC2(CCCO2)CC1)N1CCN(C(=O)C2CC2)CC1] | (4-(cyclopropanecarbonyl)piperazin-1-yl)(6-fluoro-4-(1-oxa-8-azaspiro[4.5]decan-8-yl)quinolin-3-yl)methanone, TFA |
| 67 | 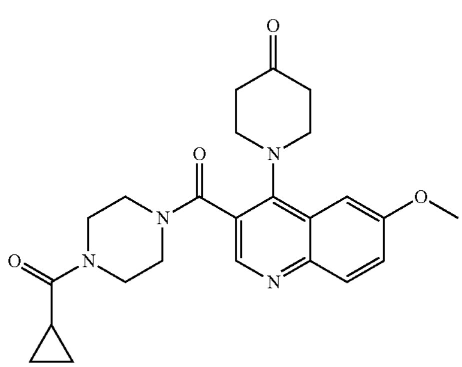 [SMILES: COc1ccc2ncc(C(=O)N3CCN(C(=O)C4CC4)CC3)c(N3CCC(=O)CC3)c2c1] | 1-(3-(4-(cyclopropanecarbonyl)piperazine-1-carbonyl)-6-methoxyquinolin-4-yl)piperidin-4-one |

TABLE 1-continued

| Cpd. ID | Structure | Compound name |
| --- | --- | --- |
| 68 | 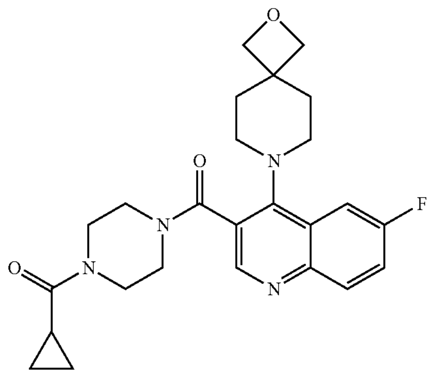 [SMILES: O=C(c1cnc2ccc(F)cc2c1N1CCC2(CC1)COC2)N1CCN(C(=O)C2CC2)CC1] | (4-(cyclopropanecarbonyl)piperazin-1-yl)(6-fluoro-4-(2-oxa-7-azaspiro[3.5]nonan-7-yl)quinolin-3-yl)methanone |
| 69 | 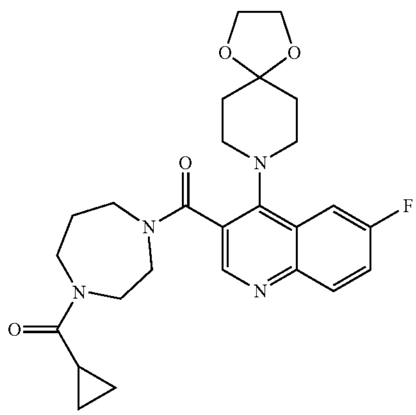 [SMILES: O=C(c1cnc2ccc(F)cc2c1N1CCC2(CC1)OCCO2)N1CCCN(C(=O)C2CC2)CC1] | (4-(cyclopropanecarbonyl)-1,4-diazepan-1-yl)(6-fluoro-4-(1,4-dioxa-8-azaspiro[4.5]decan-8-yl)quinolin-3-yl)methanone, TFA |
| 70 | 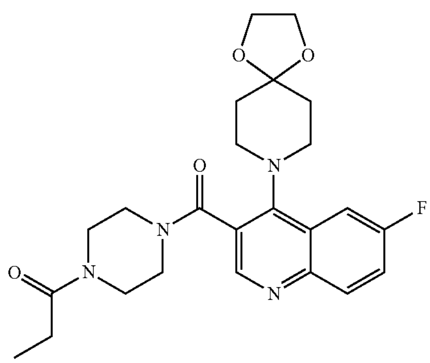 | 1-(4-(6-fluoro-4-(1,4-dioxa-8-azaspiro[4.5]decan-8-yl)quinoline-3-carbonyl)piperazin-1-yl)propan-1-one, TFA |
| 71 | 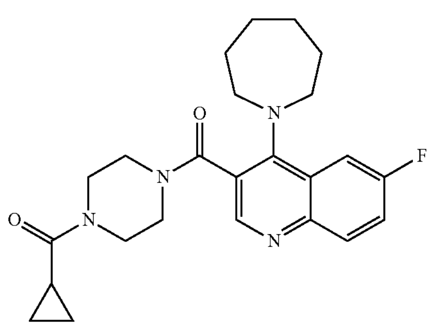 [SMILES: O=C(c1cnc2ccc(F)cc2c1N1CCCCCC1)N1CCN(C(=O)C2CC2)CC1] | (4-(azepan-1-yl)-6-fluoroquinolin-3-yl)(4-(cyclopropanecarbonyl)piperazin-1-yl)methanone, TFA |

TABLE 1-continued

| Cpd. ID | Structure | Compound name |
|---|---|---|
| 72 | 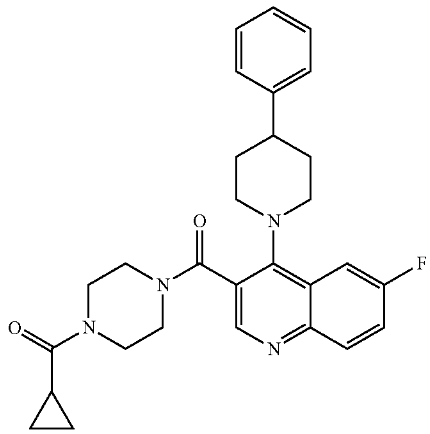 [SMILES: O=C(c1cnc2ccc(F)cc2c1N1CCC(c2ccccc2)CC1)N1CCN(C(=O)C2CC2)CC1] | (4-(cyclopropanecarbonyl)piperazin-1-yl)(6-fluoro-4-(4-phenylpiperidin-1-yl)quinolin-3-yl)methanone, TFA |
| 73 | 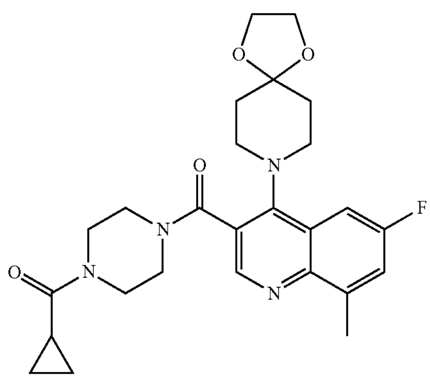 [SMILES: Cc1cc(F)cc2c(N3CCC4(CC3)OCCO4)c(C(=O)N3CCN(C(=O)C4CC4)CC3)cnc12] | (4-(cyclopropanecarbonyl)piperazin-1-yl)(6-fluoro-8-methyl-4-(1,4-dioxa-8-azaspiro[4.5]decan-8-yl)quinolin-3-yl)methanone, TFA |
| 74 | 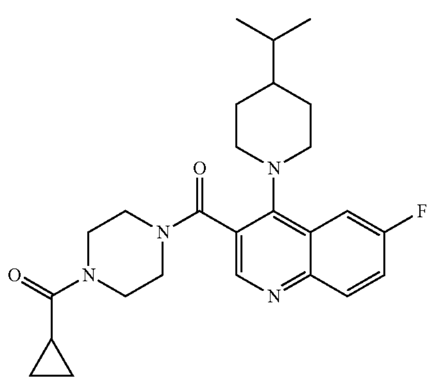 [SMILES: CC(C)C1CCN(c2c(C(=O)N3CCN(C(=O)C4CC4)CC3)cnc3ccc(F)cc23)CC1] | (4-(cyclopropanecarbonyl)piperazin-1-yl)(6-fluoro-4-(4-isopropylpiperidin-1-yl)quinolin-3-yl)methanone, TFA |
| 75 | 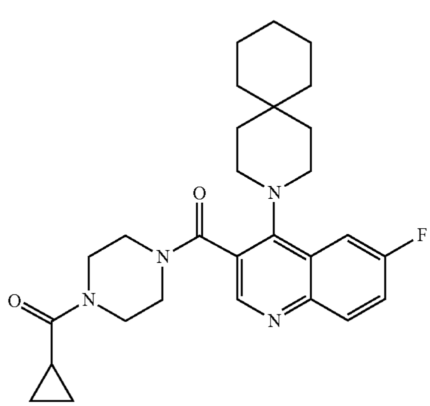 [SMILES: O=C(c1cnc2ccc(F)cc2c1N1CCC2(CCCCC2)CC1)N1CCN(C(=O)C2CC2)CC1] | (4-(cyclopropanecarbonyl)piperazin-1-yl)(6-fluoro-4-(3-azaspiro[5.5]undecan-3-yl)quinolin-3-yl)methanone, TFA |

TABLE 1-continued

| Cpd. ID | Structure | Compound name |
|---|---|---|
| 76 | 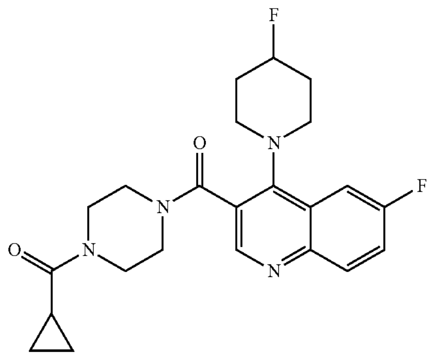 [SMILES: O=C(c1cnc2ccc(F)cc2c1N1CCC(F)CC1)N1CCN(C(=O)C2CC2)CC1] | (4-(cyclopropanecarbonyl)piperazin-1-yl)(6-fluoro-4-(4-fluoropiperidin-1-yl)quinolin-3-yl)methanone, TFA |
| 77 | 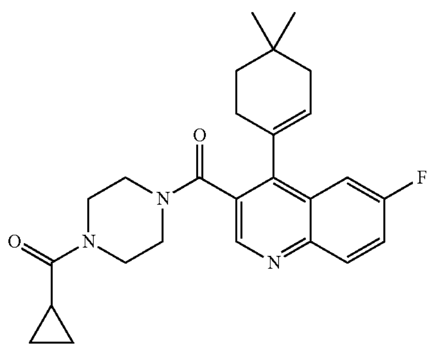 [SMILES: CC1(C)CC=C(c2c(C(=O)N3CCN(C(=O)C4CC4)CC3)cnc3ccc(F)cc23)CC1] | (4-(cyclopropanecarbonyl)piperazin-1-yl)(4-(4,4-dimethylcyclohex-1-en-1-yl)-6-fluoroquinolin-3-yl)methanone |
| 78 | 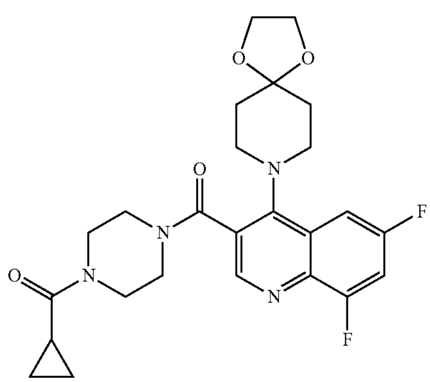 [SMILES: O=C(c1cnc2c(F)cc(F)cc2c1N1CCC2(CC1)OCCO2)N1CCN(C(=O)C2CC2)CC1] | (4-(cyclopropanecarbonyl)piperazin-1-yl)(6,8-difluoro-4-(1,4-dioxa-8-azaspiro[4.5]decan-8-yl)quinolin-3-yl)methanone, TFA |
| 79 | 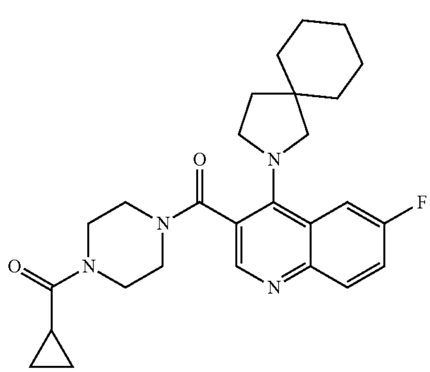 [SMILES: O=C(c1cnc2ccc(F)cc2c1N1CCC2(CCCCC2)C1)N1CCN(C(=O)C2CC2)CC1] | (4-(cyclopropanecarbonyl)piperazin-1-yl)(6-fluoro-4-(2-azaspiro[4.5]decan-2-yl)quinolin-3-yl)methanone, TFA |

TABLE 1-continued

| Cpd. ID | Structure | Compound name |
|---|---|---|
| 80 | 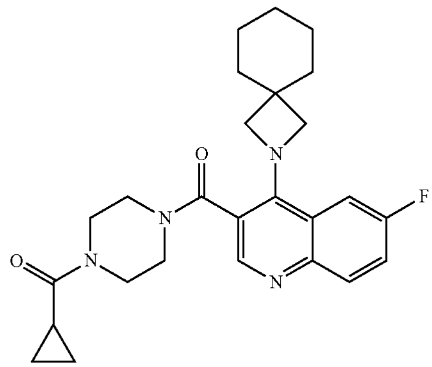 [SMILES: O=C(c1cnc2ccc(F)cc2c1N1CC2(CCCCC2)C1)N1CCN(C(=O)C2CC2)CC1] | (4-(cyclopropanecarbonyl)piperazin-1-yl)(6-fluoro-4-(2-azaspiro[3.5]nonan-2-yl)quinolin-3-yl)methanone, TFA |
| 81 | 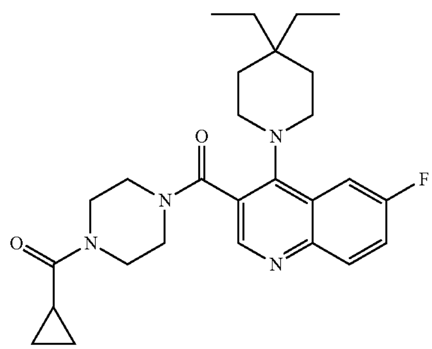 [SMILES: CCC1(CC)CCN(c2c(C(=O)N3CCN(C(=O)C4CC4)CC3)cnc3ccc(F)cc23)CC1] | (4-(cyclopropanecarbonyl)piperazin-1-yl)(4-(4,4-diethylpiperidin-1-yl)-6-fluoroquinolin-3-yl)methanone, TFA |
| 82 | 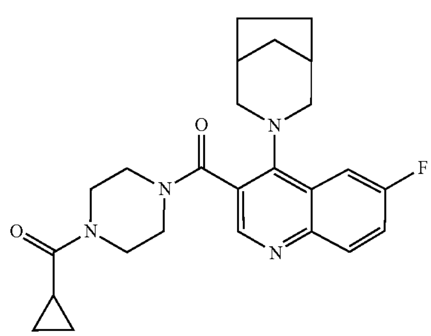 [SMILES: O=C(c1cnc2ccc(F)cc2c1N1CC2CCC(C2)C1)N1CCN(C(=O)C2CC2)CC1] | (4-(3-azabicyclo[3.2.1]octan-3-yl)-6-fluoroquinolin-3-yl)(4-(cyclopropanecarbonyl)piperazin-1-yl)methanone, TFA |
| 83 | 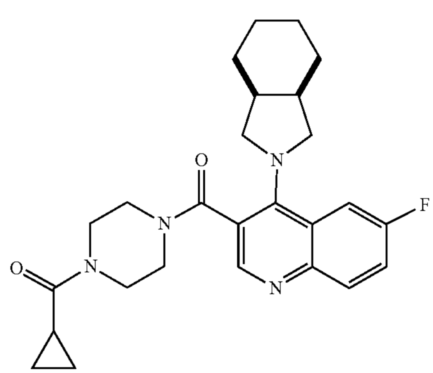 [SMILES: O=C(c1cnc2ccc(F)cc2c1N1C[C@H]2CCCC[C@H]2C1)N1CCN(C(=O)C2CC2)CC1] | (4-(cyclopropanecarbonyl)piperazin-1-yl)(6-fluoro-4-((3aR*,7aS*)-hexahydro-1H-isoindol-2(3H)-yl)quinolin-3-yl)methanone |

TABLE 1-continued

| Cpd. ID | Structure | Compound name |
|---|---|---|
| 84 | 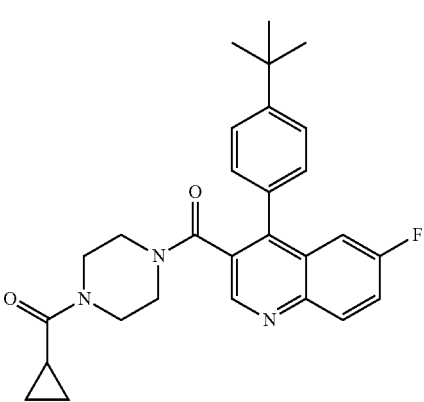 [SMILES: CC(C)(C)c1ccc(-c2c(C(=O)N3CCN(C(=O)C4CC4)CC3)cnc3ccc(F)cc23)cc1] | (4-(4-(tert-butyl)phenyl)-6-fluoroquinolin-3-yl)(4-(cyclopropanecarbonyl)piperazin-1-yl)methanone, TFA |
| 85 | 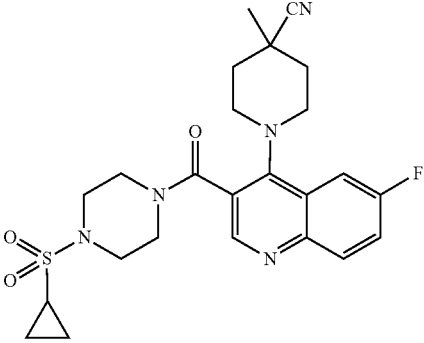 [SMILES: CC1(C#N)CCN(c2c(C(=O)N3CCN(S(=O)(=O)C4CC4)CC3)cnc3ccc(F)cc23)CC1] | 1-(3-(4-(cyclopropylsulfonyl)piperazine-1-carbonyl)-6-fluoroquinolin-4-yl)-4-methylpiperidine-4-carbonitrile, TFA |
| 86 | 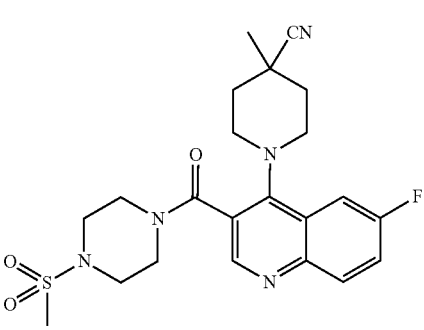 [SMILES: CC1(C#N)CCN(c2c(C(=O)N3CCN(S(C)(=O)=O)CC3)cnc3ccc(F)cc23)CC1] | 1-(6-fluoro-3-(4-(methylsulfonyl)piperazine-1-carbonyl)quinolin-4-yl)-4-methylpiperidine-4-carbonitrile, TFA |
| 87 | 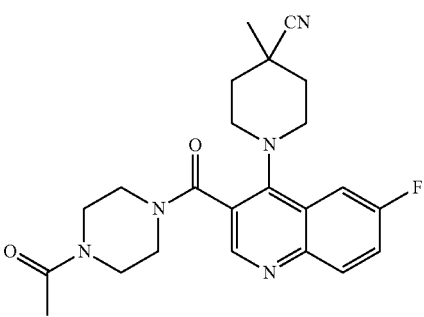 [SMILES: CC(=O)N1CCN(C(=O)c2cnc3ccc(F)cc3c2N2CCC(C)(C#N)CC2)CC1] | 1-(3-(4-acetylpiperazine-1-carbonyl)-6-fluoroquinolin-4-yl)-4-methylpiperidine-4-carbonitrile, TFA |

TABLE 1-continued

| Cpd. ID | Structure | Compound name |
|---|---|---|
| 88 | 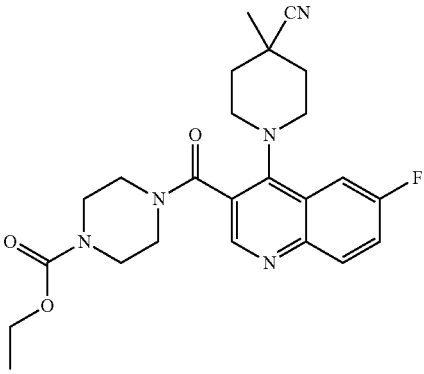 [SMILES: CCOC(=O)N1CCN(C(=O)c2cnc3ccc(F)cc3c2N2CCC(C)(C#N)CC2)CC1] | ethyl 4-(4-(4-cyano-4-methylpiperidin-1-yl)-6-fluoroquinoline-3-carbonyl)piperazine-1-carboxylate, TFA |
| 89 | 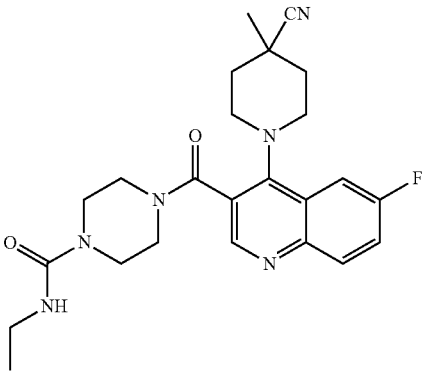 [SMILES: CCNC(=O)N1CCN(C(=O)c2cnc3ccc(F)cc3c2N2CCC(C)(C#N)CC2)CC1] | 4-(4-(4-cyano-4-methylpiperidin-1-yl)-6-fluoroquinoline-3-carbonyl)-N-ethylpiperazine-1-carboxamide, TFA |
| 90 | 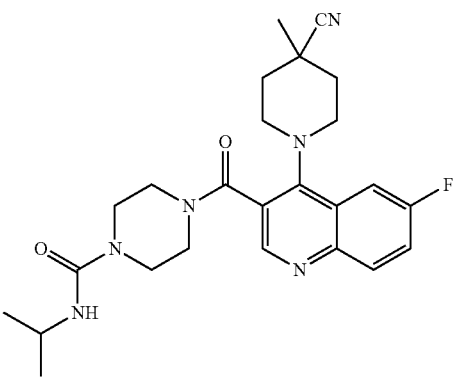 [SMILES: CC(C)NC(=O)N1CCN(C(=O)c2cnc3ccc(F)cc3c2N2CCC(C)(C#N)CC2)CC1] | 4-(4-(4-cyano-4-methylpiperidin-1-yl)-6-fluoroquinoline-3-carbonyl)-N-isopropylpiperazine-1-carboxamide, TFA |
| 91 | 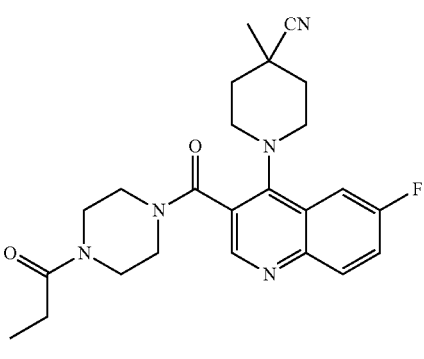 [SMILES: CCC(=O)N1CCN(C(=O)c2cnc3ccc(F)cc3c2N2CCC(C)(C#N)CC2)CC1] | 1-(6-fluoro-3-(4-propionylpiperazine-1-carbonyl)quinolin-4-yl)-4-methylpiperidine-4-carbonitrile, TFA |

TABLE 1-continued

| Cpd. ID | Structure | Compound name |
|---|---|---|
| 92 | 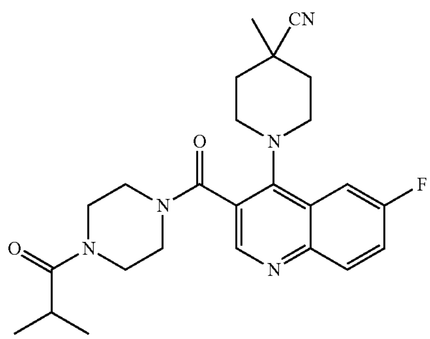 [SMILES: CC(C)C(=O)N1CCN(C(=O)c2cnc3ccc(F)cc3c2N2CCC(C)(C#N)CC2)CC1] | 1-(6-fluoro-3-(4-isobutyrylpiperazine-1-carbonyl)quinolin-4-yl)-4-methylpiperidine-4-carbonitrile, TFA |
| 93 | 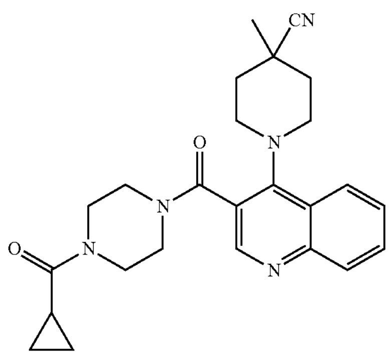 [SMILES: CC1(C#N)CCN(c2c(C(=O)N3CCN(C(=O)C4CC4)CC3)cnc3ccccc23)CC1] | 1-(3-(4-(cyclopropanecarbonyl)piperazine-1-carbonyl)quinolin-4-yl)-4-methylpiperidine-4-carbonitrile, TFA |
| 94 | 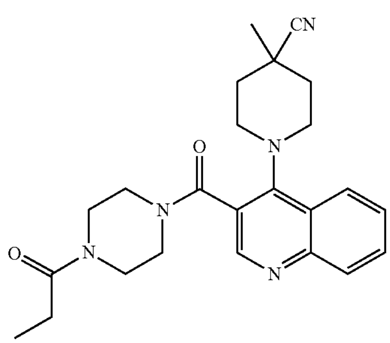 [SMILES: CCC(=O)N1CCN(C(=O)c2cnc3ccccc3c2N2CCC(C)(C#N)CC2)CC1] | 4-methyl-1-(3-(4-propionylpiperazine-1-carbonyl)quinolin-4-yl)piperidine-4-carbonitrile, TFA |
| 95 | 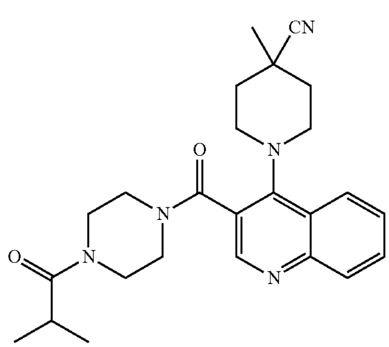 [SMILES: CC(C)C(=O)N1CCN(C(=O)c2cnc3ccccc3c2N2CCC(C)(C#N)CC2)CC1] | 1-(3-(4-isobutyrylpiperazine-1-carbonyl)quinolin-4-yl)-4-methylpiperidine-4-carbonitrile, TFA |

TABLE 1-continued

| Cpd. ID | Structure | Compound name |
|---|---|---|
| 96 | 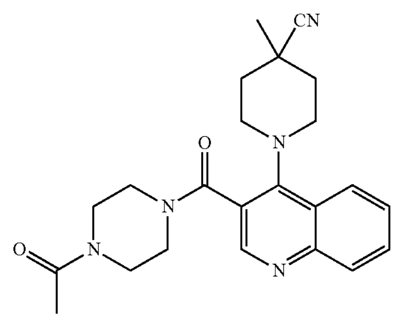 [SMILES: CC(=O)N1CCN(C(=O)c2cnc3ccccc3c2N2CCC(C)(C#N)CC2)CC1] | 1-(3-(4-acetylpiperazine-1-carbonyl)quinolin-4-yl)-4-methylpiperidine-4-carbonitrile, TFA |
| 97 | 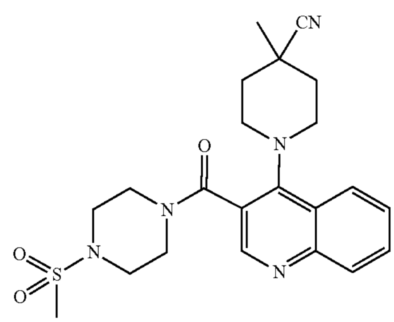 [SMILES: CC1(C#N)CCN(c2c(C(=O)N3CCN(S(C)(=O)=O)CC3)cnc3ccccc23)CC1] | 4-methyl-1-(3-(4-(methylsulfonyl)piperazine-1-carbonyl)quinolin-4-yl)piperidine-4-carbonitrile, TFA |
| 98 | 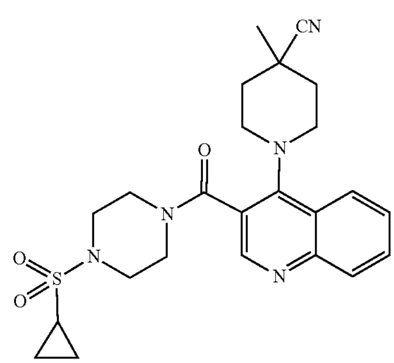 [SMILES: CC1(C#N)CCN(c2c(C(=O)N3CCN(S(=O)(=O)C4CC4)CC3)cnc3ccccc23)CC1] | 1-(3-(4-(cyclopropylsulfonyl)piperazine-1-carbonyl)quinolin-4-yl)-4-methylpiperidine-4-carbonitrile, TFA |
| 99 | 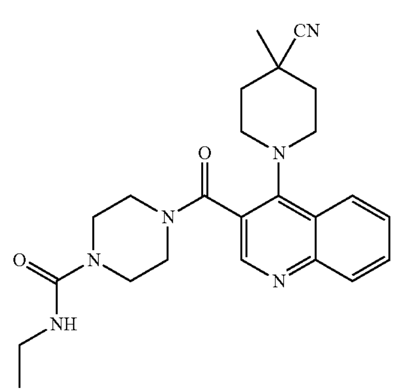 [SMILES: CCNC(=O)N1CCN(C(=O)c2cnc3ccccc3c2N2CCC(C)(C#N)CC2)CC1] | 4-(4-(4-cyano-4-methylpiperidin-1-yl)quinoline-3-carbonyl)-N-ethylpiperazine-1-carboxamide, TFA |

TABLE 1-continued

| Cpd. ID | Structure | Compound name |
|---|---|---|
| 100 | 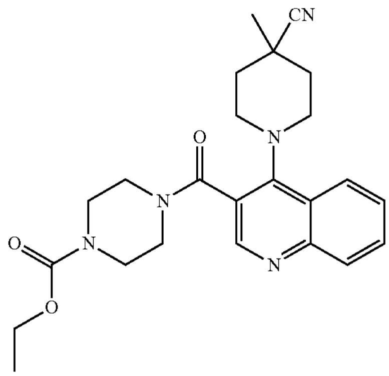 [SMILES: CCOC(=O)N1CCN(C(=O)c2cnc3ccccc3c2N2CCC(C)(C#N)CC2)CC1] | ethyl 4-(4-(4-cyano-4-methylpiperidin-1-yl)quinoline-3-carbonyl)piperazine-1-carboxylate, TFA |
| 101 | 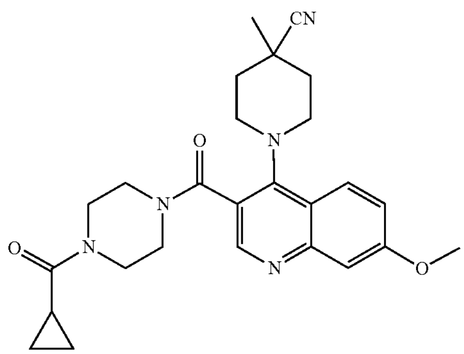 [SMILES: COc1ccc2c(N3CCC(C)(C#N)CC3)c(C(=O)N3CCN(C(=O)C4CC4)CC3)cnc2c1] | 1-(3-(4-(cyclopropanecarbonyl)piperazine-1-carbonyl)-7-methoxyquinolin-4-yl)-4-methylpiperidine-4-carbonitrile, TFA |
| 102 | 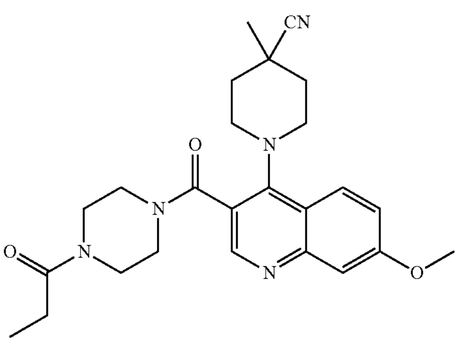 [SMILES: CCC(=O)N1CCN(C(=O)c2cnc3cc(OC)ccc3c2N2CCC(C)(C#N)CC2)CC1] | 1-(7-methoxy-3-(4-propionylpiperazine-1-carbonyl)quinolin-4-yl)-4-methylpiperidine-4-carbonitrile, TFA |
| 103 | 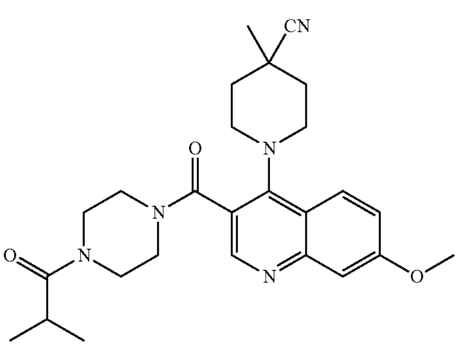 [SMILES: COc1ccc2c(N3CCC(C)(C#N)CC3)c(C(=O)N3CCN(C(=O)C(C)C)CC3)cnc2c1] | 1-(3-(4-isobutyrylpiperazine-1-carbonyl)-7-methoxyquinolin-4-yl)-4-methylpiperidine-4-carbonitrile, TFA |

TABLE 1-continued

| Cpd. ID | Structure | Compound name |
|---|---|---|
| 104 | 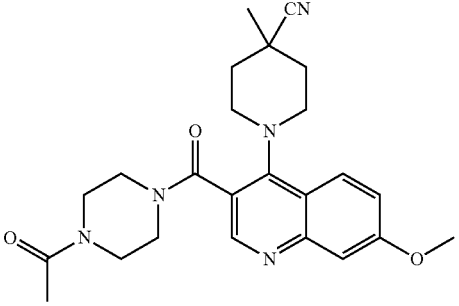 [SMILES: COc1ccc2c(N3CCC(C)(C#N)CC3)c(C(=O)N3CCN(C(C)=O)CC3)cnc2c1] | 1-(3-(4-acetylpiperazine-1-carbonyl)-7-methoxyquinolin-4-yl)-4-methylpiperidine-4-carbonitrile, TFA |
| 105 | 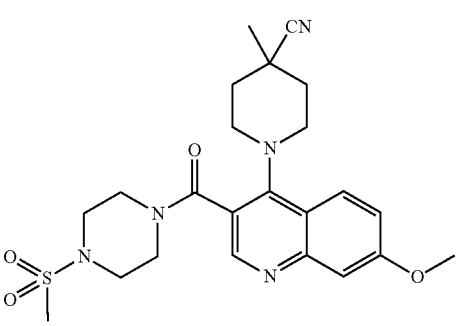 [SMILES: COc1ccc2c(N3CCC(C)(C#N)CC3)c(C(=O)N3CCN(S(C)(=O)=O)CC3)cnc2c1] | 1-(7-methoxy-3-(4-(methylsulfonyl)piperazine-1-carbonyl)quinolin-4-yl)-4-methylpiperidine-4-carbonitrile, TFA |
| 106 | 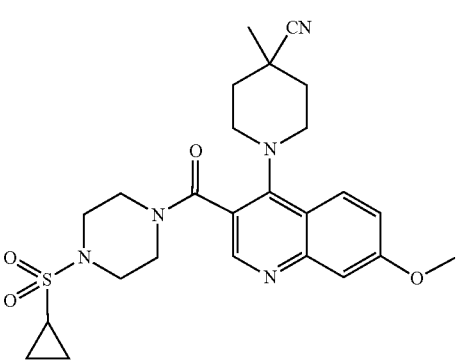 [SMILES: COc1ccc2c(N3CCC(C)(C#N)CC3)c(C(=O)N3CCN(S(=O)(=O)C4CC4)CC3)cnc2c1] | 1-(3-(4-(cyclopropylsulfonyl)piperazine-1-carbonyl)-7-methoxyquinolin-4-yl)-4-methylpiperidine-4-carbonitrile, TFA |
| 107 | 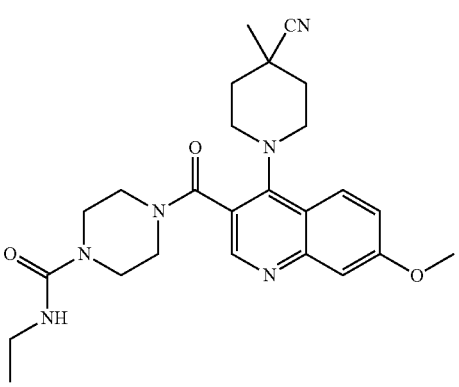 [SMILES: CCNC(=O)N1CCN(C(=O)c2cnc3cc(OC)ccc3c2N2CCC(C)(C#N)CC2)CC1] | 4-(4-(4-cyano-4-methylpiperidin-1-yl)-7-methoxyquinoline-3-carbonyl)-N-ethylpiperazine-1-carboxamide, TFA |

TABLE 1-continued

| Cpd. ID | Structure | Compound name |
|---|---|---|
| 108 | 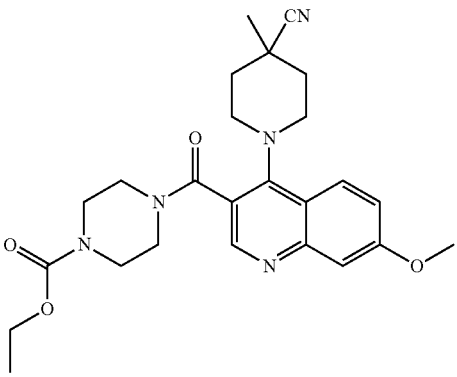 [SMILES: CCOC(=O)N1CCN(C(=O)c2cnc3cc(OC)ccc3c2N2CCC(C)(C#N)CC2)CC1] | ethyl 4-(4-(4-cyano-4-methylpiperidin-1-yl)-7-methoxyquinoline-3-carbonyl)piperazine-1-carboxylate, TFA |
| 109 | 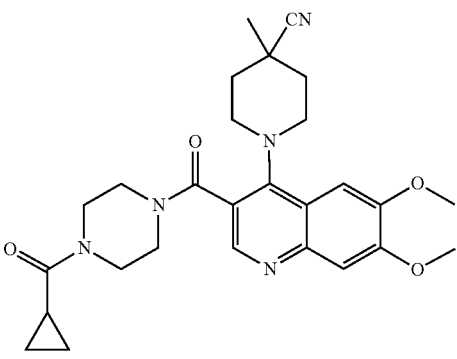 [SMILES: COc1cc2ncc(C(=O)N3CCN(C(=O)C4CC4)CC3)c(N3CCC(C)(C#N)CC3)c2cc1OC] | 1-(3-(4-(cyclopropanecarbonyl)piperazine-1-carbonyl)-6,7-dimethoxyquinolin-4-yl)-4-methylpiperidine-4-carbonitrile, TFA |
| 110 | 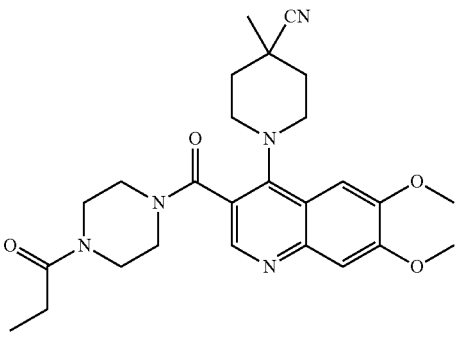 [SMILES: CCC(=O)N1CCN(C(=O)c2cnc3cc(OC)c(OC)cc3c2N2CCC(C)(C#N)CC2)CC1] | 1-(6,7-dimethoxy-3-(4-propionylpiperazine-1-carbonyl)quinolin-4-yl)-4-methylpiperidine-4-carbonitrile, TFA |
| 111 | 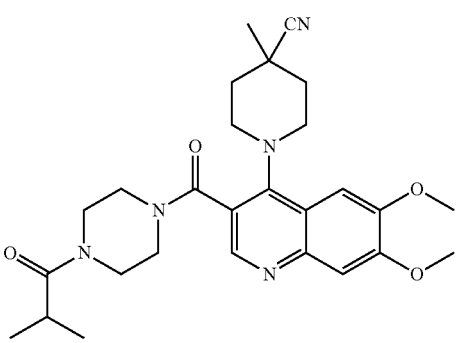 [SMILES: COc1cc2ncc(C(=O)N3CCN(C(=O)C(C)C)CC3)c(N3CCC(C)(C#N)CC3)c2cc1OC] | 1-(3-(4-isobutyrylpiperazine-1-carbonyl)-6,7-dimethoxyquinolin-4-yl)-4-methylpiperidine-4-carbonitrile, TFA |

TABLE 1-continued

| Cpd. ID | Structure | Compound name |
|---|---|---|
| 112 | 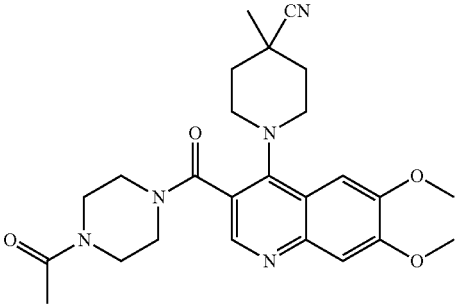 [SMILES: COc1cc2ncc(C(=O)N3CCN(C(C)=O)CC3)c(N3CCC(C)(C#N)CC3)c2cc1OC] | 1-(3-(4-acetylpiperazine-1-carbonyl)-6,7-dimethoxyquinolin-4-yl)-4-methylpiperidine-4-carbonitrile, TFA |
| 113 | 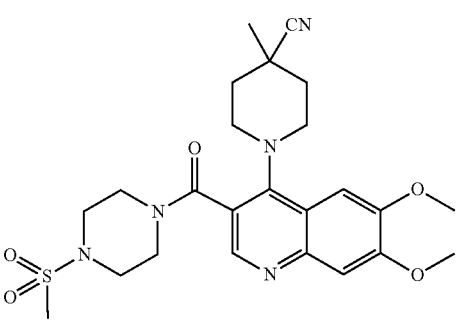 [SMILES: COc1cc2ncc(C(=O)N3CCN(S(C)(=O)=O)CC3)c(N3CCC(C)(C#N)CC3)c2cc1OC] | 1-(6,7-dimethoxy-3-(4-(methylsulfonyl)piperazine-1-carbonyl)quinolin-4-yl)-4-methylpiperidine-4-carbonitrile, TFA |
| 114 | 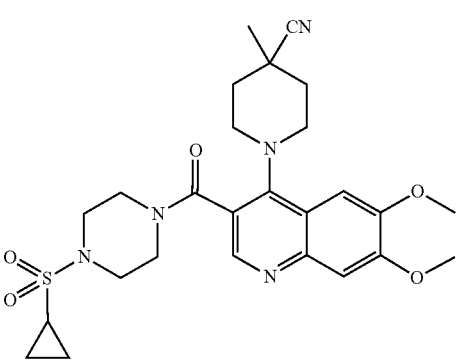 [SMILES: COc1cc2ncc(C(=O)N3CCN(S(=O)(=O)C4CC4)CC3)c(N3CCC(C)(C#N)CC3)c2cc1OC] | 1-(3-(4-(cyclopropylsulfonyl)piperazine-1-carbonyl)-6,7-dimethoxyquinolin-4-yl)-4-methylpiperidine-4-carbonitrile, TFA |
| 115 | 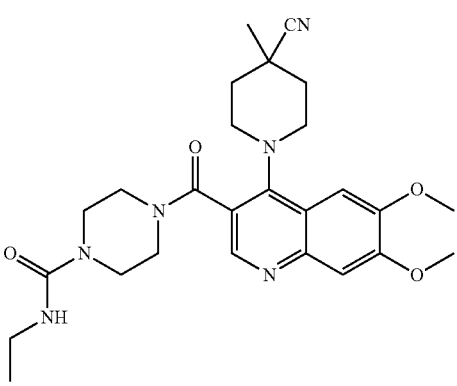 [SMILES: CCNC(=O)N1CCN(C(=O)c2cnc3cc(OC)c(OC)cc3c2N2CCC(C)(C#N)CC2)CC1] | 4-(4-(4-cyano-4-methylpiperidin-1-yl)-6,7-dimethoxyquinoline-3-carbonyl)-N-ethylpiperazine-1-carboxamide, TFA |

TABLE 1-continued

| Cpd. ID | Structure | Compound name |
|---|---|---|
| 116 | 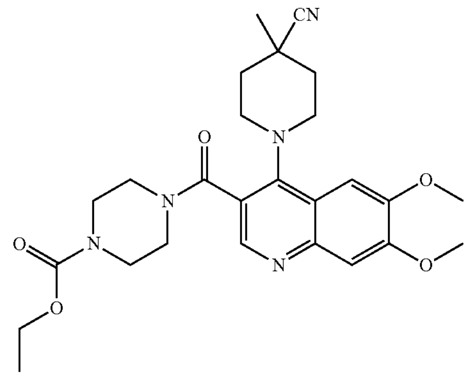 [SMILES: CCOC(=O)N1CCN(C(=O)c2cnc3cc(OC)c(OC)cc3c2N2CCC(C)(C#N)CC2)CC1] | ethyl 4-(4-(4-cyano-4-methylpiperidin-1-yl)-6,7-dimethoxyquinoline-3-carbonyl)piperazine-1-carboxylate, TFA |
| 117 | 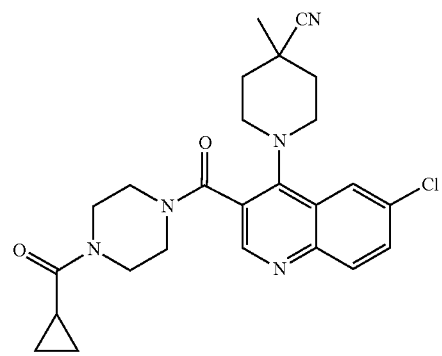 [SMILES: CC1(C#N)CCN(c2c(C(=O)N3CCN(C(=O)C4CC4)CC3)cnc3ccc(Cl)cc23)CC1] | 1-(6-chloro-3-(4-(cyclopropanecarbonyl)piperazine-1-carbonyl)quinolin-4-yl)-4-methylpiperidine-4-carbonitrile, TFA |
| 118 | 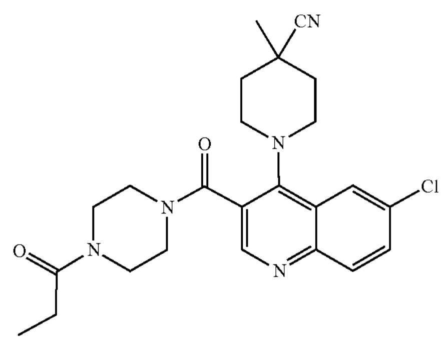 [SMILES: CCC(=O)N1CCN(C(=O)c2cnc3ccc(Cl)cc3c2N2CCC(C)(C#N)CC2)CC1] | 1-(6-chloro-3-(4-propionylpiperazine-1-carbonyl)quinolin-4-yl)-4-methylpiperidine-4-carbonitrile, TFA |
| 119 | 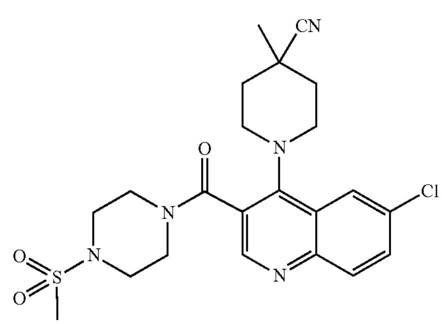 [SMILES: CC1(C#N)CCN(c2c(C(=O)N3CCN(S(C)(=O)=O)CC3)cnc3ccc(Cl)cc23)CC1] | 1-(6-chloro-3-(4-(methylsulfonyl)piperazine-1-carbonyl)quinolin-4-yl)-4-methylpiperidine-4-carbonitrile, TFA |

TABLE 1-continued

| Cpd. ID | Structure | Compound name |
|---|---|---|
| 120 | 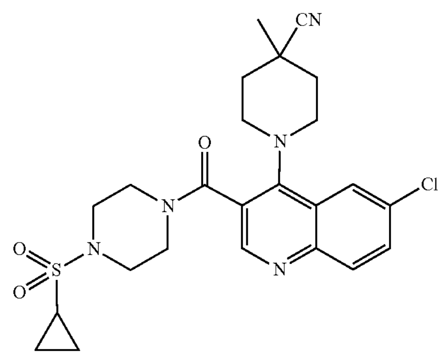 [SMILES: CC1(C#N)CCN(c2c(C(=O)N3CCN(S(=O)(=O)C4CC4)CC3)cnc3ccc(Cl)cc23)CC1] | 1-(6-chloro-3-(4-(cyclopropylsulfonyl)piperazine-1-carbonyl)quinolin-4-yl)-4-methylpiperidine-4-carbonitrile, TFA |
| 121 | 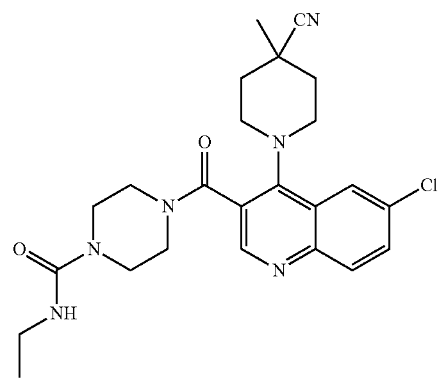 [SMILES: CCNC(=O)N1CCN(C(=O)c2cnc3ccc(Cl)cc3c2N2CCC(C)(C#N)CC2)CC1] | 4-(6-chloro-4-(4-cyano-4-methylpiperidin-1-yl)quinoline-3-carbonyl)-N-ethylpiperazine-1-carboxamide, TFA |
| 122 | 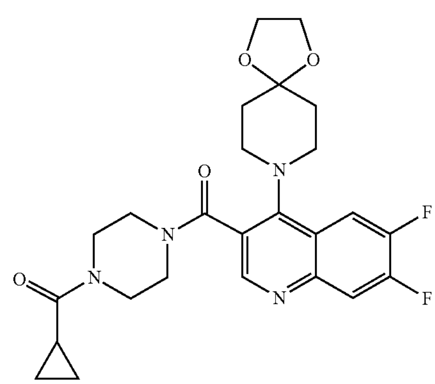 [SMILES: O=C(c1cnc2cc(F)c(F)cc2c1N1CCC2(CC1)OCCO2)N1CCN(C(=O)C2CC2)CC1] | (4-(cyclopropanecarbonyl)piperazin-1-yl)(6,7-difluoro-4-(1,4-dioxa-8-azaspiro[4.5]decan-8-yl)quinolin-3-yl)methanone, TFA |
| 123 | 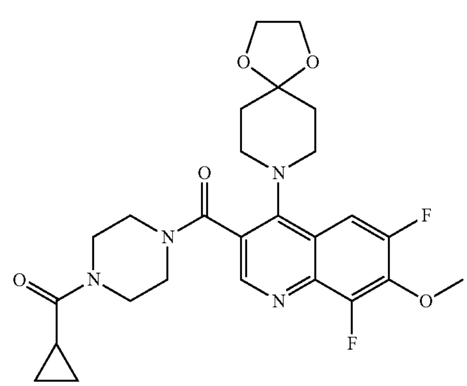 [SMILES: COc1c(F)cc2c(N3CCC4(CC3)OCCO4)c(C(=O)N3CCN(C(=O)C4CC4)CC3)cnc2c1F] | (4-(cyclopropanecarbonyl)piperazin-1-yl)(6,8-difluoro-7-methoxy-4-(1,4-dioxa-8-azaspiro[4.5]decan-8-yl)quinolin-3-yl)methanone, TFA |

TABLE 1-continued

| Cpd. ID | Structure | Compound name |
|---|---|---|
| 124 | 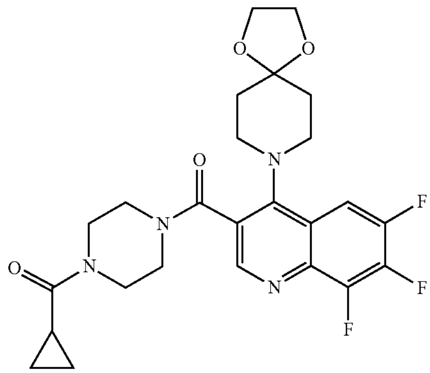 [SMILES: O=C(c1cnc2c(F)c(F)c(F)cc2c1N1CCC2(CC1)OCCO2)N1CCN(C(=O)C2CC2)CC1] | (4-(cyclopropanecarbonyl)piperazin-1-yl)(6,7,8-trifluoro-4-(1,4-dioxa-8-azaspiro[4.5]decan-8-yl)quinolin-3-yl)methanone, TFA |
| 125 | 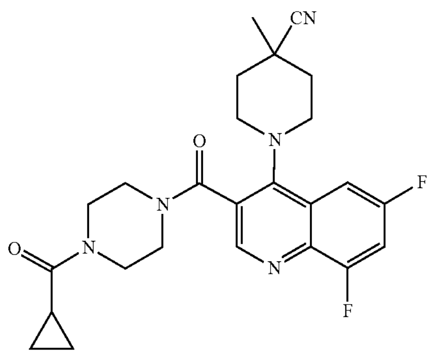 [SMILES: CC1(C#N)CCN(c2c(C(=O)N3CCN(C(=O)C4CC4)CC3)cnc3c(F)cc(F)cc23)CC1] | 1-(3-(4-(cyclopropanecarbonyl)piperazine-1-carbonyl)-6,8-difluoroquinolin-4-yl)-4-methylpiperidine-4-carbonitrile, TFA |
| 126 | 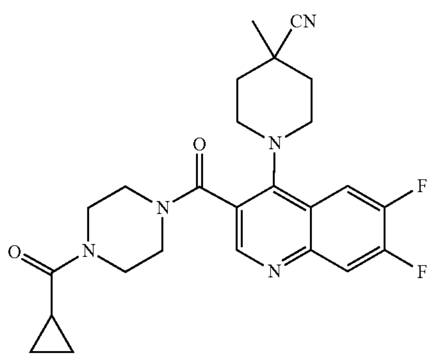 [SMILES: CC1(C#N)CCN(c2c(C(=O)N3CCN(C(=O)C4CC4)CC3)cnc3cc(F)c(F)cc23)CC1] | 1-(3-(4-(cyclopropanecarbonyl)piperazine-1-carbonyl)-6,7-difluoroquinolin-4-yl)-4-methylpiperidine-4-carbonitrile, TFA |
| 127 | 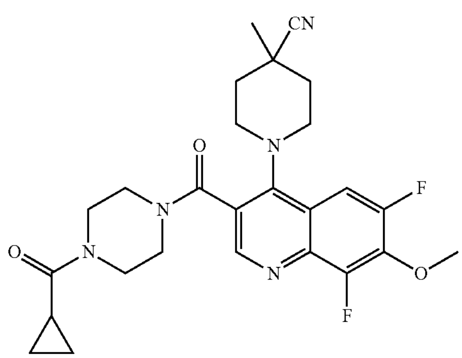 [SMILES: COc1c(F)cc2c(N3CCC(C)(C#N)CC3)c(C(=O)N3CCN(C(=O)C4CC4)CC3)cnc2c1F] | 1-(3-(4-(cyclopropanecarbonyl)piperazine-1-carbonyl)-6,8-difluoro-7-methoxyquinolin-4-yl)-4-methylpiperidine-4-carbonitrile, TFA |

TABLE 1-continued

| Cpd. ID | Structure | Compound name |
|---|---|---|
| 128 | 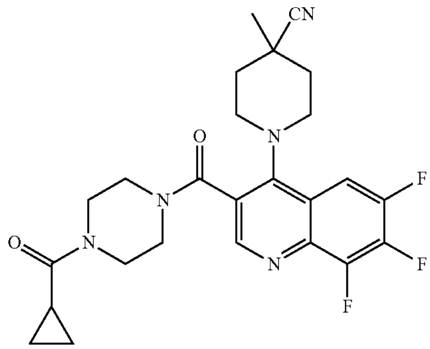 [SMILES: CC1(C#N)CCN(c2c(C(=O)N3CCN(C(=O)C4CC4)CC3)cnc3c(F)c(F)c(F)cc23)CC1] | 1-(3-(4-(cyclopropanecarbonyl)piperazine-1-carbonyl)-6,7,8-trifluoroquinolin-4-yl)-4-methylpiperidine-4-carbonitrile, TFA |
| 129 | 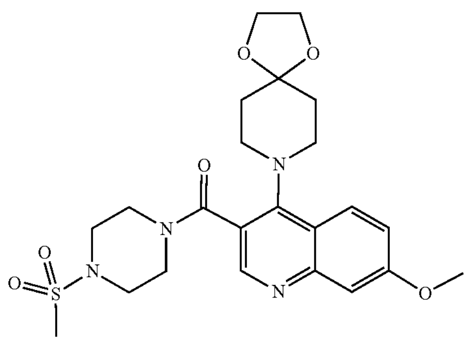 [SMILES: COc1ccc2c(N3CCC4(CC3)OCCO4)c(C(=O)N3CCN(S(C)(=O)=O)CC3)cnc2c1] | (7-methoxy-4-(1,4-dioxa-8-azaspiro[4.5]decan-8-yl)quinolin-3-yl)(4-(methylsulfonyl)piperazin-1-yl)methanone, TFA |
| 130 | 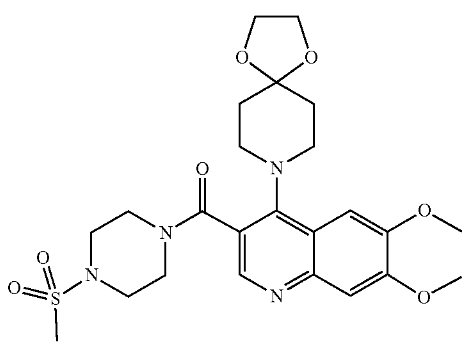 [SMILES: COc1cc2ncc(C(=O)N3CCN(S(C)(=O)=O)CC3)c(N3CCC4(CC3)OCCO4)c2cc1OC] | (6,7-dimethoxy-4-(1,4-dioxa-8-azaspiro[4.5]decan-8-yl)quinolin-3-yl)(4-(methylsulfonyl)piperazin-1-yl)methanone, TFA |
| 131 | 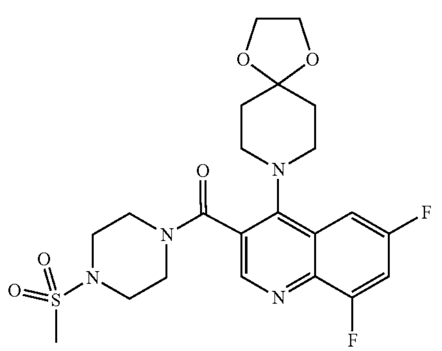 [SMILES: CS(=O)(=O)N1CCN(C(=O)c2cnc3c(F)cc(F)cc3c2N2CCC3(CC2)OCCO3)CC1] | (6,8-difluoro-4-(1,4-dioxa-8-azaspiro[4.5]decan-8-yl)quinolin-3-yl)(4-(methylsulfonyl)piperazin-1-yl)methanone, TFA |

TABLE 1-continued

| Cpd. ID | Structure | Compound name |
| --- | --- | --- |
| 132 | 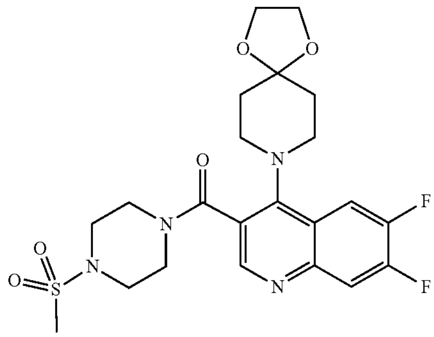 [SMILES: CS(=O)(=O)N1CCN(C(=O)c2cnc3cc(F)c(F)cc3c2N2CCC3(CC2)OCCO3)CC1] | (6,7-difluoro-4-(1,4-dioxa-8-azaspiro[4.5]decan-8-yl)quinolin-3-yl)(4-(methylsulfonyl)piperazin-1-yl)methanone, TFA |
| 133 | 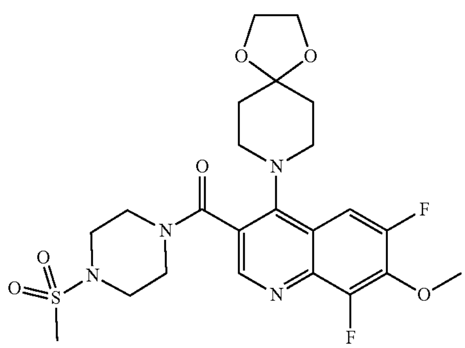 [SMILES: COc1c(F)cc2c(N3CCC4(CC3)OCCO4)c(C(=O)N3CCN(S(C)(=O)=O)CC3)cnc2c1F] | (6,8-difluoro-7-methoxy-4-(1,4-dioxa-8-azaspiro[4.5]decan-8-yl)quinolin-3-yl)(4-(methylsulfonyl)piperazin-1-yl)methanone, TFA |
| 134 | 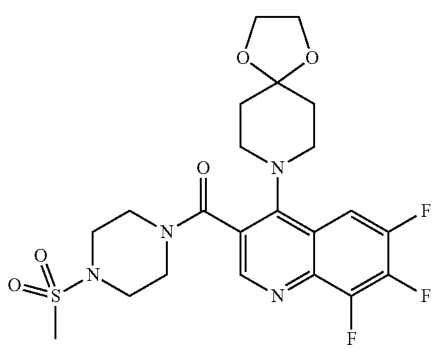 [SMILES: CS(=O)(=O)N1CCN(C(=O)c2cnc3c(F)c(F)c(F)cc3c2N2CCC3(CC2)OCCO3)CC1] | (4-(methylsulfonyl)piperazin-1-yl)(6,7,8-trifluoro-4-(1,4-dioxa-8-azaspiro[4.5]decan-8-yl)quinolin-3-yl)methanone, TFA |
| 135 | 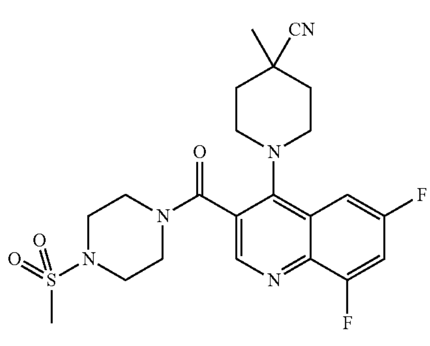 [SMILES: CC1(C#N)CCN(c2c(C(=O)N3CCN(S(C)(=O)=O)CC3)cnc3c(F)cc(F)cc23)CC1] | 1-(6,8-difluoro-3-(4-(methylsulfonyl)piperazine-1-carbonyl)quinolin-4-yl)-4-methylpiperidine-4-carbonitrile, TFA |

TABLE 1-continued

| Cpd. ID | Structure | Compound name |
|---|---|---|
| 136 | 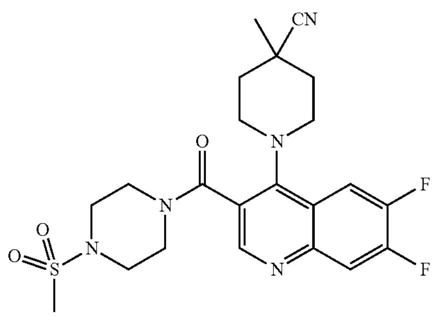 [SMILES: CC1(C#N)CCN(c2c(C(=O)N3CCN(S(C)(=O)=O)CC3)cnc3cc(F)c(F)cc23)CC1] | 1-(6,7-difluoro-3-(4-(methylsulfonyl)piperazine-1-carbonyl)quinolin-4-yl)-4-methylpiperidine-4-carbonitrile, TFA |
| 137 | 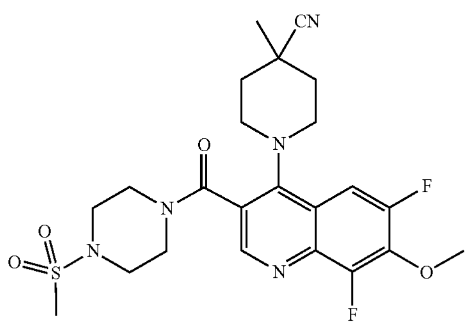 [SMILES: COc1c(F)cc2c(N3CCC(C)(C#N)CC3)c(C(=O)N3CCN(S(C)(=O)=O)CC3)cnc2c1F] | 1-(6,8-difluoro-7-methoxy-3-(4-(methylsulfonyl)piperazine-1-carbonyl)quinolin-4-yl)-4-methylpiperidine-4-carbonitrile, TFA |
| 138 | 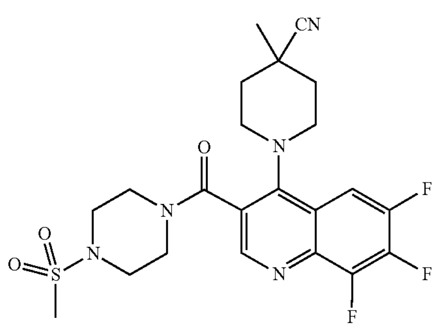 [SMILES: CC1(C#N)CCN(c2c(C(=O)N3CCN(S(C)(=O)=O)CC3)cnc3c(F)c(F)c(F)cc23)CC1] | 4-methyl-1-(6,7,8-trifluoro-3-(4-(methylsulfonyl)piperazine-1-carbonyl)quinolin-4-yl)piperidine-4-carbonitrile, TFA |
| 139 | 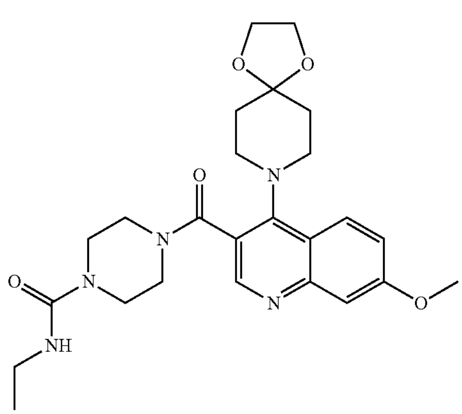 [SMILES: CCNC(=O)N1CCN(C(=O)c2cnc3cc(OC)ccc3c2N2CCC3(CC2)OCCO3)CC1] | N-ethyl-4-(7-methoxy-4-(1,4-dioxa-8-azaspiro[4.5]decan-8-yl)quinoline-3-carbonyl)piperazine-1-carboxamide, TFA |

TABLE 1-continued

| Cpd. ID | Structure | Compound name |
|---|---|---|
| 140 | 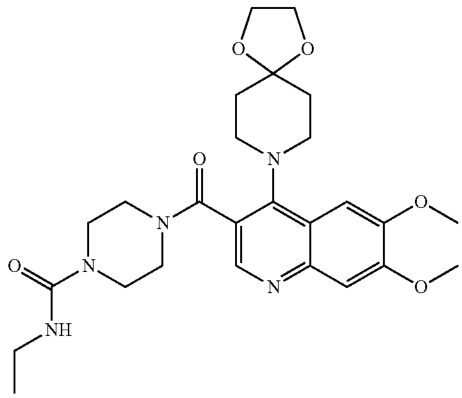 [SMILES: CCNC(=O)N1CCN(C(=O)c2cnc3cc(OC)c(OC)cc3c2N2CCC3(CC2)OCCO3)CC1] | 4-(6,7-dimethoxy-4-(1,4-dioxa-8-azaspiro[4.5]decan-8-yl)quinoline-3-carbonyl)-N-ethylpiperazine-1-carboxamide, TFA |
| 141 | 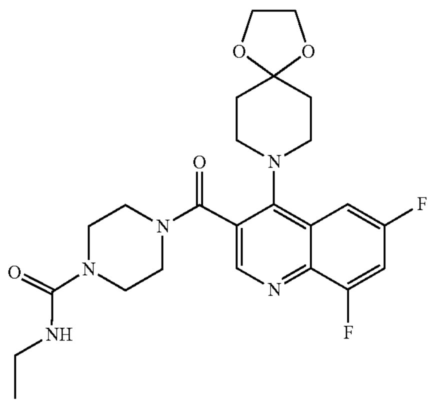 [SMILES: CCNC(=O)N1CCN(C(=O)c2cnc3c(F)cc(F)cc3c2N2CCC3(CC2)OCCO3)CC1] | 4-(6,8-difluoro-4-(1,4-dioxa-8-azaspiro[4.5]decan-8-yl)quinoline-3-carbonyl)-N-ethylpiperazine-1-carboxamide, TFA |
| 142 | 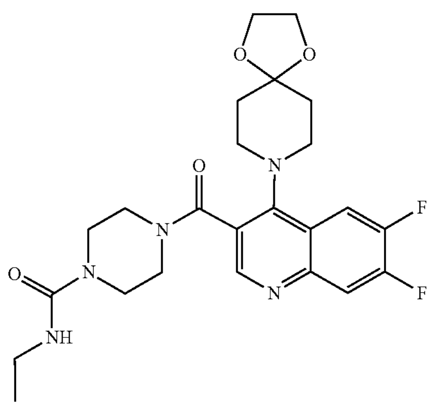 [SMILES: CCNC(=O)N1CCN(C(=O)c2cnc3cc(F)c(F)cc3c2N2CCC3(CC2)OCCO3)CC1] | 4-(6,7-difluoro-4-(1,4-dioxa-8-azaspiro[4.5]decan-8-yl)quinoline-3-carbonyl)-N-ethylpiperazine-1-carboxamide, TFA |
| 143 | 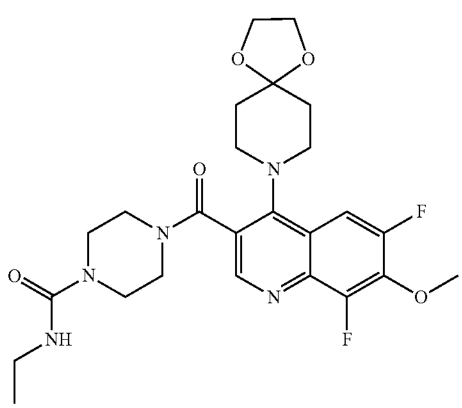 [SMILES: CCNC(=O)N1CCN(C(=O)c2cnc3c(F)c(OC)c(F)cc3c2N2CCC3(CC2)OCCO3)CC1] | 4-(6,8-difluoro-7-methoxy-4-(1,4-dioxa-8-azaspiro[4.5]decan-8-yl)quinoline-3-carbonyl)-N-ethylpiperazine-1-carboxamide, TFA |

TABLE 1-continued

| Cpd. ID | Structure | Compound name |
|---|---|---|
| 144 | 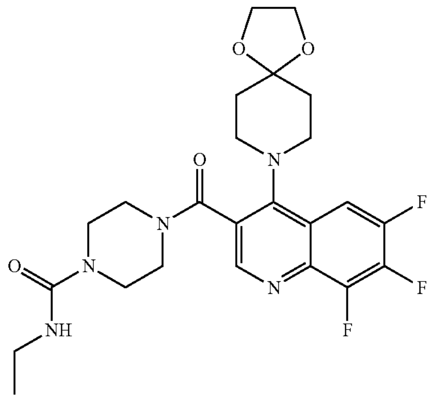 [SMILES: CCNC(=O)N1CCN(C(=O)c2cnc3c(F)c(F)c(F)cc3c2N2CCC3(CC2)OCCO3)CC1] | N-ethyl-4-(6,7,8-trifluoro-4-(1,4-dioxa-8-azaspiro[4.5]decan-8-yl)quinoline-3-carbonyl)piperazine-1-carboxamide, TFA |
| 145 | 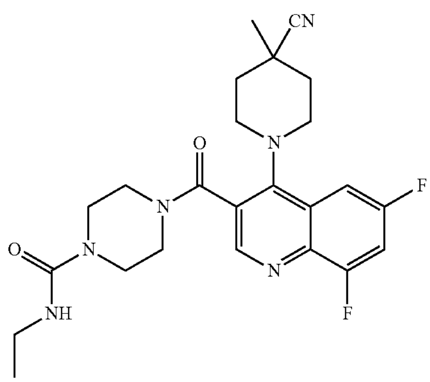 [SMILES: CCNC(=O)N1CCN(C(=O)c2cnc3c(F)cc(F)cc3c2N2CCC(C)(C#N)CC2)CC1] | 4-(4-(4-cyano-4-methylpiperidin-1-yl)-6,8-difluoroquinoline-3-carbonyl)-N-ethylpiperazine-1-carboxamide, TFA |
| 146 | 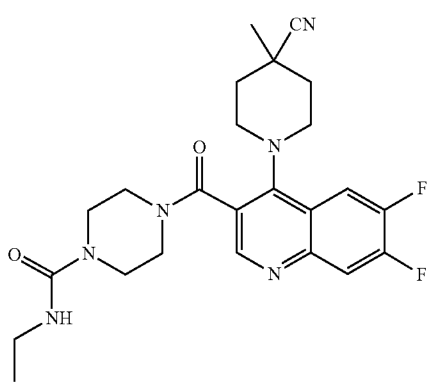 [SMILES: CCNC(=O)N1CCN(C(=O)c2cnc3cc(F)c(F)cc3c2N2CCC(C)(C#N)CC2)CC1] | 4-(4-(4-cyano-4-methylpiperidin-1-yl)-6,7-difluoroquinoline-3-carbonyl)-N-ethylpiperazine-1-carboxamide, TFA |
| 147 | 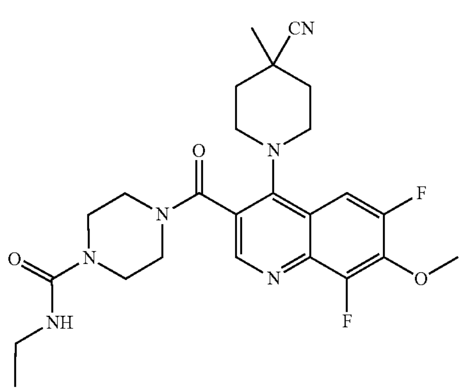 [SMILES: CCNC(=O)N1CCN(C(=O)c2cnc3c(F)c(OC)c(F)cc3c2N2CCC(C)(C#N)CC2)CC1] | 4-(4-(4-cyano-4-methylpiperidin-1-yl)-6,8-difluoro-7-methoxyquinoline-3-carbonyl)-N-ethylpiperazine-1-carboxamide, TFA |

TABLE 1-continued

| Cpd. ID | Structure | Compound name |
|---|---|---|
| 148 | 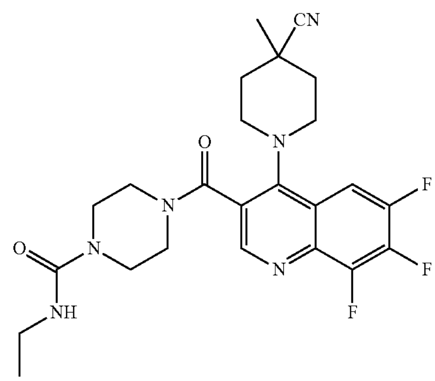 [SMILES: CCNC(=O)N1CCN(C(=O)c2cnc3c(F)c(F)c(F)cc3c2N2CCC(C)(C#N)CC2)CC1] | 4-(4-(4-cyano-4-methylpiperidin-1-yl)-6,7,8-trifluoroquinoline-3-carbonyl)-N-ethylpiperazine-1-carboxamide, TFA |
| 149 | 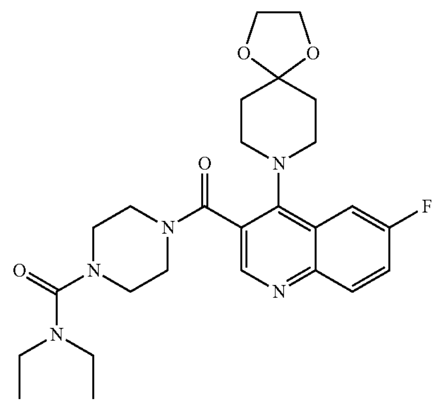 [SMILES: CCN(CC)C(=O)N1CCN(C(=O)c2cnc3ccc(F)cc3c2N2CCC3(CC2)OCCO3)CC1] | N,N-diethyl-4-(6-fluoro-4-(1,4-dioxa-8-azaspiro[4.5]decan-8-yl)quinoline-3-carbonyl)piperazine-1-carboxamide, TFA |
| 150 | 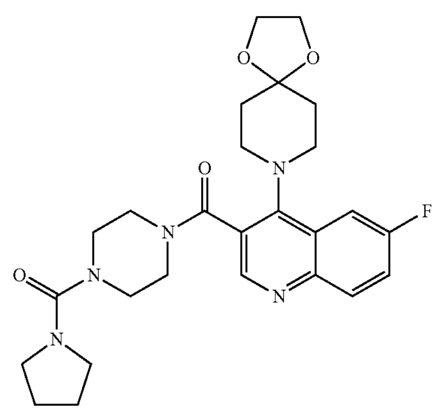 [SMILES: O=C(c1cnc2ccc(F)cc2c1N1CCC2(CC1)OCCO2)N1CCN(C(=O)N2CCCC2)CC1] | (6-fluoro-4-(1,4-dioxa-8-azaspiro[4.5]decan-8-yl)quinolin-3-yl)(4-(pyrrolidine-1-carbonyl)piperazin-1-yl)methanone, TFA |
| 151 | 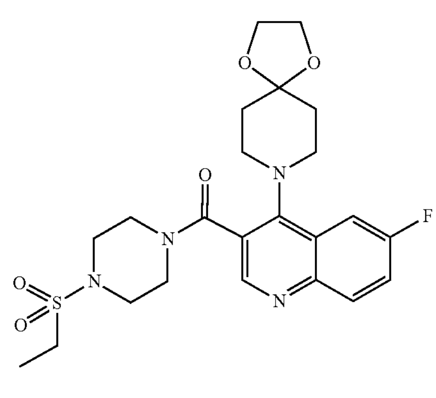 [SMILES: CCS(=O)(=O)N1CCN(C(=O)c2cnc3ccc(F)cc3c2N2CCC3(CC2)OCCO3)CC1] | (4-(ethylsulfonyl)piperazin-1-yl)(6-fluoro-4-(1,4-dioxa-8-azaspiro[4.5]decan-8-yl)quinolin-3-yl)methanone, TFA |

TABLE 1-continued

| Cpd. ID | Structure | Compound name |
|---|---|---|
| 152 | 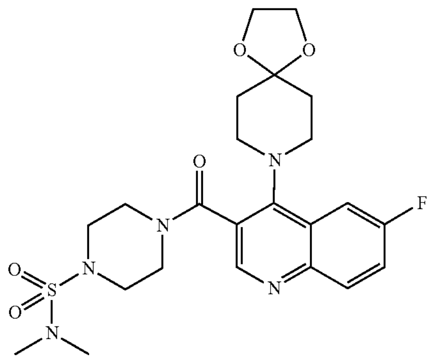 [SMILES: CN(C)S(=O)(=O)N1CCN(C(=O)c2cnc3ccc(F)cc3c2N2CCC3(CC2)OCCO3)CC1] | 4-(6-fluoro-4-(1,4-dioxa-8-azaspiro[4.5]decan-8-yl)quinoline-3-carbonyl)-N,N-dimethylpiperazine-1-sulfonamide, TFA |
| 153 | 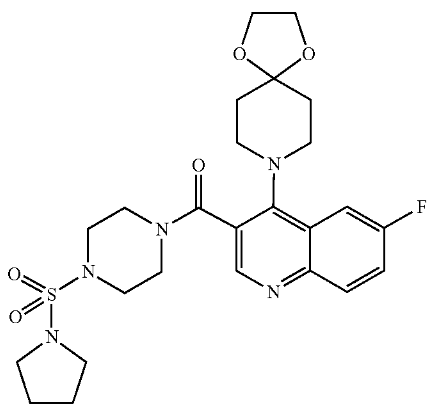 [SMILES: O=C(c1cnc2ccc(F)cc2c1N1CCC2(CC1)OCCO2)N1CCN(S(=O)(=O)N2CCCC2)CC1] | (6-fluoro-4-(1,4-dioxa-8-azaspiro[4.5]decan-8-yl)quinolin-3-yl)(4-(pyrrolidin-1-ylsulfonyl)piperazin-1-yl)methanone, TFA |
| 154 | 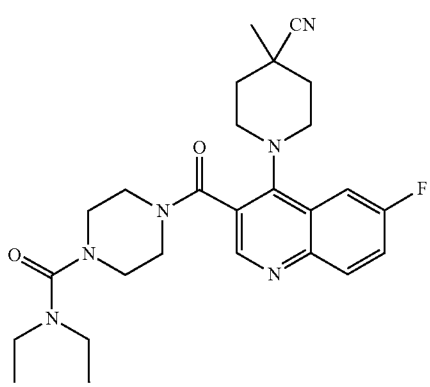 [SMILES: CCN(CC)C(=O)N1CCN(C(=O)c2cnc3ccc(F)cc3c2N2CCC(C)(C#N)CC2)CC1] | 4-(4-(4-cyano-4-methylpiperidin-1-yl)-6-fluoroquinoline-3-carbonyl)-N,N-diethylpiperazine-1-carboxamide, TFA |
| 155 | 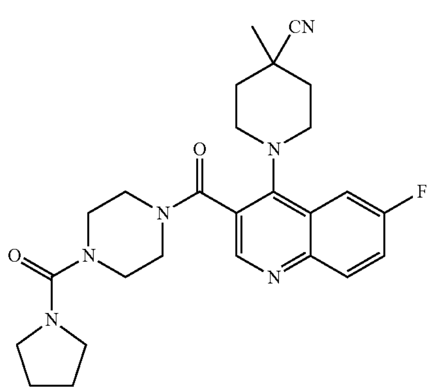 [SMILES: CC1(C#N)CCN(c2c(C(=O)N3CCN(C(=O)N4CCCC4)CC3)cnc3ccc(F)cc23)CC1] | 1-(6-fluoro-3-(4-(pyrrolidine-1-carbonyl)piperazine-1-carbonyl)quinolin-4-yl)-4-methylpiperidine-4-carbonitrile, TFA |

TABLE 1-continued

| Cpd. ID | Structure | Compound name |
| --- | --- | --- |
| 156 | 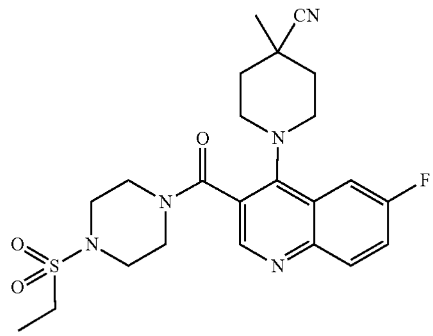 [SMILES: CCS(=O)(=O)N1CCN(C(=O)c2cnc3ccc(F)cc3c2N2CCC(C)(C#N)CC2)CC1] | 1-(3-(4-(ethylsulfonyl)piperazine-1-carbonyl)-6-fluoroquinolin-4-yl)-4-methylpiperidine-4-carbonitrile, TFA |
| 157 | 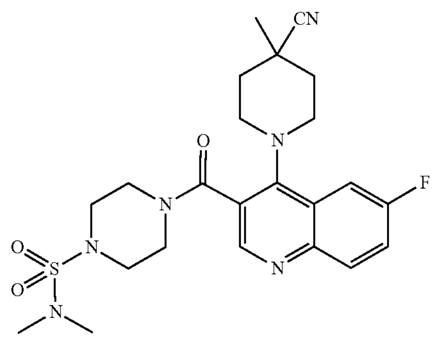 [SMILES: CN(C)S(=O)(=O)N1CCN(C(=O)c2cnc3ccc(F)cc3c2N2CCC(C)(C#N)CC2)CC1] | 4-(4-(4-cyano-4-methylpiperidin-1-yl)-6-fluoroquinoline-3-carbonyl)-N,N-dimethylpiperazine-1-sulfonamide, TFA |
| 158 | 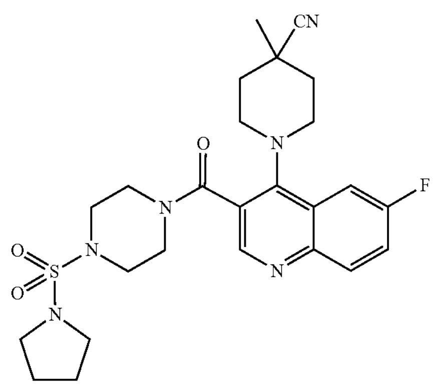 [SMILES: CC1(C#N)CCN(c2c(C(=O)N3CCN(S(=O)(=O)N4CCCC4)CC3)cnc3ccc(F)cc23)CC1] | 1-(6-fluoro-3-(4-(pyrrolidin-1-ylsulfonyl)piperazine-1-carbonyl)quinolin-4-yl)-4-methylpiperidine-4-carbonitrile, TFA |
| 159 | 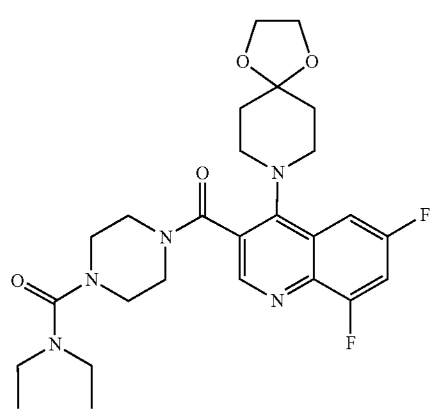 [SMILES: CCN(CC)C(=O)N1CCN(C(=O)c2cnc3c(F)cc(F)cc3c2N2CCC3(CC2)OCCO3)CC1] | 4-(6,8-difluoro-4-(1,4-dioxa-8-azaspiro[4.5]decan-8-yl)quinoline-3-carbonyl)-N,N-diethylpiperazine-1-carboxamide, TFA |

TABLE 1-continued

| Cpd. ID | Structure | Compound name |
| --- | --- | --- |
| 160 | 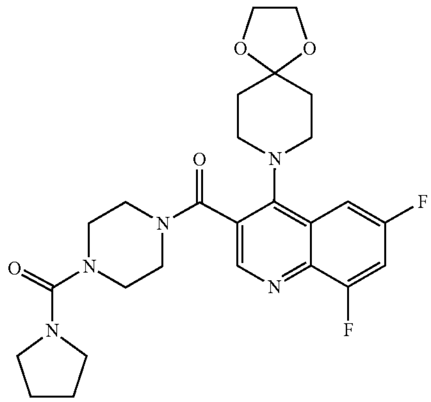 [SMILES: O=C(c1cnc2c(F)cc(F)cc2c1N1CCC2(CC1)OCCO2)N1CCN(C(=O)N2CCCC2)CC1] | (6,8-difluoro-4-(1,4-dioxa-8-azaspiro[4.5]decan-8-yl)quinolin-3-yl)(4-(pyrrolidine-1-carbonyl)piperazin-1-yl)methanone, TFA |
| 161 | 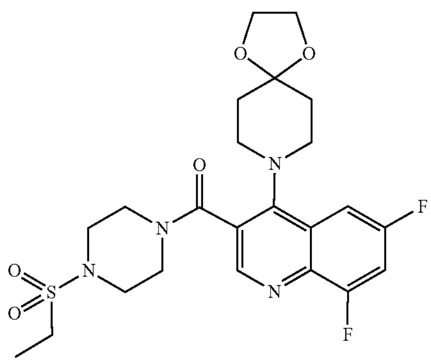 [SMILES: CCS(=O)(=O)N1CCN(C(=O)c2cnc3c(F)cc(F)cc3c2N2CCC3(CC2)OCCO3)CC1] | (6,8-difluoro-4-(1,4-dioxa-8-azaspiro[4.5]decan-8-yl)quinolin-3-yl)(4-(ethylsulfonyl)piperazin-1-yl)methanone, TFA |
| 162 | 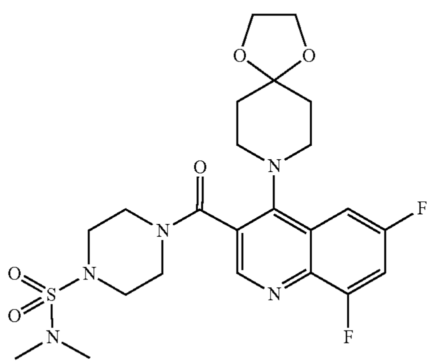 [SMILES: CN(C)S(=O)(=O)N1CCN(C(=O)c2cnc3c(F)cc(F)cc3c2N2CCC3(CC2)OCCO3)CC1] | 4-(6,8-difluoro-4-(1,4-dioxa-8-azaspiro[4.5]decan-8-yl)quinoline-3-carbonyl)-N,N-dimethylpiperazine-1-sulfonamide, TFA |
| 163 | 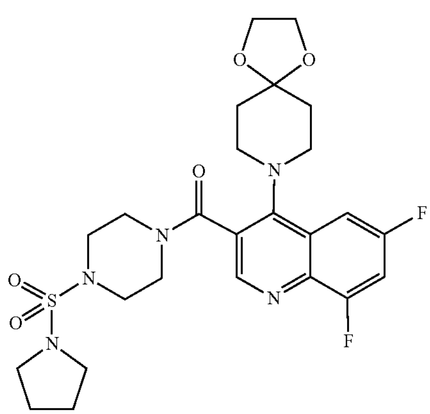 [SMILES: O=C(c1cnc2c(F)cc(F)cc2c1N1CCC2(CC1)OCCO2)N1CCN(S(=O)(=O)N2CCCC2)CC1] | (6,8-difluoro-4-(1,4-dioxa-8-azaspiro[4.5]decan-8-yl)quinolin-3-yl)(4-(pyrrolidin-1-ylsulfonyl)piperazin-1-yl)methanone, TFA |

TABLE 1-continued

| Cpd. ID | Structure | Compound name |
|---|---|---|
| 164 | 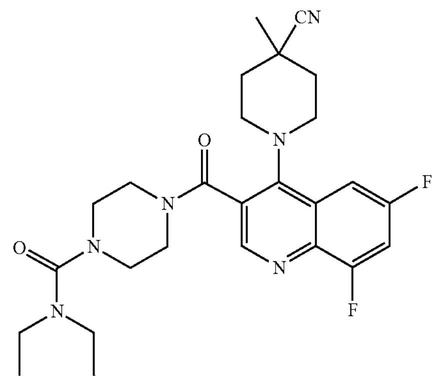 [SMILES: CCN(CC)C(=O)N1CCN(C(=O)c2cnc3c(F)cc(F)cc3c2N2CCC(C)(C#N)CC2)CC1] | 4-(4-(4-cyano-4-methylpiperidin-1-yl)-6,8-difluoroquinoline-3-carbonyl)-N,N-diethylpiperazine-1-carboxamide, TFA |
| 165 | 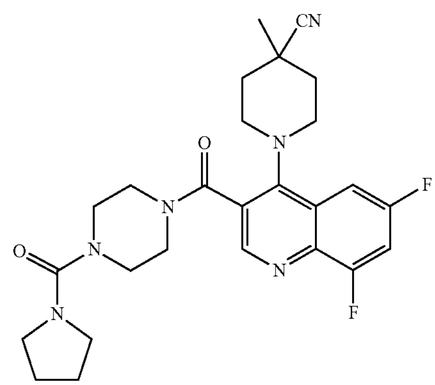 [SMILES: CC1(C#N)CCN(c2c(C(=O)N3CCN(C(=O)N4CCCC4)CC3)cnc3c(F)cc(F)cc23)CC1] | 1-(6,8-difluoro-3-(4-(pyrrolidine-1-carbonyl)piperazine-1-carbonyl)quinolin-4-yl)-4-methylpiperidine-4-carbonitrile, TFA |
| 166 | 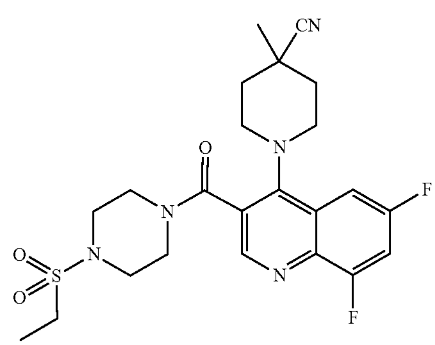 [SMILES: CCS(=O)(=O)N1CCN(C(=O)c2cnc3c(F)cc(F)cc3c2N2CCC(C)(C#N)CC2)CC1] | 1-(3-(4-(ethylsulfonyl)piperazine-1-carbonyl)-6,8-difluoroquinolin-4-yl)-4-methylpiperidine-4-carbonitrile, TFA |
| 167 | 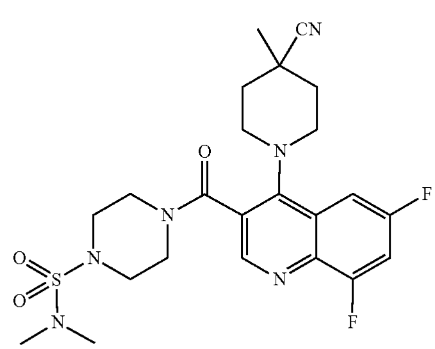 [SMILES: CN(C)S(=O)(=O)N1CCN(C(=O)c2cnc3c(F)cc(F)cc3c2N2CCC(C)(C#N)CC2)CC1] | 4-(4-(4-cyano-4-methylpiperidin-1-yl)-6,8-difluoroquinoline-3-carbonyl)-N,N-dimethylpiperazine-1-sulfonamide, TFA |

TABLE 1-continued

| Cpd. ID | Structure | Compound name |
|---|---|---|
| 168 | 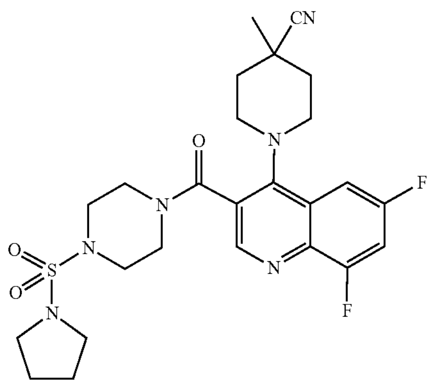 [SMILES: CC1(C#N)CCN(c2c(C(=O)N3CCN(S(=O)(=O)N4CCCC4)CC3)cnc3c(F)cc(F)cc23)CC1] | 1-(6,8-difluoro-3-(4-(pyrrolidin-1-ylsulfonyl)piperazine-1-carbonyl)quinolin-4-yl)-4-methylpiperidine-4-carbonitrile, TFA |
| 169 | 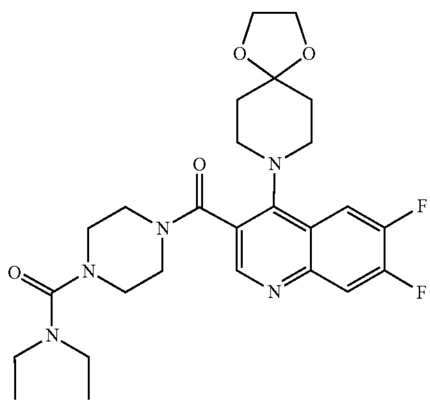 [SMILES: CCN(CC)C(=O)N1CCN(C(=O)c2cnc3cc(F)c(F)cc3c2N2CCC3(CC2)OCCO3)CC1] | 4-(6,7-difluoro-4-(1,4-dioxa-8-azaspiro[4.5]decan-8-yl)quinoline-3-carbonyl)-N,N-diethylpiperazine-1-carboxamide, TFA |
| 170 | 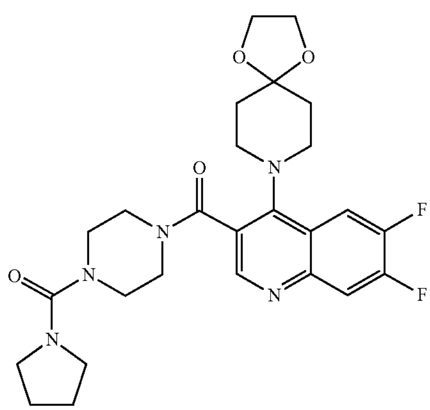 [SMILES: O=C(c1cnc2cc(F)c(F)cc2c1N1CCC2(CC1)OCCO2)N1CCN(C(=O)N2CCCC2)CC1] | (6,7-difluoro-4-(1,4-dioxa-8-azaspiro[4.5]decan-8-yl)quinolin-3-yl)(4-(pyrrolidine-1-carbonyl)piperazin-1-yl)methanone, TFA |
| 171 | 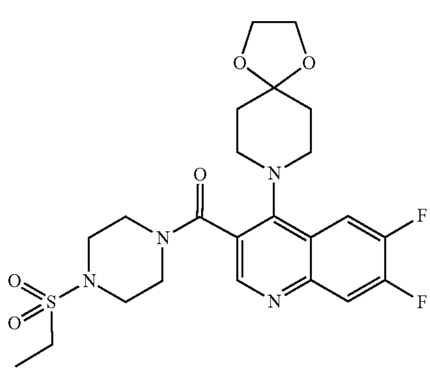 [SMILES: CCS(=O)(=O)N1CCN(C(=O)c2cnc3cc(F)c(F)cc3c2N2CCC3(CC2)OCCO3)CC1] | (6,7-difluoro-4-(1,4-dioxa-8-azaspiro[4.5]decan-8-yl)quinolin-3-yl)(4-(ethylsulfonyl)piperazin-1-yl)methanone, TFA |

TABLE 1-continued

| Cpd. ID | Structure | Compound name |
|---|---|---|
| 172 | 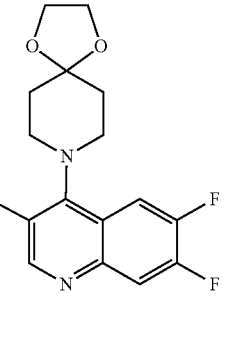 | 4-(6,7-difluoro-4-(1,4-dioxa-8-azaspiro[4.5]decan-8-yl)quinoline-3-carbonyl)-N,N-dimethylpiperazine-1-sulfonamide, TFA |
| 173 | 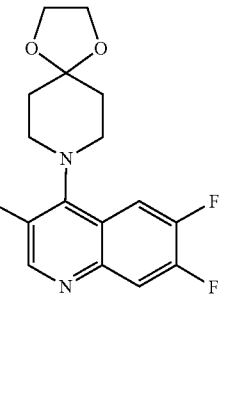 | (6,7-difluoro-4-(1,4-dioxa-8-azaspiro[4.5]decan-8-yl)quinolin-3-yl)(4-(pyrrolidin-1-ylsulfonyl)piperazin-1-yl)methanone, TFA |
| 174 | 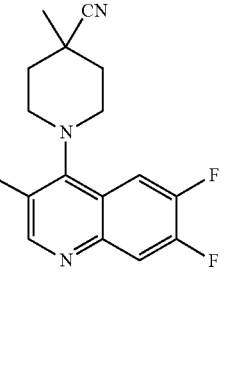 | 4-(4-(4-cyano-4-methylpiperidin-1-yl)-6,7-difluoroquinoline-3-carbonyl)-N,N-diethylpiperazine-1-carboxamide, TFA |
| 175 | 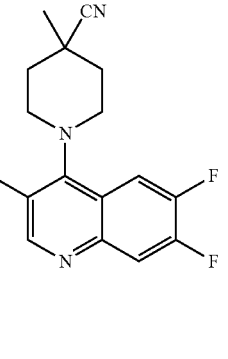 | 1-(6,7-difluoro-3-(4-(pyrrolidine-1-carbonyl)piperazine-1-carbonyl)quinolin-4-yl)-4-methylpiperidine-4-carbonitrile, TFA |

TABLE 1-continued

| Cpd. ID | Structure | Compound name |
|---|---|---|
| 176 | 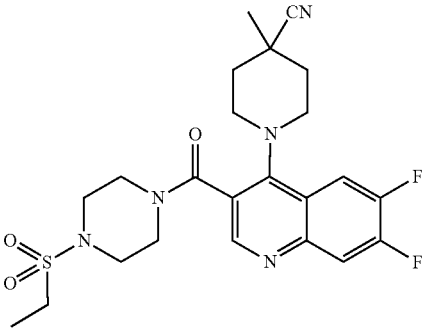 [SMILES: CCS(=O)(=O)N1CCN(C(=O)c2cnc3cc(F)c(F)cc3c2N2CCC(C)(C#N)CC2)CC1] | 1-(3-(4-(ethylsulfonyl)piperazine-1-carbonyl)-6,7-difluoroquinolin-4-yl)-4-methylpiperidine-4-carbonitrile, TFA |
| 177 | 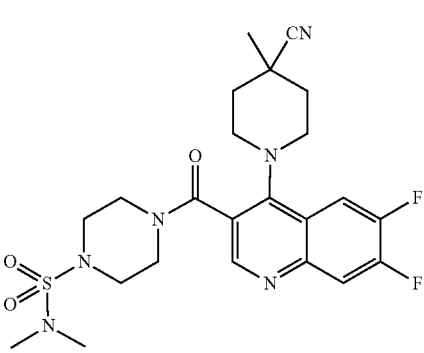 [SMILES: CN(C)S(=O)(=O)N1CCN(C(=O)c2cnc3cc(F)c(F)cc3c2N2CCC(C)(C#N)CC2)CC1] | 4-(4-(4-cyano-4-methylpiperidin-1-yl)-6,7-difluoroquinoline-3-carbonyl)-N,N-dimethylpiperazine-1-sulfonamide, TFA |
| 178 | 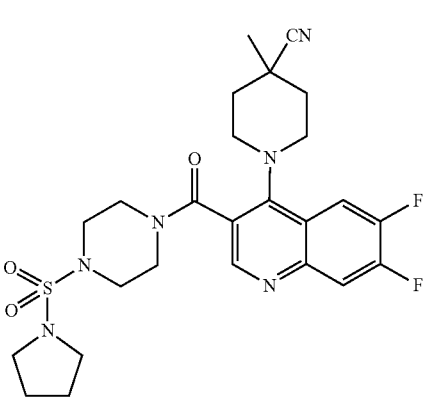 [SMILES: CC1(C#N)CCN(c2c(C(=O)N3CCN(S(=O)(=O)N4CCCC4)CC3)cnc3cc(F)c(F)cc23)CC1] | 1-(6,7-difluoro-3-(4-(pyrrolidin-1-ylsulfonyl)piperazine-1-carbonyl)quinolin-4-yl)-4-methylpiperidine-4-carbonitrile, TFA |
| 179 | 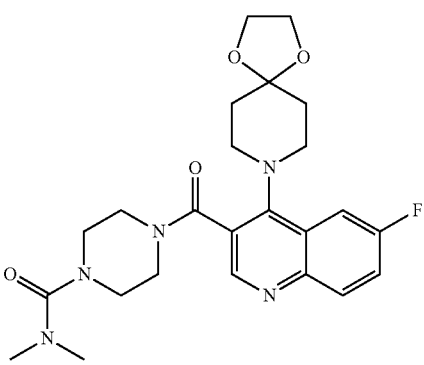 [SMILES: CN(C)C(=O)N1CCN(C(=O)c2cnc3ccc(F)cc3c2N2CCC3(CC2)OCCO3)CC1] | 4-(6-fluoro-4-(1,4-dioxa-8-azaspiro[4.5]decan-8-yl)quinoline-3-carbonyl)-N,N-dimethylpiperazine-1-carboxamide, TFA |

TABLE 1-continued

| Cpd. ID | Structure | Compound name |
| --- | --- | --- |
| 180 | 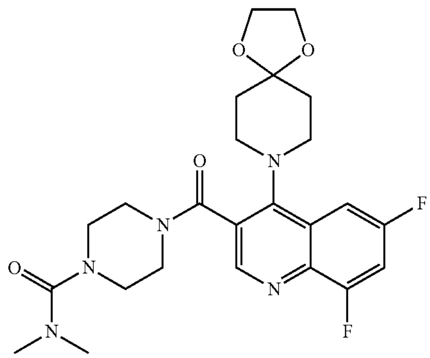 [SMILES: CN(C)C(=O)N1CCN(C(=O)c2cnc3c(F)cc(F)cc3c2N2CCC3(CC2)OCCO3)CC1] | 4-(6,8-difluoro-4-(1,4-dioxa-8-azaspiro[4.5]decan-8-yl)quinoline-3-carbonyl)-N,N-dimethylpiperazine-1-carboxamide, TFA |
| 181 | 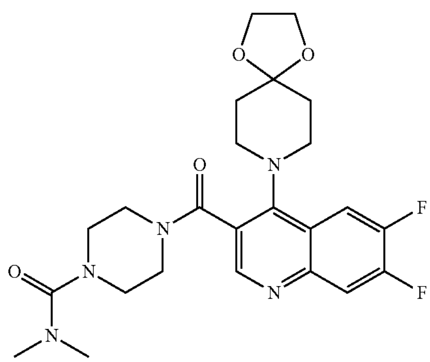 [SMILES: CN(C)C(=O)N1CCN(C(=O)c2cnc3cc(F)c(F)cc3c2N2CCC3(CC2)OCCO3)CC1] | 4-(6,7-difluoro-4-(1,4-dioxa-8-azaspiro[4.5]decan-8-yl)quinoline-3-carbonyl)-N,N-dimethylpiperazine-1-carboxamide, TFA |
| 182 | 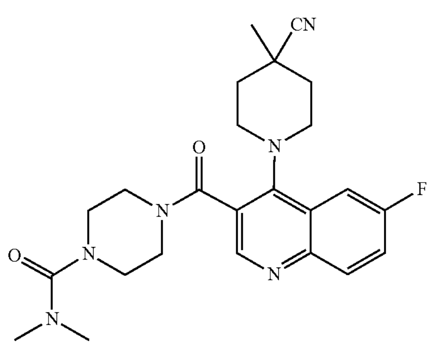 [SMILES: CN(C)C(=O)N1CCN(C(=O)c2cnc3ccc(F)cc3c2N2CCC(C)(C#N)CC2)CC1] | 4-(4-(4-cyano-4-methylpiperidin-1-yl)-6-fluoroquinoline-3-carbonyl)-N,N-dimethylpiperazine-1-carboxamide, TFA |
| 183 | 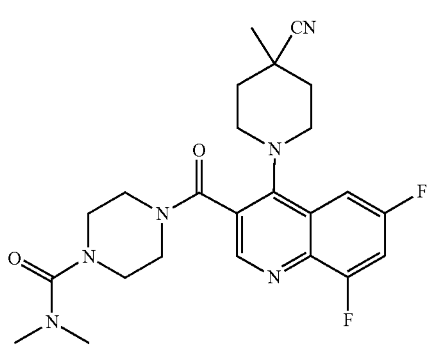 [SMILES: CN(C)C(=O)N1CCN(C(=O)c2cnc3c(F)cc(F)cc3c2N2CCC(C)(C#N)CC2)CC1] | 4-(4-(4-cyano-4-methylpiperidin-1-yl)-6,8-difluoroquinoline-3-carbonyl)-N,N-dimethylpiperazine-1-carboxamide, TFA |

TABLE 1-continued

| Cpd. ID | Structure | Compound name |
|---|---|---|
| 184 | 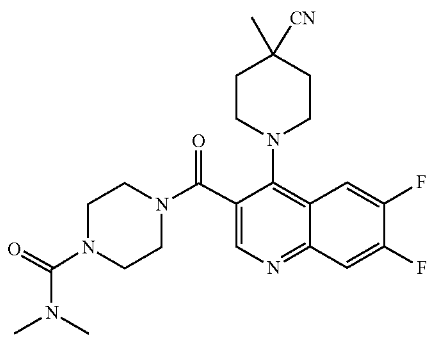 [SMILES: CN(C)C(=O)N1CCN(C(=O)c2cnc3cc(F)c(F)cc3c2N2CCC(C)(C#N)CC2)CC1] | 4-(4-(4-cyano-4-methylpiperidin-1-yl)-6,7-difluoroquinoline-3-carbonyl)-N,N-dimethylpiperazine-1-carboxamide, TFA |
| 185 | 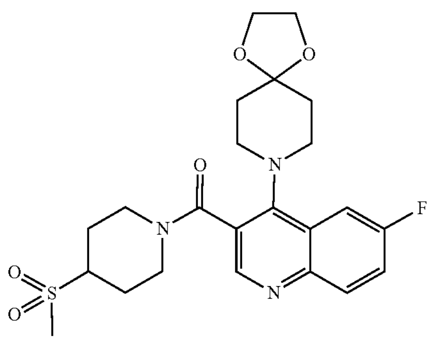 [SMILES: CS(=O)(=O)C1CCN(C(=O)c2cnc3ccc(F)cc3c2N2CCC3(CC2)OCCO3)CC1] | (6-fluoro-4-(1,4-dioxa-8-azaspiro[4.5]decan-8-yl)quinolin-3-yl)(4-(methylsulfonyl)piperidin-1-yl)methanone, TFA |
| 186 | 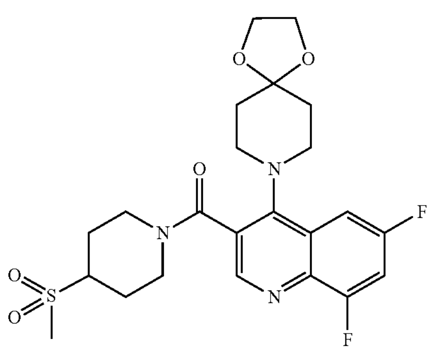 [SMILES: CS(=O)(=O)C1CCN(C(=O)c2cnc3c(F)cc(F)cc3c2N2CCC3(CC2)OCCO3)CC1] | (6,8-difluoro-4-(1,4-dioxa-8-azaspiro[4.5]decan-8-yl)quinolin-3-yl)(4-(methylsulfonyl)piperidin-1-yl)methanone, TFA |
| 187 | 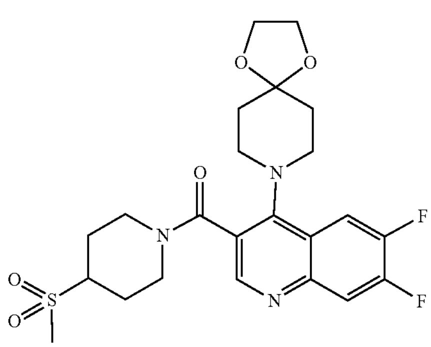 [SMILES: CS(=O)(=O)C1CCN(C(=O)c2cnc3cc(F)c(F)cc3c2N2CCC3(CC2)OCCO3)CC1] | (6,7-difluoro-4-(1,4-dioxa-8-azaspiro[4.5]decan-8-yl)quinolin-3-yl)(4-(methylsulfonyl)piperidin-1-yl)methanone, TFA |

TABLE 1-continued

| Cpd. ID | Structure | Compound name |
|---|---|---|
| 188 | 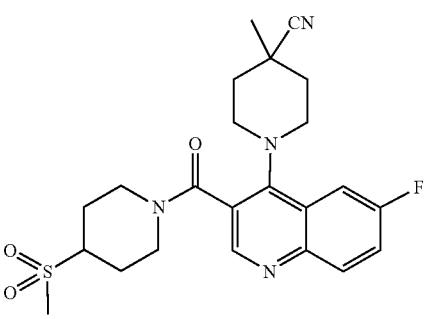 [SMILES: CC1(C#N)CCN(c2c(C(=O)N3CCC(S(C)(=O)=O)CC3)cnc3ccc(F)cc23)CC1] | 1-(6-fluoro-3-(4-(methylsulfonyl)piperidine-1-carbonyl)quinolin-4-yl)-4-methylpiperidine-4-carbonitrile, TFA |
| 189 | 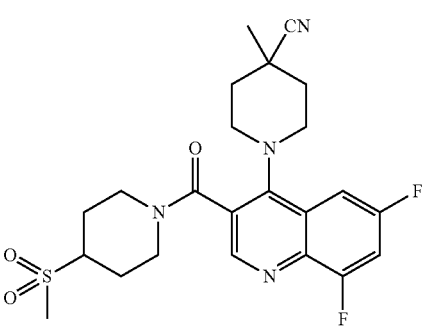 [SMILES: CC1(C#N)CCN(c2c(C(=O)N3CCC(S(C)(=O)=O)CC3)cnc3c(F)cc(F)cc23)CC1] | 1-(6,8-difluoro-3-(4-(methylsulfonyl)piperidine-1-carbonyl)quinolin-4-yl)-4-methylpiperidine-4-carbonitrile, TFA |
| 190 | 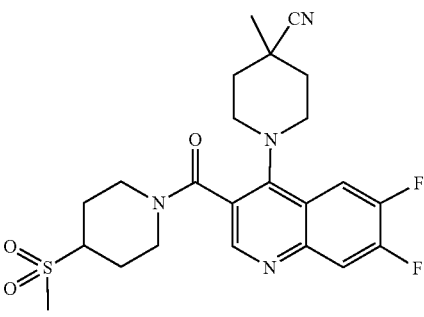 [SMILES: CC1(C#N)CCN(c2c(C(=O)N3CCC(S(C)(=O)=O)CC3)cnc3cc(F)c(F)cc23)CC1] | 1-(6,7-difluoro-3-(4-(methylsulfonyl)piperidine-1-carbonyl)quinolin-4-yl)-4-methylpiperidine-4-carbonitrile, TFA |
| 191 | 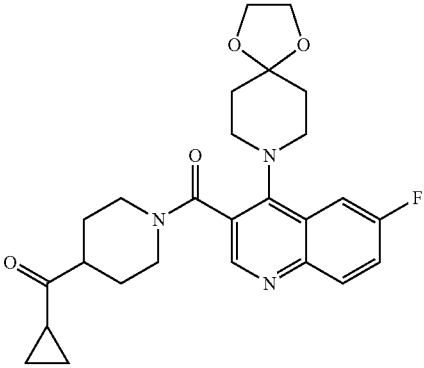 [SMILES: O=C(C1CC1)C1CCN(C(=O)c2cnc3ccc(F)cc3c2N2CCC3(CC2)OCCO3)CC1] | (4-(cyclopropanecarbonyl)piperidin-1-yl)(6-fluoro-4-(1,4-dioxa-8-azaspiro[4.5]decan-8-yl)quinolin-3-yl)methanone, TFA |

TABLE 1-continued

| Cpd. ID | Structure | Compound name |
|---|---|---|
| 192 | 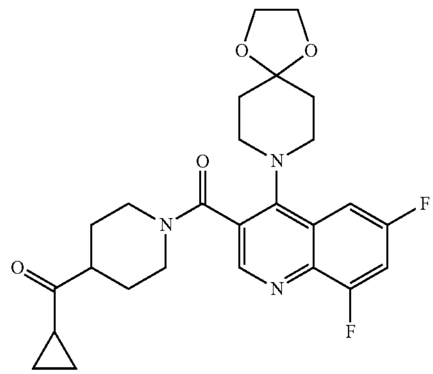 [SMILES: O=C(C1CC1)C1CCN(C(=O)c2cnc3c(F)cc(F)cc3c2N2CCC3(CC2)OCCO3)CC1] | (4-(cyclopropanecarbonyl)piperidin-1-yl)(6,8-difluoro-4-(1,4-dioxa-8-azaspiro[4.5]decan-8-yl)quinolin-3-yl)methanone, TFA |
| 193 | 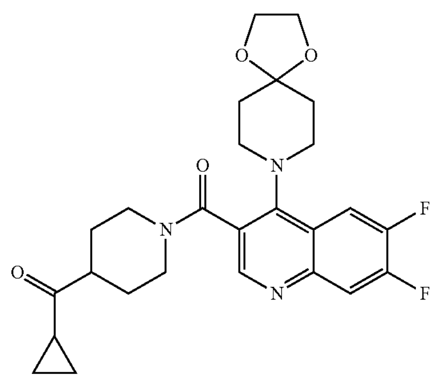 [SMILES: O=C(C1CC1)C1CCN(C(=O)c2cnc3cc(F)c(F)cc3c2N2CCC3(CC2)OCCO3)CC1] | (4-(cyclopropanecarbonyl)piperidin-1-yl)(6,7-difluoro-4-(1,4-dioxa-8-azaspiro[4.5]decan-8-yl)quinolin-3-yl)methanone, TFA |
| 194 | 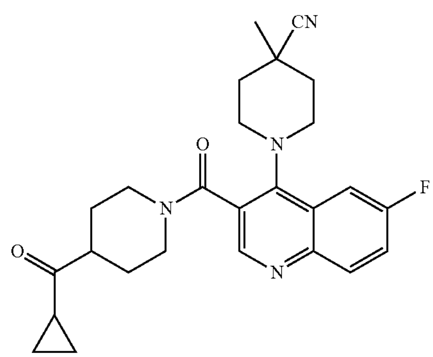 [SMILES: CC1(C#N)CCN(c2c(C(=O)N3CCC(C(=O)C4CC4)CC3)cnc3ccc(F)cc23)CC1] | 1-(3-(4-(cyclopropanecarbonyl)piperidine-1-carbonyl)-6-fluoroquinolin-4-yl)-4-methylpiperidine-4-carbonitrile, TFA |
| 195 | 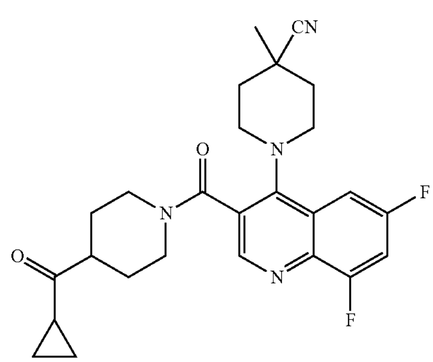 [SMILES: CC1(C#N)CCN(c2c(C(=O)N3CCC(C(=O)C4CC4)CC3)cnc3c(F)cc(F)cc23)CC1] | 1-(3-(4-(cyclopropanecarbonyl)piperidine-1-carbonyl)-6,8-difluoroquinolin-4-yl)-4-methylpiperidine-4-carbonitrile, TFA |

TABLE 1-continued

| Cpd. ID | Structure | Compound name |
|---|---|---|
| 196 | 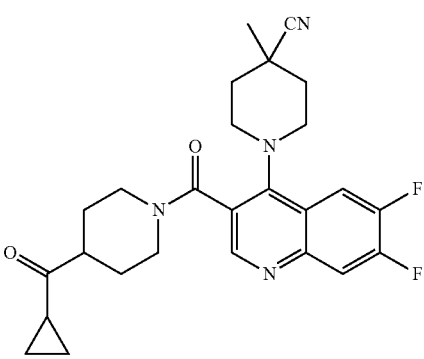 [SMILES: CC1(C#N)CCN(c2c(C(=O)N3CCC(C(=O)C4CC4)CC3)cnc3cc(F)c(F)cc23)CC1] | 1-(3-(4-(cyclopropanecarbonyl)piperidine-1-carbonyl)-6,7-difluoroquinolin-4-yl)-4-methylpiperidine-4-carbonitrile, TFA |
| 197 | 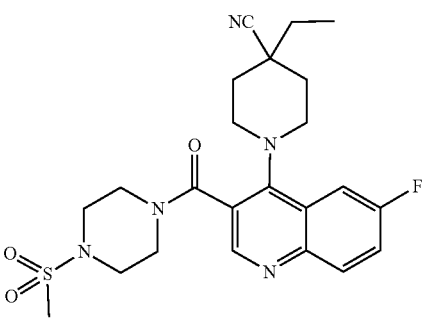 [SMILES: CCC1(C#N)CCN(c2c(C(=O)N3CCN(S(C)(=O)=O)CC3)cnc3ccc(F)cc23)CC1] | 4-ethyl-1-(6-fluoro-3-(4-(methylsulfonyl)piperazine-1-carbonyl)quinolin-4-yl)piperidine-4-carbonitrile, TFA, |
| 198 | 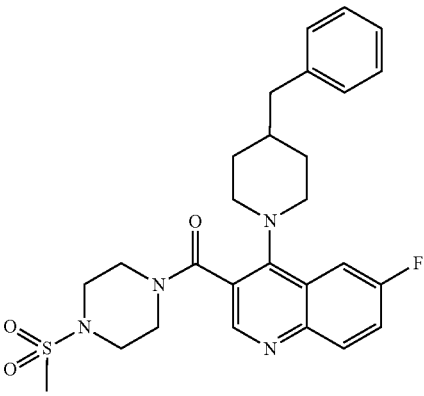 [SMILES: CS(=O)(=O)N1CCN(C(=O)c2cnc3ccc(F)cc3c2N2CCC(Cc3ccccc3)CC2)CC1] | (4-(4-benzylpiperidin-1-yl)-6-fluoroquinolin-3-yl)(4-(methylsulfonyl)piperazin-1-yl)methanone, TFA |
| 199 | 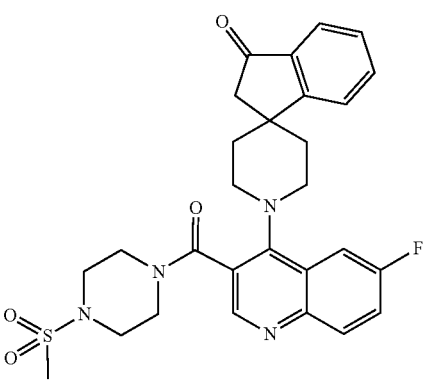 [SMILES: CS(=O)(=O)N1CCN(C(=O)c2cnc3ccc(F)cc3c2N2CCC3(CC2)CC(=O)c2ccccc23)CC1] | 1'-(6-fluoro-3-(4-(methylsulfonyl)piperazine-1-carbonyl)quinolin-4-yl)spiro[indene-1,4'-piperidin]-3(2H)-one, TFA |

TABLE 1-continued

| Cpd. ID | Structure | Compound name |
|---|---|---|
| 200 | 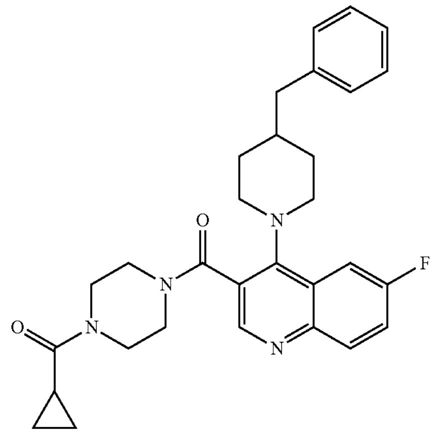 [SMILES: O=C(c1cnc2ccc(F)cc2c1N1CCC(Cc2ccccc2)CC1)N1CCN(C(=O)C2CC2)CC1] | (4-(4-benzylpiperidin-1-yl)-6-fluoroquinolin-3-yl)(4-(cyclopropanecarbonyl)piperazin-1-yl)methanone, TFA |
| 201 | 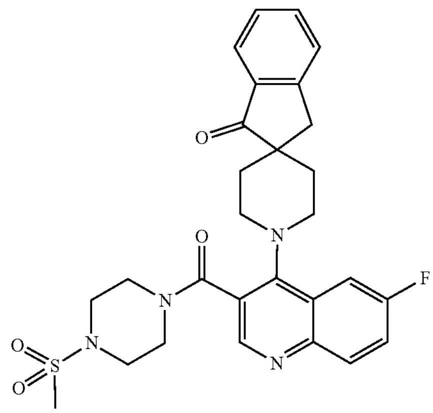 [SMILES: CS(=O)(=O)N1CCN(C(=O)c2cnc3ccc(F)cc3c2N2CCC3(CC2)Cc2ccccc2C3=O)CC1] | 1'-(6-fluoro-3-(4-(methylsulfonyl)piperazine-1-carbonyl)quinolin-4-yl)spiro[indene-2,4'-piperidin]-1(3H)-one, TFA |
| 202 | 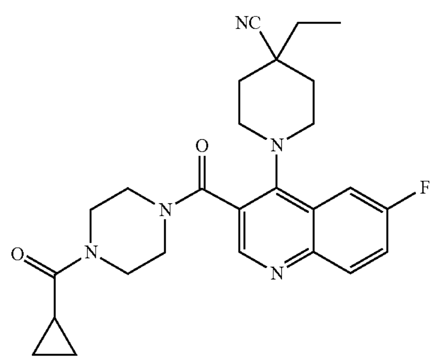 [SMILES: CCC1(C#N)CCN(c2c(C(=O)N3CCN(C(=O)C4CC4)CC3)cnc3ccc(F)cc23)CC1] | 1-(3-(4-(cyclopropanecarbonyl)piperazine-1-carbonyl)-6-fluoroquinolin-4-yl)-4-ethylpiperidine-4-carbonitrile, TFA |
| 203 | 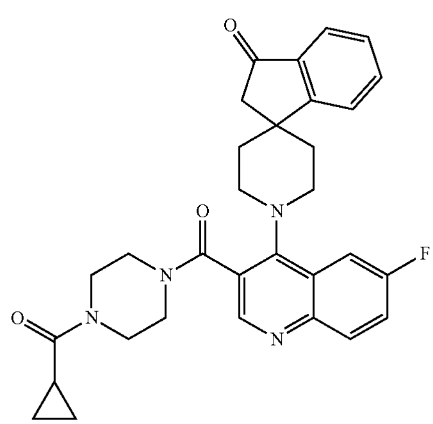 [SMILES: O=C1CC2(CCN(c3c(C(=O)N4CCN(C(=O)C5CC5)CC4)cnc4ccc(F)cc34)CC2)c2ccccc21] | 1'-(3-(4-(cyclopropanecarbonyl)piperazine-1-carbonyl)-6-fluoroquinolin-4-yl)spiro[indene-1,4'-piperidin]-3(2H)-one, TFA |

TABLE 1-continued

| Cpd. ID | Structure | Compound name |
|---|---|---|
| 204 | 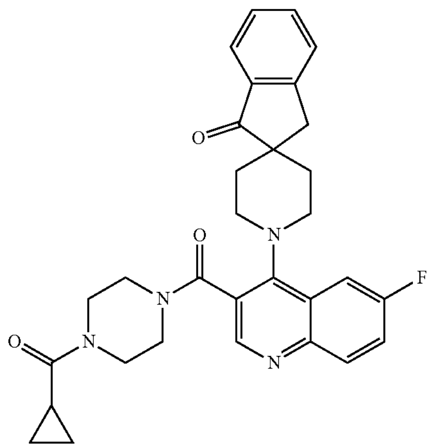 [SMILES: O=C(c1cnc2ccc(F)cc2c1N1CCC2(CC1)Cc1ccccc1C2=O)N1CCN(C(=O)C2CC2)CC1] | 1'-(3-(4-(cyclopropanecarbonyl)piperazine-1-carbonyl)-6-fluoroquinolin-4-yl)spiro[indene-2,4'-piperidin]-1(3H)-one, TFA |
| 205 | 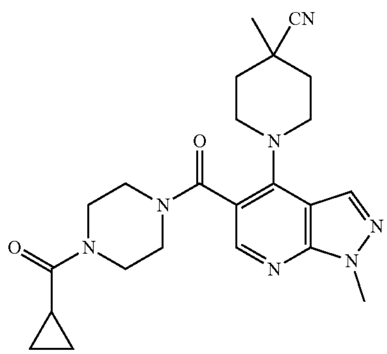 [SMILES: Cn1ncc2c(N3CCC(C)(C#N)CC3)c(C(=O)N3CCN(C(=O)C4CC4)CC3)cnc21] | 1-(5-(4-(cyclopropanecarbonyl)piperazine-1-carbonyl)-1-methyl-1H-pyrazolo[3,4-b]pyridin-4-yl)-4-methylpiperidine-4-carbonitrile, TFA |
| 206 | 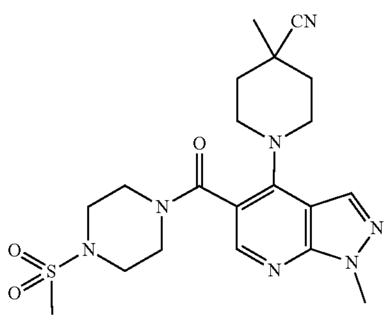 [SMILES: Cn1ncc2c(N3CCC(C)(C#N)CC3)c(C(=O)N3CCN(S(C)(=O)=O)CC3)cnc21] | 4-methyl-1-(1-methyl-5-(4-(methylsulfonyl)piperazine-1-carbonyl)-1H-pyrazolo[3,4-b]pyridin-4-yl)piperidine-4-carbonitrile, TFA |
| 207 | 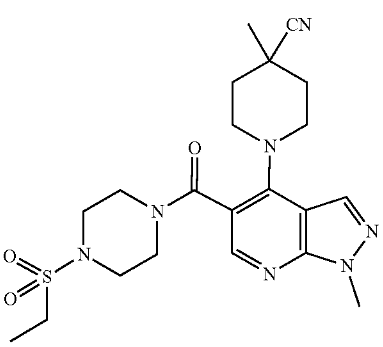 [SMILES: CCS(=O)(=O)N1CCN(C(=O)c2cnc3c(cnn3C)c2N2CCC(C)(C#N)CC2)CC1] | 1-(5-(4-(ethylsulfonyl)piperazine-1-carbonyl)-1-methyl-1H-pyrazolo[3,4-b]pyridin-4-yl)-4-methylpiperidine-4-carbonitrile, TFA |

TABLE 1-continued

| Cpd. ID | Structure | Compound name |
| --- | --- | --- |
| 208 | 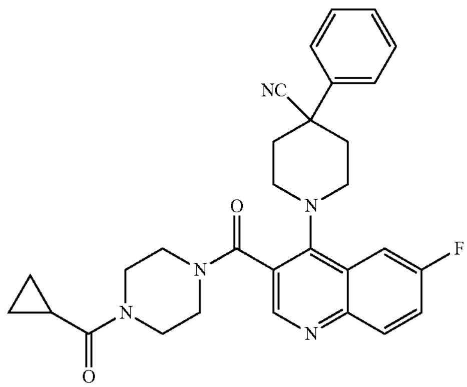 [SMILES: N#CC1(c2ccccc2)CCN(c2c(C(=O)N3CCN(C(=O)C4CC4)CC3)cnc3ccc(F)cc23)CC1] | 1-(3-(4-(cyclopropanecarbonyl)piperazine-1-carbonyl)-6-fluoroquinolin-4-yl)-4-phenylpiperidine-4-carbonitrile, TFA |
| 209 | 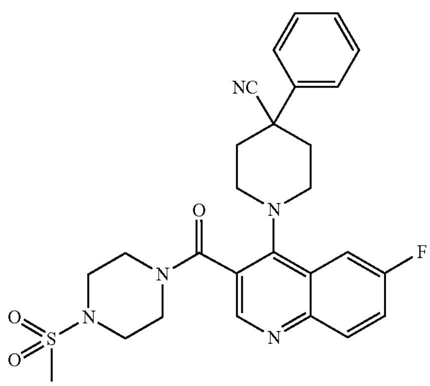 [SMILES: CS(=O)(=O)N1CCN(C(=O)c2cnc3ccc(F)cc3c2N2CCC(C#N)(c3ccccc3)CC2)CC1] | 1-(6-fluoro-3-(4-(methylsulfonyl)piperazine-1-carbonyl)quinolin-4-yl)-4-phenylpiperidine-4-carbonitrile, TFA |
| 210 | 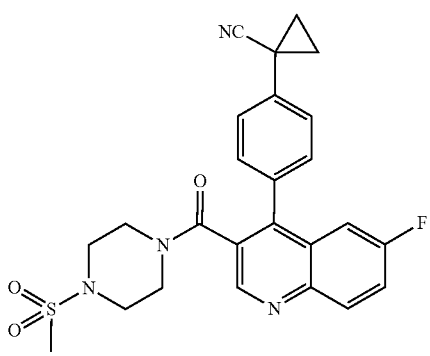 [SMILES: CS(=O)(=O)N1CCN(C(=O)c2cnc3ccc(F)cc3c2-c2ccc(C3(C#N)CC3)cc2)CC1] | 1-(4-(6-fluoro-3-(4-(methylsulfonyl)piperazine-1-carbonyl)quinolin-4-yl)phenyl)cyclopropanecarbonitrile, TFA |
| 211 | 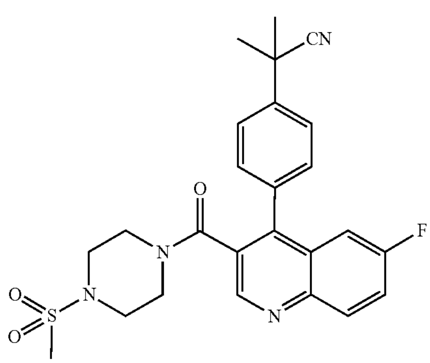 [SMILES: CC(C)(C#N)c1ccc(-c2c(C(=O)N3CCN(S(C)(=O)=O)CC3)cnc3ccc(F)cc23)cc1] | 2-(4-(6-fluoro-3-(4-(methylsulfonyl)piperazine-1-carbonyl)quinolin-4-yl)phenyl)-2-methylpropanenitrile, TFA |

TABLE 1-continued

| Cpd. ID | Structure | Compound name |
|---|---|---|
| 212 | 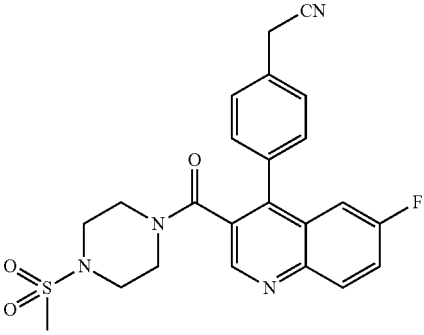 [SMILES: CS(=O)(=O)N1CCN(C(=O)c2cnc3ccc(F)cc3c2-c2ccc(CC#N)cc2)CC1] | 2-(4-(6-fluoro-3-(4-(methylsulfonyl)piperazine-1-carbonyl)quinolin-4-yl)phenyl)acetonitrile, TFA |
| 213 | 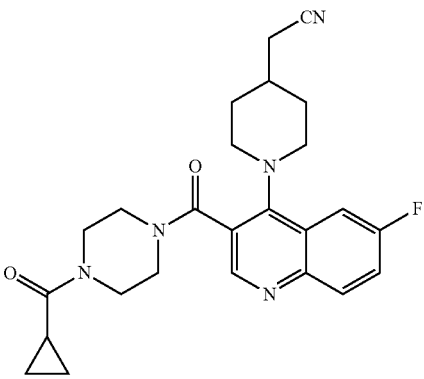 [SMILES: N#CCC1CCN(c2c(C(=O)N3CCN(C(=O)C4CC4)CC3)cnc3ccc(F)cc23)CC1] | 2-(1-(3-(4-(cyclopropanecarbonyl)piperazine-1-carbonyl)-6-fluoroquinolin-4-yl)piperidin-4-yl)acetonitrile, TFA |
| 214 | 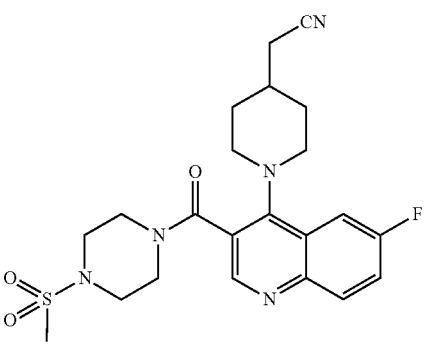 [SMILES: CS(=O)(=O)N1CCN(C(=O)c2cnc3ccc(F)cc3c2N2CCC(CC#N)CC2)CC1] | 2-(1-(6-fluoro-3-(4-(methylsulfonyl)piperazine-1-carbonyl)quinolin-4-yl)piperidin-4-yl)acetonitrile, TFA |
| 215 | 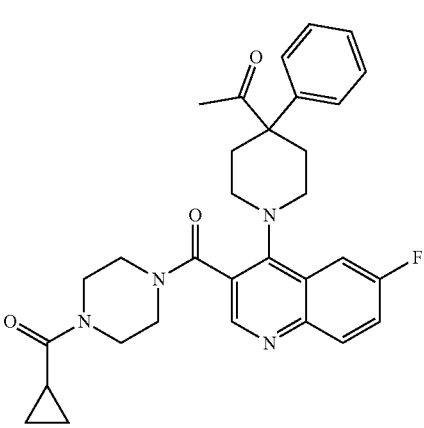 [SMILES: CC(=O)C1(c2ccccc2)CCN(c2c(C(=O)N3CCN(C(=O)C4CC4)CC3)cnc3ccc(F)cc23)CC1] | 1-(1-(3-(4-(cyclopropanecarbonyl)piperazine-1-carbonyl)-6-fluoroquinolin-4-yl)-4-phenylpiperidin-4-yl)ethanone, TFA |

TABLE 1-continued

| Cpd. ID | Structure | Compound name |
|---|---|---|
| 216 | 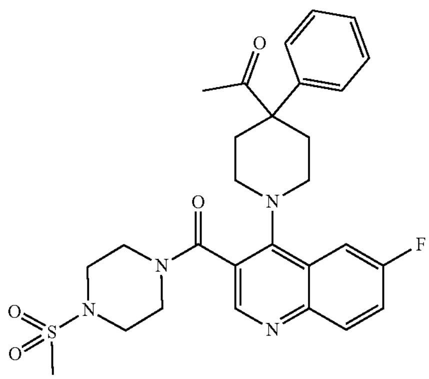 [SMILES: CC(=O)C1(c2ccccc2)CCN(c2c(C(=O)N3CCN(S(C)(=O)=O)CC3)cnc3ccc(F)cc23)CC1] | 1-(1-(6-fluoro-3-(4-(methylsulfonyl)piperazine-1-carbonyl)quinolin-4-yl)-4-phenylpiperidin-4-yl)ethanone, TFA |
| 217 | 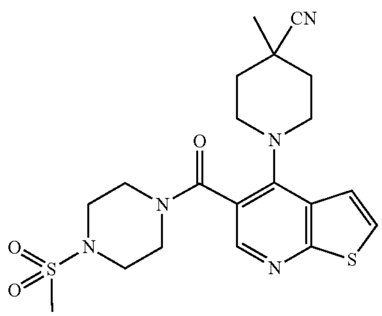 [SMILES: CC1(C#N)CCN(c2c(C(=O)N3CCN(S(C)(=O)=O)CC3)cnc3sccc23)CC1] | 4-methyl-1-(5-(4-(methylsulfonyl)piperazine-1-carbonyl)thieno[2,3-b]pyridin-4-yl)piperidine-4-carbonitrile, TFA |
| 218 | 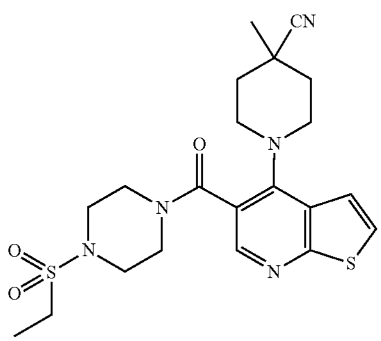 [SMILES: CCS(=O)(=O)N1CCN(C(=O)c2cnc3sccc3c2N2CCC(C)(C#N)CC2)CC1] | 1-(5-(4-(ethylsulfonyl)piperazine-1-carbonyl)thieno[2,3-b]pyridin-4-yl)-4-methylpiperidine-4-carbonitrile, TFA |
| 219 | 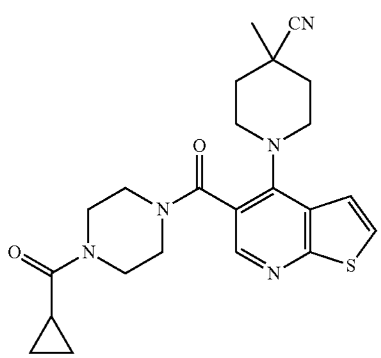 [SMILES: CC1(C#N)CCN(c2c(C(=O)N3CCN(C(=O)C4CC4)CC3)cnc3sccc23)CC1] | 1-(5-(4-(cyclopropanecarbonyl)piperazine-1-carbonyl)thieno[2,3-b]pyridin-4-yl)-4-methylpiperidine-4-carbonitrile, TFA |

TABLE 1-continued

| Cpd. ID | Structure | Compound name |
|---|---|---|
| 220 | 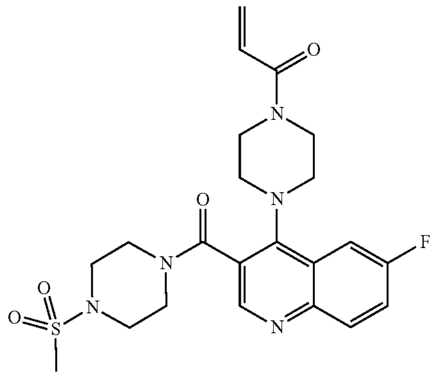 [SMILES: C=CC(=O)N1CCN(c2c(C(=O)N3CCN(S(C)(=O)=O)CC3)cnc3ccc(F)cc23)CC1] | 1-(4-(6-fluoro-3-(4-(methylsulfonyl)piperazine-1-carbonyl)quinolin-4-yl)piperazin-1-yl)prop-2-en-1-one |
| 221 | 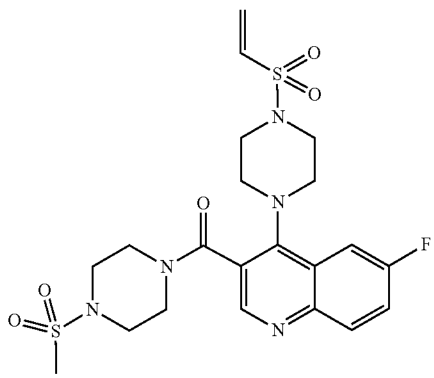 [SMILES: C=CS(=O)(=O)N1CCN(c2c(C(=O)N3CCN(S(C)(=O)=O)CC3)cnc3ccc(F)cc23)CC1] | (6-fluoro-4-(4-(vinylsulfonyl)piperazin-1-yl)quinolin-3-yl)(4-(methylsulfonyl)piperazin-1-yl)methanone |
| 222 | 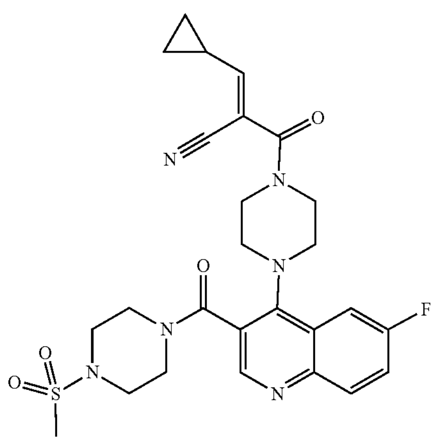 [SMILES: CS(=O)(=O)N1CCN(C(=O)c2cnc3ccc(F)cc3c2N2CCN(C(=O)/C(C#N)=C/C3CC3)CC2)CC1] | (E)-3-cyclopropyl-2-(4-(6-fluoro-3-(4-(methylsulfonyl)piperazine-1-carbonyl)quinolin-4-yl)piperazine-1-carbonyl)acrylonitrile |
| 223 | 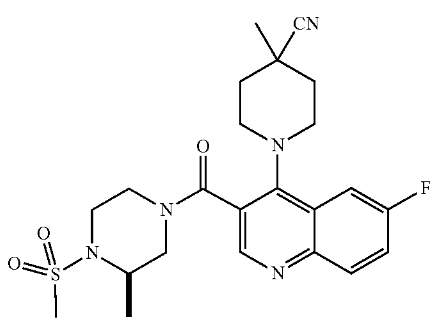 | (R)-1-(6-fluoro-3-(3-methyl-4-(methylsulfonyl)piperazine-1-carbonyl)quinolin-4-yl)-4-methylpiperidine-4-carbonitrile, TFA |

TABLE 1-continued

| Cpd. ID | Structure | Compound name |
|---|---|---|
| 224 | 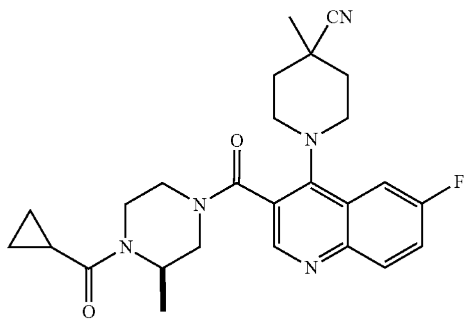 [SMILES: C[C@@H]1CN(C(=O)c2cnc3ccc(F)cc3c2N2CCC(C)(C#N)CC2)CCN1C(=O)C1CC1] | (R)-1-(3-(4-(cyclopropanecarbonyl)-3-methylpiperazine-1-carbonyl)-6-fluoroquinolin-4-yl)-4-methylpiperidine-4-carbonitrile, TFA |
| 225 | 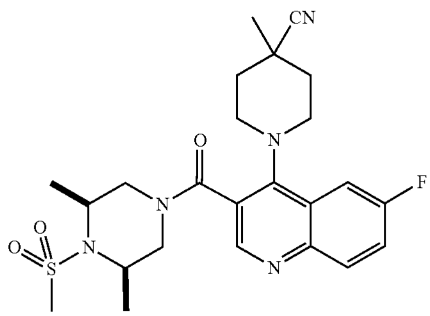 [SMILES: C[C@@H]1CN(C(=O)c2cnc3ccc(F)cc3c2N2CCC(C)(C#N)CC2)C[C@H](C)N1S(C)(=O)=O] | 1-(3-((3R*,5S*)-3,5-dimethyl-4-(methylsulfonyl)piperazine-1-carbonyl)-6-fluoroquinolin-4-yl)-4-methylpiperidine-4-carbonitrile, TFA |
| 226 | 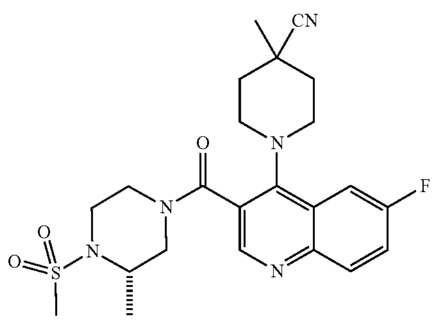 [SMILES: C[C@H]1CN(C(=O)c2cnc3ccc(F)cc3c2N2CCC(C)(C#N)CC2)CCN1S(C)(=O)=O] | (S)-1-(6-fluoro-3-(3-methyl-4-(methylsulfonyl)piperazine-1-carbonyl)quinolin-4-yl)-4-methylpiperidine-4-carbonitrile, TFA |
| 227 | 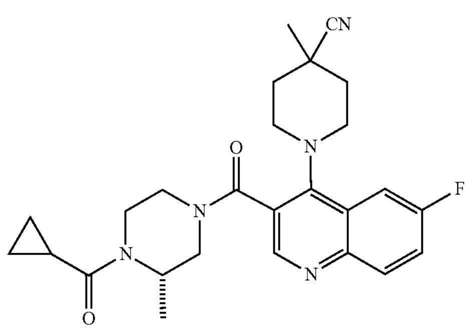 [SMILES: C[C@H]1CN(C(=O)c2cnc3ccc(F)cc3c2N2CCC(C)(C#N)CC2)CCN1C(=O)C1CC1] | (S)-1-(3-(4-(cyclopropanecarbonyl)-3-methylpiperazine-1-carbonyl)-6-fluoroquinolin-4-yl)-4-methylpiperidine-4-carbonitrile, TFA |
| 228 | 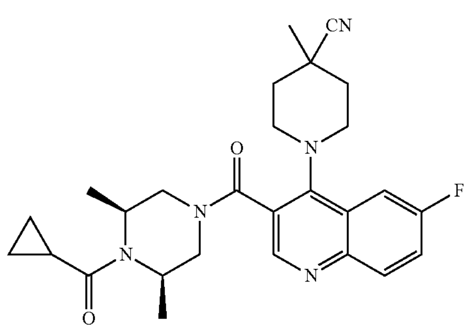 [SMILES: C[C@@H]1CN(C(=O)c2cnc3ccc(F)cc3c2N2CCC(C)(C#N)CC2)C[C@H](C)N1C(=O)C1CC1] | XSW1-20<br>1-(3-((3R*,5S*)-4-(cyclopropanecarbonyl)-3,5-dimethylpiperazine-1-carbonyl)-6-fluoroquinolin-4-yl)-4-methylpiperidine-4-carbonitrile, TFA |

TABLE 1-continued

| Cpd. ID | Structure | Compound name |
|---|---|---|
| 229 | 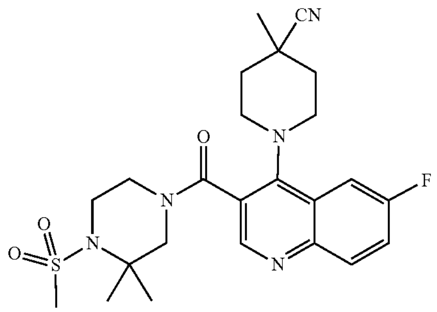 [SMILES: CC1(C#N)CCN(c2c(C(=O)N3CCN(S(C)(=O)=O)C(C)(C)C3)cnc3ccc(F)cc23)CC1] | 1-(3-(3,3-dimethyl-4-(methylsulfonyl)piperazine-1-carbonyl)-6-fluoroquinolin-4-yl)-4-methylpiperidine-4-carbonitrile, TFA |
| 230 | 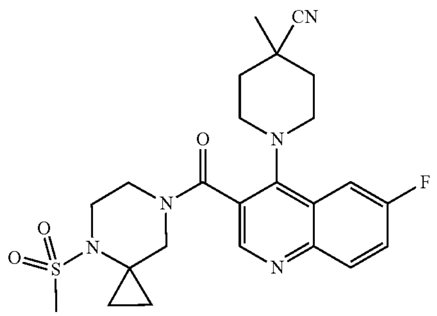 [SMILES: CC1(C#N)CCN(c2c(C(=O)N3CCN(S(C)(=O)=O)C4(CC4)C3)cnc3ccc(F)cc23)CC1] | 1-(6-fluoro-3-(4-(methylsulfonyl)-4,7-diazaspiro[2.5]octane-7-carbonyl)quinolin-4-yl)-4-methylpiperidine-4-carbonitrile, TFA |
| 231 | 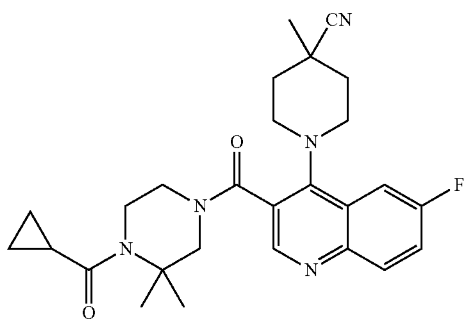 [SMILES: CC1(C#N)CCN(c2c(C(=O)N3CCN(C(=O)C4CC4)C(C)(C)C3)cnc3ccc(F)cc23)CC1] | 1-(3-(4-(cyclopropanecarbonyl)-3,3-dimethylpiperazine-1-carbonyl)-6-fluoroquinolin-4-yl)-4-methylpiperidine-4-carbonitrile, TFA |
| 232 | 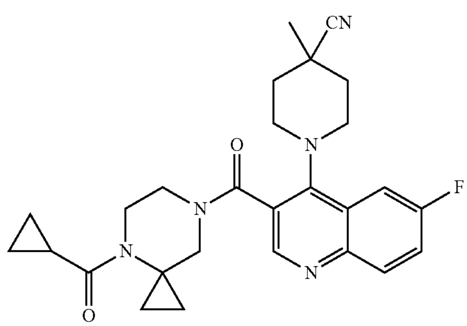 [SMILES: CC1(C#N)CCN(c2c(C(=O)N3CCN(C(=O)C4CC4)C4(CC4)C3)cnc3ccc(F)cc23)CC1] | 1-(3-(4-(cyclopropanecarbonyl)-4,7-diazaspiro[2.5]octane-7-carbonyl)-6-fluoroquinolin-4-yl)-4-methylpiperidine-4-carbonitrile, TFA |
| 233 | 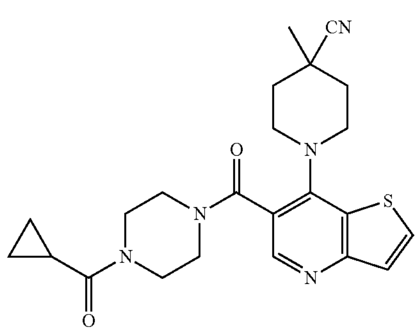 [SMILES: CC1(C#N)CCN(c2c(C(=O)N3CCN(C(=O)C4CC4)CC3)cnc3ccsc23)CC1] | 1-(6-(4-(cyclopropanecarbonyl)piperazine-1-carbonyl)thieno[3,2-b]pyridin-7-yl)-4-methylpiperidine-4-carbonitrile, TFA |

TABLE 1-continued

| Cpd. ID | Structure | Compound name |
|---|---|---|
| 234 | 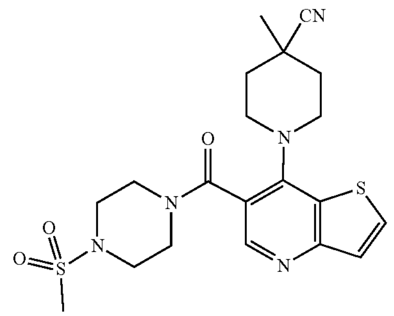 [SMILES: CC1(C#N)CCN(c2c(C(=O)N3CCN(S(C)(=O)=O)CC3)cnc3ccsc23)CC1] | 4-methyl-1-(6-(4-(methylsulfonyl)piperazine-1-carbonyl)thieno[3,2-b]pyridin-7-yl)piperidine-4-carbonitrile, TFA |
| 235 | 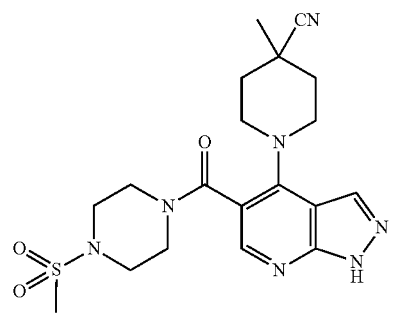 [SMILES: CC1(C#N)CCN(c2c(C(=O)N3CCN(S(C)(=O)=O)CC3)cnc3[nH]ncc23)CC1] | 4-methyl-1-(5-(4-(methylsulfonyl)piperazine-1-carbonyl)-1H-pyrazolo[3,4-b]pyridin-4-yl)piperidine-4-carbonitrile, TFA |
| 236 | 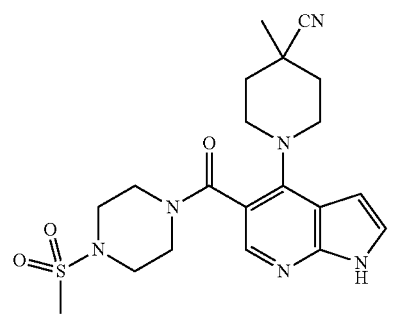 [SMILES: CC1(C#N)CCN(c2c(C(=O)N3CCN(S(C)(=O)=O)CC3)cnc3[nH]ccc23)CC1] | 4-methyl-1-(5-(4-(methylsulfonyl)piperazine-1-carbonyl)-1H-pyrrolo[2,3-b]pyridin-4-yl)piperidine-4-carbonitrile, TFA |
| 237 | 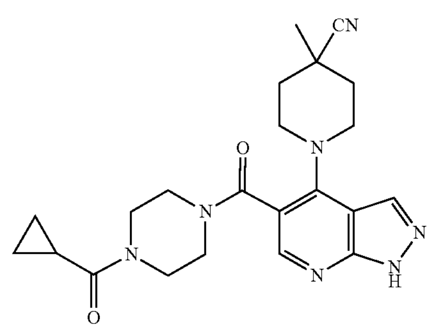 [SMILES: CC1(C#N)CCN(c2c(C(=O)N3CCN(C(=O)C4CC4)CC3)cnc3[nH]ncc23)CC1] | 1-(5-(4-(cyclopropanecarbonyl)piperazine-1-carbonyl)-1H-pyrazolo[3,4-b]pyridin-4-yl)-4-methylpiperidine-4-carbonitrile, TFA |
| 238 | 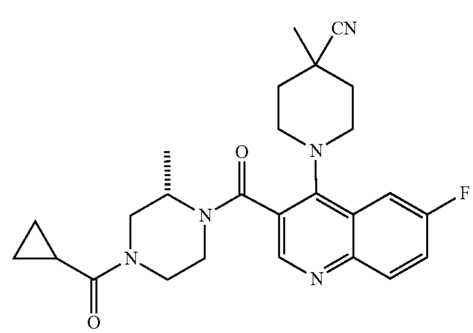 [SMILES: C[C@H]1CN(C(=O)C2CC2)CCN1C(=O)c1cnc2ccc(F)cc2c1N1CCC(C)(C#N)CC1] | (S)-1-(3-(4-(cyclopropanecarbonyl)-2-methylpiperazine-1-carbonyl)-6-fluoroquinolin-4-yl)-4-methylpiperidine-4-carbonitrile, TFA |

TABLE 1-continued

| Cpd. ID | Structure | Compound name |
|---|---|---|
| 239 | 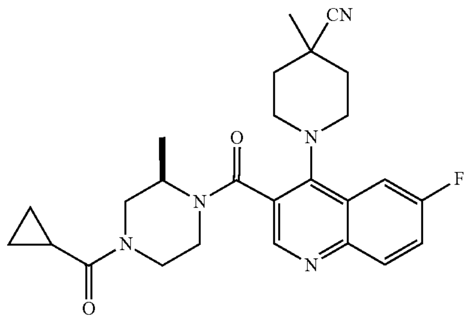 [SMILES: C[C@@H]1CN(C(=O)C2CC2)CCN1C(=O)c1cnc2ccc(F)cc2c1N1CCC(C)(C#N)CC1] | (R)-1-(3-(4-(cyclopropanecarbonyl)-2-methylpiperazine-1-carbonyl)-6-fluoroquinolin-4-yl)-4-methylpiperidine-4-carbonitrile, TFA |
| 240 | 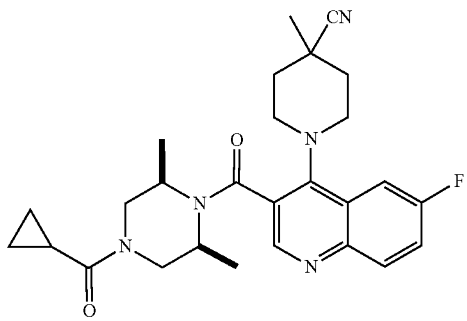 [SMILES: C[C@@H]1CN(C(=O)C2CC2)C[C@H](C)N1C(=O)c1cnc2ccc(F)cc2c1N1CCC(C)(C#N)CC1] | 1-(3-((2S*,6R*)-4-(cyclopropanecarbonyl)-2,6-dimethylpiperazine-1-carbonyl)-6-fluoroquinolin-4-yl)-4-methylpiperidine-4-carbonitrile, TFA |
| 241 | 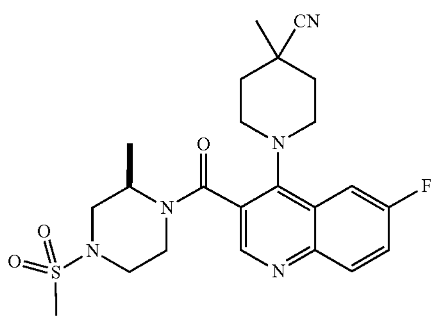 [SMILES: C[C@@H]1CN(S(C)(=O)=O)CCN1C(=O)c1cnc2ccc(F)cc2c1N1CCC(C)(C#N)CC1] | (R)-1-(6-fluoro-3-(2-methyl-4-(methylsulfonyl)piperazine-1-carbonyl)quinolin-4-yl)-4-methylpiperidine-4-carbonitrile, TFA |
| 242 | 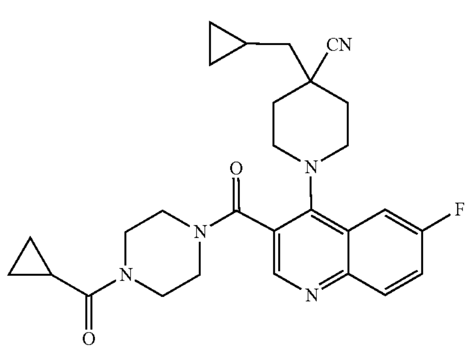 [SMILES: N#CC1(CC2CC2)CCN(c2c(C(=O)N3CCN(C(=O)C4CC4)CC3)cnc3ccc(F)cc23)CC1] | 1-(3-(4-(cyclopropanecarbonyl)piperazine-1-carbonyl)-6-fluoroquinolin-4-yl)-4-(cyclopropylmethyl)piperidine-4-carbonitrile |

TABLE 1-continued

| Cpd. ID | Structure | Compound name |
|---|---|---|
| 243 | 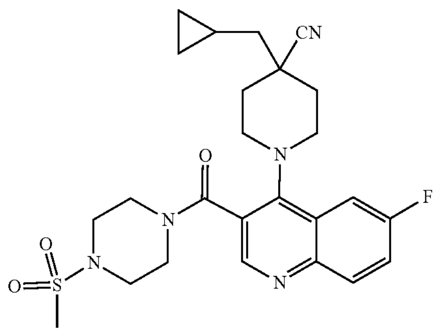 [SMILES: CS(=O)(=O)N1CCN(C(=O)c2cnc3ccc(F)cc3c2N2CCC(C#N)(CC3CC3)CC2)CC1] | 4-(cyclopropylmethyl)-1-(6-fluoro-3-(4-(methylsulfonyl)piperazine-1-carbonyl)quinolin-4-yl)piperidine-4-carbonitrile, TFA |
| 244 | 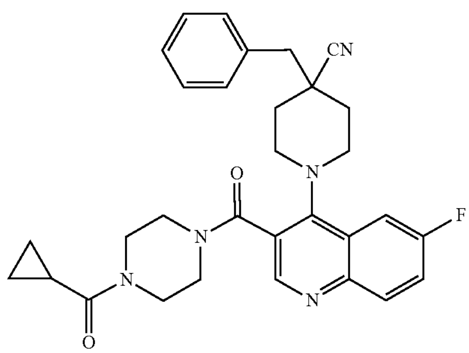 [SMILES: N#CC1(Cc2ccccc2)CCN(c2c(C(=O)N3CCN(C(=O)C4CC4)CC3)cnc3ccc(F)cc23)CC1] | 4-benzyl-1-(3-(4-(cyclopropanecarbonyl)piperazine-1-carbonyl)-6-fluoroquinolin-4-yl)piperidine-4-carbonitrile, TFA |
| 245 | 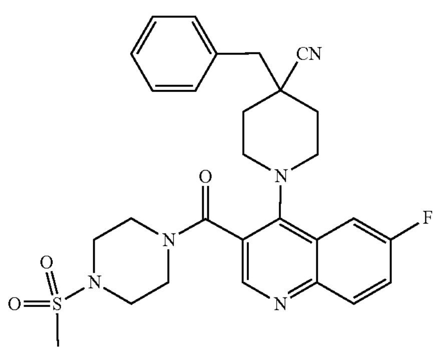 [SMILES: CS(=O)(=O)N1CCN(C(=O)c2cnc3ccc(F)cc3c2N2CCC(C#N)(Cc3ccccc3)CC2)CC1] | 4-benzyl-1-(6-fluoro-3-(4-(methylsulfonyl)piperazine-1-carbonyl)quinolin-4-yl)piperidine-4-carbonitrile, TFA |
| 246 | 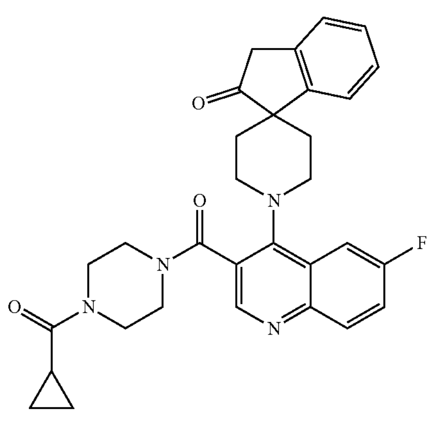 [SMILES: O=C(c1cnc2ccc(F)cc2c1N1CCC2(CC1)C(=O)Cc1ccccc12)N1CCN(C(=O)C2CC2)CC1] | 1'-(3-(4-(cyclopropanecarbonyl)piperazine-1-carbonyl)-6-fluoroquinolin-4-yl)spiro[indene-1,4'-piperidin]-2(3H)-one, TFA |

TABLE 1-continued

| Cpd. ID | Structure | Compound name |
| --- | --- | --- |
| 247 | 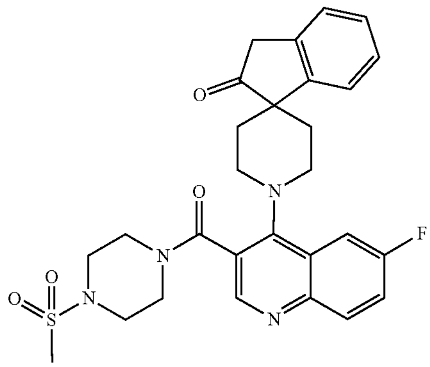 [SMILES: CS(=O)(=O)N1CCN(C(=O)c2cnc3ccc(F)cc3c2N2CCC3(CC2)C(=O)Cc2ccccc23)CC1] | 1'-(6-fluoro-3-(4-(methylsulfonyl)piperazine-1-carbonyl)quinolin-4-yl)spiro[indene-1,4'-piperidin]-2(3H)-one, TFA |
| 248 | 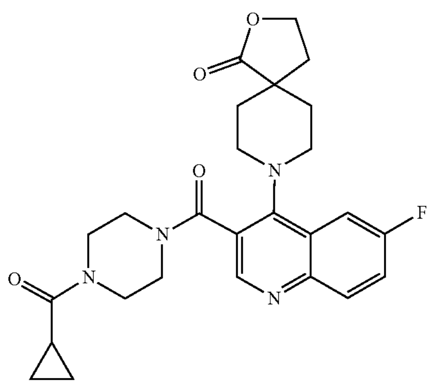 [SMILES: O=C(c1cnc2ccc(F)cc2c1N1CCC2(CCOC2=O)CC1)N1CCN(C(=O)C2CC2)CC1] | 8-(3-(4-(cyclopropanecarbonyl)piperazine-1-carbonyl)-6-fluoroquinolin-4-yl)-2-oxa-8-azaspiro[4.5]decan-1-one, TFA |
| 249 | 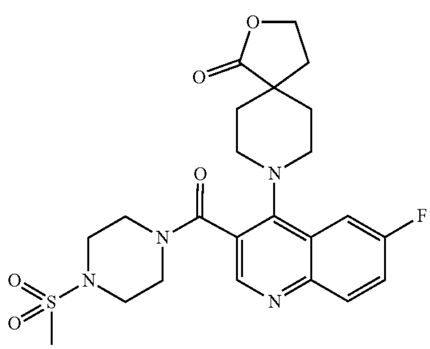 [SMILES: CS(=O)(=O)N1CCN(C(=O)c2cnc3ccc(F)cc3c2N2CCC3(CCOC3=O)CC2)CC1] | 8-(6-fluoro-3-(4-(methylsulfonyl)piperazine-1-carbonyl)quinolin-4-yl)-2-oxa-8-azaspiro[4.5]decan-1-one, TFA |
| 250 | 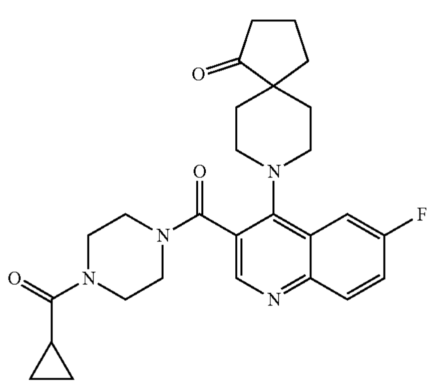 [SMILES: O=C(c1cnc2ccc(F)cc2c1N1CCC2(CCCC2=O)CC1)N1CCN(C(=O)C2CC2)CC1] | 8-(3-(4-(cyclopropanecarbonyl)piperazine-1-carbonyl)-6-fluoroquinolin-4-yl)-8-azaspiro[4.5]decan-1-one, TFA |

TABLE 1-continued

| Cpd. ID | Structure | Compound name |
|---|---|---|
| 251 | 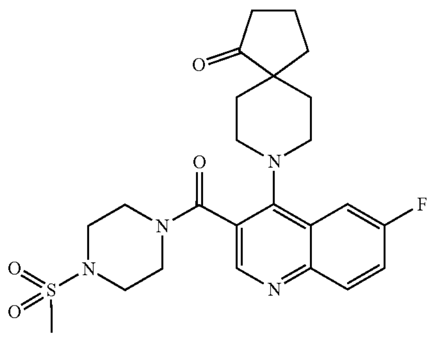 [SMILES: CS(=O)(=O)N1CCN(C(=O)c2cnc3ccc(F)cc3c2N2CCC3(CCCC3=O)CC2)CC1] | 8-(6-fluoro-3-(4-(methylsulfonyl)piperazine-1-carbonyl)quinolin-4-yl)-8-azaspiro[4.5]decan-1-one, TFA |
| 252 | 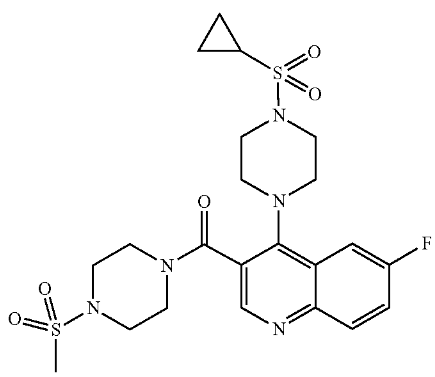 [SMILES: CS(=O)(=O)N1CCN(C(=O)c2cnc3ccc(F)cc3c2N2CCN(S(=O)(=O)C3CC3)CC2)CC1] | (4-(4-(cyclopropylsulfonyl)piperazin-1-yl)-6-fluoroquinolin-3-yl)(4-(methylsulfonyl)piperazin-1-yl)methanone, TFA |
| 253 | 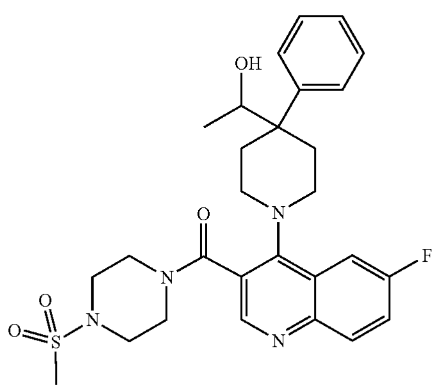 [SMILES: CC(O)C1(c2ccccc2)CCN(c2c(C(=O)N3CCN(S(C)(=O)=O)CC3)cnc3ccc(F)cc23)CC1] | (6-fluoro-4-(4-(1-hydroxyethyl)-4-phenylpiperidin-1-yl)quinolin-3-yl)(4-(methylsulfonyl)piperazin-1-yl)methanone |
| 254 | 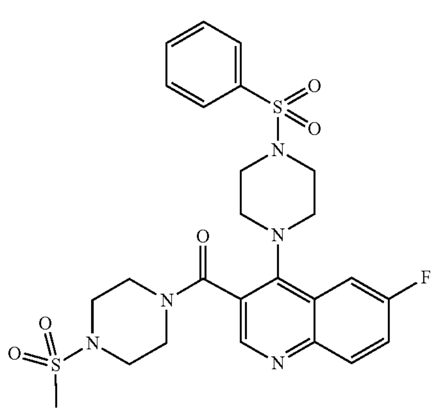 [SMILES: CS(=O)(=O)N1CCN(C(=O)c2cnc3ccc(F)cc3c2N2CCN(S(=O)(=O)c3ccccc3)CC2)CC1] | (6-fluoro-4-(4-(phenylsulfonyl)piperazin-1-yl)quinolin-3-yl)(4-(methylsulfonyl)piperazin-1-yl)methanone |

| Cpd. ID | Structure | Compound name |
|---|---|---|
| 255 | 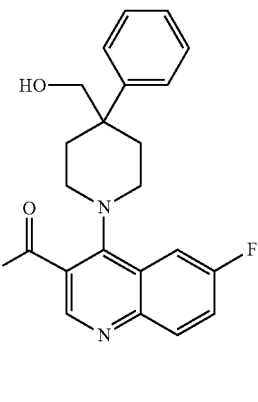 | (4-(cyclopropanecarbonyl)piperazin-1-yl)(6-fluoro-4-(4-(hydroxymethyl)-4-phenylpiperidin-1-yl)quinolin-3-yl)methanone, TFA |
| 256 | 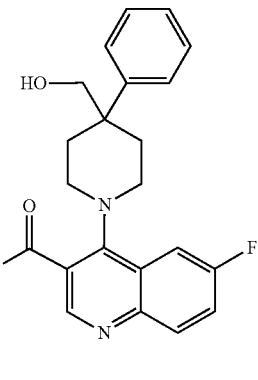 | (6-fluoro-4-(4-(hydroxymethyl)-4-phenylpiperidin-1-yl)quinolin-3-yl)(4-(methylsulfonyl)piperazin-1-yl)methanone, TFA |
| 257 | 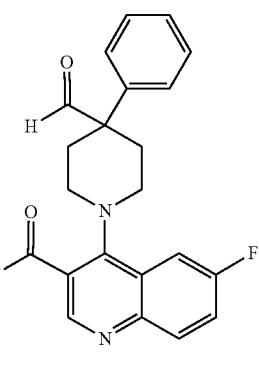 | 1-(6-fluoro-3-(4-(methylsulfonyl)piperazine-1-carbonyl)quinolin-4-yl)-4-phenylpiperidine-4-carbaldehyde |
| 258 | 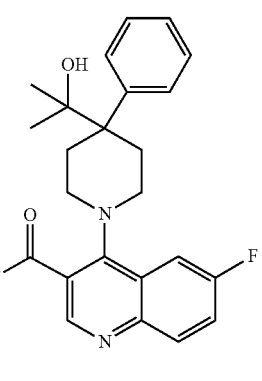 | (6-fluoro-4-(4-(2-hydroxypropan-2-yl)-4-phenylpiperidin-1-yl)quinolin-3-yl)(4-(methylsulfonyl)piperazin-1-yl)methanone, TFA |

TABLE 1-continued

| Cpd. ID | Structure | Compound name |
|---|---|---|
| 259 | 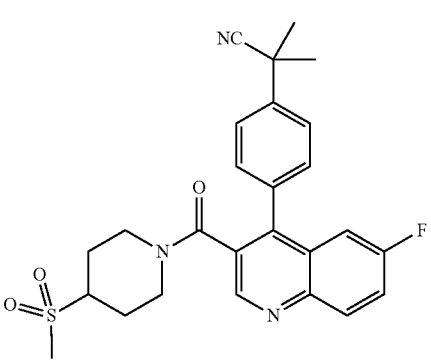 [SMILES: CC(C)(C#N)c1ccc(-c2c(C(=O)N3CCC(S(C)(=O)=O)CC3)cnc3ccc(F)cc23)cc1] | 2-(4-(6-fluoro-3-(4-(methylsulfonyl)piperidine-1-carbonyl)quinolin-4-yl)phenyl)-2-methylpropanenitrile, TFA |
| 260 | 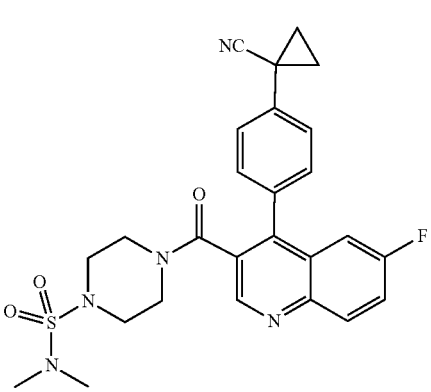 [SMILES: CN(C)S(=O)(=O)N1CCN(C(=O)c2cnc3ccc(F)cc3c2-c2ccc(C3(C#N)CC3)cc2)CC1] | 4-(4-(4-(1-cyanocyclopropyl)phenyl)-6-fluoroquinoline-3-carbonyl)-N,N-dimethylpiperazine-1-sulfonamide, TFA |
| 261 | 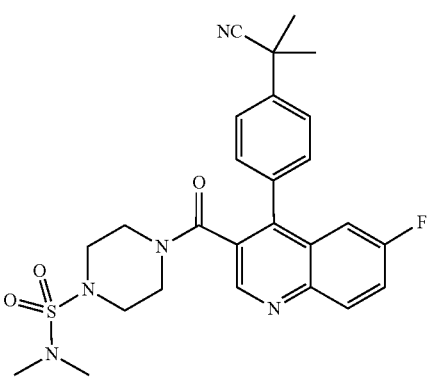 [SMILES: CN(C)S(=O)(=O)N1CCN(C(=O)c2cnc3ccc(F)cc3c2-c2ccc(C(C)(C)C#N)cc2)CC1] | 4-(4-(4-(2-cyanopropan-2-yl)phenyl)-6-fluoroquinoline-3-carbonyl)-N,N-dimethylpiperazine-1-sulfonamide, TFA |
| 262 | 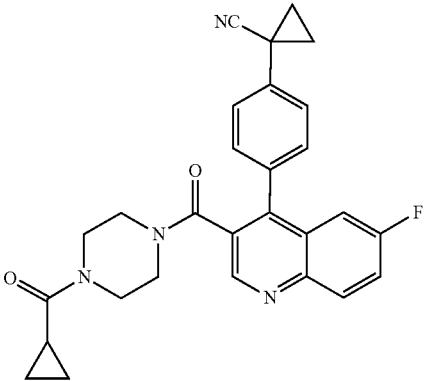 [SMILES: N#CC1(c2ccc(-c3c(C(=O)N4CCN(C(=O)C5CC5)CC4)cnc4ccc(F)cc34)cc2)CC1] | 1-(4-(3-(4-(cyclopropanecarbonyl)piperazine-1-carbonyl)-6-fluoroquinolin-4-yl)phenyl)cyclopropanecarbonitrile, TFA |

TABLE 1-continued

| Cpd. ID | Structure | Compound name |
|---|---|---|
| 263 | 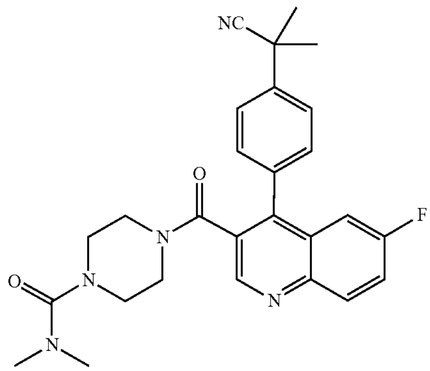 [SMILES: CN(C)C(=O)N1CCN(C(=O)c2cnc3ccc(F)cc3c2-c2ccc(C(C)(C)C#N)cc2)CC1] | 4-(4-(4-(2-cyanopropan-2-yl)phenyl)-6-fluoroquinoline-3-carbonyl)-N,N-dimethylpiperazine-1-carboxamide, TFA |
| 264 | 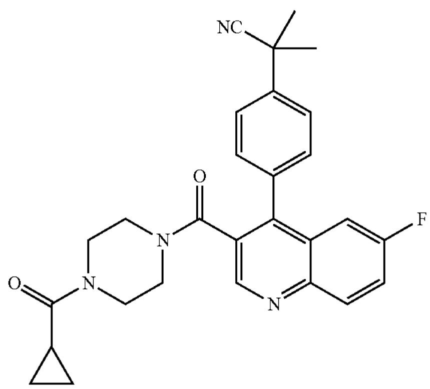 [SMILES: CC(C)(C#N)c1ccc(-c2c(C(=O)N3CCN(C(=O)C4CC4)CC3)cnc3ccc(F)cc23)cc1] | 2-(4-(3-(4-(cyclopropanecarbonyl)piperazine-1-carbonyl)-6-fluoroquinolin-4-yl)phenyl)-2-methylpropanenitrile, TFA |
| 265 | 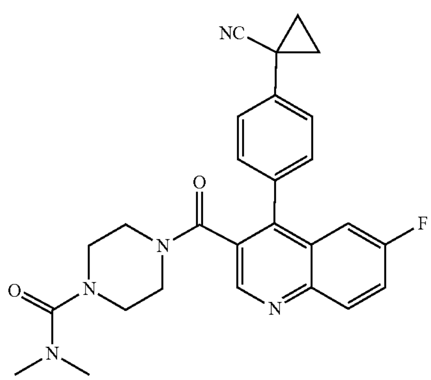 [SMILES: CN(C)C(=O)N1CCN(C(=O)c2cnc3ccc(F)cc3c2-c2ccc(C3(C#N)CC3)cc2)CC1] | 4-(4-(4-(1-cyanocyclopropyl)phenyl)-6-fluoroquinoline-3-carbonyl)-N,N-dimethylpiperazine-1-carboxamide, TFA |
| 266 | 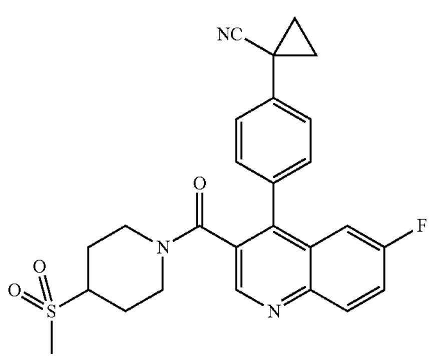 [SMILES: CS(=O)(=O)C1CCN(C(=O)c2cnc3ccc(F)cc3c2-c2ccc(C3(C#N)CC3)cc2)CC1] | 1-(4-(6-fluoro-3-(4-(methylsulfonyl)piperidine-1-carbonyl)quinolin-4-yl)phenyl)cyclopropanecarbonitrile, TFA |

TABLE 1-continued
| Cpd. ID | Structure | Compound name |
|---|---|---|
| 267 | 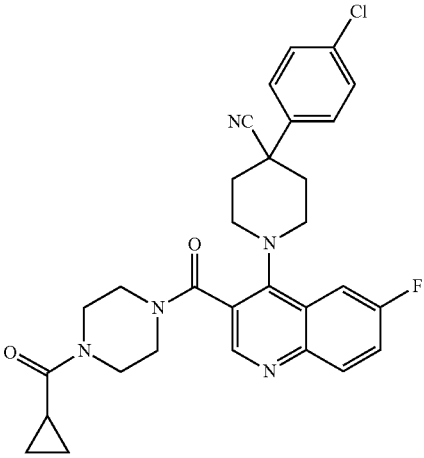 [SMILES: N#CC1(c2ccc(Cl)cc2)CCN(c2c(C(=O)N3CCN(C(=O)C4CC4)CC3)cnc3ccc(F)cc23)CC1] | 4-(4-chlorophenyl)-1-(3-(4-(cyclopropanecarbonyl)piperazine-1-carbonyl)-6-fluoroquinolin-4-yl)piperidine-4-carbonitrile, TFA |
| 268 | 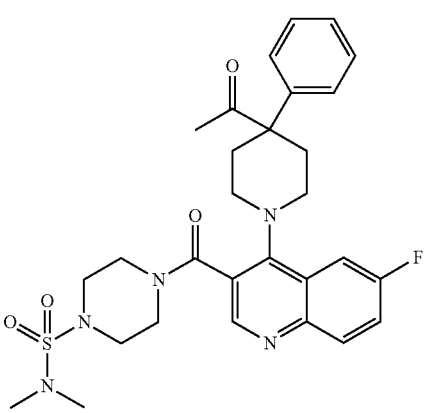 [SMILES: CC(=O)C1(c2ccccc2)CCN(c2c(C(=O)N3CCN(S(=O)(=O)N(C)C)CC3)cnc3ccc(F)cc23)CC1] | 4-(4-(4-acetyl-4-phenylpiperidin-1-yl)-6-fluoroquinoline-3-carbonyl)-N,N-dimethylpiperazine-1-sulfonamide, TFA |
| 269 | 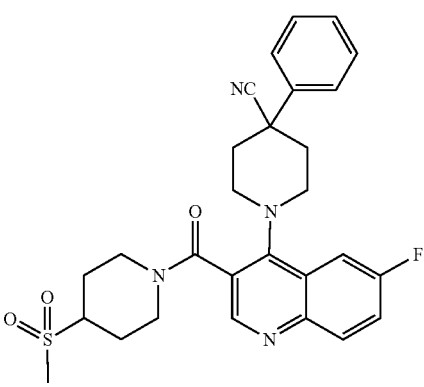 [SMILES: CS(=O)(=O)C1CCN(C(=O)c2cnc3ccc(F)cc3c2N2CCC(C#N)(c3ccccc3)CC2)CC1] | 1-(6-fluoro-3-(4-(methylsulfonyl)piperidine-1-carbonyl)quinolin-4-yl)-4-phenylpiperidine-4-carbonitrile, TFA |

TABLE 1-continued

| Cpd. ID | Structure | Compound name |
|---|---|---|
| 270 | 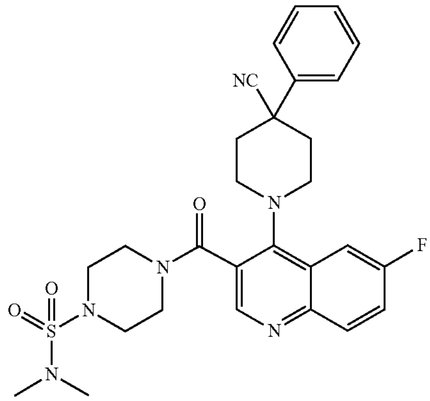 [SMILES: CN(C)S(=O)(=O)N1CCN(C(=O)c2cnc3ccc(F)cc3c2N2CCC(C#N)(c3ccccc3)CC2)CC1] | 4-(4-(4-cyano-4-phenylpiperidin-1-yl)-6-fluoroquinoline-3-carbonyl)-N,N-dimethylpiperazine-1-sulfonamide, TFA |
| 271 | 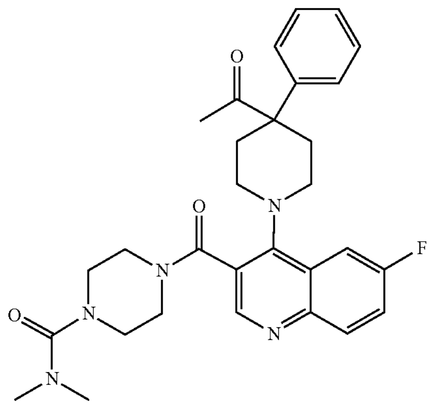 [SMILES: CC(=O)C1(c2ccccc2)CCN(c2c(C(=O)N3CCN(C(=O)N(C)C)CC3)cnc3ccc(F)cc23)CC1] | 4-(4-(4-acetyl-4-phenylpiperidin-1-yl)-6-fluoroquinoline-3-carbonyl)-N,N-dimethylpiperazine-1-carboxamide, TFA |
| 272 | 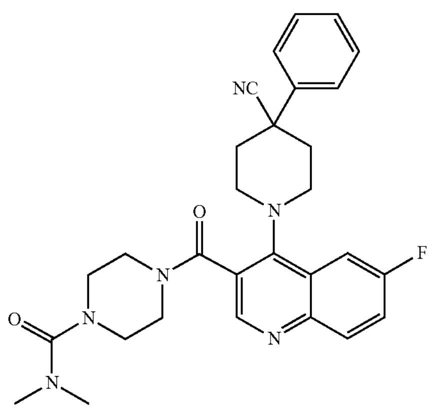 [SMILES: CN(C)C(=O)N1CCN(C(=O)c2cnc3ccc(F)cc3c2N2CCC(C#N)(c3ccccc3)CC2)CC1] | 4-(4-(4-cyano-4-phenylpiperidin-1-yl)-6-fluoroquinoline-3-carbonyl)-N,N-dimethylpiperazine-1-carboxamide, TFA |
| 273 | 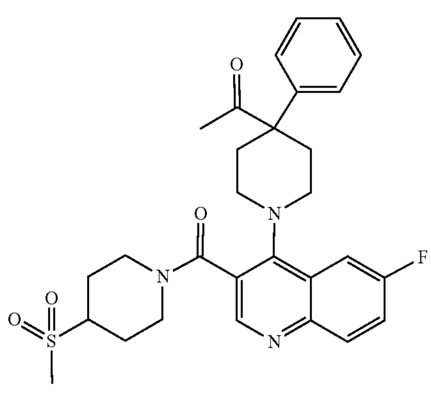 [SMILES: CC(=O)C1(c2ccccc2)CCN(c2c(C(=O)N3CCC(S(C)(=O)=O)CC3)cnc3ccc(F)cc23)CC1] | 1-(1-(6-fluoro-3-(4-(methylsulfonyl)piperidine-1-carbonyl)quinolin-4-yl)-4-phenylpiperidin-4-yl)ethanone, TFA |

TABLE 1-continued

| Cpd. ID | Structure | Compound name |
|---|---|---|
| 274 | 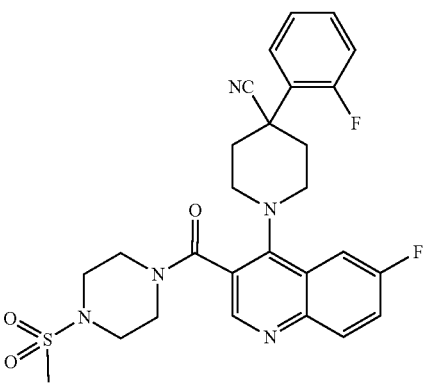 [SMILES: CS(=O)(=O)N1CCN(C(=O)c2cnc3ccc(F)cc3c2N2CCC(C#N)(c3ccccc3F)CC2)CC1] | 1-(6-fluoro-3-(4-(methylsulfonyl)piperazine-1-carbonyl)quinolin-4-yl)-4-(2-fluorophenyl)piperidine-4-carbonitrile, TFA |
| 275 | 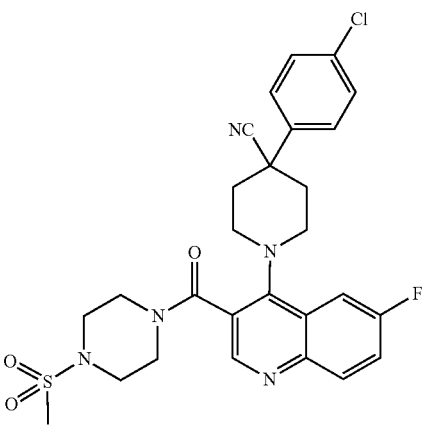 [SMILES: CS(=O)(=O)N1CCN(C(=O)c2cnc3ccc(F)cc3c2N2CCC(C#N)(c3ccc(Cl)cc3)CC2)CC1] | 4-(4-chlorophenyl)-1-(6-fluoro-3-(4-(methylsulfonyl)piperazine-1-carbonyl)quinolin-4-yl)piperidine-4-carbonitrile, TFA |
| 276 | 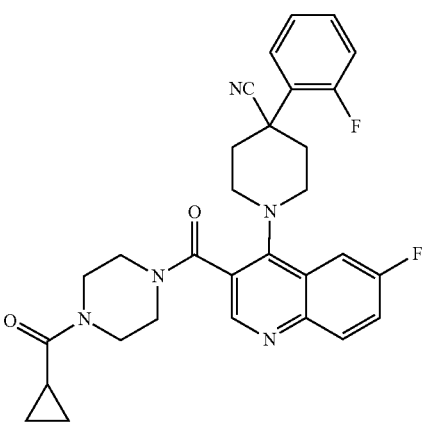 [SMILES: N#CC1(c2ccccc2F)CCN(c2c(C(=O)N3CCN(C(=O)C4CC4)CC3)cnc3ccc(F)cc23)CC1] | 1-(3-(4-(cyclopropanecarbonyl)piperazine-1-carbonyl)-6-fluoroquinolin-4-yl)-4-(2-fluorophenyl)piperidine-4-carbonitrile, TFA |

| Cpd. ID | Structure | Compound name |
|---|---|---|
| 277 | 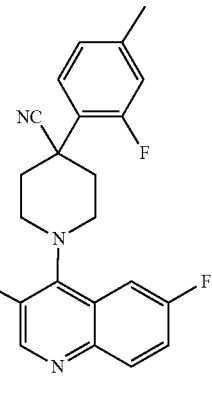 | 1-(6-fluoro-3-(4-(methylsulfonyl)piperazine-1-carbonyl)quinolin-4-yl)-4-(2-fluoro-4-methylphenyl)piperidine-4-carbonitrile, TFA |
| 278 | 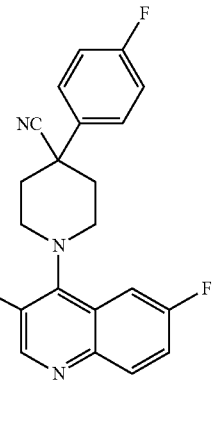 | 1-(3-(4-(cyclopropanecarbonyl)piperazine-1-carbonyl)-6-fluoroquinolin-4-yl)-4-(4-fluorophenyl)piperidine-4-carbonitrile, TFA |
| 279 | 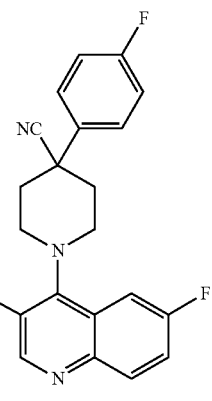 | 1-(6-fluoro-3-(4-(methylsulfonyl)piperazine-1-carbonyl)quinolin-4-yl)-4-(4-fluorophenyl)piperidine-4-carbonitrile, TFA |

TABLE 1-continued

| Cpd. ID | Structure | Compound name |
|---|---|---|
| 280 | 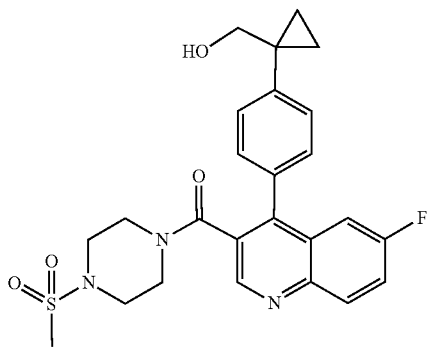 [SMILES: CS(=O)(=O)N1CCN(C(=O)c2cnc3ccc(F)cc3c2-c2ccc(C3(CO)CC3)cc2)CC1] | (6-fluoro-4-(4-(1-(hydroxymethyl)cyclopropyl)phenyl)quinolin-3-yl)(4-(methylsulfonyl)piperazin-1-yl)methanone, TFA |
| 281 | 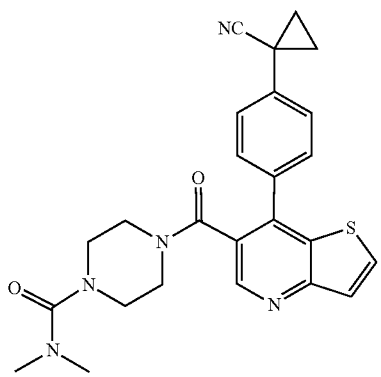 [SMILES: CN(C)C(=O)N1CCN(C(=O)c2cnc3ccsc3c2-c2ccc(C3(C#N)CC3)cc2)CC1] | 4-(7-(4-(1-cyanocyclopropyl)phenyl)thieno[3,2-b]pyridine-6-carbonyl)-N,N-dimethylpiperazine-1-carboxamide, TFA |
| 282 | 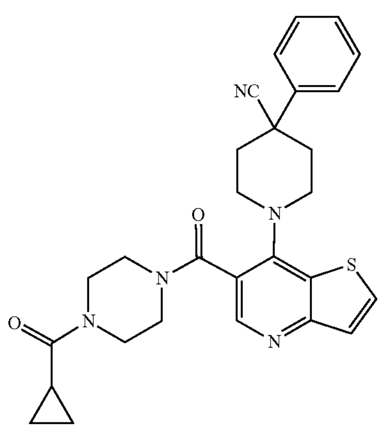 [SMILES: N#CC1(c2ccccc2)CCN(c2c(C(=O)N3CCN(C(=O)C4CC4)CC3)cnc3ccsc23)CC1] | 1-(6-(4-(cyclopropanecarbonyl)piperazine-1-carbonyl)thieno[3,2-b]pyridin-7-yl)-4-phenylpiperidine-4-carbonitrile, TFA |
| 283 | 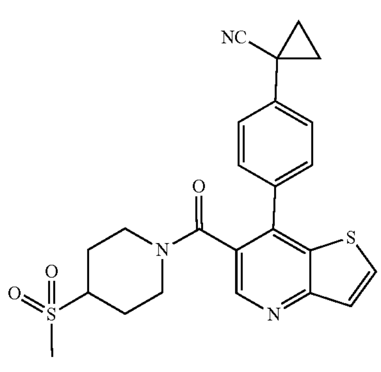 [SMILES: CS(=O)(=O)C1CCN(C(=O)c2cnc3ccsc3c2-c2ccc(C3(C#N)CC3)cc2)CC1] | 1-(4-(6-(4-(methylsulfonyl)piperidine-1-carbonyl)thieno[3,2-b]pyridin-7-yl)phenyl)cyclopropanecarbonitrile, TFA |

TABLE 1-continued

| Cpd. ID | Structure | Compound name |
|---|---|---|
| 284 | 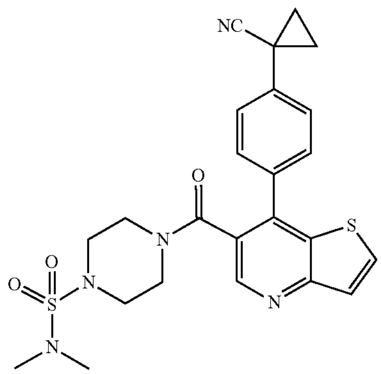 [SMILES: CN(C)S(=O)(=O)N1CCN(C(=O)c2cnc3ccsc3c2-c2ccc(C3(C#N)CC3)cc2)CC1] | 4-(7-(4-(1-cyanocyclopropyl)phenyl)thieno[3,2-b]pyridine-6-carbonyl)-N,N-dimethylpiperazine-1-sulfonamide, TFA |
| 285 | 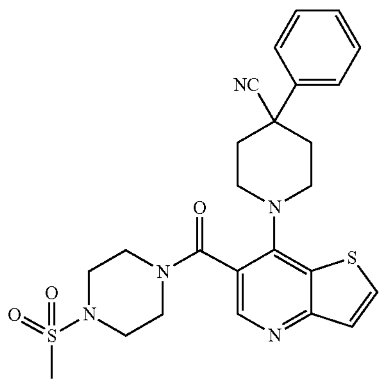 [SMILES: CS(=O)(=O)N1CCN(C(=O)c2cnc3ccsc3c2N2CCC(C#N)(c3ccccc3)CC2)CC1] | 1-(6-(4-(methylsulfonyl)piperazine-1-carbonyl)thieno[3,2-b]pyridin-7-yl)-4-phenylpiperidine-4-carbonitrile, TFA |
| 286 | 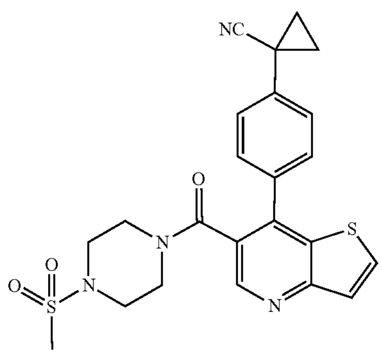 [SMILES: CS(=O)(=O)N1CCN(C(=O)c2cnc3ccsc3c2-c2ccc(C3(C#N)CC3)cc2)CC1] | 1-(4-(6-(4-(methylsulfonyl)piperazine-1-carbonyl)thieno[3,2-b]pyridin-7-yl)phenyl)cyclopropanecarbonitrile, TFA |
| 287 | 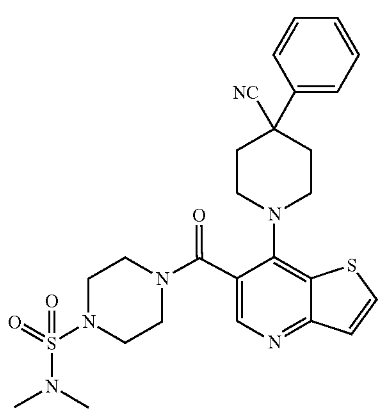 [SMILES: CN(C)S(=O)(=O)N1CCN(C(=O)c2cnc3ccsc3c2N2CCC(C#N)(c3ccccc3)CC2)CC1] | 4-(7-(4-cyano-4-phenylpiperidin-1-yl)thieno[3,2-b]pyridine-6-carbonyl)-N,N-dimethylpiperazine-1-sulfonamide, TFA |

TABLE 1-continued

| Cpd. ID | Structure | Compound name |
|---|---|---|
| 288 | 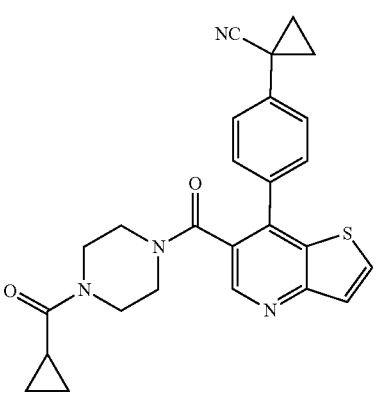 [SMILES: N#CC1(c2ccc(-c3c(C(=O)N4CCN(C(=O)C5CC5)CC4)cnc4ccsc34)cc2)CC1] | 1-(4-(6-(4-(cyclopropanecarbonyl)piperazine-1-carbonyl)thieno[3,2-b]pyridin-7-yl)phenyl)cyclopropanecarbonitrile, TFA |
| 289 | 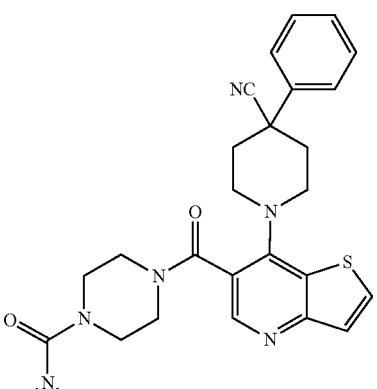 | 4-(7-(4-cyano-4-phenylpiperidin-1-yl)thieno[3,2-b]pyridine-6-carbonyl)-N,N-dimethylpiperazine-1-carboxamide, TFA |
| 290 | 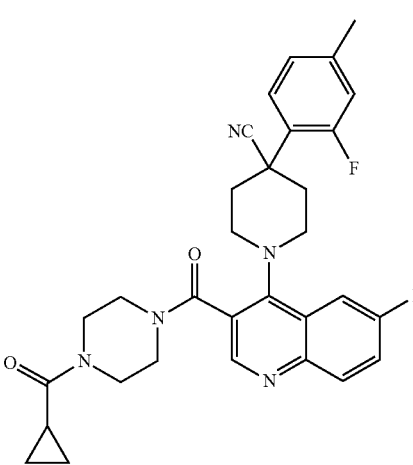 | 1-(3-(4-(cyclopropanecarbonyl)piperazine-1-carbonyl)-6-fluoroquinolin-4-yl)-4-(2-fluoro-4-methylphenyl)piperidine-4-carbonitrile, TFA |

TABLE 1-continued

| Cpd. ID | Structure | Compound name |
|---|---|---|
| 291 | 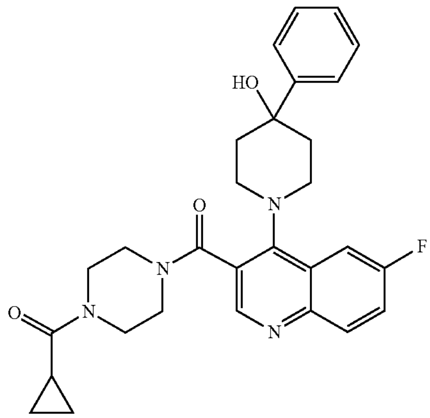 [SMILES: O=C(c1cnc2ccc(F)cc2c1N1CCC(O)(c2ccccc2)CC1)N1CCN(C(=O)C2CC2)CC1] | (4-(cyclopropanecarbonyl)piperazin-1-yl)(6-fluoro-4-(4-hydroxy-4-phenylpiperidin-1-yl)quinolin-3-yl)methanone, TFA |
| 292 | 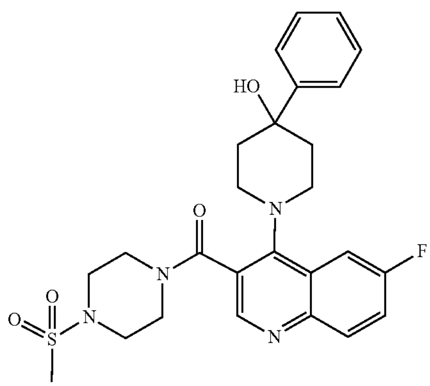 [SMILES: CS(=O)(=O)N1CCN(C(=O)c2cnc3ccc(F)cc3c2N2CCC(O)(c3ccccc3)CC2)CC1] | (6-fluoro-4-(4-hydroxy-4-phenylpiperidin-1-yl)quinolin-3-yl)(4-(methylsulfonyl)piperazin-1-yl)methanone, TFA |
| 293 | 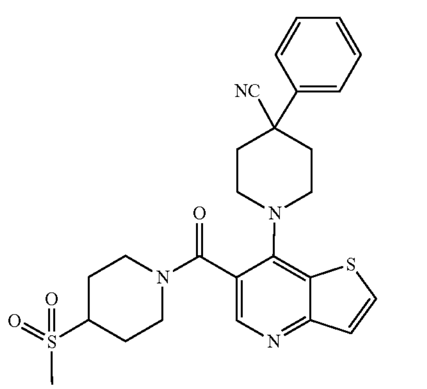 [SMILES: CS(=O)(=O)C1CCN(C(=O)c2cnc3ccsc3c2N2CCC(C#N)(c3ccccc3)CC2)CC1] | 1-(6-(4-(methylsulfonyl)piperidine-1-carbonyl)thieno[3,2-b]pyridin-7-yl)-4-phenylpiperidine-4-carbonitrile, TFA |
| 294 | 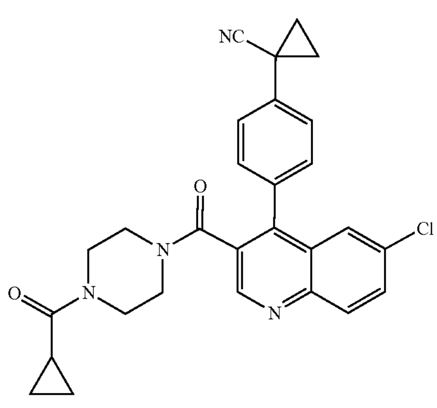 [SMILES: N#CC1(c2ccc(-c3c(C(=O)N4CCN(C(=O)C5CC5)CC4)cnc4ccc(Cl)cc34)cc2)CC1] | 1-(4-(6-chloro-3-(4-(cyclopropanecarbonyl)piperazine-1-carbonyl)quinolin-4-yl)phenyl)cyclopropanecarbonitrile, TFA |

TABLE 1-continued

| Cpd. ID | Structure | Compound name |
|---|---|---|
| 295 | 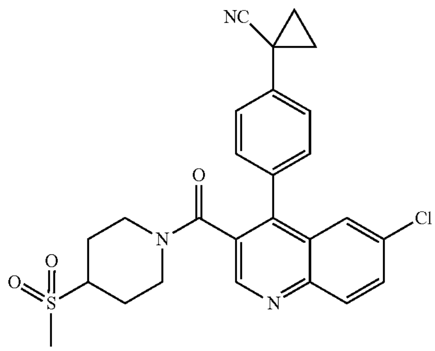 [SMILES: CS(=O)(=O)C1CCN(C(=O)c2cnc3ccc(Cl)cc3c2-c2ccc(C3(C#N)CC3)cc2)CC1] | 1-(4-(6-chloro-3-(4-(methylsulfonyl)piperidine-1-carbonyl)quinolin-4-yl)phenyl)cyclopropanecarbonitrile, TFA |
| 296 | 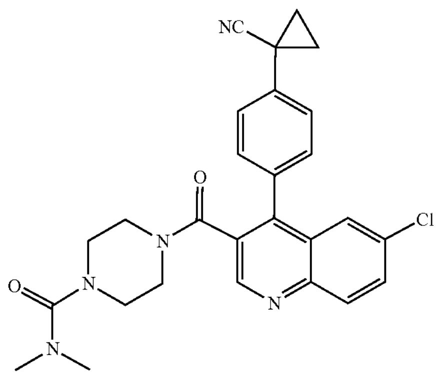 [SMILES: CN(C)C(=O)N1CCN(C(=O)c2cnc3ccc(Cl)cc3c2-c2ccc(C3(C#N)CC3)cc2)CC1] | 4-(6-chloro-4-(4-(1-cyanocyclopropyl)phenyl)quinoline-3-carbonyl)-N,N-dimethylpiperazine-1-carboxamide, TFA |
| 297 | 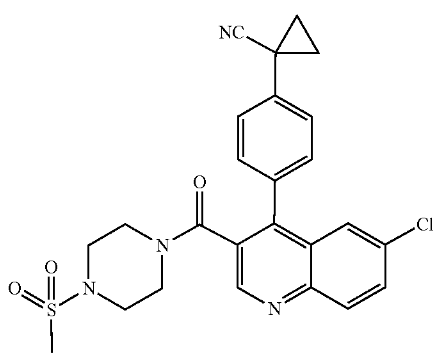 [SMILES: CS(=O)(=O)N1CCN(C(=O)c2cnc3ccc(Cl)cc3c2-c2ccc(C3(C#N)CC3)cc2)CC1] | 1-(4-(6-chloro-3-(4-(methylsulfonyl)piperazine-1-carbonyl)quinolin-4-yl)phenyl)cyclopropanecarbonitrile, TFA |
| 298 | 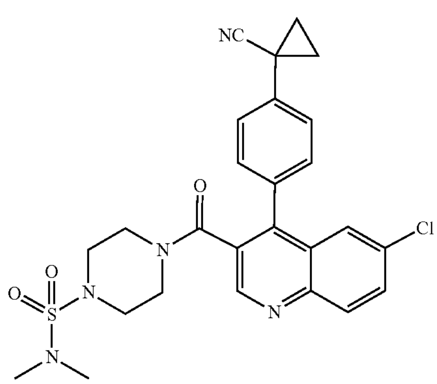 [SMILES: CN(C)S(=O)(=O)N1CCN(C(=O)c2cnc3ccc(Cl)cc3c2-c2ccc(C3(C#N)CC3)cc2)CC1] | 4-(6-chloro-4-(4-(1-cyanocyclopropyl)phenyl)quinoline-3-carbonyl)-N,N-dimethylpiperazine-1-sulfonamide, TFA |

TABLE 1-continued

| Cpd. ID | Structure | Compound name |
|---|---|---|
| 299 | 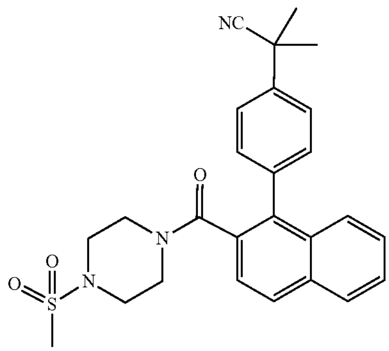 [SMILES: CC(C)(C#N)c1ccc(-c2c(C(=O)N3CCN(S(C)(=O)=O)CC3)ccc3ccccc23)cc1] | 2-methyl-2-(4-(2-(4-(methylsulfonyl)piperazine-1-carbonyl)naphthalen-1-yl)phenyl)propanenitrile |
| 300 | 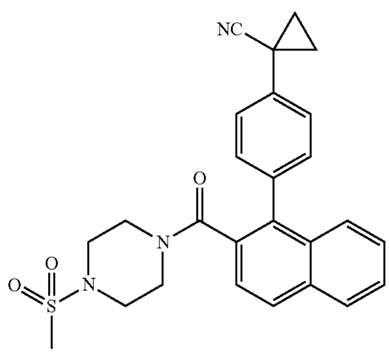 [SMILES: CS(=O)(=O)N1CCN(C(=O)c2ccc3ccccc3c2-c2ccc(C3(C#N)CC3)cc2)CC1] | 1-(4-(2-(4-(methylsulfonyl)piperazine-1-carbonyl)naphthalen-1-yl)phenyl)cyclopropanecarbonitrile |
| 301 | 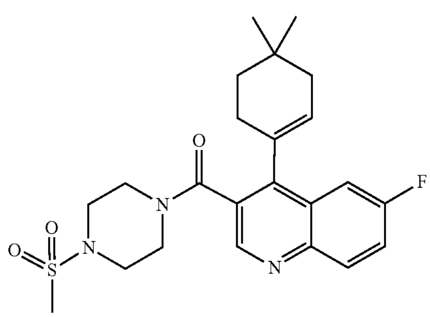 [SMILES: CC1(C)CC=C(c2c(C(=O)N3CCN(S(C)(=O)=O)CC3)cnc3ccc(F)cc23)CC1] | (4-(4,4-dimethylcyclohex-1-en-1-yl)-6-fluoroquinolin-3-yl)(4-(methylsulfonyl)piperazin-1-yl)methanone, TFA |
| 302 | 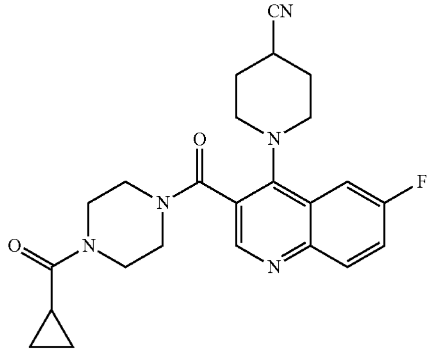 [SMILES: N#CC1CCN(c2c(C(=O)N3CCN(C(=O)C4CC4)CC3)cnc3ccc(F)cc23)CC1] | 1-(3-(4-(cyclopropanecarbonyl)piperazine-1-carbonyl)-6-fluoroquinolin-4-yl)piperidine-4-carbonitrile, TFA |

TABLE 1-continued

| Cpd. ID | Structure | Compound name |
|---|---|---|
| 303 | 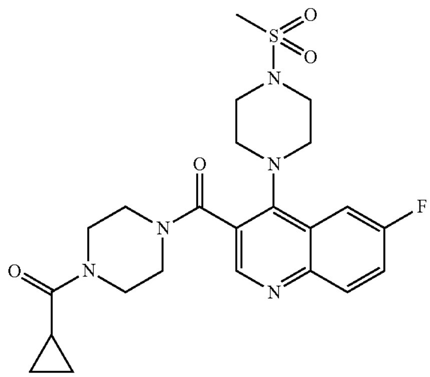 [SMILES: CS(=O)(=O)N1CCN(c2c(C(=O)N3CCN(C(=O)C4CC4)CC3)cnc3ccc(F)cc23)CC1] | (4-(cyclopropanecarbonyl)piperazin-1-yl)(6-fluoro-4-(4-(methylsulfonyl)piperazin-1-yl)quinolin-3-yl)methanone, TFA |
| 304 | 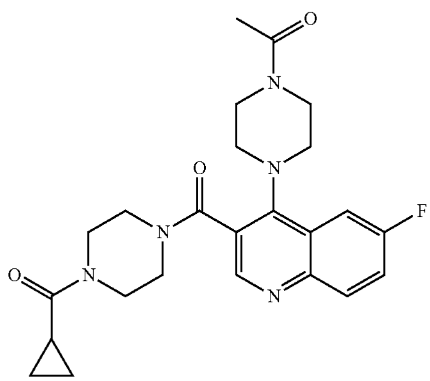 [SMILES: CC(=O)N1CCN(c2c(C(=O)N3CCN(C(=O)C4CC4)CC3)cnc3ccc(F)cc23)CC1] | 1-(4-(3-(4-(cyclopropanecarbonyl)piperazine-1-carbonyl)-6-fluoroquinolin-4-yl)piperazin-1-yl)ethanone, TFA |
| 305 | 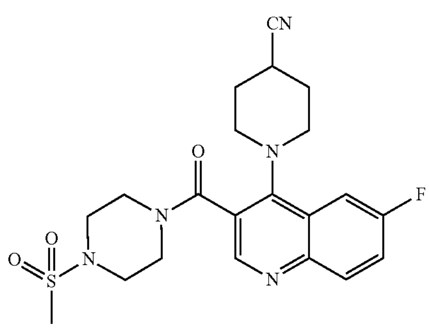 [SMILES: CS(=O)(=O)N1CCN(C(=O)c2cnc3ccc(F)cc3c2N2CCC(C#N)CC2)CC1] | 1-(6-fluoro-3-(4-(methylsulfonyl)piperazine-1-carbonyl)quinolin-4-yl)piperidine-4-carbonitrile, TFA |
| 306 | 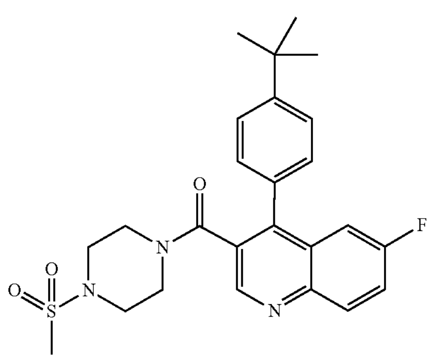 [SMILES: CC(C)(C)c1ccc(-c2c(C(=O)N3CCN(S(C)(=O)=O)CC3)cnc3ccc(F)cc23)cc1] | (4-(4-(tert-butyl)phenyl)-6-fluoroquinolin-3-yl)(4-(methylsulfonyl)piperazin-1-yl)methanone, TFA |

TABLE 1-continued

| Cpd. ID | Structure | Compound name |
|---|---|---|
| 307 | 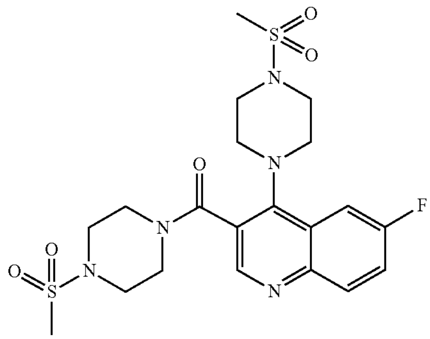 [SMILES: CS(=O)(=O)N1CCN(C(=O)c2cnc3ccc(F)cc3c2N2CCN(S(C)(=O)=O)CC2)CC1] | (6-fluoro-4-(4-(methylsulfonyl)piperazin-1-yl)quinolin-3-yl)(4-(methylsulfonyl)piperazin-1-yl)methanone, TFA |
| 308 | 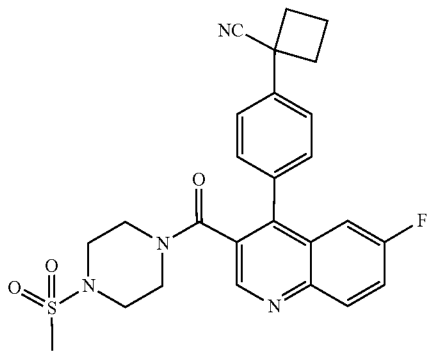 [SMILES: CS(=O)(=O)N1CCN(C(=O)c2cnc3ccc(F)cc3c2-c2ccc(C3(C#N)CCC3)cc2)CC1] | 1-(4-(6-fluoro-3-(4-(methylsulfonyl)piperazine-1-carbonyl)quinolin-4-yl)phenyl)cyclobutanecarbonitrile, TFA |
| 309 | 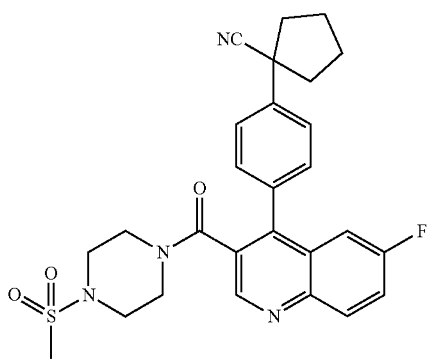 [SMILES: CS(=O)(=O)N1CCN(C(=O)c2cnc3ccc(F)cc3c2-c2ccc(C3(C#N)CCCC3)cc2)CC1] | 1-(4-(6-fluoro-3-(4-(methylsulfonyl)piperazine-1-carbonyl)quinolin-4-yl)phenyl)cyclopentanecarbonitrile, TFA |
| 310 | 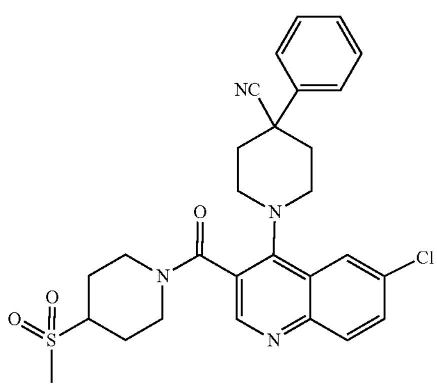 [SMILES: CS(=O)(=O)C1CCN(C(=O)c2cnc3ccc(Cl)cc3c2N2CCC(C#N)(c3ccccc3)CC2)CC1] | 1-(6-chloro-3-(4-(methylsulfonyl)piperidine-1-carbonyl)quinolin-4-yl)-4-phenylpiperidine-4-carbonitrile, TFA |

TABLE 1-continued

| Cpd. ID | Structure | Compound name |
|---|---|---|
| 311 | 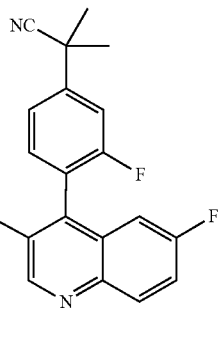 | 2-(3-fluoro-4-(6-fluoro-3-(4-(methylsulfonyl)piperazine-1-carbonyl)quinolin-4-yl)phenyl)-2-methylpropanenitrile, TFA |
| 312 | 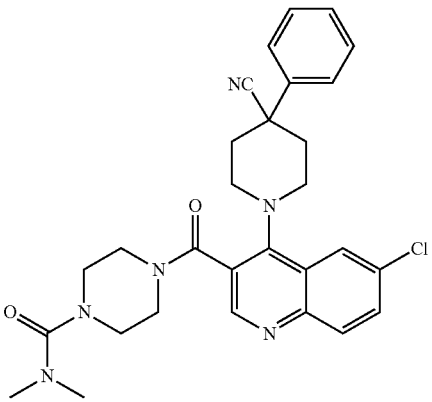 [SMILES: CN(C)C(=O)N1CCN(C(=O)c2cnc3ccc(Cl)cc3c2N2CCC(C#N)(c3ccccc3)CC2)CC1] | 4-(6-chloro-4-(4-cyano-4-phenylpiperidin-1-yl)quinoline-3-carbonyl)-N,N-dimethylpiperazine-1-carboxamide, TFA |
| 313 | 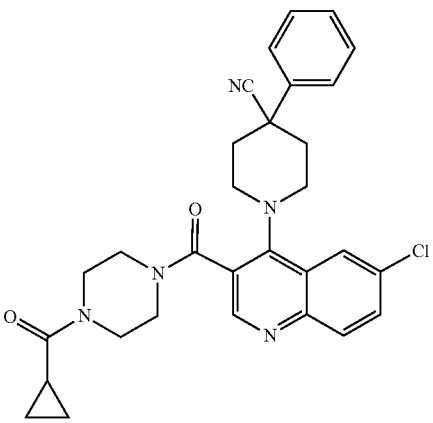 [SMILES: N#CC1(c2ccccc2)CCN(c2c(C(=O)N3CCN(C(=O)C4CC4)CC3)cnc3ccc(Cl)cc23)CC1] | 1-(6-chloro-3-(4-(cyclopropanecarbonyl)piperazine-1-carbonyl)quinolin-4-yl)-4-phenylpiperidine-4-carbonitrile, TFA |
| 314 | 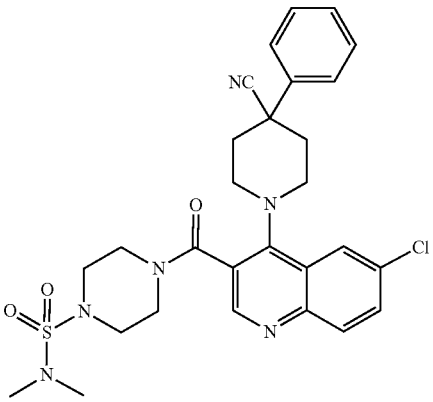 [SMILES: CN(C)S(=O)(=O)N1CCN(C(=O)c2cnc3ccc(Cl)cc3c2N2CCC(C#N)(c3ccccc3)CC2)CC1] | 4-(6-chloro-4-(4-cyano-4-phenylpiperidin-1-yl)quinoline-3-carbonyl)-N,N-dimethylpiperazine-1-sulfonamide, TFA |

TABLE 1-continued

| Cpd. ID | Structure | Compound name |
| --- | --- | --- |
| 315 | 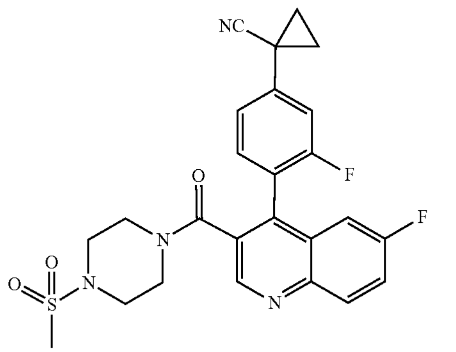 [SMILES: CS(=O)(=O)N1CCN(C(=O)c2cnc3ccc(F)cc3c2-c2ccc(C3(C#N)CC3)cc2F)CC1] | 1-(3-fluoro-4-(6-fluoro-3-(4-(methylsulfonyl)piperazine-1-carbonyl)quinolin-4-yl)phenyl)cyclopropanecarbonitrile, TFA |
| 316 | 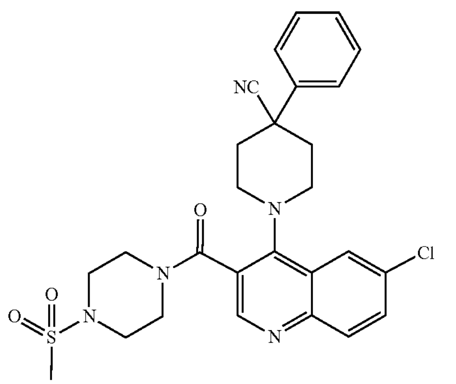 [SMILES: CS(=O)(=O)N1CCN(C(=O)c2cnc3ccc(Cl)cc3c2N2CCC(C#N)(c3ccccc3)CC2)CC1] | 1-(6-chloro-3-(4-(methylsulfonyl)piperazine-1-carbonyl)quinolin-4-yl)-4-phenylpiperidine-4-carbonitrile, TFA |
| 317 | 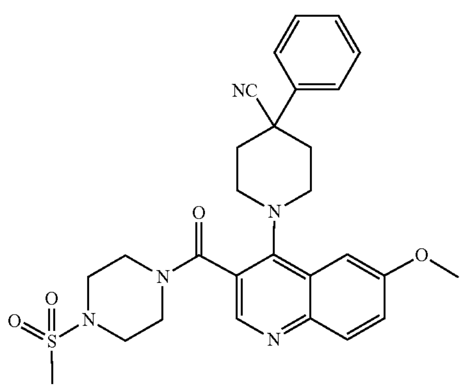 [SMILES: COc1ccc2ncc(C(=O)N3CCN(S(C)(=O)=O)CC3)c(N3CCC(C#N)(c4ccccc4)CC3)c2c1] | 1-(6-methoxy-3-(4-(methylsulfonyl)piperazine-1-carbonyl)quinolin-4-yl)-4-phenylpiperidine-4-carbonitrile, HCl |
| 318 | 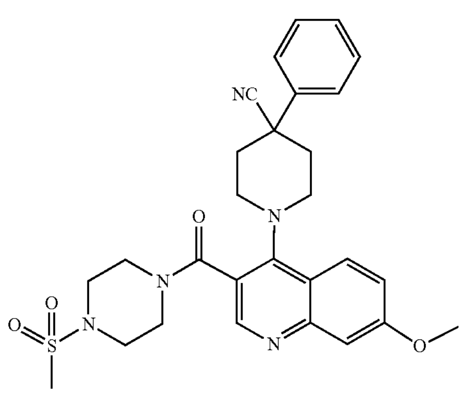 [SMILES: COc1ccc2c(N3CCC(C#N)(c4ccccc4)CC3)c(C(=O)N3CCN(S(C)(=O)=O)CC3)cnc2c1] | 1-(7-methoxy-3-(4-(methylsulfonyl)piperazine-1-carbonyl)quinolin-4-yl)-4-phenylpiperidine-4-carbonitrile, HCl |

TABLE 1-continued

| Cpd. ID | Structure | Compound name |
|---|---|---|
| 319 | 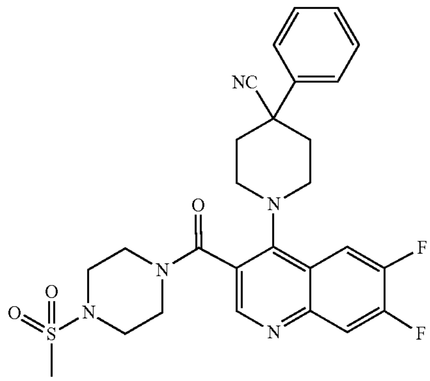 [SMILES: CS(=O)(=O)N1CCN(C(=O)c2cnc3cc(F)c(F)cc3c2N2CCC(C#N)(c3ccccc3)CC2)CC1] | 1-(6,7-difluoro-3-(4-(methylsulfonyl)piperazine-1-carbonyl)quinolin-4-yl)-4-phenylpiperidine-4-carbonitrile, HCl |
| 320 | 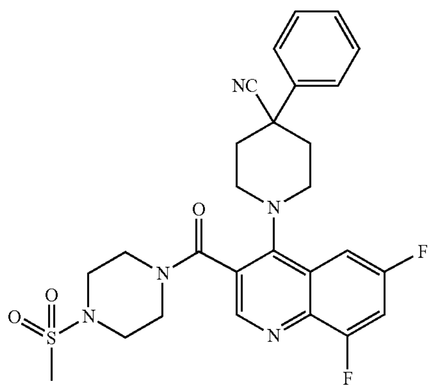 [SMILES: CS(=O)(=O)N1CCN(C(=O)c2cnc3c(F)cc(F)cc3c2N2CCC(C#N)(c3ccccc3)CC2)CC1] | 1-(6,8-difluoro-3-(4-(methylsulfonyl)piperazine-1-carbonyl)quinolin-4-yl)-4-phenylpiperidine-4-carbonitrile, HCl |
| 321 | 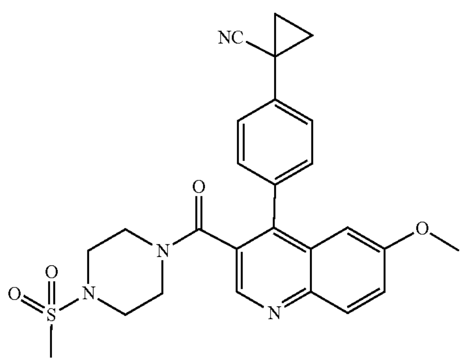 [SMILES: COc1ccc2ncc(C(=O)N3CCN(S(C)(=O)=O)CC3)c(-c3ccc(C4(C#N)CC4)cc3)c2c1] | 1-(4-(6-methoxy-3-(4-(methylsulfonyl)piperazine-1-carbonyl)quinolin-4-yl)phenyl)cyclopropane-1-carbonitrile, HCl |
| 322 | 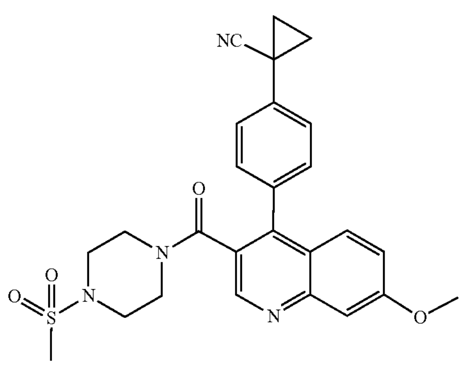 [SMILES: COc1ccc2c(-c3ccc(C4(C#N)CC4)cc3)c(C(=O)N3CCN(S(C)(=O)=O)CC3)cnc2c1] | 1-(4-(7-methoxy-3-(4-(methylsulfonyl)piperazine-1-carbonyl)quinolin-4-yl)phenyl)cyclopropane-1-carbonitrile, HCl |

TABLE 1-continued

| Cpd. ID | Structure | Compound name |
|---|---|---|
| 323 | 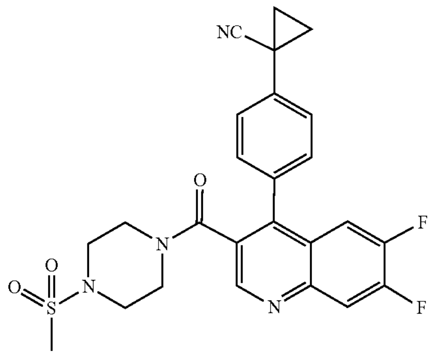 [SMILES: CS(=O)(=O)N1CCN(C(=O)c2cnc3cc(F)c(F)cc3c2-c2ccc(C3(C#N)CC3)cc2)CC1] | 1-(4-(6,7-difluoro-3-(4-(methylsulfonyl)piperazine-1-carbonyl)quinolin-4-yl)phenyl)cyclopropane-1-carbonitrile, HCl |
| 324 | 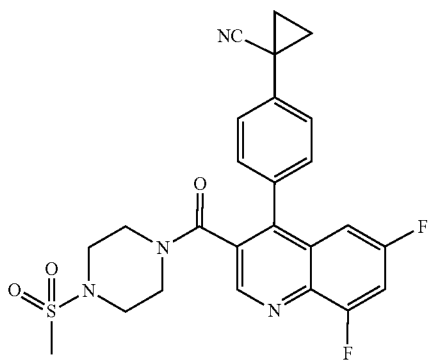 [SMILES: CS(=O)(=O)N1CCN(C(=O)c2cnc3c(F)cc(F)cc3c2-c2ccc(C3(C#N)CC3)cc2)CC1] | 1-(4-(6,8-difluoro-3-(4-(methylsulfonyl)piperazine-1-carbonyl)quinolin-4-yl)phenyl)cyclopropane-1-carbonitrile, HCl |
| 325 | 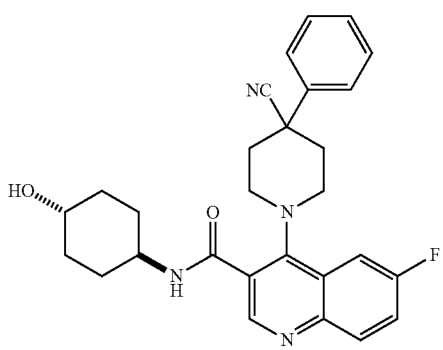 [SMILES: N#CC1(c2ccccc2)CCN(c2c(C(=O)N[C@H]3CC[C@H](O)CC3)cnc3ccc(F)cc23)CC1] | 4-(4-cyano-4-phenylpiperidin-1-yl)-6-fluoro-N-((1r,4r)-4-hydroxycyclohexyl)quinoline-3-carboxamide, TFA |
| 326 | 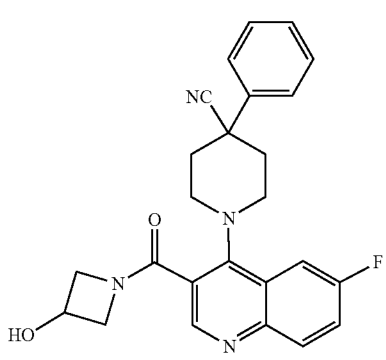 [SMILES: N#CC1(c2ccccc2)CCN(c2c(C(=O)N3CC(O)C3)cnc3ccc(F)cc23)CC1] | 1-(6-fluoro-3-(3-hydroxyazetidine-1-carbonyl)quinolin-4-yl)-4-phenylpiperidine-4-carbonitrile, TFA |

TABLE 1-continued

| Cpd. ID | Structure | Compound name |
|---|---|---|
| 327 | 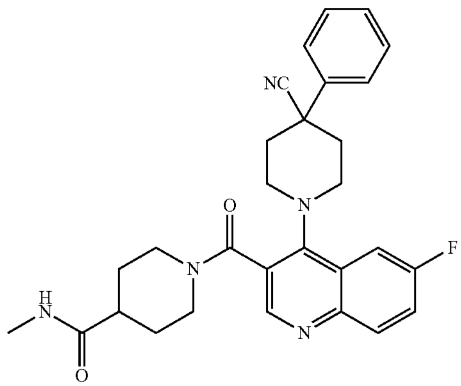 [SMILES: CNC(=O)C1CCN(C(=O)c2cnc3ccc(F)cc3c2N2CCC(C#N)(c3ccccc3)CC2)CC1] | 1-(4-(4-cyano-4-phenylpiperidin-1-yl)-6-fluoroquinoline-3-carbonyl)-N-methylpiperidine-4-carboxamide, TFA |
| 328 | 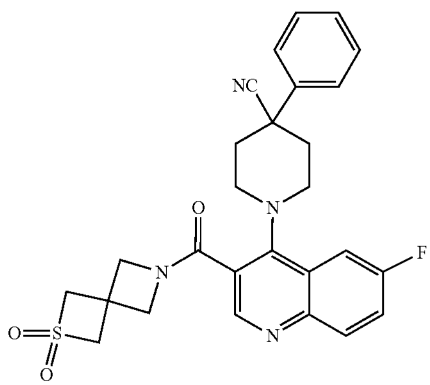 [SMILES: N#CC1(c2ccccc2)CCN(c2c(C(=O)N3CC4(C3)CS(=O)(=O)C4)cnc3ccc(F)cc23)CC1] | 1-(3-(2,2-dioxido-2-thia-6-azaspiro[3.3]heptane-6-carbonyl)-6-fluoroquinolin-4-yl)-4-phenylpiperidine-4-carbonitrile, TFA |
| 329 | 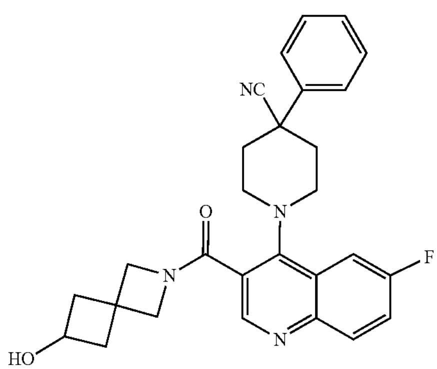 [SMILES: N#CC1(c2ccccc2)CCN(c2c(C(=O)N3CC4(CC(O)C4)C3)cnc3ccc(F)cc23)CC1] | 1-(6-fluoro-3-(6-hydroxy-2-azaspiro[3.3]heptane-2-carbonyl)quinolin-4-yl)-4-phenylpiperidine-4-carbonitrile, TFA |
| 330 | 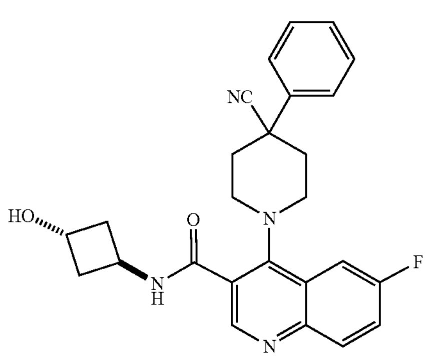 [SMILES: N#CC1(c2ccccc2)CCN(c2c(C(=O)N[C@H]3C[C@H](O)C3)cnc3ccc(F)cc23)CC1] | 4-(4-cyano-4-phenylpiperidin-1-yl)-6-fluoro-N-((1r,3r)-3-hydroxycyclobutyl)quinoline-3-carboxamide, TFA |

TABLE 1-continued

| Cpd. ID | Structure | Compound name |
|---|---|---|
| 331 | 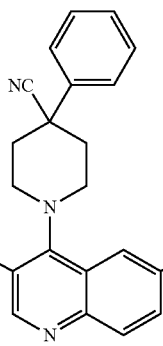 | 1-(6-fluoro-3-(4-hydroxypiperidine-1-carbonyl)quinolin-4-yl)-4-phenylpiperidine-4-carbonitrile, TFA |
| 332 | 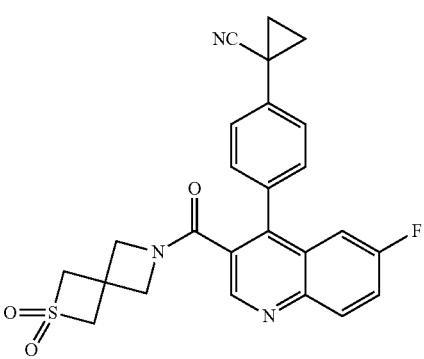 [SMILES: N#CC1(c2ccc(-c3c(C(=O)N4CC5(C4)CS(=O)(=O)C5)cnc4ccc(F)cc34)cc2)CC1] | 1-(4-(3-(2,2-dioxido-2-thia-6-azaspiro[3.3]heptane-6-carbonyl)-6-fluoroquinolin-4-yl)phenyl)cyclopropane-1-carbonitrile, TFA |
| 333 | 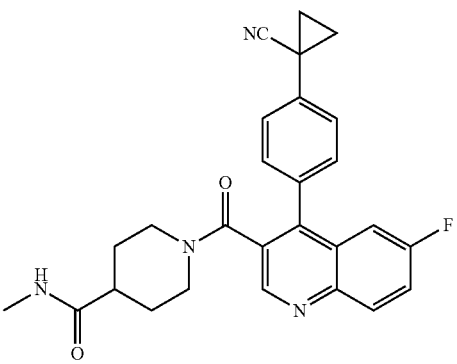 [SMILES: CNC(=O)C1CCN(C(=O)c2cnc3ccc(F)cc3c2-c2ccc(C3(C#N)CC3)cc2)CC1] | 1-(4-(4-(1-cyanocyclopropyl)phenyl)-6-fluoroquinoline-3-carbonyl)-N-methylpiperidine-4-carboxamide, TFA |
| 334 | 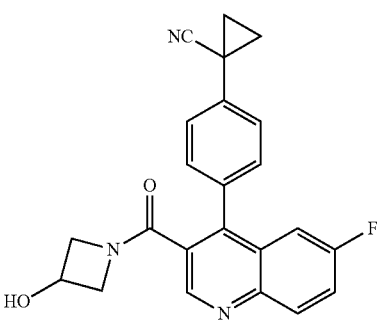 | 1-(4-(6-fluoro-3-(3-hydroxyazetidine-1-carbonyl)quinolin-4-yl)phenyl)cyclopropane-1-carbonitrile, TFA |

TABLE 1-continued

| Cpd. ID | Structure | Compound name |
|---|---|---|
| 335 | 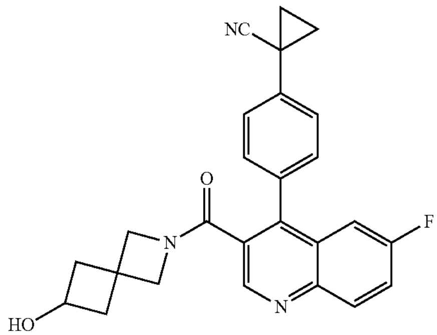 [SMILES: N#CC1(c2ccc(-c3c(C(=O)N4CC5(CC(O)C5)C4)cnc4ccc(F)cc34)cc2)CC1] | 1-(4-(6-fluoro-3-(6-hydroxy-2-azaspiro[3.3]heptane-2-carbonyl)quinolin-4-yl)phenyl)cyclopropane-1-carbonitrile |
| 336 | 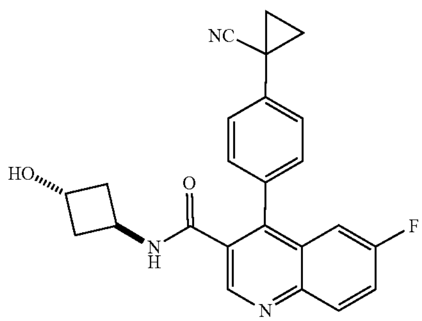 [SMILES: N#CC1(c2ccc(-c3c(C(=O)N[C@H]4C[C@H](O)C4)cnc4ccc(F)cc34)cc2)CC1] | 4-(4-(1-cyanocyclopropyl)phenyl)-6-fluoro-N-((1r,3r)-3-hydroxycyclobutyl)quinoline-3-carboxamide |
| 337 | 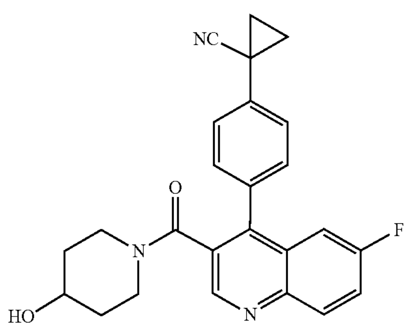 [SMILES: N#CC1(c2ccc(-c3c(C(=O)N4CCC(O)CC4)cnc4ccc(F)cc34)cc2)CC1] | 1-(4-(6-fluoro-3-(4-hydroxypiperidine-1-carbonyl)quinolin-4-yl)phenyl)cyclopropane-1-carbonitrile |
| 338 | 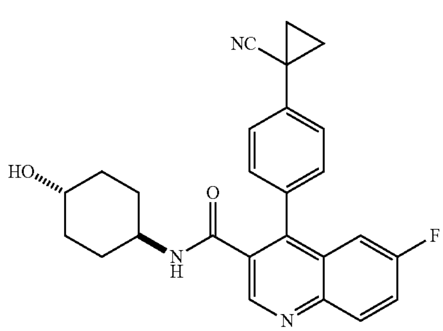 [SMILES: N#CC1(c2ccc(-c3c(C(=O)N[C@H]4CC[C@H](O)CC4)cnc4ccc(F)cc34)cc2)CC1] | 4-(4-(1-cyanocyclopropyl)phenyl)-6-fluoro-N-((1r,4r)-4-hydroxycyclohexyl)quinoline-3-carboxamide |

TABLE 1-continued

| Cpd. ID | Structure | Compound name |
|---|---|---|
| 339 | 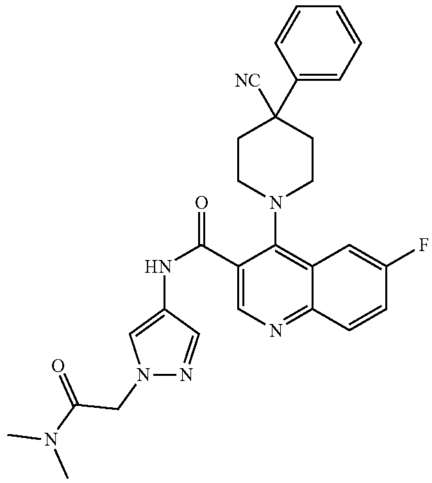 [SMILES: CN(C)C(=O)Cn1cc(NC(=O)c2cnc3ccc(F)cc3c2N2CCC(C#N)(c3ccccc3)CC2)cn1] | 4-(4-cyano-4-phenylpiperidin-1-yl)-N-(1-(2-(dimethylamino)-2-oxoethyl)-1H-pyrazol-4-yl)-6-fluoroquinoline-3-carboxamide, TFA |
| 340 | 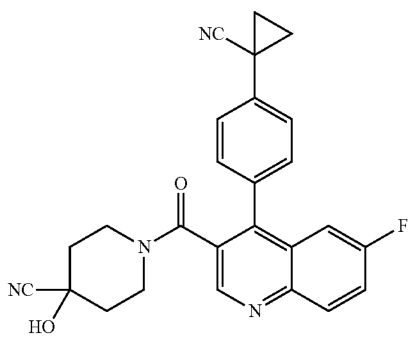 [SMILES: N#CC1(O)CCN(C(=O)c2cnc3ccc(F)cc3c2-c2ccc(C3(C#N)CC3)cc2)CC1] | 1-(4-(4-(1-cyanocyclopropyl)phenyl)-6-fluoroquinoline-3-carbonyl)-4-hydroxypiperidine-4-carbonitrile, TFA |
| 341 | 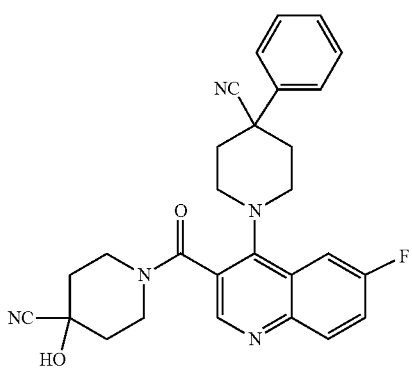 [SMILES: N#CC1(O)CCN(C(=O)c2cnc3ccc(F)cc3c2N2CCC(C#N)(c3ccccc3)CC2)CC1] | 1-(3-(4-cyano-4-hydroxypiperidine-1-carbonyl)-6-fluoroquinolin-4-yl)-4-phenylpiperidine-4-carbonitrile, TFA |
| 342 | 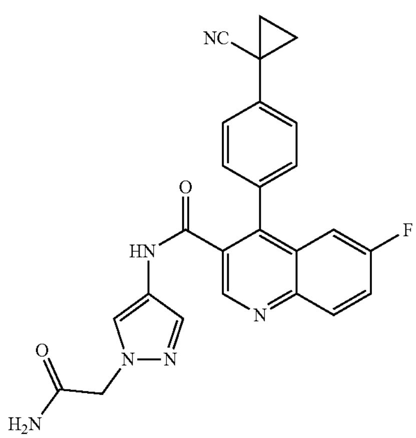 [SMILES: N#CC1(c2ccc(-c3c(C(=O)Nc4cnn(CC(N)=O)c4)cnc4ccc(F)cc34)cc2)CC1] | N-(1-(2-amino-2-oxoethyl)-1H-pyrazol-4-yl)-4-(4-(1-cyanocyclopropyl)phenyl)-6-fluoroquinoline-3-carboxamide, TFA |

TABLE 1-continued
| Cpd. ID | Structure | Compound name |
|---|---|---|
| 343 | 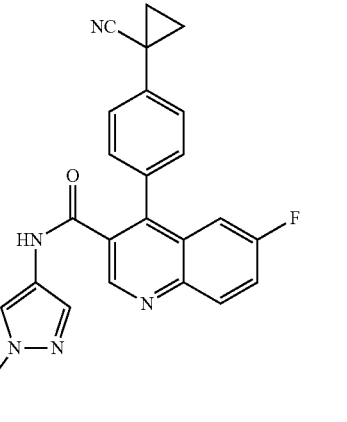 | 4-(4-(1-cyanocyclopropyl)phenyl)-6-fluoro-N-(1-(2-hydroxyethyl)-1H-pyrazol-4-yl)quinoline-3-carboxamide, TFA |
| 344 | 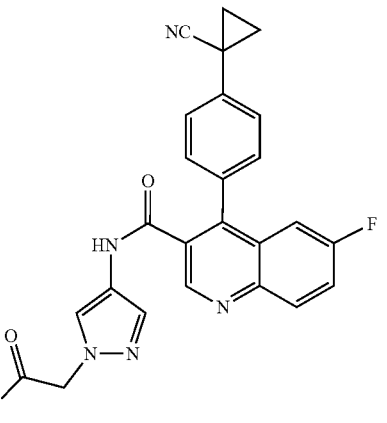 | 4-(4-(1-cyanocyclopropyl)phenyl)-N-(1-(2-(cyclopropylamino)-2-oxoethyl)-1H-pyrazol-4-yl)-6-fluoroquinoline-3-carboxamide, TFA |
| 345 | 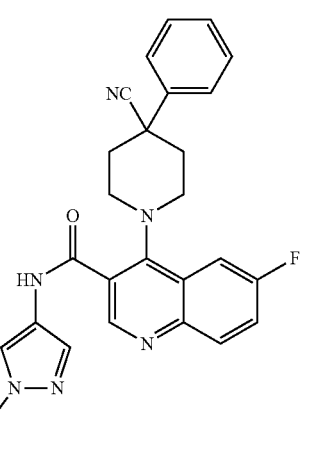 | 4-(4-cyano-4-phenylpiperidin-1-yl)-6-fluoro-N-(1-(2-hydroxyethyl)-1H-pyrazol-4-yl)quinoline-3-carboxamide, TFA |

TABLE 1-continued
| Cpd. ID | Structure | Compound name |
|---|---|---|
| 346 | 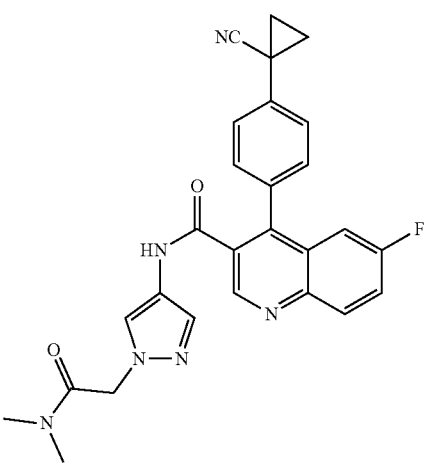 [SMILES: CN(C)C(=O)Cn1cc(NC(=O)c2cnc3ccc(F)cc3c2-c2ccc(C3(C#N)CC3)cc2)cn1] | 4-(4-(1-cyanocyclopropyl)phenyl)-N-(1-(2-(dimethylamino)-2-oxoethyl)-1H-pyrazol-4-yl)-6-fluoroquinoline-3-carboxamide, TFA |
| 347 | 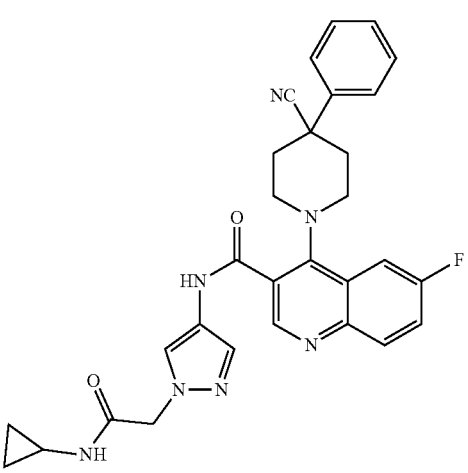 [SMILES: N#CC1(c2ccccc2)CCN(c2c(C(=O)Nc3cnn(CC(=O)NC4CC4)c3)cnc3ccc(F)cc23)CC1] | 4-(4-cyano-4-phenylpiperidin-1-yl)-N-(1-(2-(cyclopropylamino)-2-oxoethyl)-1H-pyrazol-4-yl)-6-fluoroquinoline-3-carboxamide |
| 348 | 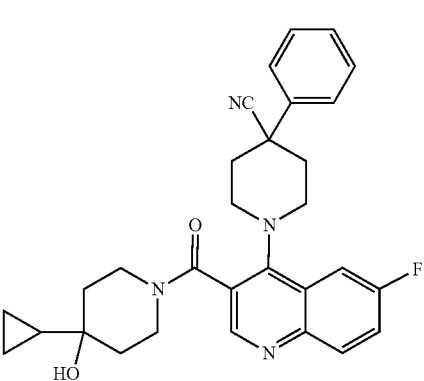 [SMILES: N#CC1(c2ccccc2)CCN(c2c(C(=O)N3CCC(O)(C4CC4)CC3)cnc3ccc(F)cc23)CC1] | 1-(3-(4-cyclopropyl-4-hydroxypiperidine-1-carbonyl)-6-fluoroquinolin-4-yl)-4-phenylpiperidine-4-carbonitrile |

TABLE 1-continued

| Cpd. ID | Structure | Compound name |
|---|---|---|
| 349 | 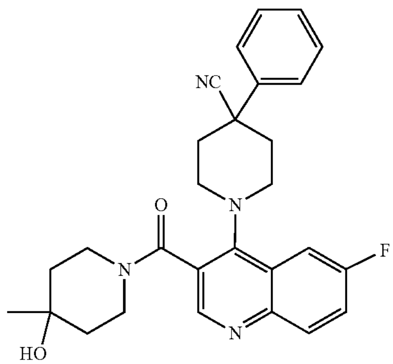 [SMILES: CC1(O)CCN(C(=O)c2cnc3ccc(F)cc3c2N2CCC(C#N)(c3ccccc3)CC2)CC1] | 1-(6-fluoro-3-(4-hydroxy-4-methylpiperidine-1-carbonyl)quinolin-4-yl)-4-phenylpiperidine-4-carbonitrile |
| 350 | 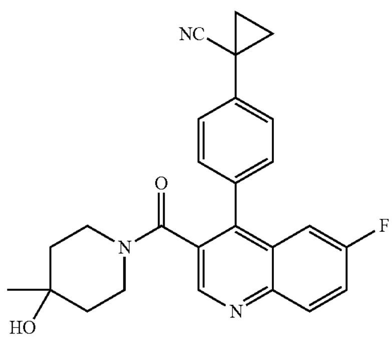 [SMILES: CC1(O)CCN(C(=O)c2cnc3ccc(F)cc3c2-c2ccc(C3(C#N)CC3)cc2)CC1] | 1-(4-(6-fluoro-3-(4-hydroxy-4-methylpiperidine-1-carbonyl)quinolin-4-yl)phenyl)cyclopropane-1-carbonitrile |
| 351 | 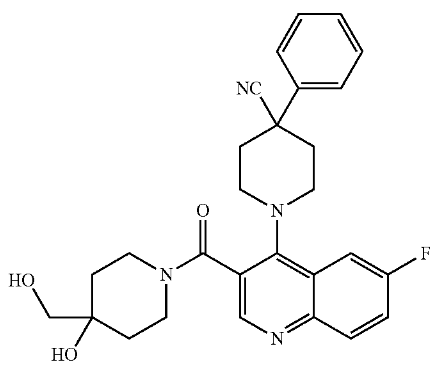 [SMILES: N#CC1(c2ccccc2)CCN(c2c(C(=O)N3CCC(O)(CO)CC3)cnc3ccc(F)cc23)CC1] | 1-(6-fluoro-3-(4-hydroxy-4-(hydroxymethyl)piperidine-1-carbonyl)quinolin-4-yl)-4-phenylpiperidine-4-carbonitrile |
| 352 | 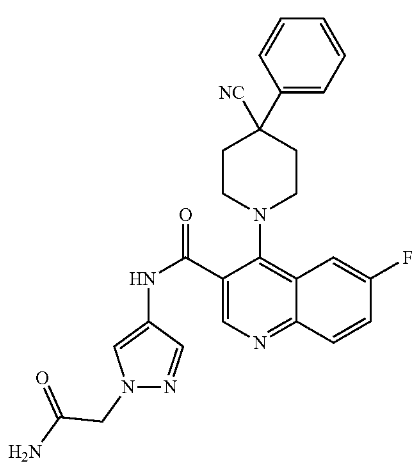 [SMILES: N#CC1(c2ccccc2)CCN(c2c(C(=O)Nc3cnn(CC(N)=O)c3)cnc3ccc(F)cc23)CC1] | N-(1-(2-amino-2-oxoethyl)-1H-pyrazol-4-yl)-4-(4-cyano-4-phenylpiperidin-1-yl)-6-fluoroquinoline-3-carboxamide |

TABLE 1-continued

| Cpd. ID | Structure | Compound name |
|---|---|---|
| 353 | 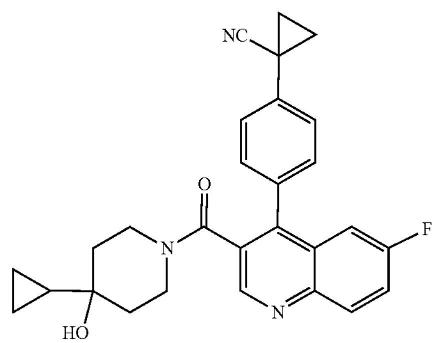 [SMILES: N#CC1(c2ccc(-c3c(C(=O)N4CCC(O)(C5CC5)CC4)cnc4ccc(F)cc34)cc2)CC1] | 1-(4-(3-(4-cyclopropyl-4-hydroxypiperidine-1-carbonyl)-6-fluoroquinolin-4-yl)phenyl)cyclopropane-1-carbonitrile |
| 354 | 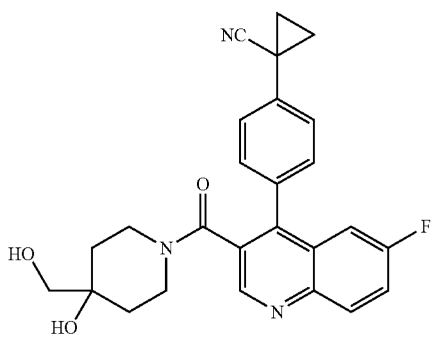 [SMILES: N#CC1(c2ccc(-c3c(C(=O)N4CCC(O)(CO)CC4)cnc4ccc(F)cc34)cc2)CC1] | 1-(4-(6-fluoro-3-(4-hydroxy-4-(hydroxymethyl)piperidine-1-carbonyl)quinolin-4-yl)phenyl)cyclopropane-1-carbonitrile |
| 355 | 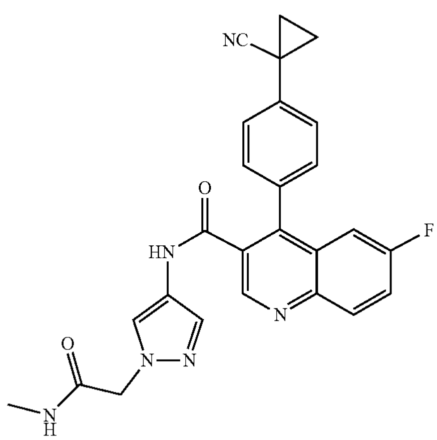 [SMILES: CNC(=O)Cn1cc(NC(=O)c2cnc3ccc(F)cc3c2-c2ccc(C3(C#N)CC3)cc2)cn1] | 4-(4-(1-cyanocyclopropyl)phenyl)-6-fluoro-N-(1-(2-(methylamino)-2-oxoethyl)-1H-pyrazol-4-yl)quinoline-3-carboxamide, TFA |
| 356 | 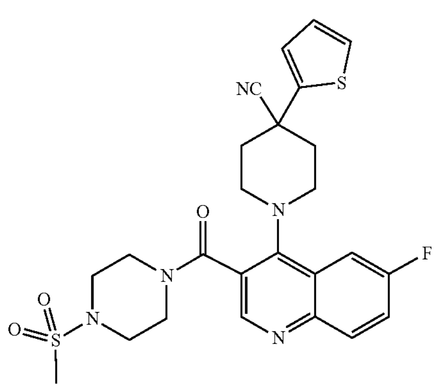 [SMILES: CS(=O)(=O)N1CCN(C(=O)c2cnc3ccc(F)cc3c2N2CCC(C#N)(c3cccs3)CC2)CC1] | 1-(6-fluoro-3-(4-(methylsulfonyl)piperazine-1-carbonyl)quinolin-4-yl)-4-(thiophen-2-yl)piperidine-4-carbonitrile, TFA |

TABLE 1-continued

| Cpd. ID | Structure | Compound name |
|---|---|---|
| 357 | 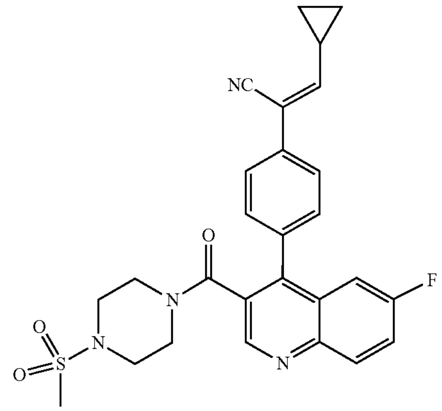 [SMILES: CS(=O)(=O)N1CCN(C(=O)c2cnc3ccc(F)cc3c2-c2ccc(/C(C#N)=C/C3CC3)cc2)CC1] | (Z)-3-cyclopropyl-2-(4-(6-fluoro-3-(4-(methylsulfonyl)piperazine-1-carbonyl)quinolin-4-yl)phenyl)acrylonitrile |

Example 358. ALDH1A1 Enzymatic Assay (In Vitro Assay)

3 μL of ALDH1A1 enzyme (final concentration 20 nM) or assay buffer (100 mM HEPES pH 7.5 with 0.01% Tween 20) were dispensed into a 1,536-well solid-bottom black plate (Greiner Bio One, Monroe, N.C.) followed by pin-tool transfer (23 nL) of candidate inhibitors (final concentration range 968 pM to 57.2 μM) and control (Bay 11-7085, final concentration range 1.31 nM to 2.86 μM). Samples were incubated (RT, protected from light) for 15 minutes followed by a 1 μL substrate addition of NAD$^+$ and Propionaldehyde (final concentrations of 1 mM and 80 μM, respectively). Plates were centrifuged at 1,000 rpm for 15 seconds, then read in kinetic mode on a ViewLux High-throughput CCD imager (Perkin-Elmer) equipped with standard UV fluorescence optics (340 nm excitation, 450 nm emission) for 10 minutes. The change in fluorescence intensity over the 10-minute reaction period was normalized against no-inhibitor and no-enzyme controls and the resulting percent inhibition data were fitted for biological activity.

Example 359. MIA PaCa2 Cell-Based Assay (In Vitro Assay)

1,536-Well High-Content Imaging ALDEFLUOR Assay

The ALDEFLUOR™ kit was purchased from STEMCELL Technologies (Vancouver, Canada; #01700). MIA PaCa-2 cells (5 μL; 1,000 cells/well) were dispensed into black, optical quality (cyclic olefin copolymer) clear bottom, medium binding TC treated 1,536-well plates (Aurora Microplates, Whitefish Mont.) using a Multidrop Combi dispenser (ThermoFisher) and incubated overnight (37° C., 5% CO$_2$, 85% RH). Media (RPMI 1640 (Life Technologies, Carlsbad, Calif.), supplemented with 2 mM L-Glutamine (Life Technologies), 10% HyClone™ fetal bovine serum (FBS, GE Healthcare, Piscataway, N.J.) and 100 U/mL penicillin and 100 μg/mL streptomycin (Life Technologies)) was subsequently removed by centrifuging plates upside down using a plate adaptor to collect media. A solution of BAAA substrate (STEMCELL Technologies) and Hoechst 33342 (ThermoFisher, final concentrations of 500 nM and 0.5 nM, respectively) in ALDEFLUOR™ buffer (STEMCELL Technologies #01700) was dispensed onto cells using a Multidrop Combi followed by immediate transfer (23 nL) of compound or control solutions using a Wako Pin-tool (final percentage of DMSO in the cell plates was 0.5%). Unless otherwise noted, all compounds were assayed as 16-point dilutions spanning a final concentration range of 1.4 nM to 47.8 μM. The neutral and positive assay controls were DMSO and DEAB (4.6 μM), respectively. Cells were incubated for 30 minutes or the indicated amount of time at 37° C., 5% CO$_2$, 85% RH to allow the conversion of BAAA into BAA. Supernatant was subsequently removed by centrifugation as described above, then ALDEFLUOR™ buffer (3 μl) was dispensed by Multidrop Combi before imaging on an IN Cell 2200 (GE Healthcare).

The above assay was modified for an online robotic screening system. After cell plating and overnight incubation, 4 μL of media were removed using a 64-tip metal aspirator head on a Wako aspirator station, leaving 1 μL remaining in the well, followed by a 4 μL dispense of BAAA and Hoechst 33342 in ALDEFLUOR™ buffer, for a final concentration of 500 nM and 0.5 nM, respectively Immediately following the dispense, 23 nL of compound or control solutions were transferred using a Wako Pin-tool. Cells were incubated for 30 minutes at 37° C., 5% CO$_2$, 85% RH, followed by a 4 μL media removal using the Wako aspirator, and a subsequent 3 μL addition of ALDEFLUOR™ buffer. Plates were then immediately read on the IN Cell 2200 as described below.

Image Acquisition and Analysis

For images captured on the IN Cell 2200 widefield automated microscope, a 10×0.45 NA Plan Apo objective lens was used to capture the entire well of the 1,536-well plate using standard DAPI (390/18×, 432/48 m) and FITC (475/28×, 525/48 m) filter sets at 50 msec and 100 msec exposures, respectively. Images were subsequently analyzed using IN Cell Investigator v1.6.2 analysis software's canned Multi-Target Analysis algorithm (GE Healthcare). Hoechst stained nuclei were identified using top hat segmentation with a minimum area of 75 μm$^2$ and sensitivity of 93. BAA-retaining cells captured via FITC channel, were identified using multiscale top hat segmentation with a minimum area of 100 μm$^2$ and a sensitivity setting of 16. Several data measures were collected and the most robust measure for ALDH activity was found to be the integrated intensity (Intensity×Area) of the FITC channel. Data were plotted using GraphPad Prism software (GraphPad, San Diego, Calif.).

Table 2: Biological Activity for Compounds of Formula (I)

Table 2 provides the biological activity of compounds of this disclosure in the ALDH1A1 enzymatic assay and MIA PaCa2 cell based assay, where ++++ represents $IC_{50} \leq 0.5$ μM; +++ represents $0.5$ μM$<IC_{50} \leq 1.0$ μM; ++ represents $1.0$ μM$<IC_{50} \leq 10$ μM; + represents $IC_{50} > 10$ μM; and NA represents the assay data is not available.

TABLE 2

| Cpd. ID | ALDH1A1 $IC_{50}$ | MIA PaCa2 $IC_{50}$ |
| --- | --- | --- |
| 1 | ++++ | ++ |
| 2 | ++++ | ++ |
| 3 | ++++ | + |
| 4 | ++++ | ++ |
| 5 | ++++ | + |
| 6 | ++++ | ++ |
| 7 | ++++ | + |
| 8 | ++ | + |
| 9 | ++ | + |
| 10 | ++++ | + |
| 11 | + | + |
| 12 | ++++ | ++ |
| 13 | ++++ | ++ |
| 14 | ++++ | + |
| 15 | ++ | + |
| 16 | ++ | NA |
| 17 | ++++ | ++ |
| 18 | ++++ | ++ |
| 19 | ++ | ++ |
| 20 | + | NA |
| 21 | + | NA |
| 22 | + | NA |
| 23 | + | + |
| 24 | ++++ | + |
| 25 | + | + |
| 26 | ++++ | + |
| 27 | ++++ | ++ |
| 28 | ++ | + |
| 29 | + | + |
| 30 | ++++ | ++ |
| 31 | ++++ | ++ |
| 32 | +++ | + |
| 33 | ++ | + |
| 34 | + | NA |
| 35 | + | NA |
| 36 | ++++ | + |
| 37 | ++++ | +++ |
| 38 | ++++ | ++ |
| 39 | +++ | + |
| 40 | ++++ | + |
| 41 | + | NA |
| 42 | ++++ | + |
| 43 | ++++ | ++ |
| 44 | + | + |
| 45 | ++++ | ++ |
| 46 | ++++ | ++ |
| 47 | ++++ | ++ |
| 48 | ++++ | ++ |
| 49 | ++++ | + |
| 50 | ++++ | + |
| 51 | ++++ | + |
| 52 | ++++ | ++ |
| 53 | +++ | + |
| 54 | ++++ | + |
| 55 | ++ | + |
| 56 | ++++ | + |
| 57 | ++++ | + |
| 58 | +++ | + |
| 59 | ++++ | + |
| 60 | + | NA |
| 61 | ++++ | + |
| 62 | ++++ | + |
| 63 | ++ | + |
| 64 | ++++ | ++ |
| 65 | ++++ | ++ |
| 66 | ++++ | ++ |
| 67 | + | + |
| 68 | ++ | + |
| 69 | ++++ | + |
| 70 | ++++ | ++ |
| 71 | +++ | ++ |
| 72 | ++++ | + |
| 73 | ++++ | ++ |
| 74 | ++++ | ++ |
| 75 | ++++ | ++ |
| 76 | ++ | + |
| 77 | ++++ | ++++ |
| 78 | ++++ | ++ |
| 79 | ++++ | + |
| 80 | ++++ | + |
| 81 | ++++ | ++ |
| 82 | ++++ | + |
| 83 | ++++ | + |
| 84 | ++++ | ++++ |
| 85 | +++ | + |
| 86 | ++++ | ++ |
| 87 | ++++ | ++ |
| 88 | ++++ | + |
| 89 | ++++ | + |
| 90 | ++ | + |
| 91 | ++++ | ++ |
| 92 | ++++ | ++ |
| 93 | ++++ | ++ |
| 94 | +++ | + |
| 95 | ++++ | + |
| 96 | ++ | + |
| 97 | ++++ | + |
| 98 | ++ | + |
| 99 | ++ | + |
| 100 | +++ | + |
| 101 | ++++ | ++ |
| 102 | ++++ | ++ |
| 103 | ++++ | ++ |
| 104 | ++++ | + |
| 105 | ++++ | ++ |
| 106 | ++++ | ++ |
| 107 | ++++ | ++ |
| 108 | ++++ | ++ |
| 109 | ++++ | ++ |
| 110 | ++++ | ++ |
| 111 | ++++ | ++ |
| 112 | ++++ | ++ |
| 113 | ++++ | ++ |
| 114 | ++++ | ++ |
| 115 | ++++ | + |
| 116 | ++++ | ++ |
| 117 | ++++ | ++ |
| 118 | ++++ | ++ |
| 119 | ++++ | ++ |
| 120 | ++++ | ++ |
| 121 | ++++ | ++ |
| 122 | ++++ | ++ |
| 123 | ++++ | ++ |
| 124 | ++++ | ++ |
| 125 | ++++ | ++ |
| 126 | ++++ | ++ |
| 127 | ++++ | ++ |
| 128 | ++++ | ++ |
| 129 | ++++ | ++ |
| 130 | ++++ | ++ |
| 131 | ++++ | ++ |
| 132 | ++++ | ++ |
| 133 | ++++ | ++ |
| 134 | ++++ | ++ |
| 135 | ++++ | ++ |
| 136 | ++++ | ++ |
| 137 | ++++ | +++ |
| 138 | ++++ | ++ |
| 139 | ++++ | ++ |
| 140 | ++++ | + |
| 141 | ++++ | ++ |
| 142 | ++++ | ++ |

TABLE 2-continued

Biological activity.

| Cpd. ID | ALDH1A1 IC$_{50}$ | MIA PaCa2 IC$_{50}$ |
| --- | --- | --- |
| 143 | ++++ | ++ |
| 144 | ++++ | ++ |
| 145 | +++ | + |
| 146 | +++ | ++ |
| 147 | ++++ | ++ |
| 148 | ++ | ++ |
| 149 | ++++ | ++ |
| 150 | ++++ | + |
| 151 | ++++ | ++ |
| 152 | ++++ | +++ |
| 153 | ++++ | + |
| 154 | ++++ | ++ |
| 155 | ++ | + |
| 156 | ++++ | ++ |
| 157 | ++++ | ++++ |
| 158 | ++ | + |
| 159 | ++++ | ++ |
| 160 | ++++ | + |
| 161 | ++++ | ++ |
| 162 | ++++ | +++ |
| 163 | ++++ | + |
| 164 | +++ | ++ |
| 165 | ++ | ++ |
| 166 | ++++ | ++ |
| 167 | ++++ | ++++ |
| 168 | ++ | + |
| 169 | ++++ | ++ |
| 170 | ++++ | ++ |
| 171 | ++++ | ++ |
| 172 | ++++ | +++ |
| 173 | ++++ | + |
| 174 | +++ | ++ |
| 175 | ++ | ++ |
| 176 | ++++ | ++ |
| 177 | ++++ | ++++ |
| 178 | ++ | + |
| 179 | ++++ | +++ |
| 180 | ++++ | ++ |
| 181 | ++++ | ++ |
| 182 | ++++ | ++ |
| 183 | ++++ | ++ |
| 184 | ++++ | ++ |
| 185 | ++++ | ++ |
| 186 | ++++ | ++ |
| 187 | ++++ | ++ |
| 188 | ++++ | ++ |
| 189 | ++++ | ++ |
| 190 | ++++ | ++ |
| 191 | ++++ | +++ |
| 192 | ++++ | +++ |
| 193 | ++++ | ++ |
| 194 | ++++ | ++ |
| 195 | ++++ | ++ |
| 196 | ++++ | ++ |
| 197 | ++++ | ++++ |
| 198 | ++++ | + |
| 199 | ++++ | ++ |
| 200 | ++ | + |
| 201 | ++++ | ++ |
| 202 | ++++ | ++++ |
| 203 | ++ | ++ |
| 204 | ++ | + |
| 205 | ++++ | ++ |
| 206 | ++++ | ++ |
| 207 | ++++ | ++ |
| 208 | ++++ | ++++ |
| 209 | ++++ | ++++ |
| 210 | ++++ | ++++ |
| 211 | ++++ | ++++ |
| 212 | ++++ | ++ |
| 213 | ++ | ++ |
| 214 | ++ | + |
| 215 | ++++ | +++ |
| 216 | ++++ | ++++ |
| 217 | ++++ | ++ |
| 218 | ++++ | ++ |
| 219 | ++++ | ++ |
| 220 | ++ | + |
| 221 | ++++ | ++ |
| 222 | ++++ | + |
| 223 | ++ | ++ |
| 224 | ++ | + |
| 225 | ++ | + |
| 226 | ++++ | ++ |
| 227 | ++++ | ++ |
| 228 | ++ | + |
| 229 | ++ | + |
| 230 | ++++ | ++ |
| 231 | + | + |
| 232 | ++++ | ++ |
| 233 | ++++ | +++ |
| 234 | ++++ | ++ |
| 235 | +++ | + |
| 236 | ++++ | ++ |
| 237 | ++ | + |
| 238 | ++ | + |
| 239 | ++++ | ++ |
| 240 | ++ | + |
| 241 | ++ | + |
| 242 | ++++ | +++ |
| 243 | ++++ | ++++ |
| 244 | ++ | + |
| 245 | +++ | ++ |
| 246 | ++++ | ++ |
| 247 | ++++ | ++ |
| 248 | ++++ | ++ |
| 249 | ++++ | ++ |
| 250 | ++++ | ++ |
| 251 | ++++ | +++ |
| 252 | ++++ | + |
| 253 | ++++ | + |
| 254 | ++++ | ++++ |
| 255 | ++ | + |
| 256 | ++++ | ++ |
| 257 | ++++ | ++++ |
| 258 | +++ | ++ |
| 259 | ++++ | ++++ |
| 260 | ++++ | ++++ |
| 261 | ++++ | ++++ |
| 262 | ++++ | ++++ |
| 263 | ++++ | ++++ |
| 264 | ++++ | ++++ |
| 265 | ++++ | ++++ |
| 266 | ++++ | ++++ |
| 267 | ++++ | ++ |
| 268 | ++++ | ++++ |
| 269 | ++++ | ++++ |
| 270 | ++++ | ++++ |
| 271 | ++++ | ++++ |
| 272 | ++++ | ++++ |
| 273 | ++++ | ++++ |
| 274 | ++++ | ++++ |
| 275 | ++++ | ++++ |
| 276 | ++++ | ++++ |
| 277 | ++++ | ++++ |
| 278 | ++++ | ++++ |
| 279 | ++++ | ++++ |
| 280 | ++++ | ++++ |
| 281 | ++++ | ++++ |
| 282 | ++++ | ++++ |
| 283 | ++++ | ++++ |
| 284 | ++++ | ++++ |
| 285 | ++++ | ++++ |
| 286 | ++++ | ++++ |
| 287 | ++++ | ++++ |
| 288 | ++++ | ++++ |
| 289 | ++++ | ++++ |
| 290 | ++++ | ++++ |
| 291 | ++++ | + |
| 292 | ++++ | ++ |
| 293 | ++++ | ++++ |
| 294 | ++++ | ++++ |

TABLE 2-continued

| | Biological activity. | |
|---|---|---|
| Cpd. ID | ALDH1A1 IC$_{50}$ | MIA PaCa2 IC$_{50}$ |
| 295 | ++++ | ++++ |
| 296 | ++++ | ++++ |
| 297 | ++++ | ++++ |
| 298 | ++++ | ++++ |
| 299 | ++++ | ++++ |
| 300 | ++++ | ++++ |
| 301 | ++++ | ++++ |
| 302 | + | + |
| 303 | ++ | ++ |
| 304 | + | + |
| 305 | ++ | + |
| 306 | ++++ | ++++ |
| 307 | ++ | + |
| 308 | ++++ | ++++ |
| 309 | ++++ | ++++ |
| 310 | ++++ | ++++ |
| 311 | ++++ | ++++ |
| 312 | ++++ | ++++ |
| 313 | ++++ | ++++ |
| 314 | ++++ | ++++ |
| 315 | ++++ | ++++ |
| 316 | ++++ | ++++ |
| 317 | ++++ | ++++ |
| 318 | ++++ | ++++ |
| 319 | ++++ | ++++ |
| 320 | ++++ | ++++ |
| 321 | ++++ | ++++ |
| 322 | ++++ | ++++ |
| 323 | ++++ | ++++ |
| 324 | ++++ | ++++ |
| 325 | ++++ | ++++ |
| 326 | ++++ | ++ |
| 327 | ++++ | ++++ |
| 328 | ++++ | ++++ |
| 329 | ++++ | ++++ |
| 330 | ++++ | ++++ |
| 331 | ++++ | +++ |
| 332 | ++++ | ++ |
| 333 | ++++ | ++++ |
| 334 | ++ | + |
| 335 | ++++ | ++ |
| 336 | ++++ | +++ |
| 337 | ++++ | ++ |
| 338 | ++++ | ++++ |
| 339 | ++++ | ++++ |
| 340 | ++++ | ++ |
| 341 | ++++ | +++ |
| 342 | ++++ | +++ |
| 343 | ++++ | ++++ |
| 344 | ++++ | ++ |
| 345 | ++++ | ++++ |
| 346 | ++ | + |
| 347 | ++++ | ++++ |
| 348 | ++++ | ++++ |
| 349 | ++++ | ++++ |
| 350 | ++++ | ++ |
| 351 | ++++ | ++++ |
| 352 | NA | ++++ |
| 353 | ++++ | ++ |
| 354 | ++++ | ++ |
| 355 | ++++ | ++ |
| 356 | ++++ | ++++ |
| 357 | ++++ | ++++ |

What is claimed is:

1. A compound or a pharmaceutically acceptable salt thereof, wherein the compound is a compound of Formula I-2

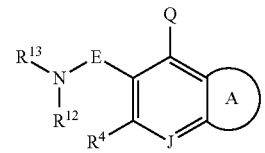

(Formula I-2)

wherein E is —C(O)—;

J is N;

Q is

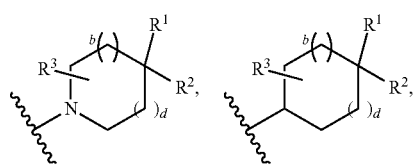

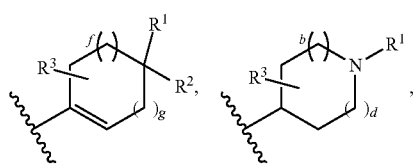

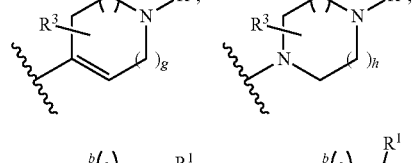

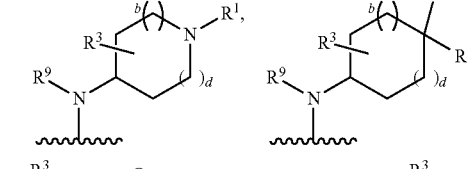

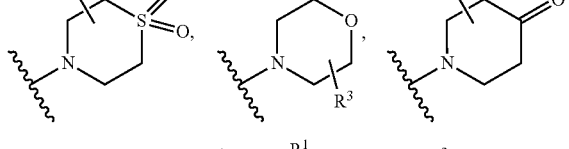

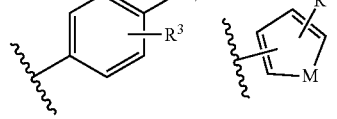

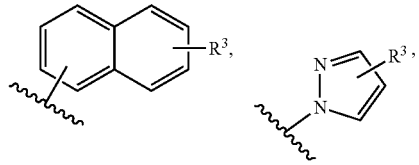

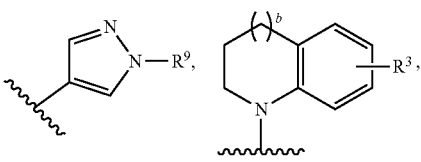

-continued

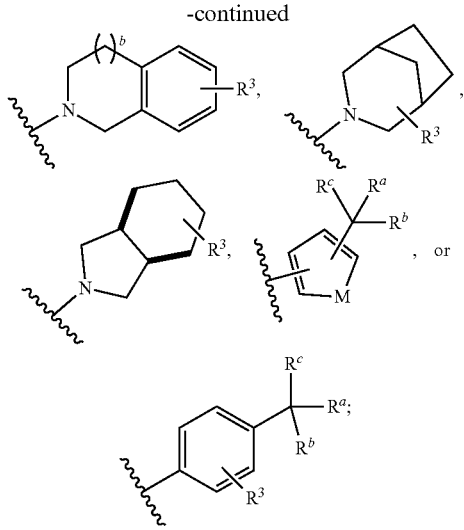

wherein b, d, and f, are each an independent integer from 0 to 2; g and h are each an independent integer from 1 to 2;

M is O, S, NH, $N(C_1\text{-}C_4\text{alkyl})$, or $N(C_3\text{-}C_5\text{cycloalkyl})$;

$R^3$ is independently chosen at each occurrence and is 0 or 1 or more substituents independently chosen from halogen, hydroxyl, cyano, amino, $C_1\text{-}C_6$alkyl, $C_1\text{-}C_6$alkoxy, $C_3\text{-}C_6$cycloalkyl, trifluoromethyl, and phenyl;

$R^a$ and $R^b$ are independently selected from hydrogen, $C_1\text{-}C_4$alkyl, $(C_3\text{-}C_6\text{cycloalkyl})C_{(0\text{-}2)}$alkyl,

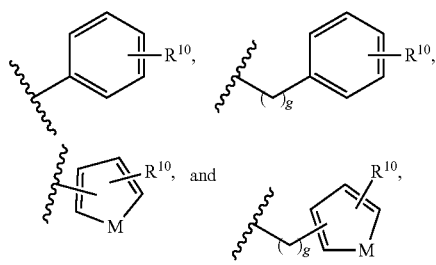

or $R^a$ and $R^b$ can be joined to form a 3- to 6-membered carbocyclic ring, or a 4- to 6-membered heterocycloalkyl ring having one heteroatom chosen from oxygen, sulfur, and nitrogen; wherein $R^{10}$ is 0 or one or more substituents independently selected from halogen, hydroxyl, oxo, CN, $OCF_3$, $CF_3$, $C_1\text{-}C_4$alkyl, $C_1\text{-}C_4$alkoxy, and $C_3\text{-}C_6$ cycloalkyl; and $R^c$ is hydrogen, CN, F, OH, $HOCH_2$—, $HO(CH_3)CH$—, $HO(Me_2)C$—, $HC(=O)$—, $C_1\text{-}C_3\text{alkylC}(=O)$, $C_1\text{-}C_4$alkyl, or $(C_{(3\text{-}6)}\text{cycloalkyl})C_{(0\text{-}2)}$alkyl;

$R^9$ is $C_1\text{-}C_4$alkyl, $C_1\text{-}C_4$alkoxy, $C_1\text{-}C_2$haloalkyl, $C_1\text{-}C_2$haloalkoxy, and $C_3\text{-}C_6$cycloalkyl;

$R^1$, when present, is hydrogen, halogen, hydroxyl, $C_1\text{-}C_6$alkyl, optionally substituted $C_3\text{-}C_6$cycloalkyl, optionally substituted phenyl, optionally substituted phenyl$SO_2$—, optionally substituted benzyl, or an optionally substituted 5- or 6-membered heterocyclic ring;

$R^2$, when present, is hydrogen, hydroxyl, halogen, cyano, or $C_1\text{-}C_4$alkyl; or $R^1$ and $R^2$ are joined to form an a oxo group, a $C_3\text{-}C_6$cycloalkyl ring or a 3- to 6-membered heterocycloalkyl ring; each of which $R^1/R^2$ ring is optionally fused to a 5- to 6-membered aryl or heteroaryl ring and is optionally substituted with one or more substituents independently chosen from halogen, hydroxyl, cyano, amino, $C_1\text{-}C_6$alkyl, and phenyl;

where each alkyl in the definition of $R^1$ and $R^2$ is straight or branched, can contain one or more double or triple bonds, can have one or more $CH_2$ group replaced by an O, S, or NH, and is optionally substituted by one or more substituents independently chosen from hydroxyl, amino, cyano, halo, oxo, and $C_3\text{-}C_6$cycloalkyl;

the A ring

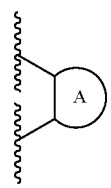

is phenyl ring or 5- or 6-membered heteroaryl ring having 1, 2, or 3 heteroatoms independently chosen from N, O, and S, which A ring is optionally substituted with one or more $R^{11}$ substituents, where $R^{11}$ is independently chosen from halogen, hydroxyl, cyano, amino, nitro, $C_1\text{-}C_6$alkyl, $C_1\text{-}C_6$alkoxy, $C_1\text{-}C_2$haloalkyl, and $C_1\text{-}C_2$haloalkoxy, provided that when Q is

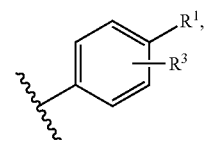

and the A ring is a phenyl ring, the A ring is substituted with one or more $R^{11}$ substituents;

$R^4$ is hydrogen, halogen, hydroxyl, or cyano;

$R^{12}$ is hydrogen or methyl; and $R^{13}$ is $C_3\text{-}C_6$cycloalkyl, phenyl, a 4-6 membered carbon-linked heterocycloalkyl group having 1 or 2 heteroatoms chosen from N, O, and S; or a 5- or 6-membered carbon-linked heteroaryl group having 1, 2, or 3 heteroatoms chosen from N, O, and S; where $R^{13}$ is optionally substituted with one or more substituents independently chosen from halogen, hydroxyl, cyano, amino, $C_1\text{-}C_4$alkyl, $C_1\text{-}C_4$alkoxy, trifluoromethyl, and trifluoromethoxy, and optionally substituted with one $C_1\text{-}C_6$alkyl substituent which has one or more $CH_2$ group replaced by an O, S, NH, or $N(C_1\text{-}C_6\text{alkyl})$ and/or is substituted by one or more substituents independently chosen from hydroxyl, amino, cyano, halo, oxo, and $C_3\text{-}C_6$cycloalkyl.

2. A compound or salt of claim 1, wherein $R^1$, when present, is hydrogen, halogen, hydroxyl, cyano, —$CF_3$, $C_1\text{-}C_4$alkyl optionally substituted with $R^{10}$, $C_1\text{-}C_4$alkoxy optionally substituted with $R^{10}$, $C_3\text{-}C_6$cycloalkyl optionally substituted with $R^{10}$, $C_3\text{-}C_6$cycloalkoxy optionally substituted with $R^{10}$, HC(O)—, $HOCH_2$-, $HO(CH_3)CH$—, $HO(Me_2)C$—, $C_1\text{-}C_3\text{alkylC}(=O)$—,

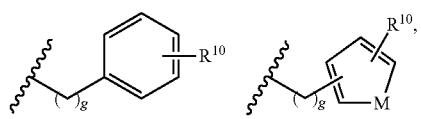

phenyl substituted with 0 to 2 $R^{10}$ substituents, pyridinyl substituted with 0 to 2 $R^{10}$ substituents, thiophenyl substituted with 0 to 1 $R^{10}$ substituents, furanyl substituted with 0 to 1 $R^{10}$ substituents; or $R^1$ and $R^2$ can be taken together to form a $C_3$-$C_6$ cycloalkyl ring substituted with 0 to 2 $R^{10}$ substituents, a 4-membered heterocycloalkyl ring containing a heteroatom selected from N, O and S and substituted with 0 to 2 $R^{10}$ substituents, or a 5- to 7-membered heterocycloalkyl ring containing 1 to 2 heteroatom selected from N, O, and S and substituted with 0 to 2 $R^{10}$ substituents.

3. A compound or salt of claim 1, wherein
$R^1$, when present, is
(i) hydrogen,
(ii) $C_1$-$C_4$alkyl, $C_3$-$C_6$ cycloalkyl, $C_1$-$C_3$alkylC(O)—, $C_3$-$C_6$ cycloalkylC(O)—

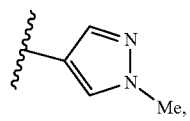

phenyl, pyridinyl, thiazolyl, oxazolyl, furanyl, thiophenyl, phenylC(O)—, heteroarylC(O)—$C_1C_4$alkyl $SO_2$, $C_3$-$C_6$ cycloalkylSO$_2$—, phenylSO$_2$—, heteroarylSO$_2$—, each of which is substituted with 0 or 1 or 2 groups independently chosen from halogen, cyano, methyl, ethyl, methoxy, ethoxy, and trifluoromethyl; or
(iii)

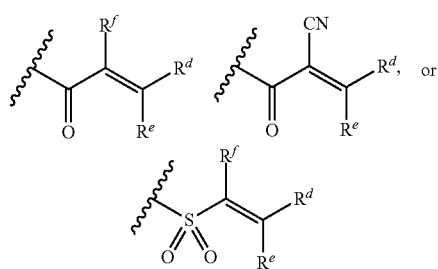

wherein $R^d$, $R^e$, and $R^f$ are independently hydrogen, $C_1$-$C_4$alkyl, or $C_3$-$C_6$cycloalkyl; and one of $R^d$ or $R^e$ can be $C_1$-$C_4$alkoxy, $(C_1$-$C_4$alkyl$)_2$N—,

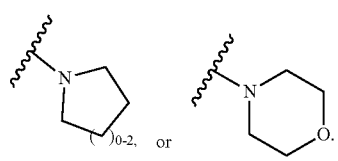

4. A compound or salt according to claim 1, wherein $R^1$ is cyano and $R^2$ is methyl.

5. A compound or salt according to claim 1, wherein the A-ring is substituted with 1, 2, or 3 substituents independently chosen from chloro, fluoro, methyl, and methoxy.

6. A compound or salt of claim 4, wherein $R^3$ is 0 or 1 or more substituents independently chosen from fluoro, trifluoromethyl, and $C_1$-$C_3$alkyl.

7. A compound or salt of claim 1, where $R^{11}$ is 1, 2, or 3 substituents independently chosen from chloro, fluoro, methyl, and methoxy.

8. A compound or salt of claim 1, wherein $R^3$ is 0 substituents.

9. A compound or salt according of claim 1, wherein $R^4$ is hydrogen.

10. A compound or salt according to claim 1, wherein the compound is a compound of Formula I-S

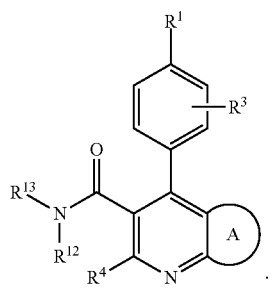

(Formula I-S)

11. A compound or pharmaceutically salt thereof, wherein the compound is a compound of Formula I-S:

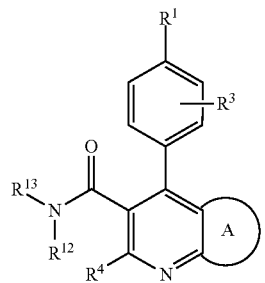

(Formula I-S)

wherein
$R^1$ is $(CN)C(CH_3)_2$—,

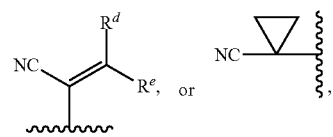

where $R^d$ and $R^e$ are independently hydrogen, $C_1$-$C_4$alkyl, or $C_3$-$C_6$cycloalkyl; and one of $R^d$ or $R^e$ can be $C_1$-$C_4$alkoxy, $(C_1$-$C_4$alkyl$)_2$N—,

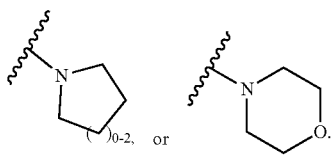

R³ is independently chosen at each occurrence and is 0 or 1 or more substituents independently chosen from halogen, hydroxyl, cyano, amino, $C_1$-$C_6$alkyl, $C_1$-$C_6$alkoxy, $C_3$-$C_6$cycloalkyl, trifluoromethyl, and phenyl;

R⁴ is hydrogen, halogen, hydroxyl, cyano, or $C_1$-$C_4$alkyl;

the A ring

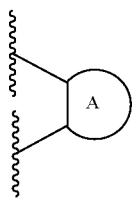

is phenyl ring or 5- or 6-membered heteroaryl ring having 1, 2, or 3 heteroatoms independently chosen from N, O, and S, which A ring is optionally substituted with one or more R¹¹ substituents, where R¹¹ is independently chosen from halogen, hydroxyl, cyano, amino, nitro, $C_1$-$C_6$alkyl, $C_1$-$C_6$alkoxy, $C_1$-$C_2$haloalkyl, and $C_1$-$C_2$haloalkoxy;

R¹² is hydrogen or methyl; and

R¹³ is $C_3$-$C_6$cycloalkyl, phenyl, a 4-6 membered carbon-linked heterocycloalkyl group having 1 or 2 heteroatoms chosen from N, O, and S; or a 5- or 6-membered carbon-linked heteroaryl group having 1, 2, or 3 heteroatoms chosen from N, O, and S; where R¹³ is optionally substituted with one or more substituents independently chosen from halogen, hydroxyl, cyano, amino, $C_1$-$C_4$alkyl, $C_1$-$C_4$alkoxy, trifluoromethyl, and trifluoromethoxy, and optionally substituted with one $C_1$-$C_6$alkyl substituent which has one or more $CH_2$ group replaced by an O, S, NH, or N($C_1$-$C_6$alkyl) and/or is substituted by one or more substituents independently chosen from hydroxyl, amino, cyano, halo, oxo, and $C_3$-$C_6$cycloalkyl.

12. A compound of Formula I-T or a pharmaceutically acceptable salt thereof

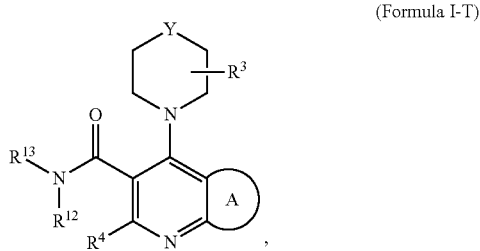

(Formula I-T)

wherein Y is NR¹, O, SO₂, or CR¹R²;

R¹, when present, is hydrogen, halogen, hydroxyl, $C_1$-$C_6$alkyl, optionally substituted $C_3$-$C_6$cycloalkyl, optionally substituted phenyl, optionally substituted phenylSO₂—, optionally substituted benzyl, or an optionally substituted 5- or 6-membered heterocyclic ring;

R², when present, is hydrogen, hydroxyl, halogen, cyano, or $C_1$-$C_4$alkyl; or R¹ and R² are joined to form an a oxo group, a $C_3$-$C_6$cycloalkyl ring or a 3- to 6-membered heterocycloalkyl ring; each of which R¹/R² ring is optionally fused to a 5- to 6-membered aryl or heteroaryl ring and is optionally substituted with one or more substituents independently chosen from halogen, hydroxyl, cyano, amino, $C_1$-$C_6$alkyl, and phenyl;

where each alkyl in the definition of R¹ and R² is straight or branched, can contain one or more double or triple bonds, can have one or more $CH_2$ group replaced by an O, S, or NH, and is optionally substituted by one or more substituents independently chosen from hydroxyl, amino, cyano, halo, oxo, and $C_3$-$C_6$cycloalkyl;

R³ is independently chosen at each occurrence and is 0 or 1 or more substituents independently chosen from halogen, hydroxyl, cyano, amino, $C_1$-$C_6$alkyl, $C_1$-$C_6$alkoxy, $C_3$-$C_6$cycloalkyl, trifluoromethyl, and phenyl;

the A ring

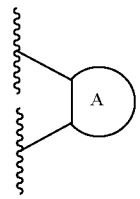

is phenyl ring or 5- or 6-membered heteroaryl ring having 1, 2, or 3 heteroatoms independently chosen from N, O, and S, which A ring is optionally substituted with one or more R¹¹ substituents, where R¹¹ is independently chosen from halogen, hydroxyl, cyano, amino, nitro, $C_1$-$C_6$alkyl, $C_1$-$C_6$alkoxy, $C_1$-$C_2$haloalkyl, and $C_1$-$C_2$haloalkoxy;

R⁴ is hydrogen, halogen, hydroxyl, cyano, or $C_1$-$C_4$alkyl;

R¹² is hydrogen or methyl; and

R¹³ is $C_3$-$C_6$cycloalkyl, phenyl, a 4-6 membered carbon-linked heterocycloalkyl group having 1 or 2 heteroatoms chosen from N, O, and S; or a 5- or 6-membered carbon-linked heteroaryl group having 1, 2, or 3 heteroatoms chosen from N, O, and S; where R¹³ is optionally substituted with one or more substituents independently chosen from halogen, hydroxyl, cyano, amino, $C_1$-$C_4$alkyl, $C_1$-$C_4$alkoxy, trifluoromethyl, and trifluoromethoxy, and optionally substituted with one $C_1$-$C_6$alkyl substituent which has one or more $CH_2$ group replaced by an O, S, NH, or N($C_1$-$C_6$alkyl) and/or is substituted by one or more substituents independently chosen from hydroxyl, amino, cyano, halo, oxo, and $C_3$-$C_6$cycloalkyl.

13. A compound or salt of claim 1, wherein the compound is a compound of Formula I-U or Formula I-V

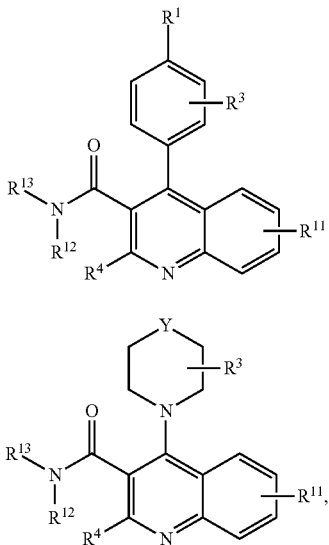

(Formula I-U)

(Formula I-V)

wherein Y is NR$^1$, O, SO$_2$, or CR$^1$R$^2$.

14. A compound or salt of claim 13, wherein the compound is a compound of Formula I-W or Formula I-Y

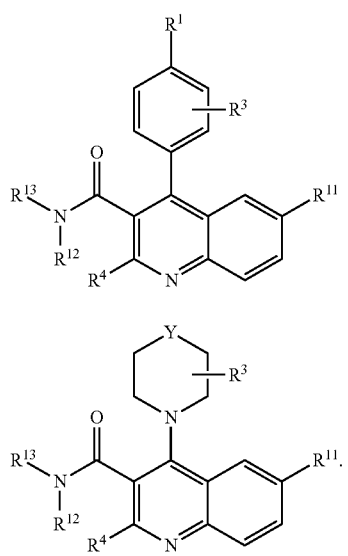

(Formula I-W)

(Formula I-Y)

15. A compound or salt of claim 13, wherein the compound is a compound of Formula I-U R$^1$ is

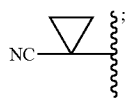

and R$^{11}$ is F, Cl, or methoxy.

16. A compound or salt of claim 12, wherein the compound is a compound of Formula I-V,

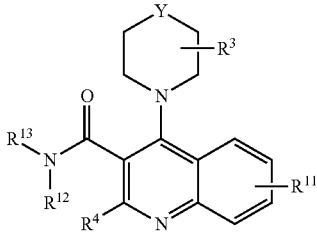

(Formula I-V)

Y is —C(R$^1$)(R$^2$)—, R$^1$ is —CN and R$^2$ is phenyl; and R$^{11}$ is F, Cl, or methoxy.

17. A compound or salt of claim 10, where R$^{12}$ is hydrogen and
R$^{13}$ is C$_3$-C$_6$cycloalkyl substituted with hydroxyl; or
R$^{13}$ is where R$^{14}$ is —CH$_2$C(O)N(CH$_3$)$_2$, —CH$_2$C(O)N(H)(CH$_3$), —CH$_2$C(O)NH$_2$, —CH$_2$C(O)N(H)(cyclopropyl), or —C$_1$-C$_4$alkylOH.

18. A compound or pharmaceutically acceptable salt thereof, wherein the compound is
6-methoxy-N-(1-methylpiperidin-4-yl)-4-(1,4-dioxa-8-azaspiro[4.5]decan-8-yl)quinoline-3-carboxamide;
4-(4-cyano-4-phenylpiperidin-1-yl)-6-fluoro-N-((1r,4r)-4-hydroxycyclohexyl)quinoline-3-carboxamide;
4-(4-cyano-4-phenylpiperidin-1-yl)-6-fluoro-N-((1r,3r)-3-hydroxycyclobutyl)quinoline-3-carboxamide;
4-(4-(1-cyanocyclopropyl)phenyl)-6-fluoro-N-((1r,3r)-3-hydroxycyclobutyl)quinoline-3-carboxamide;
4-(4-(1-cyanocyclopropyl)phenyl)-6-fluoro-N-((1r,4r)-4-hydroxycyclohexyl)quinoline-3-carboxamide;
4-(4-cyano-4-phenylpiperidin-1-yl)-N-(1-(2-(dimethylamino)-2-oxoethyl)-1H-pyrazol-4-yl)-6-fluoroquinoline-3-carboxamide;
N-(1-(2-amino-2-oxoethyl)-1H-pyrazol-4-yl)-4-(4-(1-cyanocyclopropyl)phenyl)-6-fluoroquinoline-3-carboxamide;
4-(4-(1-cyanocyclopropyl)phenyl)-6-fluoro-N-(1-(2-hydroxyethyl)-1H-pyrazol-4-yl)quinoline-3-carboxamide;
4-(4-(1-cyanocyclopropyl)phenyl)-N-(1-(2-(cyclopropylamino)-2-oxoethyl)-1H-pyrazol-4-yl)-6-fluoroquinoline-3-carboxamide;
4-(4-cyano-4-phenylpiperidin-1-yl)-6-fluoro-N-(1-(2-hydroxyethyl)-1H-pyrazol-4-yl)quinoline-3-carboxamide;
4-(4-(1-cyanocyclopropyl)phenyl)-N-(1-(2-(dimethylamino)-2-oxoethyl)-1H-pyrazol-4-yl)-6-fluoroquinoline-3-carboxamide;
4-(4-cyano-4-phenylpiperidin-1-yl)-N-(1-(2-(cyclopropylamino)-2-oxoethyl)-1H-pyrazol-4-yl)-6-fluoroquinoline-3-carboxamide;

N-(1-(2-amino-2-oxoethyl)-1H-pyrazol-4-yl)-4-(4-cyano-4-phenylpiperidin-1-yl)-6-fluoroquinoline-3-carboxamide; or 4-(4-(1-cyanocyclopropyl)phenyl)-6-fluoro-N-(1-(2-(methylamino)-2-oxoethyl)-1H-pyrazol-4-yl)quinoline-3-carboxamide.

19. A pharmaceutical composition comprising a pharmaceutically acceptable carrier and a compound or salt of claim 1.

20. A pharmaceutical composition comprising a pharmaceutically acceptable carrier and a compound or salt of claim 11.

21. A pharmaceutical composition comprising a pharmaceutically acceptable carrier and a compound or salt of claim 12.

22. A pharmaceutical composition comprising a pharmaceutically acceptable carrier and a compound or salt of claim 18.

* * * * *